(12) United States Patent
Shook et al.

(10) Patent No.: US 9,957,281 B2
(45) Date of Patent: May 1, 2018

(54) BENZODIAZEPINE DERIVATIVES AS RSV INHIBITORS

(71) Applicant: Enanta Pharmaceuticals, Inc., Watertown, MA (US)

(72) Inventors: Brian C. Shook, Holliston, MA (US); In Jong Kim, Lexington, MA (US); Thomas P. Blaisdell, Brighton, MA (US); Jianming Yu, Plainsboro, NJ (US); Joseph Panarese, Malden, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days. days.

(21) Appl. No.: 15/216,119

(22) Filed: Jul. 21, 2016

(65) Prior Publication Data

US 2017/0022221 A1   Jan. 26, 2017

Related U.S. Application Data

(60) Provisional application No. 62/195,648, filed on Jul. 22, 2015, provisional application No. 62/335,227, filed on May 12, 2016.

(51) Int. Cl.

| | | |
|---|---|---|
| *C07D 243/24* | (2006.01) | |
| *C07D 403/12* | (2006.01) | |
| *C07D 513/04* | (2006.01) | |
| *A61K 31/5513* | (2006.01) | |
| *A61K 45/06* | (2006.01) | |
| *C07D 243/16* | (2006.01) | |
| *C07D 413/12* | (2006.01) | |
| *C07D 413/14* | (2006.01) | |
| *C07D 417/14* | (2006.01) | |
| *C07D 471/08* | (2006.01) | |
| *C07D 491/048* | (2006.01) | |
| *C07D 495/04* | (2006.01) | |
| *C07D 498/08* | (2006.01) | |
| *A61K 31/56* | (2006.01) | |
| *A61K 31/58* | (2006.01) | |

(52) U.S. Cl.
CPC ........ *C07D 513/04* (2013.01); *A61K 31/5513* (2013.01); *A61K 31/56* (2013.01); *A61K 31/58* (2013.01); *A61K 45/06* (2013.01); *C07D 243/16* (2013.01); *C07D 413/12* (2013.01); *C07D 413/14* (2013.01); *C07D 417/14* (2013.01); *C07D 471/08* (2013.01); *C07D 491/048* (2013.01); *C07D 495/04* (2013.01); *C07D 498/08* (2013.01)

(58) Field of Classification Search
CPC ............................ C07D 243/24; C07D 403/12
See application file for complete search history.

(56) References Cited

U.S. PATENT DOCUMENTS

| | | | |
|---|---|---|---|
| 2007/0142403 | A1 | 6/2007 | Powell et al. |
| 2007/0185094 | A1 | 8/2007 | Lattmann et al. |
| 2008/0139536 | A1 | 6/2008 | Dowdell et al. |
| 2010/0015063 | A1 | 1/2010 | Carter et al. |
| 2012/0196846 | A1 | 8/2012 | Mackman et al. |
| 2015/0065504 | A1 | 3/2015 | Wang et al. |

FOREIGN PATENT DOCUMENTS

| | | |
|---|---|---|
| WO | 2006081389 A1 | 8/2006 |
| WO | 2014047369 A1 | 3/2014 |
| WO | 2014125444 A1 | 8/2014 |
| WO | 2014184350 A1 | 11/2014 |

OTHER PUBLICATIONS

U.S. Appl. No. 15/405,526, filed Jan. 13, 2017.
Xiong, et al., "Discover of a potent respiratory syncytial virus RNA polymerase inhibitor," Bioorganic & Medicinal Chemistry Letters, 23:6789-6793, 2013.

*Primary Examiner* — Bruck Kifle
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula (I), or pharmaceutically acceptable salts, esters, or prodrugs thereof:

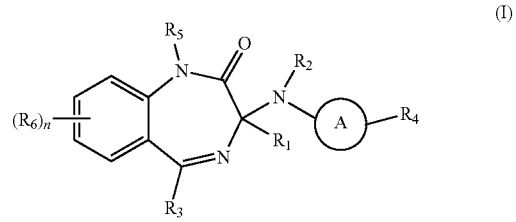

(I)

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

18 Claims, No Drawings

BENZODIAZEPINE DERIVATIVES AS RSV INHIBITORS

RELATED APPLICATION(S)

This application claims the benefit of U.S. Provisional Application No. 62/195,648, filed on Jul. 22, 2015 and 62/335,227, filed on May 12, 2016. The entire teachings of the above applications are incorporated herein by reference.

TECHNICAL FIELD

The present invention relates generally to compounds and pharmaceutical compositions useful as Respiratory Syncytial Virus (RSV) inhibitors. Specifically, the present invention relates to benzodiazepine derivatives that can inhibit RSV activities and for treating RSV infection.

BACKGROUND OF THE INVENTION

Human respiratory syncytial virus (HRSV) is a negative-sense, single stranded, RNA paramyxovirus (K M. Empey, et al., *Rev. Anti-Infective Agents*, 2010, 50(1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, and *J. Med. Chem.* 2015, 58, 1630-1643. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2013/242525 and *J. Med. Chem.* 2015, 58, 1862-1878.

There is a need for the development of effective treatments for HRSV. The present invention has identified compounds that are aminoheteroaryl substituted benzodiazepines, and inhibit HRSV. The invention includes methods to prepare the compounds as well as methods of using these compounds to treat disease.

SUMMARY OF THE INVENTION

The present invention provides compounds represented by Formula (I), and pharmaceutically acceptable salts, esters or prodrugs thereof that can be used to treat or prevent viral (particularly HRSV) infection:

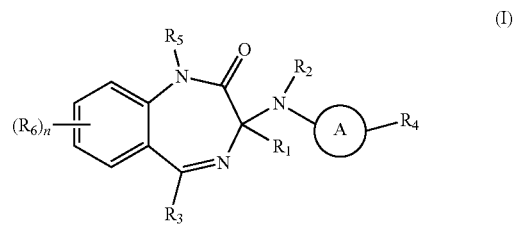

wherein:
$R_1$ is selected from the group consisting of:
 1) Hydrogen;
 2) Halogen;
 3) CN;
 4) Optionally substituted —$C_1$-$C_8$ alkyl; and
 5) Optionally substituted —$C_1$-$C_8$ alkyl O—$R_{11}$;
$R_2$ and $R_5$ are each independently selected from the group consisting of:
 1) Hydrogen; and
 2) Optionally substituted —$C_1$-$C_8$ alkyl;
A is selected from the group consisting of:
 1) Optionally substituted —$C_3$-$C_{12}$ cycloalkyl;
 2) Optionally substituted —$C_3$-$C_{12}$ cycloalkenyl;
 3) Optionally substituted 3- to 12-membered heterocycloalkyl;
 4) Optionally substituted aryl; and
 5) Optionally substituted heteroaryl;
$R_3$ is hydrogen or $R_{11}$;
$R_4$ is selected from the group consisting of:
 1) Hydrogen;
 2) Optionally substituted —$C_1$-$C_8$ alkyl;
 3) Optionally substituted —$C_2$-$C_8$ alkenyl;
 4) Optionally substituted —$C_2$-$C_8$ alkynyl;
 5) Optionally substituted —$C_3$-$C_{12}$ cycloalkyl;
 6) Optionally substituted —$C_3$-$C_{12}$ cycloalkenyl;
 7) Optionally substituted 3- to 12-membered heterocyclyl;
 8) Optionally substituted aryl;
 9) Optionally substituted heteroaryl;
 10) —$NR_{13}R_{14}$;
 11) —CO—$NR_{13}R_{14}$; and
 12) —$SO_2$—$NR_{13}R_{14}$;
Each $R_6$ is the same or different and independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —$NHC_1$-$C_8$ alkyl, optionally substituted —S—(—$C_1$-$C_8$ alkyl), optionally substituted —$SO_2$—(—$C_1$-$C_8$ alkyl), optionally substituted —$SO_2$—NH—(—$C_1$-$C_8$ alkyl), optionally substituted —NH—$SO_2$—(—$C_1$-$C_8$ alkyl), —$CO_2R_{12}$, and $NR_{13}R_{14}$, and —CO—$NR_{13}R_{14}$;
$R_{11}$ and $R_{12}$ are each independently selected from the group consisting of:

1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;
7) Optionally substituted aryl; and
8) Optionally substituted heteroaryl;

$R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted —$C_1$-$C_8$-alkoxy, —C(O)$R_{12}$, —S(O)$_2R_{12}$, and —S(O)$_2$NH$R_{12}$; alternatively, $R_{13}$ and $R_{14}$ are taken together with the nitrogen atom to which they are attached to form an optionally substituted heterocyclic ring; and n is 0, 1, 2, 3 or 4.

Each preferred group stated above can be taken in combination with one, any or all other preferred groups.

DETAILED DESCRIPTION OF THE INVENTION

In one embodiment of the present invention is a compound represented by Formula (I) as described above, or a pharmaceutically acceptable salt, ester or prodrug thereof.

The carbon atom at position 3 of the benzodiazepine ring system of the compounds of the invention is chiral. Thus, compounds of the invention can have the stereochemistry depicted in Formula (Ia) or (Ib):

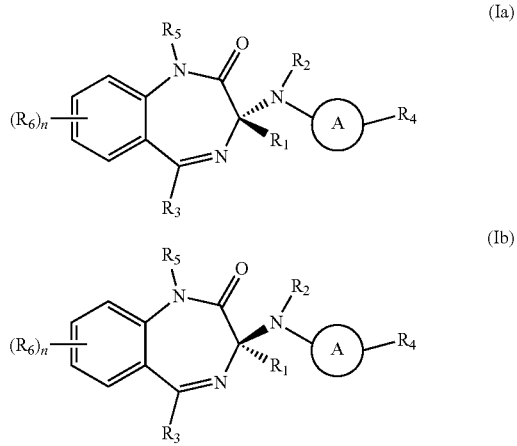

wherein $R_1$, $R_2$, $R_3$, $R_4$, $R_5$, $R_6$, A and n are previously defined. A composition of the invention can comprise a compound of the invention as a racemic mixture of Formula Ia and Formula Ib, a pure enantiomer of either Formula Ia or Formula Ib, or an excess of one enantiomer over the other. For example, the composition can comprise the compound in an enantiomeric excess of at least 5, 10, 20, 30, 40, 50, 60, 70, 80 or 90%. In one embodiment, the enantiomeric excess is at least 95%. In compounds of the invention having two or more chiral atoms, such compounds can be present in a composition as a pure stereoisomer or a mixture of stereoisomers, such as a racemic mixture or a mixture of diastereomers. In one embodiment, a composition of the invention comprises a racemic mixture, a single stereoisomer or enantiomers with an enantiomeric excess of at least 5, 10, 20, 30, 40, 50, 60, 70, 80, 90 or 95%.

In a preferred embodiment, a compound of the invention is represented by Formula (Ib). Compositions of the invention preferably comprise a substantially pure compound of Formula (Ib), or a mixture of a compound of Formula (Ib) and the corresponding compound of Formula (Ia), with an enantiomeric excess of the compound of Formula (Ib) as discussed above.

In certain embodiments, the present invention relates to compounds of Formula (I), and pharmaceutically acceptable salts thereof, wherein $R_1$ is not hydrogen. In other embodiments, $R_1$ is hydrogen, optionally substituted —$C_1$-$C_8$-alkoxy, or optionally substituted CH$_3$. In certain embodiments, the present invention relates to compounds of Formula (I) and pharmaceutically acceptable salts thereof, wherein $R_1$ is optionally substituted —$C_1$-$C_8$-alkoxy, or optionally substituted CH$_3$, such as, for example, CF$_3$.

In certain embodiments, the present invention relates to compounds of Formula (I), and pharmaceutically acceptable salts thereof, wherein $R_2$ is hydrogen, or optionally substituted CH$_3$.

In certain embodiments, the present invention relates to compounds of Formula (I), and pharmaceutically acceptable salts thereof, wherein $R_5$ is hydrogen or optionally substituted CH$_3$.

In certain embodiments, the present invention relates to compounds of Formula (I), and pharmaceutically acceptable salts thereof, wherein $R_1$ is hydrogen or optionally substituted CH$_3$, $R_2$ is hydrogen and $R_5$ is hydrogen.

In certain embodiments, the present invention relates to compounds of Formula (I), and pharmaceutically acceptable salts thereof, wherein $R_3$ is optionally substituted aryl or heteroaryl. Preferably $R_3$ is phenyl and optionally substituted with one to three substituents selected from the group consisting of hydrogen, halo, —CF$_3$, —OCF$_3$, —CH$_3$, —SO$_2$Me, and cyano.

In certain embodiments, the present invention relates to compounds of Formula (I), and pharmaceutically acceptable salts thereof, wherein A is optionally substituted aryl, optionally substituted heteroaryl, optionally substituted —$C_3$-$C_8$ cycloalkyl or optionally substituted 3- to 8-membered heterocyclyl. Preferably A is optionally substituted aryl or optionally substituted heteroaryl. More preferably A is optionally substituted monocyclic 5-membered heteroaryl, a monocyclic 6-membered heteroaryl or an 8-10-membered fused heteroaryl. In one embodiment, A is a five-membered nitrogen containing heteroaryl group.

In another embodiment, the present invention relates to compounds of Formula (I), or a pharmaceutically acceptable salt thereof, wherein A is derived from one of the following by removal of two hydrogen atoms:

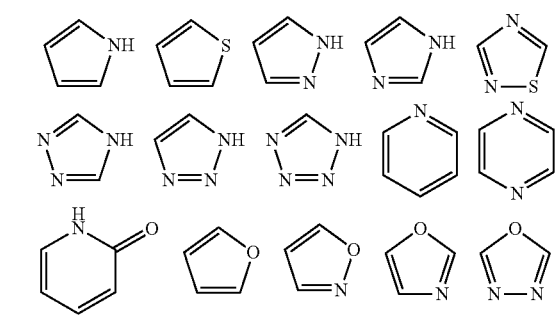

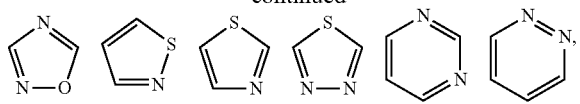

wherein each of the above shown monocyclic heteroaryl is optionally substituted when possible.

In certain embodiments, A is selected from, but not limited to, the groups set forth below, where one of the indicated valences is the point of attachment of the heteroaryl group to $R_4$ and the other is the point of attachment to the amino nitrogen atom. Each of these groups is optionally additionally substituted when possible. The atom of A which connects A to $R_4$ can be a carbon atom or, when possible, a nitrogen atom:

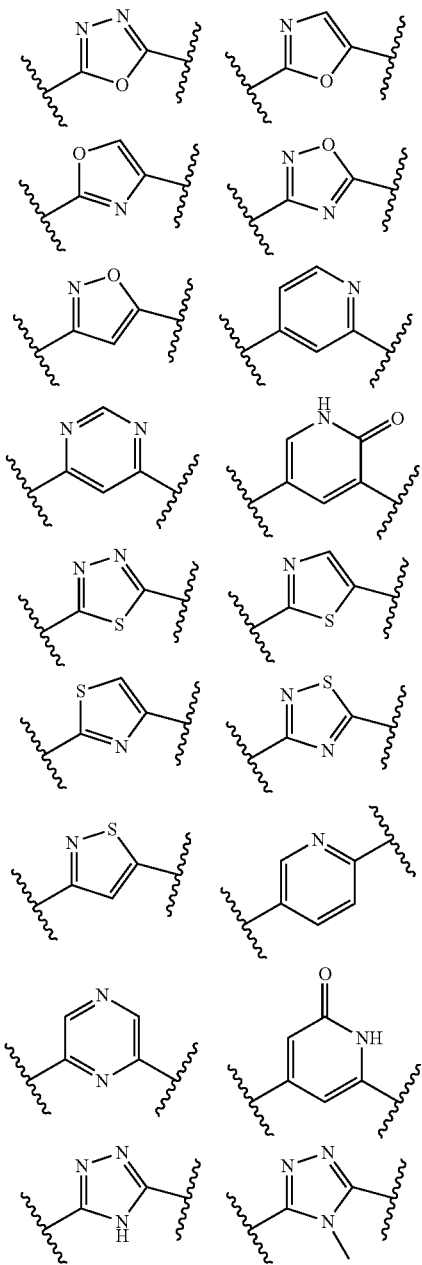
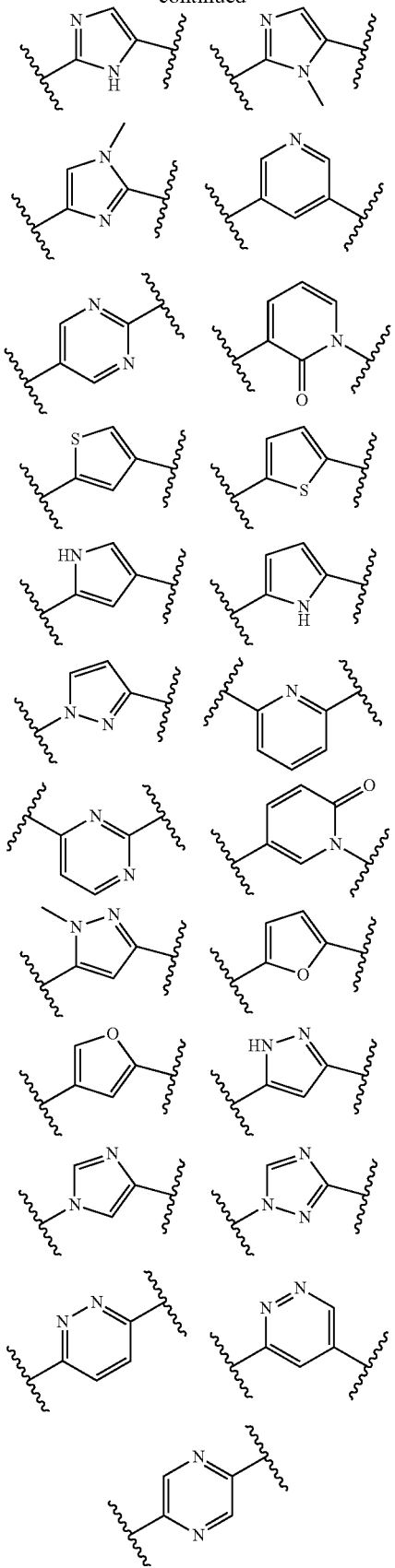

Preferably the optional substituents are independently selected from halo, —CH$_3$, —CF$_3$, —OCF$_3$, —CN, —SO$_2$Me, —CH$_2$N(CH$_3$)$_2$, optionally substituted —C$_1$-C$_8$-alkoxy, and —C(O)CH$_3$. It is to be understood that depending on the heteroaryl group, there can be 0, 1, 2 or 3 substituents. In preferred embodiments, there are 0 to 2 substituents and, more preferably, 0 or 1 substituent.

In another particular embodiment, the present invention relates to compounds of Formula (I), or a pharmaceutically acceptable salt thereof, wherein A is derived from a fused bicyclic group selected from one of the following by removal of two hydrogen atoms.

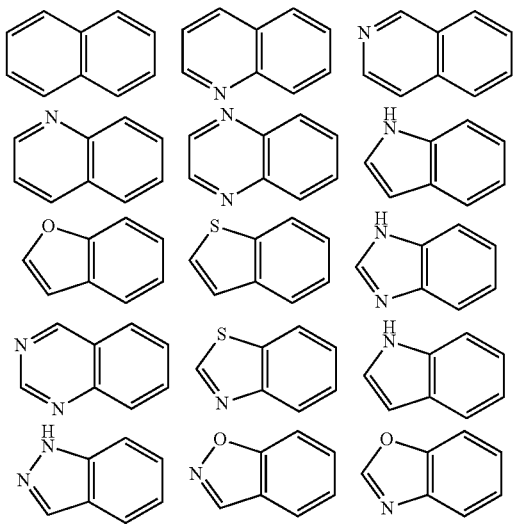

In this embodiment, A is attached to the amino nitrogen atom and R$_4$ via any available ring atoms. In the 5/6 fused rings, A is preferably attached to the amino nitrogen atom via an available atom in the 5-membered ring. In the 6/6 fused rings, A is preferably attached to the amino nitrogen atom via a carbon atom of the nitrogen-containing ring.

In certain embodiments, A is selected from the groups set forth below.

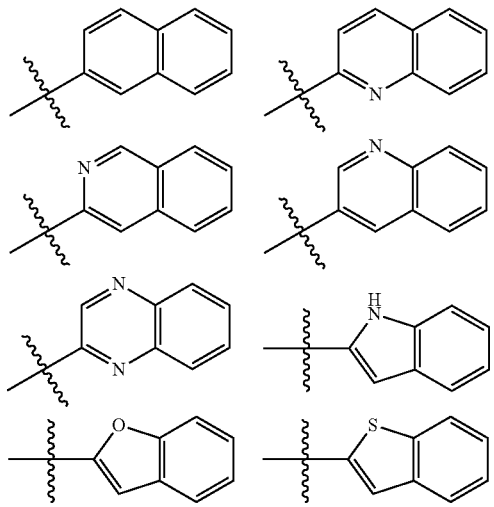

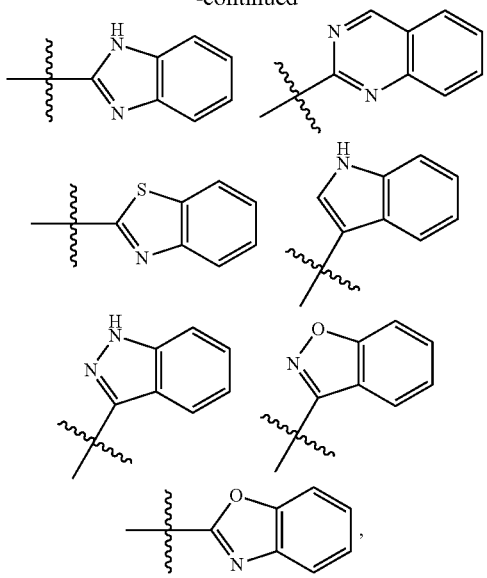

wherein the point of attachment to the amino nitrogen atom is shown and R$_4$ is attached to any other available ring position and is preferably hydrogen. In one embodiment, R$_4$ is attached to an atom of the benzo ring. When A is naphthyl, R$_4$ and the amino nitrogen atom are preferably attached to carbon atoms from different rings. Each of the above shown groups is optionally substituted, and preferably the optional substituents are independently selected from halo, —CH$_3$, —CF$_3$, —OCF$_3$, —CN, —NH$_2$, —OH, —CH$_2$N(CH$_3$)$_2$, —C(O)CH$_3$, —NH—(C$_1$-C$_6$)alkyl, —SO$_2$—(C$_1$-C$_6$)alkyl, —SO$_2$—NH—(C$_1$-C$_6$)alkyl, —NH—SO$_2$—(C$_1$-C$_6$)alkyl, and —C$_1$-C$_8$-alkoxy. Preferably, in addition to R$_4$, there are 0, 1, 2 or 3 substituents, more preferably 0, 1 or 2 substituents, and more preferably 0 or 1 substituent.

In certain embodiments of the compounds of the invention, R$_4$ is not hydrogen. In certain embodiments of the compounds of the invention, R$_4$ is an optionally substituted aryl, optionally substituted heteroaryl, optionally substituted 3- to 12-membered heterocycloalkyl, optionally substituted —C$_3$-C$_{12}$-cycloalkyl, optionally substituted —C$_3$-C$_{12}$ cycloalkenyl, optionally substituted aryl-O—, optionally substituted heteroaryl-O, optionally substituted aryl-C$_1$-C$_4$-alkyl or optionally substituted heteroaryl-C$_1$-C$_4$-alkyl. In certain embodiments, R$_4$ is phenyl, naphthyl, 5-membered heteroaryl or 6-membered heteroaryl, each of which is optionally substituted. In certain embodiments, R$_4$ is an optionally substituted 5- or 6-membered heteroaryl fused with a 6-membered aryl, heteroaryl, carbocyclic or heterocyclic ring, such as a benzo-fused-5- or 6-membered heteroaryl or a pyrido-fused 5- or 6-membered heteroaryl.

In certain embodiments of the compounds of the invention, R$_4$ is a group derived from one of the following by removal of one hydrogen atom:

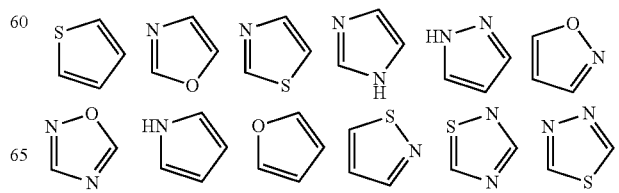

-continued

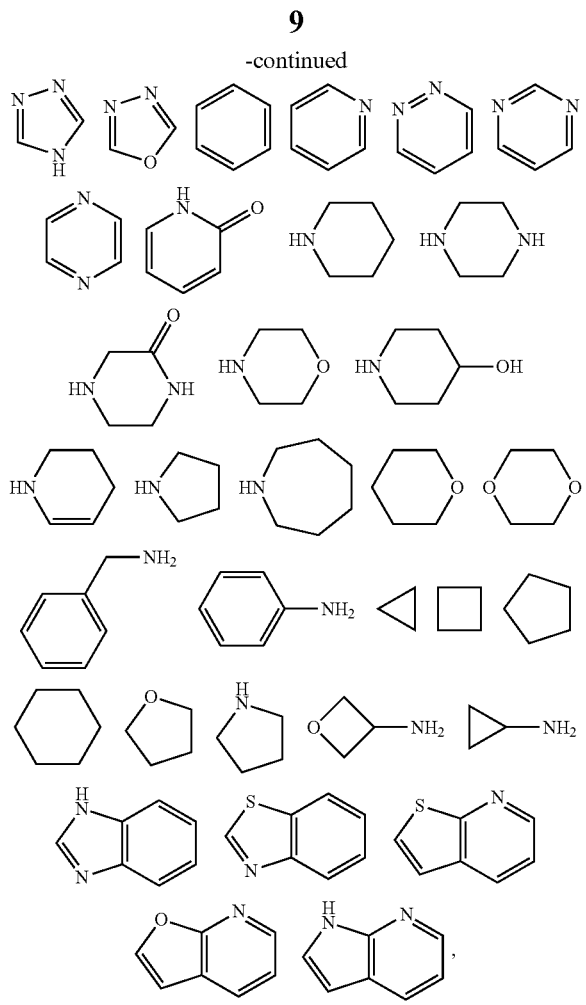

wherein each of the above shown is optionally substituted when possible.

In certain embodiments, $R_4$ is selected from the groups shown below, each of which is optionally substituted,

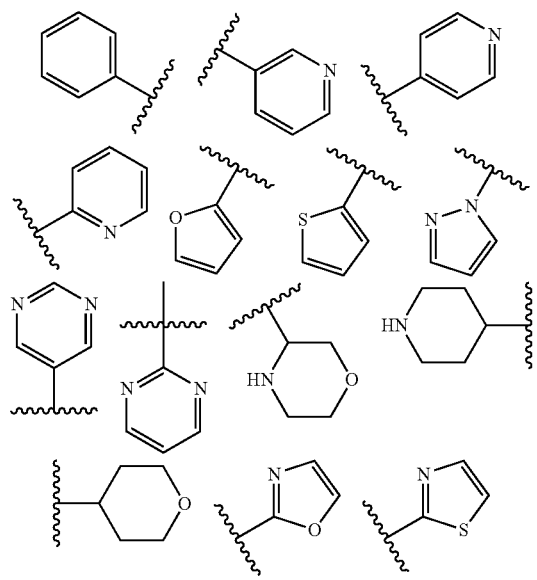

-continued

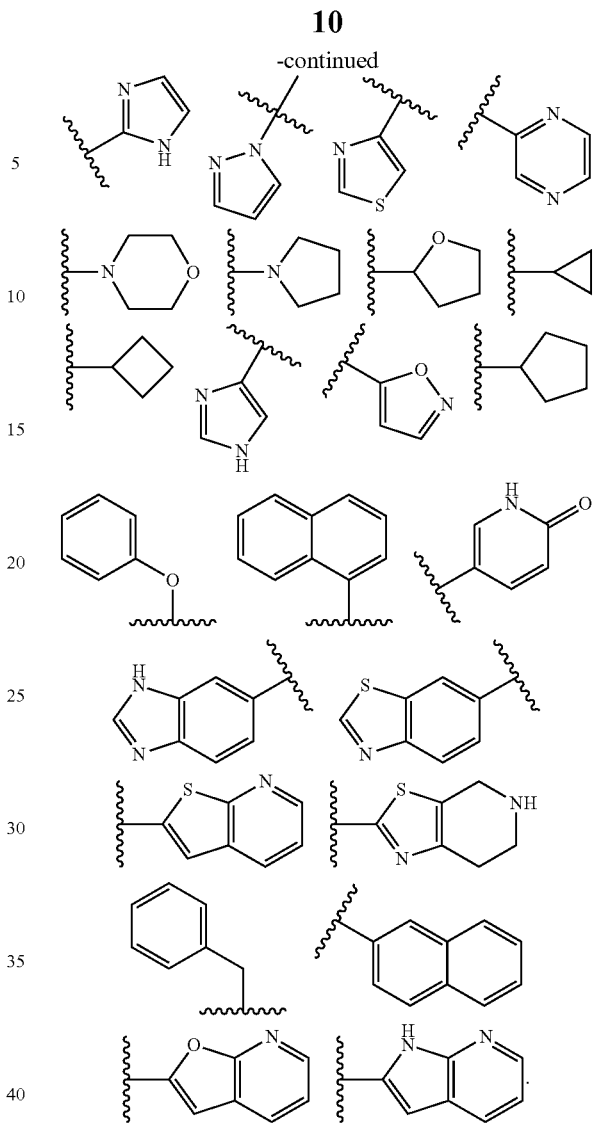

In certain embodiments, $R_4$ is optionally substituted with one or more substituents independently selected from halo, —$CH_3$, —$CF_3$, —$OCF_3$, —CN, —$NH_2$, —OH, —$CH_2N$ $(CH_3)_2$, —C(O)$CH_3$, optionally substituted —NH—($C_1$-$C_6$) alkyl, optionally substituted —NH—($C_1$-$C_6$)alkyl-($C_1$-$C_6$) alkoxy, optionally substituted —$SO_2$—($C_1$-$C_6$)alkyl, optionally substituted —$SO_2$—NH—($C_1$-$C_6$)alkyl, optionally substituted —NH—$SO_2$—($C_1$-$C_6$)alkyl, optionally substituted 3- to 12-membered heterocycloalkyl, optionally substituted aryl, optionally substituted heteroaryl, optionally substituted —$C_1$-$C_8$-alkyl, optionally substituted —$C_1$-$C_8$-alkenyl, optionally substituted —$C_3$-$C_8$-cycloalkyl, optionally substituted —$C_3$-$C_8$-cycloalkenyl, and optionally substituted —$C_1$-$C_8$-alkoxy. In another embodiment, the substituents are independently selected from $CH_3$, CN, fluoro, chloro, $CH_3O$—, $CH_3C(O)$—, $CH_3OCH_2$—, $CH_3OCH_2CH_2O$—, —$CF_3$, $CF_3O$—,

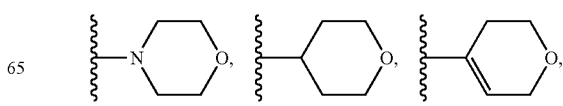

-continued

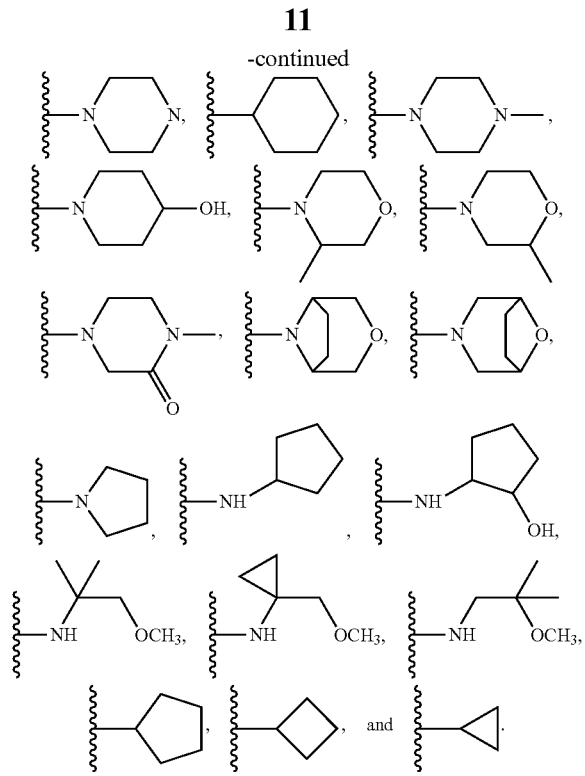
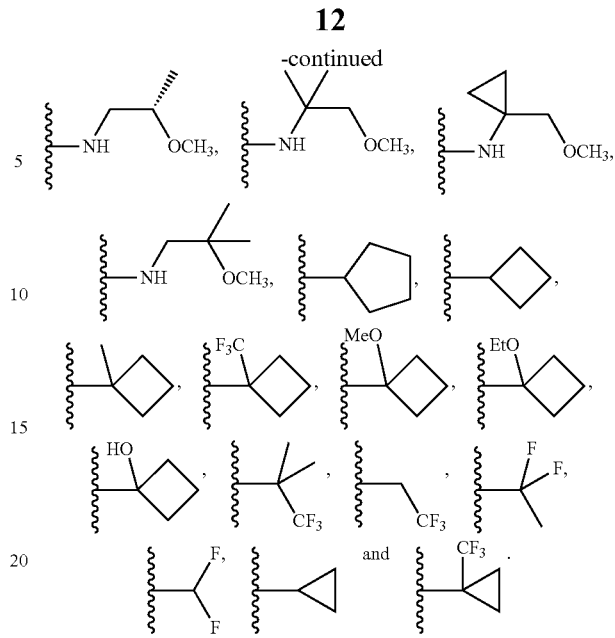

In another embodiment, the substituents are independently selected from CH₃, CN, fluoro, chloro, CH₃O—, CH₃C(O)—, CH₃OCH₂—, CH₃OCH₂CH₂O—, —CF₃, CF₃O—

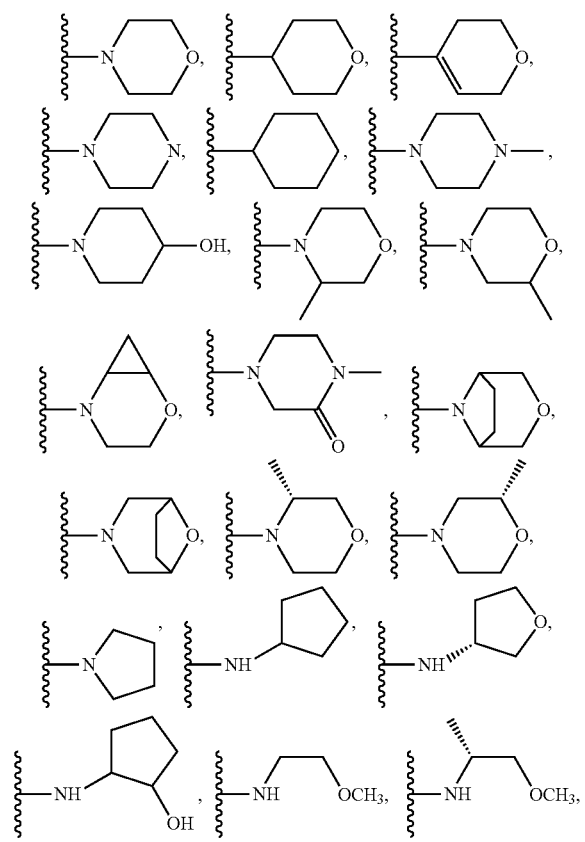

In certain embodiments, there are 0 to 4, 0 to 3, 0 to 2, 1 or 0 substituents. Preferably, there are 0 to 2 substituents and more preferably, 0 or 1 substituent. More preferably optionally substituted groups can be more than one.

In certain embodiments of the compounds of the invention, A is optionally substituted aryl, optionally substituted heteroaryl, optionally substituted —$C_3$-$C_8$ cycloalkyl or optionally substituted 3- to 8-membered heterocyclyl, as described above. In this embodiment, $R_4$ is an optionally substituted aryl, heteroaryl, 3- to 12-membered heterocycloalkyl, $C_3$-$C_{12}$-cycloalkyl, $C_3$-$C_{12}$ cycloalkenyl, aryl-O—, heteroaryl-O, aryl-$C_1$-$C_4$-alkyl or heteroaryl-$C_1$-$C_4$-alkyl, as described above. In this embodiment, $R_4$ is preferably optionally substituted aryl, heteroaryl, 3- to 12-membered heterocycloalkyl, $C_3$-$C_{12}$-cycloalkyl, or $C_3$-$C_{12}$ cycloalkenyl.

In certain embodiments of the compounds of the invention, each $R_6$ is independently halo, optionally substituted methyl, CN or $CF_3$. In certain embodiments, n is 0 to 3, 0 to 2, 1 or 0. More preferably, n is 0.

In certain embodiments of the compounds of the invention, A is a monocyclic 5-membered heteroaryl, optionally substituted with one to two substituents independently selected from the group consisting of halo, $CF_3$, $OCF_3$, $SO_2Me$, cyano, optionally substituted —$C_1$-$C_8$-alkoxy, and optionally substituted methyl; $R_1$ is hydrogen or optionally substituted methyl; $R_2$ is hydrogen; $R_3$ is optionally substituted aryl; $R_4$ is optionally substituted aryl or optionally substituted heteroaryl; $R_5$ is hydrogen; n is 0. Preferably A is optionally substituted triazole, optionally substituted oxadiazolyl, optionally substituted oxazolyl, or optionally substituted thiadiazolyl.

In certain embodiments of the compounds of the invention, A is a monocyclic 6-membered heteroaryl optionally independently substituted with one to two substituents selected from the group consisting of halo, $CF_3$, $OCF_3$, $SO_2Me$, cyano, optionally substituted —$C_1$-$C_8$-alkoxy, and optionally substituted methyl; $R_1$ is hydrogen or optionally substituted methyl; $R_2$ is hydrogen; $R_3$ is optionally substituted aryl; $R_4$ is optionally substituted aryl or optionally substituted heteroaryl; $R_5$ is hydrogen; $R_6$ is hydrogen. Preferably A is optionally substituted pyridyl or optionally substituted pyrimidyl.

In another embodiment of the invention is a compound represented by Formulas (IIa-1), (IIa-2), (IIb-1) and (IIb-2) or a pharmaceutically acceptable salt, ester or prodrug thereof:

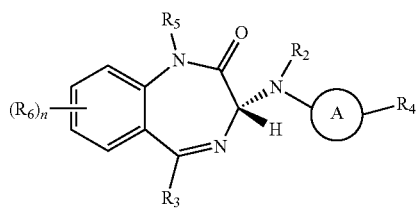
(IIa-1)

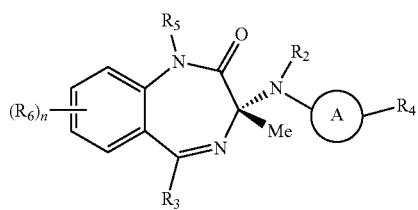
(IIa-2)

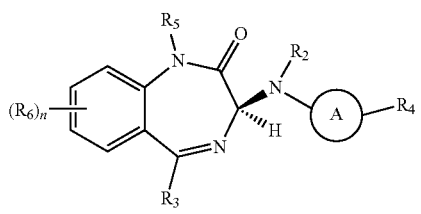
(IIb-1)

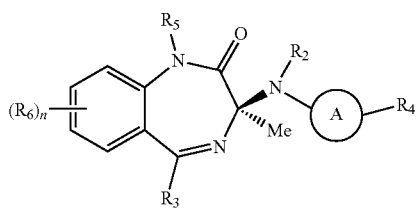
(IIb-2)

wherein $R_2$, $R_3$, $R_4$, $R_5$, $R_6$, A and n are as previously defined.

In another embodiment of the invention is a compound represented by Formulas (IIIa-1), (IIIa-2), (IIIb-1), and (IIIb-2) or a pharmaceutically acceptable salt, ester or prodrug thereof:

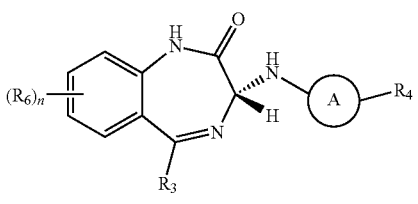
(IIIa-1)

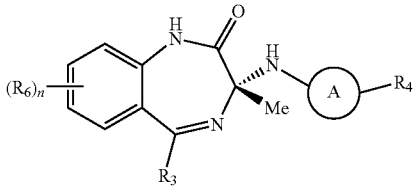
(IIIa-2)

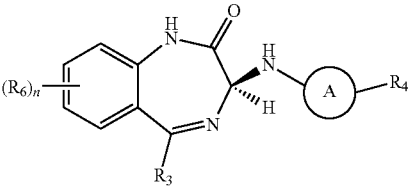
(IIIb-1)

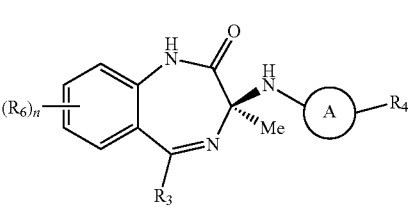
(IIIb-2)

wherein $R_3$, $R_4$, $R_6$, A and n are as previously defined.

In another embodiment of the invention is a compound represented by Formulas (IV-1)~(IV-4), (IVa-1)~(IVa-4), and (IVb-1)~(IVb-4), or a pharmaceutically acceptable salt, ester or prodrug thereof:

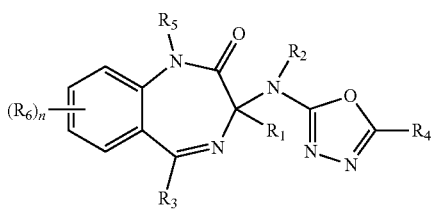
(IV-1)

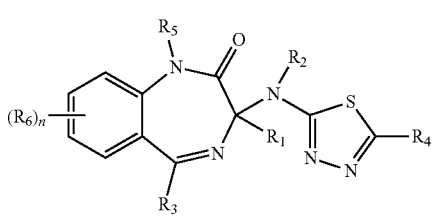
(IV-2)

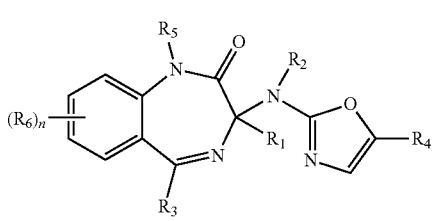
(IV-3)

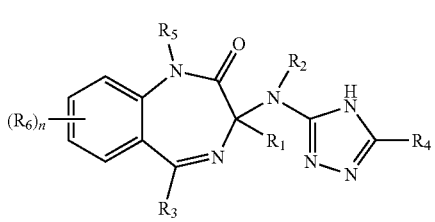
(IV-4)

-continued
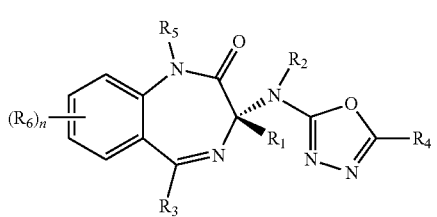
(IVa-1)
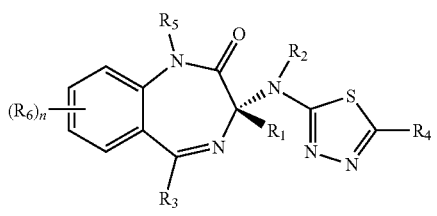
(IVa-2)
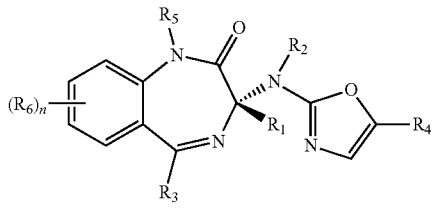
(IVa-3)
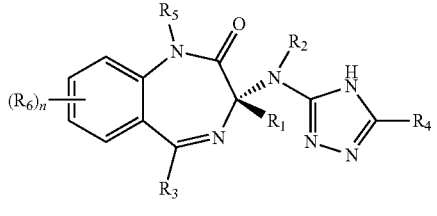
(IVa-4)
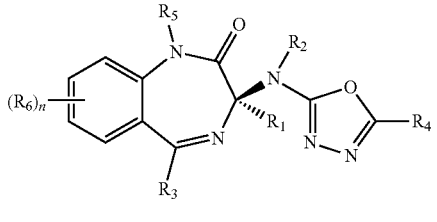
(IVb-1)
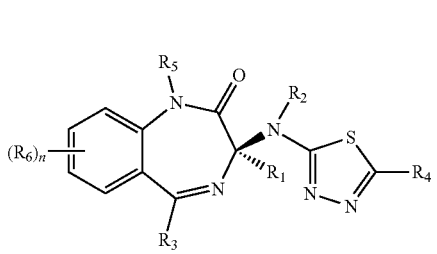
(IVb-2)
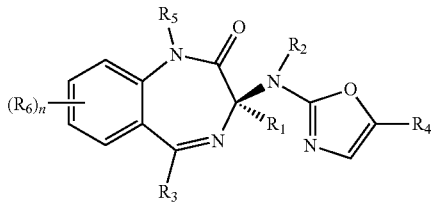
(IVb-3)
-continued
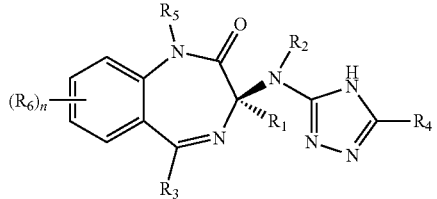
(IVb-4)
wherein, $R_1$, $R_2$, $R_3$, $R_4$, $R_5$, $R_6$ and n are as previously defined.
In another embodiment of the invention is a compound represented by Formulas (V-1)~(V-3), (Va-1)~(Va-3), and (Vb-1)~(Vb-3), or a pharmaceutically acceptable salt, ester or prodrug thereof:
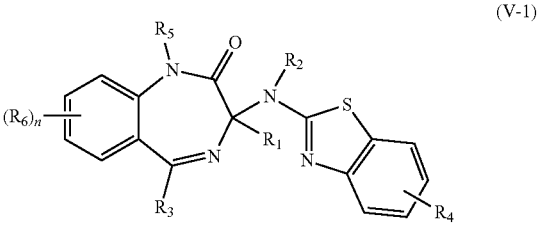
(V-1)
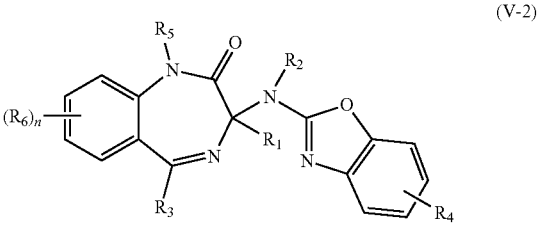
(V-2)
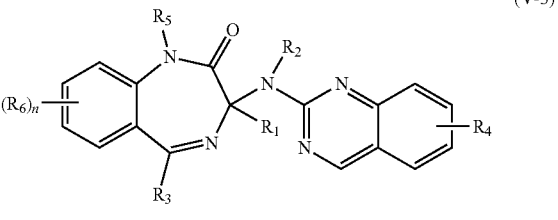
(V-3)
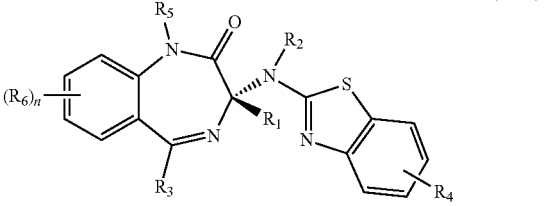
(Va-1)
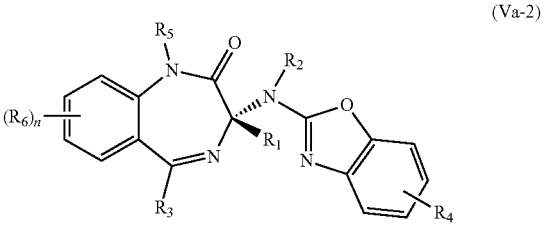
(Va-2)

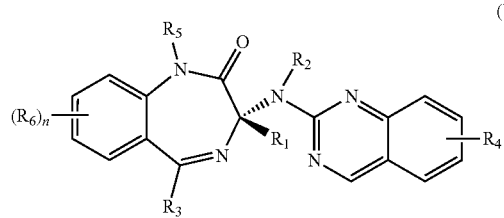
(Va-3)
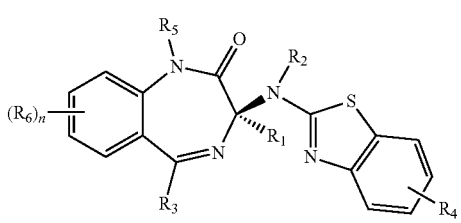
(Vb-1)
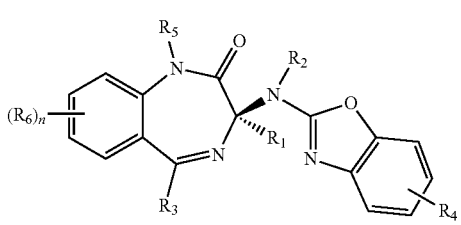
(Vb-2)
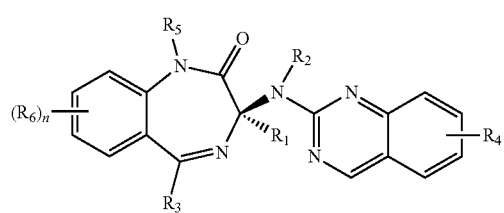
(Vb-3)
wherein, $R_1$, $R_2$, $R_3$, $R_4$, $R_5$, $R_6$ and n are as previously defined.
In another embodiment of the invention is a compound represented by Formula (VIa-1)~(VIa-8), Formula (VIb-1)~(VIb-8), or a pharmaceutically acceptable salt, ester or prodrug thereof:
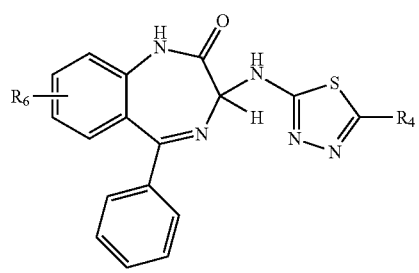
(VIa-1)
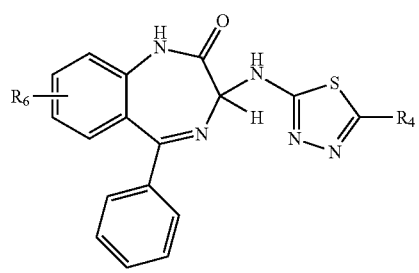
(VIa-2)
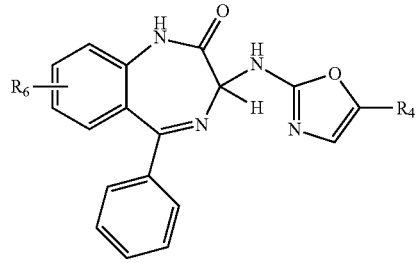
(VIa-3)
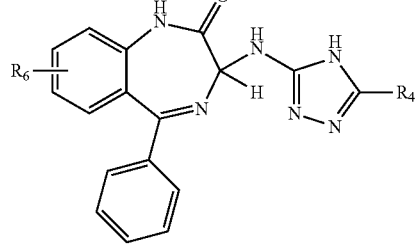
(VIa-4)
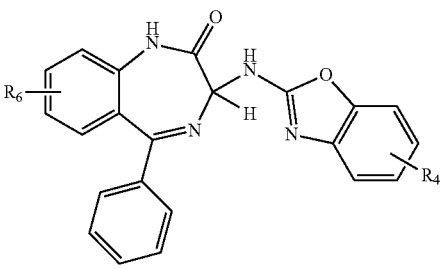
(VIa-5)
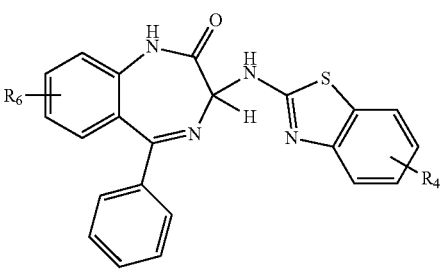
(VIa-6)
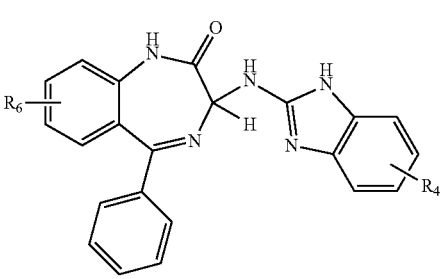
(VIa-7)

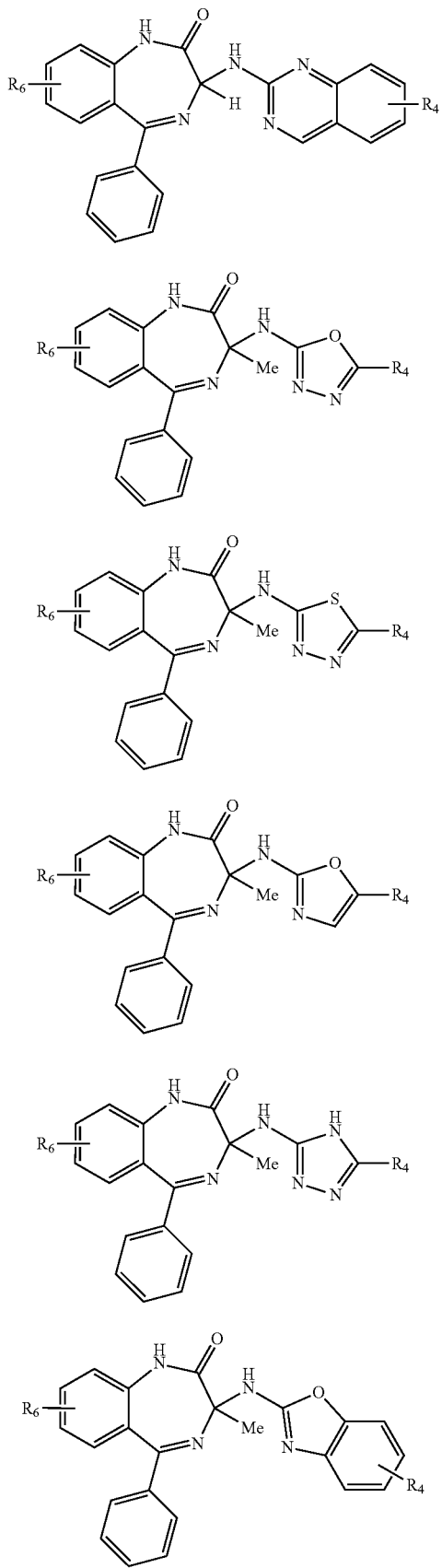
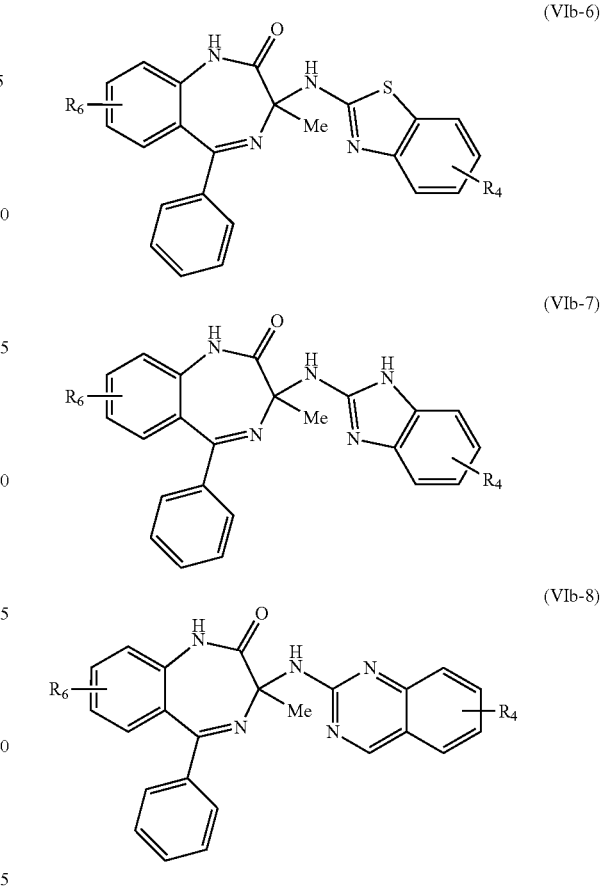

wherein $R_6$ and $R_4$ are as previously defined, except that $R_6$ can be absent, corresponding to n=0 in Formula (I). Preferably $R_6$ is absent, halo, —CN, —OH, —NH$_2$, optionally substituted methoxy, or optionally substituted methyl; more preferably $R_6$ is absent. In the compounds of Formulas (VIa-5) to (VIa-8) and (VIb-5) to (VIb-8), $R_4$ can be attached to any available ring atom and is preferably attached to a carbon atom of the benzo ring. In particular embodiments, $R_4$ for each Formula (VIa-1)~(VIa-8), (VIb-1)~(VIb-8) is selected from the groups set forth in Table 1 and can be further optionally substituted (Entry 1 to Entry 184 in Table 1).

TABLE 1

| Entry | $R_4$ |
|---|---|
| 1 |  |
| 2 |  |

TABLE 1-continued
| Entry | R4 |
|---|---|
| 3 | 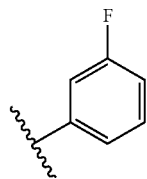 [SMILES: *c1cccc(F)c1] |
| 4 | 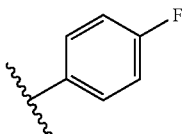 [SMILES: *c1ccc(F)cc1] |
| 5 | 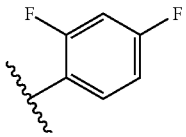 [SMILES: *c1ccc(F)cc1F] |
| 6 | 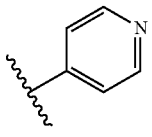 [SMILES: *c1ccncc1] |
| 7 | 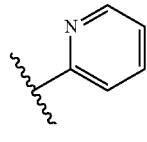 [SMILES: *c1ccccn1] |
| 8 | 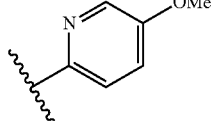 |
| 9 | 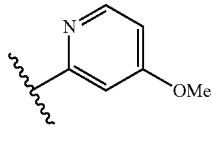 [SMILES: *c1cc(OC)ccn1] |
| 10 | 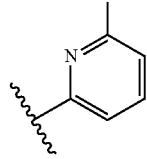 |
| 11 | 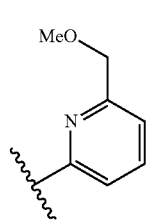 [SMILES: *c1cccc(COC)n1] |
| 12 | 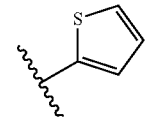 |
| 13 | 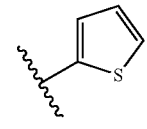 |
| 14 | 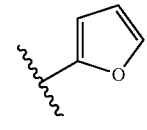 |
| 15 | 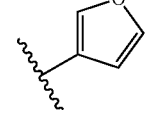 |
| 16 | 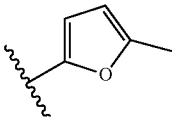 [SMILES: *c1ccc(C)o1] |
| 17 | 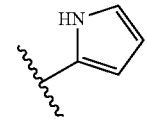 |
| 18 | 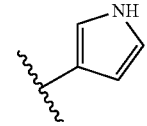 |
| 19 | 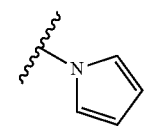 [SMILES: *n1cccc1] |
| 20 | 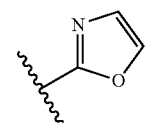 |
| 21 | 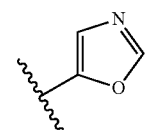 [SMILES: *c1cnco1] |
| 22 | 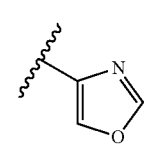 |

TABLE 1-continued
| Entry | R4 |
|---|---|
| 23 | 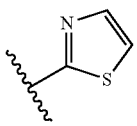 |
| 24 | 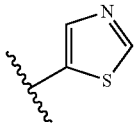 |
| 25 | 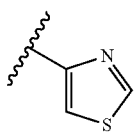 [SMILES: *c1cscn1] |
| 26 | 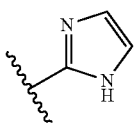 |
| 27 | 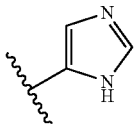 [SMILES: *c1cnc[nH]1] |
| 28 | 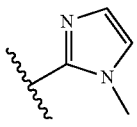 [SMILES: *c1nccn1C] |
| 29 | 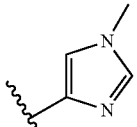 |
| 30 | 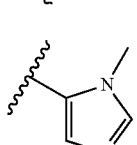 |
| 31 | 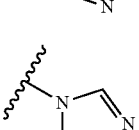 |
| 32 | 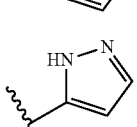 |
| 33 | 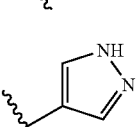 |
| 34 | 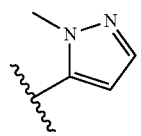 |
| 35 | 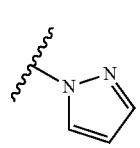 [SMILES: *n1cccn1] |
| 36 | 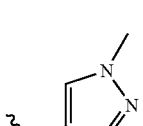 |
| 37 | 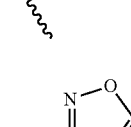 |
| 38 | 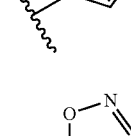 |
| 39 | 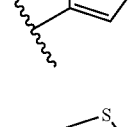 |
| 40 | 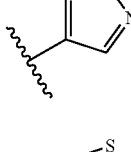 |
| 41 | 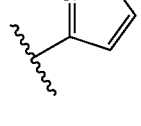 |
| 42 | 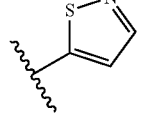 |
| 43 | 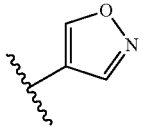 [SMILES: *c1cnoc1] |

TABLE 1-continued
| Entry | R4 |
|---|---|
| 44 | 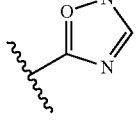 |
| 45 | 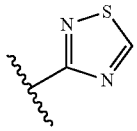 |
| 46 | 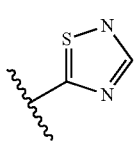 |
| 47 | 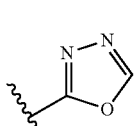 |
| 48 | 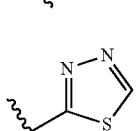 |
| 49 | 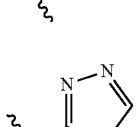 |
| 50 | 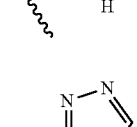 |
| 51 | 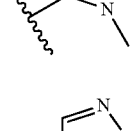 |
| 52 | 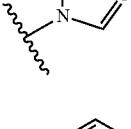 |
| 53 | 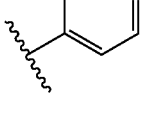 |
| 54 | 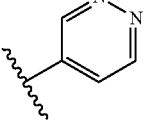 |
| 55 | 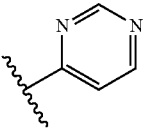 [SMILES: *c1ccncn1] |
| 56 | 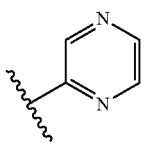 [SMILES: *c1cnccn1] |
| 57 | 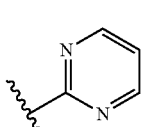 |
| 58 | 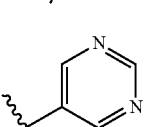 |
| 59 | 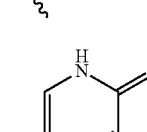 |
| 60 | 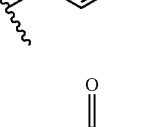 |
| 61 | 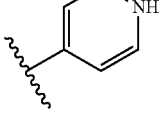 |
| 62 | 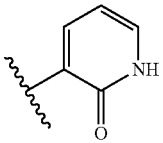 [SMILES: *c1ccc[nH]c1=O] |
| 63 | 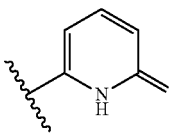 |

TABLE 1-continued

| Entry | R₄ |
|---|---|
| 64 | piperidin-1-yl |
| 65 | 4-fluoropiperidin-1-yl |
| 66 | piperazin-1-yl |
| 67 | 4-methylpiperazin-1-yl |
| 68 | 3-oxopiperazin-1-yl |
| 69 | morpholin-4-yl |
| 70 | 3,6-dihydro-2H-pyridin-1-yl |
| 71 | 4-hydroxypiperidin-1-yl |
| 72 | pyrrolidin-1-yl |
| 73 | azepan-1-yl |
| 74 | tetrahydro-2H-pyran-4-yl |
| 75 | morpholin-3-yl |
| 76 | 4-methylmorpholin-3-yl |
| 77 | piperidin-4-yl |
| 78 | 1-methylpiperidin-4-yl |
| 79 | 1-acetylpiperidin-4-yl |
| 80 | cyclohexyl |
| 81 | 4,4-difluorocyclohexyl |
| 82 | cyclopropyl |
| 83 | tetrahydrofuran-2-yl |
| 84 | pyrrolidin-2-yl |
| 85 | pyrrolidin-3-yl |
| 86 | 1-methylpyrrolidin-3-yl |
| 87 | 1-methylpyrrolidin-2-yl |
| 88 | benzylamino |
| 89 | cyclopropylamino |

TABLE 1-continued

| Entry | R₄ |
|---|---|
| 90 | NH-phenyl |
| 91 | NH-oxetan-3-yl |
| 92 | benzyl (CH₂-phenyl) |
| 93 | -C(O)NH-(3-fluorophenyl) |
| 94 | -S(O)₂-NH-R₁₁ |
| 95 | 4-methoxyphenyl |
| 96 | 3-methoxyphenyl |
| 97 | -C(O)-N(piperidinyl) |
| 98 | 2-methoxyphenyl |

TABLE 1-continued

| Entry | R₄ |
|---|---|
| 99 | 3-methoxy-4-fluorophenyl |
| 100 | 2,3-difluorophenyl |
| 101 | 3,4-difluorophenyl |
| 102 | 4-chlorophenyl |
| 103 | 4-(trifluoromethyl)phenyl |
| 104 | 4-cyanophenyl |
| 105 | 4-(trifluoromethoxy)phenyl |
| 106 | 4-(methylsulfonyl)phenyl |
| 107 | 4-sulfamoylphenyl |

TABLE 1-continued

| Entry | R₄ |
|---|---|
| 108 | 4-(1H-pyrazol-1-yl)phenyl |
| 109 | 4-methylphenyl |
| 110 | 3-methylphenyl |
| 111 | 3-chlorophenyl |
| 112 | 3-(trifluoromethyl)phenyl |
| 113 | 3-cyanophenyl |
| 114 | 3-(trifluoromethoxy)phenyl |
| 115 | 3-(methylsulfonyl)phenyl |
| 116 | 3-isopropoxyphenyl |
| 117 | 3-(2-methoxyethoxy)phenyl |
| 118 | 5-fluoropyridin-2-yl |
| 119 | 5-(trifluoromethyl)pyridin-2-yl |
| 120 | 5-cyanopyridin-2-yl |
| 121 | 5-(methylsulfonyl)pyridin-2-yl |
| 122 | 5-sulfamoylpyridin-2-yl |
| 123 | 5-(trifluoromethoxy)pyridin-2-yl |
| 124 | 5-(dimethylamino)pyridin-2-yl |

TABLE 1-continued
| Entry | R4 |
|---|---|
| 125 | 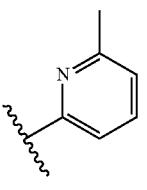 [SMILES: *c1cccc(C)n1] |
| 126 | 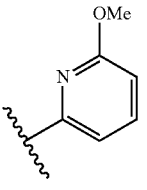 |
| 127 | 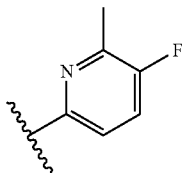 [SMILES: *c1ccc(F)c(C)n1] |
| 128 | 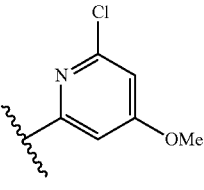 [SMILES: *c1cc(OC)cc(Cl)n1] |
| 129 | 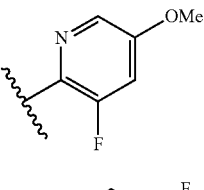 |
| 130 | 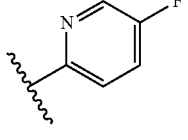 |
| 131 | 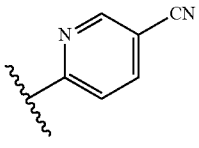 [SMILES: *c1ccc(C#N)cn1] |
| 132 | 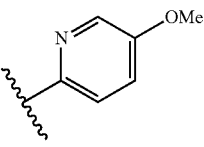 [SMILES: *c1ccc(OC)cn1] |
| 133 | 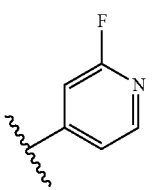 |
| 134 | 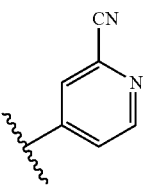 [SMILES: *c1ccnc(C#N)c1] |
| 135 | 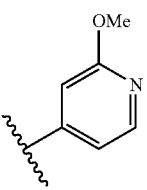 [SMILES: *c1ccnc(OC)c1] |
| 136 | 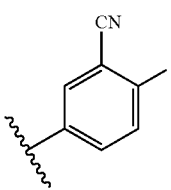 |
| 137 | 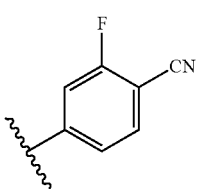 [SMILES: *c1ccc(C#N)c(F)c1] |
| 138 | 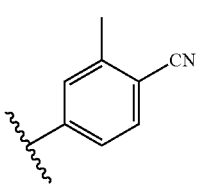 [SMILES: *c1ccc(C#N)c(C)c1] |
| 139 | 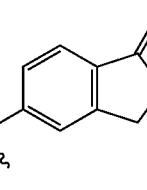 |
| 140 | 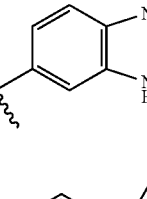 |
| 141 | 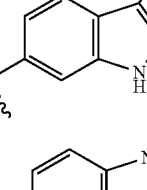 |
| 142 | 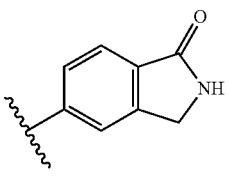 [SMILES: *c1ccc2c(c1)CNC2=O] |

TABLE 1-continued

| Entry | R4 |
|---|---|
| 143 | thieno[2,3-b]pyridin-2-yl |
| 144 | 5-methyl-4,5,6,7-tetrahydrothiazolo[5,4-c]pyridin-2-yl |
| 145 | 5-cyanothiophen-2-yl |
| 146 | 5-(trifluoromethyl)thiophen-2-yl |
| 147 | -C(O)NH-phenyl |
| 148 | -C(O)NH-(2-fluorophenyl) |
| 149 | -C(O)NH-(4-fluorophenyl) |
| 150 | -C(O)NH-(pyridin-2-yl) |
| 151 | -C(O)NH-(pyridin-3-yl) |
| 152 | -C(O)NH-(pyridin-4-yl) |
| 153 | -C(O)NH-(tetrahydro-2H-pyran-4-yl) |
| 154 | -C(O)-morpholin-4-yl |
| 155 | -S(O)2NH-phenyl |
| 156 | -S(O)2NH-(2-fluorophenyl) |
| 157 | -S(O)2NH-(3-fluorophenyl) |

TABLE 1-continued

| Entry | R4 |
|---|---|
| 158 | 4-fluorophenyl sulfonamide |
| 159 | pyridin-2-yl sulfonamide |
| 160 | pyridin-3-yl sulfonamide |
| 161 | pyridin-4-yl sulfonamide |
| 162 | tetrahydropyran-4-yl sulfonamide |
| 163 | morpholinyl sulfonyl |
| 164 | 3-methylisoxazol-5-yl |
| 165 | 4-(dimethylamino)phenyl |
| 166 | 6-(1H-pyrazol-1-yl)pyridin-3-yl |
| 167 | 5-(1H-pyrazol-1-yl)pyridin-2-yl |
| 168 | 4-(pyrrolidin-1-yl)phenyl |
| 169 | 4-morpholinophenyl |
| 170 | 4-(1H-imidazol-1-yl)phenyl |
| 171 | 4-(3-(trifluoromethyl)-1H-pyrazol-1-yl)phenyl |
| 172 | 4-(1H-1,2,4-triazol-1-yl)phenyl |

TABLE 1-continued

| Entry | R₄ |
|---|---|
| 173 | (4-(tetrazol-5-yl)phenyl) |
| 174 | (2-methylbenzothiazol-6-yl) |
| 175 | (2-methyl-3-cyanopyridin-6-yl) |
| 176 | (5-(methoxymethyl)furan-2-yl) |
| 177 | (5-((dimethylamino)methyl)furan-2-yl) |
| 178 | (isopropyl) |
| 179 | (5-methylthiophen-2-yl) |
| 180 | (cyclopentyl) |
| 181 | (cyclobutyl) |
| 182 | (5-chlorofuran-2-yl) |
| 183 | (naphthalen-1-yl) |
| 184 | (naphthalen-2-yl) |

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule. For example, in Formula (V-1) when n is 2, each of the two $R_6$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection is subjects. The method comprises administering a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon radicals. Preferred alkyl radicals include $C_1$-$C_6$ alkyl and $C_1$-$C_8$ alkyl radicals. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl groups include, but are not limited to, methyl, ethyl, propyl, isopropyl, n-butyl, tert-butyl, neopentyl, n-hexyl, heptyl, and octyl radicals.

The term "alkenyl" as used herein, refers to straight- or branched-chain hydrocarbon radicals having at least one carbon-carbon double bond by the removal of a single hydrogen atom. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl" as used herein, refers to straight- or branched-chain hydrocarbon radicals having at least one carbon-carbon triple bond by the removal of a single hydrogen atom. Preferred alkynyl radicals include $C_2$-$C_6$ alkynyl and $C_2$-$C_8$ alkynyl radicals. Representative alkynyl radicals include, but are not limited to, for example, ethynyl, 1-propynyl, 1-butynyl, heptynyl, octynyl and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "alkynylene" refers to an alkynyl group from which an additional hydrogen atom has been removed to form a diradical group. Alkynylene groups include, but are not limited to, for example, ethynylene, propynylene, butynylene, 1-methyl-2-butyn-1-ylene, heptynylene, octynylene, and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure, the carbocycle group can be attached to the two other elements through any two substitutable ring atoms. A $C_4$-$C_6$ carbocycle has 4-6 ring atoms.

The term "cycloalkyl", as used herein, refers to a monocyclic or polycyclic saturated carbocyclic ring compound, and the carbon atoms may be optionally oxo-substituted. A polycyclic cycloalkenyl can comprise fused rings. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl", as used herein, refers to monocyclic or polycyclic carbocyclic ring compound having at least one carbon-carbon double bond and the carbon atoms may be optionally oxo-substituted. A polycyclic cycloalkenyl can comprise fused rings, covalently attached rings or a combination thereof. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "heterocycloalkyl" and "heterocyclic" can be used interchangeably and refer to a non-aromatic 3-, 4-, 5-, 6-, 7- or 8- or 9-12 membered ring or a bi- or tri-cyclic group fused or bridged or spiro system, where: (i) each ring contains between one and three heteroatoms independently selected from oxygen, sulfur and nitrogen, (ii) each 5-membered ring has 0 to 1 double bonds and each 6-, 7-, 8-, or 9-12 membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, 8-azabicyclo[3.2.1]octyl, 5-azaspiro[2.5]octyl, 1-oxa-7-azaspiro[4.4]nonanyl, and tetrahydrofuryl. Such heterocyclic groups may be further substituted to give substituted heterocyclic. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, indenyl and the like. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. A polycyclic heteroaryl can comprise fused rings, covalently attached rings or a combination thereof.

In accordance with the invention, aromatic groups can be substituted or unsubstituted.

The term "arylalkyl," as used herein, refers to functional group wherein an alkylene chain is attached to an aryl group. Examples include, but are not limited to, benzyl, phenethyl and the like. The term "substituted arylalkyl" means an arylalkyl functional group in which the aryl group is substituted. Similarly, the term "heteroarylalkyl" means a functional group wherein an alkylene chain is attached to a heteroaryl group. Examples include, but are not limited to, pyridinylmethyl, pyrimidinylethyl and the like. The term "substituted heteroarylalkyl" means a heteroarylalkyl functional group in which the heteroaryl group is substituted.

The term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "halo" or halogen" alone or as part of another substituent, as used herein, refers to a fluorine, chlorine, bromine, or iodine atom.

The term "hydrogen" includes hydrogen and deuterium. In addition, the recitation of an atom includes other isotopes of that atom so long as the resulting compound is pharmaceutically acceptable.

The term "substituted" as used herein, refers to independent replacement of one, two, three or more of the hydrogen atoms thereon with substituents including, but not limited to, deuterium, tritium, —F, —Cl, —Br, —I, —OH, protected hydroxy, —NO₂, —CN, —NH₂, —N₃, protected amino, alkoxy, thioalkoxy, oxo, thioxo, —$C_1$-$C_{12}$-alkyl, —$C_2$-$C_{12}$-alkenyl, —$C_2$-$C_{12}$-alkynyl, —$C_3$-$C_{12}$-cycloalkyl-halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$), and the like.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, including the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc. "Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Meth-* ods of Purification, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BAST for bis(2-methoxyethyl)aminosulfur trifluoride
BME for 2-mercaptoethanol;
BOP for benzotriazol-1-yloxy-tris(dimethylamino)phosphonium hexafluorophosphate;
BTC for bis(trichloromethyl)carbonate; triphosgene;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-;
1-O-(2-cyanoethyl)-(N,N-diisopropyl)-phosphoramidite;
DBU for 1, 8-Diazabicycloundec-7-ene;
DCC for N, N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;

DMA for N,N-dimethyl acetamide;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
DUPHOS for

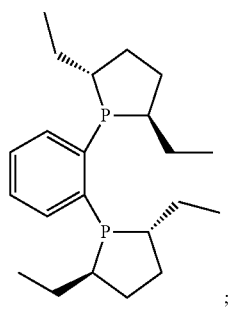 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc or EA for ethyl acetate;
EtOH for ethyl alcohol;
HATU for O (7-Azabenzotriazole-1-yl)-N,N,N',N' tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
PE for petroleum ether;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethyl amine;
Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or PPh$_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene; and
Zhan 1 B for

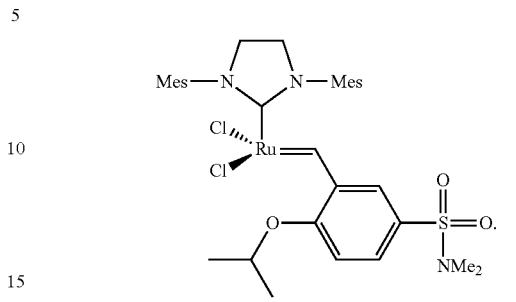

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel RSV analogs of the compounds of formula 10 or 11 are prepared starting from compounds 1, 2, and 3. A procedure similar to that described by Sherrill and Sugg (J. Org. Chem. 1995, 60, 730-734) was followed to get to the intermediate having the formula 8. Firstly, 1, 2, and 3 are heated in an appropriate solvent like, but not limited to, toluene to form compound 4. Compound 4 is converted to the corresponding acid chloride, using the appropriate conditions, and is then reacted with 5, wherein n, R$_3$, R$_5$, and R$_6$ are as previously defined, to form compound 6. Compound 6 is reacted with ammonia, followed by reaction with ammonium acetate in acetic acid to form compound 7. The Cbz group in 7 is removed using HBr in acetic acid to afford the intermediate amine 8. Compound 8 is a common intermediate that will be used in various ways to access compounds of the formula (10 or 11). Following Path 1, 8 is reacted with 9 via a displacement of the halogen (X) or via suitable coupling conditions using Pd or Cu catalysts to afford compounds of formula 10, wherein A and R$_4$ are defined as previously described. Compounds 10 can be reacted further via alkylation with reagents like, but not limited to, alkyl halides, mesylates and tosylates or via reductive amination with aldehydes and ketones to install R$_2$, wherein R$_2$ is defined as previously described, to give compounds of formula 11. Following Path 2 reverses the reaction sequence by alkylating 8 with reagents like, but not limited to, alkyl halides, mesylates and tosylates or via reductive amination with aldehydes and ketones to install R$_2$, wherein R$_2$ is defined as previously described, giving 12 which is reacted further with 9, via displacement or Pd/Cu catalyzed reactions, to give compounds of formula 11.

Scheme 1
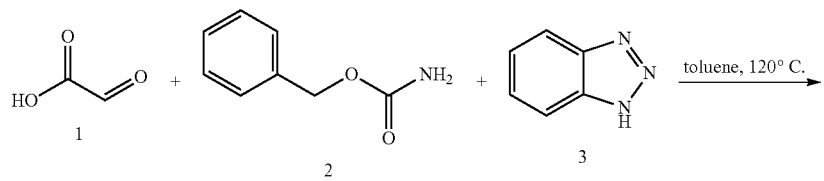
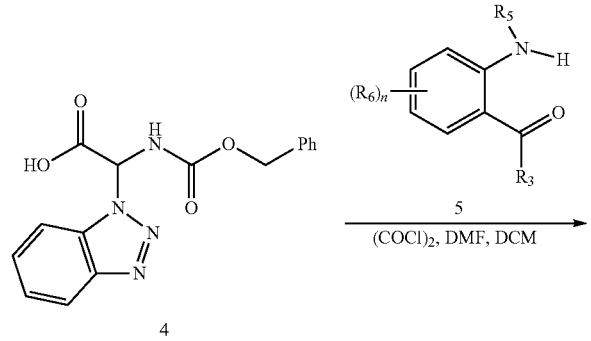
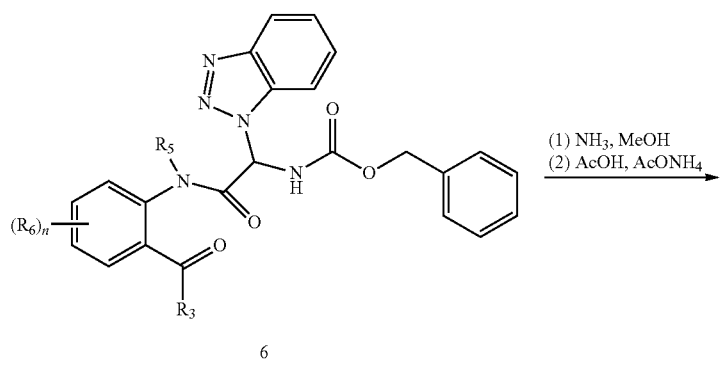
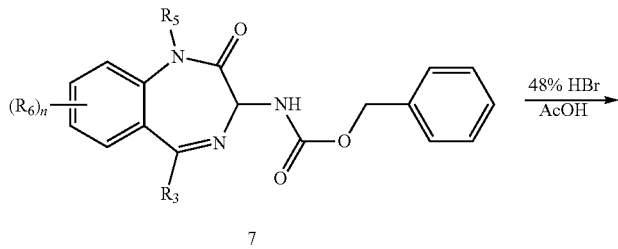
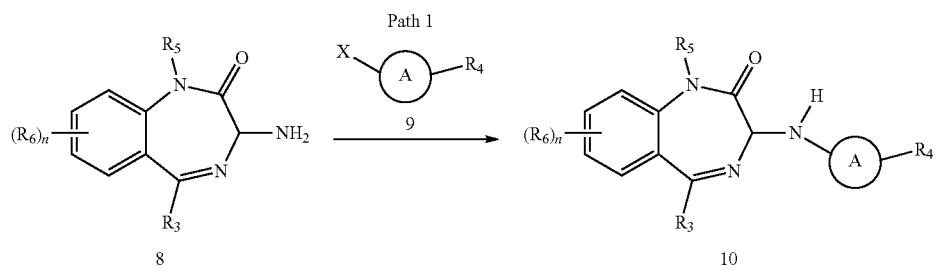

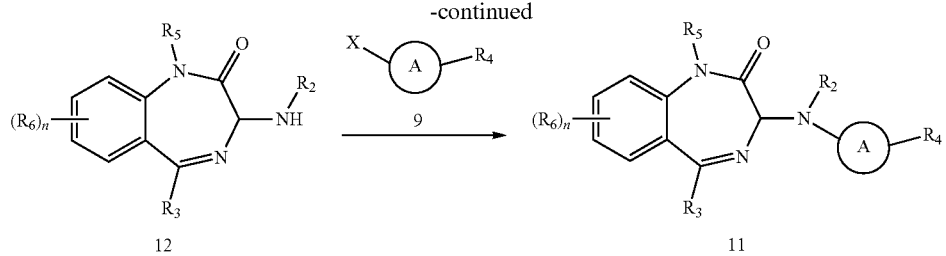

Scheme 2 illustrates alternative methods, wherein n, $R_2$, $R_3$, $R_4$, $R_5$, $R_6$, and A are defined as previously described, to prepare compounds of formula (11). Following Path 1, compound 12 is reacted with the di-halide 13, where X is a halogen that may or may not be the same, via displacement of one halogen (X) or via suitable coupling conditions using Pd or Cu catalysts to afford compounds of formula 14.

reagents, and organozinc reagents in combination with copper (I) thiophenecarboxylate (CuTC) and the appropriate Pd, Ni, or Cu catalyst to afford compounds of formula 11. Alternatively, compound 16 can be oxidized to the corresponding sulfoxide or sulfone using an appropriate oxidant like, but not limited to, m-CPBA, $H_2O_2$, or Oxone, followed by displacement with an appropriate amine, alcohol, or thiol to form 11.

Scheme 2

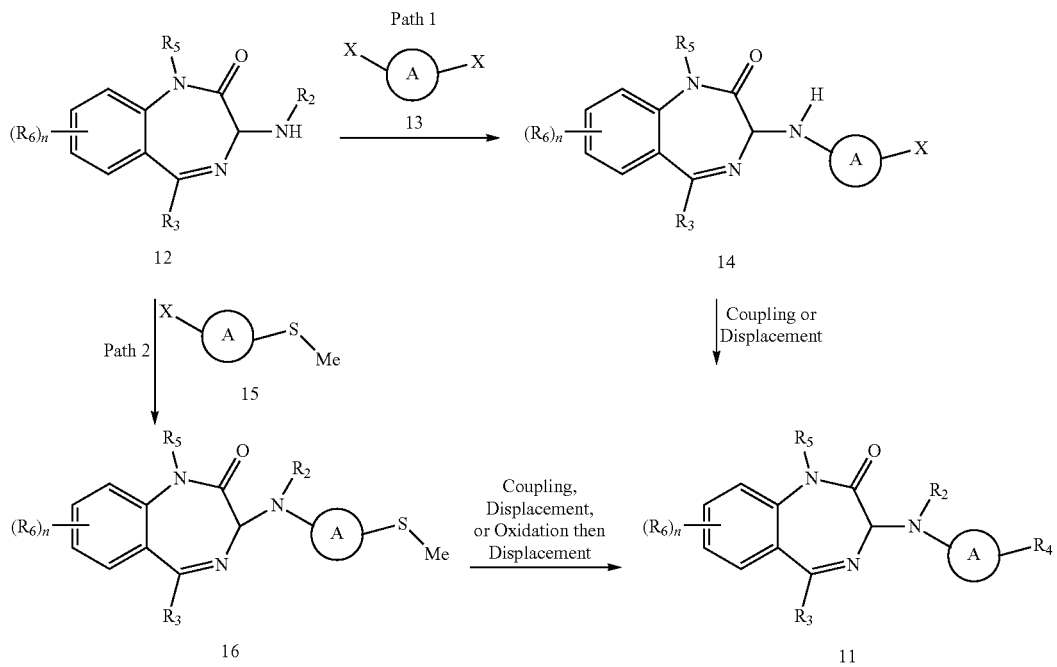

Compound 14 is reacted further with appropriate coupling partners selected from, but not limited to, boronic acids, boronic esters, organotin reagents, organozinc reagents, organomagnesium reagents, organo silicon reagents, amines, and alcohols, in combination with the appropriate Pd, Ni, or Cu catalyst to afford compounds of formula 11. The aforementioned reaction can also be run in an atmosphere of carbon monoxide to afford corresponding ketones, amides, and esters of formula 11. Compound 14 can also reacted with an appropriate amine, alcohol, or thiol to form 11 via a displacement reaction. Following path 2, 12 is reacted with halide 15 via a displacement of the halogen (X) or via suitable coupling conditions using Pd or Cu catalysts to afford compounds of formula 16. Compound 16 is reacted further with appropriate coupling partners selected from, but not limited to, boronic acids, boronic esters, organotin Scheme 3 illustrates methods, wherein n, $R_2$, $R_3$, $R_4$, $R_5$, and $R_6$ are defined as previously described, to prepare compounds of formulas 20, 21, 22 and 23. Following Path 1 amine 8 is reacted with 1,1'-thiocarbonyldiimidazole (TCDI) to generate the intermediate 17 that is reacted directly with hydrazides to afford compounds of formula 18. Compounds of formula 18 can be reacted with 1-Ethyl-3-(3-dimethylaminopropyl)carbodiimide (EDCI) to give the oxadiazoles of formula 20. Compound 20 can be reacted further via alkylation or reductive amination to install $R_2$, wherein $R_2$ is defined as previously described, to give compounds of formula 21. Compounds of formula 18 can also be reacted with tosyl chloride (TsCl) to afford the thiadiazoles of formula 22 that can be reacted further via alkylation with reagents like, but not limited to, alkyl halides, mesylates and tosylates or via reductive amination with aldehydes and ketones to install $R_2$, wherein $R_2$ is defined as previously described, to give compounds of formula 23. Following Path 2 the intermediate 17 is reacted directly with hydrazine to form compound 19. Compound 19 is then coupled to a carboxylic acid using an appropriate coupling reagent such as, but not limited to, EDCI with HOBt or HATU to afford compound 18 which is converted to the compounds 20, 21, 22, and 23 as described above.

reacted with oxadiazolones is the presence of a coupling reagent such as, but not limited to, (Benzotriazol-1-yloxy)tris(dimethylamino)phosphonium hexafluorophosphate (BOP) to afford compounds of formula 20 and can be reacted further via alkylation with reagents like, but not limited to, alkyl halides, mesylates and tosylates or via reductive amination with aldehydes and ketones to install $R_2$, wherein $R_2$ is defined as previously described, to give

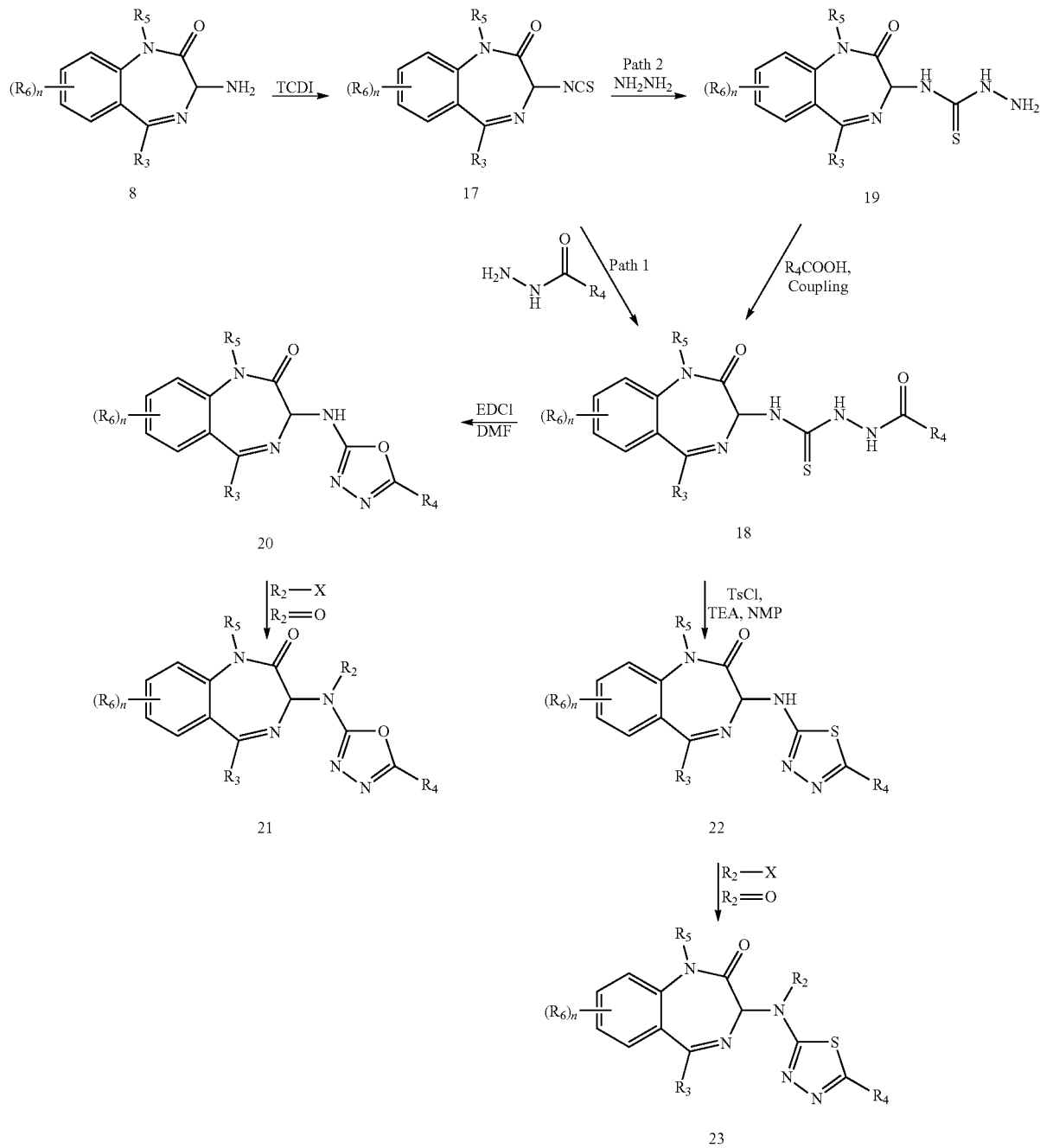

Scheme 3

Scheme 4 illustrates methods, wherein n, $R_2$, $R_3$, $R_4$, $R_5$, and $R_6$ are defined as previously described, to prepare compounds of formula 20 and (21). Compounds 8 or (can be compounds of formula 21. Alternatively compounds 12 can be reacted with oxadiazolones is the presence of (BOP) to afford compounds of formula 21.

Scheme 4

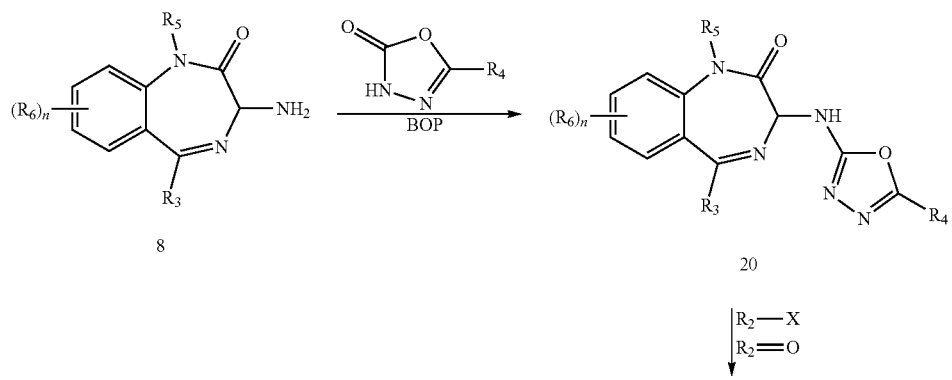

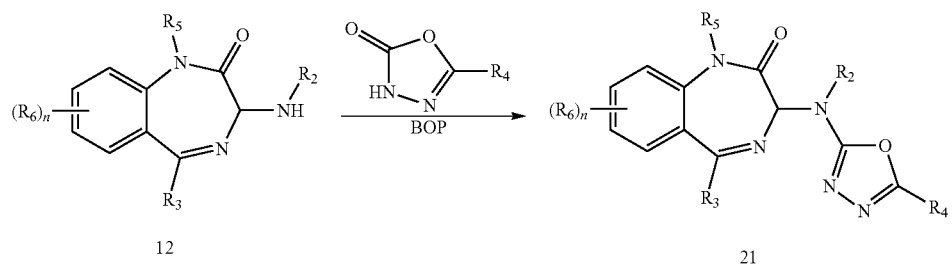

Scheme 5 illustrates methods, wherein n, $R_2$, $R_3$, $R_4$, $R_5$, and $R_6$ are defined as previously described, to prepare compounds of formula 23, 24, 26, and, 27. Following Path 1, amine 8 is reacted with TCDI to generate the intermediate 17 that is reacted with alpha-azido ketones to generate the oxazole 23. Compound 23 can be reacted further via alkylation with reagents like, but not limited to, alkyl halides, mesylates and tosylates or via reductive amination with aldehydes and ketones to install $R_2$, wherein $R_2$ is defined as previously described, to give compounds of formula 24. Following Path 2, 8 is reacted with TCDI to generate the intermediate thiourea 25 which is reacted further with alpha-bromo ketones to form the thiazoles having a formula like 26, that can react further via alkylation with reagents like, but not limited to, alkyl halides, mesylates and tosylates or via reductive amination with aldehydes and ketones to install $R_2$, wherein $R_2$ is defined as previously described, to give compounds of formula 27.

Scheme 5

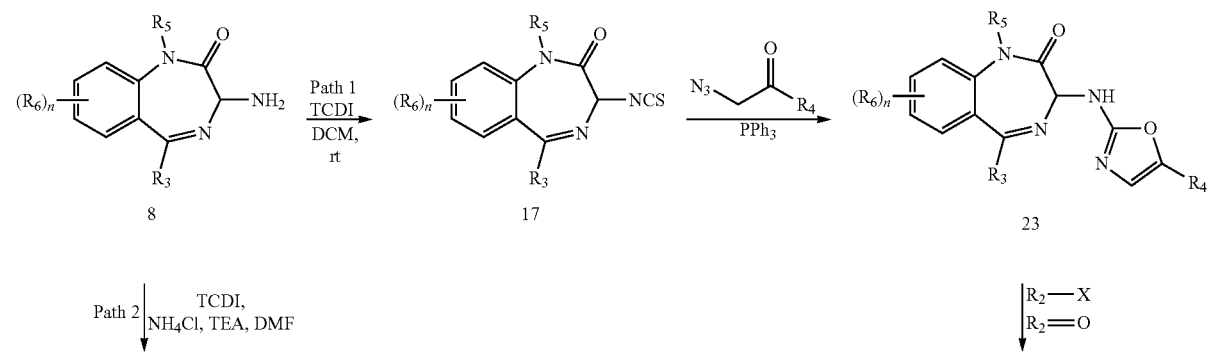

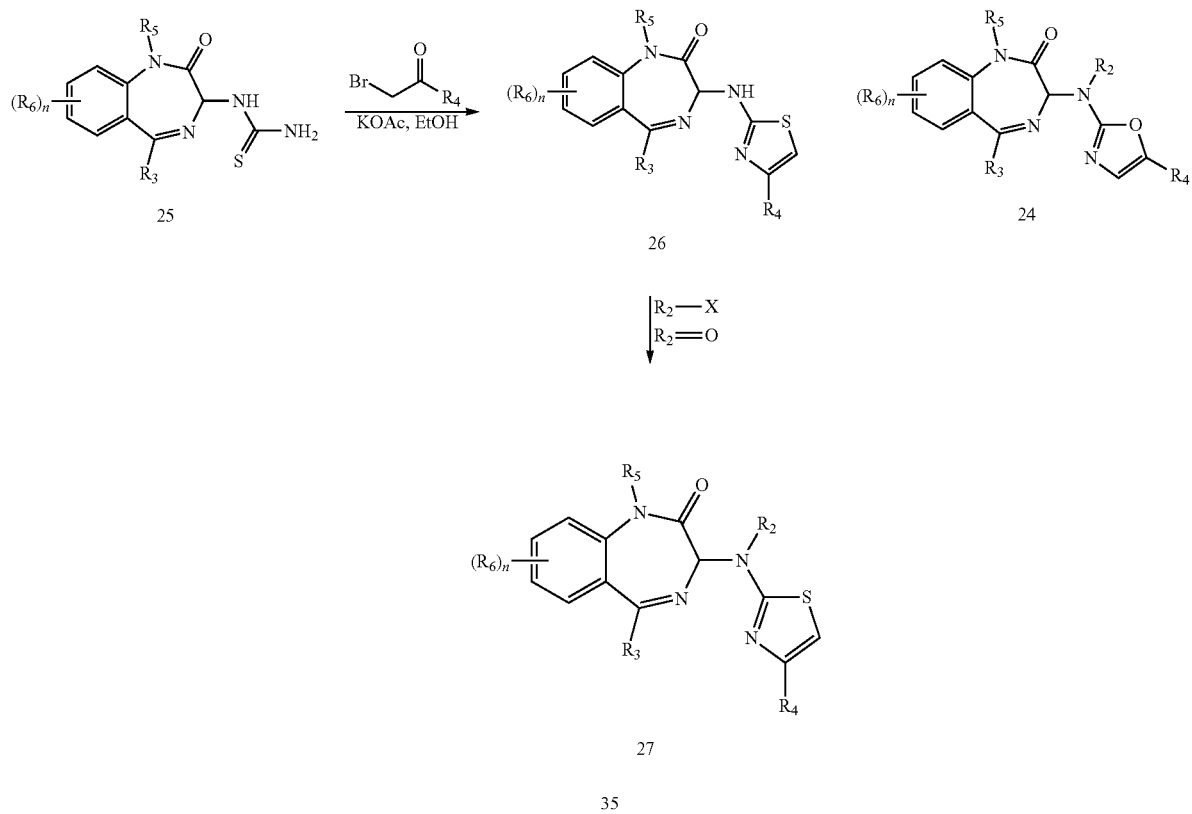

Scheme 6 illustrates methods, wherein n, $R_2$, $R_3$, $R_4$, $R_5$, and $R_6$ are defined as previously described, to prepare compounds of formula 29, 30, 32, and 33. Following Path 1, amine 8 is reacted with isothiocyanates to give the intermediate (28) that is reacted further with hydrazine to give triazoles having the formula 29. Compound 29 can be reacted further via alkylation with reagents like, but not limited to, alkyl halides, mesylates and tosylates or via reductive amination with aldehydes and ketones to install $R_2$, wherein $R_2$ is defined as previously described, to give compounds of formula 30. Following Path 2, (8) is reacted with TCDI followed by alpha-amino ketones to give the thioureas 31. Reaction of 31 with sulfuric acid affords the thiazoles having the formula 32 that can be reacted further via alkylation with reagents like, but not limited to, alkyl halides, mesylates and tosylates or via reductive amination with aldehydes and ketones to install $R_2$, wherein $R_2$ is defined as previously described, to give compounds of formula 33.

Scheme 6

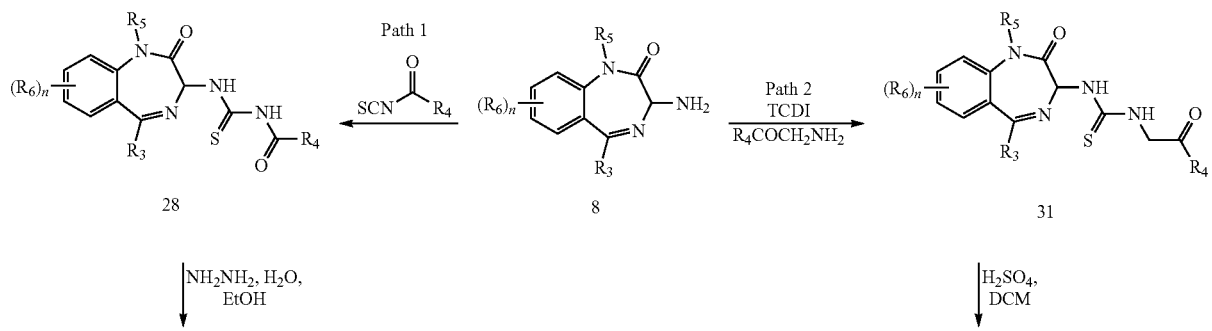

-continued

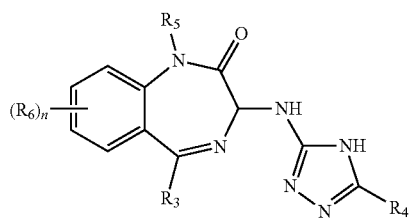

29

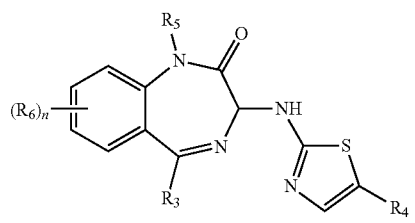

32

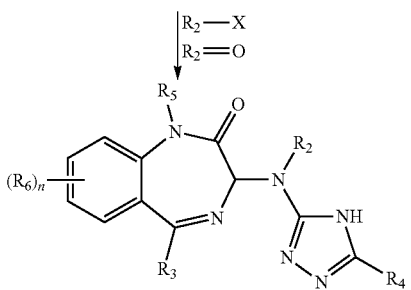

30

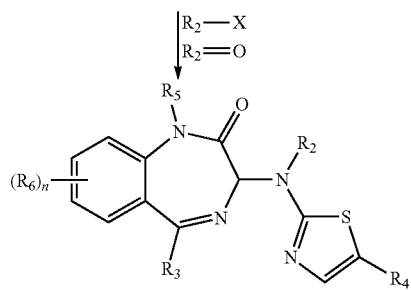

33

Scheme 7 illustrates methods, wherein n, $R_2$, $R_3$, $R_4$, $R_5$, and $R_6$ are defined as previously described, to prepare compounds of formulas 20 and 21. Amine 8 is reacted with BTC to give the intermediate isocyanate 34 that is reacted further with hydrazides to give intermediates 35. Reaction of 35 with $PPh_3$ and $CCl_4$ affords the oxadiazoles 20 that can then be reacted further via alkylation with reagents like, but not limited to, alkyl halides, mesylates and tosylates or via reductive amination with aldehydes and ketones to install $R_2$, wherein $R_2$ is defined as previously described, to give compounds of formula 33.

Scheme 7

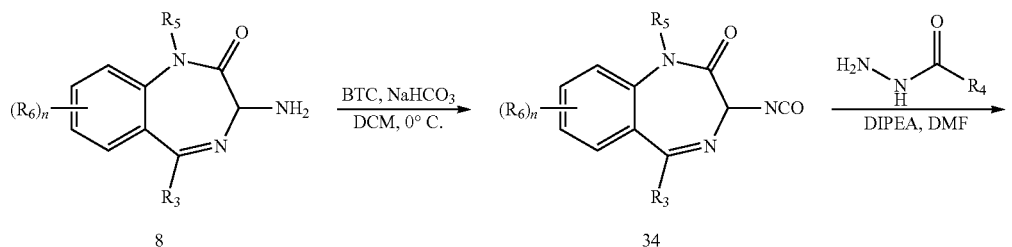

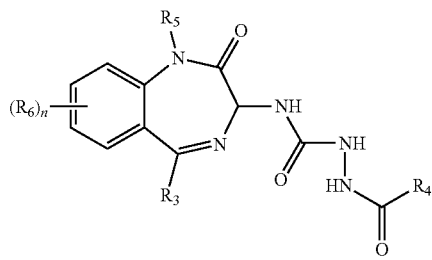

35

PPh$_3$, CCl$_4$,
TEA, MeCN

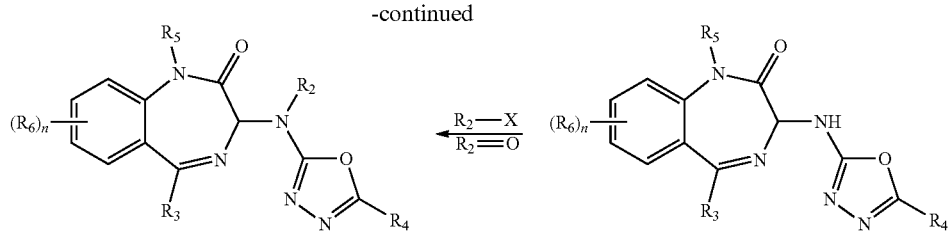

Scheme 8 illustrates methods, wherein n, $R_2$, $R_3$, $R_4$, $R_5$, and $R_6$ are defined as previously described, to prepare compounds of formula 37 and 38. Amine 8 is reacted with isothiocyanates to give the intermediate 28 that is reacted further with methyl iodide to give intermediates 36. Reaction of 36 with hydroxyl amine-HCl salt affords the 1,2,4-oxadiazoles 37 that can then be reacted further via alkylation with reagents like, but not limited to, alkyl halides, mesylates and tosylates or via reductive amination with aldehydes and ketones to install $R_2$, wherein $R_2$ is defined as previously described, to give compounds of formula 38.

Scheme 9 illustrates methods, wherein n, $R_1$, $R_2$, $R_3$, $R_4$, $R_5$, and $R_6$ are defined as previously described, to prepare compounds of formula 43. The compound 39 is reacted under basic conditions with alkyl halides to give compound 40. Compound 40 is reacted again under basic conditions with electrophilic azide sources (like trisyl azide) to afford the intermediate azide 41. Reduction of 41 with $PPh_3$, or some other suitable reductant, gives the amine 42 that can be reacted similarly to that described in schemes 1-8 to afford the target compounds 43.

Scheme 8

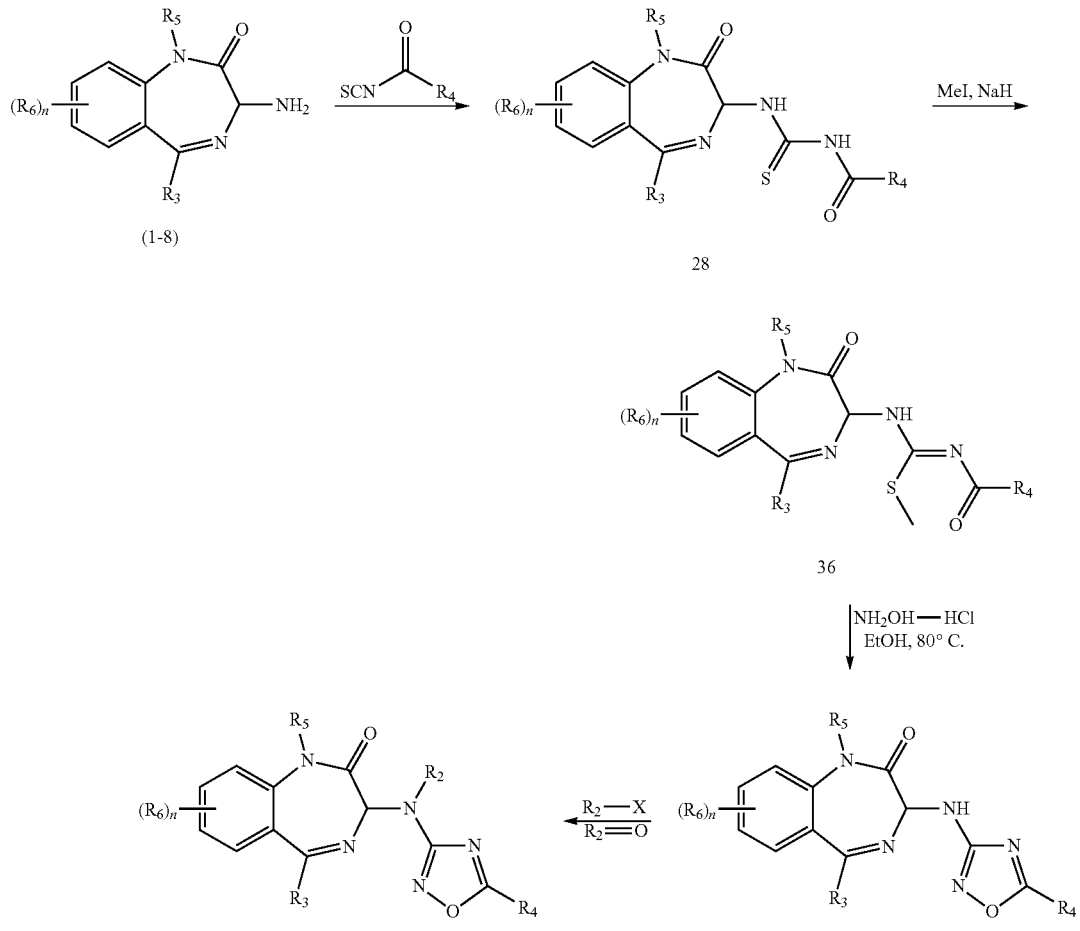

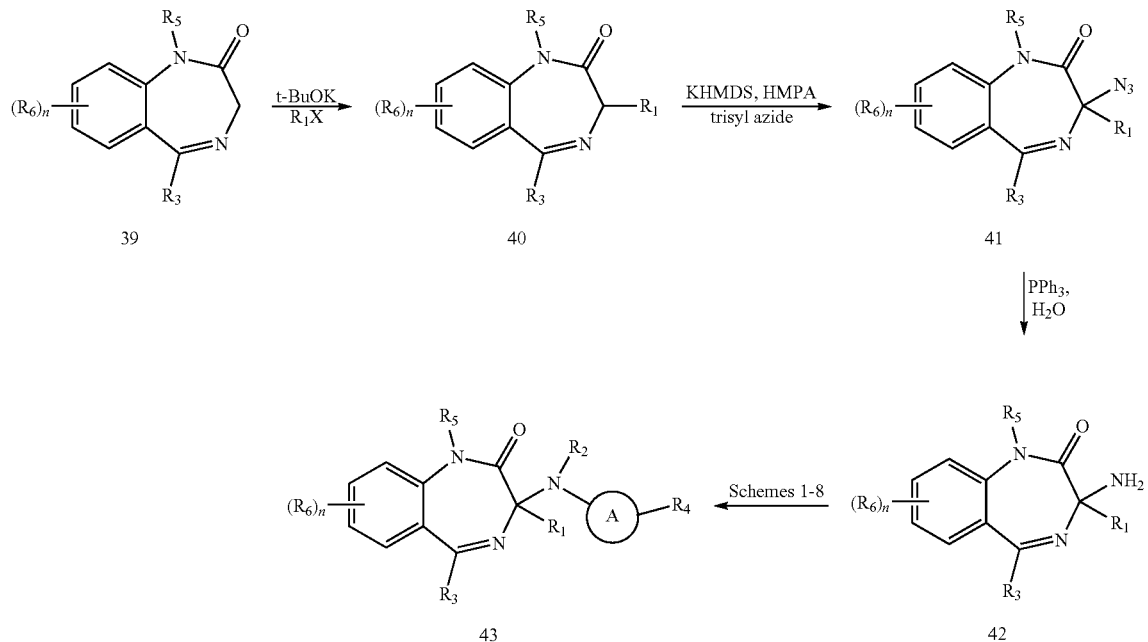

Scheme 10 illustrates methods, wherein n, $R_1$, $R_2$, $R_3$, $R_4$, $R_5$, and $R_6$ are defined as previously described, to prepare compounds of formula 43. The amine 8 is condensed with an aryl aldehyde give the corresponding imine 44. The imine 44 is reacted under basic conditions with alkyl halides to give compound 45. Hydrolysis of the imine 45 under acidic conditions affords the amine 42 that can be reacted similarly to that described in schemes 1-8 to afford the target compounds 43.

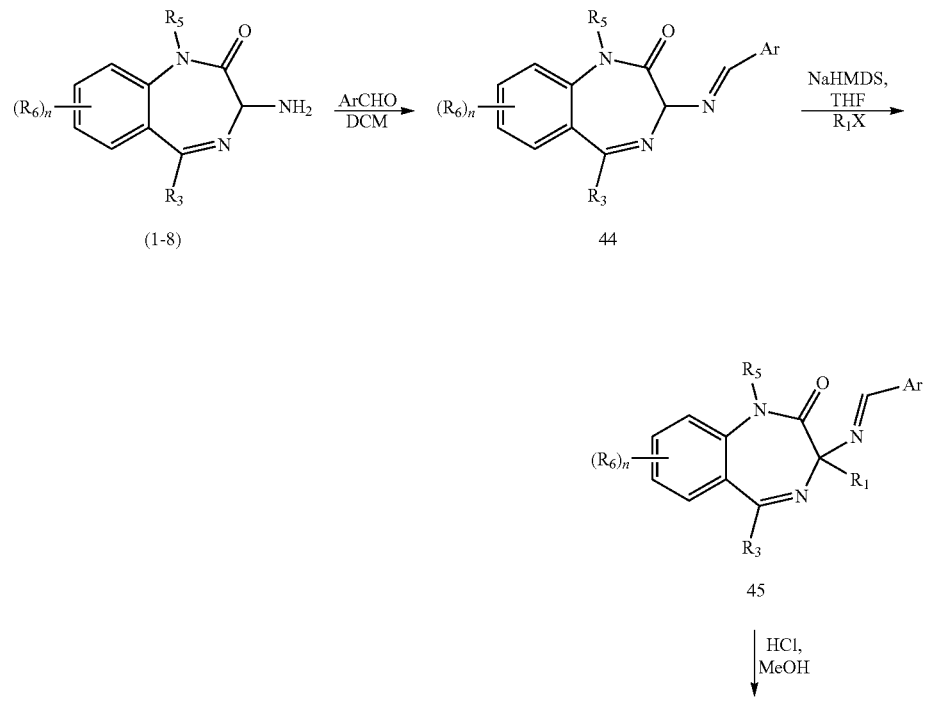

-continued

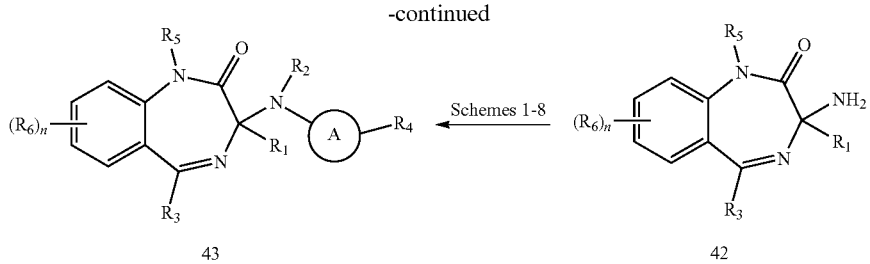

Scheme 11 illustrates methods, wherein n, $R_3$, $R_4$, $R_5$, and $R_6$ are defined as previously described, to prepare compounds of formula 48. The racemic amine 8 is converted to the enantiomerically pure amine 44 by two different paths 1 and 2. Following path 1 uses the method described by Sherrill and Sugg (J. Org. Chem. 1995, 60, 730-734) to access the chiral amine 44. Alternatively, chiral amine 44 can be accessed by SFC separation of the racemic amine 8. Amine 44 is reacted with CDI to afford intermediate 45 that is reacted further with the hydrazides 46 to give the corresponding amino semicarbazides 47. The amino semicarbazides 47 can be cyclized to the corresponding oxadiazoles 48 using TsCl, POCl$_3$, and related activating agents.

Scheme 11

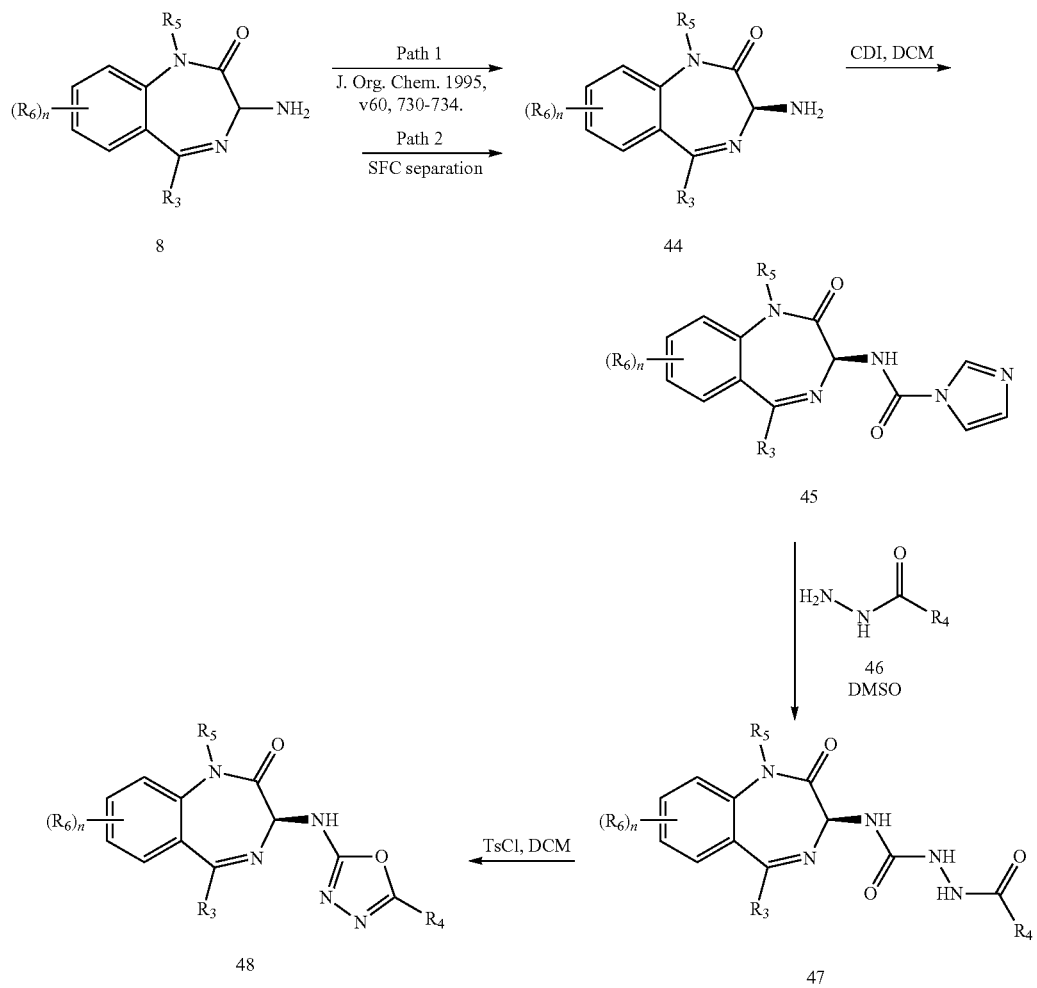

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Unless otherwise indicated, each of the compounds of the examples below was prepared and tested as a racemic mixture or, when possible, a diastereomeric mixture.

Example 1

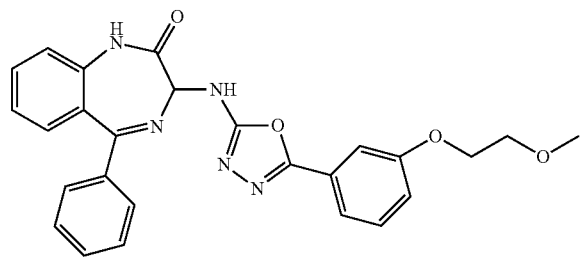 [SMILES: COCCOc1cccc(-c2nnc(NC3N=C(c4ccccc4)c4ccccc4NC3=O)o2)c1]

Example 1 Step a

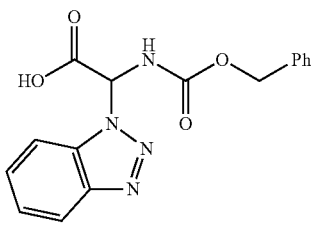 [SMILES: O=C(NC(C(=O)O)n1nnc2ccccc21)OCc1ccccc1]

To a 250 mL flask equipped mechanical stirring, was added 2-oxoacetic acid hydrate (9.2 g, 0.1 mol), benzyl carbamate (15.1 g, 0.1 mol) and 1H-benzo[d][1,2,3]triazole (9.2 g, 0.1 mol), and toluene (300 mL). The resulting solution was stirred for 2 h at 120° C. in an oil bath. The resulting mixture was filtered and the solid residue was washed with petroleum ether (3×), and dried in vacuo to give 2-(1H-benzo[d][1,2,3]triazol-1-yl)-2-(benzyloxycarbonylamino)acetic acid (28.6 g, 87%) as a white solid that was used without further purification. ESI-MS m/z: 327 [M+H]⁺.

Example 1 Step b

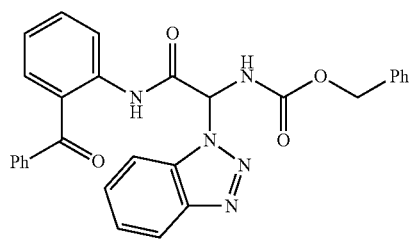 [SMILES: O=C(NC(C(=O)Nc1ccccc1C(=O)c1ccccc1)n1nnc2ccccc21)OCc1ccccc1]

To a 500-mL 3-necked round-bottom flask, was added 2-(1H-1,2,3-benzotriazol-1-yl)-2-[[(benzyloxy)carbonyl]amino]acetic acid (46.3 g, 91.94 mmol) and tetrahydrofuran (200 mL). The reaction mixture was cooled to 0° C. and a solution of oxalyl chloride (17.6 g, 1.00 equiv) in tetrahydrofuran (40 mL) was added dropwise, followed by the addition of DMF (8 mL). The resulting solution was stirred for 2 h at 0° C. then treated with a THF solution (160 mL) of N-methylmorpholine (28.6 g, 280.7 mmol) and 2-benzoylaniline (22.3 g, 80.0 mmol) in portions at 0° C. The cold bath was removed and the resulting solution stirred for 30 min at room temperature. The solids were filtered off and the filtrate was evaporated to dryness to afford benzyl N-[[(2-benzoylphenyl)carbamoyl](1H-1,2,3-benzotriazol-1-yl)methyl]carbamate (40.4 g, 87%) as a yellow oil that was used without further purification. ESI-MS m/z: 504 [M−H]⁻.

Example 1 Step c

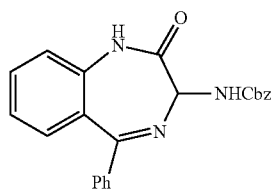 [SMILES: O=C(NC1N=C(c2ccccc2)c2ccccc2NC1=O)OCc1ccccc1]

To a 250-mL round-bottom flask, was added benzyl N-[[(2-benzoylphenyl)carbamoyl](1H-1,2,3-benzotriazol-1-yl)methyl]carbamate (40.4. g, 80.00 mmol), methanol (200 mL), and ammonia (200 mL). The reaction mixture was stirred for 3 h at room temperature, concentrated in vacuo, and the residue was diluted with EtOAc (200 mL). The resulting solution was washed with 1M sodium hydroxide (2×100 mL), dried over anhydrous sodium sulfate, and filtered. The filtrate was concentrated in vacuo to give benzyl N-[amino[(2-benzoylphenyl)carbamoyl]methyl]carbamate (30.2 g, 93%) as yellow oil that was used without further purification. To a 500-mL round-bottom flask, was added benzyl N-[amino[(2-benzoylphenyl)carbamoyl]methyl]carbamate (30.2 g, 74.8 mmol), acetic acid (200 mL), and $CH_3COONH_4$ (28.00 g, 363.3 mmol). The reaction mixture was stirred for 16 h at room temperature, concentrated in vacuo, and the residue was diluted with EtOAc:ether=1:3 (100 mL). The pH value of the solution was adjusted to 8 with 1M sodium hydroxide and the precipitate was collected by filtration to afford of (Z)-benzyl 2-oxo-5-phenyl-2,3-dihydro-1H-benzo[e][1,4]diazepin-3-ylcarbamate (14.5 g, 50%) as a pink solid that was used without further purification. ESI-MS m/z: 386 [M+H]⁺.

Example 1 Step d

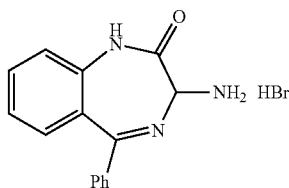 [SMILES: NC1N=C(c2ccccc2)c2ccccc2NC1=O ; Br]

Into a 50 mL round-bottom flask, was placed (Z)-benzyl 2-oxo-5-phenyl-2,3-dihydro-1H-benzo[e][1,4]diazepin-3-ylcarbamate (300 mg, 0.60 mmol), HBr/HOAc (20 mL). The resulting solution was stirred for 30 min at 70° C. in an oil bath. The solution was diluted with 20 mL of ether. The solids were collected by filtration to give 270 mg (crude) of (Z)-3-amino-5-phenyl-1H-benzo[e][1,4]diazepin-2(3H)-one hydrobromide as a yellow solid that was used without further purification. ESI-MS m/z: 252 [M+H]⁺.

Example 1 Step e

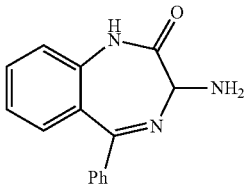 [SMILES: NC1N=C(c2ccccc2)c2ccccc2NC1=O]

The crude (Z)-3-amino-5-phenyl-1H-benzo[e][1,4]diazepin-2(3H)-one hydrobromide from step d (38.7 g) was dissolved in 50 mL water, then NH$_3$.H$_2$O was added slowly in ice-water bath to adjust the PH to 14. The solid was filtered and washed with a small amount of water. The solid was collected and dried under vacuum to afford (Z)-3-amino-5-phenyl-1H-benzo[e][1,4]diazepin-2(3H)-one (16.8 g) as yellow solid and used without further purification. ESI-MS m/z: 252 [M+H]⁺.

Example 1 Step f

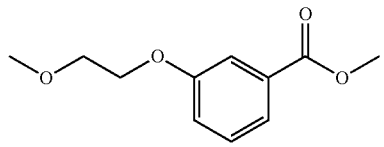

A solution of methyl 3-hydroxybenzoate (4 g, 26.3 mmol), 2-bromoethyl methyl ether (7.3 g, 52.6 mmol) and K$_2$CO$_3$ in acetone (50 mL) was refluxed for 16 hours, the mixture was cooled to room temperature and filtered. The filtrate was concentrated, dissolved in DCM, and washed with saturated aqueous NaHCO$_3$ (×2). The organic layer was dried (Na$_2$SO$_4$), concentrated, and purified by column chromatography (silica, petroleum ether: EtOAc) to give desired compound as light yellow oil (3.3 g, 59.6%). ESI-MS m/z: 252.2 [M+MeCN+H]⁺.

Example 1 Step g

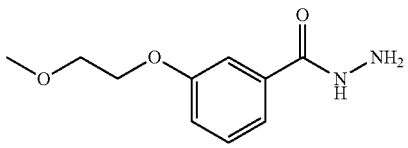

A solution of the compound from step f (3.3 g, 15.7 mmol) in EtOH (20 mL) and NH$_2$NH$_2$.H$_2$O (2 mL) was refluxed for 48 hours. The mixture was concentrated, diluted with ether (100 mL), and the resulting precipitate was collected by filtration to give the desired compound (2.6 g, 79%) as a white solid, which was used directly in the next step without further purification. ESI-MS m/z: 211.1 [M+H]⁺.

Example 1 Step h

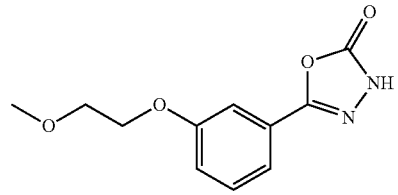 [SMILES: COCCOc1cccc(-c2n[nH]c(=O)o2)c1]

Triphosgene (3.7 g, 12.4 mmol) in THF (10 mL) was added dropwise to the solution of the compound from step g (1.3 g, 6.2 mmol) and Et$_3$N (1.7 mL, 12.4 mmol) in THF (30 mL) at 0° C. and it was heated to reflux for 16 hours. The reaction was quenched with water and concentrated, and the resulting residue was dissolved in EtOAc. The organic layer was washed with water, dried (Na$_2$SO$_4$), and concentrated to give 5-(3-(2-methoxyethoxy)phenyl)-1,3,4-oxadiazol-2(3H)-one as a yellow solid (600 mg, 41%) that was used without further purification. ESI-MS m/z: 237.2 [M+H]⁺.

Example 1 Step i

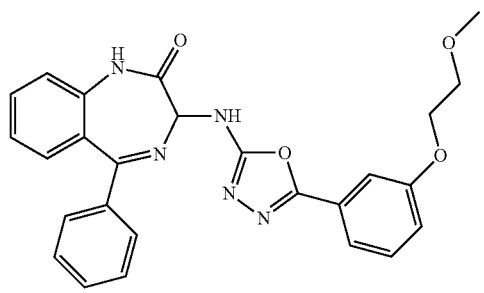 [SMILES: COCCOc1cccc(-c2nnc(NC3N=C(c4ccccc4)c4ccccc4NC3=O)o2)c1]

A solution of the compound from step h (350 mg, 1.48 mmol), BOP (654 mg, 1.48 mmol), (Z)-3-amino-5-phenyl-1H-benzo[e][1,4]diazepin-2(3H)-one (149 mg, 0.59 mmol) and DIPEA (305 mg, 2.37 mmol) in DMF (3 mL) was stirred for 36 hours at room temperature. Then the reaction mixture was purified by prep-HPLC to give the title compound as a white solid (10 mg, 4%). ESI-MS m/z: 470.3 [M+H]⁺. ¹H NMR (300 MHz, DMSO-d$_6$) δ 3.33 (s, 3H), 3.68 (m, 2H), 4.11-4.21 (m, 2H), 5.16 (d, J=8.6 Hz, 1H), 7.13 (d, J=8.0 Hz, 1H), 7.22-7.57 (m, 9H), 7.61-7.71 (m, 1H), 9.12 (d, J=8.4 Hz, 1H), 11.00 (s, 1H).

Example 2

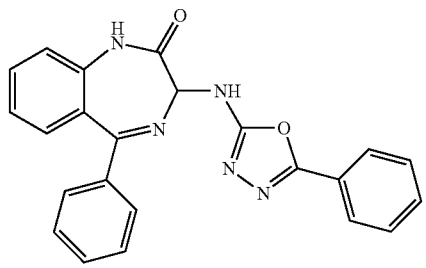 [SMILES: O=C1Nc2ccccc2C(c2ccccc2)=NC1Nc1nnc(-c2ccccc2)o1]

Example 2 was prepared using a procedure similar to that used to prepare Example 1 where 5-phenyl-1,3,4-oxadiazol-2(3H)-one was used in place of 5-(3-(2-methoxyethoxy)phenyl)-1,3,4-oxadiazol-2(3H)-one. ESI-MS m/z: 396.1 [M+H]+.

Example 3

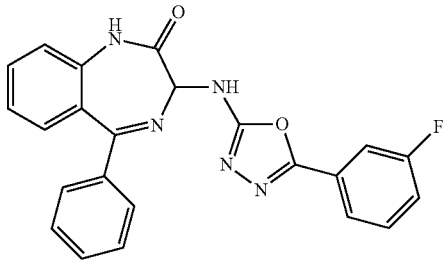 [SMILES: O=C1Nc2ccccc2C(c2ccccc2)=NC1Nc1nnc(-c2cccc(F)c2)o1]

Example 3 was prepared using a procedure similar to that used to prepare Example 1 where 5-(3-fluorophenyl)-1,3,4-oxadiazol-2(3H)-one was used in place of 5-(3-(2-methoxyethoxy)phenyl)-1,3,4-oxadiazol-2(3H)-one. ESI-MS m/z: 414.1 [M+H]+.

Example 4

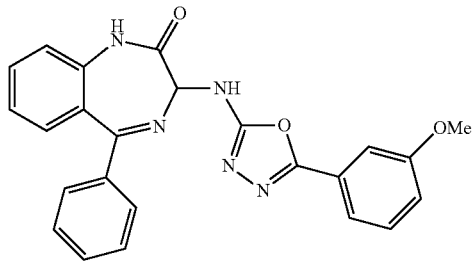 [SMILES: COc1cccc(-c2nnc(NC3N=C(c4ccccc4)c4ccccc4NC3=O)o2)c1]

Example 4 was prepared using a procedure similar to that used to prepare Example 1 where 5-(3-methoxyphenyl)-1,3,4-oxadiazol-2(3H)-one was used in place of 5-(3-(2-methoxyethoxy)phenyl)-1,3,4-oxadiazol-2(3H)-one. ESI-MS m/z: 426.2 [M+H]+.

Example 5

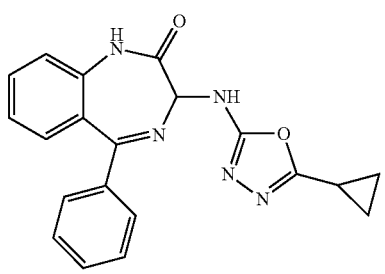 [SMILES: O=C1Nc2ccccc2C(c2ccccc2)=NC1Nc1nnc(C2CC2)o1]

Example 5 was prepared using a procedure similar to that used to prepare Example 1 where 5-cyclopropyl-1,3,4-oxadiazol-2(3H)-one was used in place of 5-(3-(2-methoxyethoxy)phenyl)-1,3,4-oxadiazol-2(3H)-one. ESI-MS m/z: 360.1 [M+H]+. $^1$H NMR (300 MHz, DMSO-$d_6$) δ 0.78-0.93 (m, 2H), 1.02 (dt, J=8.3, 3.2 Hz, 2H), 2.05 (tt, J=8.4, 5.0 Hz, 1H), 5.04 (d, J=8.7 Hz, 1H), 7.20-7.38 (m, 3H), 7.39-7.61 (m, 5H), 7.67 (ddd, J=8.4, 7.0, 1.8 Hz, 1H), 8.67 (d, J=8.7 Hz, 1H), 10.93 (s, 1H).

Example 6

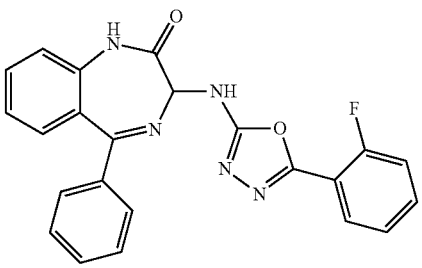 [SMILES: O=C1Nc2ccccc2C(c2ccccc2)=NC1Nc1nnc(-c2ccccc2F)o1]

Example 6 was prepared using a procedure similar to that used to prepare Example 1 where 5-(2-fluorophenyl)-1,3,4-oxadiazol-2(3H)-one was used in place of 5-(3-(2-methoxyethoxy)phenyl)-1,3,4-oxadiazol-2(3H)-one. ESI-MS m/z: 414.1 [M+H]+. $^1$H NMR (300 MHz, DMSO-$d_6$) δ 5.19 (d, J=8.4 Hz, 1H), 7.25-7.55 (m, 10H), 7.58-7.72 (m, 2H), 7.87 (m, 1H), 9.23 (d, J=8.5 Hz, 1H), 11.00 (s, 1H).

Example 7

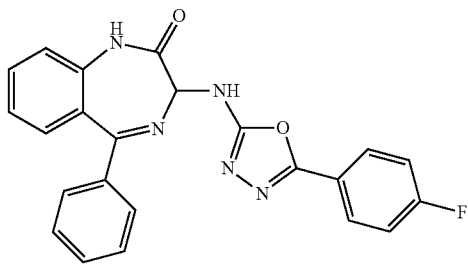

Example 7 was prepared using a procedure similar to that used to prepare Example 1 where 5-(4-fluorophenyl)-1,3,4-oxadiazol-2(3H)-one was used in place of 5-(3-(2-methoxyethoxy)phenyl)-1,3,4-oxadiazol-2(3H)-one. ESI-MS m/z: 414.1 [M+H]+. $^1$H NMR (300 MHz, DMSO-$d_6$) δ 5.17 (dd, J=8.2, 5.2 Hz, 1H), 7.23-7.60 (m, 10H), 7.69 (ddd, J=8.5, 7.0, 1.7 Hz, 1H), 7.89 (ddd, J=7.0, 5.4, 2.8 Hz, 2H), 9.17 (d, J=8.5 Hz, 1H), 10.89 (s, 1H).

Example 7a

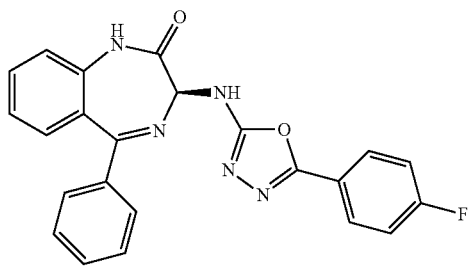 [SMILES: O=C1Nc2ccccc2C(c2ccccc2)=N[C@@H]1Nc1nnc(-c2ccc(F)cc2)o1]

Example 7a was separated from racemic Example 7 using a reverse phase chiral column (Gemini-NX C18 110A). ESI-MS m/z: 414.2 [M+H]$^+$.

Example 7b

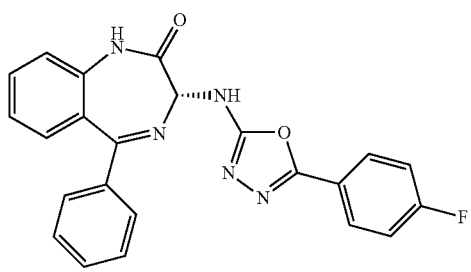 [SMILES: O=C1Nc2ccccc2C(c2ccccc2)=N[C@H]1Nc1nnc(-c2ccc(F)cc2)o1]

Example 7b was separated from racemic Example 7 using a reverse phase chiral column (Gemini-NX C18 110A). ESI-MS m/z: 414.2 [M+H]$^+$.

Example 8

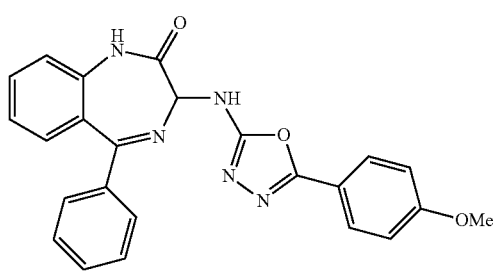 [SMILES: COc1ccc(-c2nnc(NC3N=C(c4ccccc4)c4ccccc4NC3=O)o2)cc1]

Example 8 was prepared using a procedure similar to that used to prepare Example 1 where 5-(4-methoxyphenyl)-1,3,4-oxadiazol-2(3H)-one was used in place of 5-(3-(2-methoxyethoxy)phenyl)-1,3,4-oxadiazol-2(3H)-one. ESI-MS m/z: 426.3 [M+H]$^+$. $^1$H NMR (300 MHz, DMSO-$d_6$) δ 5.16 (d, J=8.4 Hz, 1H), 7.09-7.19 (m, 2H), 7.24-7.42 (m, 3H), 7.43-7.60 (m, 5H), 7.69 (ddd, J=8.6, 7.1, 1.8 Hz, 1H), 7.75-7.85 (m, 2H), 9.02 (d, J=8.6 Hz, 1H), 10.99 (s, 1H).

Example 9

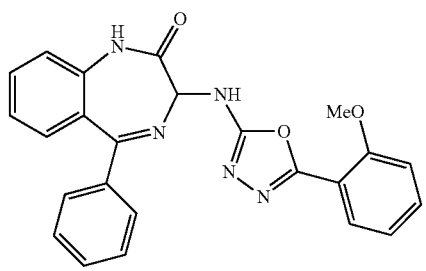 [SMILES: COc1ccccc1-c1nnc(NC2N=C(c3ccccc3)c3ccccc3NC2=O)o1]

Example 9 was prepared using a procedure similar to that used to prepare Example 1 where 5-(2-methoxyphenyl)-1,3,4-oxadiazol-2(3H)-one was used in place of 5-(3-(2-methoxyethoxy)phenyl)-1,3,4-oxadiazol-2(3H)-one. ESI-MS m/z: 426.3 [M+H]$^+$. $^1$H NMR (300 MHz, DMSO-$d_6$) δ 3.84 (s, 3H), 5.14 (d, J=8.5 Hz, 1H), 7.08 (t, J=7.5 Hz, 1H), 7.15-7.40 (m, 4H), 7.42-7.58 (m, 6H), 7.67 (td, J=7.4, 1.7 Hz, 2H), 8.98 (d, J=8.6 Hz, 1H), 10.98 (s, 1H).

Example 10

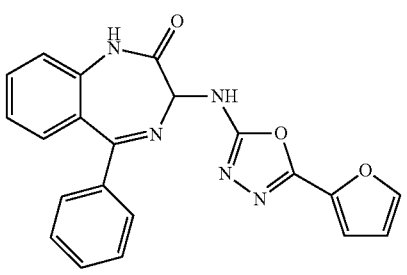 [SMILES: O=C1Nc2ccccc2C(c2ccccc2)=NC1Nc1nnc(-c2ccco2)o1]

Example 10 was prepared using a procedure similar to that used to prepare Example 1 where 5-(furan-2-yl)-1,3,4-oxadiazol-2(3H)-one was used in place of 5-(3-(2-methoxyethoxy)phenyl)-1,3,4-oxadiazol-2(3H)-one. ESI-MS m/z: 386.1 [M+H]$^+$. $^1$H NMR (300 MHz, DMSO-$d_6$) δ 5.14 (d, J=8.4 Hz, 1H), 6.72 (dd, J=3.5, 1.8 Hz, 1H), 7.06 (dd, J=3.5, 0.8 Hz, 1H), 7.22-7.40 (m, 3H), 7.40-7.61 (m, 5H), 7.66 (ddd, J=8.5, 7.0, 1.8 Hz, 1H), 7.94 (dd, J=1.8, 0.8 Hz, 1H), 9.21 (d, J=8.5 Hz, 1H), 10.99 (s, 1H).

Example 10a

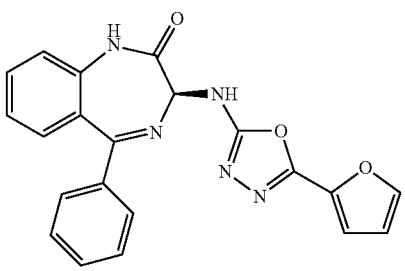 [SMILES: O=C1Nc2ccccc2C(c2ccccc2)=N[C@@H]1Nc1nnc(-c2ccco2)o1]

Example 10a was separated from racemic Example 10 using a reverse phase chiral column (Gemini-NX C18 110A). ESI-MS m/z: 386.2 [M+H]$^+$.

Example 10b

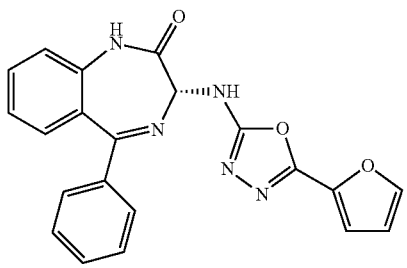

Example 10b was separated from racemic Example 10 using a reverse phase chiral column (Gemini-NX C18 110A). ESI-MS m/z: 386.2 [M+H]+.

Example 11

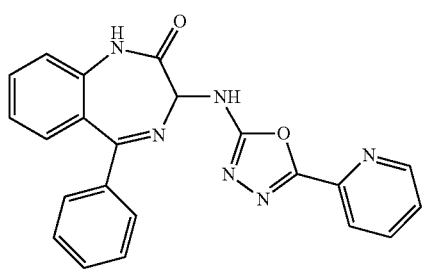

Example 11 was prepared using a procedure similar to that used to prepare Example 1 where 5-(pyridin-2-yl)-1,3,4-oxadiazol-2(3H)-one was used in place of 5-(3-(2-methoxyethoxy)phenyl)-1,3,4-oxadiazol-2(3H)-one. ESI-MS m/z: 397.1 [M+H]+. $^1$H NMR (400 MHz, DMSO-$d_6$) δ 5.20 (d, J=8.5 Hz, 1H), 6.99 (d, J=2.3 Hz, 1H), 7.12 (d, J=2.2 Hz, 1H), 7.22-7.33 (m, 2H), 7.33-7.42 (m, 2H), 7.42-7.60 (m, 5H), 7.69 (ddd, J=8.5, 7.2, 1.7 Hz, 1H), 7.94-8.05 (m, 2H), 8.71 (dt, J=4.7, 1.4 Hz, 1H), 9.32 (d, J=8.5 Hz, 1H), 11.01 (s, 1H).

Example 12

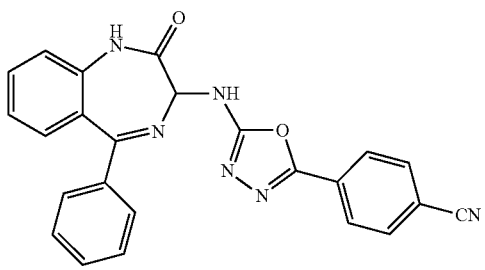 [SMILES: N#Cc1ccc(-c2nnc(NC3N=C(c4ccccc4)c4ccccc4NC3=O)o2)cc1]

Example 12 was prepared using a procedure similar to that used to prepare Example 1 where 4-(5-oxo-4,5-dihydro-1,3,4-oxadiazol-2-yl)benzonitrile was used in place of 5-(3-(2-methoxyethoxy)phenyl)-1,3,4-oxadiazol-2(3H)-one. ESI-MS m/z: 421.2 [M+H]+. $^1$H NMR (300 MHz, DMSO-$d_6$) δ 5.21 (d, J=8.1 Hz, 1H), 7.23-7.42 (m, 3H), 7.42-7.61 (m, 5H), 7.69 (ddd, J=8.5, 7.0, 1.8 Hz, 1H), 7.95-8.09 (m, 4H), 9.37 (d, J=8.3 Hz, 1H), 11.02 (s, 1H).

Example 13

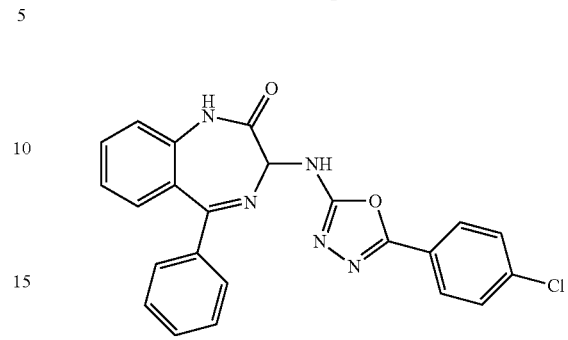

Example 13 was prepared using a procedure similar to that used to prepare Example 1 where 5-(4-chlorophenyl)-1,3,4-oxadiazol-2(3H)-one was used in place of 5-(3-(2-methoxyethoxy)phenyl)-1,3,4-oxadiazol-2(3H)-one. ESI-MS m/z: 430.2 [M+H]+. $^1$H NMR (400 MHz, DMSO-$d_6$) δ 5.18 (d, J=8.5 Hz, 1H), 7.23-7.41 (m, 3H), 7.41-7.60 (m, 5H), 7.61-7.75 (m, 3H), 7.79-7.89 (m, 2H), 9.20 (d, J=8.5 Hz, 1H), 11.00 (s, 1H).

Example 14

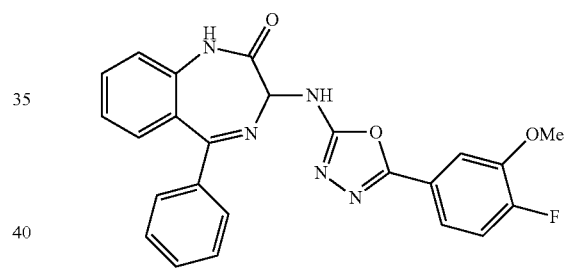

Example 14 was prepared using a procedure similar to that used to prepare Example 1 where 5-(4-fluoro-3-methoxyphenyl)-1,3,4-oxadiazol-2(3H)-one was used in place of 5-(3-(2-methoxyethoxy)phenyl)-1,3,4-oxadiazol-2(3H)-one. ESI-MS m/z: 444.2 [M+H]+. $^1$H NMR (300 MHz, DMSO-$d_6$) δ 3.94 (s, 3H), 5.18 (d, J=8.4 Hz, 1H), 7.23-7.63 (m, 11H), 7.69 (ddd, J=8.4, 7.0, 1.7 Hz, 1H), 9.12 (d, J=8.5 Hz, 1H), 11.01 (s, 1H).

Example 15

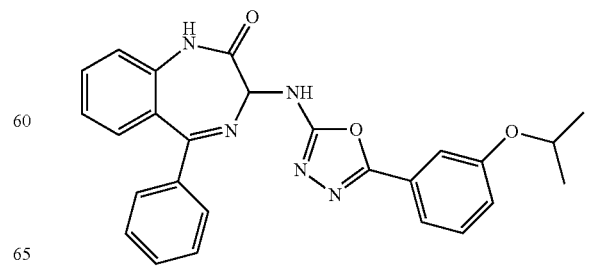

Example 15 was prepared using a procedure similar to that used to prepare Example 1 where 5-(3-isopropoxyphenyl)-1,3,4-oxadiazol-2(3H)-one was used in place of 5-(3-(2-methoxyethoxy)phenyl)-1,3,4-oxadiazol-2(3H)-one. ESI-MS m/z: 454.2 [M+H]$^+$. $^1$H NMR (400 MHz, DMSO-$d_6$) δ 1.30 (d, J=5.9 Hz, 6H), 4.68 (p, J=6.0 Hz, 1H), 5.17 (d, J=8.4 Hz, 1H), 7.10 (ddd, J=8.2, 2.6, 1.0 Hz, 1H), 7.25-7.32 (m, 2H), 7.33-7.41 (m, 3H), 7.42-7.58 (m, 6H), 7.68 (ddd, J=8.3, 7.2, 1.7 Hz, 1H), 9.09 (d, J=8.4 Hz, 1H), 11.00 (s, 1H).

Example 16

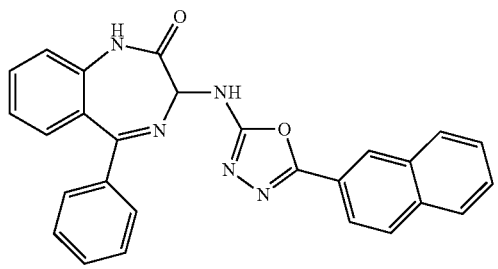 [SMILES: O=C1Nc2ccccc2C(c2ccccc2)=NC1Nc1nnc(-c2ccc3ccccc3c2)o1]

Example 16 was prepared using a procedure similar to that used to prepare Example 1 where 5-(naphthalen-2-yl)-1,3,4-oxadiazol-2(3H)-one was used in place of 5-(3-(2-methoxyethoxy)phenyl)-1,3,4-oxadiazol-2(3H)-one. ESI-MS m/z: 446.3 [M+H]$^+$. $^1$H NMR (300 MHz, DMSO-$d_6$) δ 5.22 (d, J=8.4 Hz, 1H), 7.24-7.42 (m, 3H), 7.44-7.60 (m, 5H), 7.60-7.76 (m, 3H), 7.92-8.07 (m, 2H), 8.11 (dd, J=8.0, 4.9 Hz, 2H), 8.34-8.45 (m, 1H), 9.21 (d, J=8.5 Hz, 1H), 11.03 (s, 1H).

Example 17

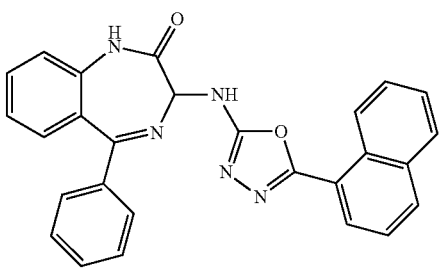 [SMILES: O=C1Nc2ccccc2C(c2ccccc2)=NC1Nc1nnc(-c2cccc3ccccc23)o1]

Example 17 was prepared using a procedure similar to that used to prepare Example 1 where 5-(naphthalen-1-yl)-1,3,4-oxadiazol-2(3H)-one was used in place of 5-(3-(2-methoxyethoxy)phenyl)-1,3,4-oxadiazol-2(3H)-one. ESI-MS m/z: 446.3[M+H]$^+$. $^1$H NMR (300 MHz, DMSO-$d_6$) δ 5.25 (d, J=8.4 Hz, 1H), 7.24-7.43 (m, 3H), 7.43-7.61 (m, 5H), 7.60-7.77 (m, 4H), 8.07 (td, J=7.6, 1.7 Hz, 2H), 8.15 (d, J=8.2 Hz, 1H), 9.02-9.13 (m, 1H), 9.23 (d, J=8.4 Hz, 1H), 11.03 (s, 1H).

Example 18

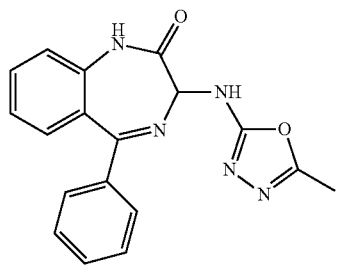 [SMILES: Cc1nnc(NC2N=C(c3ccccc3)c3ccccc3NC2=O)o1]

Example 18 was prepared using a procedure similar to that used to prepare Example 1 where 5-methyl-1,3,4-oxadiazol-2(3H)-one was used in place of 5-(3-(2-methoxyethoxy)phenyl)-1,3,4-oxadiazol-2(3H)-one. ESI-MS m/z: 334.2 [M+H]$^+$. $^1$H NMR (300 MHz, DMSO-$d_6$) δ 2.32 (s, 3H), 5.03 (d, J=8.7 Hz, 1H), 7.20-7.37 (m, 3H), 7.38-7.60 (m, 5H), 7.65 (ddd, J=8.6, 7.0, 1.8 Hz, 1H), 8.73 (d, J=8.7 Hz, 1H), 10.92 (s, 1H).

Example 19

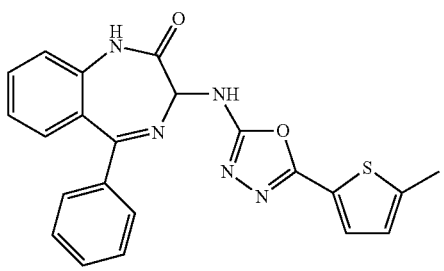 [SMILES: Cc1ccc(-c2nnc(NC3N=C(c4ccccc4)c4ccccc4NC3=O)o2)s1]

Example 19 was prepared using a procedure similar to that used to prepare Example 1 where 5-(5-methylthiophen-2-yl)-1,3,4-oxadiazol-2(3H)-one was used in place of 5-(3-(2-methoxyethoxy)phenyl)-1,3,4-oxadiazol-2(3H)-one. ESI-MS m/z: 416.3 [M+H]$^+$. $^1$H NMR (300 MHz, DMSO-$d_6$) δ 2.52 (s, 3H), 5.14 (d, J=8.5 Hz, 1H), 6.95 (dd, J=3.6, 1.3 Hz, 1H), 7.23-7.61 (m, 9H), 7.68 (m, 1H), 9.11 (d, J=8.5 Hz, 1H), 10.99 (s, 1H).

Example 20

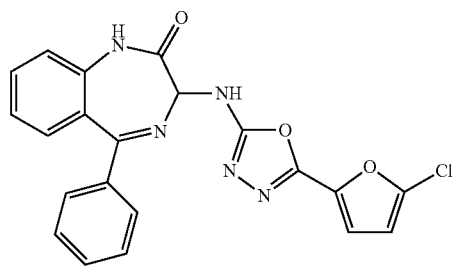 [SMILES: O=C1Nc2ccccc2C(c2ccccc2)=NC1Nc1nnc(-c2ccc(Cl)o2)o1]

Example 20 Step a

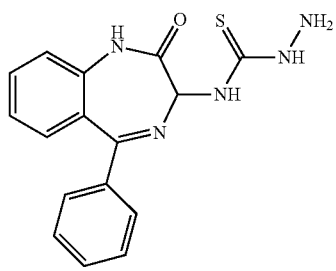 [SMILES: NNC(=S)NC1N=C(c2ccccc2)c2ccccc2NC1=O]

A solution of (Z)-3-amino-5-phenyl-1H-benzo[e][1,4]diazepin-2(3H)-one (5.1 g, 20.3 mmol), 1,1'-thiocarbonyldiimidazole (5.4 g, 30.3 mmol) in DMF (20 mL) was stirred for 20 minutes before hydrazinemonohydrate (2 mL) was added. The mixture was stirred for 30 minutes, diluted with EtOAc, and washed with water (×2). The organic layer was dried (Na$_2$SO$_4$) and concentrated to give desired compound as a light yellow solid (5 g, 76%) that was used without further purification. ESI-MS m/z: 326.1 [M+H]$^+$.

Example 20 Step b

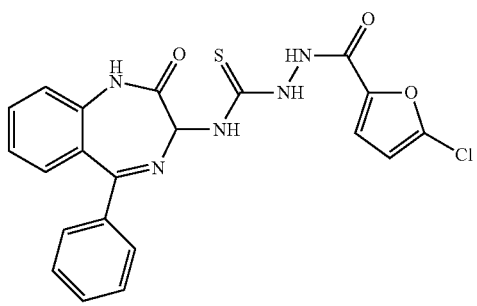 [SMILES: O=C(NNC(=S)NC1N=C(c2ccccc2)c2ccccc2NC1=O)c1ccc(Cl)o1]

A solution of the compound from step a (100 mg, 0.3 mmol), 5-chlorofuran-2-carboxylic acid (54 mg, 0.4 mmol), HOBt (61 mg, 0.48 mmol) and EDCI (86 mg, 0.45 mmol) in DMF (2 mL) was stirred for 2 hours. The mixture was purified by reverse phase C18 column chromatography (MeCN:H$_2$O) to give desired compound as a white solid (110 mg, 80%). ESI-MS m/z: 454.2 [M+H]$^+$.

Example 20 Step c

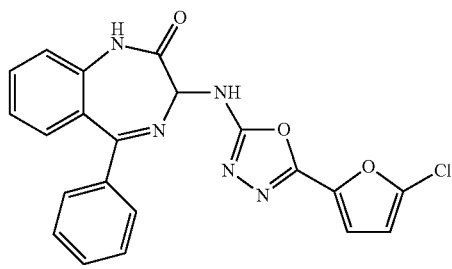 [SMILES: O=C1Nc2ccccc2C(c2ccccc2)=NC1Nc1nnc(-c2ccc(Cl)o2)o1]

A solution of the compound from step b (110 mg, 0.24 mmol) and EDCI (70 mg, 0.36 mmol) in DMF (5 mL) was stirred for 30 minutes at 60° C. It was purified by prep-HPLC to give the title compound as a yellow solid (27 mg, 27%). ESI-MS m/z: 420.2 [M+H]$^+$. $^1$H NMR (400 MHz, DMSO-d$_6$) δ 5.15 (d, J=8.4 Hz, 1H), 6.79 (d, J=3.6 Hz, 1H), 7.17 (d, J=3.6 Hz, 1H), 7.23-7.39 (m, 3H), 7.50 (m, 5H), 7.62-7.72 (m, 1H), 9.28 (d, J=8.4 Hz, 1H), 10.99 (s, 1H).

Example 21

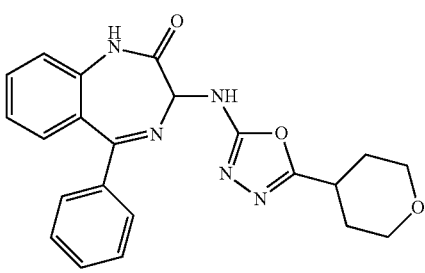 [SMILES: O=C1Nc2ccccc2C(c2ccccc2)=NC1Nc1nnc(C2CCOCC2)o1]

Example 21 Step a

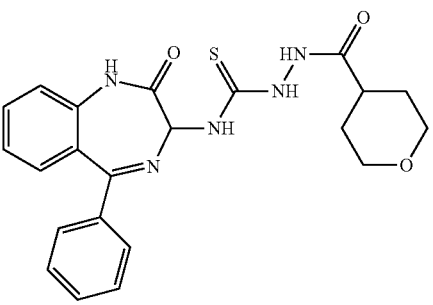 [SMILES: O=C(NNC(=S)NC1N=C(c2ccccc2)c2ccccc2NC1=O)C1CCOCC1]

A solution of (Z)-3-amino-5-phenyl-1H-benzo[e][1,4]diazepin-2(3H)-one (200 mg, 0.8 mmol), 1,1'-thiocarbonyldiimidazole (178 mg, 1.0 mmol) in DMF (3 mL) was stirred for 20 minutes before tetrahydro-2H-pyran-4-carbohydrazide (159 mg, 1.1 mmol) was added. The resulting mixture was stirred for 30 minutes and used directly in the next step. ESI-MS m/z: 438.2 [M+H]$^+$.

Example 21 Step b

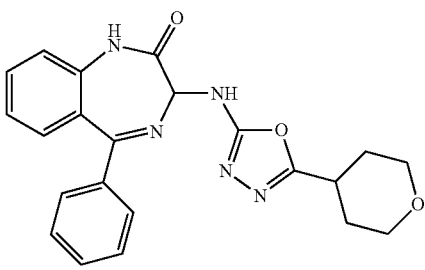 [SMILES: O=C1Nc2ccccc2C(c2ccccc2)=NC1Nc1nnc(C2CCOCC2)o1]

A solution of the compound from step a (350 mg, 0.8 mmol) and EDCI (192 mg, 1.0 mmol) in DMF (3 mL) was stirred for 60 minutes at 60° C. It was purified by directly by prep-HPLC to give the title compound as a white solid (54 mg, 17%). ESI-MS m/z: 404.2 [M+H]+. 1H NMR (300 MHz, DMSO-d6) δ 1.69 (tdd, J=13.2, 10.9, 5.5 Hz, 2H), 1.80-1.95 (m, 2H), 3.09 (tt, J=10.9, 4.0 Hz, 1H), 3.45 (td, J=11.3, 2.3 Hz, 2H), 3.88 (dt, J=11.6, 3.6 Hz, 2H), 5.07 (d, J=8.2 Hz, 1H), 7.21-7.40 (m, 3H), 7.41-7.61 (m, 5H), 7.67 (ddd, J=8.5, 7.0, 1.8 Hz, 1H), 8.81 (d, J=8.7 Hz, 1H), 10.95 (s, 1H).

Example 22

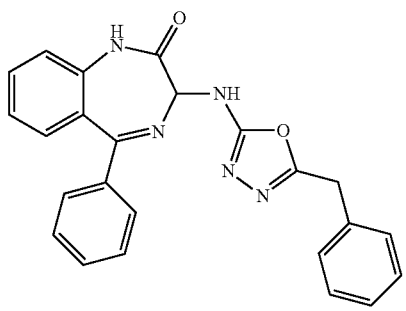 [SMILES: O=C1Nc2ccccc2C(c2ccccc2)=NC1Nc1nnc(Cc2ccccc2)o1]

Example 22 was prepared using a procedure similar to that used to prepare Example 21 where 2-phenylacetohydrazide was used in place of tetrahydro-2H-pyran-4-carbohydrazide. ESI-MS m/z: 410.2 [M+H]+. 1H NMR (300 MHz, DMSO-d6) δ 4.11 (s, 2H), 5.05 (d, J=8.6 Hz, 1H), 7.23-7.41 (m, 8H), 7.43-7.57 (m, 5H), 7.67 (ddd, J=8.5, 6.9, 1.9 Hz, 1H), 8.78 (d, J=8.7 Hz, 1H), 10.85-11.02 (m, 1H).

Example 23

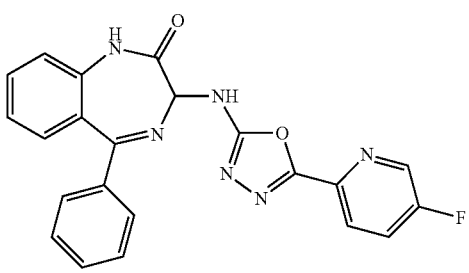 [SMILES: O=C1Nc2ccccc2C(c2ccccc2)=NC1Nc1nnc(-c2ccc(F)cn2)o1]

Example 23 was prepared using a procedure similar to that used to prepare Example 20 where 5-fluoropicolinic acid was used in place of 5-chlorofuran-2-carboxylic acid ESI-MS m/z: 415.0 [M+H]+. 1H NMR (300 MHz, DMSO-d6) δ 5.20 (d, J=7.9 Hz, 1H), 7.24-7.61 (m, 8H), 7.69 (m, 1H), 7.94 (m, 1H), 8.09 (dd, J=8.8, 4.4 Hz, 1H), 8.74 (d, J=2.8 Hz, 1H), 9.32 (d, J=8.4 Hz, 1H), 10.96 (s, 1H).

Example 24

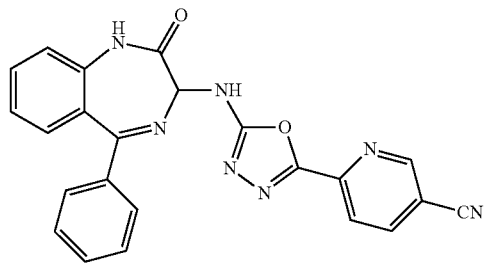 [SMILES: N#Cc1ccc(-c2nnc(NC3N=C(c4ccccc4)c4ccccc4NC3=O)o2)nc1]

Example 24 was prepared using a procedure similar to that used to prepare Example 20 where 5-cyanopicolinic acid was used in place of 5-chlorofuran-2-carboxylic acid. ESI-MS m/z: 422.3 [M+H]+. 1H NMR (300 MHz, DMSO-d6) δ 5.23 (d, J=7.5 Hz, 1H), 7.24-7.42 (m, 3H), 7.52 (dq, J=12.0, 6.8, 5.5 Hz, 5H), 7.70 (t, J=7.3 Hz, 1H), 8.16 (d, J=8.3 Hz, 1H), 8.48 (dd, J=8.3, 2.1 Hz, 1H), 9.13-9.22 (m, 1H), 9.58 (d, J=8.3 Hz, 1H), 11.04 (s, 1H).

Example 25

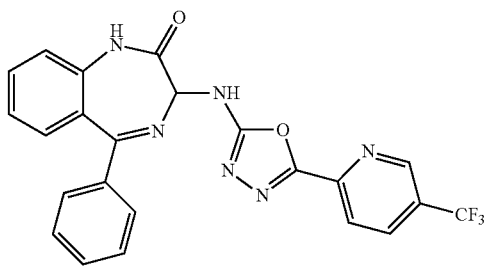 [SMILES: O=C1Nc2ccccc2C(c2ccccc2)=NC1Nc1nnc(-c2ccc(C(F)(F)F)cn2)o1]

Example 25 was prepared using a procedure similar to that used to prepare Example 20 where 5-(trifluoromethyl) picolinic acid was used in place of 5-chlorofuran-2-carboxylic acid. ESI-MS m/z: 465.3 [M+H]+. 1H NMR (300 MHz, DMSO-d6) δ 5.21 (d, J=7.6 Hz, 1H), 7.22-7.41 (m, 3H), 7.39-7.60 (m, 5H), 7.68 (m, 1H), 8.18 (d, J=8.4 Hz, 1H), 8.38 (m, 1H), 9.11 (m, 1H), 9.52 (d, J=8.3 Hz, 1H), 11.01 (s, 1H).

Example 26

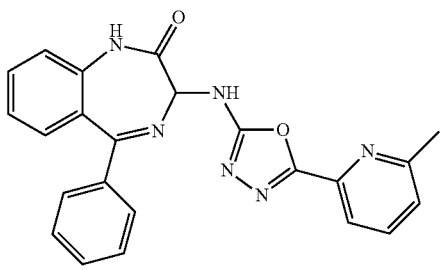 [SMILES: Cc1cccc(-c2nnc(NC3N=C(c4ccccc4)c4ccccc4NC3=O)o2)n1]

Example 26 was prepared using a procedure similar to that used to prepare Example 20 where 6-methylpicolinic acid was used in place of 5-chlorofuran-2-carboxylic acid.

ESI-MS m/z: 411.1 [M+H]+. 1H NMR (300 MHz, DMSO-d6) δ 2.54 (s, 3H), 5.18 (d, J=8.5 Hz, 1H), 7.21-7.75 (m, 10H), 7.74-7.92 (m, 2H), 9.27 (d, J=8.5 Hz, 1H), 10.99 (s, 1H).

Example 27

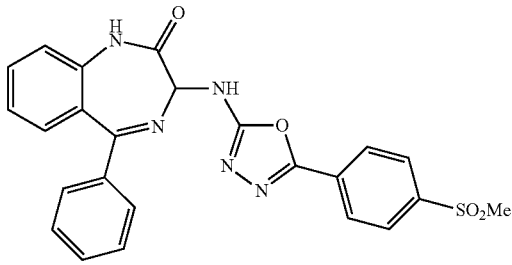 [SMILES: CS(=O)(=O)c1ccc(-c2nnc(NC3N=C(c4ccccc4)c4ccccc4NC3=O)o2)cc1]

Example 27 was prepared using a procedure similar to that used to prepare Example 21 where 4-(methylsulfonyl)benzohydrazide was used in place of tetrahydro-2H-pyran-4-carbohydrazide. ESI-MS m/z: 474.2 [M+H]+. 1H NMR (300 MHz, DMSO-d6) δ 5.21 (s, 1H), 7.23-7.43 (m, 3H), 7.43-7.61 (m, 5H), 7.69 (ddd, J=8.4, 7.0, 1.7 Hz, 1H), 8.02-8.19 (m, 4H), 9.37 (s, 1H), 10.96 (s, 1H).

Example 28

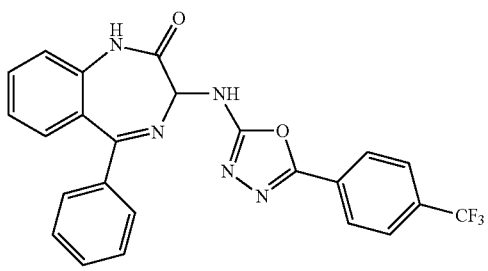 [SMILES: O=C1Nc2ccccc2C(c2ccccc2)=NC1Nc1nnc(-c2ccc(C(F)(F)F)cc2)o1]

Example 28 was prepared using a procedure similar to that used to prepare Example 20 where 4-(trifluoromethyl)benzoic acid was used in place of 5-chlorofuran-2-carboxylic acid. ESI-MS m/z: 464.1 [M+H]+. 1H NMR (300 MHz, DMSO-d6) δ 5.19 (d, J=11.2 Hz, 1H), 7.20-7.60 (m, 8H), 7.65-7.75 (m, 1H), 7.90-8.00 (m, 2H), 8.00-8.10 (m, 2H), 9.34 (d, J=11.2 Hz, 1H), 11.02 (s, 1H).

Example 29

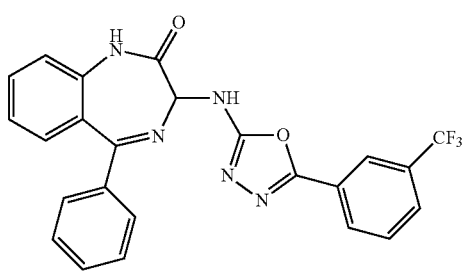 [SMILES: O=C1Nc2ccccc2C(c2ccccc2)=NC1Nc1nnc(-c2cccc(C(F)(F)F)c2)o1]

Example 29 was prepared using a procedure similar to that used to prepare Example 20 where 3-(trifluoromethyl)benzoic acid was used in place of 5-chlorofuran-2-carboxylic acid. ESI-MS m/z: 464.3 [M+H]+. 1H NMR (300 MHz, DMSO-d6) δ 5.19 (d, J=11.2 Hz, 1H), 7.20-7.40 (m, 3H), 7.40-7.60 (m, 5H), 7.65-7.75 (m, 1H), 7.90-8.00 (m, 2H), 8.00-8.10 (m, 2H), 9.30-9.40 (d, J=11.6 Hz, 1H), 11.02 (s, 1H).

Example 30

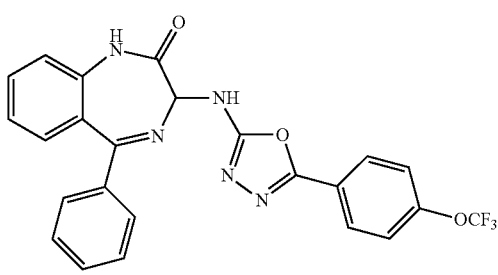 [SMILES: O=C1Nc2ccccc2C(c2ccccc2)=NC1Nc1nnc(-c2ccc(OC(F)(F)F)cc2)o1]

Example 30 was prepared using a procedure similar to that used to prepare Example 20 where 4-(trifluoromethoxy)benzoic acid was used in place of 5-chlorofuran-2-carboxylic acid. ESI-MS m/z: 480.2 [M+H]+. 1H NMR (300 MHz, DMSO-d6) δ 5.17 (d, J=8.4 Hz, 1H), 7.22-7.61 (m, 11H), 7.67 (m, 1H), 7.88-8.00 (m, 2H), 9.23 (d, J=8.5 Hz, 1H), 11.00 (s, 1H).

Example 31

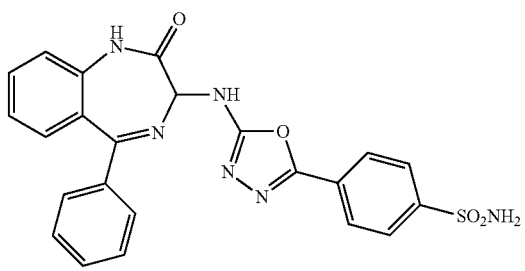 [SMILES: NS(=O)(=O)c1ccc(-c2nnc(NC3N=C(c4ccccc4)c4ccccc4NC3=O)o2)cc1]

Example 31 was prepared using a procedure similar to that used to prepare Example 20 where 4-sulfamoylbenzoic acid was used in place of 5-chlorofuran-2-carboxylic acid. ESI-MS m/z: 475.3 [M+H]+. 1H NMR (300 MHz, DMSO-d6) δ 5.19 (s, 1H), 7.20-7.80 (m, 12H), 7.90-8.10 (m, 4H), 9.20-9.60 (m, 1H).

Example 32

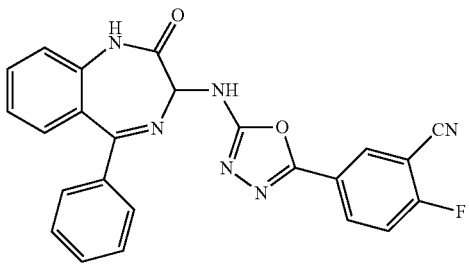 [SMILES: N#Cc1cc(-c2nnc(NC3N=C(c4ccccc4)c4ccccc4NC3=O)o2)ccc1F]

Example 32 was prepared using a procedure similar to that used to prepare Example 20 where 3-cyano-4-fluorobenzoic acid was used in place of 5-chlorofuran-2-carboxylic acid. ESI-MS m/z: 439.1 [M+H]+. 1H NMR (300 MHz, DMSO-$d_6$) δ 5.18 (d, J=8.2 Hz, 1H), 7.26-7.60 (m, 8H), 7.71 (dt, J=14.3, 7.9 Hz, 2H), 8.17 (m, 1H), 8.30 (dd, J=6.0, 2.3 Hz, 1H), 9.30 (d, J=8.4 Hz, 1H), 11.02 (s, 1H).

Example 33

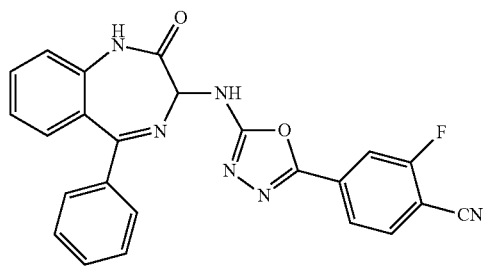 [SMILES: N#Cc1ccc(-c2nnc(NC3N=C(c4ccccc4)c4ccccc4NC3=O)o2)cc1F]

Example 33 was prepared using a procedure similar to that used to prepare Example 20 where 4-cyano-3-fluorobenzoic acid was used in place of 5-chlorofuran-2-carboxylic acid. ESI-MS m/z: 439.1 [M+H]+. 1H NMR (300 MHz, DMSO-$d_6$) δ 5.19 (s, 1H), 7.22-7.59 (m, 9H), 7.67 (m, 1H), 7.82 (m, 2H), 8.12 (dd, J=8.1, 6.7 Hz, 1H), 9.49 (s, 1H), 11.01 (s, 1H).

Example 34

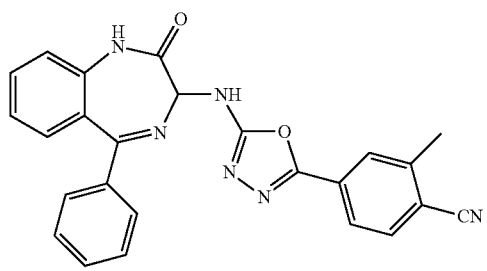 [SMILES: Cc1cc(-c2nnc(NC3N=C(c4ccccc4)c4ccccc4NC3=O)o2)ccc1C#N]

Example 34 was prepared using a procedure similar to that used to prepare Example 20 where 4-cyano-3-methylbenzoic acid was used in place of 5-chlorofuran-2-carboxylic acid. ESI-MS m/z: 435.2 [M+H]+. 1H NMR (300 MHz, DMSO-$d_6$) δ 2.57 (s, 3H), 5.19 (d, J=8.3 Hz, 1H), 7.23-7.60 (m, 8H), 7.62-7.81 (m, 2H), 7.87-8.00 (m, 2H), 9.36 (d, J=8.4 Hz, 1H), 11.03 (s, 1H).

Example 35

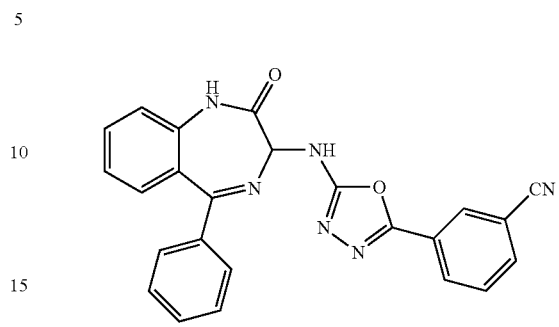

Example 35 was prepared using a procedure similar to that used to prepare Example 20 where 3-cyanobenzoic acid was used in place of 5-chlorofuran-2-carboxylic acid. ESI-MS m/z: 421.3 [M+H]+. 1H NMR (300 MHz, DMSO-$d_6$) δ 5.20 (s, 1H), 7.25-7.33 (m, 1H), 7.37 (dd, J=8.1, 2.2 Hz, 2H), 7.43-7.60 (m, 5H), 7.69 (ddd, J=8.4, 7.1, 1.7 Hz, 1H), 7.79 (t, J=7.9 Hz, 1H), 8.03 (dt, J=7.7, 1.4 Hz, 1H), 8.14 (dt, J=8.0, 1.4 Hz, 1H), 8.20 (t, J=1.6 Hz, 1H), 9.31 (s, 1H), 11.03 (s, 1H).

Example 36

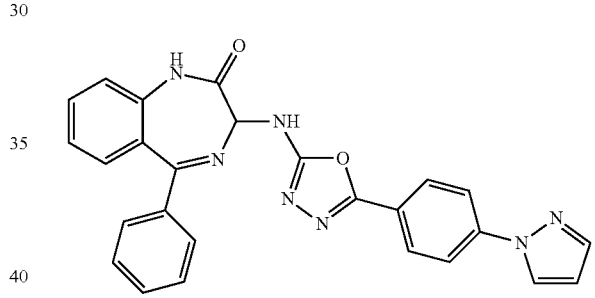

Example 36 was prepared using a procedure similar to that used to prepare Example 20 where 4-(1H-pyrazol-1-yl)benzoic acid was used in place of 5-chlorofuran-2-carboxylic acid. ESI-MS m/z: 462.3 [M+H]+. 1H NMR (300 MHz, DMSO-$d_6$) δ 5.19 (d, J=8.4 Hz, 1H), 6.62 (t, J=2.2 Hz, 1H), 7.24-7.42 (m, 3H), 7.43-7.62 (m, 5H), 7.70 (ddd, J=8.4, 7.1, 1.7 Hz, 1H), 7.83 (d, J=1.7 Hz, 1H), 7.89-8.01 (m, 2H), 8.02-8.12 (m, 2H), 8.63 (d, J=2.6 Hz, 1H), 9.18 (d, J=8.6 Hz, 1H), 11.01 (s, 1H).

Example 37

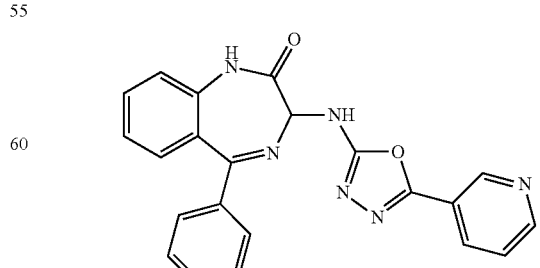

Example 37 was prepared using a procedure similar to that used to prepare Example 20 where nicotinic acid was used in place of 5-chlorofuran-2-carboxylic acid. ESI-MS m/z: 397.2 [M+H]+. 1H NMR (300 MHz, DMSO-d6) δ 5.19 (d, J=8.4 Hz, 1H), 7.23-7.74 (m, 10H), 8.14-8.23 (m, 1H), 8.72 (d, J=4.7 Hz, 1H), 9.01 (s, 1H), 9.26 (d, J=8.4 Hz, 1H), 11.01 (s, 1H).

Example 38

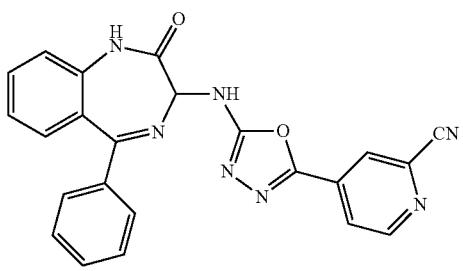 [SMILES: N#Cc1cc(-c2nnc(NC3N=C(c4ccccc4)c4ccccc4NC3=O)o2)ccn1]

Example 38 was prepared using a procedure similar to that used to prepare Example 20 where 2-cyanoisonicotinic acid was used in place of 5-chlorofuran-2-carboxylic acid. ESI-MS m/z: 422.3 [M+H]+. 1H NMR (300 MHz, DMSO-d6) δ 5.24 (s, 1H), 7.16-7.43 (m, 3H), 7.52 (hept, J=7.6, 7.0 Hz, 5H), 7.70 (t, J=7.3 Hz, 1H), 8.03 (dd, J=5.1, 1.8 Hz, 1H), 8.33 (s, 1H), 8.50 (s, OH), 8.93 (d, J=5.2 Hz, 1H), 9.61 (s, 1H), 11.09 (s, 1H).

Example 39

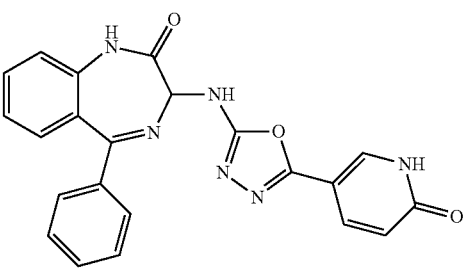 [SMILES: O=C1Nc2ccccc2C(c2ccccc2)=NC1Nc1nnc(-c2ccc(=O)[nH]c2)o1]

Example 39 was prepared using a procedure similar to that used to prepare Example 20 where 6-oxo-1,6-dihydropyridine-3-carboxylic acid was used in place of 5-chlorofuran-2-carboxylic acid. ESI-MS m/z: 413.2 [M+H]+. 1H NMR (400 MHz, DMSO-d6) δ 5.13 (d, J=8.6 Hz, 1H), 6.45-6.53 (m, 1H), 7.24-7.39 (m, 3H), 7.42-7.59 (m, 5H), 7.68 (m, 1H), 7.76-7.84 (m, 2H), 9.00 (d, J=8.7 Hz, 1H), 11.01 (s, 1H), 12.05 (s, 1H).

Example 40

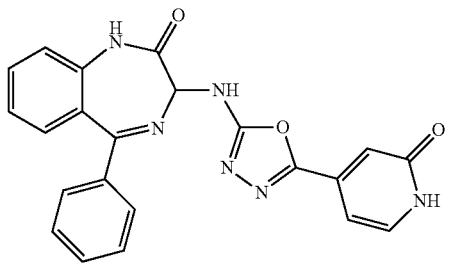 [SMILES: O=C1Nc2ccccc2C(c2ccccc2)=NC1Nc1nnc(-c2cc[nH]c(=O)c2)o1]

Example 40 was prepared using a procedure similar to that used to prepare Example 20 where 2-oxo-1,2-dihydropyridine-4-carboxylic acid was used in place of 5-chlorofuran-2-carboxylic acid. ESI-MS m/z: 413.2 [M+H]+. 1H NMR (400 MHz, DMSO-d6) δ 5.18 (s, 1H), 6.53-6.63 (m, 2H), 7.24-7.40 (m, 3H), 7.42-7.59 (m, 6H), 7.68 (m, 1H), 9.41 (s, 1H), 11.39 (s, 2H).

Example 41

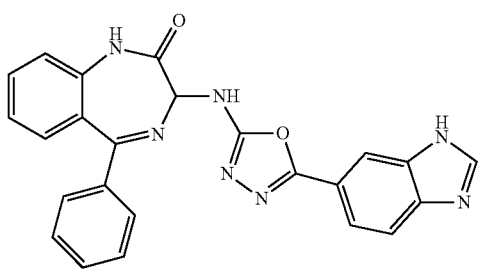 [SMILES: O=C1Nc2ccccc2C(c2ccccc2)=NC1Nc1nnc(-c2ccc3nc[nH]c3c2)o1]

Example 41 was prepared using a procedure similar to that used to prepare Example 20 where 1H-benzo[d]imidazole-6-carboxylic acid was used in place of 5-chlorofuran-2-carboxylic acid. ESI-MS m/z: 436.3 [M+H]+. 1H NMR (300 MHz, DMSO-d6) δ 5.17 (d, J=11.6 Hz, 1H), 7.20-7.40 (m, 3H), 7.40-7.60 (m, 5H), 7.60-7.85 (m, 3H), 8.01 (s, 1H), 8.37 (s, 1H), 9.06 (d, J=11.6 Hz, 1H), 11.02 (s, 1H).

Example 42

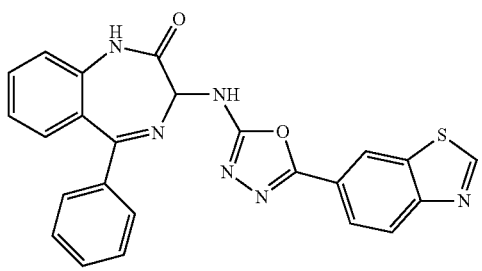 [SMILES: O=C1Nc2ccccc2C(c2ccccc2)=NC1Nc1nnc(-c2ccc3ncsc3c2)o1]

Example 42 was prepared using a procedure similar to that used to prepare Example 20 where benzo[d]thiazole-6-carboxylic acid was used in place of 5-chlorofuran-2-carboxylic acid. ESI-MS m/z: 453.2 [M+H]+. 1H NMR (300 MHz, DMSO-d6) δ 5.21 (d, J=8.4 Hz, 1H), 7.24-7.62 (m, 9H), 7.70 (ddd, J=8.5, 7.2, 1.8 Hz, 1H), 8.00 (dd, J=8.6, 1.8 Hz, 1H), 8.25 (d, J=8.6 Hz, 1H), 8.69 (d, J=1.7 Hz, 1H), 9.26 (d, J=8.5 Hz, 1H), 9.54 (s, 1H), 11.02 (s, 1H).

Example 43

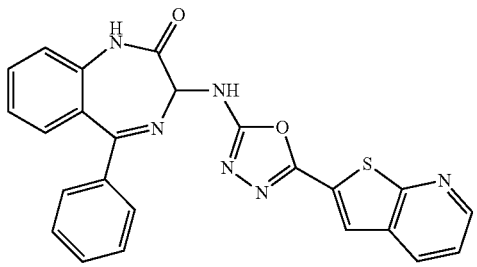 [SMILES: O=C1Nc2ccccc2C(c2ccccc2)=NC1Nc1nnc(-c2cc3cccnc3s2)o1]

Example 43 was prepared using a procedure similar to that used to prepare Example 20 where thieno[2,3-b]pyridine-2-carboxylic acid was used in place of 5-chlorofuran-2-carboxylic acid. ESI-MS m/z: 453.1 [M+H]$^+$. $^1$H NMR (300 MHz, DMSO-d$_6$) δ 2.53 (s, 2H), 5.19 (d, J=6.3 Hz, 1H), 7.21-7.59 (m, 9H), 7.68 (ddd, J=8.4, 7.0, 1.7 Hz, 1H), 7.92-8.01 (m, 2H), 8.55 (d, J=5.5 Hz, 1H), 9.33 (t, J=0.9 Hz, 1H), 9.53 (s, 1H), 11.03 (s, 1H).

Example 44

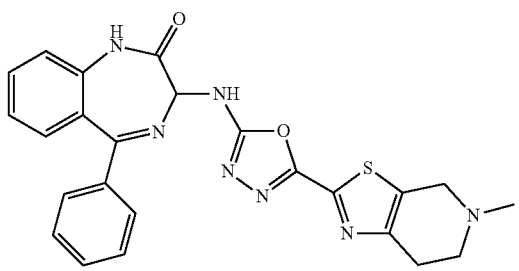 [SMILES: CN1CCc2nc(-c3nnc(NC4N=C(c5ccccc5)c5ccccc5NC4=O)o3)sc2C1]

Example 44 was prepared using a procedure similar to that used to prepare Example 20 where 5-methyl-4,5,6,7-tetrahydrothiazolo[5,4-c]pyridine-2-carboxylic acid was used in place of 5-chlorofuran-2-carboxylic acid. ESI-MS m/z: 472.2 [M+H]$^+$. $^1$H NMR (300 MHz, DMSO-d$_6$) δ 2.40 (s, 3H), 2.81 (dt, J=28.9, 5.9 Hz, 4H), 3.68 (s, 2H), 5.17 (d, J=8.3 Hz, 1H), 7.22-7.60 (m, 8H), 7.65-7.70 (m, 1H), 9.44 (d, J=8.3 Hz, 1H), 11.00 (s, 1H).

Example 45

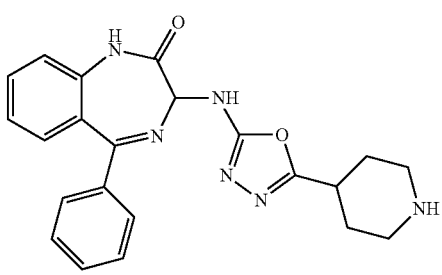 [SMILES: O=C1Nc2ccccc2C(c2ccccc2)=NC1Nc1nnc(C2CCNCC2)o1]

Example 45 was prepared using a procedure similar to that used to prepare Example 21 where piperidine-4-carbohydrazide was used in place of tetrahydro-2H-pyran-4-carbohydrazide. ESI-MS m/z: 403.2 [M+H]$^+$. $^1$H NMR (300 MHz, DMSO-d$_6$) δ 1.75-1.93 (m, 2H), 2.04-2.18 (m, 2H), 3.04 (q, J=11.2 Hz, 2H), 3.20 (tt, J=10.9, 4.0 Hz, 1H), 3.33 (d, J=13.2 Hz, 2H), 5.07 (d, J=8.4 Hz, 1H), 7.23-7.41 (m, 3H), 7.41-7.60 (m, 5H), 7.67 (ddd, J=8.4, 7.0, 1.8 Hz, 1H), 8.55 (d, J=10.8 Hz, 1H), 8.87 (d, J=8.7 Hz, 2H), 10.97 (s, 1H).

Example 46

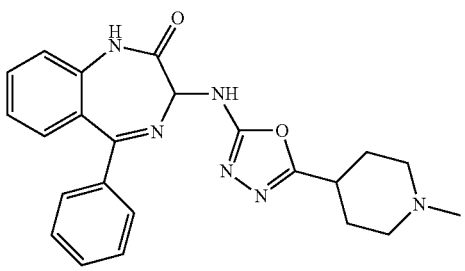 [SMILES: CN1CCC(c2nnc(NC3N=C(c4ccccc4)c4ccccc4NC3=O)o2)CC1]

Example 46 was prepared using a procedure similar to that used to prepare Example 20 where 1-methylpiperidine-4-carboxylic acid was used in place of 5-chlorofuran-2-carboxylic acid. ESI-MS m/z: 417.3 [M+H]$^+$. $^1$H NMR (300 MHz, DMSO-d$_6$) δ 1.58-1.76 (m, 2H), 1.85-1.97 (m, 2H), 1.97-2.11 (m, 2H), 2.20 (s, 3H), 2.77 (td, J=10.9, 5.3 Hz, 3H), 5.06 (d, J=8.7 Hz, 1H), 7.18-7.40 (m, 3H), 7.41-7.60 (m, 5H), 7.67 (ddd, J=8.5, 7.0, 1.8 Hz, 1H), 8.75 (d, J=8.7 Hz, 1H), 10.94 (s, 1H).

Example 47

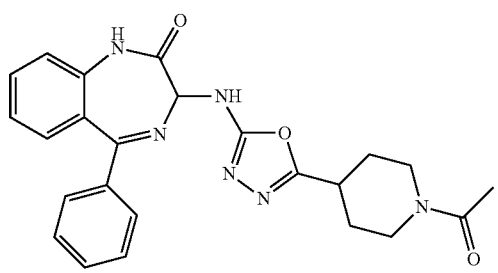 [SMILES: CC(=O)N1CCC(c2nnc(NC3N=C(c4ccccc4)c4ccccc4NC3=O)o2)CC1]

Example 47 was prepared using a procedure similar to that used to prepare Example 21 where 1-acetylpiperidine-4-carbohydrazide was used in place of tetrahydro-2H-pyran-4-carbohydrazide. ESI-MS m/z: 445.3 [M+H]$^+$. $^1$H NMR (300 MHz, DMSO-d$_6$) δ 1.26-1.26 (m, 2H), 1.92-2.09 (m, 4H), 2.72-2.88 (m, 1H), 3.03-3.28 (m, 2H), 4.25 (d, J=13.3 Hz, 1H), 5.07 (d, J=7.8 Hz, 1H), 7.31 (dtd, J=15.2, 7.9, 5.4 Hz, 2H), 7.40-7.61 (m, 4H), 7.67 (ddd, J=8.4, 7.0, 1.8 Hz, 1H), 8.83 (d, J=8.7 Hz, 1H), 10.95 (s, 1H).

Example 48

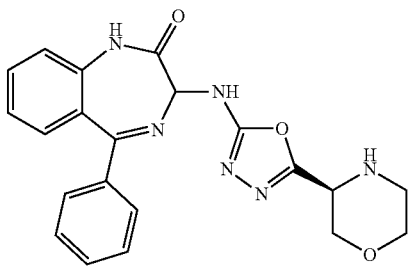 [SMILES: O=C1Nc2ccccc2C(c2ccccc2)=NC1Nc1nnc([C@@H]2COCCN2)o1]

Example 48 was prepared using a procedure similar to that used to prepare Example 20 where (S)-4-(tert-butoxycarbonyl)morpholine-3-carboxylic acid was used in place of 5-chlorofuran-2-carboxylic acid. The Boc-protected intermediate (126 mg, 0.5 mmol) was dissolved in DCM (20 mL) and then HCl (gas) saturated dioxane (10 mL) was added to the mixture and it was stirred at r.t for 2 h. Solid $K_2CO_3$ was added to neutralize the HCl, and the solid was filtered off. The filtrate was concentrated and the resulting residue was purified by prep-HPLC to give the title compound as a white solid (49 mg, 48%). ESI-MS m/z: 405.1 [M+H]$^+$. $^1$H NMR (400 MHz, DMSO-d6) δ 2.70-2.81 (m, 1H), 2.83-2.95 (m, 2H), 3.49 (m, 1H), 3.63 (m, 2H), 3.86 (m, 1H), 3.97 (dd, J=8.3, 3.2 Hz, 1H), 5.07 (dd, J=8.6, 1.4 Hz, 1H), 7.23-7.38 (m, 3H), 7.41-7.58 (m, 5H), 7.66 (m, 1H), 8.86 (dd, J=8.7, 1.7 Hz, 1H), 10.94 (s, 1H).

Example 49

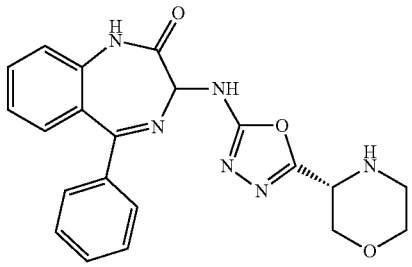 [SMILES: O=C1Nc2ccccc2C(c2ccccc2)=NC1Nc1nnc([C@H]2COCCN2)o1]

Example 49 was prepared using a procedure similar to that used to prepare Example 20 where (R)-4-(tert-butoxycarbonyl)morpholine-3-carboxylic acid was used in place of 5-chlorofuran-2-carboxylic acid. The Boc-protected intermediate was de-protected using a procedure similar to that described in Example 48. ESI-MS m/z: 405.0 [M+H]$^+$. $^1$H NMR (300 MHz, DMSO-$d_6$) δ 2.66-2.81 (m, 1H), 2.86 (d, J=13.1 Hz, 1H), 3.41-3.71 (m, 3H), 3.79-3.90 (m, 1H), 3.96 (m, 1H), 5.06 (m, 1H), 7.20-7.38 (m, 3H), 7.38-7.58 (m, 5H), 7.65 (m, 1H), 8.45 (S, 0.23H), 8.79-8.89 (m, 1H), 10.94 (d, J=6.0 Hz, 1H).

Example 50

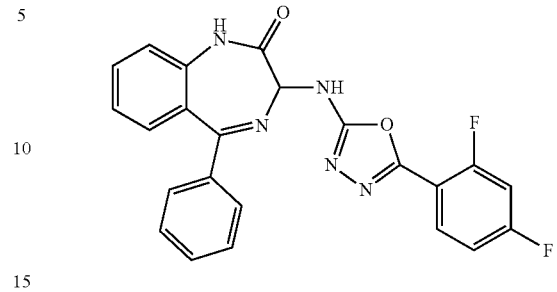

Example 50 was prepared using a procedure similar to that used to prepare Example 20 where 2,4-difluorobenzoic acid was used in place of 5-chlorofuran-2-carboxylic acid. ESI-MS m/z: 432.2 [M+H]$^+$. $^1$H NMR (300 MHz, DMSO-$d_6$) δ 5.18 (d, J=8.4 Hz, 1H), 7.20-7.61 (m, 10H), 7.61-7.77 (m, 1H), 7.92 (td, J=8.6, 6.3 Hz, 1H), 9.22 (d, J=8.5 Hz, 1H), 11.01 (s, 1H).

Example 51

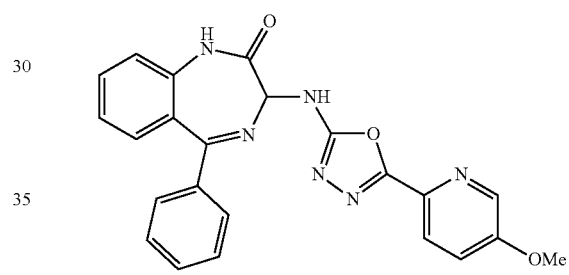

Example 51 was prepared using a procedure similar to that used to prepare Example 20 where 5-methoxypicolinic acid was used in place of 5-chlorofuran-2-carboxylic acid. ESI-MS m/z: 427.3 [M+H]$^+$. $^1$H NMR (300 MHz, DMSO-$d_6$) δ 3.91 (s, 3H), 5.17 (d, J=8.5 Hz, 1H), 7.22-7.61 (m, 9H), 7.68 (m, 1H), 7.95 (d, J=8.8 Hz, 1H), 8.41 (d, J=2.9 Hz, 1H), 9.18 (d, J=8.6 Hz, 1H), 11.00 (s, 1H).

Example 52

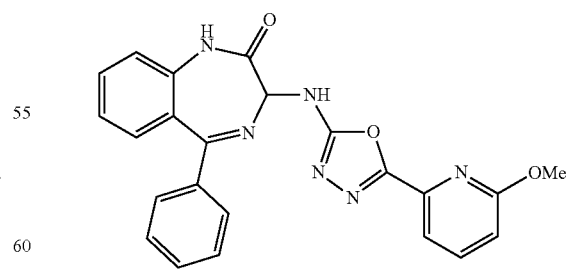

Example 52 was prepared using a procedure similar to that used to prepare Example 20 where 6-methoxypicolinic acid was used in place of 5-chlorofuran-2-carboxylic acid. ESI-MS m/z: 427.1 [M+H]$^+$. $^1$H NMR (300 MHz, DMSO-$d_6$) δ 3.91 (s, 3H), 5.18 (d, J=8.4 Hz, 1H), 6.97 (dd, J=8.4, 0.8 Hz, 1H), 7.21-7.73 (m, 10H), 7.87 (dd, J=8.4, 7.4 Hz, 1H), 9.28 (d, J=8.5 Hz, 1H), 10.99 (s, 1H).

Example 53

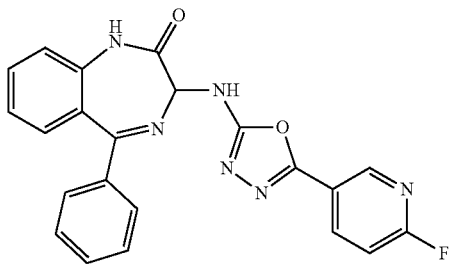 [SMILES: O=C1Nc2ccccc2C(c2ccccc2)=NC1Nc1nnc(-c2ccc(F)nc2)o1]

Example 53 was prepared using a procedure similar to that used to prepare Example 20 where 6-fluoronicotinic acid was used in place of 5-chlorofuran-2-carboxylic acid. ESI-MS m/z: 415.3 [M+H]$^+$. $^1$H NMR (300 MHz, DMSO-d$_6$) δ 5.17 (d, J=8.4 Hz, 1H), 7.22-7.59 (m, 9H), 7.67 (m, 1H), 8.21 (s, 0.518H), 8.37 (m, 1H), 8.66 (d, J=2.4 Hz, 1H), 9.28 (d, J=8.4 Hz, 1H), 11.01 (s, 1H).

Example 54

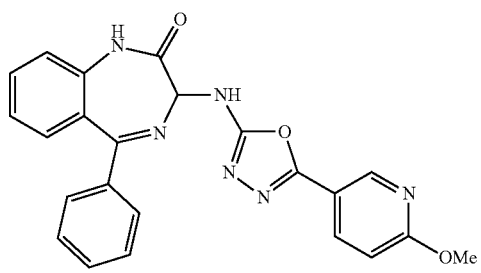 [SMILES: COc1ccc(-c2nnc(NC3N=C(c4ccccc4)c4ccccc4NC3=O)o2)cn1]

Example 54 was prepared using a procedure similar to that used to prepare Example 20 where 6-methoxynicotinic acid was used in place of 5-chlorofuran-2-carboxylic acid. ESI-MS m/z: 427.3 [M+H]$^+$. $^1$H NMR (300 MHz, DMSO-d$_6$) δ 3.93 (s, 3H), 5.16 (d, J=8.2 Hz, 1H), 7.01 (d, J=8.7 Hz, 1H), 7.22-7.59 (m, 8H), 7.65-7.70 (m, 1H), 8.10 (dd, J=8.7, 2.5 Hz, 1H), 8.61 (d, J=2.4 Hz, 1H), 9.14 (d, J=8.5 Hz, 1H), 10.97 (s, 1H).

Example 55

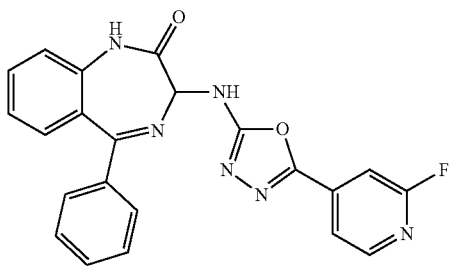 [SMILES: O=C1Nc2ccccc2C(c2ccccc2)=NC1Nc1nnc(-c2ccnc(F)c2)o1]

Example 55 was prepared using a procedure similar to that used to prepare Example 20 where 2-fluoroisonicotinic acid was used in place of 5-chlorofuran-2-carboxylic acid. ESI-MS m/z: 415.3 [M+H]$^+$. $^1$H NMR (300 MHz, DMSO-d$_6$) δ 5.20 (s, 1H), 7.22-7.76 (m, 11H), 8.44 (d, J=5.2 Hz, 1H), 9.48 (s, 1H), 11.00 (s, 1H).

Example 56

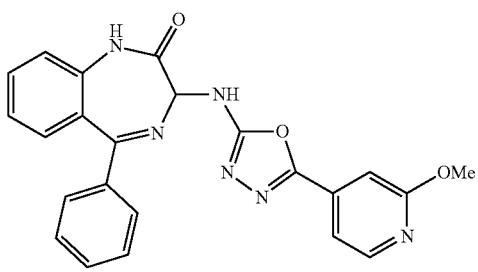 [SMILES: COc1cc(-c2nnc(NC3N=C(c4ccccc4)c4ccccc4NC3=O)o2)ccn1]

Example 56 was prepared using a procedure similar to that used to prepare Example 20 where 2-methoxyisonicotinic acid was used in place of 5-chlorofuran-2-carboxylic acid. ESI-MS m/z: 427.1 [M+H]$^+$. $^1$H NMR (300 MHz, DMSO-d$_6$) δ 3.91 (s, 3H), 5.18 (d, J=8.2 Hz, 1H), 7.07 (t, J=1.0 Hz, 1H), 7.22-7.59 (m, 9H), 7.67 (ddd, J=8.4, 7.0, 1.8 Hz, 1H), 8.34 (d, J=5.3 Hz, 1H), 9.38 (d, J=8.4 Hz, 1H), 11.02 (s, 1H).

Example 57

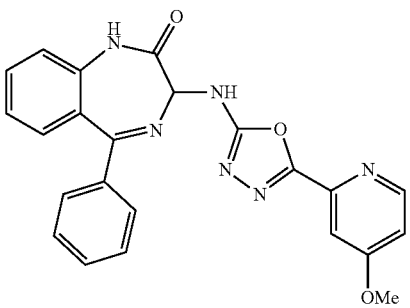 [SMILES: COc1ccnc(-c2nnc(NC3N=C(c4ccccc4)c4ccccc4NC3=O)o2)c1]

Example 57 was prepared using a procedure similar to that used to prepare Example 20 where 4-methoxypicolinic acid was used in place of 5-chlorofuran-2-carboxylic acid. ESI-MS m/z: 427.2 [M+H]$^+$. $^1$H NMR (300 MHz, DMSO-d$_6$) δ 3.91 (s, 3H), 5.19 (d, J=8.4 Hz, 1H), 7.12 (dd, J=5.8, 2.5 Hz, 1H), 7.22-7.59 (m, 9H), 7.68 (m, 1H), 8.51 (d, J=5.7 Hz, 1H), 9.27 (d, J=8.5 Hz, 1H), 10.97-11.04 (m, 1H).

Example 58

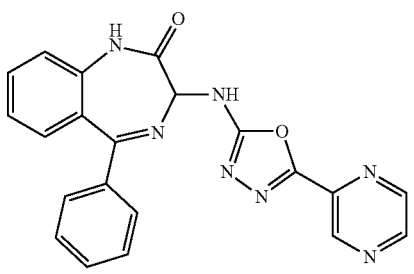 [SMILES: O=C1Nc2ccccc2C(c2ccccc2)=NC1Nc1nnc(-c2cnccn2)o1]

Example 58 was prepared using a procedure similar to that used to prepare Example 20 where pyrazine-2-carboxylic acid was used in place of 5-chlorofuran-2-carboxylic acid. ESI-MS m/z: 398.2 [M+H]+. $^1$H NMR (300 MHz, DMSO-$d_6$) δ 5.20 (d, J=8.1 Hz, 1H), 7.22-7.59 (m, 8H), 7.67 (m, 1H), 8.72-8.82 (m, 2H), 9.19 (d, J=1.3 Hz, 1H), 9.46 (d, J=8.3 Hz, 1H), 11.01 (s, 1H).

Example 59

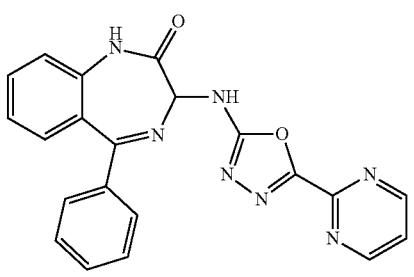 [SMILES: O=C1Nc2ccccc2C(c2ccccc2)=NC1Nc1nnc(-c2ncccn2)o1]

Example 59 was prepared using a procedure similar to that used to prepare Example 20 where pyrimidine-2-carboxylic acid was used in place of 5-chlorofuran-2-carboxylic acid. ESI-MS m/z: 398.2 [M+H]+. $^1$H NMR (300 MHz, DMSO-$d_6$) δ 5.23 (d, J=8.4 Hz, 1H), 7.23-7.43 (m, 3H), 7.43-7.62 (m, 5H), 7.60-7.77 (m, 2H), 8.98 (d, J=4.9 Hz, 2H), 9.47 (d, J=8.4 Hz, 1H), 11.01 (s, 1H).

Example 60

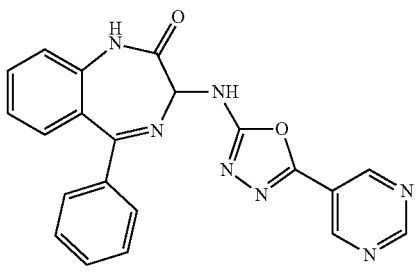 [SMILES: O=C1Nc2ccccc2C(c2ccccc2)=NC1Nc1nnc(-c2cncnc2)o1]

Example 60 was prepared using a procedure similar to that used to prepare Example 20 where pyrimidine-5-carboxylic acid was used in place of 5-chlorofuran-2-carboxylic acid. ESI-MS m/z: 398.1 [M+H]+. $^1$H NMR (300 MHz, DMSO-$d_6$) δ 5.20 (d, J=7.7 Hz, 1H), 7.21-7.59 (m, 8H), 7.67 (m, 1H), 9.17 (s, 2H), 9.35 (d, J=19.3 Hz, 2H), 11.00 (s, 1H).

Example 61

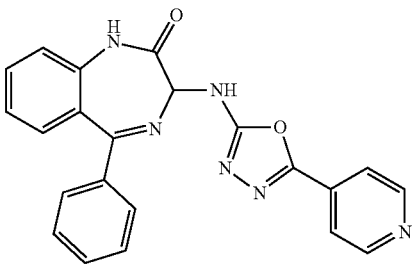 [SMILES: O=C1Nc2ccccc2C(c2ccccc2)=NC1Nc1nnc(-c2ccncc2)o1]

Example 61 was prepared using a procedure similar to that used to prepare Example 20 where isonicotinic acid was used in place of 5-chlorofuran-2-carboxylic acid. ESI-MS m/z: 397.1 [M+H]+. $^1$H NMR (300 MHz, DMSO-d6) δ 5.21 (d, J=8.3 Hz, 1H), 7.24-7.61 (m, 8H), 7.63-7.80 (m, 3H), 8.73-8.88 (m, 2H), 9.41 (d, J=8.4 Hz, 1H), 11.02 (s, 1H).

Example 62

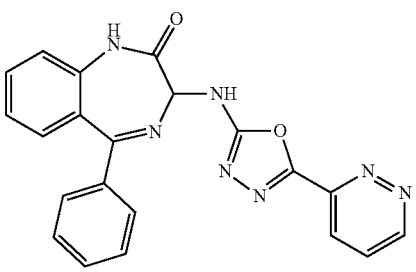 [SMILES: O=C1Nc2ccccc2C(c2ccccc2)=NC1Nc1nnc(-c2cccnn2)o1]

Example 62 was prepared using a procedure similar to that used to prepare Example 20 where pyridazine-3-carboxylic acid was used in place of 5-chlorofuran-2-carboxylic acid. ESI-MS m/z: 398.2 [M+H]+. $^1$H NMR (300 MHz, DMSO-$d_6$) δ 5.24 (d, J=8.2 Hz, 1H), 7.24-7.43 (m, 3H), 7.43-7.62 (m, 5H), 7.70 (ddd, J=8.4, 7.0, 1.7 Hz, 1H), 7.89 (dd, J=8.6, 5.0 Hz, 1H), 8.25 (dd, J=8.6, 1.6 Hz, 1H), 9.36 (dd, J=5.0, 1.6 Hz, 1H), 9.55 (d, J=8.4 Hz, 1H), 11.04 (s, 1H).

Example 63

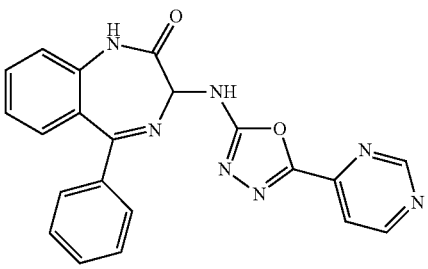 [SMILES: O=C1Nc2ccccc2C(c2ccccc2)=NC1Nc1nnc(-c2ccncn2)o1]

Example 63 was prepared using a procedure similar to that used to prepare Example 20 where pyrimidine-4-carboxylic acid was used in place of 5-chlorofuran-2-carboxylic acid. ESI-MS m/z: 398.1 [M+H]⁺. ¹H NMR (300 MHz, DMSO-d6) δ 5.23 (s, 1H), 7.24-7.62 (m, 8H), 7.69 (m, 1H), 8.02 (dd, J=5.3, 1.5 Hz, 1H), 8.99 (d, J=5.3 Hz, 1H), 9.34 (d, J=1.4 Hz, 1H), 9.60 (s, 1H), 11.03 (s, 1H).

Example 64

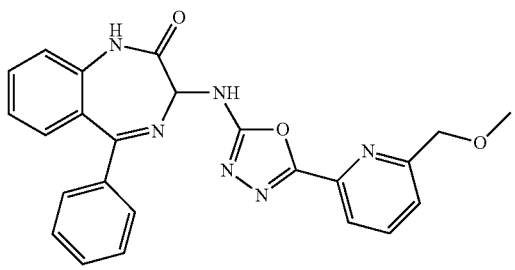 [SMILES: COCc1cccc(-c2nnc(NC3N=C(c4ccccc4)c4ccccc4NC3=O)o2)n1]

Example 64 was prepared using a procedure similar to that used to prepare Example 20 where 6-(methoxymethyl)picolinic acid was used in place of 5-chlorofuran-2-carboxylic acid. ESI-MS m/z: 441.1 [M+H]⁺. ¹H NMR (300 MHz, DMSO-d₆) δ 3.40 (s, 3H), 4.57 (s, 2H), 5.19 (d, J=8.4 Hz, 1H), 7.22-7.59 (m, 10H), 7.68 (m, 1H), 7.86-8.05 (m, 2H), 9.29 (d, J=8.5 Hz, 1H), 10.98 (s, 1H).

Example 65

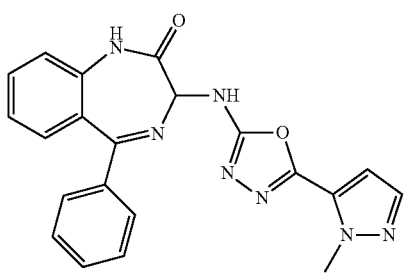 [SMILES: Cn1nccc1-c1nnc(NC2N=C(c3ccccc3)c3ccccc3NC2=O)o1]

Example 65 was prepared using a procedure similar to that used to prepare Example 20 where 1-methyl-1H-pyrazole-5-carboxylic acid was used in place of 5-chlorofuran-2-carboxylic acid. ESI-MS m/z: 400.2 [M+H]⁺. ¹H NMR (300 MHz, DMSO-d₆) δ 4.11 (s, 3H), 5.17 (d, J=8.2 Hz, 1H), 6.74 (d, J=2.0 Hz, 1H), 7.22-7.74 (m, 10H), 9.24 (d, J=8.4 Hz, 1H), 11.00 (s, 1H).

Example 66

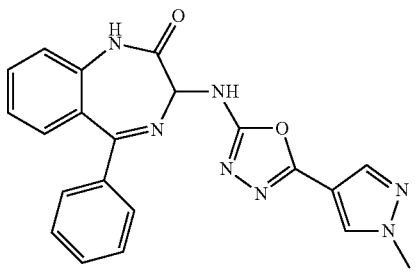 [SMILES: Cn1cc(-c2nnc(NC3N=C(c4ccccc4)c4ccccc4NC3=O)o2)cn1]

Example 66 was prepared using a procedure similar to that used to prepare Example 20 where 1-methyl-1H-pyrazole-4-carboxylic acid was used in place of 5-chlorofuran-2-carboxylic acid. ESI-MS m/z: 400.3 [M+H]⁺. ¹H NMR (300 MHz, DMSO-d₆) δ 3.92 (s, 3H), 5.12 (d, J=8.6 Hz, 1H), 7.21-7.60 (m, 8H), 7.67 (m, 1H), 7.84 (d, J=0.8 Hz, 1H), 8.28 (s, 1H), 8.92 (d, J=8.6 Hz, 1H), 10.96 (s, 1H).

Example 67

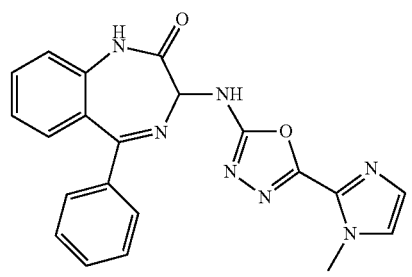 [SMILES: Cn1ccnc1-c1nnc(NC2N=C(c3ccccc3)c3ccccc3NC2=O)o1]

Example 67 was prepared using a procedure similar to that used to prepare Example 20 where 1-methyl-1H-imidazole-2-carboxylic acid was used in place of 5-chlorofuran-2-carboxylic acid. ESI-MS m/z: 400.3 [M+H]⁺. ¹H NMR (300 MHz, DMSO-d₆) δ 3.92 (s, 3H), 5.15 (d, J=8.1 Hz, 1H), 7.09 (d, J=1.1 Hz, 1H), 7.21-7.59 (m, 9H), 7.67 (m, 1H), 9.24 (d, J=8.5 Hz, 1H), 10.96 (s, 1H).

Example 68

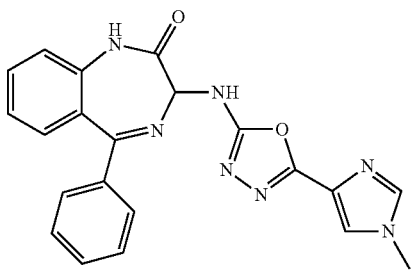 [SMILES: Cn1cnc(-c2nnc(NC3N=C(c4ccccc4)c4ccccc4NC3=O)o2)c1]

Example 68 was prepared using a procedure similar to that used to prepare Example 20 where 1-methyl-1H-imidazole-4-carboxylic acid was used in place of 5-chlorofuran-2-carboxylic acid. ESI-MS m/z: 400.3 [M+H]⁺. ¹H NMR (300 MHz, DMSO-d$_6$) δ 3.72 (s, 3H), 5.12 (d, J=8.6 Hz, 1H), 7.21-7.59 (m, 8H), 7.60-7.79 (m, 3H), 8.91 (d, J=8.7 Hz, 1H), 10.97 (s, 1H).

Example 69

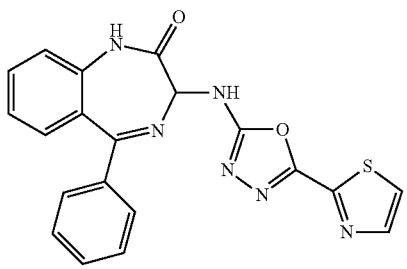

Example 69 was prepared using a procedure similar to that used to prepare Example 20 where thiazole-2-carboxylic acid was used in place of 5-chlorofuran-2-carboxylic acid. ESI-MS m/z: 403.0 [M+H]$^+$. $^1$H NMR (300 MHz, DMSO-d6) δ 5.20 (s, 1H), 7.23-7.61 (m, 8H), 7.69 (m, 1H), 7.99-8.15 (m, 2H), 9.50 (s, 1H), 11.02 (s, 1H).

Example 70

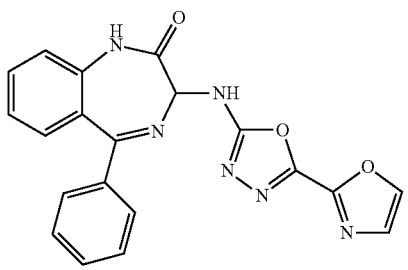

Example 70 was prepared using a procedure similar to that used to prepare Example 20 where oxazole-2-carboxylic acid was used in place of 5-chlorofuran-2-carboxylic acid. ESI-MS m/z: 387.4 [M+H]$^+$. $^1$H NMR (300 MHz, DMSO-d$_6$) δ 3.34 (d, J=14.0 Hz, 1H), 5.20 (d, J=8.3 Hz, 1H), 7.22-7.62 (m, 10H), 7.69 (ddd, J=8.4, 7.1, 1.8 Hz, 1H), 8.41 (d, J=0.8 Hz, 1H), 9.61 (d, J=8.3 Hz, 1H), 11.03 (s, 1H).

Example 71

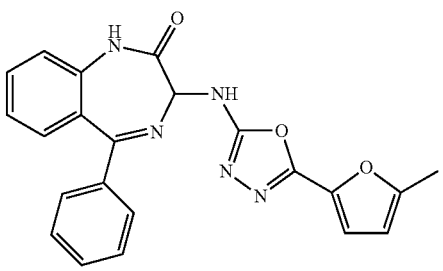 [SMILES: Cc1ccc(-c2nnc(NC3N=C(c4ccccc4)c4ccccc4NC3=O)o2)o1]

Example 71 was prepared using a procedure similar to that used to prepare Example 20 where 5-methylfuran-2-carboxylic acid was used in place of 5-chlorofuran-2-carboxylic acid. ESI-MS m/z: 400.0 [M+H]$^+$. $^1$H NMR (300 MHz, DMSO-d6) δ 2.39 (s, 3H), 5.14 (d, J=8.5 Hz, 1H), 6.36 (dd, J=3.3, 1.2 Hz, 1H), 6.95 (d, J=3.3 Hz, 1H), 7.23-7.61 (m, 8H), 7.68 (m, 1H), 9.13 (d, J=8.5 Hz, 1H), 10.98 (s, 1H).

Example 72

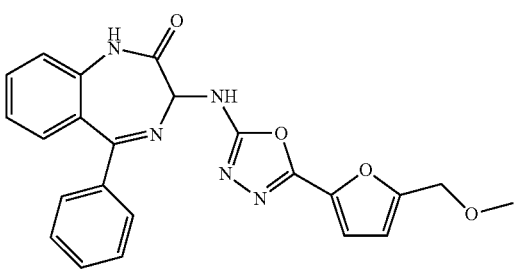 [SMILES: COCc1ccc(-c2nnc(NC3N=C(c4ccccc4)c4ccccc4NC3=O)o2)o1]

Example 72 was prepared using a procedure similar to that used to prepare Example 20 where 5-(methoxymethyl)furan-2-carboxylic acid was used in place of 5-chlorofuran-2-carboxylic acid. ESI-MS m/z: 430.1 [M+H]$^+$. $^1$H NMR (300 MHz, DMSO-d$_6$) δ 3.28 (s, 3H), 4.44 (s, 2H), 5.14 (s, 1H), 6.68 (d, J=3.5 Hz, 1H), 7.02 (d, J=3.4 Hz, 1H), 7.21-7.59 (m, 8H), 7.67 (m, 1H), 9.26 (s, 2H).

Example 73

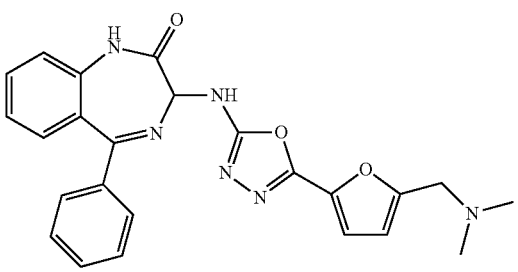 [SMILES: CN(C)Cc1ccc(-c2nnc(NC3N=C(c4ccccc4)c4ccccc4NC3=O)o2)o1]

Example 73 was prepared using a procedure similar to that used to prepare Example 20 where 5-((dimethylamino)methyl)furan-2-carboxylic acid was used in place of 5-chlorofuran-2-carboxylic acid. ESI-MS m/z: 443.3 [M+H]$^+$. $^1$H NMR (300 MHz, DMSO-d$_6$) δ 2.79 (s, 6H), 4.50 (s, 2H), 5.15 (d, J=8.4 Hz, 1H), 6.94 (d, J=3.5 Hz, 1H), 7.13 (d, J=3.5 Hz, 1H), 7.22-7.60 (m, 8H), 7.61-7.74 (m, 1H), 9.30 (d, J=8.5 Hz, 1H), 10.33 (s, 1H), 10.99 (s, 1H).

Example 74

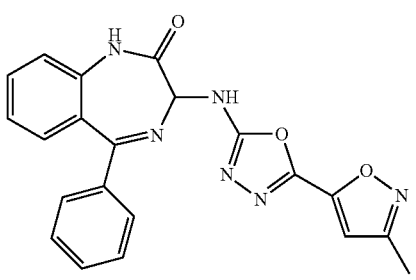 [SMILES: Cc1cc(-c2nnc(NC3N=C(c4ccccc4)c4ccccc4NC3=O)o2)on1]

Example 74 was prepared using a procedure similar to that used to prepare Example 20 where 3-methylisoxazole-5-carboxylic acid was used in place of 5-chlorofuran-2-carboxylic acid. ESI-MS m/z: 401.2 [M+H]$^+$. $^1$H NMR (300 MHz, DMSO-d$_6$) δ 2.34 (s, 3H), 5.16 (s, 1H), 7.02 (s, 1H), 7.23-7.36 (m, 3H), 7.43-7.56 (m, 5H), 7.66 (t, J=7.4 Hz, 1H), 9.76 (s, 1H), 10.89 (s, 1H).

Example 75

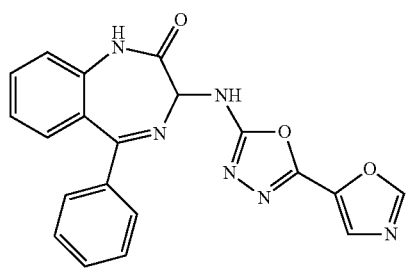

Example 75 was prepared using a procedure similar to that used to prepare Example 20 where oxazole-5-carboxylic acid was used in place of 5-chlorofuran-2-carboxylic acid. ESI-MS m/z: 387.2 [M+H]$^+$. $^1$H NMR (300 MHz, DMSO-d$_6$) δ 5.17 (d, J=8.3 Hz, 1H), 7.23-7.43 (m, 3H), 7.43-7.63 (m, 5H), 7.69 (td, J=7.7, 7.0, 1.8 Hz, 1H), 7.85 (s, 1H), 8.69 (s, 1H), 9.41 (d, J=8.4 Hz, 1H), 11.01 (s, 1H).

Example 76

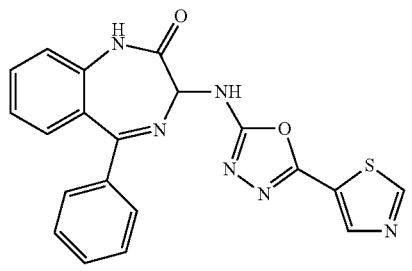

Example 76 was prepared using a procedure similar to that used to prepare Example 20 where thiazole-5-carboxylic acid was used in place of 5-chlorofuran-2-carboxylic acid. ESI-MS m/z: 403.2 [M+H]$^+$. $^1$H NMR (300 MHz, DMSO-d$_6$) δ 5.15 (d, J=8.2 Hz, 1H), 7.21-7.59 (m, 8H), 7.66 (m, 1H), 8.35 (s, 1H), 9.27 (d, J=7.9 Hz, 2H), 10.99 (s, 1H).

Example 77

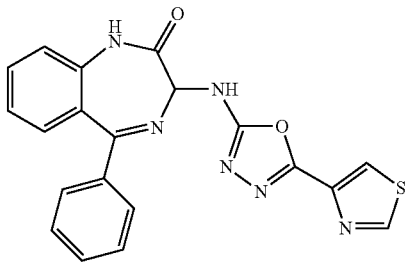 [SMILES: O=C1Nc2ccccc2C(c2ccccc2)=NC1Nc1nnc(-c2cscn2)o1]

Example 77 was prepared using a procedure similar to that used to prepare Example 20 where thiazole-4-carboxylic acid was used in place of 5-chlorofuran-2-carboxylic acid. ESI-MS m/z: 403.2 [M+H]$^+$. $^1$H NMR (300 MHz, DMSO-d$_6$) δ 5.18 (d, J=8.5 Hz, 1H), 7.20-7.43 (m, 3H), 7.42-7.61 (m, 5H), 7.69 (ddd, J=8.5, 7.0, 1.7 Hz, 1H), 8.33 (d, J=1.9 Hz, 1H), 9.20 (d, J=8.5 Hz, 1H), 9.30 (d, J=1.9 Hz, 1H), 10.99 (s, 1H).

Example 78

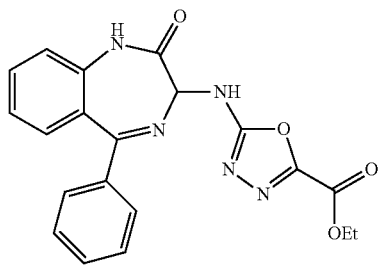 [SMILES: CCOC(=O)c1nnc(NC2N=C(c3ccccc3)c3ccccc3NC2=O)o1]

Example 78 was prepared using a procedure similar to that used to prepare Example 20 where 2-ethoxy-2-oxoacetic acid was used in place of 5-chlorofuran-2-carboxylic acid. ESI-MS m/z: 392.21 [M+H]$^+$. $^1$H NMR (300 MHz, DMSO-d$_6$) δ 1.31 (t, J=7.1 Hz, 3H), 4.36 (q, J=7.1 Hz, 2H), 5.18 (s, 1H), 7.22-7.40 (m, 3H), 7.40-7.60 (m, 5H), 7.64-7.70 (m, 1H), 9.70 (s, 1H), 11.04 (s, 1H).

Example 79

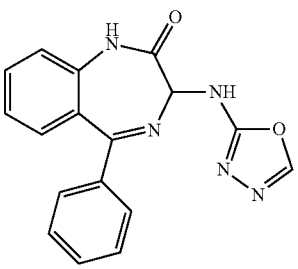 [SMILES: O=C1Nc2ccccc2C(c2ccccc2)=NC1Nc1nnco1]

Example 79 Step a

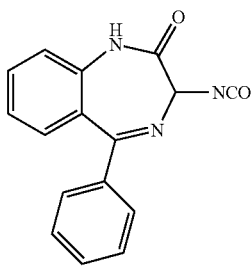

A solution of (Z)-3-amino-5-phenyl-1H-benzo[e][1,4]diazepin-2(3H)-one (300 mg, 1.195 mmol), BTC (116.7 mg, 0.394 mmol) and saturated NaHCO$_3$ (3 mL) in DCM (10 mL) was stirred for 30 minutes at 0° C. It was diluted with water, extracted with DCM (×2). The organic layer was dried, concentrated to give desired compound as orange solid (331 mg, 100%) that was used without further purification. ESI-MS m/z: 278.1 [M+H]$^+$.

Example 79 Step b

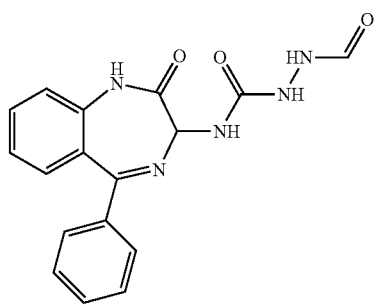 [SMILES: O=CNNC(=O)NC1N=C(c2ccccc2)c2ccccc2NC1=O]

A solution of the isocyanate from step a (331 mg, 1.20 mmol), formylhydrazine (108 mg, 1.79 mmol) and DIPEA (1 mL) in DMF (5 mL) was stirred for 2 hours. The reaction mixture was purified by reverse phase C18 column chromatography (MeCN:H$_2$O) to give the desired compound as a white solid (220 mg, 55%). ESI-MS m/z: 338.1 [M+H]$^+$.

Example 79 Step c

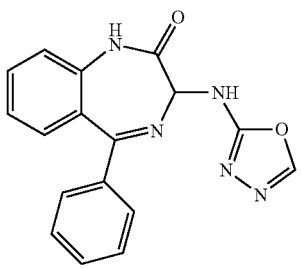 [SMILES: O=C1Nc2ccccc2C(c2ccccc2)=NC1Nc1nnco1]

A solution of the compound from step b (190 mg, 0.56 mmol), PPh$_3$ (443 mg, 1.69 mmol), CCl$_4$ (0.4 mL), and TEA (0.5 mL) in MeCN (5 mL) was stirred for 30 minutes. Water was added and the aqueous phase was extracted with EtOAc (×2) and the organics were dried (Na$_2$SO$_4$), concentrated, and purified by prep-HPLC to give the title compound as a yellow solid (12 mg, 7%). ESI-MS m/z: 320.3 [M+H]$^+$. $^1$H NMR (300 MHz, DMSO-d$_6$) δ 5.08 (d, J=8.6 Hz, 1H), 7.18-7.78 (m, 9H), 8.57 (s, 1H), 8.94 (d, J=8.6 Hz, 1H), 10.96 (s, 1H).

Example 80

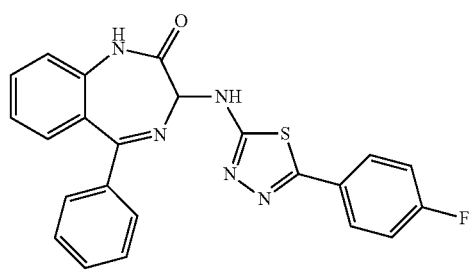

Example 80 Step a

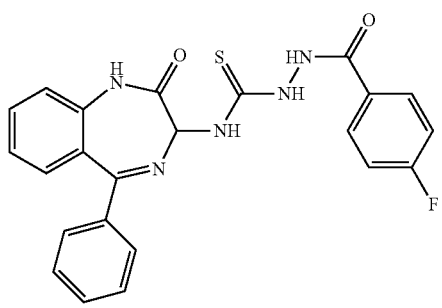 [SMILES: O=C(NNC(=S)NC1N=C(c2ccccc2)c2ccccc2NC1=O)c1ccc(F)cc1]

Example 80 was prepared using a procedure similar to that used to prepare Example 20 where 4-fluorobenzoic acid was used in place of 5-chlorofuran-2-carboxylic acid. The title compound was also used to prepare Example 7.

Example 80 Step b

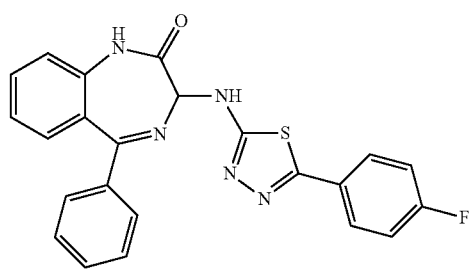

To a NMP solution (3 mL) of 2-(4-fluorobenzoyl)-N-(2-oxo-5-phenyl-2,3-dihydro-1H-benzo[e][1,4]diazepin-3-yl)hydrazine-1-carbothioamide (447 mg, 1.0 mmol), prepared in step a, was added TEA (0.28 mL, 2.0 mmol) and then TsCl (229 mg, 1.2 mmol). The mixture was stirred for 2 h at room temperature. DCM was added and the mixture was washed with water and brine. The organic phase was dried (Na$_2$SO$_4$), concentrated and purified by prep-HPLC to desired compound as light yellow solid (142 mg, 33%). ESI-MS m/z: 430.1 [M+H]$^+$. $^1$H-NMR (300 MHz, DMSO-d$_6$) δ 5.37 (d, J=7.6 Hz, 1H), 7.23-7.39 (m, 5H), 7.44-7.55 (m, 5H), 7.68 (m, 1H), 7.82 (dd, J=8.7, 5.5 Hz, 2H), 9.16 (d, J=7.7 Hz, 1H), 10.98 (s, 1H).

Example 81

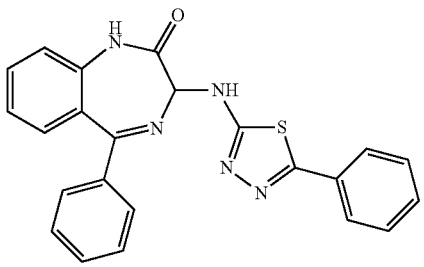

Example 81 was prepared using a procedure similar to that used to prepare Example 80 where benzoic acid was used in place of 4-fluorobenzoic acid. ESI-MS m/z: 412.3 [M+H]$^+$. $^1$H NMR (300 MHz, DMSO-d$_6$) δ 5.40 (d, J=7.6 Hz, 1H), 7.34 (dd, J=19.8, 7.9 Hz, 3H), 7.42-7.64 (m, 8H), 7.63-7.74 (m, 1H), 7.73-7.94 (m, 2H), 9.16 (d, J=7.7 Hz, 1H), 10.98 (s, 1H).

Example 82

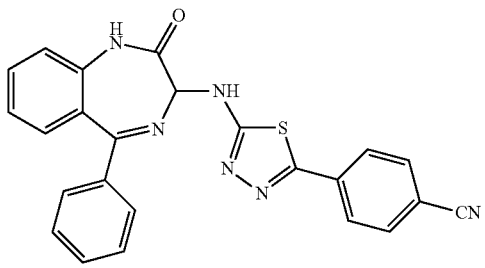

Example 82 was prepared using a procedure similar to that used to prepare Example 80 where 4-cyanobenzoic acid was used in place of 4-fluorobenzoic acid. ESI-MS m/z: 437.2 [M+H]$^+$. $^1$H NMR (300 MHz, CD3OD:CDCl3=2:1) δ 5.46 (s, 1H), 7.20-7.35 (m, 2H), 7.35-7.50 (m, 3H), 7.50-7.60 (m, 3H), 7.60-7.70 (m, 1H), 7.75-7.95 (m, 2H), 7.95-8.10 (m, 2H).

Example 83

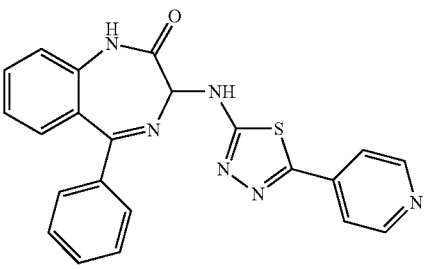 [SMILES: O=C1Nc2ccccc2C(c2ccccc2)=NC1Nc1nnc(-c2ccncc2)s1]

Example 83 was prepared using a procedure similar to that used to prepare Example 80 where isonicotinic acid was used in place of 4-fluorobenzoic acid. ESI-MS m/z: 413.1 [M+H]$^+$. $^1$H NMR (300 MHz, DMSO-d$_6$) δ 5.41 (d, J=7.4 Hz, 1H), 7.24-7.46 (m, 5H), 7.47-7.62 (m, 5H), 7.63-7.79 (m, 3H), 8.63-8.72 (m, 2H), 9.42 (d, J=7.5 Hz, 1H), 11.03 (s, 1H).

Example 84

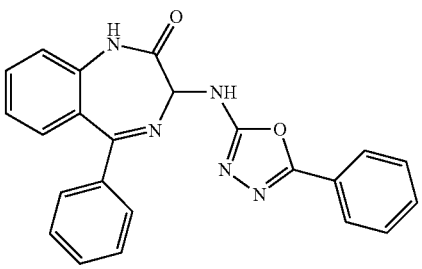 [SMILES: O=C1Nc2ccccc2C(c2ccccc2)=NC1Nc1nnc(-c2ccccc2)o1]

Example 84 Step a

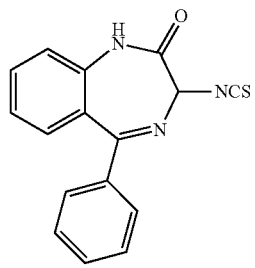

A solution of (Z)-3-amino-5-phenyl-1H-benzo[e][1,4]diazepin-2(3H)-one (251 mg, 1.0 mmol) in DCM (20 mL) was added di(1H-imidazol-1-yl)methanethione (178 mg, 1.0 mmol) at 0° C. The cold bat was removed and the reaction stirred at room temperature for 30 minutes. Water was added to the mixture and it was extracted with EtOAc. The organic layer was washed with brine, dried (Na$_2$SO$_4$) and concentrated to afford the desired product as yellow foam (320 mg), which is used directly without any further purification. ESI-MS m/z: 294.2 [M+H]$^+$.

Example 84 Step b

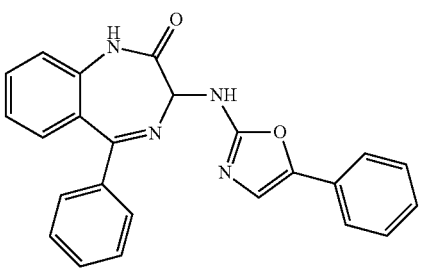 [SMILES: O=C1Nc2ccccc2C(c2ccccc2)=NC1Nc1ncc(-c2ccccc2)o1]

2-azido-1-phenylethanone (161 mg, 1.0 mmol) and PPh$_3$ (262 mg, 1.0 mmol) were added to the solution of compound from step a (293 mg, 1.0 mmol) in dioxane (10 mL). The mixture was heated to 90° C. for 30 minutes under $N_2$. The reaction mixture was concentrated and the residue was purified by prep-HPLC to afford title product as white solid (20 mg, 5%). ESI-MS m/z: 395.1 [M+H]$^+$. $^1$H NMR (300 MHz, DMSO-d6) δ 5.19 (d, J=8.7 Hz, 1H), 7.12-7.31 (m, 3H), 7.31-7.58 (m, 11H), 7.66 (m, 1H), 8.65 (d, J=8.7 Hz, 1H), 10.83-11.08 (m, 1H).

Example 85

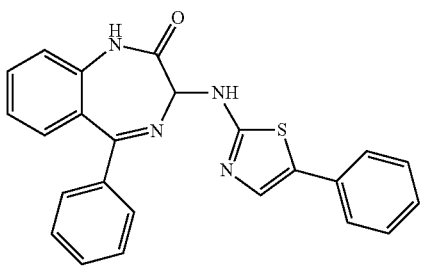 [SMILES: O=C1Nc2ccccc2C(c2ccccc2)=NC1Nc1ncc(-c2ccccc2)s1]

Example 85 Step a

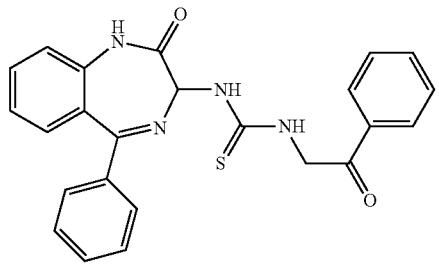 [SMILES: O=C(CNC(=S)NC1N=C(c2ccccc2)c2ccccc2NC1=O)c1ccccc1]

A solution of (Z)-3-amino-5-phenyl-1H-benzo[e][1,4]diazepin-2(3H)-one (251 mg, 1.0 mmol) in DMF (5 mL) was added di(1H-imidazol-1-yl)methanethione (214 mg, 1.2 mmol) at 0° C. After stirring for 30 minutes, 2-amino-1-phenylethanone as the HCl salt (342 mg, 2.0 mmol) and TEA (303 mg, 3.0 mmol) were added. The mixture was stirred at room temperature for 30 minutes, then it was purified by reverse phase C18 column chromatography (MeCN:H$_2$O) to afford product as yellow solid (180 mg, 42%). ESI-MS m/z: 429.3 [M+H]$^+$.

Example 85 Step b

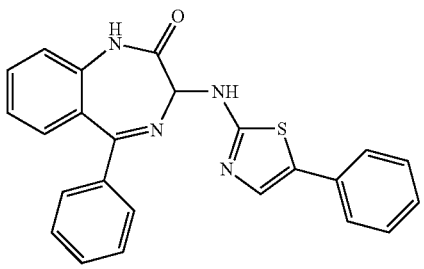 [SMILES: O=C1Nc2ccccc2C(c2ccccc2)=NC1Nc1ncc(-c2ccccc2)s1]

A solution of the compound from step a (80 mg, 0.18 mmol) in 5 mL DCM was added 50 mg $H_2SO_4$ (98%) at 0° C. After stirring for 30 minutes, it was diluted with DCM and washed with water, dried (Na$_2$SO$_4$), concentrated, and purified by prep-HPLC to afford title product as white solid (35 mg, 46%). ESI-MS m/z: 411.2 [M+H]$^+$. $^1$H NMR (300 MHz, DMSO-d$_6$) δ 5.37 (d, J=8.0 Hz, 1H), 7.10-7.59 (m, 14H), 7.66 (m, 1H), 8.94 (d, J=8.0 Hz, 1H), 10.90 (s, 1H).

Example 86

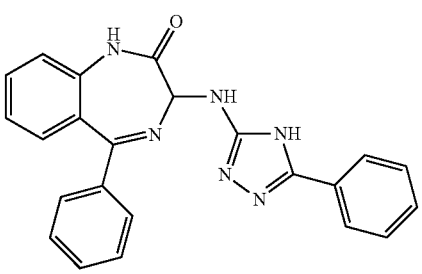 [SMILES: O=C1Nc2ccccc2C(c2ccccc2)=NC1Nc1nnc(-c2ccccc2)[nH]1]

Example 86 Step a

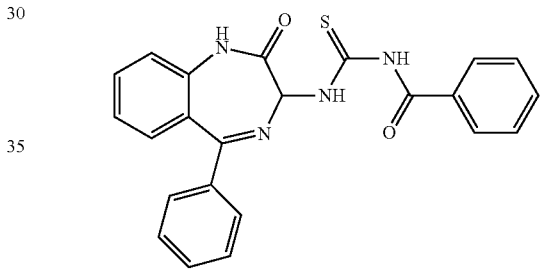

A solution of (Z)-3-amino-5-phenyl-1H-benzo[e][1,4]diazepin-2(3H)-one (200 mg, 0.80 mmol), benzoyl isothiocyanate (0.11 mL, 0.80 mmol) in DCM (10 mL) was stirred for 2 hours at room temperature. The reaction mixture was concentrated and the resulting residue was purified by column chromatography (silica, petroleum ether:EtOAc) to give the desired compound as a yellow solid (390 mg, 100%). ESI-MS m/z: 415.2 [M+H]$^+$.

Example 86 Step b

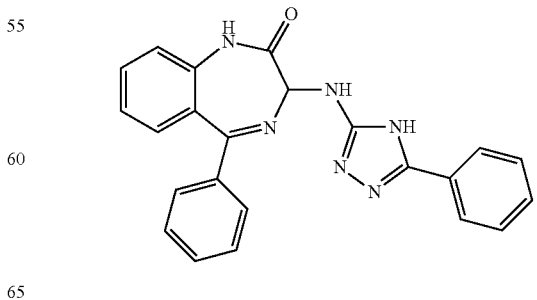

A solution of the compound from step a (300 mg, 0.73 mmol) and NH$_2$NH$_2$.H$_2$O (0.1 mL) in EtOH (5 mL) was stirred for 3 hours at 60° C. The reaction mixture was concentrated, diluted with water, extracted with EtOAc (×4), dried (Na$_2$SO$_4$), and concentrated. The crude product was purified by prep-HPLC to give the title compound as a pink solid (30 mg, 10%). ESI-MS m/z: 395.3 [M+H]$^+$. $^1$H NMR (300 MHz, DMSO-d$_6$) δ 5.20 (d, J=8.8 Hz, 1H), 7.21-7.72 (m, 13H), 7.78-7.88 (m, 2H), 8.37 (s, 0.185H), 10.94 (s, 1H).

Example 87

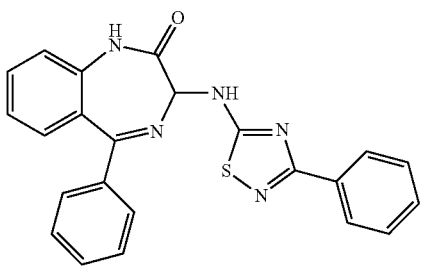 [SMILES: O=C1Nc2ccccc2C(c2ccccc2)=NC1Nc1nc(-c2ccccc2)ns1]

To a 20 mL vial was placed (Z)-3-amino-5-phenyl-1H-benzo[e][1,4]diazepin-2(3H)-one (141 mg, 0.56 mmol), 5-chloro-3-phenyl-1,2,4-thiadiazole (100 mg, 0.51 mmol), and TEA (0.14 mL, 1.02 mmol) in DMF (2.5 mL) and the resulting mixture was heated to 70° C. overnight. The mixture was diluted with EtOAc, washed with water and brine, dried (Na$_2$SO$_4$), concentrated, and purified via column chromatography (silica, hexanes:EtOAc) to give the title compound (35 mg, 15%) as an off-white solid. ESI-MS m/z: 412.1 [M+H]$^+$.

Example 88

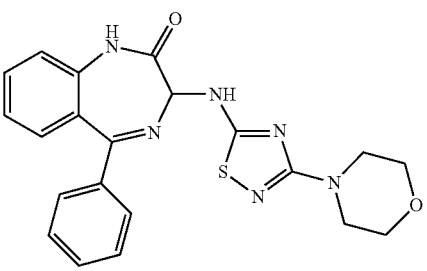 [SMILES: O=C1Nc2ccccc2C(c2ccccc2)=NC1Nc1nc(N2CCOCC2)ns1]

Example 88 Step a

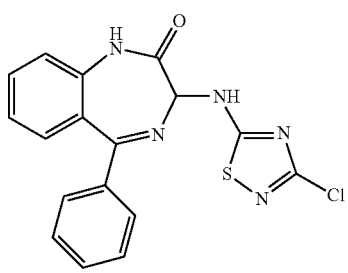 [SMILES: O=C1Nc2ccccc2C(c2ccccc2)=NC1Nc1nc(Cl)ns1]

To a 20 mL vial was placed (Z)-3-amino-5-phenyl-1H-benzo[e][1,4]diazepin-2(3H)-one (324 mg, 1.29 mmol), 3,5-dichloro-1,2,4-thiadiazole (200 mg, 1.29 mmol), and Et$_3$N (0.36 mL, 2.58 mmol) in DMF (5 mL) and the resulting mixture was heated to 40° C. for 5 h. The mixture was diluted with EtOAc, washed with water and brine, dried (Na$_2$SO$_4$), concentrated, and purified via column chromatography (silica, hexanes: EtOAc) to give the title compound (190 mg, 40%) as a yellow solid. ESI-MS m/z: 370.0 [M+H]$^+$.

Example 88 Step b

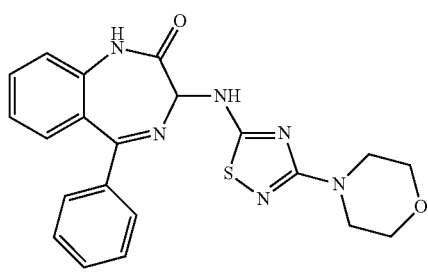 [SMILES: O=C1Nc2ccccc2C(c2ccccc2)=NC1Nc1nc(N2CCOCC2)ns1]

To a 20 mL vial was placed the compound from step a (35 mg, 0.10 mmol) and morpholine (0.16 mL, 1.9 mmol) in dioxane (0.75 mL) and the resulting mixture was heated to 80° C. for 16 h. The mixture was diluted with EtOAc, washed with water and brine, dried (Na$_2$SO$_4$), concentrated, and purified via column chromatography (silica, hexanes: EtOAc) to give the title compound (17 mg, 43%) as a yellow solid. ESI-MS m/z: 421.1 [M+H]$^+$.

Example 89

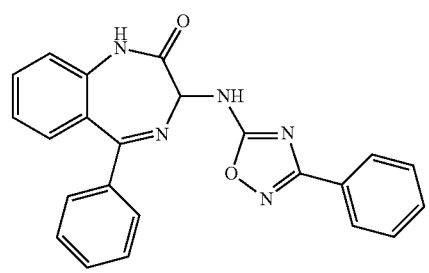 [SMILES: O=C1Nc2ccccc2C(c2ccccc2)=NC1Nc1nc(-c2ccccc2)no1]

Example 89 was prepared using a procedure similar to that used to prepare Example 87 where 5-chloro-3-phenyl-1,2,4-oxadiazole was used in place of 5-chloro-3-phenyl-1,2,4-thiadiazole. ESI-MS m/z: 396.1 [M+H]$^+$.

Example 90

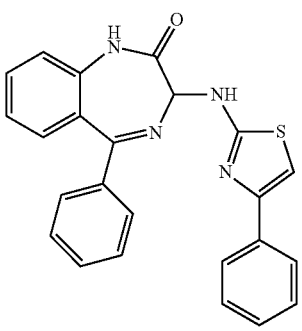 [SMILES: O=C1Nc2ccccc2C(c2ccccc2)=NC1Nc1nc(-c2ccccc2)cs1]

Example 90 Step a

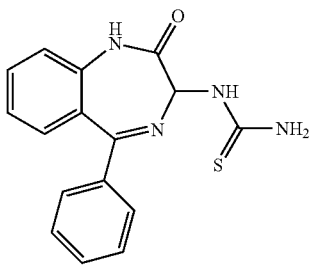 [SMILES: NC(=S)NC1N=C(c2ccccc2)c2ccccc2NC1=O]

Solid di(1H-imidazol-1-yl)methanethione (196 mg, 1.1 mmol) was added to (Z)-3-amino-5-phenyl-1H-benzo[e][1,4]diazepin-2(3H)-one (251 mg, 1.0 mmol) in DMF (30 mL). The mixture was stirred for 1 h at room temperature. Solid NH$_4$C$_1$ (1.6 g, 30 mmol) and TEA (5.1 g, 50 mmol) were added to the mixture and stirred for 3 h at room temperature. The reaction mixture was poured into water, and extracted with EtOAc (×3). The organic layer was dried (Na$_2$SO$_4$) and concentrated to give crude product as a brown solid (250 mg, 81%) that was used without further purification. ESI-MS m/z: 311.0 [M+H]$^+$.

Example 90 Step b

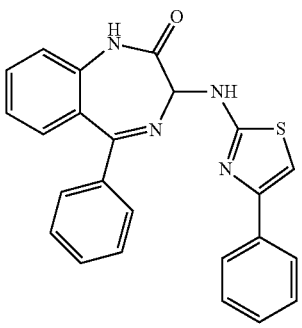 [SMILES: O=C1Nc2ccccc2C(c2ccccc2)=NC1Nc1nc(-c2ccccc2)cs1]

A solution of compound from step a (248 mg, 0.8 mmol) was added to 2-bromo-1-phenylethanone (158 mg, 0.8 mmol) and AcOK (94 mg, 0.96 mmol) in EtOH (20 mL). The mixture was stirred for 1 h at 80° C., then it was poured into water. The mixture was extracted with EtOAc (×3), and the organic layer was dried (Na$_2$SO$_4$), concentrated, and the resulting residue was purified by reverse phase C18 column chromatography (MeCN:H$_2$O) to give title compound as a light yellow solid (142 mg, 43%). ESI-MS m/z: 411.0 [M+H]$^+$. $^1$H NMR (300 MHz, DMSO-d6) δ 5.40 (d, J=7.7 Hz, 1H), 7.10-7.60 (m, 12H), 7.63-7.75 (m, 3H), 8.74 (d, J=7.8 Hz, 1H), 10.95 (s, 1H).

Example 91

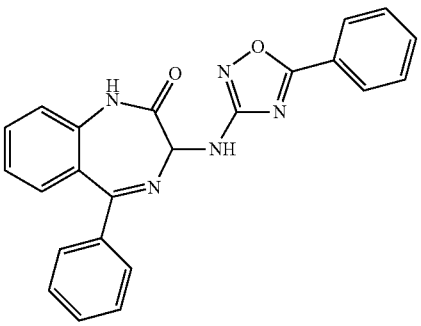 [SMILES: O=C1Nc2ccccc2C(c2ccccc2)=NC1Nc1noc(-c2ccccc2)n1]

Example 91 Step a

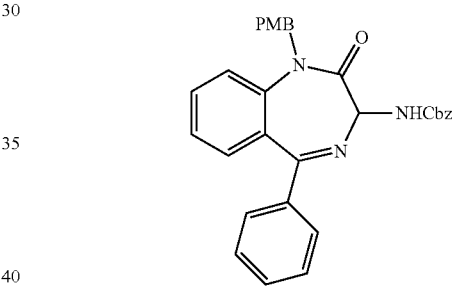

A solution of (Z)-benzyl 2-oxo-5-phenyl-2,3-dihydro-1H-benzo[e][1,4]diazepin-3-ylcarbamate (6.0 g, 7.8 mmol; from Example 1 step c), PMBCl (3.7 g, 23.4 mmol) and K$_2$CO$_3$ (4.3 g, 31.2 mmol) in DMF (100 mL) was heated to 50° C. overnight. The solution was poured into water and extracted with EtOAc. The organic layer was dried (Na$_2$SO$_4$), concentrated, and it was purified by column chromatography (silica, petroleum ether:EtOAc) to give the desired product (5.0 g, 64%) as yellow solid. ESI-MS m/z: 506.4 [M+H]$^+$.

Example 91 Step b

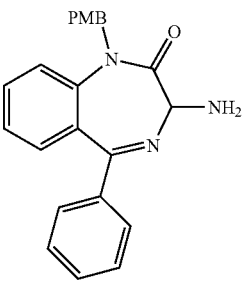

A solution of the compound from step a (5.8 g, 11.5 mmol) in 48% HBr/AcOH (50 mL) was heated to 70° C. for 30 minutes. Ether was added to the solution and the resulting solid was collected by filtration. The collected solid was added to the saturated NaHCO₃, and was extracted with EtOAc. The organic layer was dried (Na₂SO₄), concentrated and the residue was purified by column chromatography (silica, DCM:MeOH) to give 3-amino-1-(4-methoxybenzyl)-5-phenyl-1,3-dihydro-2H-benzo[e][1,4]diazepin-2-one (2.4 g, 56%) as yellow foam. ESI-MS m/z: 372.2 [M+H]⁺.

Example 91 Step c

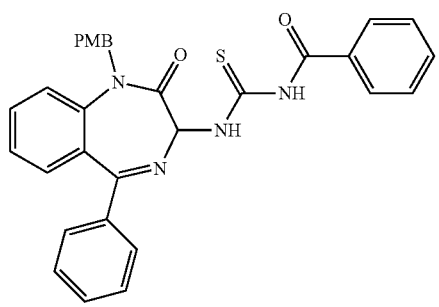

A solution of (Z)-3-amino-1-(4-methoxybenzyl)-5-phenyl-1H-benzo[e][1,4]diazepin-2(3H)-one, from step b, (185 mg, 0.5 mmol) and benzoyl isothiocyanate (82 mg, 0.5 mmol) in DCM (20 mL) was stirred at room temperature for 2 h. The reaction mixture was concentrated and purified by reverse phase C18 column chromatography (MeCN:H₂O) to obtain desired product as yellow solid (155 mg, 58%). ESI-MS m/z: 535.3 [M+H]⁺.

Example 91 Step d

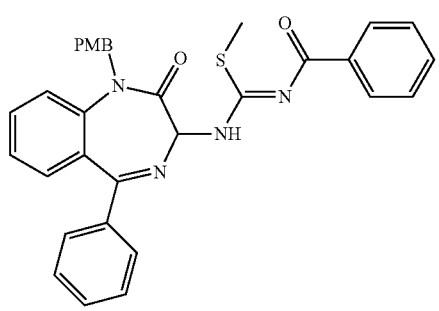

Solid NaH (15 mg, 0.58 mmol) was added to the compound from step c (155 mg, 0.29 mmol) in THF (20 ml) at 0° C. After stirring for 30 minutes, neat MeI (82 mg, 0.58 mmol) was added. The mixture was stirred at room temperature for 3 h. The solvent was removed and the residue was used directly in the next step. ESI-MS m/z: 549.3 [M+H]⁺.

Example 91 Step e

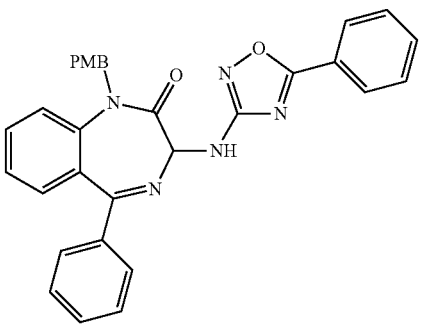

The crude compound from step d was dissolved in ethanol (5 mL). Hydroxylamine hydrochloride (40 mg, 0.58 mmol) was added and the mixture was heated at 75° C. for 3 h. The resulting mixture was concentrated under vacuum and water was added. The resulting precipitate was filtered off to give the desired compound (100 mg, 67%) as a light yellow solid. ESI-MS m/z: 516.4 [M+H]⁺.

Example 91 Step f

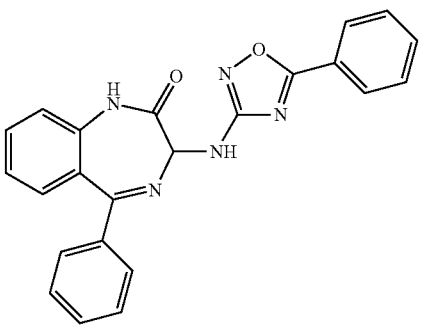 [SMILES: O=C1Nc2ccccc2C(c2ccccc2)=NC1Nc1noc(-c2ccccc2)n1]

To the compound from step e (100 mg, 0.19 mmol) in MeCN (10 mL) and water (10 mL) was added CAN (153 mg, 0.28 mmol). The resulting solution was stirred at room temperature for 4 h. The solution was diluted with 20 mL of EtOAc, washed with water, dried (Na₂SO₄), concentrated and purified by prep-HPLC to obtain the title product as a white solid (27 mg, 19%). ESI-MS m/z: 396.3 [M+H]⁺. ¹H NMR (300 MHz, DMSO-d₆): δ 5.06 (d, J=8.7 Hz, 1H), 7.20-7.80 (m, 12H), 7.93-8.14 (m, 3H), 10.96 (s, 1H).

Example 92

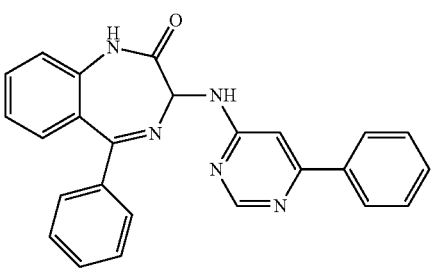 [SMILES: O=C1Nc2ccccc2C(c2ccccc2)=NC1Nc1cc(-c2ccccc2)ncn1]

Example 92 Step a

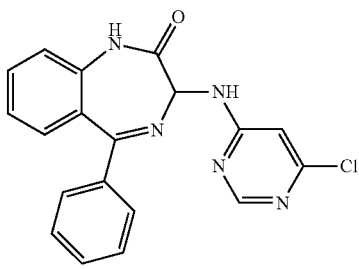 [SMILES: O=C1Nc2ccccc2C(c2ccccc2)=NC1Nc1cc(Cl)ncn1]

To a solution of Z)-3-amino-5-phenyl-1H-benzo[e][1,4]diazepin-2(3H)-one (1.0 g, 4.0 mmol) in PrOH (60 mL) was added to 4,6-dichloropyrimidine (1.2 g, 2.0 mmol) and DIPEA (1.3 g, 2.5 mmol). The mixture was stirred for 18 h at 90° C. The reaction was concentrated and the residue was triturated with Et$_2$O (20 mL) and H$_2$O (3 mL), and dried under vacuum to give desired compound as a white solid (800 mg, 55%). ESI-MS m/z: 364.2 [M+H]$^+$.

Example 92 Step b

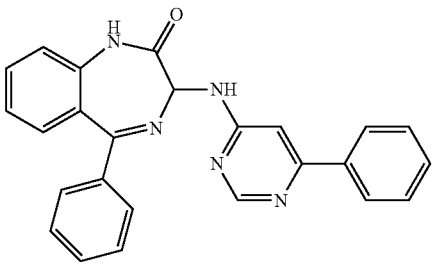 [SMILES: O=C1Nc2ccccc2C(c2ccccc2)=NC1Nc1cc(-c2ccccc2)ncn1]

To a solution of compound from step a (109 mg, 0.30 mmol) in dioxane (4 mL) and H$_2$O (1 mL) was added to phenylboronic acid (73.2 mg, 0.60 mmol), Pd(dtbpf)Cl$_2$ (20 mg, 0.03 mmol) and KF (174 mg, 3.0 mmol). The mixture was heated to 100° C. in the microwave for 1 h. The reaction mixture was purified directly by reverse phase C18 column chromatography (MeCN:H$_2$O) to give desired compound as a white solid (22 mg, 18%). ESI-MS m/z: 406.1 [M+H]$^+$. $^1$H NMR (300 MHz, DMSO-d$_6$) δ 5.65 (d, J=7.6 Hz, 1H), 7.23-7.61 (m, 12H), 7.68 (m, 1H), 7.96-8.11 (m, 2H), 8.47 (d, J=1.1 Hz, 1H), 8.57 (s, 1H), 10.90-10.97 (m, 1H).

Example 93

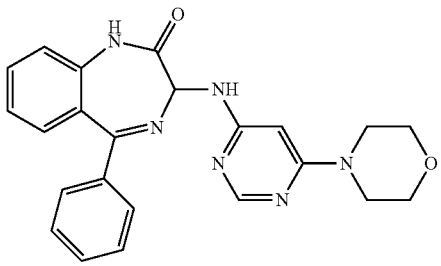 [SMILES: O=C1Nc2ccccc2C(c2ccccc2)=NC1Nc1cc(N2CCOCC2)ncn1]

To a solution of the compound from Example 92 step a (182 mg, 0.5 mmol) in DMF (5 mL) was added K$_2$CO$_3$ (138 mg, 1.0 mmol) and morpholine (2 mL). The mixture was heated to 140° C. for 1 h in the microwave, then it was poured into water and extracted with EtOAc (×3). The organic layer was dried (Na$_2$SO$_4$), concentrated, and purified by reverse phase C18 column chromatography (MeCN:H$_2$O) to give the title compound as white solid (63 mg, 30%). ESI-MS m/z: 415.1 [M+H]$^+$. $^1$H NMR (300 MHz, DMSO-d$_6$) δ 3.43 (m, 4H), 3.68 (dd, J=5.8, 3.9 Hz, 4H), 5.59 (d, J=8.1 Hz, 1H), 6.05-6.12 (m, 1H), 7.20-7.60 (m, 8H), 7.66 (m, 1H), 7.78 (s, 1H), 7.97 (s, 1H), 10.86 (s, 1H).

Example 94

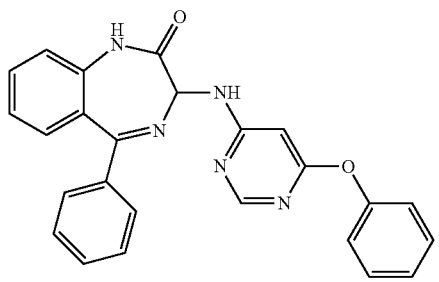 [SMILES: O=C1Nc2ccccc2C(c2ccccc2)=NC1Nc1cc(Oc2ccccc2)ncn1]

To a solution of the compound from Example 92 step a (182 mg, 0.5 mmol) in DMF (6 mL) was added K$_2$CO$_3$ (414 mg, 3.0 mmol) and phenol (282 mg, 3.0 mmol). The mixture was heated for 3 h at 130° C. in the microwave. The reaction mixture was purified directly by reverse phase C18 column chromatography (MeCN:H$_2$O) to give desired compound as a white solid (20 mg, 10%). ESI-MS m/z: 415.1 [M+H]$^+$. $^1$H NMR (300 MHz, DMSO-d$_6$) δ 5.56 (s, 1H), 6.26 (s, 1H), 7.10-7.37 (m, 6H), 7.37-7.57 (m, 7H), 7.64 (m, 1H), 8.07 (s, 1H), 8.52 (s, 1H), 10.86 (s, 1H).

Example 95

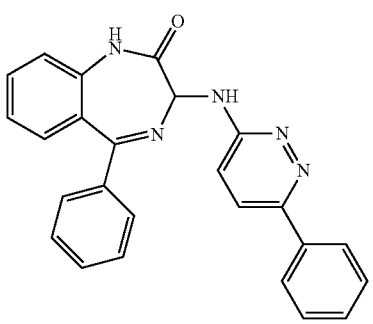 [SMILES: O=C1Nc2ccccc2C(c2ccccc2)=NC1Nc1ccc(-c2ccccc2)nn1]

Example 95 Step a

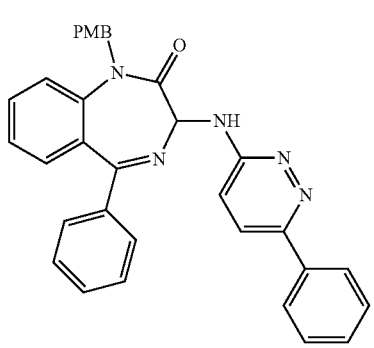

A solution of 3-amino-1-(4-methoxybenzyl)-5-phenyl-1,3-dihydro-2H-benzo[e][1,4]diazepin-2-one, from Example 91 step b, (500 mg, 1.35 mmol), 3-chloro-6-phenylpyridazine (257 mg, 1.35 mmol), Brettphos (72 mg, 0.14 mmol) and $K_2CO_3$ (372 mg, 2.70 mmol) in t-BuOH (5 mL) were stirred under nitrogen for 30 minutes at room temperature before 3rd Generation Brettphos precatalyst (122 mg, 0.14 mmol) was added. The reaction was stirred for 12 hours at 90° C. The mixture was diluted with EtOAc, washed with water (×2), dried ($Na_2SO_4$), concentrated and purified by reverse phase C18 column chromatography (MeCN:$H_2O$) to give desired compound as light yellow solid (100 mg, 14%). ESI-MS m/z: 526.4 [M+H]$^+$.

Example 95 Step b

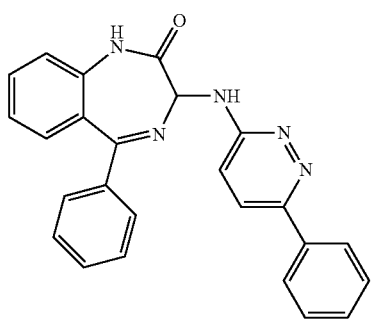 [SMILES: O=C1Nc2ccccc2C(c2ccccc2)=NC1Nc1ccc(-c2ccccc2)nn1]

To a solution of the compound from step a (87 mg, 0.17 mmol) in anisole (5 mL) was added $AlCl_3$ (220 mg, 1.65 mmol) and the mixture was stirred for 3 hours at 70° C. The reaction mixture was purified directly by prep-HPLC to give the title compound as a white solid (31 mg, 47%). ESI-MS m/z: 406.3 [M+H]$^+$. $^1$H NMR (300 MHz, DMSO-$d_6$) 5.69 (d, J=7.7 Hz, 1H), 7.25-7.70 (m, 13H), 7.91-7.98 (m, 3H), 8.12 (d, J=7.7 Hz, 1H), 10.92 (s, 1H).

Example 96

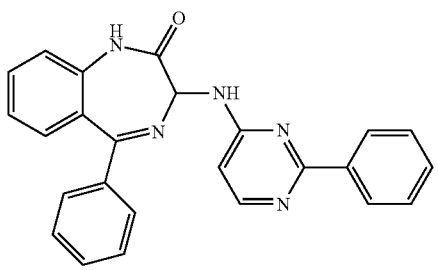 [SMILES: O=C1Nc2ccccc2C(c2ccccc2)=NC1Nc1ccnc(-c2ccccc2)n1]

Example 96 Step a

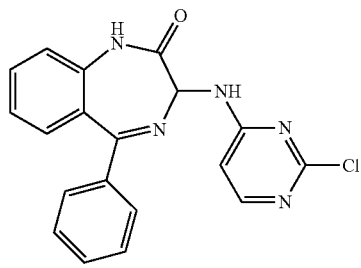 [SMILES: O=C1Nc2ccccc2C(c2ccccc2)=NC1Nc1ccnc(Cl)n1]

A solution of Z)-3-amino-5-phenyl-1H-benzo[e][1,4]diazepin-2(3H)-one (500 mg, 2.0 mmol), 2,4-dichloropyrimidine (600 mg, 4.0 mmol), DIEA (1.5 ml, 9.0 mmol) in $^i$PrOH (60 mL) were heated to 90° C. overnight. The reaction mixture was cooled to room temperature, diluted with DCM, and washed with water (×2). The organic layer was dried ($Na_2SO_4$), concentrated, and purified by reverse phase C18 column chromatography (MeCN:$H_2O$) to give desired compound as a beige solid (530 mg, 41%). ESI-MS m/z: 364.1 [M+H]$^+$.

Example 96 Step b

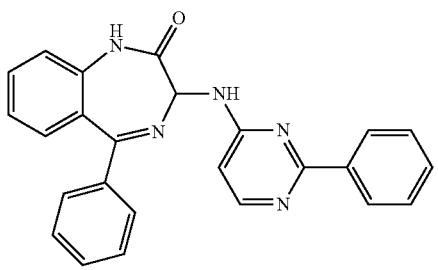 [SMILES: O=C1Nc2ccccc2C(c2ccccc2)=NC1Nc1ccnc(-c2ccccc2)n1]

A solution of the compound from step a (200 mg, 0.55 mmol), phenylboronic acid (300 mg, 2.46 mmol), Pd(dtbpf)Cl$_2$ (80 mg, 0.06 mmol), KF (500 mg, 8.2 mmol), in $H_2O$ (1 mL) and 1.4-dioxane (5 mL) was heated to 100° C. in the microwave for 1.5 hours. The reaction mixture was purified by prep-HPLC to give the title compound as a white solid (26 mg, 11%). ESI-MS m/z: 406.2 [M+H]$^+$. $^1$H NMR (300 MHz, Methanol-$d_4$) δ 5.80 (s, 1H), 6.79 (s, 1H), 7.28-7.58

(m, 21H), 7.70 (ddd, J=8.4, 7.2, 1.6 Hz, 2H), 8.11 (d, J=7.6 Hz, 3H), 8.25 (d, J=6.1 Hz, 2H).

Example 97

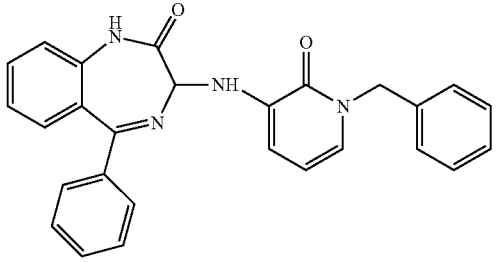 [SMILES: O=C1Nc2ccccc2C(c2ccccc2)=NC1Nc1cccn(Cc2ccccc2)c1=O]

Example 97 Step a

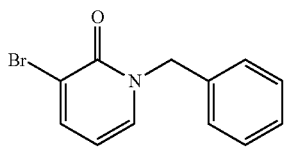 [SMILES: O=c1c(Br)cccn1Cc1ccccc1]

A solution of 3-bromo-2-hydroxypyridine (2.0 g, 12 mmol), benzyl bromide (1.9 g, 12 mmol), and K$_2$CO$_3$ (4.9 g, 36 mmol) in DMF (100 mL) was stirred for 3 hour at rt. The reaction mixture was diluted with water and extracted with EtOAc (×3). The organic layer was dried (Na$_2$SO$_4$), concentrated, and purified by column chromatography (silica, petroleum ether:EtOAc) to give desired compound as yellow oil (3 g, 95%). ESI-MS m/z: 264.1 [M+H]$^+$.

Example 97 Step b

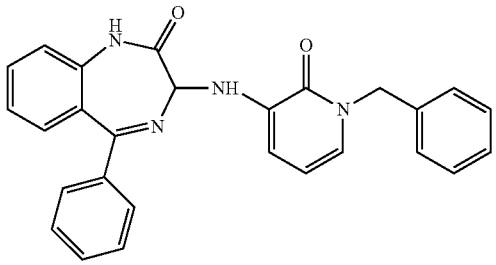 [SMILES: O=C1Nc2ccccc2C(c2ccccc2)=NC1Nc1cccn(Cc2ccccc2)c1=O]

A solution of the compound from step a (87 mg, 0.33 mmol), Z)-3-amino-5-phenyl-1H-benzo[e][1,4]diazepin-2(3H)-one (100 mg, 0.40 mmol), Pd(OAc)$_2$ (11 mg, 0.05 mmol), and CsCO$_3$ (220 mg, 0.66 mmol) in DMF (5 mL) was stirred for 5 h at 120° C. The mixture was purified directly by prep-HPLC to give the title compound as a white solid (5 mg, 4%). ESI-MS m/z: 435.3 [M+H]$^+$. $^1$H NMR (300 MHz, DMSO-d$_6$) δ 11.08 (s, 1H), 8.48 (s, 1H), 7.64 (m, 1H), 7.56-7.21 (m, 14H), 7.12 (dd, J=5.9, 2.6 Hz, 1H), 6.58 (d, J=6.9 Hz, 1H), 6.20-6.07 (m, 2H), 5.17 (s, 2H), 4.91 (d, J=6.9 Hz, 1H).

Example 98

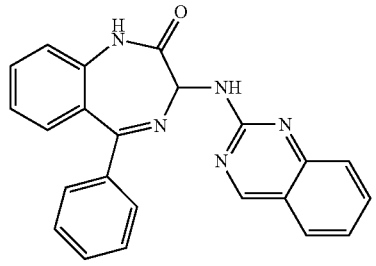 [SMILES: O=C1Nc2ccccc2C(c2ccccc2)=NC1Nc1ncc2ccccc2n1]

To a solution of Z)-3-amino-5-phenyl-1H-benzo[e][1,4]diazepin-2(3H)-one (502 mg, 2.0 mmol) in $^i$PrOH (20 mL) was added 2-chloroquinazoline (164 mg, 1.0 mmol) and TsOH (1.0 mmol). The mixture was stirred for 24 h at 80° C. The reaction mixture was concentrated and purified by prep-HPLC to give desired compound as white solid (17 mg, 4%). ESI-MS m/z: 445.1 [M+H]$^+$. $^1$H NMR (300 MHz, DMSO-d$_6$) δ 5.63 (d, J=7.9 Hz, 1H), 7.24-7.59 (m, 10H), 7.59-7.80 (m, 3H), 7.87 (d, J=8.0 Hz, 1H), 8.48 (s, 1H), 9.23 (s, 1H), 10.92 (s, 1H).

Example 99

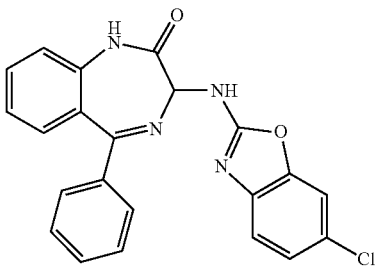 [SMILES: O=C1Nc2ccccc2C(c2ccccc2)=NC1Nc1nc2ccc(Cl)cc2o1]

To a solution of Z)-3-amino-5-phenyl-1H-benzo[e][1,4]diazepin-2(3H)-one (502 mg, 2.0 mmol) in DMF (8 mL) was added 2,6-dichlorobenzo[d]oxazole (449 mg, 2.4 mmol) and TEA (404 mg, 2 mmol). The mixture was stirred at 60° C. for 1 h, then poured into water. The mixture was extracted with EtOAc (×3), the organic layer was dried (Na$_2$SO$_4$) and concentrated. The residue was purified by prep-HPLC to give desired compound as white solid (500 mg, 62%). ESI-MS m/z: 403.2 [M+H]$^+$. 1H NMR (300 MHz, DMSO-d6) δ 5.31 (d, J=8.3 Hz, 1H), 7.12-7.76 (m, 12H), 9.50 (d, J=8.3 Hz, 1H), 10.98 (s, 1H).

Example 100

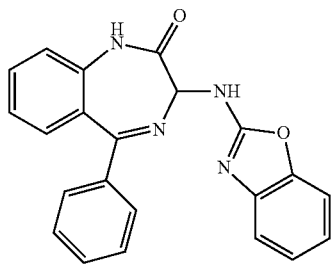 [SMILES: O=C1Nc2ccccc2C(c2ccccc2)=NC1Nc1nc2ccccc2o1]

Example 100 was prepared using a procedure similar to that used to prepare Example 99 where 2-chlorobenzo[d]oxazole was used in place of 2,6-dichlorobenzo[d]oxazole. ESI-MS m/z: 369.1 [M+H]$^+$.

Example 101

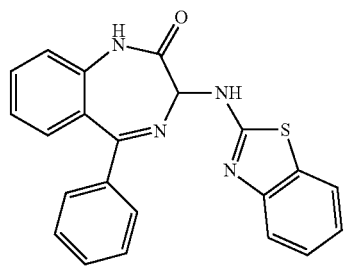 [SMILES: O=C1Nc2ccccc2C(c2ccccc2)=NC1Nc1nc2ccccc2s1]

To a solution of Z)-3-amino-5-phenyl-1H-benzo[e][1,4]diazepin-2(3H)-one (50 mg, 0.2 mmol) in DMSO (1 mL) was added to 1-iodo-2-isothiocyanatobenzene (46 mg, 0.3 mmol), ″Bu$_4$NBr (91 mg, 0.3 mmol), and CuBr (7 mg, 0.05 mmol) and the resulting mixture was stirred at 60° C. for 2 h. The reaction mixture was purified by prep-HPLC to give desired compound as light yellow solid (12 mg, 17%). ESI-MS m/z: 385.2 [M+H]$^+$. $^1$H NMR (300 MHz, DMSO-d$_6$) δ 5.52 (d, J=7.9 Hz, 1H), 7.05 (m, 1H), 7.14-7.61 (m, 10H), 7.64-7.77 (m, 2H), 9.26 (d, J=7.9 Hz, 1H), 10.96 (s, 1H).

Example 102

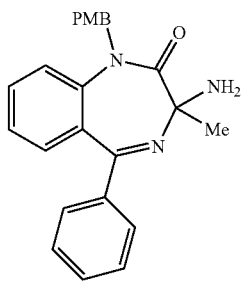

Example 102 Step a

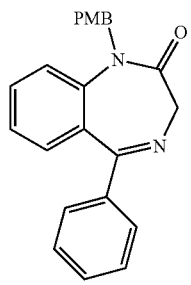

To a 100 mL round-bottomed flask were added 5-phenyl-1,3-dihydro-2H-benzo[e][1,4]diazepin-2-one (1.05 g, 4.4 mmol) and DMF (40 mL) and cooled to 0° C. The reaction mixture was treated with NaH 60% in oil (213 mg, 5.3 mmol), stirred for 20 min., allowed to warm to room temperature, treated with PMB-Cl (0.72 mL, 5.3 mmol) and stirred for 3.5 hrs. The reaction was cooled to 0° C., quenched by addition of sat. NH$_4$C$_1$ sol'n (10 mL), diluted with ethyl acetate-MTBE (100 mL) and filtered. The filtrate was washed with H$_2$O (3×30 mL) and brine. Dried over Na$_2$SO$_4$, filtered and evaporated to dryness. The residue was purified by column chromatography (silica, hexanes:EtOAc) to give the title compound (1.262 g) as a colorless solid. ESI MS m/z=357.16 [M+H]$^+$.

Example 102 Step b

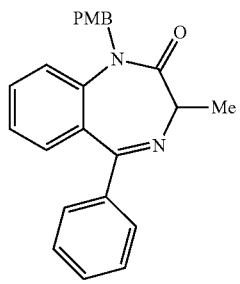

To a 25 mL round-bottomed flask were added the compound from step a (0.569 g, 1.0 equiv., 1.6 mmol) and THF (8 mL) and cooled to −65° C. The reaction mixture was treated with t-BuOK (1.68 mL, 1M in THF, 1.7 mmol) and stirred for 30 min. Methyl iodide (0.109 mL, 1.8 mmol) in THF (2 mL) was added to the reaction via cannular, slowly allowed to warm to 2° C. for 1.5 hour and stirred at room temperature for 15 min. The reaction was cooled to 0° C., quenched by addition of sat. NH$_4$C$_1$ sol'n (2 mL), diluted with ethyl acetate, washed with H$_2$O and brine. Dried over Na$_2$SO$_4$, filtered and evaporated to dryness. The residue was purified by column chromatography (silica, hexanes:acetone) to give the title compound (519.6 mg) as a colorless solid. ESI MS m/z=371.17 [M+H]$^+$.

Example 102 Step c

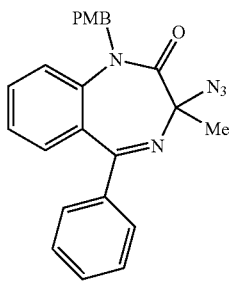

To a 25 mL round-bottomed flask were added the compound from step b (0.1 g, 1.0 equiv., 0.27 mmol), DME (6 mL)-THF (1 mL), HMPA (0.28 mL, 1.62 mmol) and cooled to −40° C. The reaction mixture was treated with KHMDS (mL, 0.5M in toluene, 1.08 mmol) and stirred for 100 min. Then, trisyl azide (570 mg, 1.84 mmol) in THF (1.5 mL) was added to the reaction via cannular and stirred for 2 hours.

The reaction mixture was treated with AcOH (0.28 mL, 4.86 mmol) and slowly allowed to warm to room temperature for 100 min. Then, the reaction was diluted with ethyl acetate, washed with sat. NaHCO$_3$ sol'n, H$_2$O and brine. Dried over Na$_2$SO$_4$, filtered and evaporated to dryness. The residue was purified by column chromatography (silica, hexanes:acetone) to give the title compound as a colorless solid (~60% purity). ESI MS m/z=412.17 [M+H]$^+$.

Example 102 Step d

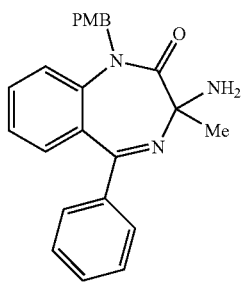

To a mixture of the compound from step c (62 mg, 60% purity) and H$_2$O (1 drop) in THF (0.9 mL) was added PPh$_3$ (200 mg, 0.76 mmol), heated at 60° C. for 2 hours and evaporated to dryness. The residue was purified by column chromatography (silica, DCM:MeOH) to give the title compound (14 mg) as a colorless solid. ESI MS m/z=386.19 [M+H]$^+$.

Example 103

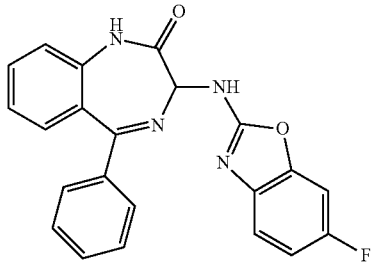 [SMILES: O=C1Nc2ccccc2C(c2ccccc2)=NC1Nc1nc2ccc(F)cc2o1]

Example 103 was prepared using a procedure similar to that used to prepare Example 99 where 2-chloro-6-fluorobenzo[d]oxazole was used in place of 2,6-dichlorobenzo[d]oxazole. ESI-MS m/z: 387.1 [M+1-1]$^+$.

Example 104

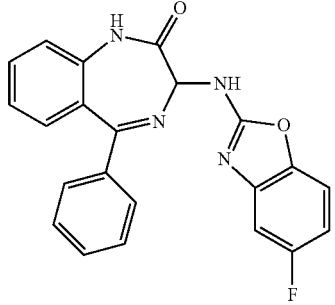 [SMILES: O=C1Nc2ccccc2C(c2ccccc2)=NC1Nc1nc2cc(F)ccc2o1]

Example 104 was prepared using a procedure similar to that used to prepare Example 99 where 2-chloro-5-fluorobenzo[d]oxazole was used in place of 2,6-dichlorobenzo[d]oxazole. ESI-MS m/z: 387.1 [M+1-1]$^+$.

Example 105

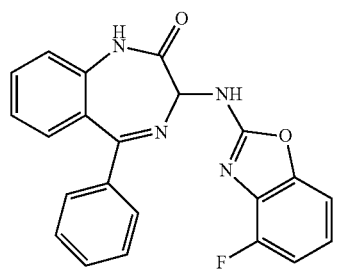 [SMILES: O=C1Nc2ccccc2C(c2ccccc2)=NC1Nc1nc2c(F)cccc2o1]

Example 105 was prepared using a procedure similar to that used to prepare Example 99 where 2-chloro-4-fluorobenzo[d]oxazole was used in place of 2,6-dichlorobenzo[d]oxazole. ESI-MS m/z: 387.1 [M+1-1]$^+$.

Example 106

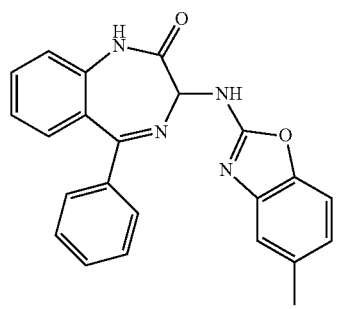 [SMILES: Cc1ccc2oc(NC3N=C(c4ccccc4)c4ccccc4NC3=O)nc2c1]

Example 106 was prepared using a procedure similar to that used to prepare Example 99 where 2-chloro-5-methylbenzo[d]oxazole was used in place of 2,6-dichlorobenzo[d]oxazole. ESI-MS m/z: 383.1 [M+H]$^+$.

Example 107

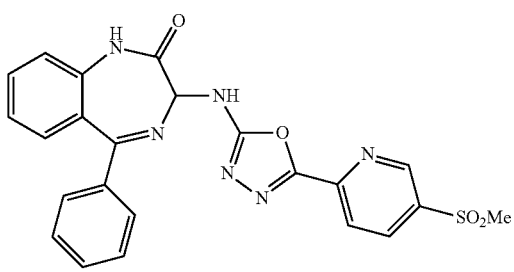

Example 107 was prepared using a procedure similar to that used to prepare Example 20 where 5-(methylsulfonyl)picolinic acid was used in place of 5-chlorofuran-2-carboxylic acid. ESI-MS m/z: 475.3 [M+H]$^+$. $^1$H NMR (300 MHz, DMSO-d$_6$) δ 3.41 (s, 3H), 5.23 (d, J=6.3 Hz, 1H), 7.26-7.42 (m, 2H), 7.43-7.59 (m, 6H), 7.70 (td, J=7.7, 7.0, 1.8 Hz, 1H), 8.25 (d, J=8.4 Hz, 1H), 8.49 (dd, J=8.4, 2.4 Hz, 1H), 9.19 (d, J=2.1 Hz, 1H), 9.59 (s, 1H), 11.04 (s, 1H).

Example 108

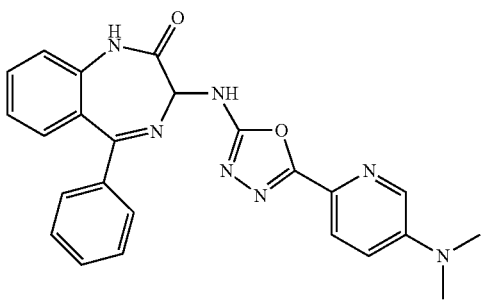 [SMILES: CN(C)c1ccc(-c2nnc(NC3N=C(c4ccccc4)c4ccccc4NC3=O)o2)nc1]

Example 108 was prepared using a procedure similar to that used to prepare Example 20 where 5-(dimethylamino)picolinic acid was used in place of 5-chlorofuran-2-carboxylic acid. ESI-MS m/z: 440.3 [M+H]⁺. ¹H NMR (300 MHz, DMSO-d₆) δ 3.02 (s, 6H), 5.14 (d, J=8.6 Hz, 1H), 7.18 (m, 1H), 7.23-7.39 (m, 3H), 7.42-7.57 (m, 5H), 7.62-7.79 (m, 2H), 8.16 (d, J=3.0 Hz, 1H), 9.03 (d, J=8.7 Hz, 1H), 10.98 (s, 1H).

Example 109

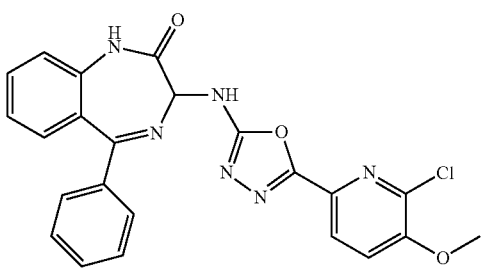 [SMILES: COc1ccc(-c2nnc(NC3N=C(c4ccccc4)c4ccccc4NC3=O)o2)nc1Cl]

Example 109 was prepared using a procedure similar to that used to prepare Example 20 where 6-chloro-5-methoxypicolinic acid was used in place of 5-chlorofuran-2-carboxylic acid. ESI-MS m/z: 461.3 [M+H]⁺. ¹H NMR (300 MHz, DMSO-d₆) δ 3.97 (s, 3H), 5.16 (d, J=8.5 Hz, 1H), 7.22-7.40 (m, 3H), 7.42-7.57 (m, 5H), 7.61-7.79 (m, 2H), 7.98 (d, J=8.5 Hz, 1H), 9.27 (d, J=8.5 Hz, 1H), 10.99 (s, 1H).

Example 110

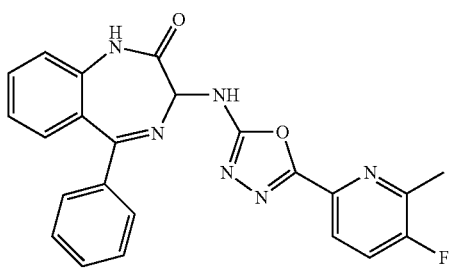 [SMILES: Cc1nc(-c2nnc(NC3N=C(c4ccccc4)c4ccccc4NC3=O)o2)ccc1F]

Example 110 was prepared using a procedure similar to that used to prepare Example 20 where 5-fluoro-6-methylpicolinic acid was used in place of 5-chlorofuran-2-carboxylic acid. ESI-MS m/z: 429.2 [M+H]⁺. ¹H NMR (300 MHz, DMSO-d₆) δ 2.50 (s, 3H), 5.17 (d, J=8.5 Hz, 1H), 7.22-7.41 (m, 3H), 7.42-7.59 (m, 5H), 7.67 (ddd, J=8.4, 7.0, 1.8 Hz, 1H), 7.81 (t, J=8.9 Hz, 1H), 7.89 (dd, J=8.6, 3.9 Hz, 1H), 9.28 (d, J=8.5 Hz, 1H), 10.99 (s, 1H).

Example 111

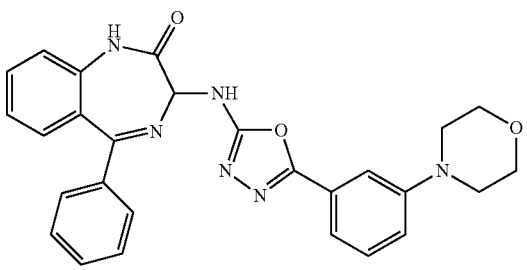 [SMILES: O=C1Nc2ccccc2C(c2ccccc2)=NC1Nc1nnc(-c2cccc(N3CCOCC3)c2)o1]

Example 111 was prepared using a procedure similar to that used to prepare Example 20 where 3-morpholinobenzoic acid was used in place of 5-chlorofuran-2-carboxylic acid. ESI-MS m/z: 481.2 [M+H]⁺. ¹H NMR (300 MHz, DMSO-d₆) δ 3.15 (t, J=4.9 Hz, 4H), 3.75 (dd, J=6.0, 3.6 Hz, 4H), 5.10-5.19 (m, 1H), 7.08-7.73 (m, 14H), 7.82 (s, 1H), 8.99-9.09 (m, 1H), 10.99 (s, 1H).

Example 112

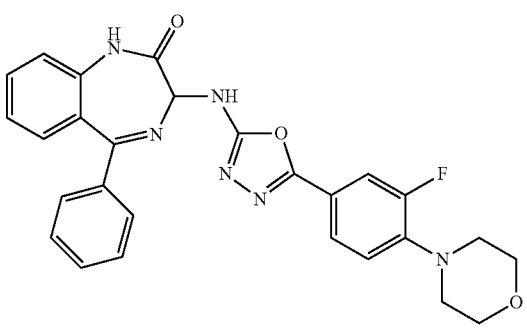 [SMILES: O=C1Nc2ccccc2C(c2ccccc2)=NC1Nc1nnc(-c2ccc(N3CCOCC3)c(F)c2)o1]

Example 112 was prepared using a procedure similar to that used to prepare Example 20 where 3-fluoro-4-morpholinobenzoic acid was used in place of 5-chlorofuran-2-carboxylic acid. ESI-MS m/z: 499.4 [M+H]⁺. ¹H NMR (300 MHz, DMSO-d₆) δ 3.11 (t, J=4.7 Hz, 4H), 3.75 (dd, J=6.0, 3.3 Hz, 4H), 5.10-5.17 (m, 1H), 7.12-7.40 (m, 4H), 7.41-7.73 (m, 8H), 9.07 (d, J=7.8 Hz, 1H), 11.00 (s, 1H).

Example 113

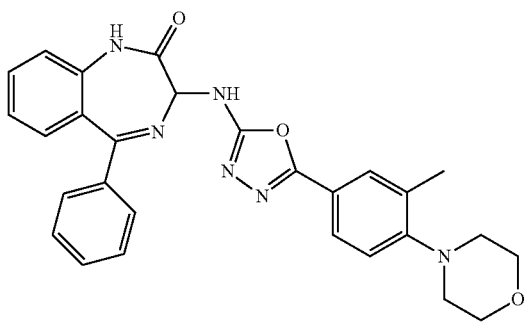 [SMILES: Cc1cc(-c2nnc(NC3N=C(c4ccccc4)c4ccccc4NC3=O)o2)ccc1N1CCOCC1]

Example 113 was prepared using a procedure similar to that used to prepare Example 20 where 3-methyl-4-morpholinobenzoic acid was used in place of 5-chlorofuran-2-carboxylic acid. ESI-MS m/z: 440.3 [M+H]$^+$. $^1$H NMR (400 MHz, DMSO-d$_6$) δ 2.33 (s, 3H), 2.81-2.99 (m, 4H), 3.71-3.84 (m, 4H), 5.15 (d, J=8.6 Hz, 1H), 7.16 (d, J=8.3 Hz, 1H), 7.25-7.39 (m, 3H), 7.43-7.57 (m, 5H), 7.59-7.73 (m, 3H), 9.03 (d, J=8.6 Hz, 1H), 10.99 (s, 1H).

Example 114

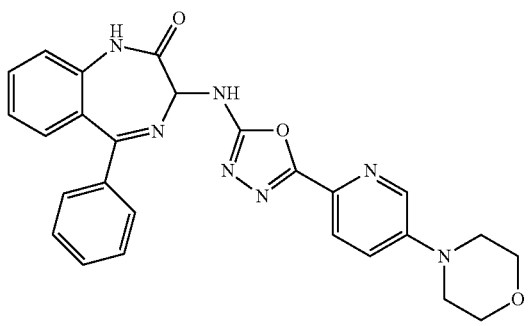 [SMILES: O=C1Nc2ccccc2C(c2ccccc2)=NC1Nc1nnc(-c2ccc(N3CCOCC3)cn2)o1]

Example 114 was prepared using a procedure similar to that used to prepare Example 20 where 5-morpholinopicolinic acid was used in place of 5-chlorofuran-2-carboxylic acid. ESI-MS m/z: 482.2 [M+H]$^+$. $^1$H NMR (300 MHz, DMSO-d$_6$) δ 3.31 (m, 4H), 3.77 (m, 4H), 5.17 (d, J=8.3 Hz, 1H), 7.21-7.87 (m, 11H), 8.41 (d, J=2.9 Hz, 1H), 9.13 (d, J=8.4 Hz, 1H), 11.01 (s, 1H).

Example 115

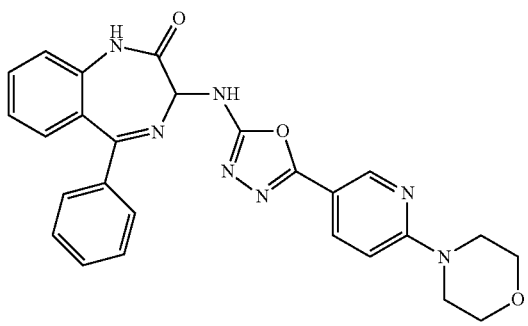 [SMILES: O=C1Nc2ccccc2C(c2ccccc2)=NC1Nc1nnc(-c2ccc(N3CCOCC3)nc2)o1]

Example 115 was prepared using a procedure similar to that used to prepare Example 20 where 6-morpholinonicotinic acid was used in place of 5-chlorofuran-2-carboxylic acid. ESI-MS m/z: 482.4[M+H]$^+$. $^1$H NMR (300 MHz, DMSO-d$_6$) δ 3.52-3.60 (m, 4H), 3.70 (dd, J=5.8, 3.8 Hz, 4H), 5.13 (d, J=8.5 Hz, 1H), 6.98 (d, J=9.1 Hz, 1H), 7.22-7.38 (m, 3H), 7.41-7.57 (m, 5H), 7.66 (ddd, J=8.5, 7.0, 1.7 Hz, 1H), 7.90 (dd, J=9.0, 2.4 Hz, 1H), 8.44-8.58 (m, 1H), 8.98 (d, J=8.6 Hz, 1H), 10.98 (s, 1H).

Example 116

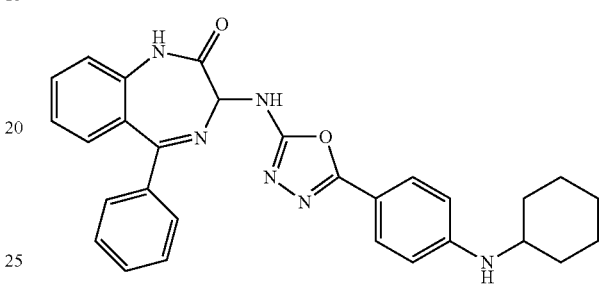

Example 116 was prepared using a procedure similar to that used to prepare Example 20 where 4-(cyclohexylamino)benzoic acid was used in place of 5-chlorofuran-2-carboxylic acid. ESI-MS m/z: 493.4[M+H]$^+$. $^1$H NMR (300 MHz, DMSO-d$_6$) δ 1.48-1.05 (m, 5H), 1.60 (d, J=12.5 Hz, 1H), 1.84-1.65 (m, 2H), 1.92 (d, J=12.0 Hz, 2H), 3.20 (m, 1H), 5.11 (d, J=8.7 Hz, 1H), 6.14 (d, J=7.8 Hz, 1H), 6.72-6.50 (m, 2H), 7.38-7.22 (m, 3H), 7.56-7.41 (m, 7H), 7.66 (m, 1H), 8.79 (d, J=8.8 Hz, 1H), 10.95 (s, 1H).

Example 117

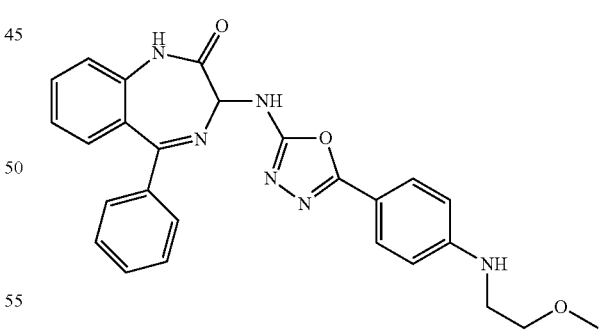

Example 117 was prepared using a procedure similar to that used to prepare Example 20 where 4-((2-methoxyethyl)amino)benzoic acid was used in place of 5-chlorofuran-2-carboxylic acid. ESI-MS m/z: 469.0 [M+H]$^+$. $^1$H NMR (300 MHz, DMSO-d$_6$) δ 3.27 (d, J=6.8 Hz, 5H), 3.49 (t, J=5.6 Hz, 2H), 5.11 (d, J=8.7 Hz, 1H), 6.34 (t, J=5.6 Hz, 1H), 6.75-6.60 (m, 1H), 7.40-7.20 (m, 3H), 7.58-7.40 (m, 7H), 7.66 (ddd, J=8.6, 7.0, 1.7 Hz, 1H), 8.83 (d, J=8.8 Hz, 1H), 10.98 (s, 1H).

Example 118

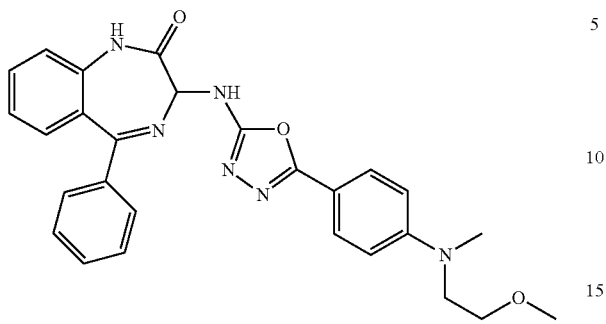

Example 118 was prepared using a procedure similar to that used to prepare Example 20 where 4-((2-methoxyethyl)(methyl)amino)benzoic acid was used in place of 5-chlorofuran-2-carboxylic acid. ESI-MS m/z: 483.4 [M+H]$^+$. $^1$H NMR (300 MHz, DMSO-d$_6$) δ 2.98 (s, 3H), 3.25 (s, 3H), 3.64-3.43 (m, 4H), 5.12 (d, J=8.7 Hz, 1H), 6.89-6.63 (m, 2H), 7.39-7.20 (m, 3H), 7.56-7.39 (m, 5H), 7.72-7.55 (m, 3H), 8.86 (d, J=8.7 Hz, 1H), 10.97 (s, 1H).

Example 119

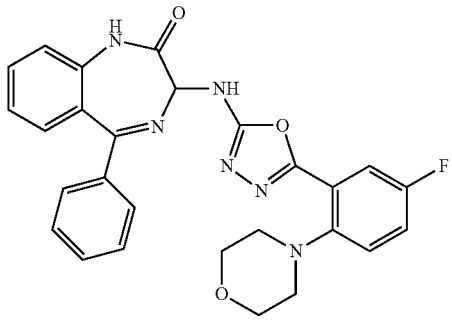 [SMILES: O=C1Nc2ccccc2C(c2ccccc2)=NC1Nc1nnc(-c2cc(F)ccc2N2CCOCC2)o1]

Example 119 was prepared using a procedure similar to that used to prepare Example 20 where 5-fluoro-2-morpholinobenzoic acid was used in place of 5-chlorofuran-2-carboxylic acid. ESI-MS m/z: 499.0 [M+H]$^+$. $^1$H NMR (300 MHz, DMSO-d$_6$) δ 2.75-2.97 (m, 4H), 3.56-3.84 (m, 4H), 5.17 (d, J=8.6 Hz, 1H), 7.19-7.41 (m, 5H), 7.42-7.57 (m, 6H), 7.67 (ddd, J=8.4, 7.0, 1.7 Hz, 1H), 9.17 (d, J=8.6 Hz, 1H), 10.99 (s, 1H).

Example 120

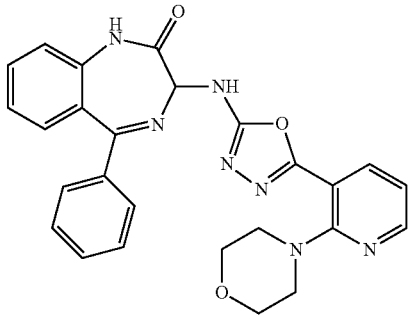 [SMILES: O=C1Nc2ccccc2C(c2ccccc2)=NC1Nc1nnc(-c2cccnc2N2CCOCC2)o1]

Example 120 was prepared using a procedure similar to that used to prepare Example 20 where 2-morpholinonicotinic acid was used in place of 5-chlorofuran-2-carboxylic acid. ESI-MS m/z: 482.3 [M+H]$^+$. $^1$H NMR (300 MHz, DMSO-d$_6$) δ 3.07-3.20 (m, 4H), 3.68 (m, 4H), 5.15 (d, J=8.6 Hz, 1H), 7.04 (dd, J=7.6, 4.8 Hz, 1H), 7.24-7.38 (m, 3H), 7.41-7.60 (m, 5H), 7.67 (ddd, J=8.5, 7.1, 1.8 Hz, 1H), 7.96 (dd, J=7.6, 1.9 Hz, 1H), 8.35 (dd, J=4.8, 1.9 Hz, 1H), 9.16 (d, J=8.6 Hz, 1H), 10.98 (s, 1H).

Example 121

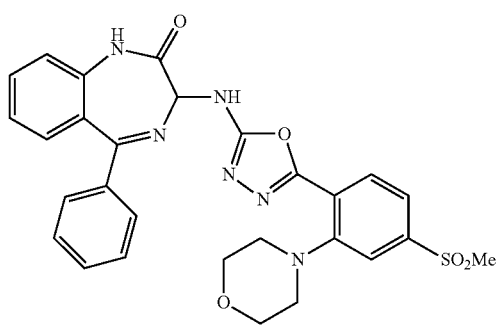 [SMILES: CS(=O)(=O)c1ccc(-c2nnc(NC3N=C(c4ccccc4)c4ccccc4NC3=O)o2)c(N2CCOCC2)c1]

Example 121 was prepared using a procedure similar to that used to prepare Example 20 where 4-(methylsulfonyl)-2-morpholinobenzoic acid was used in place of 5-chlorofuran-2-carboxylic acid. ESI-MS m/z: 559.4 [M+H]$^+$. $^1$H NMR (300 MHz, DMSO-d$_6$) δ 2.86-3.07 (m, 4H), 3.27 (s, 3H), 3.72 (t, J=4.7 Hz, 4H), 5.18 (d, J=8.3 Hz, 1H), 7.24-7.39 (m, 3H), 7.42-7.71 (m, 8H), 7.92 (d, J=8.1 Hz, 1H), 9.31 (d, J=8.5 Hz, 1H), 11.00 (s, 1H).

Example 122

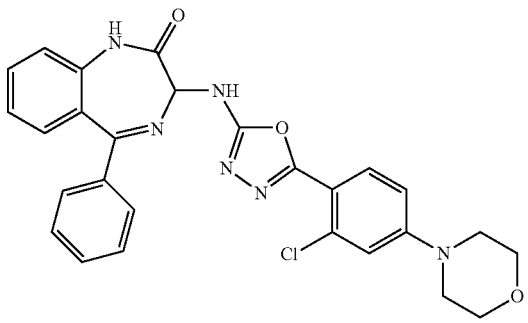 [SMILES: O=C1Nc2ccccc2C(c2ccccc2)=NC1Nc1nnc(-c2ccc(N3CCOCC3)cc2Cl)o1]

Example 122 was prepared using a procedure similar to that used to prepare Example 20 where 2-chloro-4-morpholinobenzoic acid was used in place of 5-chlorofuran-2-carboxylic acid. ESI-MS m/z: 515.5 [M+H]$^+$. $^1$H NMR (300 MHz, DMSO-d$_6$) δ 3.72 (t, J=4.8 Hz, 4H), 5.14 (d, J=8.5 Hz, 1H), 6.99-7.16 (m, 2H), 7.19-7.60 (m, 8H), 7.58-7.79 (m, 2H), 9.01 (d, J=8.5 Hz, 1H), 10.98 (s, 1H).

Example 123

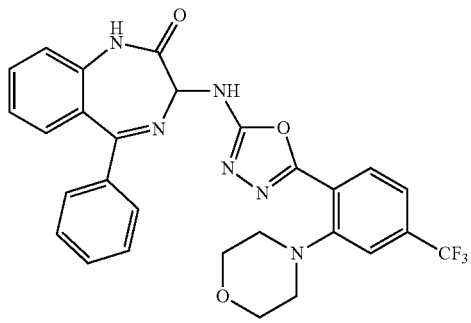 [SMILES: O=C1Nc2ccccc2C(c2ccccc2)=NC1Nc1nnc(-c2ccc(C(F)(F)F)cc2N2CCOCC2)o1]

Example 123 was prepared using a procedure similar to that used to prepare Example 20 where 2-morpholino-4-(trifluoromethyl)benzoic acid was used in place of 5-chlorofuran-2-carboxylic acid. ESI-MS m/z: 549.2 [M+H]$^+$. $^1$H NMR (300 MHz, DMSO-d$_6$) δ 2.97 (s, 3H), 5.18 (d, J=8.3 Hz, 1H), 7.13-7.82 (m, 11H), 8.22 (d, J=1.9 Hz, 1H), 9.47 (d, J=8.4 Hz, 1H), 11.00 (s, 1H).

Example 124

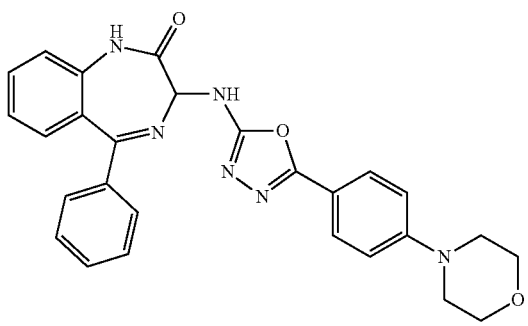 [SMILES: O=C1Nc2ccccc2C(c2ccccc2)=NC1Nc1nnc(-c2ccc(N3CCOCC3)cc2)o1]

Example 124 was prepared using a procedure similar to that used to prepare Example 20 where 4-morpholinobenzoic acid was used in place of 5-chlorofuran-2-carboxylic acid. ESI-MS m/z: 481.2 [M+H]$^+$. $^1$H NMR (400 MHz, DMSO-d$_6$) δ 3.22-3.24 (m, 4H), 3.73-3.75 (m, 4H), 5.12-5.14 (d, J=8.0 Hz, 1H), 7.06-7.08 (m, 2H), 7.26-7.29 (m, 1H), 7.33-7.36 (m, 2H), 7.44-7.49 (m, 5H), 7.51-7.77 (m, 1H), 8.93-8.95 (d, J=8.0 Hz, 1H) 10.98 (s, 1H).

Example 124a

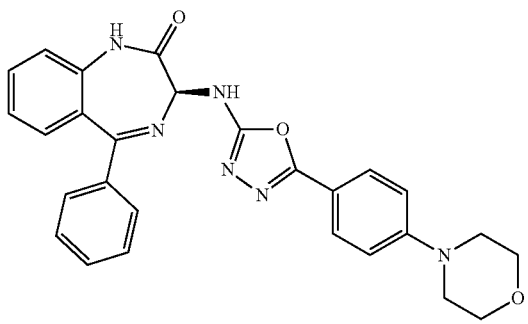 [SMILES: O=C1Nc2ccccc2C(c2ccccc2)=N[C@@H]1Nc1nnc(-c2ccc(N3CCOCC3)cc2)o1]

Example 124a was separated from racemic Example 7 using a Chiralpak IC2*25 cm, 5 um Chiral-P(IC) 004S90IC0SCJ-QF001 column. ESI-MS m/z: 481.2 [M+H]$^+$.

Example 124b

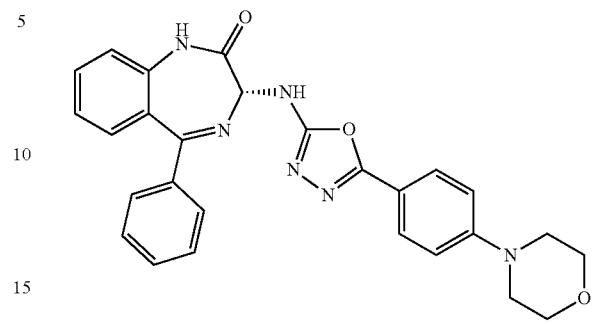

Example 124b was separated from racemic Example 7 using a Chiralpak IC2*25 cm, 5 um Chiral-P(IC) 004S90IC0SCJ-QF001 column. ESI-MS m/z: 481.2 [M+H]$^+$.

Example 125

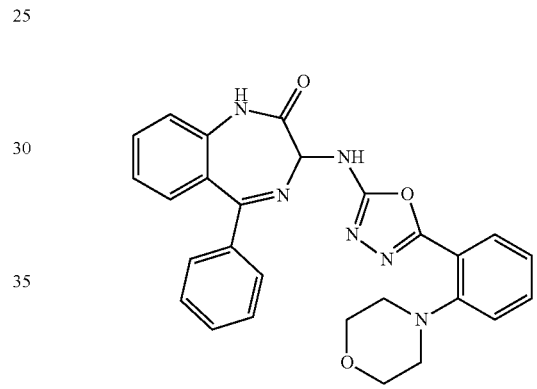

Example 125 was prepared using a procedure similar to that used to prepare Example 20 where 2-morpholinobenzoic acid was used in place of 5-chlorofuran-2-carboxylic acid. ESI-MS m/z: 481.3 [M+H]$^+$. $^1$H NMR (300 MHz, DMSO-d$_6$) δ 2.90 (dd, J=5.7, 3.4 Hz, 4H), 3.71 (t, J=4.6 Hz, 4H), 5.18 (d, J=8.7 Hz, 1H), 7.08-7.24 (m, 2H), 7.24-7.42 (m, 3H), 7.42-7.61 (m, 6H), 7.61-7.83 (m, 2H), 9.10 (d, J=8.8 Hz, 1H), 10.99 (s, 1H).

Example 125a

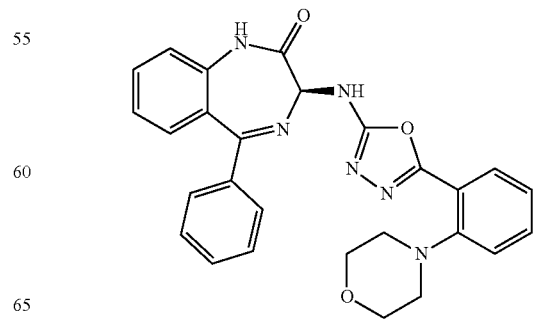

Example 125a was separated from racemic Example 7 using a Chiralpak IC2*25 cm, 5 um Chiral-P(IC) 004S90IC0SCJ-QF001 column. ESI-MS m/z: 481.3 [M+H]⁺.

Example 125b

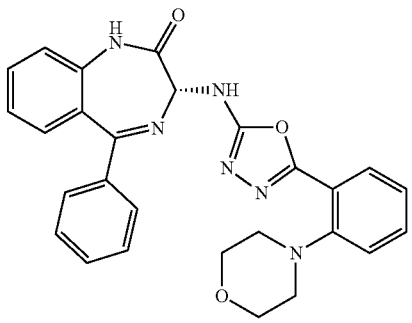 [SMILES: O=C1Nc2ccccc2C(c2ccccc2)=N[C@H]1Nc1nnc(-c2ccccc2N2CCOCC2)o1]

Example 125b was separated from racemic Example 7 using a Chiralpak IC2*25 cm, 5 um Chiral-P(IC) 004S90IC0SCJ-QF001 column. ESI-MS m/z: 481.3 [M+H]⁺.

Example 126

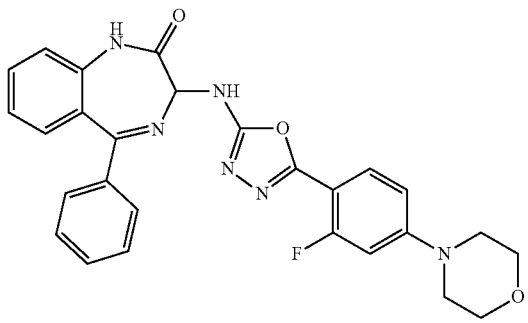 [SMILES: O=C1Nc2ccccc2C(c2ccccc2)=NC1Nc1nnc(-c2ccc(N3CCOCC3)cc2F)o1]

Example 126 was prepared using a procedure similar to that used to prepare Example 20 where 2-fluoro-4-morpholinobenzoic acid was used in place of 5-chlorofuran-2-carboxylic acid. ESI-MS m/z: 499.4 [M+H]⁺. ¹H NMR (400 MHz, DMSO-d₆) δ 2.90 (t, J=4.5 Hz, 4H), 3.69 (td, J=4.2, 2.0 Hz, 4H), 5.16 (d, J=8.7 Hz, 1H), 6.92-7.03 (m, 2H), 7.24-7.39 (m, 3H), 7.42-7.59 (m, 5H), 7.63-7.74 (m, 2H), 9.11 (d, J=8.7 Hz, 1H), 10.98 (s, 1H).

Example 126a

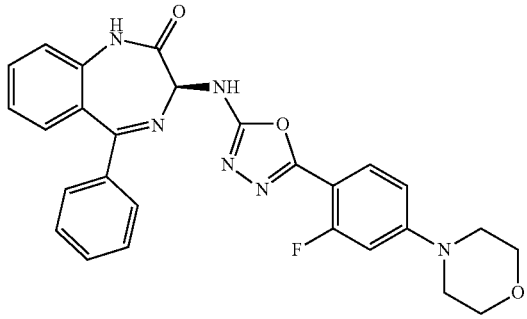 [SMILES: O=C1Nc2ccccc2C(c2ccccc2)=N[C@@H]1Nc1nnc(-c2ccc(N3CCOCC3)cc2F)o1]

Example 126a was separated from racemic Example 7 using a Chiralpak IB-3 100*3 mm, 3 m, column. ESI-MS m/z: 499.2 [M+H]⁺.

Example 126b

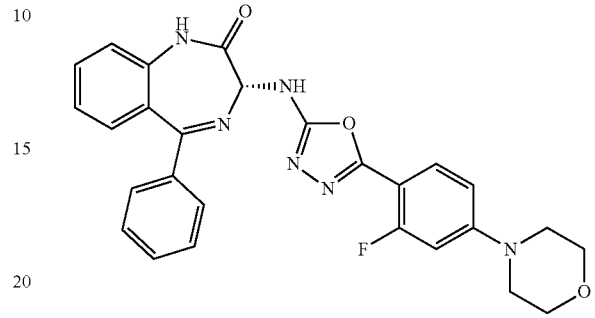

Example 126b was separated from racemic Example 7 using a Chiralpak IB-3 100*3 mm, 3 μm, column. ESI-MS m/z: 499.2 [M+H]⁺.

Example 127

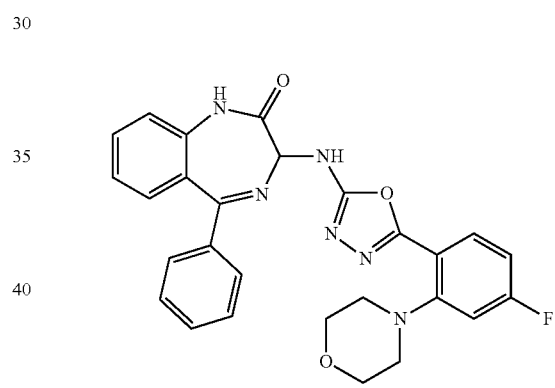

Example 127 Step a

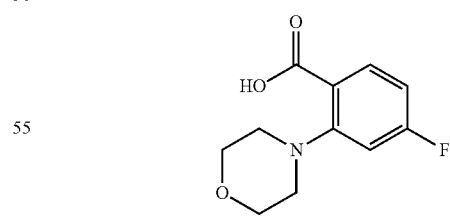

A solution of compound 2-chloro-4-fluorobenzoic acid (5.2 g, 30 mmol), CuI (570 mg, 3 mmol), K₂CO₃ (1.8 g, 90 mmol) and morpholine (10 mL) in DMF (100 mL) was stirred for 2 hours at 90° C. The mixture was concentrated and purified by reverse phase C18 column chromatography (MeCN:H₂O) to give 4-fluoro-2-morpholinobenzoic acid as a white solid (900 mg, 13%). ESI-MS m/z: 226.0 [M+H]⁺.

Example 127 Step b

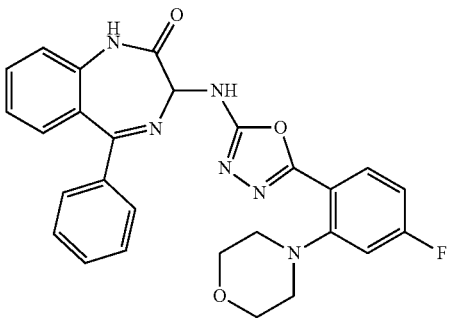 [SMILES: O=C1Nc2ccccc2C(c2ccccc2)=NC1Nc1nnc(-c2ccc(F)cc2N2CCOCC2)o1]

Example 127 was prepared using a procedure similar to that used to prepare Example 20 where 4-fluoro-2-morpholinobenzoic acid was used in place of 5-chlorofuran-2-carboxylic acid. ESI-MS m/z: 499.2 [M+H]$^+$. $^1$H NMR (300 MHz, DMSO-d6) δ 2.92 (d, J=4.6 Hz, 4H), 3.71 (m, 4H), 5.17 (d, J=8.7 Hz, 1H), 6.91-7.06 (m, 2H), 7.23-7.41 (m, 3H), 7.42-7.62 (m, 5H), 7.63-7.77 (m, 2H), 9.13 (d, J=8.8 Hz, 1H), 11.00 (s, 1H).

Example 128

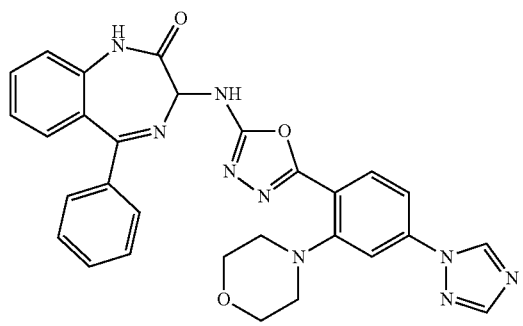 [SMILES: O=C1Nc2ccccc2C(c2ccccc2)=NC1Nc1nnc(-c2ccc(-n3cncn3)cc2N2CCOCC2)o1]

Example 128 Step a

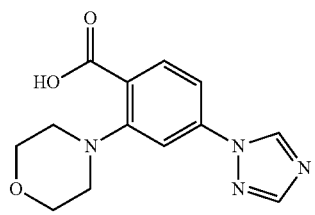 [SMILES: O=C(O)c1ccc(-n2cncn2)cc1N1CCOCC1]

A solution of the 2-chloro-4-(1H-1, 2, 4-triazol-1-yl)benzoic acid (300 mg, 1.34 mmol) in morpholine (5 mL) was stirred at 120° C. for 2 hours. Water (20 mL) was added to the mixture and it was extracted with EtOAc (×3). The organic layer was dried and purified by reverse phase C18 column chromatography to give 2-chloro-4-(1H-1,2,4-triazol-1-yl)benzoic acid as off-white solid (200 mg, 54%). ESI-MS m/z: 275.1 [M+H]$^+$.

Example 128 Step b

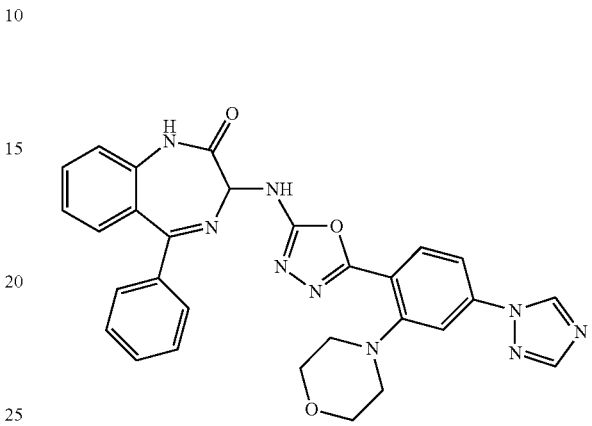

Example 128 was prepared using a procedure similar to that used to prepare Example 20 where 2-chloro-4-(1H-1, 2,4-triazol-1-yl)benzoic acid was used in place of 5-chlorofuran-2-carboxylic acid. ESI-MS m/z: 548.1 [M+H]$^+$. $^1$H NMR (400 MHz, DMSO-d$_6$) δ 2.97-2.99 (m, 4H), 3.74 (s, 4H), 5.16-5.18 (d, J=8.0 Hz, 1H), 7.26-7.28 (m, 1H), 7.30-7.34 (m, 2H), 7.36-7.48 (m, 5H), 7.51-7.53 (m, 3H), 7.54-7.60 (m, 1H), 8.29 (s, 1H), 9.17-9.19 (m, 1H), 9.44 (s, 1H) 10.99 (s, 1H).

Example 129

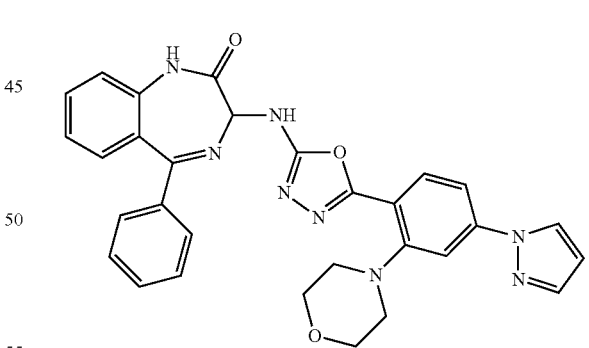

Example 129 was prepared using a procedure similar to that used to prepare Example 20 where 2-morpholino-4-(1H-pyrazol-1-yl)benzoic acid, which was prepared similarly to 2-chloro-4-(1H-1,2,4-triazol-1-yl)benzoic acid from Example 128 step a, was used in place of 5-chlorofuran-2-carboxylic acid. ESI-MS m/z: 547.1 [M+H]$^+$. $^1$H NMR (400 MHz, DMSO-d$_6$) δ 2.96-2.98 (m, 4H), 3.73 (s, 4H), 5.16-5.18 (d, J=8.0 Hz, 1H), 6.59-6.60 (m, 1H), 7.26-7.36 (m, 2H), 7.44-7.48 (m, 2H), 7.51-7.54 (m, 6H), 7.58-7.59 (m, 2H), 7.60-7.69 (m, 1H), 7.77-7.80 (m, 2H), 8.64 (s, 1H), 9.12-9.14 (m, 1H), 9.44 (s, 1H) 10.99 (s, 1H).

Example 130

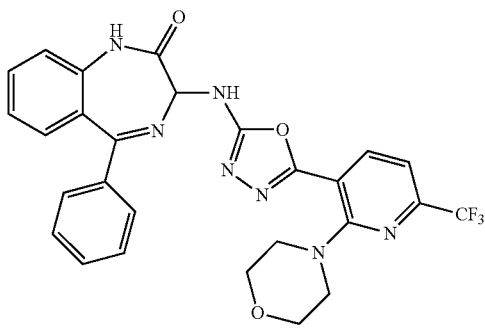 [SMILES: O=C1Nc2ccccc2C(c2ccccc2)=NC1Nc1nnc(-c2ccc(C(F)(F)F)nc2N2CCOCC2)o1]

Example 130 was prepared using a procedure similar to that used to prepare Example 20 where 2-morpholino-6-(trifluoromethyl)nicotinic acid, which was prepared similarly to 2-chloro-4-(1H-1,2,4-triazol-1-yl)benzoic acid from Example 128 step a, was used in place of 5-chlorofuran-2-carboxylic acid. ESI-MS m/z: 550.1 [M+H]$^+$. $^1$H NMR (400 MHz, DMSO-d$_6$) δ 3.18-3.22 (m, 4H), 3.66-3.72 (m, 4H), 5.16-5.18 (d, J=8.0 Hz, 1H), 7.26-7.28 (m, 1H), 7.30-7.34 (m, 2H), 7.36-7.48 (m, 6H), 7.50-7.70 (m, 1H), 8.18-8.20 (m, 1H), 9.33-9.35 (d, J=8.0 Hz, 1H), 11.01 (s, 1H).

Example 131

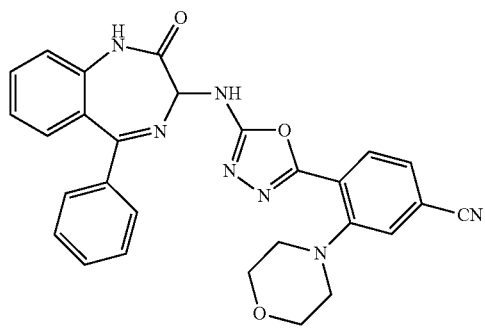 [SMILES: N#Cc1ccc(-c2nnc(NC3N=C(c4ccccc4)c4ccccc4NC3=O)o2)c(N2CCOCC2)c1]

Example 131 was prepared using a procedure similar to that used to prepare Example 20 where 4-cyano-2-morpholinobenzoic acid, which was prepared similarly to 2-chloro-4-(1H-1,2,4-triazol-1-yl)benzoic acid from Example 128 step a, was used in place of 5-chlorofuran-2-carboxylic acid. ESI-MS m/z: 506.2 [M+H]$^+$. $^1$H NMR (400 MHz, DMSO-d$_6$) δ 2.92-2.94 (m, 4H), 3.71-3.75 (m, 4H), 5.17-5.19 (d, J=8.0 Hz, 1H), 7.26-7.28 (m, 1H), 7.30-7.34 (m, 2H), 7.35-7.48 (m, 7H), 7.50-7.59 (m, 1H), 7.65-7.69 (m, 1H), 9.29-9.31 (d, J=8.0 Hz, 1H), 10.99 (s, 1H).

Example 132

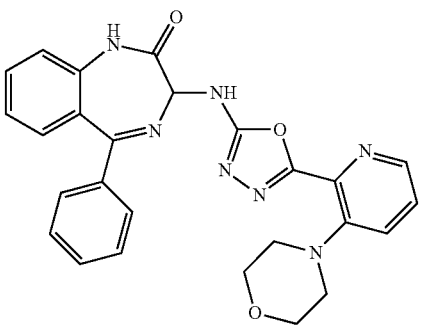 [SMILES: O=C1Nc2ccccc2C(c2ccccc2)=NC1Nc1nnc(-c2ncccc2N2CCOCC2)o1]

Example 132 Step a

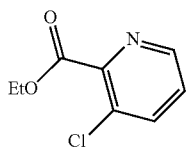

A solution of 3-chloropicolinic acid (1 g, 6.37 mmol) and H$_2$SO$_4$ (1 mL) in EtOH (20 mL) was refluxed for 3 hours. It was concentrated and purified by reverse phase C18 column chromatography (MeCN/H$_2$O) to give ethyl 3-chloropicolinate as a yellow oil (0.85 g, 72%). ESI-MS m/z: 186.0 [M+H]$^+$.

Example 132 Step b

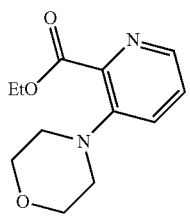

A solution of ethyl 3-chloropicolinate (400 mg, 2.16 mmol) in morpholine (neat) (2 ml) was stirred overnight at 120° C. It was concentrated under vacuum and the crude product was purified by prep-TLC(PE/EtOAc=2/1) to give ethyl 3-morpholinopicolinate a yellow solid (0.17 g, 35%). ESI-MS m/z: 237.1 [M+H]$^+$.

Example 132 Step c

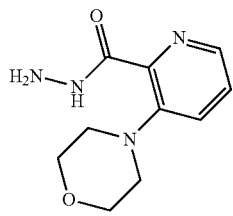 [SMILES: NNC(=O)c1ncccc1N1CCOCC1]

A solution of ethyl 3-morpholinopicolinate (0.17 g, 0.72 mmol) and NH$_2$NH$_2$.H$_2$O (1 mL) in EtOH (10 mL) was refluxed overnight. The crude product was purified by reverse phase C18 column chromatography (MeCN/H$_2$O) to give 3-morpholinopicolinohydrazide as a yellow oil (0.11 g, 80%). ESI-MS m/z: 223.1 [M+H]$^+$.

Example 132 Step d

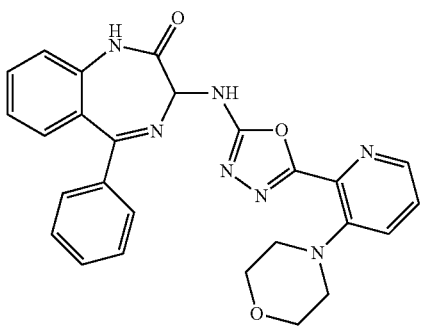 [SMILES: O=C1Nc2ccccc2C(c2ccccc2)=NC1Nc1nnc(-c2ncccc2N2CCOCC2)o1]

Example 132 was prepared using a procedure similar to that used to prepare Example 21 where 3-morpholinopicolinohydrazide was used in place of tetrahydro-2H-pyran-4-carbohydrazide. ESI-MS m/z: 482.5 [M+H]$^+$. $^1$H NMR (400 MHz, DMSO-d$_6$) δ 2.87-3.08 (m, 4H), 3.71 (dd, J=5.7, 3.2 Hz, 4H), 5.20 (d, J=8.5 Hz, 1H), 7.24-7.42 (m, 3H), 7.43-7.61 (m, 6H), 7.62-7.75 (m, 2H), 8.35 (dd, J=4.5, 1.3 Hz, 1H), 9.21 (d, J=8.6 Hz, 1H), 11.00 (s, 1H).

Example 133

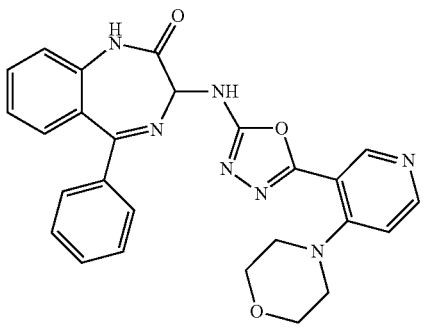 [SMILES: O=C1Nc2ccccc2C(c2ccccc2)=NC1Nc1nnc(-c2cnccc2N2CCOCC2)o1]

Example 133 Step a

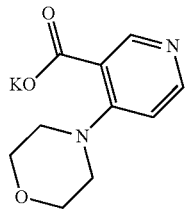

A solution of 4-chloronicotinic acid (1.00 g, 6.0 mmol), morpholine (1.26 g, 14.0 mmol) and K$_2$CO$_3$ (1.33 g, 9.6 mmol) in DMSO (5 mL) was stirred for 12 hours at 120° C. It was diluted with EtOH, the solid was filtered out. The filtrate was concentrated, and it was precipitated by adding MeCN (20 mL) to give 1.06 g (71%) as white solid. ESI-MS m/z: 208.9 [M+H]$^+$.

Example 133 Step b

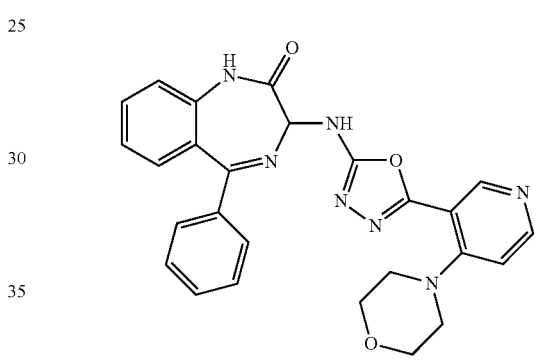

Example 133 was prepared using a procedure similar to that used to prepare Example 20 where potassium 4-morpholinonicotinate was used in place of 5-chlorofuran-2-carboxylic acid. ESI-MS m/z: 482.3 [M+H]$^+$. $^1$H NMR (300 MHz, DMSO-d$_6$) δ 3.03 (s, 4H), 3.69 (s, 4H), 5.15 (d, J=8.7 Hz, 1H), 7.03 (d, J=5.7 Hz, 1H), 7.29 (m, 1H), 7.35 (m, 2H), 7.39-7.62 (m, 5H), 7.67 (m, 1H), 8.42 (d, 1H), 8.56 (s, 1H), 9.18 (d, 1H), 10.99 (s, 1H).

Example 134

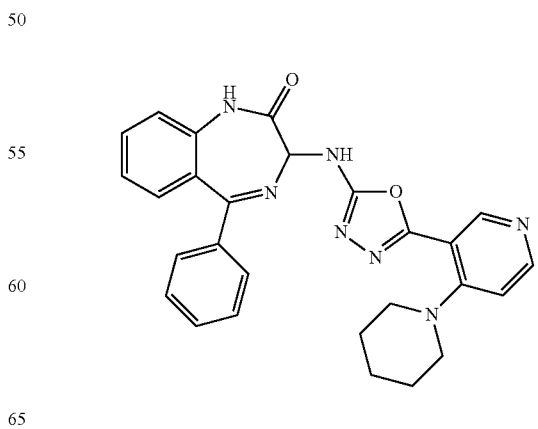

Example 134 was prepared using a procedure similar to that used to prepare Example 20 where potassium 4-(piperidin-1-yl)nicotinate, which was prepared similarly to potassium 4-morpholinonicotinate from Example 133 step a, was used in place of 5-chlorofuran-2-carboxylic acid. ESI-MS m/z: 480.4 [M+H]+. 1H NMR (300 MHz, DMSO-d6) δ 1.57 (s, 4H), 3.15 (s, 4H), 5.15 (d, 1H), 7.15 (d, J=6.5 Hz, 1H), 7.19-7.40 (m, 3H), 7.40-7.60 (m, 5H), 7.62-7.71 (m, 1H), 8.35 (d, J=6.5 Hz, 1H), 8.52 (s, 1H), 9.21 (d, J=8.6 Hz, 1H), 10.99 (s, 1H).

Example 135

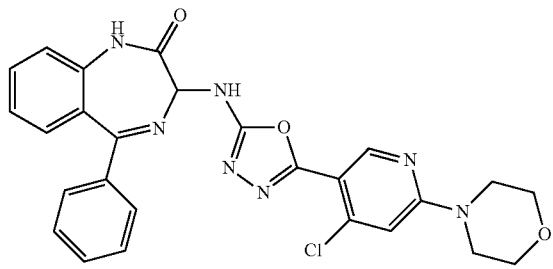 [SMILES: O=C1Nc2ccccc2C(c2ccccc2)=NC1Nc1nnc(-c2cnc(N3CCOCC3)cc2Cl)o1]

Example 135 Step a

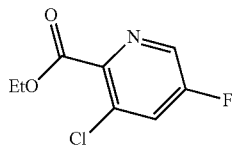 [SMILES: CCOC(=O)c1ncc(F)cc1Cl]

A solution of the 3-chloro-5-fluoropicolinic acid (500 mg, 2.85 mmol), H2SO4 (1 mL) in EtOH (5 mL) was stirred at 80° C. for 4 hours. Then H2O (20 ml) was added to the mixture and it was extracted with EtOAc (×3). The organic layer was dried and by reverse phase C18 column chromatography (MeCN/H2O) to give ethyl 3-chloro-5-fluoropicolinate as off-white solid (400 mg, 69%). ESI-MS m/z: 203.9 [M+H]+.

Example 135 Step b

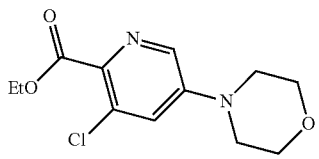

A solution of ethyl 3-chloro-5-fluoropicolinate (100 mg, 0.49 mmol), morpholine (43 mg, 0.49 mmol), K2CO3 (135 mg, 0.98 mmol) in DMSO (5 mL) was stirred at 100° C. for 2 hours. Then H2O (20 ml) was added to the mixture and it was extracted with EtOAc (×3). The organic layer was dried and purified by reverse phase C18 column chromatography (MeCN/H2O) to give ethyl 3-chloro-5-morpholinopicolinate as off-white solid (120 mg, 91%). ESI-MS m/z: 270.9 [M+H]+.

Example 135 Step c

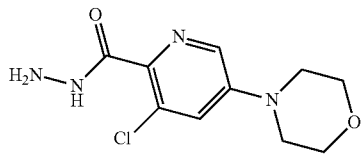 [SMILES: NNC(=O)c1ncc(N2CCOCC2)cc1Cl]

A solution of ethyl 3-chloro-5-morpholinopicolinate (120 mg, 0.44 mmol), hydrazine hydrate (1 mL) in EtOH (3 mL) was stirred at 80° C. for 1 hour. The solution was concentrated and purified by reverse phase C18 column chromatography (MeCN/H2O) to give 3-chloro-5-morpholinopicolinohydrazide as off-white solid (100 mg, 89%). ESI-MS m/z: 279.0[M+H]+.

Example 135 Step d

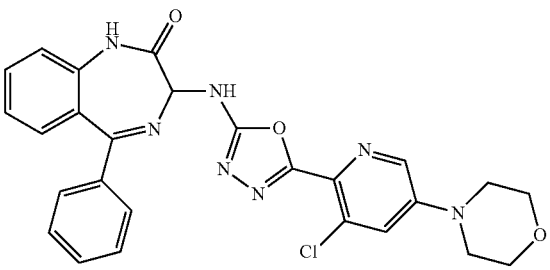 [SMILES: O=C1Nc2ccccc2C(c2ccccc2)=NC1Nc1nnc(-c2ncc(N3CCOCC3)cc2Cl)o1]

Example 135 was prepared using a procedure similar to that used to prepare Example 21 where 3-chloro-5-morpholinopicolinohydrazide was used in place of tetrahydro-2H-pyran-4-carbohydrazide. ESI-MS m/z: 516.2 [M+H]+. 1H NMR (400 MHz, DMSO-d6) δ 3.28-3.38 (m, 4H), 3.73-3.75 (m, 4H), 5.15-5.17 (d, J=8.0 Hz, 1H), 7.26-7.29 (m, 1H), 7.33-7.36 (m, 2H), 7.44-7.55 (m, 6H), 7.66-7.69 (m, 1H), 8.40-8.41 (m, 1H), 9.15-9.17 (m, 1H), 10.99 (s, 1H).

Example 136

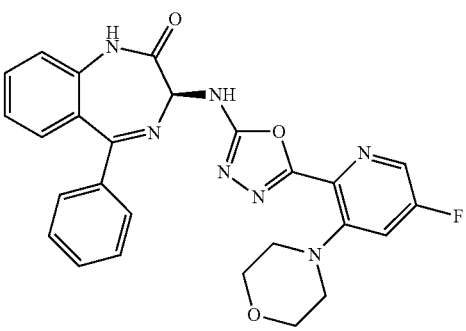 [SMILES: O=C1Nc2ccccc2C(c2ccccc2)=N[C@@H]1Nc1nnc(-c2ncc(F)cc2N2CCOCC2)o1]

Example 136 Step a

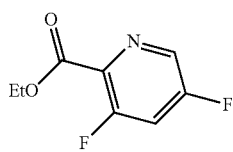 [SMILES: CCOC(=O)c1ncc(F)cc1F]

A solution of 3,5-difluoropicolinic acid (3.3 g, 20.75 mmol), $H_2SO_4$ (5 mL) in EtOH (20 mL) was stirred for 2 hours at 80° C. Then solvent was removed. The residue was diluted with EtOAc and it was washed with brine (×2). The organic layers was concentrated to give ethyl 3,5-difluoropicolinate as a pale yellow solid (3.44 g, 88%). ESI-MS m/z: 188.0 [M+H]$^+$.

Example 136 Step b

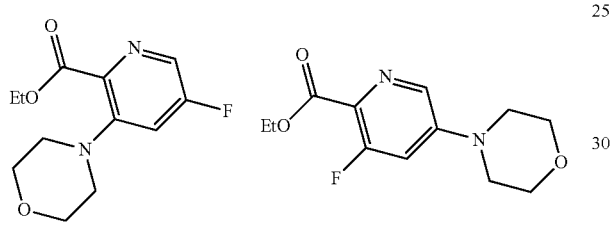

A solution of ethyl 3,5-difluoropicolinate (3.1 g, 16.6 mmol), morpholine (1.44 g, 16.6 mmol) and $K_2CO_3$ (6.87 g, 49.8 mmol) in DMF (4 mL) and DMSO (6 mL) was stirred for overnight at room temperature. It was poured into water and extracted with EtOAc. The organic layer was dried over $Na_2SO_4$ and concentrated to give a mixture of ethyl 5-fluoro-3-morpholinopicolinate and the isomer ethyl 3-fluoro-5-morpholinopicolinate as a pale yellow solid (3.37 g). ESI-MS m/z: 255.2 [M+H]$^+$.

Example 136 Step c

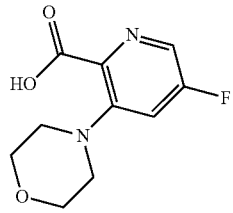 [SMILES: O=C(O)c1ncc(F)cc1N1CCOCC1]

A solution of the mixture of isomers from step b (3.37 g, 13.3 mmol) and NaOH (796 mg, 19.9 mmol) in THF (10 mL) and $H_2O$ (15 mL) was stirred for 2 hours at room temperature. It was adjusted pH to 2-3 with HCl and purified by Prep-HPLC (MeCN/$H_2O$) to give 817 mg of the desired compound 5-fluoro-3-morpholinopicolinic acid as a white solid. ESI-MS m/z: 227.0[M+H]$^+$.

Example 136 Step d

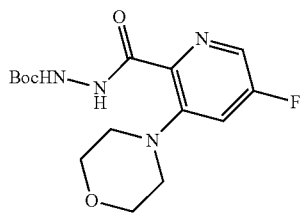 [SMILES: CC(C)(C)OC(=O)NNC(=O)c1ncc(F)cc1N1CCOCC1]

A solution of 5-fluoro-3-morpholinopicolinic acid (817 mg, 3.62 mmol) and $NH_2NHBoc$ (956 mg, 7.24 mol), DIPEA (934 mg, 7.24 mol) and HATU (1.44 g, 3.80 mol) in DMF (10 mL) was stirred for half an hour at room temperature. It was diluted with $H_2O$ (×3), extracted with EtOAc and purified by reverse phase C18 column chromatography (MeCN/$H_2O$) to give tert-butyl 2-(5-fluoro-3-morpholinopicolinoyl)hydrazine-1-carboxylate as a need amount white solid. ESI-MS m/z: 341.2 [M+H]$^+$.

Example 136 Step e

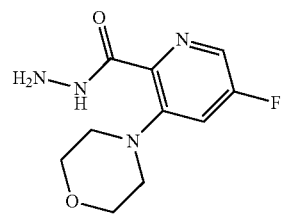 [SMILES: NNC(=O)c1ncc(F)cc1N1CCOCC1]

A solution of tert-butyl 2-(5-fluoro-3-morpholinopicolinoyl)hydrazine-1-carboxylate in EA (10 mL) was added HCl (3 mL, conc.). Then it was stirred for half an hour at room temperature. Solvent was removed and the residue was purified by reverse phase C18 column chromatography (MeCN/$H_2O$) to give 5-fluoro-3-morpholinopicolinohydrazide as a pale yellow solid (293 mg). ESI-MS m/z: 241.0[M+H]$^+$.

Example 136 Step f

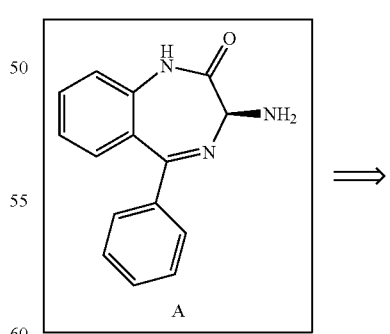

A

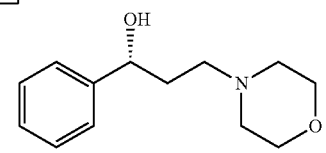

The above compound (S)-3-amino-5-phenyl-1,3-dihydro-2H-benzo[e][1,4]diazepin-2-one (A) was made several ways including the procedures described by Sherrill and Sugg (*J. Org. Chem.* 1995, 60, 730-734), Rittle and Evans (*Tetrahedron Lett.* 1987, 28, 521-522), and the method described below.

Neat (R)-3-chloro-1-phenylpropan-1-ol (12.6 g, 73.8 mmol) was dissolved in morpholine (60 mL) and the mixture was heated to 80° C. overnight. The mixture was cooled to rt, diluted with EtOAc % and washed with water and brine. The organic layer was dried ($Na_2SO_4$), concentrated, and pumped on the high vacuum for 3 h. The material (R)-3-morpholino-1-phenylpropan-1-ol (14.0 g, 86%) was used directly without further purification.

Example 136 Step g

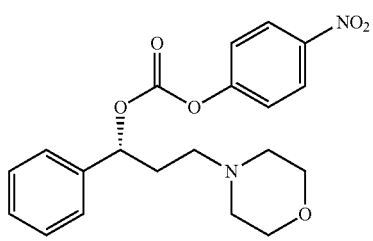 [SMILES: O=C(Oc1ccc([N+](=O)[O-])cc1)O[C@H](CCN1CCOCC1)c1ccccc1]

Solid p-nitrophenyl chloroformate (16.4 g, 41 mmol) was added to a DCA solution (200 mL) of (R)-3-morpholino-1-phenylpropan-1-ol (7.0 g, 31.6 mmol) and i-$Pr_2NEt$ (8.3 mL, 47.4 mmol) and the mixture was stirred at rt overnight. The mixture was diluted with DCM, and washed with water and brine dried ($Na_2SO_4$), concentrated, and purified via column chromatography to give the desired material (R)-3-morpholino-1-phenyl propyl (4-nitrophenyl) carbonate (10.2 g, 84%) as a yellow gum Which will be used directly for the next step.

Example 136 Step h

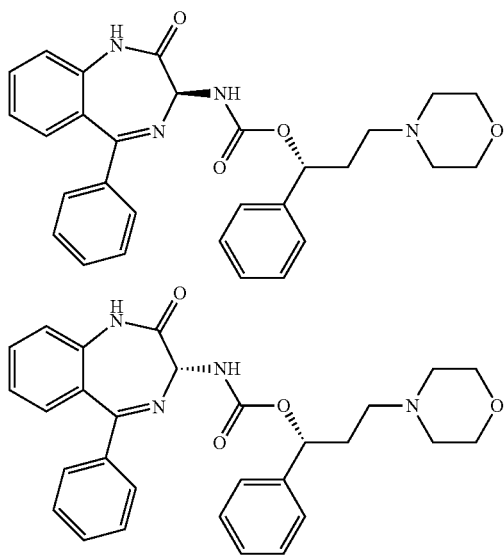

Neat i-$Pr_2NEt$ (4.1 mL, 23.2 mmol) was added to a DMF solution (140 mL) of (R)-3-morpholino-1-phenylpropyl (4-nitrophenyl) carbonate (6.9 g, 17.9 mmol) and racemic amine (Z)-3-amino-5-phenyl-1H-benzo[e][1,4]diazepin-2(3H)-one (4.5 g, 17.9 mmol) and the mixture was heated to 60° C. overnight. The mixture was cooled to it, diluted with EtOAc, and washed with water and brine, dried ($Na_2SO_4$), concentrated, and purified via column chromatography (0-100% EtOAc/hexanes) to give the (R)-3-morpholino-1-phenylpropyl ((S)-2-oxo-5-phenyl-2,3-dihydro-1H-benzo[e][1,4]diazepin-3-yl)carbamate (3.92 g, 44% yield, first and less polar spot) and (R)-3-morpholino-1-phenylpropyl ((R)-2-oxo-5-phenyl-2,3-dihydro-1H-benzo[e][1,4]diazepin-3-yl)carbamate (3.56 g, 40% yield, second and more polar spot) as light yellow solids. ESI MS m/z=499.2395 $[M+H]^+$ for R)-3-morpholino-1-phenylpropyl ((S)-2-oxo-5-phenyl-2,3-dihydro-1H-benzo[e][1,4]diazepin-3-yl)carbamate and m/z=499.2379 [M+H]+ for (R)-3-morpholino-1-phenylpropyl ((R)-2-oxo-5-phenyl-2,3-dihydro-1H-benzo[e][1,4]diazepin-3-yl)carbamate.

Example 136 Step i

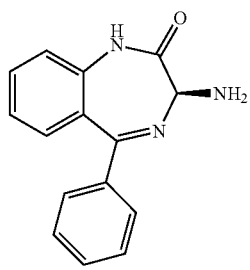

A

Neat (R)-3-morpholino-1-phenylpropyl ((S)-2-oxo-5-phenyl-2,3-dihydro-1H-benzo[e][1,4]diazepin-3-yl)carbamate (4.4 g, 8.8 mmol) was dissolved in 33% HBr in AcOH (30 mL) and the mixture was stirred at rt. After 2 h, the mixture became heterogeneous and the solution was cooled with ice bath and adjusted to pH~8 by adding saturated aqueous $NaHCO_3$ dropwise. After overnight, a white solid was precipitated which was filtered, washed with cold water, cold MeOH and dried under high vacuum to afford pure (S)-3-amino-5-phenyl-1,3-dihydro-2H-benzo[e][1,4]diazepin-2-one (A) (2.81 g, 79% yield) as a white solid. ESI MS m/z=252.1529 $[M+H]^+$. ee %=98.4% (retention time 9.39 min, Method A); $[α]_D$=−195.56 (c=0.19, MeOH).

Example 136 Step j

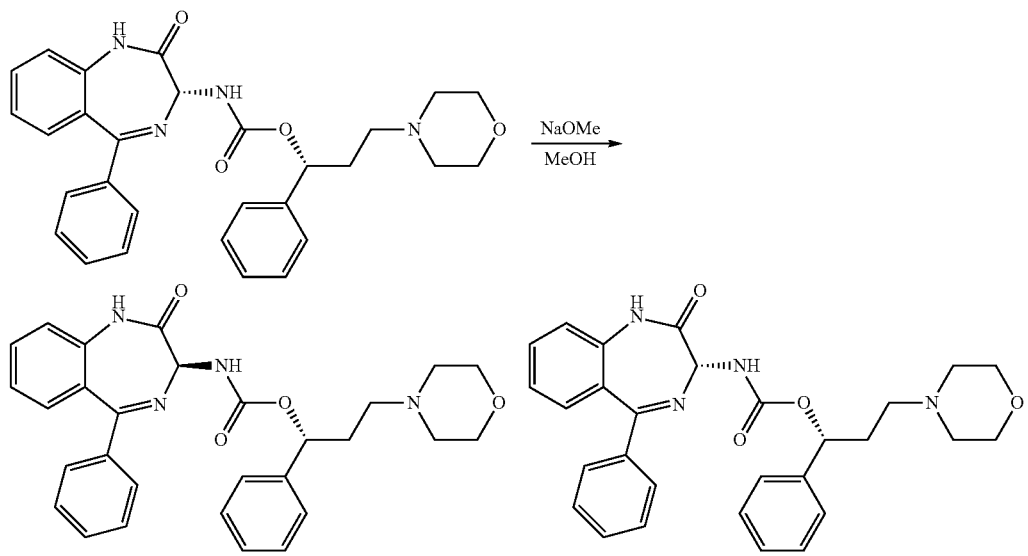

Compound (R)-3-morpholino-1-phenylpropyl ((R)-2-oxo-5-phenyl-2,3-dihydro-1H-benzo[e][1,4]diazepin-3-yl)carbamate (2.0 g, 4.0 mmol) was dissolved in MeOH (40 mL), and then 25% wt NaOMe in MeOH (2.2 mL) was slowly added. The resulting mixture was stirred at rt for 20 hrs and confirmed with $^1$H NMR that the ratio of diastereomers was near 1:1. Diluted with EtOAc, washed with brine, dried and evaporated. The residue was purified by combiflash eluting with 0-10% MeOH/DCM to obtain (R)-3-morpholino-1-phenylpropyl ((S)-2-oxo-5-phenyl-2,3-dihydro-1H-benzo[e][1,4]diazepin-3-yl)carbamate (0.90 g, 45% yield) and recycled (R)-3-morpholino-1-phenylpropyl ((R)-2-oxo-5-phenyl-2,3-dihydro-1H-benzo[e][1,4]diazepin-3-yl)carbamate (0.84 g, 42% yield). The (R)-3-morpholino-1-phenylpropyl ((S)-2-oxo-5-phenyl-2,3-dihydro-1H-benzo[e][1,4]diazepin-3-yl)carbamate was re-subjected to example 136 step i to obtain the desired (S)-3-amino-5-phenyl-1,3-dihydro-2H-benzo[e][1,4]diazepin-2-one.

Example 136 Step k

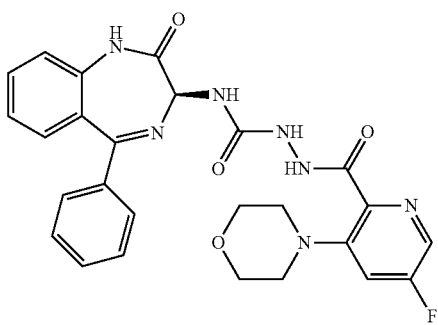 [SMILES: O=C(NNC(=O)c1ncc(F)cc1N1CCOCC1)N[C@H]1N=C(c2ccccc2)c2ccccc2NC1=O]

CDI (196 mg, 1.2 mmol) was added to a solution of (S)-3-amino-5-phenyl-1,3-dihydro-2H-benzo[e][1,4]diazepin-2-one (A) (276 mg, 1.1 mmol) in MeCN (3 mL) and DMF (0.6 mL), and then it was stirred for 1 hour at room temperature. The compound from step e (293 mg, 1.2 mmol) was added and then stirred for 48 hours. The crude product was purified by reverse phase C18 column chromatography (MeCN/H$_2$O) to give (S)-2-(5-fluoro-3-morpholinopicolinoyl)-N-(2-oxo-5-phenyl-2,3-dihydro-1H-benzo[e][1,4]diazepin-3-yl)hydrazine-1-carboxamide as a light yellow solid (371 mg). ESI-MS m/z: 518.3 [M+H]$^+$.

Example 136 Step l

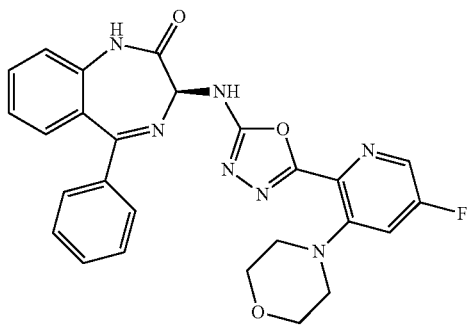 [SMILES: O=C1Nc2ccccc2C(c2ccccc2)=N[C@@H]1Nc1nnc(-c2ncc(F)cc2N2CCOCC2)o1]

A solution of (S)-2-(5-fluoro-3-morpholinopicolinoyl)-N-(2-oxo-5-phenyl-2,3-dihydro-1H-benzo[e][1,4]diazepin-3-yl)hydrazine-1-carboxamide (371 mg, 0.72 mmol), DMAP (20 mg) and TEA (181 mg, 1.78 mmol) in DCM (5 mL) was added TsCl (204 mg, 1.07 mmol). It was stirred for 1 hour before concentrated. The crude product was purified by Prep-HPLC (MeCN/H$_2$O) to give (S)-3-((5-(5-fluoro-3-morpholinopyridin-2-yl)-1,3,4-oxadiazol-2-yl)amino)-5-phenyl-1,3-dihydro-2H-benzo[e][1,4]diazepin-2-one as a white solid (122 mg, 34%). ESI-MS m/z: 500.4 [M+H]$^+$. $^1$H NMR (300 MHz, DMSO-d6) δ 2.07 (s, 1H), 2.85-3.07 (m, 4H), 3.61-3.78 (m, 4H), 5.17 (d, 1H), 7.06-7.81 (m, 9H), 8.34 (d, 1H), 9.21 (d, 1H), 10.97 (s, 1H).

Examples 137 and 138

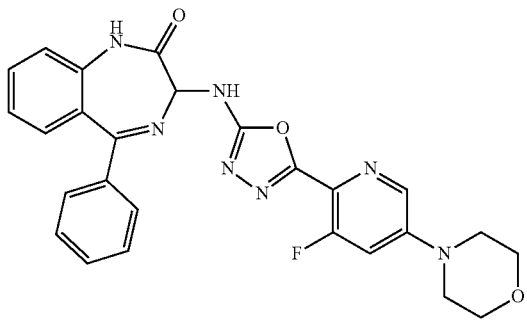

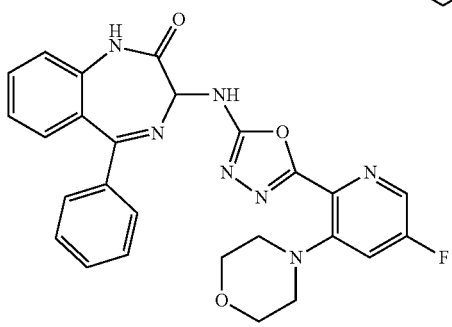

Examples 137 and 138 Step a

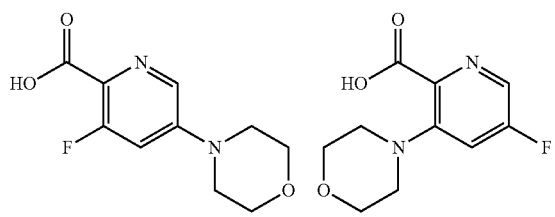

A solution of 3,5-difluoropicolinic acid (1.60 g, 10.0 mol), morpholine (0.870 g, 10.0 mol) and K$_2$CO$_3$ (2.42 g, 176 mol) in DMSO (15 mL) was stirred for 1 hour at 100° C. It was purified by reverse phase C18 column chromatography (MeCN/H$_2$O) to give the mixture of 3-fluoro-5-morpholinopicolinic acid and 5-fluoro-3-morpholinopicolinic acid as a yellow solid (1.90 g, 84%). ESI-MS m/z: 226.1 [M+H]$^+$.

Examples 137 and 138 Step b

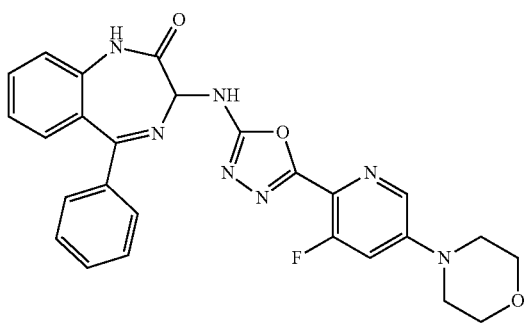

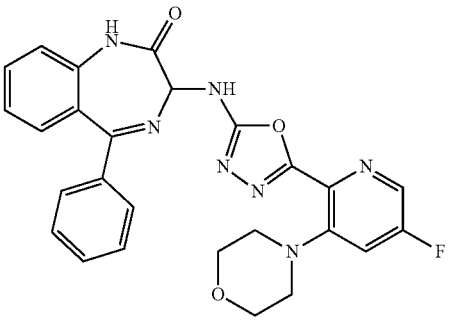

Examples 137 and 138 were prepared using a procedure similar to that used to prepare Example 20 where 3-fluoro-5-morpholinopicolinic acid and 5-fluoro-3-morpholinopicolinic acid were used, respectively, in place of 5-chlorofuran-2-carboxylic acid. Example 137: ESI-MS m/z: 500.3[M+H]$^+$. $^1$H NMR (400 MHz, DMSO-d$_6$) δ 3.32 (t, J=4.9 Hz, 4H), 3.76 (t, J=4.9 Hz, 4H), 5.17 (d, J=8.5 Hz, 1H) 7.61-7.17 (m, 9H), 7.82-7.62 (m, 1H), 8.36-8.22 (m, 1H), 9.18 (d, J=8.6 Hz, 1H), 10.99 (s, 1H). Example 138: ESI-MS m/z: 500.2[M+H]$^+$. $^1$H NMR (400 MHz, DMSO-d$_6$) δ 3.10-2.88 (m, 4H), 3.71 (dd, J=5.9, 3.3 Hz, 4H), 5.19 (d, J=8.6 Hz, 1H), 7.44-7.23 (m, 3H), 7.76-7.44 (m, 7H), 8.36 (d, J=2.3 Hz, 1H) 9.25 (d, J=8.6 Hz, 1H), 11.00 (s, 1H).

Example 139

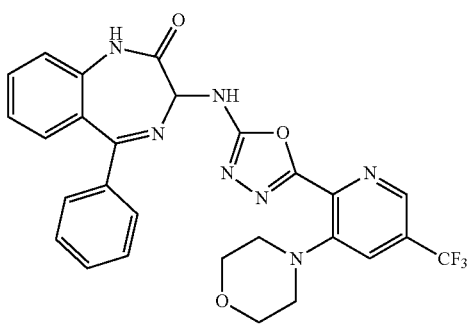

Example 139 was prepared using a procedure similar to that used to prepare Example 20 where 3-morpholino-5-(trifluoromethyl)picolinic acid, which was prepared similarly to 2-chloro-4-(1H-1,2,4-triazol-1-yl)benzoic acid from Example 128 step a, was used in place of 5-chlorofuran-2-carboxylic acid. ESI-MS m/z: 550.4 [M+H]$^+$. $^1$H NMR (300 MHz, DMSO-d$_6$) δ 3.09 (d, J=4.6 Hz, 4H), 3.73 (d, J=4.6 Hz, 3H), 5.22 (d, J=8.4 Hz, 1H), 7.22-7.44 (m, 3H), 7.44-7.65 (m, 5H), 7.66-7.80 (m, 1H), 7.91 (d, J=1.9 Hz, 1H), 8.71 (s, 1H), 9.43 (d, J=8.6 Hz, 1H), 11.01 (s, 1H).

Example 140

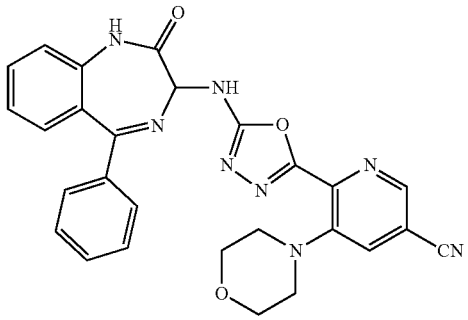 [SMILES: N#Cc1cnc(-c2nnc(NC3N=C(c4ccccc4)c4ccccc4NC3=O)o2)c(N2CCOCC2)c1]

Example 140 was prepared using a procedure similar to that used to prepare Example 20 where 5-cyano-3-morpholinopicolinic acid, which was prepared similarly to 2-chloro-4-(1H-1,2,4-triazol-1-yl)benzoic acid from Example 128 step a, was used in place of 5-chlorofuran-2-carboxylic acid. ESI-MS m/z: 507.2 [M+H]+. 1H NMR (400 MHz, DMSO-d6) δ 3.02-3.04 (m, 4H), 3.71-3.73 (m, 4H), 5.19-5.21 (d, J=8.0 Hz, 1H), 7.24-7.28 (m, 1H), 7.30-7.37 (m, 5H), 7.42-7.90 (m, 1H), 8.00-8.13 (m, 1H), 8.47 (s, 1H), 9.42-9.44 (m, 2H), 10.99 (s, 1H).

Example 141

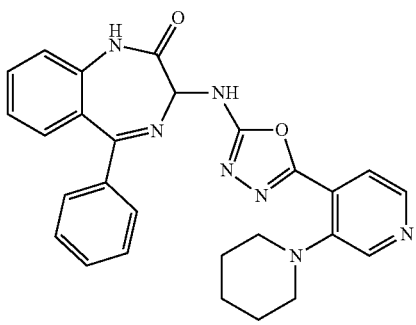

Example 141 Step a

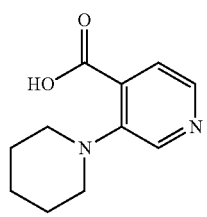 [SMILES: O=C(O)c1ccncc1N1CCCCC1]

A solution of 3-fluoroisonicotinic acid (1.30 g, 1.0 mol), piperidine (1.16 g, 13.3 mol) and K2CO3 (2.25 g, 17.6 mol) in DMSO (15 mL) was stirred for 1 hour at 120° C. It was purified by reverse phase C18 column chromatography (MeCN/H2O) to give 3-(piperidin-1-yl)isonicotinic acid as a white solid (1.12 g, 49%). ESI-MS m/z: 207.1 [M+H]+.

Example 141 Step b

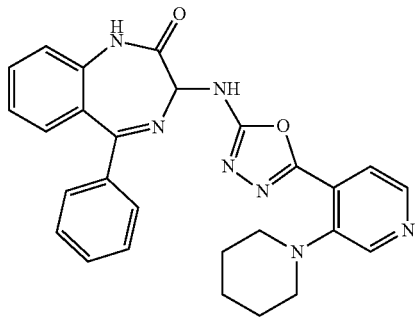 [SMILES: O=C1Nc2ccccc2C(c2ccccc2)=NC1Nc1nnc(-c2ccncc2N2CCCCC2)o1]

Example 141 was prepared using a procedure similar to that used to prepare Example 20 where 3-(piperidin-1-yl)isonicotinic acid was used in place of 5-chlorofuran-2-carboxylic acid. ESI-MS m/z: 480.0 [M+H]+. 1H NMR (300 MHz, DMSO-d6) δ 2.97 (s, 3H), 5.18 (d, J=8.3 Hz, 1H), 7.13-7.82 (m, 11H), 8.22 (d, J=1.9 Hz, 1H), 9.47 (d, J=8.4 Hz, 1H), 11.00 (s, 1H).

Example 142

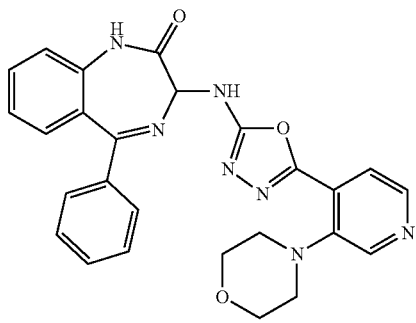 [SMILES: O=C1Nc2ccccc2C(c2ccccc2)=NC1Nc1nnc(-c2ccncc2N2CCOCC2)o1]

Example 142 was prepared using a procedure similar to that used to prepare Example 20 where 3-morpholinoisonicotinic acid, which was prepared similarly to 3-(piperidin-1-yl)isonicotinic acid from Example 141 step a, was used in place of 5-chlorofuran-2-carboxylic acid. ESI-MS m/z: 482.3 [M+H]+. 1H NMR (300 MHz, DMSO-d6) δ 3.05 (t, J=4.4 Hz, 4H), 3.75 (t, J=4.5 Hz, 4H), 5.22 (d, J=8.5 Hz, 1H), 7.43-7.18 (m, 2H), 7.51 (ddt, J=14.6, 9.1, 5.2 Hz, 5H), 7.85-7.65 (m, 2H), 8.49 (d, J=37.4 Hz, 2H), 9.46 (d, J=8.5 Hz, 1H), 11.04 (s, 1H).

Example 143

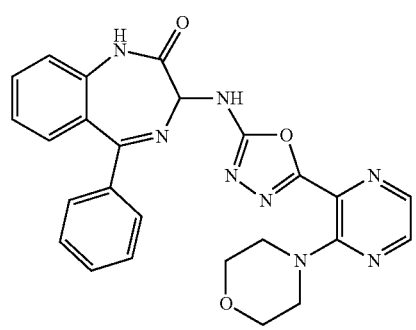 [SMILES: O=C1Nc2ccccc2C(c2ccccc2)=NC1Nc1nnc(-c2nccnc2N2CCOCC2)o1]

Example 143 was prepared using a procedure similar to that used to prepare Example 20 where 3-morpholinopyrazine-2-carboxylic acid, which was prepared similarly to 3-(piperidin-1-yl)isonicotinic acid from Example 141 step a, was used in place of 5-chlorofuran-2-carboxylic acid. ESI-MS m/z: 483.1 [M+H]+. 1H NMR (400 MHz, DMSO-d6) δ 3.27-3.33 (m, 4H), 3.67-3.70 (m, 4H), 5.17-5.19 (d, J=8.0 Hz, 1H), 7.26-7.28 (m, 1H), 7.30-7.36 (m, 2H), 7.44-7.55 (m, 5H), 8.22-8.23 (m, 1H), 8.35 (s, 1H), 9.33-9.35 (d, J=8.0 Hz, 1H), 10.99 (s, 1H).

pholinonicotinic acid was used in place of 5-chlorofuran-2-carboxylic acid. ESI-MS m/z: 496.1 [M+H]+. 1H NMR (300 MHz, DMSO-d6) δ 2.43 (s, 3H), 3.14 (m, 4H), 3.64-3.74 (m, 4H), 5.16 (d, J=8.7 Hz, 1H), 6.92 (d, J=7.7 Hz, 1H), 7.24-7.41 (m, 3H), 7.41-7.62 (m, 5H), 7.69 (m, 1H), 7.86 (d, J=7.7 Hz, 1H), 9.14 (d, J=8.8 Hz, 1H), 11.00 (s, 1H).

Example 144

Example 145

Example 144 Step a

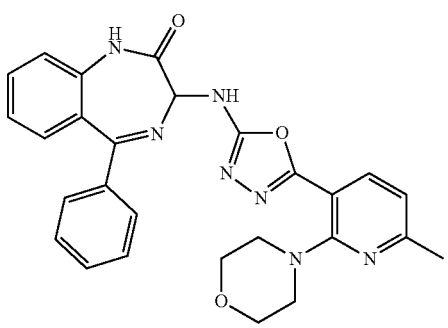 [SMILES: Cc1ccc(-c2nnc(NC3N=C(c4ccccc4)c4ccccc4NC3=O)o2)c(N2CCOCC2)n1]

Example 145 Step a

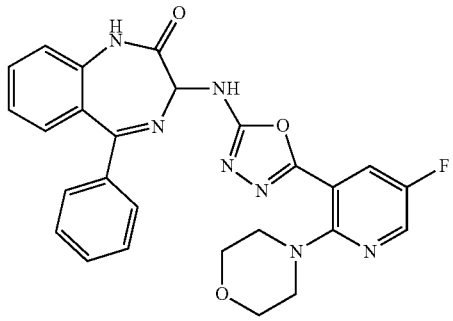

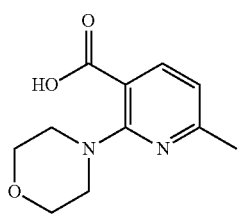 [SMILES: Cc1ccc(C(=O)O)c(N2CCOCC2)n1]

A solution of 2-chloro-6-methylnicotinic acid (855 mg, 5 mmol), K2CO3 (1.38 g, 10 mmol) and morpholine (2 mL) in DMF (20 mL) was stirred for 3 hours at 130° C. Solid was filtered out and the solvent were removed and the residue was washed with Et2O (50 mL) to give 6-methyl-2-morpholinonicotinic acid as a white solid (666 mg, 60%). ESI-MS m/z: 223.1 [M+H]+.

A solution of 2-chloro-5-fluoronicotinic acid (1050 mg, 6 mmol) and morpholine (3 mL) in DMF (15 mL) was stirred for 1 hour at 120° C. The solvent was removed to give 5-fluoro-2-morpholinonicotinic acid as a white solid (904 mg, 67%). ESI-MS m/z: 227.1 [M+H]+.

Example 144 Step b

Example 145 Step b

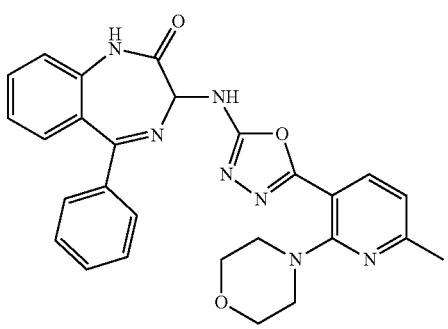 [SMILES: Cc1ccc(-c2nnc(NC3N=C(c4ccccc4)c4ccccc4NC3=O)o2)c(N2CCOCC2)n1]

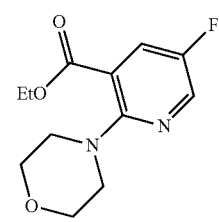 [SMILES: CCOC(=O)c1cc(F)cnc1N1CCOCC1]

Example 144 was prepared using a procedure similar to that used to prepare Example 20 where 6-methyl-2-mor- A solution of 5-fluoro-2-morpholinonicotinic acid (904 mg, 4 mmol) and H2SO4 (2 mL) in EtOH (50 mL) was stirred for 18 hours at 80° C. Then it was adjusted to PH=9, extracted with EtOAc (3×), dried Na2SO4, filtered to give ethyl 5-fluoro-2-morpholinonicotinate as a white solid (762 mg, 75%). ESI-MS m/z: 255.1 [M+H]+.

Example 145 Step c

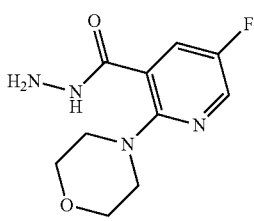 [SMILES: NNC(=O)c1cc(F)cnc1N1CCOCC1]

A solution of ethyl 5-fluoro-2-morpholinonicotinate (762 mg, 3 mmol) and NH$_2$NH$_2$H$_2$O (3 mL) in EtOH (10 mL) was stirred for 18 hours at 80° C. The solvent was removed and it was washed with Et$_2$O (20 mL) to give 5-fluoro-2-morpholinonicotinohydrazide as a white solid (480 mg, 67%). ESI-MS m/z: 241.2 [M+H]$^+$.

Example 145 Step d

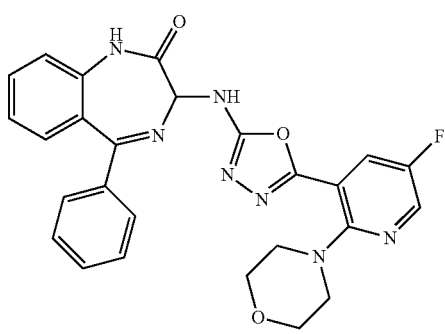 [SMILES: O=C1Nc2ccccc2C(c2ccccc2)=NC1Nc1nnc(-c2cc(F)cnc2N2CCOCC2)o1]

Example 145 was prepared using a procedure similar to that used to prepare Example 21 where 5-fluoro-2-morpholinonicotinohydrazide was used in place of tetrahydro-2H-pyran-4-carbohydrazide. ESI-MS m/z: 500.1[M+H]$^+$. $^1$H NMR (300 MHz, DMSO-d6) δ 3.09 (m, 4H), 3.70 (m, 4H), 5.18 (d, J=8.5 Hz, 1H), 7.24-7.45 (m, 3H), 7.42-7.75 (m, 6H), 7.94 (m, 1H), 8.43 (d, J=3.0 Hz, 1H), 9.29 (d, J=8.6 Hz, 1H), 11.01 (s, 1H).

Example 146

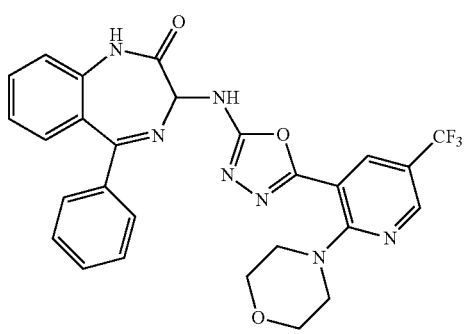 [SMILES: O=C1Nc2ccccc2C(c2ccccc2)=NC1Nc1nnc(-c2cc(C(F)(F)F)cnc2N2CCOCC2)o1]

Example 146 was prepared using a procedure similar to that used to prepare Example 20 where 2-morpholino-5-(trifluoromethyl)nicotinic acid, which was prepared similarly to 3-(piperidin-1-yl)isonicotinic acid from Example 141 step a, was used in place of 5-chlorofuran-2-carboxylic acid. ESI-MS m/z: 550.4 [M+H]$^+$. $^1$H NMR (300 MHz, DMSO-d$_6$) δ 3.31 (d, J=3.7 Hz, 4H), 3.68 (m, 4H), 5.14 (d, J=6.1 Hz, 1H), 7.19-7.39 (m, 3H), 7.41-7.57 (m, 5H), 7.66 (m, 1H), 8.15 (d, J=2.4 Hz, 1H), 8.66 (m, 1H), 9.21 (s, 1H), 10.97 (s, 1H).

Example 147

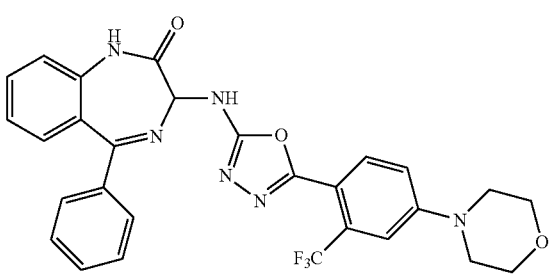 [SMILES: O=C1Nc2ccccc2C(c2ccccc2)=NC1Nc1nnc(-c2ccc(N3CCOCC3)cc2C(F)(F)F)o1]

Example 147 Step a

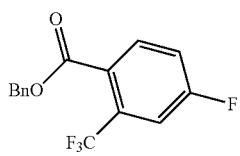

A solution of 4-fluoro-2-(trifluoromethyl)benzoic acid (500 mg, 2.5 mol), HATU (1.90 g, 5 mmol), DIPEA (650 mg, 5 mmol) and BnOH (200 uL) in DMF (10 mL) was stirred for 0.5 hour. It was added water, extracted by EtOAc to give 300 mg (crude) of benzyl 4-fluoro-2-(trifluoromethyl)benzoate as yellow oil, which was used directly in the next step.

Example 147 Step b

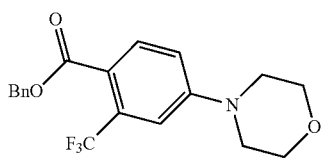 [SMILES: O=C(OCc1ccccc1)c1ccc(N2CCOCC2)cc1C(F)(F)F]

A solution of benzyl 4-fluoro-2-(trifluoromethyl)benzoate (300 mg, crude) in morpholine (5 mL) was stirred for 1 hour at 100° C. The mixture was added water and extracted by EA to give desired compound benzyl 4-morpholino-2-(trifluoromethyl)benzoate as yellow oil (1.07 g, crude). ESI-MS m/z: 366.2 [M+H]$^+$.

Example 147 Step c

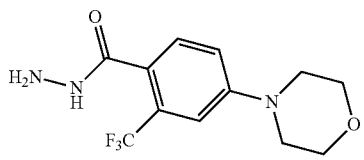 [SMILES: NNC(=O)c1ccc(N2CCOCC2)cc1C(F)(F)F]

A solution of benzyl 4-morpholino-2-(trifluoromethyl) benzoate (1.07 g, crude), NH₂NH₂·H₂O (10 ml) in EtOH (10 mL) was stirred at 80° C. for 1 hour. The solvent was removed and the crude product was purified by reverse phase C18 column chromatography (MeCN/H₂O) to give desired compound 4-morpholino-2-(trifluoromethyl)benzohydrazide as a white solid (139 mg). ESI-MS m/z: 290.1 [M+H]⁺.

Example 147 Step d

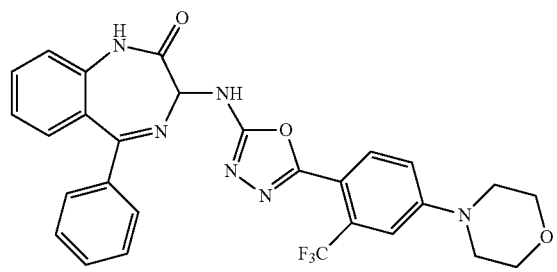 [SMILES: O=C1Nc2ccccc2C(c2ccccc2)=NC1Nc1nnc(-c2ccc(N3CCOCC3)cc2C(F)(F)F)o1]

Example 147 was prepared using a procedure similar to that used to prepare Example 21 where 4-morpholino-2-(trifluoromethyl)benzohydrazide was used in place of tetrahydro-2H-pyran-4-carbohydrazide. ESI-MS m/z: 549.2[M+H]⁺. ¹H NMR (400 MHz, DMSO-d₆) δ3.32-3.34 (m, 4H), 3.65-3.82 (m, 4H), 5.13 (d, J=8.5 Hz, 1H), 7.23-7.41 (m, 5H), 7.41-7.61 (m, 5H), 7.67 (m, 1H), 7.75 (d, J=9.4 Hz, 1H), 9.07 (d, J=8.6 Hz, 1H), 10.99 (s, 1H).

Example 148

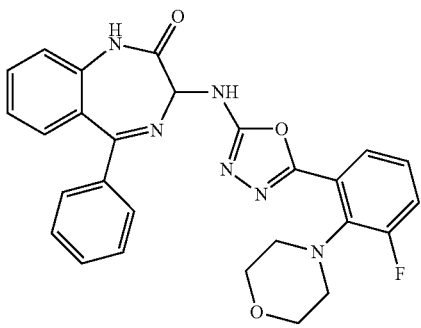 [SMILES: O=C1Nc2ccccc2C(c2ccccc2)=NC1Nc1nnc(-c2cccc(F)c2N2CCOCC2)o1]

Example 148 Step a

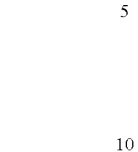

A solution of 2-chloro-3-fluorobenzoic acid (1 g, 5.75 mmol) and H₂SO₄ (1 mL) in EtOH (10 mL) were refluxed for 16 hours. It was concentrated and purified by reverse phase C18 column chromatography (MeCN/H₂O) to give ethyl 2-chloro-3-fluorobenzoate as a yellow oil (1.1 g, 95%). ESI-MS m/z: 202.9[M+H]⁺.

Example 148 Step b

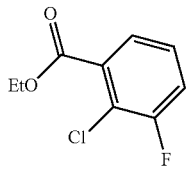

A solution of ethyl 2-chloro-3-fluorobenzoate (1.1 g, 5.44 mmol) in morpholine (neat) (6 ml) was stirred overnight at 120° C. It was concentrated under vacuum and the crude product was purified by prep-TLC(PE/EA=2/1) to give ethyl 3-fluoro-2-morpholinobenzoate a yellow solid (0.25 g, 18%). ESI-MS m/z: 254.0[M+H]⁺.

Example 148 Step c

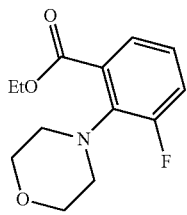

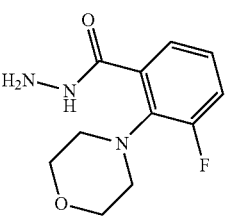 [SMILES: NNC(=O)c1cccc(F)c1N1CCOCC1]

A solution of ethyl 3-fluoro-2-morpholinobenzoate (0.25 g, 0.99 mmol) and NH₂NH₂·H₂O (1 mL) in EtOH (10 mL) was refluxed overnight. The crude product was purified by reverse phase C18 column chromatography (MeCN/H₂O) to give 3-fluoro-2-morpholinobenzohydrazide as a white solid (0.16 g, 68%). ESI-MS m/z: 240.0[M+H]⁺.

Example 148 Step d

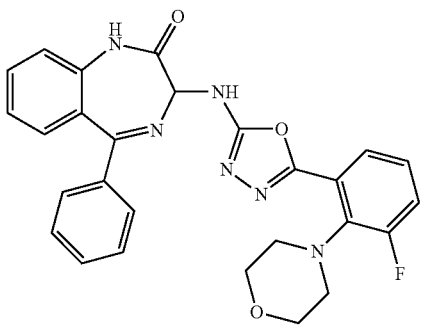 [SMILES: O=C1Nc2ccccc2C(c2ccccc2)=NC1Nc1nnc(-c2cccc(F)c2N2CCOCC2)o1]

Example 148 was prepared using a procedure similar to that used to prepare Example 21 where 3-fluoro-2-morpholinobenzohydrazide was used in place of tetrahydro-2H-pyran-4-carbohydrazide. ESI-MS m/z: 499.0[M+H]$^+$. $^1$H NMR (400 MHz, DMSO-d$_6$) δ 3.02 (m, 4H), 3.55-3.73 (m, 4H), 5.19 (d, J=8.5 Hz, 1H), 7.24-7.62 (m, 11H), 7.62-7.74 (m, 1H), 9.18 (d, J=8.6 Hz, 1H), 11.02 (s, 1H).

Examples 149 and 150

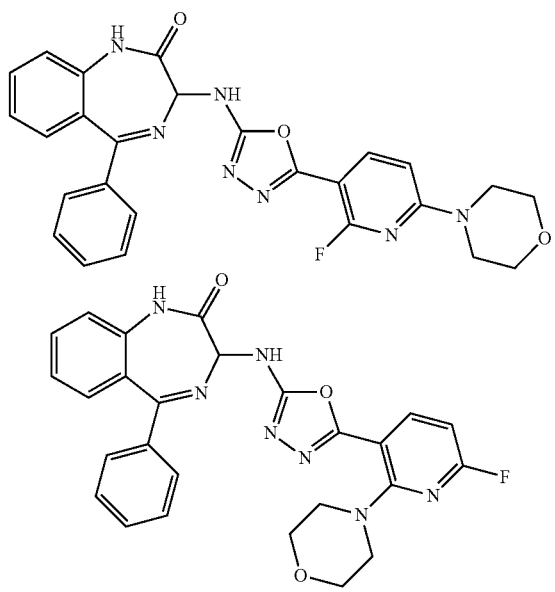

Examples 149 and 150 were prepared using a procedure similar to that used to prepare Example 20 where 2-fluoro-6-morpholinonicotinic acid and 6-fluoro-2-morpholinonicotinic acid, which were prepared similarly to 3-fluoro-5-morpholinopicolinic acid and 5-fluoro-3-morpholinopicolinic acid in Examples, 137 and 138, were used, respectively, in place of 5-chlorofuran-2-carboxylic acid. Example 137: ESI-MS m/z: 500.5[M+H]$^+$. $^1$H NMR (300 MHz, DMSO-d$_6$) δ 3.58 (d, J=4.8 Hz, 4H), 3.69 (m, 4H), 5.13 (d, J=8.6 Hz, 1H), 6.87 (d, J=8.8 Hz, 1H), 7.21-7.39 (m, 3H), 7.41-7.57 (m, 5H), 7.58-7.74 (m, 1H), 8.01 (m 1H), 9.02 (d, J=8.6 Hz, 1H), 10.97 (s, 1H). Example 138: ESI-MS m/z: 500.5[M+H]$^+$. $^1$H NMR (300 MHz, DMSO-d$_6$) δ 3.09-3.23 (m, 4H), 3.66 (m, 4H), 5.14 (d, J=8.5 Hz, 1H), 6.70 (m, 1H), 7.21-7.40 (m, 3H), 7.39-7.59 (m, 5H), 7.67 (m, 1H), 8.08 (m, 1H), 8.45 (s, 0.35H), 9.15 (d, J=8.6 Hz, 1H), 10.94 (s, 1H).

Example 151

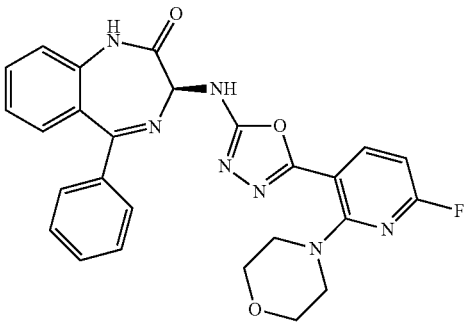 [SMILES: O=C1Nc2ccccc2C(c2ccccc2)=N[C@@H]1Nc1nnc(-c2ccc(F)nc2N2CCOCC2)o1]

Example 151 Step a

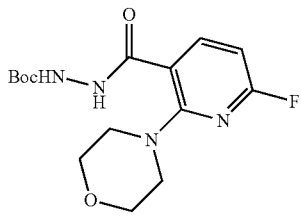 [SMILES: CC(C)(C)OC(=O)NNC(=O)c1ccc(F)nc1N1CCOCC1]

A solution of 6-fluoro-2-morpholinonicotinic acid, which was prepared similarly as 5-fluoro-2-morpholinonicotinic acid described in Example 145 step a, (280 mg, 1.22 mmol), tert-butyl hydrazinecarboxylate (161 mg, 1.22 mmol), HATU (464 mg, 1.22 mmol) and DIPEA (0.34 mL, 2.04 mmol) in DMF (5 mL) was stirred for 1 hour at room temperature. It was purified by reverse phase C18 column chromatography (MeCN/H$_2$O) to give tert-butyl 2-(6-fluoro-2-morpholinonicotinoyl)hydrazine-1-carboxylate as a white solid (400 mg, 96%). ESI-MS m/z: 341.2 [M+H]$^+$.

Example 151 Step b

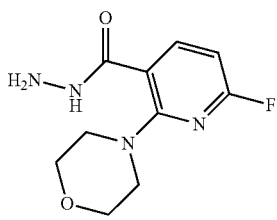 [SMILES: NNC(=O)c1ccc(F)nc1N1CCOCC1]

A solution of tert-butyl 2-(6-fluoro-2-morpholinonicotinoyl)hydrazine-1-carboxylate (400 mg, 1.18 mmol) and conc. HCl (0.4 mL) in EA (2 mL) was stirred for 1 hour. It was concentrated, adjusted to PH=7-8 with saturated aqueous NaHCO$_3$. The crude product was purified by reverse phase C18 column chromatography (MeCN/H$_2$O) to give 6-fluoro-2-morpholinonicotinohydrazide as a pale yellow solid (210 mg, 75%). ESI-MS m/z: 241.2 [M+H]+.

Example 151 Step c

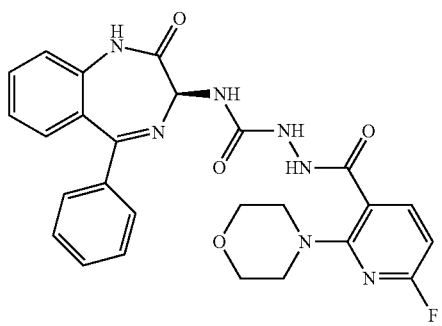 [SMILES: O=C(NNC(=O)c1ccc(F)nc1N1CCOCC1)N[C@H]1N=C(c2ccccc2)c2ccccc2NC1=O]

CDI (160 mg, 0.96 mmol) was added to a solution of (S)-3-amino-5-phenyl-1,3-dihydro-2H-benzo[e][1,4]diazepin-2-one (A) from Example 136 steps f and/or i (242 mg, 0.96 mmol), in MeCN (3 mL) and DMF (0.6 mL), and then stirred for 1 hour at room temperature. Then 6-fluoro-2-morpholinonicotinohydrazide (210 mg, 0.88 mmol) was added and then stirred for 48 hours at room temperature. The crude product was purified by reverse phase C18 column chromatography (MeCN/H$_2$O) to give (S)-2-(6-fluoro-2-morpholinonicotinoyl)-N-(2-oxo-5-phenyl-2,3-dihydro-1H-benzo[e][1,4]diazepin-3-yl)hydrazine-1-carboxamide as a light yellow solid (300 mg). ESI-MS m/z: 518.2 [M+H]+.

Example 151 Step d

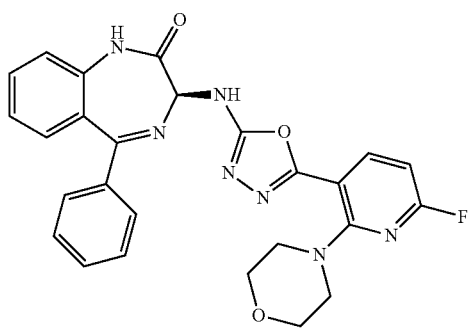

A solution of (S)-2-(6-fluoro-2-morpholinonicotinoyl)-N-(2-oxo-5-phenyl-2,3-dihydro-1H-benzo[e][1,4]diazepin-3-yl)hydrazine-1-carboxamide (300 mg, 0.58 mmol), TsCl (166 mg, 0.87 mmol) and TEA (117 mg, 1.16 mmol) in DCM (5 mL) was stirred for 1 hour before concentrated. The crude product was purified by Prep-HPLC (MeCN/H$_2$O) to give (S)-3-((5-(6-fluoro-2-morpholinopyridin-3-yl)-1,3,4-oxadiazol-2-yl)amino)-5-phenyl-1,3-dihydro-2H-benzo[e][1,4]diazepin-2-one as a white solid (59 mg, 20%). ESI-MS m/z: 500.3 [M+H]+. $^1$H NMR (300 MHz, DMSO-d$_6$) δ 3.11-3.23 (m, 4H), 3.66 (m, 4H), 5.14 (d, J=8.6 Hz, 1H), 6.70 (m, 1H), 7.18-7.38 (m, 3H), 7.41-7.59 (m, 5H), 7.67 (m, 1H), 8.08 (m, 1H), 9.14 (d, J=8.6 Hz, 1H), 10.96 (s, 1H).

Example 152

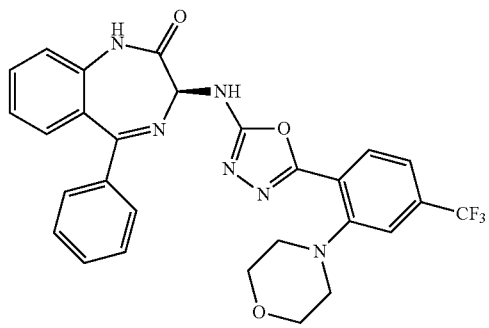 [SMILES: O=C1Nc2ccccc2C(c2ccccc2)=N[C@@H]1Nc1nnc(-c2ccc(C(F)(F)F)cc2N2CCOCC2)o1]

Example 152 Step a

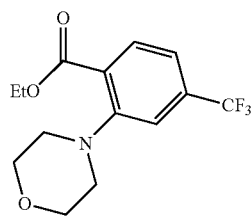

A solution of 2-morpholino-4-(trifluoromethyl)benzoic acid (1.0 g, 0.35 mol), H$_2$SO$_4$ (3 mL) in EtOH (10 mL) was stirred for 4 hours at 80° C. It was diluted with water, extracted with EA (×3), washed with brine (×2). The organic layer was dried and concentrated to give 869 mg (crude) of ethyl 2-morpholino-4-(trifluoromethyl)benzoate as yellow oil, which was used directly in the next step. ESI-MS m/z: 304.2 [M+H]+.

Example 152 Step b

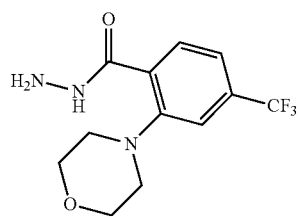 [SMILES: NNC(=O)c1ccc(C(F)(F)F)cc1N1CCOCC1]

A solution of the compound from step 1 (869 mg, 2.87 mmol) and NH$_2$NH$_2$.H$_2$O (5 mL) in EtOH (15 mL) was refluxed for 13 hours. The crude product was purified by reverse phase C18 column chromatography (MeCN/H$_2$O) to give desired compound as a white solid (651 mg, 78%). ESI-MS m/z: 290.1 [M+H]+.

Example 152 Step c

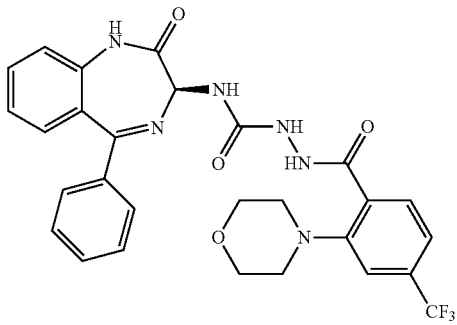 [SMILES: O=C(NNC(=O)c1ccc(C(F)(F)F)cc1N1CCOCC1)N[C@H]1N=C(c2ccccc2)c2ccccc2NC1=O]

CDI (180 mg, 0.80 mmol) was added to a solution of (S)-3-amino-5-phenyl-1,3-dihydro-2H-benzo[e][1,4]diazepin-2-one (A) from Example 136 steps f and/or i (200 mg, 0.80 mmol) in MeCN (3 mL) and DMF (0.6 mL) and then stirred for 1 hour. The compound from step b (315 mg, 1.10 mmol) was added and then stirred for 72 hours. The crude product was purified by reverse phase C18 column chromatography (MeCN/H$_2$O) to give desired compound as a light yellow solid (283 mg, 63%). ESI-MS m/z: 567.3 [M+H]$^+$.

Example 152 Step d

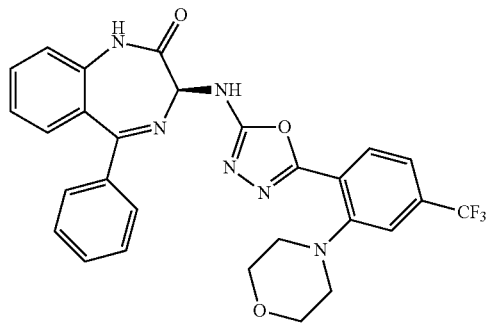

A solution of the compound from step c (283 mg, 0.50 mmol), TsCl (285 mg, 0.75 mmol) and TEA (0.5 mL) in DCM (5 mL) was stirred for 16 hours before concentrated. The crude product was purified by Prep-HPLC (MeCN/H$_2$O) to give the title compound as a light yellow solid (205 mg, 75%). ESI-MS m/z: 549.2 [M+H]$^+$. $^1$H NMR (300 MHz, DMSO-d$_6$) δ 2.95 (dd, J=6.3, 3.0 Hz, 4H), 3.71 (dd, J=5.7, 3.5 Hz, 4H), 5.18 (d, J=8.5 Hz, 1H), 7.18-7.63 (m, 10H), 7.67 (ddd, J=8.5, 7.1, 1.7 Hz, 1H), 7.86-7.98 (m, 1H), 9.26 (d, J=8.6 Hz, 1H), 10.97 (s, 1H).

Example 153

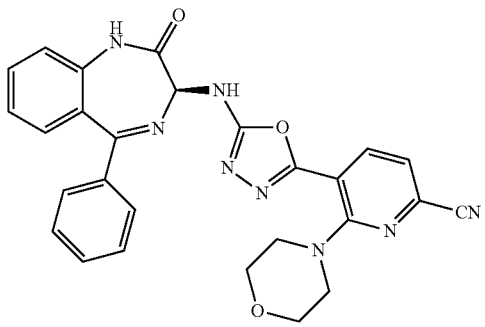 [SMILES: N#Cc1ccc(-c2nnc(N[C@H]3N=C(c4ccccc4)c4ccccc4NC3=O)o2)c(N2CCOCC2)n1]

Example 153 Step a

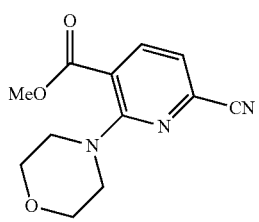 [SMILES: COC(=O)c1ccc(C#N)nc1N1CCOCC1]

A solution morpholine (0.85 g, 9.8 mmol) in DMF (20 mL) was added dropwise to methyl 2,6-dichloronicotinate (2 g, 9.8 mmol) in DMF (100 mL). It was stirred for 1 hour at rt. The mixture was diluted with water, extracted with EA (×3) and washed with bine (×2). The organic layer was dried and concentrated. The residue was chromatographed (silica gel, PE:EA=10:1) to give methyl 6-chloro-2-morpholinonicotinate as light yellow solid (0.6 g, 24%). ESI-MS m/z: 257.2 [M+H]$^+$.

Example 153 Step b

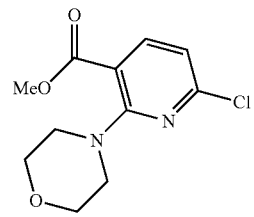 [SMILES: COC(=O)c1ccc(Cl)nc1N1CCOCC1]

A solution of methyl 6-chloro-2-morpholinonicotinate (0.6 g, 2.34 mmol), Zn(CN)$_2$ (0.54 g, 4.68 mmol), Pd(PPh$_3$)$_4$ (0.53 g, 0.46 mmol) in DMF (30 mL) was stirred for 2 hours at 80° C. under nitrogen. It was diluted with EA and washed with water (×2). The organic layer was dried, concentrated and purified by Prep-TLC (PE/EA=3:1) to give methyl 6-cyano-2-morpholinonicotinate. ESI-MS m/z: 248.2[M+H]$^+$.

Example 153 Step c

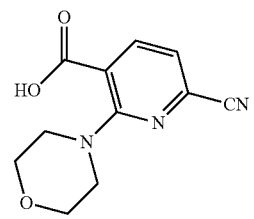 [SMILES: N#Cc1ccc(C(=O)O)c(N2CCOCC2)n1]

A solution of methyl 6-cyano-2-morpholinonicotinate, LiOH (0.1 g, 2.68 mmol) in THF (5 mL) and water (2 mL) was stirred at room temperature for 5 hours. The solvent was remove and the crude product was purified by reverse phase C18 column chromatography (MeCN/H$_2$O) to give 6-cyano-2-morpholinonicotinic acid as a white solid (0.4 g). ESI-MS m/z: 234.2 [M+H]$^+$.

Example 153 Step d

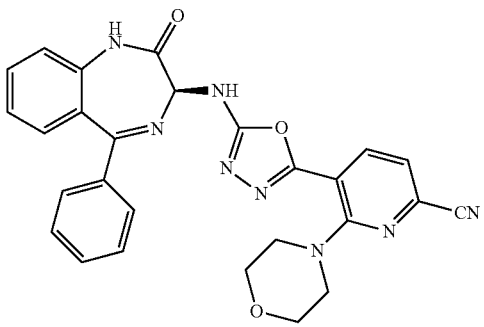 [SMILES: N#Cc1ccc(-c2nnc(N[C@H]3N=C(c4ccccc4)c4ccccc4NC3=O)o2)c(N2CCOCC2)n1]

Example 153 was prepared using a procedure similar to that used to prepare Example 151 where 6-cyano-2-morpholinonicotinic acid was used in place of 6-fluoro-2-morpholinonicotinic acid. ESI-MS m/z: 507.4 [M+H]⁺. $^1$H NMR (400 MHz, DMSO-d$_6$) δ 3.21 (m, 4H), 3.71 (m, 4H), 5.19 (s, 1H), 7.33 (m, 3H), 7.50 (m, 5H), 7.62 (d, J=7.8 Hz, 1H), 7.69 (m, 1H), 8.16 (d, J=7.7 Hz, 1H), 9.38 (s, 1H), 10.91 (s, 1H).

Example 154

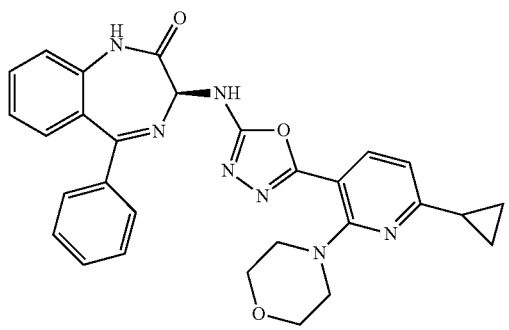 [SMILES: O=C1Nc2ccccc2C(c2ccccc2)=N[C@@H]1Nc1nnc(-c2ccc(C3CC3)nc2N2CCOCC2)o1]

Example 154 Step a

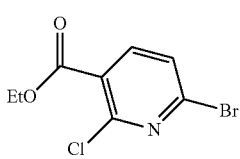

A solution of compound 1 (940 mg, 4 mmol) and H$_2$SO$_4$ (2 mL) in EtOH (20 mL) was stirred for 18 hours at 80° C. Then it was adjusted PH to 8~9, extracted with EA (3×), dried Na$_2$SO$_4$, filtered and concentrated to give desired compound as a white solid (1052 mg, 100%). ESI-MS m/z: X [M+H]⁺.

Example 154 Step b

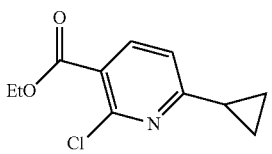 [SMILES: CCOC(=O)c1ccc(C2CC2)nc1Cl]

A solution of compound from step a (526 mg, 2 mmol), cyclopropylboronic acid (860 mg, 10 mmol), Pd(dppf)Cl$_2$ (146 mg, 0.2 mmol) and K$_2$CO$_3$ (550 mg, 4 mmol) in dioxane (12 mL) was heated to 70° C. by microwave for 1.5 hours. Then it was poured into water and extracted with EA (3×). The residue was purified by reverse phase C18 column chromatography (MeCN/H$_2$O) to give desired compound as brown oil. (315 mg, 70%). ESI-MS m/z: 225.9 [M+H]⁺.

Example 154 Step c

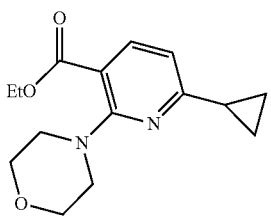 [SMILES: CCOC(=O)c1ccc(C2CC2)nc1N1CCOCC1]

A solution of compound from step b (315 mg, 1.4 mmol) in morpholine (10 mL) was stirred for 2 hours at 80° C. The solvents were removed and it was purified by reverse phase C18 column chromatography (MeCN/H$_2$O) to give desired compound as brown oil. (331 mg, 86%). ESI-MS m/z: 277.2 [M+H]⁺.

Example 154 Step d

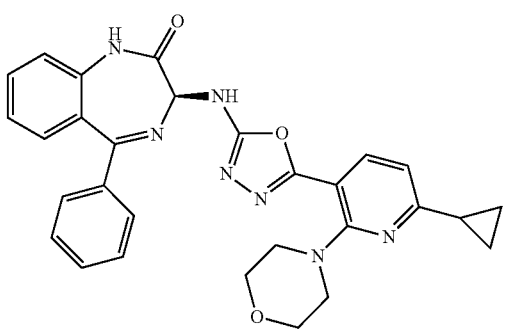 [SMILES: O=C1Nc2ccccc2C(c2ccccc2)=N[C@@H]1Nc1nnc(-c2ccc(C3CC3)nc2N2CCOCC2)o1]

Example 154 was prepared using a procedure similar to that used to prepare Example 152 where ethyl 6-cyclopropyl-2-morpholinonicotinate was used in place of ethyl 2-morpholino-4-(trifluoromethyl)benzoate. ESI-MS m/z: 522.4 [M+H]⁺. $^1$H NMR (300 MHz, Methanol-d4) δ 0.87-1.13 (m, 4H), 2.04 (m, 1H), 3.22 (m, 4H), 3.77 (m, 4H), 4.82 (s, 1H), 5.28 (s, 1H), 6.92 (d, J=7.9 Hz, 1H), 7.22-7.71 (m, 9H), 7.87 (d, J=7.9 Hz, 1H).

Example 155

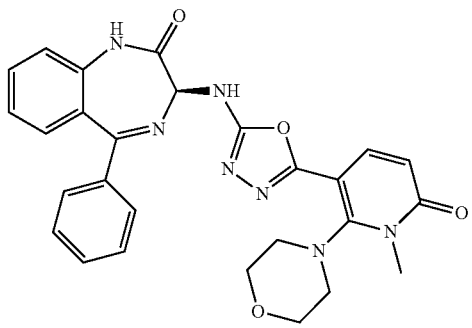 [SMILES: Cn1c(N2CCOCC2)c(-c2nnc(N[C@H]3N=C(c4ccccc4)c4ccccc4NC3=O)o2)ccc1=O]

Example 155 Step a

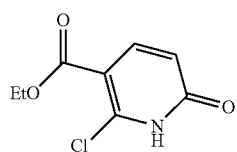

A solution of the 2-chloro-6-oxo-1, 6-dihydropyridine-3-carboxylic acid (1.0 g, 5.78 mmol), H$_2$SO$_4$ (5 mL) in EtOH (20 mL) was stirred at 80° C. for 4 hours. Then H$_2$O (100 mL) was added to the mixture and it was extracted with EA (×3). The organic layer was dried and purified by reverse phase C18 column chromatography (MeCN/H$_2$O) to give ethyl 2-chloro-6-oxo-1,6-dihydropyridine-3-carboxylate as yellow oil (950 mg, 81%). ESI-MS m/z: 201.9 [M+H]$^+$.

Example 155 Step b

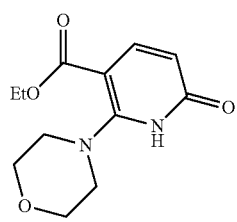

A solution of ethyl 2-chloro-6-oxo-1,6-dihydropyridine-3-carboxylate (402 mg, 2.0 mmol) in morpholine (5 mL) was stirred at 100° C. for 2 hours. Then H$_2$O (20 mL) was added to the mixture and it was extracted with EA (×3). The organic layer was dried and purified by reverse phase C18 column chromatography (MeCN/H$_2$O) to give ethyl 2-morpholino-6-oxo-1,6-dihydropyridine-3-carboxylate as yellow oil (450 mg, 89%). ESI-MS m/z: 253.0 [M+H]$^+$.

Example 155 Step c

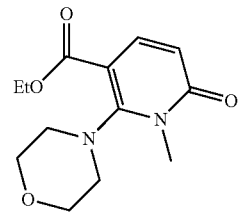

A solution of ethyl 2-morpholino-6-oxo-1,6-dihydropyridine-3-carboxylate (400 mg, 1.58 mmol), iodomethane (1127 mg, 7.93 mmol), t-BuONa (303 mg, 3.16 mmol) in DMF (10 mL) was stirred at rt for 2 hours. Then H$_2$O (20 mL) was added to the mixture and it was extracted with EA (×3). The organic layer was dried and purified by flash to give ethyl 1-methyl-2-morpholino-6-oxo-1,6-dihydropyridine-3-carboxylate as yellow oil (320 mg, 76%). ESI-MS m/z: 267.0 [M+H]$^+$.

Example 155 Step d

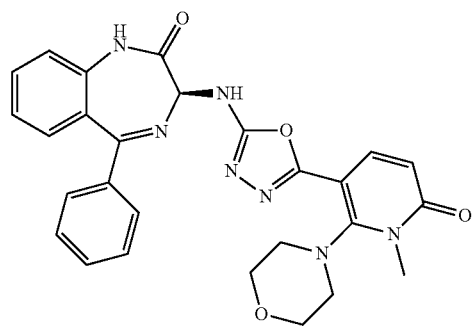 [SMILES: Cn1c(N2CCOCC2)c(-c2nnc(N[C@H]3N=C(c4ccccc4)c4ccccc4NC3=O)o2)ccc1=O]

Example 155 was prepared using a procedure similar to that used to prepare Example 152 where ethyl 1-methyl-2-morpholino-6-oxo-1,6-dihydropyridine-3-carboxylate was used in place of ethyl 2-morpholino-4-(trifluoromethyl)benzoate. ESI-MS m/z: 512.3 [M+H]$^+$. $^1$H NMR (300 MHz, DMSO-d$_6$) δ 3.21-3.23 (d, J=6.0 Hz, 4H), 3.67-3.70 (m, 4H), 3.88 (s, 1H), 5.12-5.15 (d, J=9.0 Hz, 1H), 6.40-6.42 (d, J=6.0 Hz, 1H), 7.26-7.37 (m, 3H), 7.44-7.57 (m, 5H), 7.65-7.68 (m, 1H), 7.70-7.86 (m, 1H), 9.01-9.04 (m, 1H), 10.96 (s, 1H).

Example 156

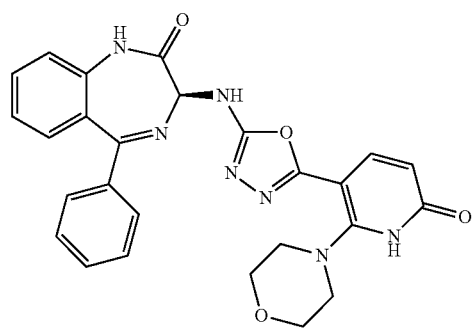 [SMILES: O=C1Nc2ccccc2C(c2ccccc2)=N[C@@H]1Nc1nnc(-c2ccc(=O)[nH]c2N2CCOCC2)o1]

Example 156 Step a

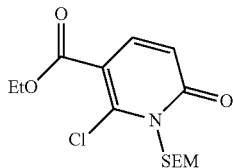

Ethyl 2-morpholino-6-oxo-1,6-dihydropyridine-3-carboxylate, from Example 155 step b, (500 mg, 1.98 mmol) was dissolved in DMF (10 mL) and cooled in an ice bath. NaH (105 mg, 2.62 mmol) was added and then SEMCl (420 mg, 2.52 mmol) was added. The mixture was warmed to rt and stirred for 2 hours. Water (10 mL) was added and the mixture was extracted with EA (20 mL×3). The combined organic phase was dried over anhydrous Na$_2$SO$_4$ and concentrated to give ethyl 2-chloro-6-oxo-1-((2-(trimethylsilyl)ethoxy)methyl)-1,6-dihydropyridine-3-carboxylate as yellow oil (510 mg, 67%). ESI-MS m/z: 383.2 [M+H]$^+$.

Example 156 Step b

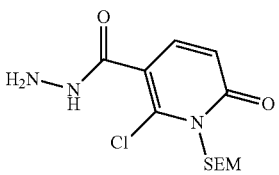 [SMILES: C[Si](C)(C)CCOCn1c(Cl)c(C(=O)NN)ccc1=O]

A solution of ethyl 2-chloro-6-oxo-1-((2-(trimethylsilyl)ethoxy)methyl)-1,6-dihydropyridine-3-carboxylate (510 mg, 1.33 mmol) and NH$_2$NH$_2$·H$_2$O (10 mL) in EtOH (10 mL) was refluxed for 5 hours. The mixture was then cooled to r.t. and concentrated. The residue was purified by reverse phase C18 column chromatography (MeCN/H$_2$O) to give 2-chloro-6-oxo-1-((2-(trimethylsilyl)ethoxy)methyl)-1,6-dihydropyridine-3-carbohydrazide as a yellow solid (300 mg, 61%). ESI-MS m/z: 369.2 [M+H]$^+$.

Example 156 Step c

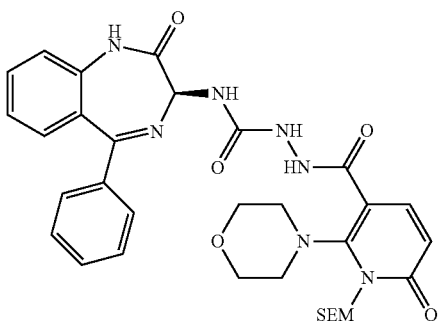 [SMILES: C[Si](C)(C)CCOCn1c(N2CCOCC2)c(C(=O)NNC(=O)N[C@H]2N=C(c3ccccc3)c3ccccc3NC2=O)ccc1=O]

CDI (132 mg, 0.81 mmol) was added to a solution of (S)-3-amino-5-phenyl-1,3-dihydro-2H-benzo[e][1,4]diazepin-2-one (A) from Example 136 steps f and/or i (186 mg, 0.74 mmol) in MeCN (3 mL) and DMF (0.6 mL) and then stirred for 1 hour. Then 2-chloro-6-oxo-1-((2-(trimethylsilyl)ethoxy)methyl)-1,6-dihydropyridine-3-carbohydrazide (300 mg, 0.81 mmol) was added and then stirred for 72 hours and then purified by reverse phase C18 column chromatography (MeCN/H$_2$O) to give (S)-2-(2-morpholino-6-oxo-1-((2-(trimethylsilyl)ethoxy)methyl)-1,6-dihydropyridine-3-carbonyl)-N-(2-oxo-5-phenyl-2,3-dihydro-1H-benzo[e][1,4]diazepin-3-yl)hydrazine-1-carboxamide as an off white solid (300 mg, 63%). ESI-MS m/z: 646.4 [M+H]$^+$.

Example 156 Step d

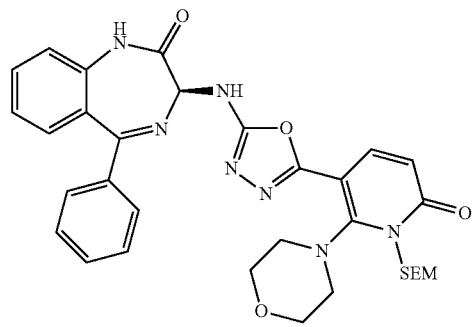 [SMILES: C[Si](C)(C)CCOCn1c(N2CCOCC2)c(-c2nnc(N[C@H]3N=C(c4ccccc4)c4ccccc4NC3=O)o2)ccc1=O]

A solution of (S)-2-(2-morpholino-6-oxo-1-((2-(trimethylsilyl)ethoxy)methyl)-1,6-dihydropyridine-3-carbonyl)-N-(2-oxo-5-phenyl-2,3-dihydro-1H-benzo[e][1,4]diazepin-3-yl)hydrazine-1-carboxamide (300 mg, 0.46 mmol), TsCl (132.8 mg, 0.69 mmol), DMAP (20 mg) and TEA (0.5 mL) in DCM (5 mL) was stirred for 2 hours and then it was concentrated. The crude product was purified by reverse phase C18 column chromatography (MeCN/H$_2$O) to give (S)-3-((5-(2-morpholino-6-oxo-1-((2-(trimethyl silyl)ethoxy)methyl)-1,6-dihydropyridin-3-yl)-1,3,4-oxadiazol-2-yl)amino)-5-phenyl-1,3-dihydro-2H-benzo[e][1,4]diazepin-2-one as a yellow solid (200 mg, 69%). ESI-MS m/z: 628.4 [M+H]$^+$.

Example 156 Step e

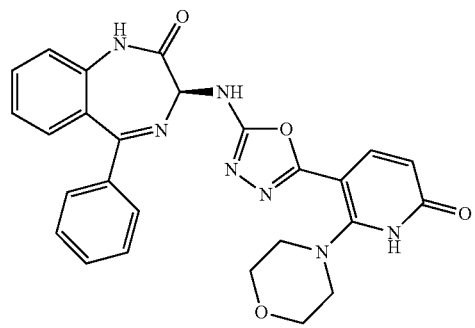 [SMILES: O=C1Nc2ccccc2C(c2ccccc2)=N[C@@H]1Nc1nnc(-c2ccc(=O)[nH]c2N2CCOCC2)o1]

(S)-3-((5-(2-morpholino-6-oxo-1-((2-(trimethylsilyl)ethoxy)methyl)-1,6-dihydropyridin-3-yl)-1,3,4-oxadiazol-2-yl)amino)-5-phenyl-1,3-dihydro-2H-benzo[e][1,4]diazepin-2-one (200 mg, 0.32 mmol) was dissolved in DCM (8 mL) and cooled to 0° C. and TFA (4 mL) was added. The mixture was stirred at rt for 1 hour and then concentrated. The residue was dissolved in DCM and then concentrated for two cycles. The residue was purified by Prep-HPLC to give (S)-3-((5-(2-morpholino-6-oxo-1,6-dihydropyridin-3-yl)-1,3,4-oxadiazol-2-yl)amino)-5-phenyl-1,3-dihydro-2H-benzo[e][1,4]diazepin-2-one as a white solid (51 mg, 32%). ESI-MS m/z: 498.2 [M+H]+. 1H NMR (300 MHz, DMSO-$d_6$) 3.12 (t, J=4.7 Hz, 4H), 3.65 (t, J=4.6 Hz, 4H), 5.12 (d, J=8.7 Hz, 1H), 6.20 (d, J=8.4 Hz, 1H), 7.21-7.39 (m, 3H), 7.39-7.59 (m, 5H), 7.60-7.78 (m, 2H), 8.96 (d, J=8.7 Hz, 1H), 10.96 (s, 1H), 11.12 (s, 1H).

Example 157

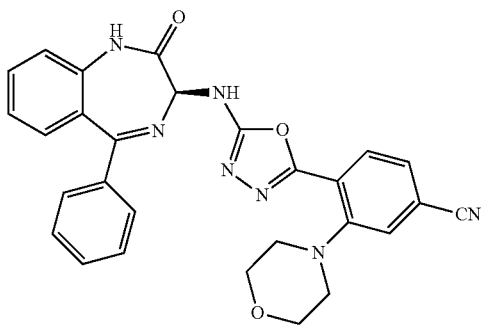 [SMILES: N#Cc1ccc(-c2nnc(N[C@H]3N=C(c4ccccc4)c4ccccc4NC3=O)o2)c(N2CCOCC2)c1]

Example 157 was prepared using a procedure similar to that used to prepare Example 151 where 4-cyano-2-morpholinobenzoic acid, which was prepared in Example 131, was used in place of 6-fluoro-2-morpholinonicotinic acid. ESI-MS m/z: 506.2 [M+H]+. 1H NMR (300 MHz, DMSO-$d_6$) δ 2.94-2.97 (m, 4H), 3.67-3.74 (m, 4H), 5.20 (d, J=8.3 Hz, 1H), 7.34-7.75 (m, 11H), 7.86 (d, J=8.0 Hz, 1H), 9.31 (d, J=8.6 Hz, 1H), 11.00 (s, 1H).

Example 158

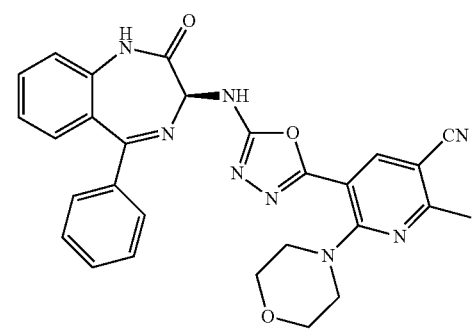 [SMILES: Cc1nc(N2CCOCC2)c(-c2nnc(N[C@H]3N=C(c4ccccc4)c4ccccc4NC3=O)o2)cc1C#N]

Example 158 Step a

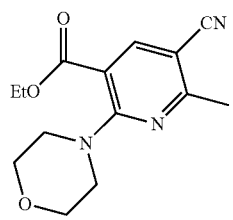 [SMILES: CCOC(=O)c1cc(C#N)c(C)nc1N1CCOCC1]

A solution of ethyl 2-chloro-5-cyano-6-methylnicotinate (1 g, 4.5 mmol) and $K_2CO_3$ (1.24 g, 9 mmol) in morpholine (5 mL) was stirred for 3 hours at 100° C. It was diluted with water and extracted with EA (×3). The organic layer was concentrated and the residue was purified by silica gel chromatography with EtOAc/PE to give 970 mg of desired compound as yellow solid. ESI-MS m/z: 276.2 [M+H]+.

Example 158 Step b

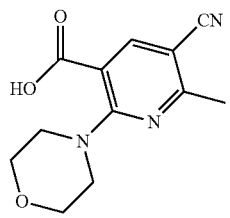 [SMILES: Cc1nc(N2CCOCC2)c(C(=O)O)cc1C#N]

A solution of the compound from step 1 (100 mg, 0.36 mmol), LiOH.$H_2O$ (31 mg, 0.73 mmol), in THF (5 mL) and water (2 mL) was stirred at room temperature overnight. Then it was adjust the pH to 2 by 0.5 M HCl. Solvent was removed. The crude product was purified by reverse phase C18 column chromatography (MeCN/$H_2O$) to give desired compound as a pink solid (80 mg, 89%). ESI-MS m/z: 248.2 [M+H]+.

Example 158 Step c

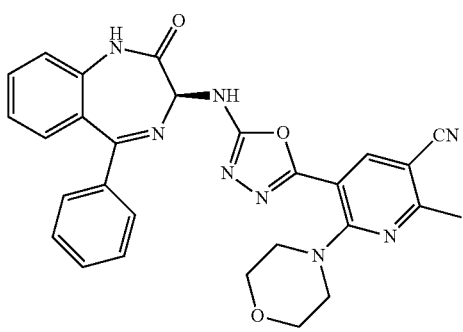 [SMILES: Cc1nc(N2CCOCC2)c(-c2nnc(N[C@H]3N=C(c4ccccc4)c4ccccc4NC3=O)o2)cc1C#N]

Example 158 was prepared using a procedure similar to that used to prepare Example 151 where 5-cyano-6-methyl-2-morpholinonicotinic acid was used in place of 6-fluoro-2-morpholinonicotinic acid. ESI-MS m/z: 521.5 [M+H]+. 1H NMR (300 MHz, DMSO-$d_6$) δ 2.55 (s, 3H), 3.33-3.40 (m, 4H), 3.66 (m, 4H), 5.14 (d, J=8.5 Hz, 1H), 7.21-7.42 (m, 3H), 7.39-7.59 (m, 5H), 7.67 (m, 1H), 8.16 (s, 1H), 9.17 (d, J=8.5 Hz, 1H), 10.98 (s, 1H).

Example 159

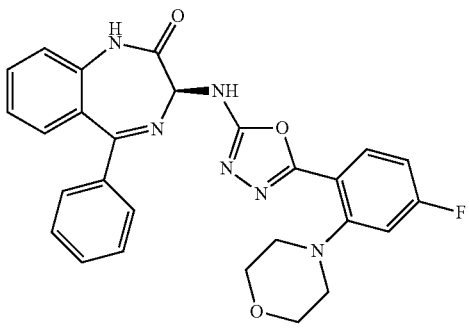 [SMILES: O=C1Nc2ccccc2C(c2ccccc2)=N[C@@H]1Nc1nnc(-c2ccc(F)cc2N2CCOCC2)o1]

Example 159 Step a

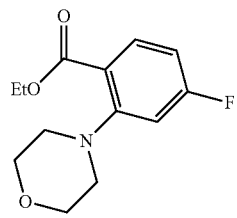 [SMILES: CCOC(=O)c1ccc(F)cc1N1CCOCC1]

A solution of 4-fluoro-2-morpholinobenzoic acid, prepared in Example 127 step a (2.25 g, 10 mmol) and H₂SO₄ (10 mL) in EtOH (50 mL) was stirred for 18 hours at 80° C. The solvent was removed, H₂O (100 mL) was added and it was extracted with EA (3×). The water layer was adjusted PH to 9~10 and extracted with EA (3×). The organic layers were combined and concentrated to give ethyl 4-fluoro-2-morpholinobenzoate as a white solid (1270 mg, 50%). ESI-MS m/z: 254.1 [M+H]$^+$.

Example 159 Step b

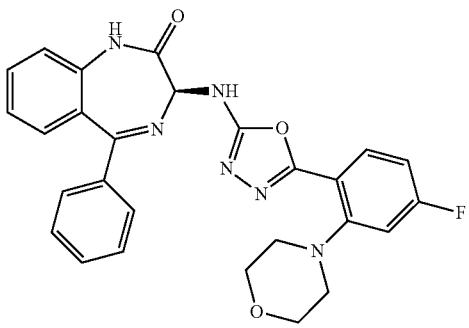 [SMILES: O=C1Nc2ccccc2C(c2ccccc2)=N[C@@H]1Nc1nnc(-c2ccc(F)cc2N2CCOCC2)o1]

Example 159 was prepared using a procedure similar to that used to prepare Example 152 where ethyl 4-fluoro-2-morpholinobenzoate was used in place of ethyl 2-morpholino-4-(trifluoromethyl)benzoate. ESI-MS m/z: 499.3 [M+H]$^+$. $^1$H NMR (300 MHz, Methanol-d4) δ 2.94-3.04 (m, 4H), 3.77-3.87 (m, 4H), 5.30 (s, 1H), 6.82-7.02 (m, 2H), 7.23-7.83 (m, 10H).

Example 160

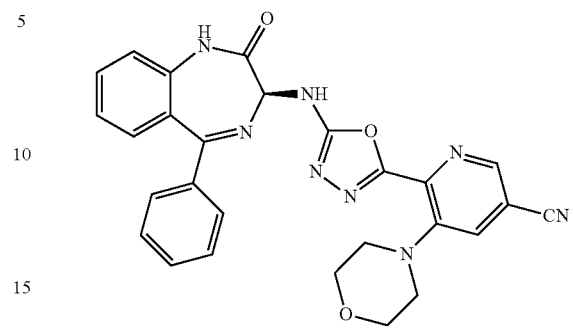

Example 160 Step a

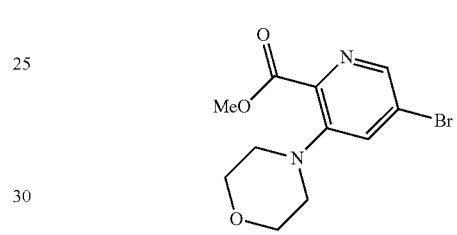

A solution of the methyl 5-bromo-3-fluoropicolinate (1.0 g, 4.29 mmol), K₂CO₃ (1.2 g, 8.58 mmol) in morpholine (10 mL) was stirred at 120° C. for 2 hours. Then H₂O (150 mL) was added to the mixture and it was extracted with EA (×3). The organic layer was dried and purified by reverse phase C18 column chromatography (MeCN/H₂O) to give desired compound as yellow oil (950 mg, 74%). ESI-MS m/z: 300.9 [M+H]$^+$.

Example 160 Step b

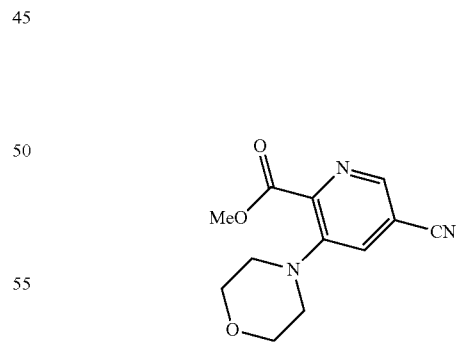

A solution of the compound from step a (900 mg, 3.00 mmol), Pd(PPh₃)₄ (693 mg, 0.60 mmol), Zn (CN)₂ (696 mg, 6.00 mmol) in DMF (5 mL) was stirred at 120° C. for 2 hours. Then H₂O (20 ml) was added to the mixture and it was extracted with EA (×3). The organic layer was dried and purified by reverse phase C18 column chromatography (MeCN/H₂O) to give desired compound as yellow oil (330 mg, 44%). ESI-MS m/z: 248.2 [M+H]$^+$.

Example 160 Step c

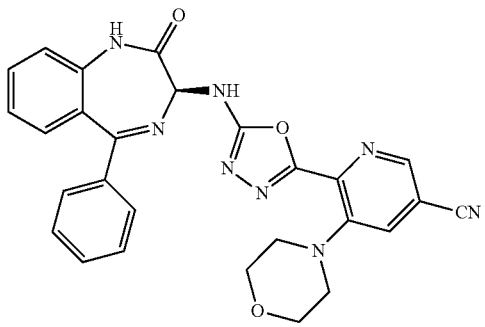

Example 160 was prepared using a procedure similar to that used to prepare Example 152 where methyl 5-cyano-3-morpholinopicolinate was used in place of ethyl 2-morpholino-4-(trifluoromethyl)benzoate. ESI-MS m/z: 507.2 [M+H]+. $^1$H NMR (400 MHz, DMSO-$d_6$) δ 3.02-3.04 (m, 4H), 3.71-3.73 (m, 4H), 5.19-5.21 (d, J=8.0 Hz, 1H), 7.26-7.30 (m, 1H), 7.34-7.36 (m, 2H), 7.44-7.55 (m, 5H), 7.65-7.70 (m, 1H), 8.13 (s, 1H), 8.72 (s, 1H), 9.42-9.45 (m, 1H), 10.98 (s, 1H).

Example 161

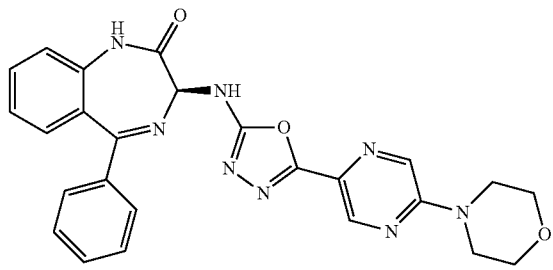 [SMILES: O=C1Nc2ccccc2C(c2ccccc2)=N[C@@H]1Nc1nnc(-c2cnc(N3CCOCC3)cn2)o1]

Example 161 Step a

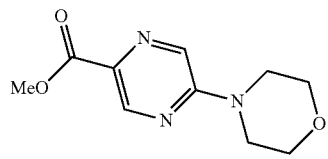 [SMILES: COC(=O)c1cnc(N2CCOCC2)cn1]

A solution of methyl 5-chloropyrazine-2-carboxylate (1.0 g, 5.79 mmol) and morpholine (756 mg, 8.69 mmol) in DMSO (10 mL) was added K$_2$CO$_3$ (2.4 g, 17.4 mmol). The mixture was heated to 100° C. for 4 hours and then cooled to r.t. Water (20 mL) was added and the mixture was extracted with EA (20 mL×3). The combined organic phase was washed with water (20 mL) and brine (20 mL). It was then dried over anhydrous Na$_2$SO$_4$ and concentrated to give the desired product as a yellow solid (850 mg) which was used directly next step. ESI-MS m/z: 224.1 [M+H]+.

Example 161 Step b

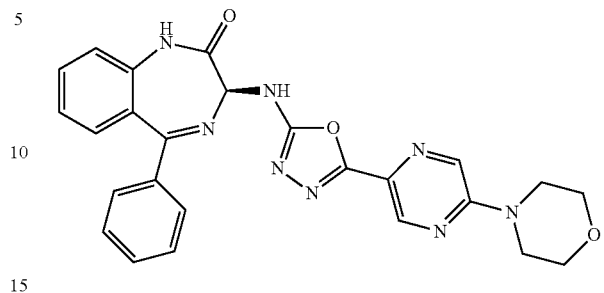

Example 161 was prepared using a procedure similar to that used to prepare Example 152 where methyl 5-morpholinopyrazine-2-carboxylate was used in place of ethyl 2-morpholino-4-(trifluoromethyl)benzoate. ESI-MS m/z: 483.2 [M+H]+. $^1$H NMR (300 MHz, DMSO-$d_6$) δ 3.62-3.79 (m, 8H), 5.17 (d, J=7.8 Hz, 1H), 7.18-7.80 (m, 9H), 8.42 (s, 1H), 8.63 (s, 1H), 9.13 (d, J=8.2 Hz, 1H), 10.83-10.93 (m, 1H).

Example 162

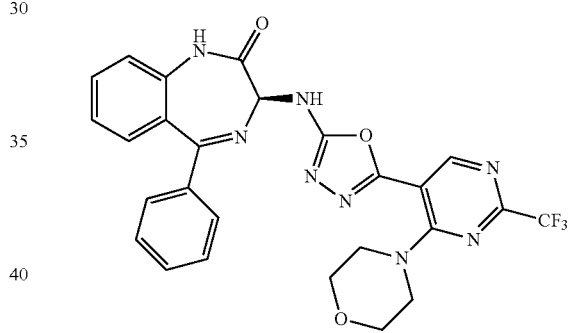

Example 162 Step a

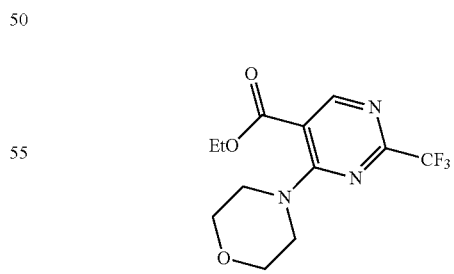

A solution of ethyl 4-chloro-2-(trifluoromethyl)pyrimidine-5-carboxylate (0.5 g, 1.97 mmol) in morpholine (5 mL) was stirred for 1 hour at rt. The mixture was concentrated. The residue was purified by prep-TLC (PE:EA=2:1) to give desired compound as light yellow solid (0.6 g, 100%). ESI-MS m/z: 306.2 [M+H]+.

Example 162 Step b

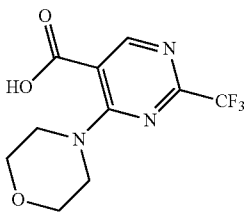 [SMILES: O=C(O)c1cnc(C(F)(F)F)nc1N1CCOCC1]

A solution of the compound from step 1 (600 mg, 1.97 mmol), LiOH (189 mg, 7.88 mmol) in THF (5 mL) and water (5 mL) were stirred at 70° C. for 3 hours. The solvent was removed and the crude product was purified by reverse phase C18 column chromatography (MeCN/H$_2$O) to give desired compound as a white solid (0.45 g, 82%). ESI-MS m/z: 278.1 [M+H]$^+$.

Example 162 Step c

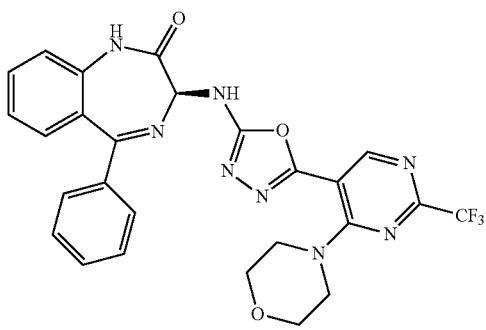 [SMILES: O=C1Nc2ccccc2C(c2ccccc2)=N[C@@H]1Nc1nnc(-c2cnc(C(F)(F)F)nc2N2CCOCC2)o1]

Example 162 was prepared using a procedure similar to that used to prepare Example 151 where 4-morpholino-2-(trifluoromethyl)pyrimidine-5-carboxylic acid was used in place of 6-fluoro-2-morpholinonicotinic acid. ESI-MS m/z: 551.6 [M+H]$^+$. $^1$H NMR (300 MHz, DMSO-d$_6$) δ 3.50 (m, 4H), 3.70 (m, 4H), 5.18 (d, J=8.0 Hz, 1H), 7.22-7.42 (m, 3H), 7.42-7.62 (m, 5H), 7.68 (m, 1H), 8.71 (s, 1H), 9.31 (d, J=8.4 Hz, 1H), 11.02 (s, 1H).

Example 163

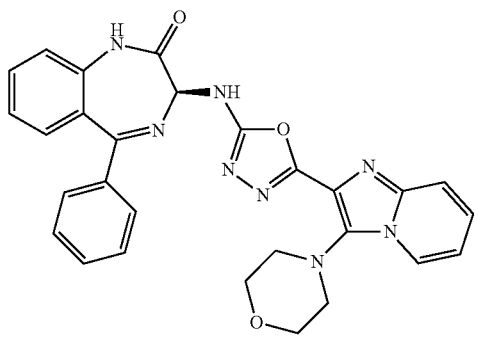 [SMILES: O=C1Nc2ccccc2C(c2ccccc2)=N[C@@H]1Nc1nnc(-c2nc3ccccn3c2N2CCOCC2)o1]

Example 163 Step a

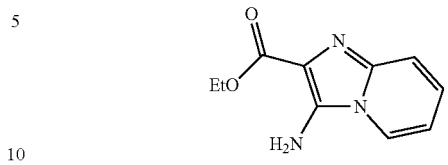

A mixture of 2-aminopyridine (940 mg, 10 mmol) and ethyl glyoxalate solution (50% solution in toluene) (2 mL, 10 mmol) was stirred at rt for 2 min. THF (20 mL) and DABCO (1.12 g, 10 mmol) were subsequently added. The reaction mixture was cooled to 0-5° C. and TMSCN (1.25 mL, 1 mmol) was added. The mixture was heated under microwave irradiation at 120° C. After completion of the reaction (monitored by TLC, 15 min), the solvent was evaporated under vacuum. The residue was purified by reverse phase C18 column chromatography (MeCN/H$_2$O) to give desired compound (600 mg) as yellow oil. ESI-MS m/z: 206.0 [M+H]$^+$.

Example 163 Step b

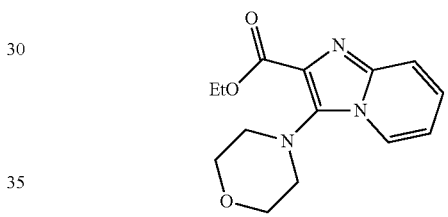

A solution of the compound from step a (600 mg, 2.92 mmol), 1-bromo-2-(2-bromoethoxy) ethane (1.01 g, 4.39 mmol) and Cs$_2$CO$_3$ (2.85 g, 8.76 mmol) in DMA (20 mL) was stirred for 4 hours at 120° C. The crude product was purified by reverse phase C18 column chromatography (MeCN/H$_2$O) to give desired compound as a yellow solid (500 mg). ESI-MS m/z: 276.2 [M+H]$^+$.

Example 163 Step c

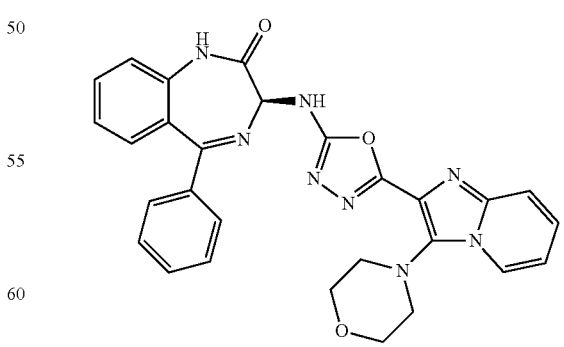

Example 163 was prepared using a procedure similar to that used to prepare Example 152 where ethyl 3-morpholinoimidazo[1,2-a]pyridine-2-carboxylate was used in place of ethyl 2-morpholino-4-(trifluoromethyl)benzoate. ESI-MS m/z: 521.5 [M+H]+. 1H NMR (300 MHz, Methanol-d4) δ 3.90 (t, J=4.6 Hz, 4H), 5.34 (s, 1H), 7.08 (td, J=6.8, 1.2 Hz, 1H), 7.26-7.33 (m, 1H), 7.34-7.70 (m, 10H), 8.46 (dt, J=7.0, 1.2 Hz, 1H).

Example 164

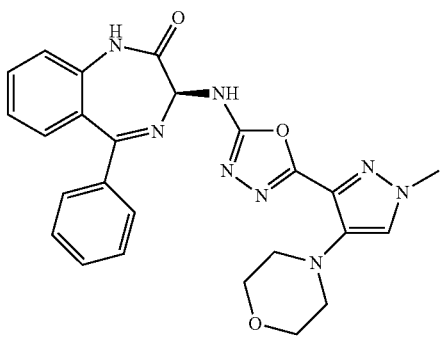 [SMILES: Cn1cc(N2CCOCC2)c(-c2nnc(N[C@H]3N=C(c4ccccc4)c4ccccc4NC3=O)o2)n1]

Example 164 Step a

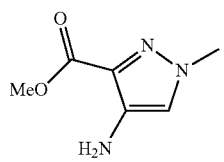

A solution of methyl 1-methyl-4-nitro-1H-pyrazole-3-carboxylate (1.0 g, 5.41 mmol) and Pd/C (200 mg) in MeOH (60 mL) was stirred for 1 hour at 25° C. Pd/C was filtered out and the filtrate was concentrated to give desired compound as a white solid (800 mg, 95%).

Example 164 Step b

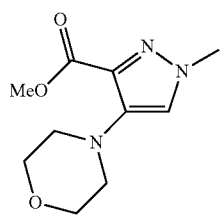 [SMILES: COC(=O)c1nn(C)cc1N1CCOCC1]

A solution of compound from step a (775 mg, 5 mmol), 1-chloro-2-(2-chloroethoxy)ethane (1420 mg, 10 mmol), KI (1660 mg, 10 mmol) and K2CO3 (2070 mg, 15 mmol) in DMF (60 mL) was stirred for 3 hours at 120° C. The solvent was removed and it was purified by reverse phase C18 column chromatography (MeCN/H2O) to give desired compound as a light yellow solid. (450 mg, 40%). ESI-MS m/z: 226.0 [M+H]+.

Example 164 Step c

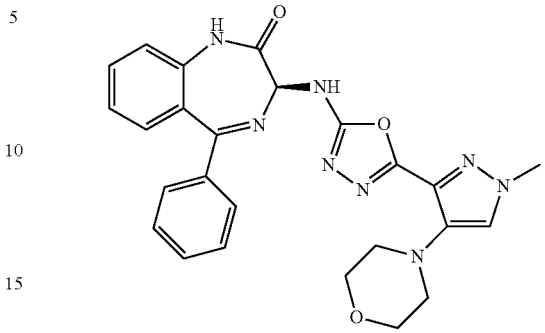

Example 164 was prepared using a procedure similar to that used to prepare Example 152 where methyl 1-methyl-4-morpholino-1H-pyrazole-3-carboxylate was used in place of ethyl 2-morpholino-4-(trifluoromethyl)benzoate. ESI-MS m/z: 485.4 [M+H]+. 1H NMR (300 MHz, DMSO-d6) δ 2.94 (m, 4H), 3.68 (m, 4H), 3.86 (d, J=2.2 Hz, 3H), 5.09-5.19 (m, 1H), 7.23-7.41 (m, 3H), 7.38-7.75 (m, 7H), 9.05 (m, 1H), 10.91 (s, 1H).

Example 165

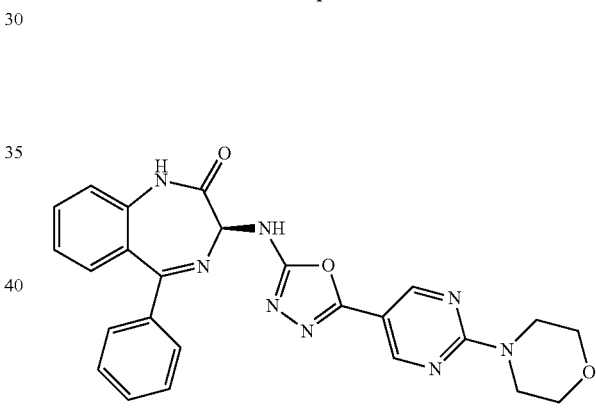

Example 165 Step a

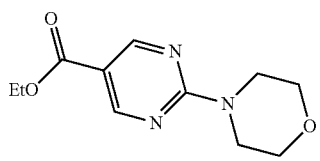 [SMILES: CCOC(=O)c1cnc(N2CCOCC2)nc1]

A solution of ethyl 4-chloropyrimidine-5-carboxylate (0.90 g, 5.0 mmol) in morpholine (5 mL) was stirred for 1 hour at rt. The mixture was concentrated. The residue was purified by prep-TLC (PE:EA=2:1) to give desired compound as light yellow solid (869 mg, 74%). ESI-MS m/z: 238.1 [M+H]+.

Example 165 Step b

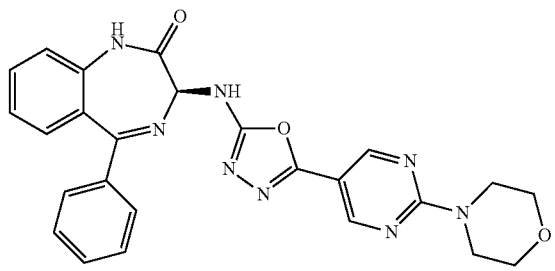 [SMILES: O=C1Nc2ccccc2C(c2ccccc2)=N[C@@H]1Nc1nnc(-c2cnc(N3CCOCC3)nc2)o1]

Example 165 was prepared using a procedure similar to that used to prepare Example 152 where ethyl 2-morpholinopyrimidine-5-carboxylate was used in place of ethyl 2-morpholino-4-(trifluoromethyl)benzoate. ESI-MS m/z: 483.1 [M+H]$^+$. $^1$H NMR (300 MHz, DMSO-d$_6$) δ 3.69 (d, J=4.9 Hz, 4H), 3.81 (t, J=4.8 Hz, 4H), 5.14 (d, J=8.4 Hz, 1H), 7.21-7.42 (m, 3H), 7.42-7.61 (m, 5H), 7.61-7.75 (m, 1H), 8.75 (s, 2H), 9.05 (d, J=8.6 Hz, 1H), 10.98 (s, 1H).

Example 166

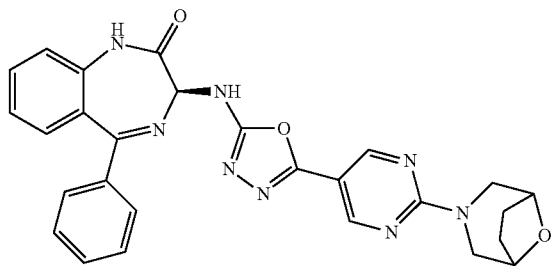 [SMILES: O=C1Nc2ccccc2C(c2ccccc2)=N[C@@H]1Nc1nnc(-c2cnc(N3CC4CCC(C3)O4)nc2)o1]

Example 166 was prepared using a procedure similar to that used to prepare Example 152 where ethyl 2-(8-oxa-3-azabicyclo[3.2.1]octan-3-yl)pyrimidine-5-carboxylate, which was prepared similarly to ethyl 2-morpholinopyrimidine-5-carboxylate in Example 165 step a, was used in place of ethyl 2-morpholino-4-(trifluoromethyl)benzoate. ESI-MS m/z: 509.2 [M+H]$^+$. $^1$H NMR (400 MHz, DMSO-d$_6$) δ 1.66 (t, J=6.6 Hz, 2H), 1.84 (dd, J=8.5, 4.3 Hz, 2H), 3.16 (dd, J=13.4, 2.5 Hz, 2H), 4.29 (d, J=13.0 Hz, 2H), 4.37-4.55 (m, 2H), 5.14 (d, J=8.5 Hz, 1H), 7.24-7.40 (m, 3H), 7.43-7.58 (m, 5H), 7.68 (ddd, J=8.4, 7.2, 1.6 Hz, 1H), 8.74 (s, 2H), 9.06 (d, J=8.5 Hz, 1H), 10.82-11.07 (m, 1H).

Example 167

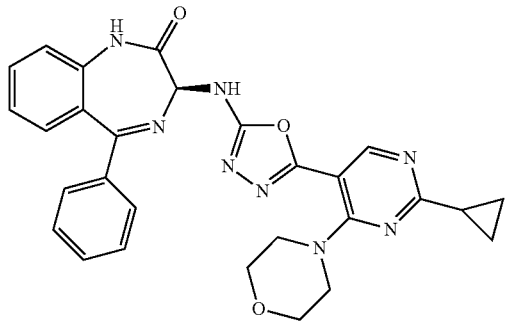

Example 167 Step a

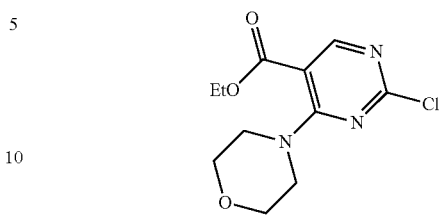

A solution morpholine (0.79 g) in DMF (20 mL) was added dropwise to ethyl 2,4-dichloropyrimidine-5-carboxylate (2 g, 9.1 mmol) in DMF (100 mL). It was stirred for 1 hour at rt. The mixture were diluted with water, extracted with EA (×3), washed with brine (×2). The organic layer was dried and concentrated. The residue was chromatographed (silica gel, PE:EA=10:1) to give desired compound as light yellow solid (1.0 g, 41%). ESI-MS m/z: 272.2 [M+H]$^+$.

Example 167 Step b

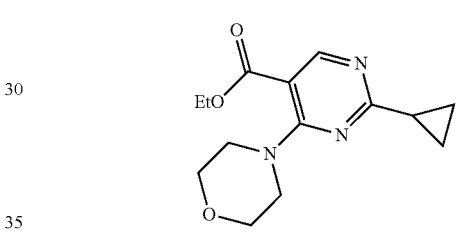

A solution of the compound from step a (0.8 g, 3.0 mmol), cyclopropylboronic acid (360 mg, 4.2 mmol), Pd(DtBPF)Cl$_2$ (196 mg, 0.3 mmol) and Cs$_2$CO$_3$ (1.47 g, 4.5 mmol) in dioxane (30 mL) was stirred for 3 hours at 100° C. under nitrogen. It was diluted with EA, washed with water (×2). The organic layer was dried, concentrated and purified by Prep-TLC (PE/EA=3:1) to give desired compound as a yellow solid (420 mg, 50%). ESI-MS m/z: 278.2 [M+H]$^+$.

Example 167 Step c

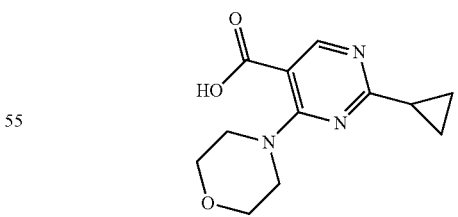

A solution of the compound from step b (400 mg, 1.44 mmol), LiOH (140 mg, 5.78 mmol) in MeOH (2 mL) and water (2 mL) was stirred at room temperature for 5 hours. The solvent was removed and the crude product was purified by reverse phase C18 column chromatography (MeCN/H$_2$O) to give desired compound as a white solid (200 mg, 50%). ESI-MS m/z: 250.2 [M+H]$^+$.

Example 167 Step d

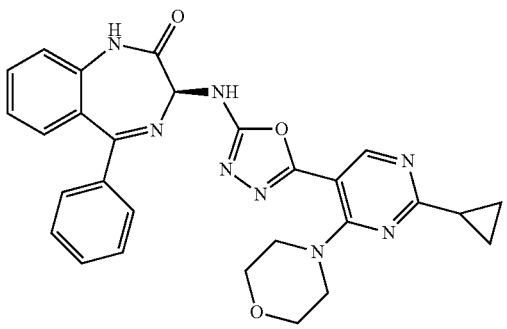

Example 167 was prepared using a procedure similar to that used to prepare Example 151 where 2-cyclopropyl-4-morpholinopyrimidine-5-carboxylic acid was used in place of 6-fluoro-2-morpholinonicotinic acid. ESI-MS m/z: 523.4 [M+H]$^+$. $^1$H NMR (300 MHz, DMSO-d$_6$) δ 0.85-1.10 (m, 4H), 2.06 (m, 1H), 3.37 (q, J=3.6 Hz, 4H), 3.64 (m, 4H), 5.13 (d, J=8.5 Hz, 1H), 7.22-7.41 (m, 3H), 7.41-7.60 (m, 5H), 7.67 (m, 1H), 8.38 (s, 1H), 9.11 (d, J=8.5 Hz, 1H), 10.98 (s, 1H).

Example 168

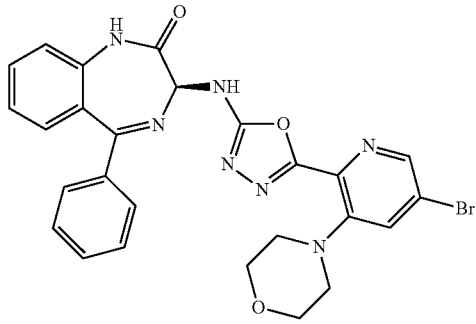 [SMILES: O=C1Nc2ccccc2C(c2ccccc2)=N[C@@H]1Nc1nnc(-c2ncc(Br)cc2N2CCOCC2)o1]

Example 168 was prepared using a procedure similar to that used to prepare Example 152 where methyl 5-bromo-3-morpholinopicolinate, prepared in Example 160 step a, was used in place of ethyl 2-morpholino-4-(trifluoromethyl)benzoate. ESI-MS m/z: 560.1 [M+H]$^+$. $^1$H NMR (300 MHz, DMSO-d$_6$) δ 3.03 (t, J=4.6 Hz, 4H), 3.72 (t, J=4.6 Hz, 4H), 5.20 (d, J=8.5 Hz, 1H), 7.25-7.60 (m, 8H), 7.69 (m, 1H), 7.86 (d, J=2.0 Hz, 1H), 8.46 (d, J=1.8 Hz, 1H), 9.27 (d, J=8.6 Hz, 1H), 10.99 (d, J=12.7 Hz, 1H).

Example 169

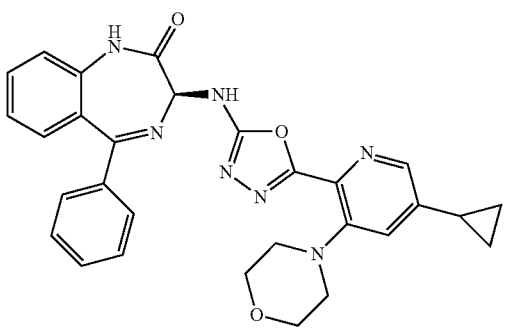

Example 169 Step a

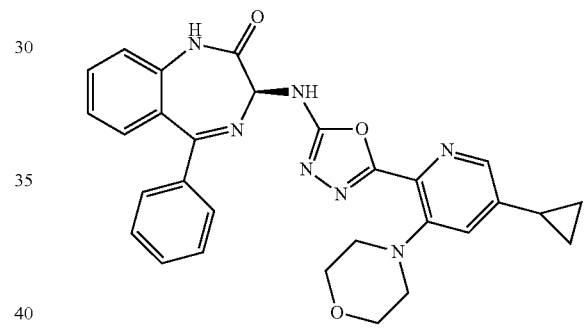

A solution of methyl 5-bromo-3-morpholinopicolinate, prepared in Example 160 step a, (753 mg, 2.5 mmol), K$_2$CO$_3$ (1.73 g, 12.5 mmol), cyclopropylboronic acid (1.07 g, 12.5 mmol) and Pd(dppf)Cl$_2$ (183 mg, 0.25 mmol) in dioxane (10 mL) was stirred for 1 hour at 80° C. in the microwave. It was concentrated under vacuum and diluted with water (100 mL). The resulting solution was extracted with EA (100 mL×3). The organic layer was dried and concentrated to give 1.0 g (crude) of desired compound, which was used directly in the next step. ESI-MS m/z: 263.0 [M+H]$^+$.

Example 169 Step b

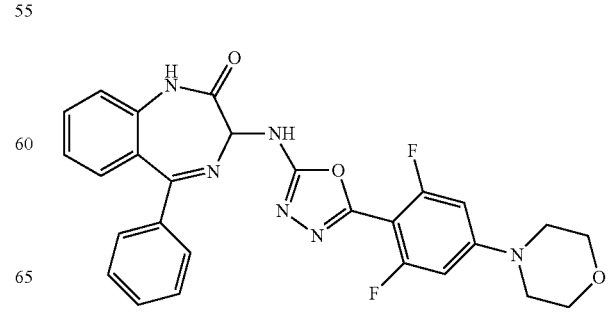

Example 169 was prepared using a procedure similar to that used to prepare Example 152 where methyl 5-cyclopropyl-3-morpholinopicolinate was used in place of ethyl 2-morpholino-4-(trifluoromethyl)benzoate. ESI-MS m/z: 522.4 [M+H]$^+$. $^1$H NMR (300 MHz, DMSO-d$_6$) δ 0.89 (dt, J=6.8, 3.3 Hz, 2H), 1.07 (dt, J=8.6, 3.2 Hz, 2H), 2.04 (tt, J=8.7, 5.0 Hz, 1H), 2.98 (t, J=4.6 Hz, 4H), 3.70 (t, J=4.5 Hz, 4H), 5.19 (d, J=8.7 Hz, 1H), 7.22-7.41 (m, 4H), 7.44-7.58 (m, 5H), 7.69 (ddd, J=8.5, 7.1, 1.8 Hz, 1H), 8.15 (d, J=1.8 Hz, 1H), 9.13 (d, J=8.7 Hz, 1H), 10.96 (s, 1H).

Examples 170 and 171

-continued

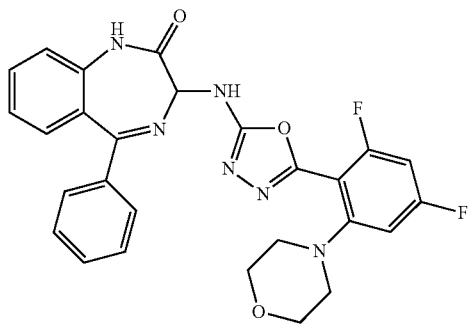

Examples 170 and 171 Step a

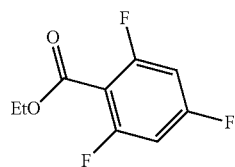 [SMILES: CCOC(=O)c1c(F)cc(F)cc1F]

A solution of 2,4,6-trifluorobenzoic acid (2.00 g, 10.1 mmol), H$_2$SO$_4$ (3 mL, 6 mmol) in EtOH (10 mL) was stirred for 12 hours at 80° C. It was diluted with water, extracted with EA (×3), washed with brine (×2). The organic layer was dried and concentrated to give 2.34 g (crude) of desired compound as yellow oil, which was used directly in the next step. ESI-MS m/z: need [M+H]$^+$.

Examples 170 and 171 Step b

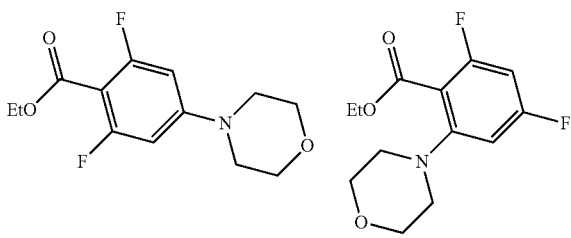

A solution of ethyl 2,4,6-trifluorobenzoate (2.34 g, 11.5 mmol), morpholine (999 mg, 11.5 mmol) and K$_2$CO$_3$ (2.76 g, 20.0 mmol) in DMF (10 mL) was stirred for 12 hours at 100° C. It was diluted with water, extracted with EA (×3), washed with brine (×2). The organic layer was dried and concentrated to give 2.31 g (crude) mixture of desired compound as yellow oil, which was used directly in the next step. ESI-MS m/z: 272.1 [M+H]$^+$.

Examples 170 and 171 Step c

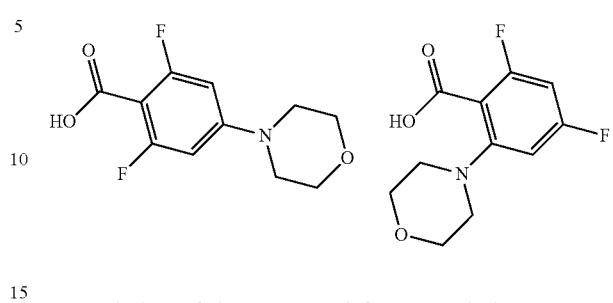

A solution of the compound from step b (2.31 g, 2.94 mmol) and NaOH (500 mg) in MeOH (5 mL) and water (5 mL) was stirred for 5 hours. The crude product was purified by reverse phase C18 column chromatography (MeCN/H$_2$O) to give desired compound as a white solid (1.79 g, 86%). ESI-MS m/z: 244.1 [M+H]$^+$.

Examples 170 and 171 Step d

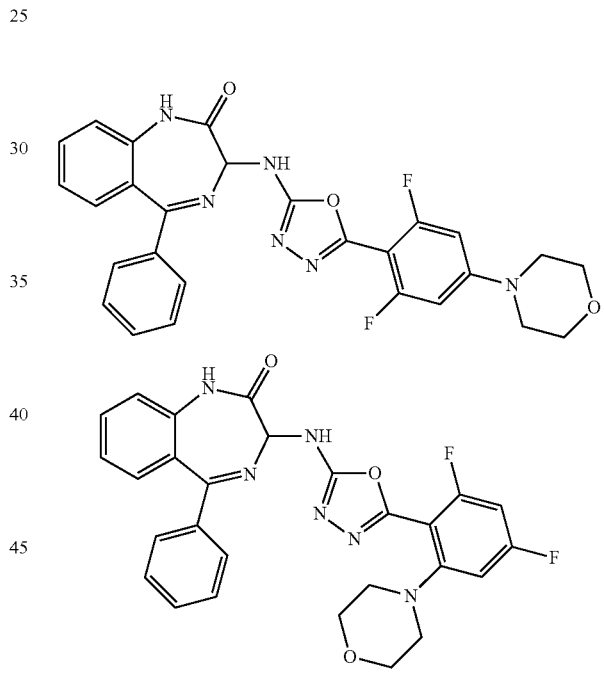

Examples 170 and 171 were prepared using a procedure similar to that used to prepare Example 151 where 2,6-difluoro-4-morpholinobenzoic acid and 2,4-difluoro-6-morpholinobenzoic acid, respectively, were used in place of 6-fluoro-2-morpholinonicotinic acid. Example 170: ESI-MS m/z: 517.3 [M+H]$^+$. $^1$H NMR (400 MHz, DMSO-d$_6$) δ3.30 (m, 4H), 3.72 (m, 4H), 5.15 (d, J=8.5 Hz, 1H), 6.85 (d, J=12.9 Hz, 2H), 7.25-7.38 (m, 3H), 7.43-7.58 (m, 5H), 7.68 (ddd, J=8.4, 7.1, 1.7 Hz, 1H), 9.10 (d, J=8.5 Hz, 1H), 10.99 (s, 1H). Example 171: ESI-MS m/z: 517.3 [M+H]$^+$. $^1$H NMR (400 MHz, DMSO-d$_6$) δ 2.91 (t, J=4.6 Hz, 4H), 3.61 (q, J=3.9 Hz, 4H), 5.16 (d, J=8.7 Hz, 1H), 6.75-7.12 (m, 2H), 7.21-7.42 (m, 3H), 7.42-7.61 (m, 5H), 7.64-7.77 (m, 1H), 9.17 (d, J=8.8 Hz, 1H), 10.99 (s, 1H).

Example 172

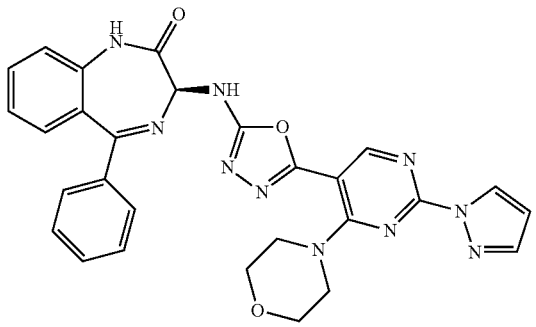 [SMILES: O=C1Nc2ccccc2C(c2ccccc2)=N[C@@H]1Nc1nnc(-c2cnc(-n3cccn3)nc2N2CCOCC2)o1]

Example 172 Step a

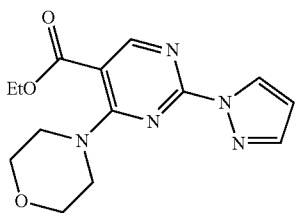 [SMILES: CCOC(=O)c1cnc(-n2cccn2)nc1N1CCOCC1]

A solution of ethyl 2-chloro-4-morpholinopyrimidine-5-carboxylate, prepared similarly to the method described in Example 145 (0.54 g, 2 mmol), 1H-pyrazole (0.27 g, 4 mmol) and $Cs_2CO_3$ (1.30 g, 4 mmol) in DMF (20 mL) was stirred for 1 hour at rt. It was diluted with water and extracted with EA (×3). The organic layer was concentrated to give yellow solid (0.6 g, 99%). ESI-MS m/z: 304.1 [M+H]$^+$.

Example 172 Step b

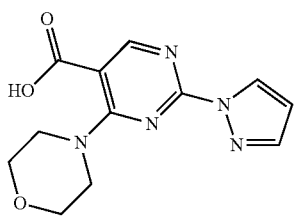 [SMILES: O=C(O)c1cnc(-n2cccn2)nc1N1CCOCC1]

A solution of the compound from step a (0.6 g, 1.98 mmol), LiOH (71 mg, 2.97 mmol), in THF (10 mL) and water (2 mL) were stirred at room temperature for 16 hours. The solvent was removed and the crude product was purified by reverse phase C18 column chromatography (MeCN/ $H_2O$) to give desired compound as a white solid (200 mg, 37%). ESI-MS m/z: 276.2 [M+H]$^+$.

Example 172 Step c

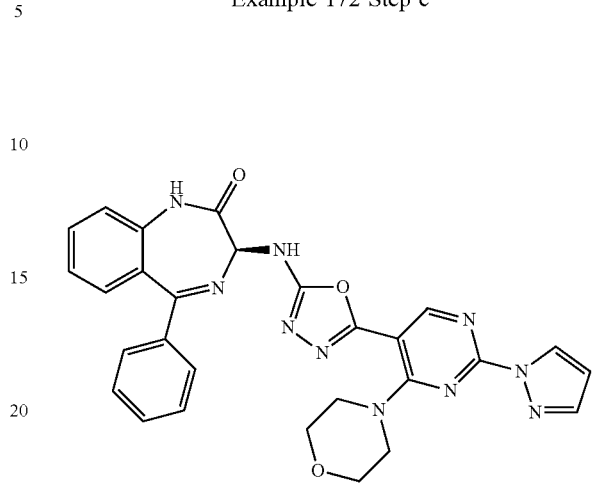

Example 172 was prepared using a procedure similar to that used to prepare Example 151 where 4-morpholino-2-(1H-pyrazol-1-yl)pyrimidine-5-carboxylic acid was used in place of 6-fluoro-2-morpholinonicotinic acid. ESI-MS m/z: 549.5 [M+H]$^+$. $^1$H NMR (400 MHz, DMSO-$d_6$) δ 3.53 (m, 4H), 3.69 (m, 4H), 5.16 (d, J=8.3 Hz, 1H), 6.55-6.67 (m, 1H), 7.29 (m, 1H), 7.36 (m, 2H), 7.46-7.55 (m, 5H), 7.63-7.73 (m, 1H), 7.86 (d, J=1.6 Hz, 1H), 8.57 (s, 1H), 8.68 (d, J=2.7 Hz, 1H), 9.19 (d, J=8.5 Hz, 1H), 11.01 (s, 1H).

Example 173

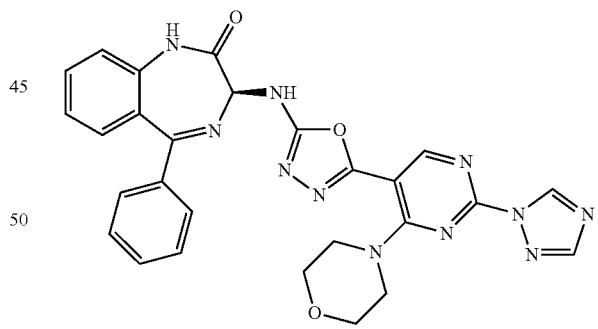

Example 173 was prepared using a procedure similar to that used to prepare Example 151 where 4-morpholino-2-(1H-1,2,4-triazol-1-yl)pyrimidine-5-carboxylic acid, which was prepared similarly to 4-morpholino-2-(1H-pyrazol-1-yl)pyrimidine-5-carboxylic acid which was described in Example 172 step b, was used in place of 6-fluoro-2-morpholinonicotinic acid. ESI-MS m/z: 550.4 [M+H]$^+$. $^1$H NMR (300 MHz, DMSO-$d_6$) δ 3.55 (m, 4H), 3.69 (d, J=4.7 Hz, 4H), 5.16 (d, J=3.8 Hz, 1H), 7.19-7.41 (m, 3H), 7.42-7.62 (m, 5H), 7.67 (m, 1H), 8.30 (s, 1H), 8.61 (s, 1H), 9.19 (s, 1H), 9.49 (s, 1H), 10.91 (s, 1H).

Example 174

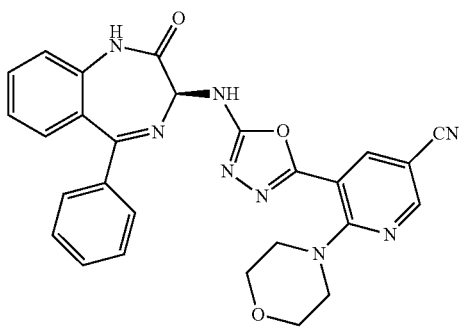 [SMILES: N#Cc1cnc(N2CCOCC2)c(-c2nnc(N[C@H]3N=C(c4ccccc4)c4ccccc4NC3=O)o2)c1]

Example 174 Step a

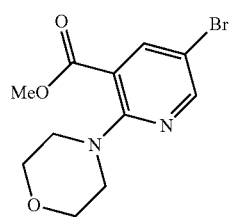 [SMILES: COC(=O)c1cc(Br)cnc1N1CCOCC1]

A solution of methyl 5-bromo-2-chloronicotinate (5.0 g, 20.0 mmol) in morpholine (20 mL) was stirred for 1 hour at 120° C. It was concentrated and purified by reverse phase C18 column chromatography (MeCN/H$_2$O) to give the desired compound as yellow solid (5.4 g, 90%). ESI-MS m/z: 302.9 [M+H]$^+$.

Example 174 Step b

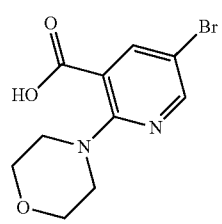

A solution of the compound from step a (1.3 g, 4.3 mmol), LiOH (517 mg, 21.6 mmol) in THF/H$_2$O (10 mL) (1/1) was stirred at rt overnight. The solution was adjusted pH value to 4 with 3N HCl and extracted with EA. The solution was concentrated and purified by reverse phase C18 column chromatography (MeCN/H$_2$O) to give the desired product as off-white solid (1.1 g, 88%). ESI-MS m/z: 287.0 [M+H]$^+$.

Example 174 Step c

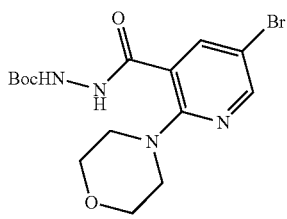 [SMILES: CC(C)(C)OC(=O)NNC(=O)c1cc(Br)cnc1N1CCOCC1]

A solution of the compound from step b (1.1 g, 3.83 mmol), tert-butyl hydrazinecarboxylate (607 mg, 4.59 mmol), HATU (1.75 g, 4.60 mmol), DIPEA (1.48 g, 11.49 mmol) in DMF (20 mL) was stirred at rt for 1 hour. The solution was purified by reverse phase C18 column chromatography (MeCN/H$_2$O) to give the desired product as off-white solid (1.3 g, 85%). ESI-MS m/z: 403.2 [M+H]$^+$.

Example 174 Step d

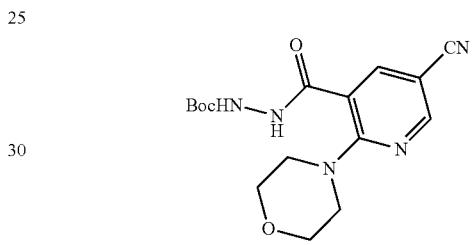

A solution of the compound from step c (1.3 g, 3.24 mmol), Zn(CN)$_2$ (752 mg, 6.28 mmol), Pd(PPh$_3$)$_4$ (750 mg, 0.62 mmol) in DMF (20 mL) was stirred at 120° C. for 1 hour. The solution was purified by reverse phase C18 column chromatography (MeCN/H$_2$O) to tert-butyl 2-(5-cyano-2-morpholinonicotinoyl)hydrazine-1-carboxylate as off-white solid (1.0 g, 89%). ESI-MS m/z: 348.3 [M+H]$^+$.

Example 174 Step e

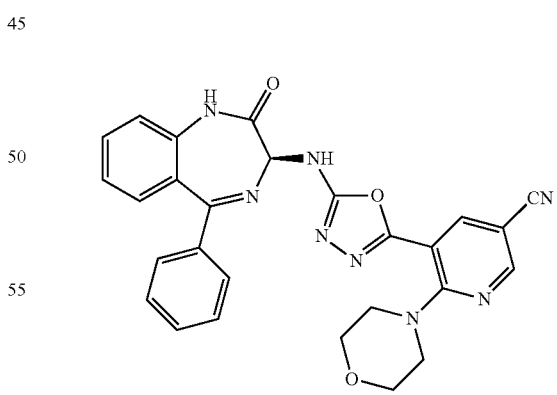

Example 174 was prepared using a procedure similar to that used to prepare Example 151 tert-butyl 2-(5-cyano-2-morpholinonicotinoyl)hydrazine-1-carboxylate was used in place of tert-butyl 2-(6-fluoro-2-morpholinonicotinoyl)hydrazine-1-carboxylate. ESI-MS m/z: 507.4 [M+H]$^+$. $^1$H NMR (400 MHz, DMSO-d$_6$) δ 3.30-3.40 (m, 4H), 3.65-3.67 (m, 4H), 5.14-5.16 (d, J=6.0 Hz, 1H), 7.26-7.30 (m, 1H), 7.33-7.36 (m, 2H), 7.44-7.55 (m, 5H), 7.65-7.69 (m, 1H) 8.25 (m, 1H), 8.69-8.70 (m, 1H), 9.22-9.24 (d, J=8.0 Hz, 1H), 10.99 (s, 1H).

Example 175

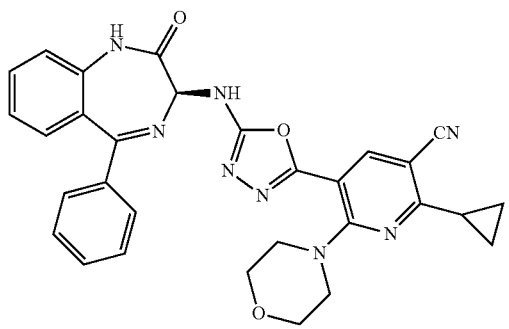 [SMILES: N#Cc1cc(-c2nnc(N[C@H]3N=C(c4ccccc4)c4ccccc4NC3=O)o2)c(N2CCOCC2)nc1C1CC1]

Example 175 Step a

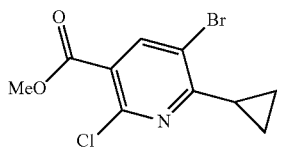 [SMILES: COC(=O)c1cc(Br)c(C2CC2)nc1Cl]

The methyl 5-bromo-2-chloronicotinate (1.2 g, 4.8 mmol) and potassium cyclopropyl trifluoroborate (2.13 g, 14.4 mmol) was dissolved in AcOH (30 mL) and water (30 mL). TFA (0.36 mL, 4.8 mmol) was added. The mixture was stirred at rt for 20 minutes. Mn(OAc)$_3$.2H$_2$O (11.6 g, 43.2 mmol) was added and the mixture was heated to 70° C. under N$_2$ atmosphere. After 48 hours the mixture was cooled to rt and saturated Na$_2$CO$_3$ solution was added and then solid was filtered out. The filtrate was extracted with EA (200 mL×3). The combined organic phase was dried over anhydrous Na$_2$SO$_4$ and concentrated. The residue was purified by silica gel chromatography (PE:EA=100:1 to 50:1) to give the desired product as white solid (269 mg,) and the starting material (696 mg). ESI-MS m/z: 292.0 [M+H]$^+$.

Example 175 Step b

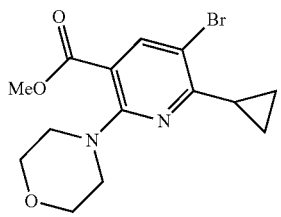 [SMILES: COC(=O)c1cc(Br)c(C2CC2)nc1N1CCOCC1]

The compound from step a (269 mg, 0.92 mmol) was dissolved in morpholine (3 mL) and it was heated to 100° C. for 1 hour. Water was added (10 mL) and the mixture was extracted with EA (20 mL×3) and the combined organic phase was dried and concentrated to give the desired product as a yellow oil (400 mg,). ESI-MS m/z: 343.1 [M+H]$^+$.

Example 175 Step c

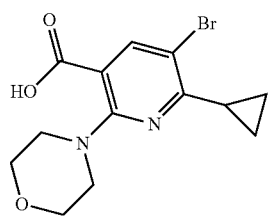 [SMILES: O=C(O)c1cc(Br)c(C2CC2)nc1N1CCOCC1]

The compound from step b (400 mg, 1.17 mmol) was dissolved in THF (3 mL) and water (1 mL). LiOH (56 mg, 2.34 mmol) was added and the mixture was heated to 50° C. overnight. The mixture was cooled to rt and 6M HCl solution was added to adjust the pH to 3 and then concentrated. The residue was purified by reverse phase C18 column chromatography (MeCN/H$_2$O) to give the desired product as a yellow solid (300 mg, 78%). ESI-MS m/z: 327.0 [M+H]$^+$.

Example 175 Step d

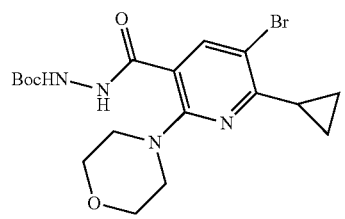 [SMILES: CC(C)(C)OC(=O)NNC(=O)c1cc(Br)c(C2CC2)nc1N1CCOCC1]

The compound from step c (300 mg, 0.92 mmol) was dissolved in DMF (5 mL) and BocNHNH$_2$ (242 mg, 1.83 mmol) was added. HATU (697 mg, 1.83 mmol) and DIPEA (0.3 mL) was added. The mixture was stirred at rt for 2 hours. Water (10 mL) was added and the mixture was extracted with EA (15 mL×3). The combined organic phase was dried over anhydrous Na$_2$SO$_4$ and concentrated. The residue was purified by gel chromatography (PE/EA=3/1) to give the desired product as a yellow solid (350 mg, 86%). ESI-MS m/z: 441.0 [M+H]$^+$.

Example 175 Step e

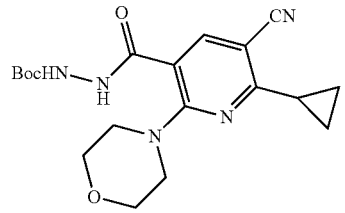 [SMILES: CC(C)(C)OC(=O)NNC(=O)c1cc(C#N)c(C2CC2)nc1N1CCOCC1]

To a stirred solution of the compound from step 4 (350 mg, 0.79 mmol) and Zn(CN)$_2$ (183 mg, 1.58 mmol) in DMF (5 mL) was added Pd(PPh$_3$)$_4$ (183.28 mg, 0.158 mmol). The mixture was heated to 120° C. for 1 hour under N₂ atmosphere. Then it was cooled to rt, Sat. FeSO₄ solution was added and the mixture was extracted with EA (50 mL×3). The combined organic phase was washed with water, brine and dried over anhydrous Na₂SO₄ and concentrated. The residue was purified by silicagel chromatography to give the desired compound as a yellow solid (290 mg, 95%). ESI-MS m/z: 388.4 [M+H]⁺.

Example 175 Step f

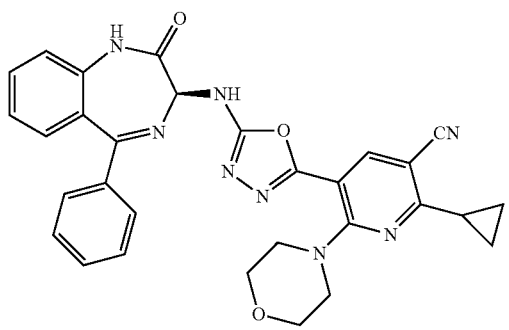 [SMILES: N#Cc1cc(-c2nnc(N[C@H]3N=C(c4ccccc4)c4ccccc4NC3=O)o2)c(N2CCOCC2)nc1C1CC1]

Example 175 was prepared using a procedure similar to that used to prepare Example 151 tert-butyl 2-(5-cyano-6-cyclopropyl-2-morpholinonicotinoyl)hydrazine-1-carboxylate was used in place of tert-butyl 2-(6-fluoro-2-morpholinonicotinoyl)hydrazine-1-carboxylate. ESI-MS m/z: 547.2 [M+H]⁺. ¹H NMR (300 MHz, DMSO-d₆) δ 0.95-1.23 (m, 4H), 2.24-2.48 (m, 1H), 3.18-3.43 (m, 4H), 3.64 (t, J=4.8 Hz, 4H), 5.15 (d, J=8.2 Hz, 1H), 7.22-7.61 (m, 8H), 7.68 (ddd, J=8.5, 7.0, 1.8 Hz, 1H), 8.12 (s, 1H), 9.17 (d, J=8.5 Hz, 1H), 10.98 (s, 1H).

Example 176

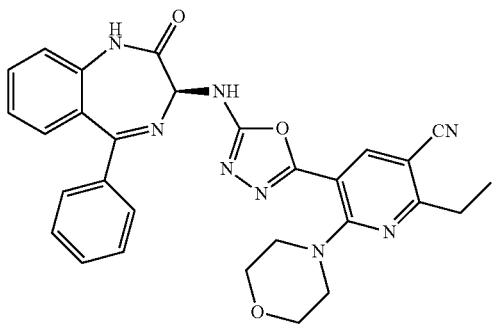 [SMILES: CCc1nc(N2CCOCC2)c(-c2nnc(N[C@H]3N=C(c4ccccc4)c4ccccc4NC3=O)o2)cc1C#N]

Example 176 was prepared using a procedure similar to that used to prepare Example 151 tert-butyl 2-(5-cyano-6-ethyl-2-morpholinonicotinoyl)hydrazine-1-carboxylate, which was prepared similarly to tert-butyl 2-(5-cyano-6-cyclopropyl-2-morpholinonicotinoyl)hydrazine-1-carboxylate as described in Example 175 step e, was used in place of tert-butyl 2-(6-fluoro-2-morpholinonicotinoyl)hydrazine-1-carboxylate. ESI-MS m/z: 535.1 [M+H]⁺. ¹H NMR (300 MHz, DMSO-d₆) δ 1.23 (m, 3H), 2.84 (m, 2H), 3.36 (m, 4H), 3.65 (m, 4H), 5.12 (d, J=8.3 Hz, 1H), 7.20-7.39 (m, 3H), 7.40-7.59 (m, 5H), 7.65 (m, 1H), 8.14 (s, 1H), 9.17 (d, J=8.5 Hz, 1H), 10.98 (s, 1H).

Example 177

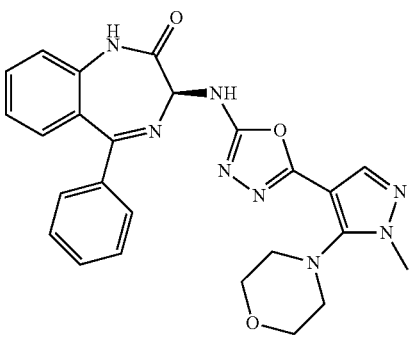 [SMILES: Cn1ncc(-c2nnc(N[C@H]3N=C(c4ccccc4)c4ccccc4NC3=O)o2)c1N1CCOCC1]

Example 177 Step a

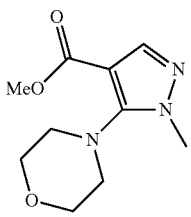 [SMILES: COC(=O)c1cnn(C)c1N1CCOCC1]

A solution of the compound ethyl 5-amino-1-methyl-1H-pyrazole-4-carboxylate (1.69 g, 10 mmol), 1-bromo-2-(2-bromoethoxy) ethane (3.45 g, 15 mmol) and Cs₂CO₃ (9.77 g, 30 mmol) in DMA (30 mL) was stirred overnight at 120° C. The crude product was purified by reverse phase C18 column chromatography (MeCN/H₂O) to give desired compound 700 mg (crude). ESI-MS m/z: 240.1 [M+H]⁺.

Example 177 Step b

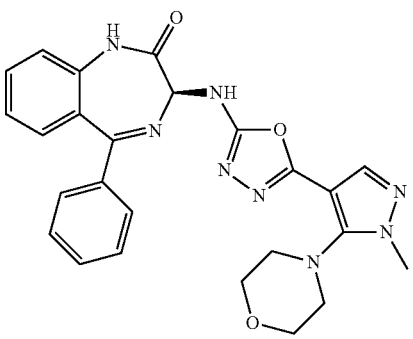 [SMILES: Cn1ncc(-c2nnc(N[C@H]3N=C(c4ccccc4)c4ccccc4NC3=O)o2)c1N1CCOCC1]

Example 177 was prepared using a procedure similar to that used to prepare Example 152 where methyl 1-methyl-5-morpholino-1H-pyrazole-4-carboxylate was used in place of ethyl 2-morpholino-4-(trifluoromethyl)benzoate. ESI-MS m/z: 485.4 [M+H]⁺. ¹H NMR (400 MHz, Methanol-d₄) δ 3.19 (dd, J=5.7, 3.5 Hz, 4H), 3.83 (d, J=6.5 Hz, 7H), 5.29 (s, 1H), 7.26-7.39 (m, 2H), 7.39-7.48 (m, 3H), 7.49-7.59 (m, 3H), 7.64-7.69 (m, 1H), 7.83 (s, 1H).

Example 178

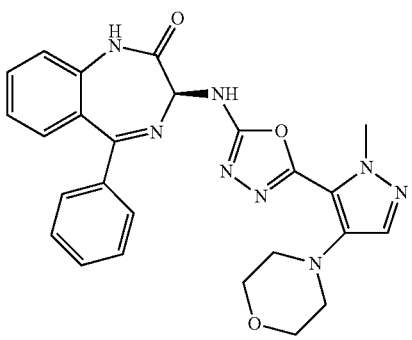 [SMILES: Cn1ncc(N2CCOCC2)c1-c1nnc(N[C@H]2N=C(c3ccccc3)c3ccccc3NC2=O)o1]

Example 178 Step a

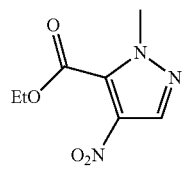

A solution of 1-methyl-4-nitro-1H-pyrazole-5-carboxylic acid (1.03 g, 6 mmol), EtBr (3 mL) and K$_2$CO$_3$ (1.66 g, 12 mmol) in DMF (30 mL) was stirred for 1 hour at 60° C. Then it was poured into water and extracted with EA (3×) to give desired compound as a light yellow solid. (995 mg, 83%). ESI-MS m/z: 200.2 [M+H]$^+$.

Example 178 Step b

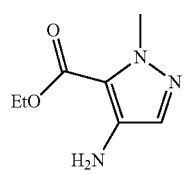

A solution of compound from step a (995 mg, 5 mmol) and Pd/C (200 mg) in EtOH (50 mL) was stirred for 3 hours at 25° C. Pd/C was filtered out and the filtrate was concentrated to give desired compound as a light brown solid. (845 mg, 100%). ESI-MS m/z: 170.2 [M+H]$^+$.

Example 178 Step c

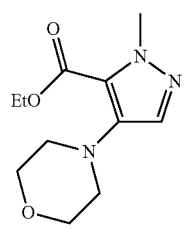 [SMILES: CCOC(=O)c1c(N2CCOCC2)cnn1C]

A solution of compound from step b (845 mg, 5 mmol), 1-bromo-2-(2-bromoethoxy)ethane (2.3 g, 10 mmol), NaI (1.5 g, 10 mmol) and K$_2$CO$_3$ (2.8 g, 20 mmol) in DMA (50 mL) was stirred for 3 hours at 120° C. The solvent was removed and the residue was purified by reverse phase C18 column chromatography (MeCN/H$_2$O) to give desired compound as brown oil. (720 mg, 60%). ESI-MS m/z: 240.2 [M+H]$^+$.

Example 178 Step d

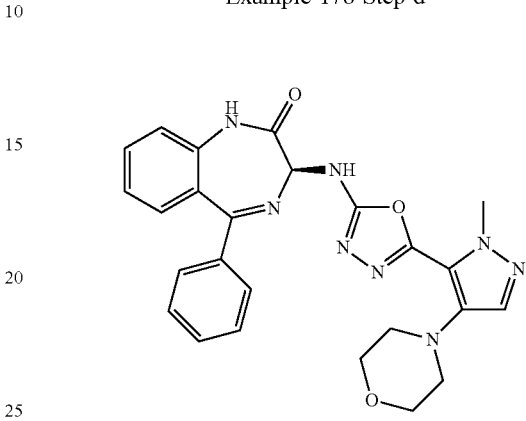

Example 178 was prepared using a procedure similar to that used to prepare Example 152 where ethyl 1-methyl-4-morpholino-1H-pyrazole-5-carboxylate was used in place of ethyl 2-morpholino-4-(trifluoromethyl)benzoate. ESI-MS m/z: 485.4 [M+H]$^+$. $^1$H NMR (300 MHz, DMSO-d6) δ 2.84-2.93 (m, 4H), 3.64 (m, 4H), 3.98 (s, 3H), 5.16 (d, J=8.3 Hz, 1H), 7.24-7.62 (m, 9H), 7.63-7.75 (m, 1H), 9.26 (d, J=8.4 Hz, 1H), 11.01 (s, 1H).

Example 179

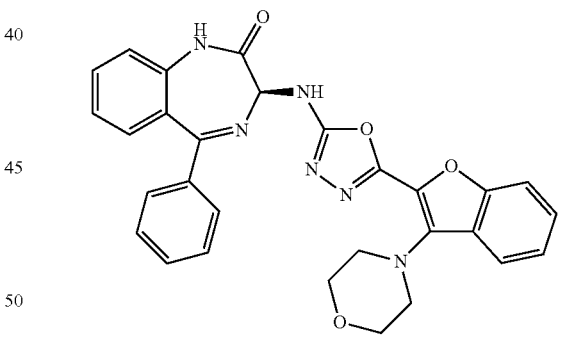

Example 179 Step a

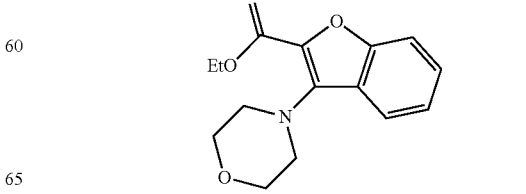

A solution of ethyl 3-aminobenzofuran-2-carboxylate (1.03 g, 5 mmol) and NaH (480 mg, 12 mmol) in DMF (30 mL) was stirred for 0.5 hour at 0° C. Then 1-bromo-2-(2-bromoethoxy)ethane (1.38 g, 6 mmol) was added to the mixture and stirred for 1 hr at rt H₂O (50 mL) was added and it was extracted with EA (3×). The organic layer was concentrated and purified by reverse phase C18 column chromatography (MeCN/H₂O) to give desired compound as light brown oil. (530 mg, 40%). ESI-MS m/z: 276.2 [M+H]⁺.

Example 179 Step b

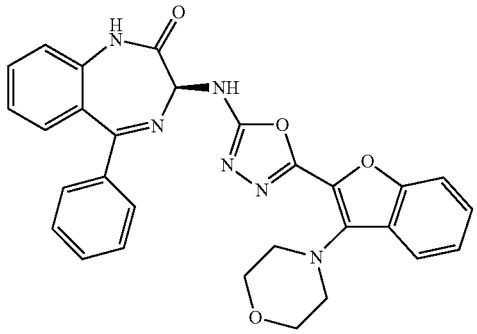 [SMILES: O=C1Nc2ccccc2C(c2ccccc2)=N[C@@H]1Nc1nnc(-c2oc3ccccc3c2N2CCOCC2)o1]

Example 179 was prepared using a procedure similar to that used to prepare Example 152 where ethyl 3-morpholinobenzofuran-2-carboxylate was used in place of ethyl 2-morpholino-4-(trifluoromethyl)benzoate. ESI-MS m/z: 521.4 [M+H]⁺. ¹H NMR (300 MHz, DMSO-d6) δ 3.32 (m, 4H), 3.74 (m, 4H), 5.17 (d, J=8.4 Hz, 1H), 7.22-7.75 (m, 12H), 7.86-8.00 (m, 1H), 9.31 (d, J=8.5 Hz, 1H), 11.00 (s, 1H).

Example 180

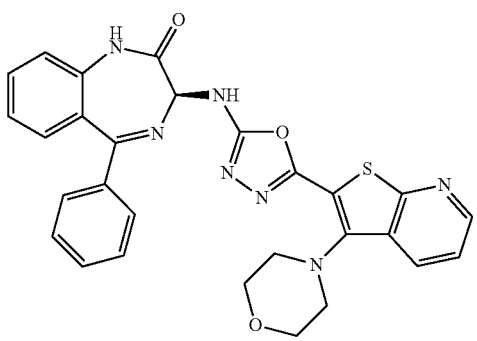 [SMILES: O=C1Nc2ccccc2C(c2ccccc2)=N[C@@H]1Nc1nnc(-c2sc3ncccc3c2N2CCOCC2)o1]

Example 180 Step a

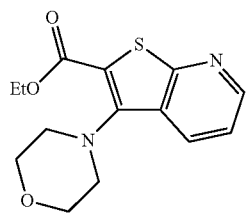 [SMILES: CCOC(=O)c1sc2ncccc2c1N1CCOCC1]

A solution of ethyl 3-aminothieno[2,3-b]pyridine-2-carboxylate (500 mg, 2.25 mmol), 1-bromo-2-(2-bromoethoxy)ethane (1.38 g, 6 mmol) and Cs₂CO₃ (1.63 g, 5 mmol) in DMA (30 mL) was stirred for 3 hours at 80° C. H₂O (50 mL) was added and it was extracted with EA (3×). The organic layer was concentrated and purified by reverse phase C18 column chromatography (MeCN/H₂O) to give desired compound as light brown oil. (500 mg, 76%). ESI-MS m/z: 293.2 [M+H]⁺.

Example 180 Step b

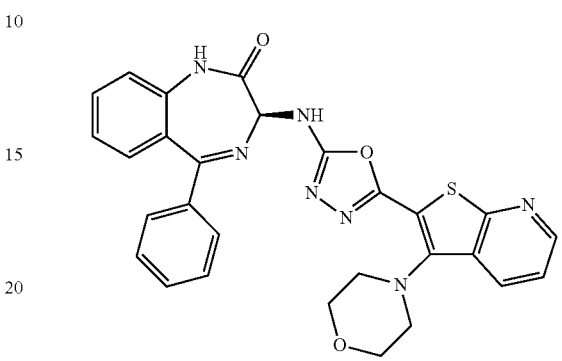

Example 180 was prepared using a procedure similar to that used to prepare Example 152 where ethyl 3-morpholinothieno[2,3-b]pyridine-2-carboxylate was used in place of ethyl 2-morpholino-4-(trifluoromethyl)benzoate. ESI-MS m/z: 538.4 [M+H]⁺. ¹H NMR (400 MHz, DMSO-d₆) δ 3.30-3.17 (m, 4H), 3.77 (d, J=6.8 Hz, 4H), 5.19 (d, J=8.2 Hz, 1H), 7.29 (t, J=7.7 Hz, 1H), 7.37 (d, J=8.0 Hz, 2H), 7.61-7.42 (m, 6H), 7.68 (t, J=7.6 Hz, 1H), 8.34 (d, J=8.1 Hz, 1H), 8.66 (d, J=4.6 Hz, 1H), 9.40 (d, J=8.1 Hz, 1H), 11.03 (s, 1H).

Example 181

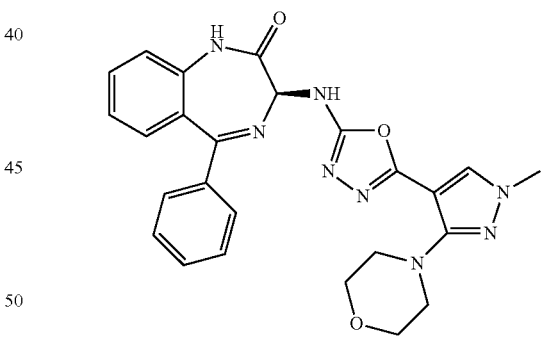

Example 181 Step a

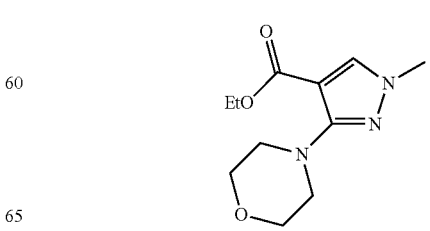

A solution of the ethyl 3-amino-1-methyl-1H-pyrazole-4-carboxylate (500 mg, 2.95 mmol), Cs$_2$CO$_3$ (2.9 g, 8.87 mmol), 1-bromo-2-(2-bromoethoxy) ethane (1.37 g, 5.90 mmol) in DMA (10 mL) as stirred at 120° C. overnight. Then H$_2$O (20 mL) was added to the mixture and it was extracted with EA (×3). The organic layer was dried and purified by flash to give desired compound as yellow oil (610 mg, 87%). ESI-MS m/z: 240.0 [M+H]$^+$.

Example 181 Step b

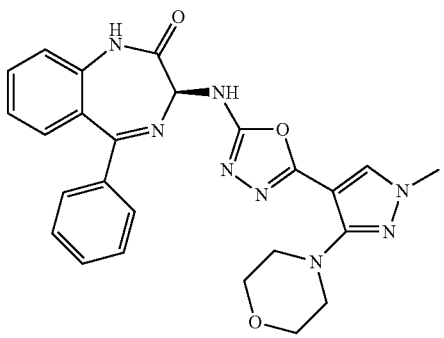 [SMILES: Cn1cc(-c2nnc(N[C@H]3N=C(c4ccccc4)c4ccccc4NC3=O)o2)c(N2CCOCC2)n1]

Example 181 was prepared using a procedure similar to that used to prepare Example 152 where ethyl 1-methyl-3-morpholino-1H-pyrazole-4-carboxylate was used in place of ethyl 2-morpholino-4-(trifluoromethyl)benzoate. ESI-MS m/z: 485.4 [M+H]$^+$. $^1$H NMR (400 MHz, DMSO-d$_6$) δ 3.14-3.15 (m, 4H), 3.65-3.67 (m, 4H), 3.77 (s, 3H), 5.07-5.09 (d, J=8.0 Hz, 1H), 7.32-7.35 (m, 3H), 7.45-7.51 (m, 6H), 8.04 (s, 1H), 8.90-8.93 (m, 1H), 10.86-11.07 (m, 1H).

Example 182

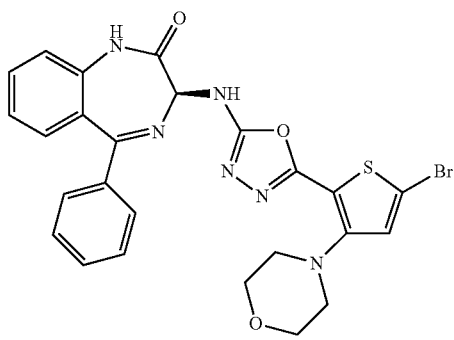 [SMILES: O=C1Nc2ccccc2C(c2ccccc2)=N[C@@H]1Nc1nnc(-c2sc(Br)cc2N2CCOCC2)o1]

Example 182 Step a

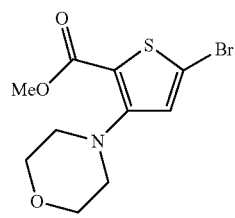 [SMILES: COC(=O)c1sc(Br)cc1N1CCOCC1]

A solution of the methyl 3-amino-5-bromothiophene-2-carboxylate (880 mg, 3.72 mmol), Cs$_2$CO$_3$ (3.64 g, 11.16 mmol), 1-bromo-2-(2-bromoethoxy) ethane (1.73 g, 7.45 mmol) in DMA (10 mL) as stirred at 80° C. overnight. Then H$_2$O (20 ml) was added to the mixture and it was extracted with EA (×3). The organic layer was dried and purified by reverse phase C18 column chromatography (MeCN/H$_2$O) to give desired compound as yellow oil (540 mg, 48%). ESI-MS m/z: 307.9 [M+H]$^+$.

Example 182 Step b

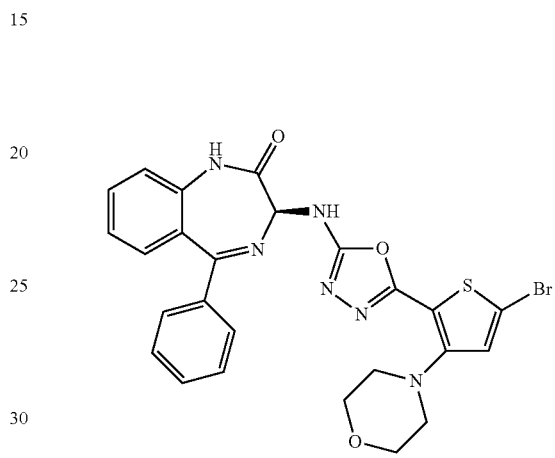

Example 182 was prepared using a procedure similar to that used to prepare Example 152 where methyl 5-bromo-3-morpholinothiophene-2-carboxylate was used in place of ethyl 2-morpholino-4-(trifluoromethyl)benzoate. ESI-MS m/z: 566.9 [M+H]$^+$. $^1$H NMR (400 MHz, DMSO-d$_6$) δ 3.06-3.07 (m, 4H), 3.64-3.70 (m, 4H), 5.09-5.11 (d, J=8.0 Hz, 1H), 7.24-7.29 (m, 2H), 7.33-7.35 (m, 2H), 7.41-7.49 (m, 5H), 7.51-7.68 (m, 1H), 9.11-9.13 (m, 1H), 10.94-10.99 (m, 1H).

Example 183

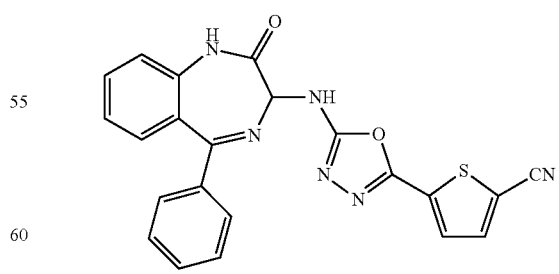

Example 183 was prepared using a procedure similar to that used to prepare Example 20 where 5-cyanothiophene-2-carboxylic acid was used in place of 5-chlorofuran-2-carboxylic acid. ESI-MS m/z: 427.1 [M+H]$^+$.

Example 184

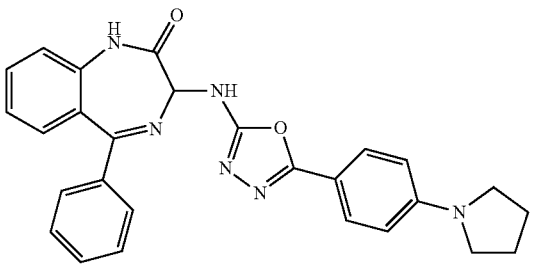 [SMILES: O=C1Nc2ccccc2C(c2ccccc2)=NC1Nc1nnc(-c2ccc(N3CCCC3)cc2)o1]

Example 184 was prepared using a procedure similar to that used to prepare Example 20 where 4-(pyrrolidin-1-yl)benzoic acid was used in place of 5-chlorofuran-2-carboxylic acid. ESI-MS m/z: 465.4 [M+H]$^+$. $^1$H NMR (300 MHz, DMSO-d$_6$) δ 1.98 (q, J=4.7, 3.1 Hz, 4H), 3.35 (q, J=4.7, 3.1 Hz, 4H), 5.13 (d, J=8.7 Hz, 1H), 6.32-6.78 (m, 2H), 7.22-7.42 (m, 3H), 7.42-7.59 (m, 5H), 7.58-7.77 (m, 3H), 8.85 (d, J=8.7 Hz, 1H), 10.98 (s, 1H).

Example 185

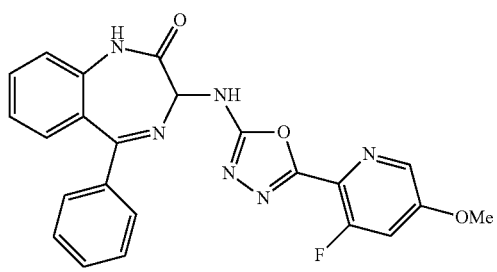 [SMILES: COc1cnc(-c2nnc(NC3N=C(c4ccccc4)c4ccccc4NC3=O)o2)c(F)c1]

Example 185 was prepared using a procedure similar to that used to prepare Example 20 where 3-fluoro-5-methoxypicolinic acid was used in place of 5-chlorofuran-2-carboxylic acid. ESI-MS m/z: 455.1 [M+H]$^+$. $^1$H NMR (300 MHz, DMSO-d$_6$) δ 3.93 (s, 3H), 5.17 (d, J=8.5 Hz, 1H), 7.22-7.39 (m, 3H), 7.40-7.58 (m, 5H), 7.60-7.72 (m, 2H), 8.32 (m, 1H), 9.26 (d, J=8.5 Hz, 1H), 11.00 (s, 1H).

Example 186

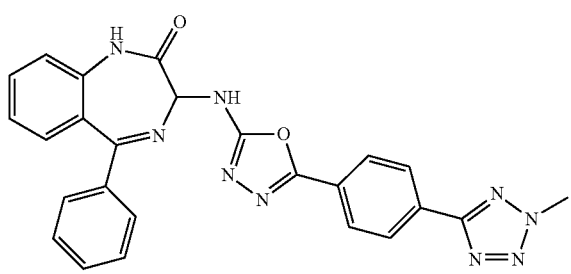 [SMILES: Cn1nnc(-c2ccc(-c3nnc(NC4N=C(c5ccccc5)c5ccccc5NC4=O)o3)cc2)n1]

Example 186 was prepared using a procedure similar to that used to prepare Example 20 where 4-(2-methyl-2H-tetrazol-5-yl)benzoic acid was used in place of 5-chlorofuran-2-carboxylic acid. ESI-MS m/z: 478.2 [M+H]$^+$. $^1$H NMR (300 MHz, DMSO-d$_6$) δ 4.45 (s, 3H), 5.18 (d, J=8.3 Hz, 1H), 7.24-7.40 (m, 3H), 7.41-7.59 (m, 5H), 7.63-7.73 (m, 1H), 8.00 (d, J=8.4 Hz, 2H), 8.23 (d, J=8.4 Hz, 2H), 9.27 (d, J=8.5 Hz, 1H), 11.02 (s, 1H).

Example 187

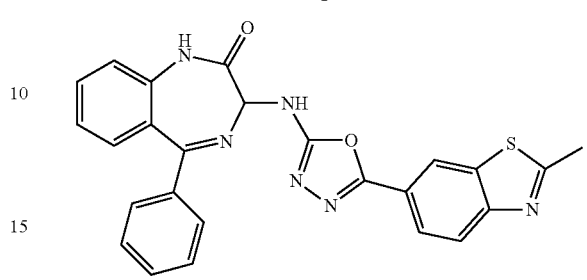

Example 187 was prepared using a procedure similar to that used to prepare Example 20 where 2-methylbenzo[d]thiazole-6-carboxylic acid was used in place of 5-chlorofuran-2-carboxylic acid. ESI-MS m/z: 467.3 [M+H]$^+$. $^1$H NMR (300 MHz, DMSO-d$_6$) δ 11.02 (s, 1H), 9.17 (s, 1H), 8.53 (d, J=1.7 Hz, 1H), 8.04 (d, J=8.5 Hz, 1H), 7.91 (dd, J=8.6, 1.8 Hz, 1H), 7.66 (ddd, J=8.4, 7.2, 1.7 Hz, 1H), 7.59-7.40 (m, 5H), 7.39-7.20 (m, 3H), 5.16 (s, 1H), 2.83 (s, 3H)

Example 188

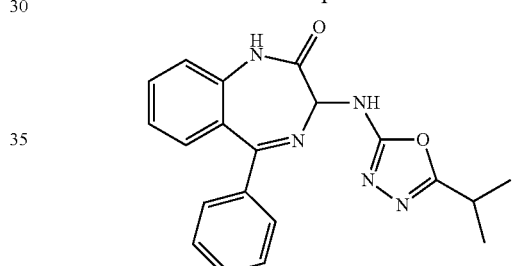

Example 188 was prepared using a procedure similar to that used to prepare Example 20 where isobutyric acid was used in place of 5-chlorofuran-2-carboxylic acid. ESI-MS m/z: 362.3 [M+H]$^+$. $^1$H NMR (300 MHz, DMSO-d$_6$) δ 1.23 (d, J=6.9 Hz, 6H), 3.02 (hept, J=6.9 Hz, 1H), 5.04 (d, J=8.7 Hz, 1H), 7.19-7.41 (m, 3H), 7.38-7.58 (m, 5H), 7.65 (ddd, J=8.4, 7.0, 1.8 Hz, 1H), 8.71 (d, J=8.7 Hz, 1H), 10.93 (s, 1H).

Example 189

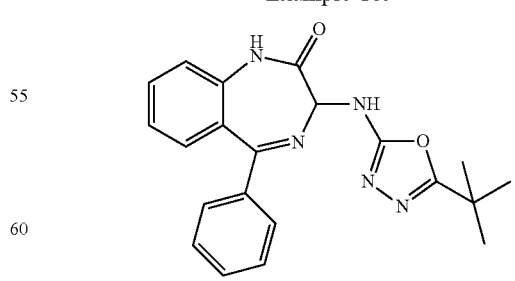

Example 189 was prepared using a procedure similar to that used to prepare Example 20 where pivalic acid was used in place of 5-chlorofuran-2-carboxylic acid. ESI-MS m/z: 376.2 [M+H]$^+$. $^1$H NMR (300 MHz, DMSO-d$_6$) δ 1.29 (s, 9H), 5.03 (d, J=8.6 Hz, 1H), 7.19-7.37 (m, 3H), 7.39-7.58 (m, 5H), 7.65 (ddd, J=8.4, 7.0, 1.8 Hz, 1H), 8.68 (d, J=8.6 Hz, 1H), 10.93 (s, 1H).

Example 190

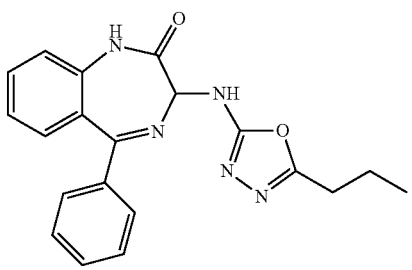 [SMILES: CCCc1nnc(NC2N=C(c3ccccc3)c3ccccc3NC2=O)o1]

Example 190 was prepared using a procedure similar to that used to prepare Example 20 where butyric acid was used in place of 5-chlorofuran-2-carboxylic acid. ESI-MS m/z: 362.2 [M+H]$^+$. $^1$H NMR (300 MHz, DMSO-d$_6$) δ 0.92 (t, J=7.4 Hz, 3H), 1.64 (h, J=7.4 Hz, 2H), 2.64 (t, J=7.3 Hz, 2H), 5.03 (d, J=8.3 Hz, 1H), 7.19-7.58 (m, 8H), 7.65 (ddd, J=8.4, 7.0, 1.8 Hz, 1H), 8.72 (d, J=8.5 Hz, 1H), 10.94 (s, 1H).

Example 191

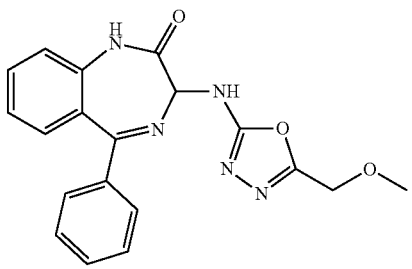 [SMILES: COCc1nnc(NC2N=C(c3ccccc3)c3ccccc3NC2=O)o1]

Example 191 was prepared using a procedure similar to that used to prepare Example 20 where 2-methoxyacetic acid was used in place of 5-chlorofuran-2-carboxylic acid. ESI-MS m/z: 364.1 [M+H]$^+$. $^1$H NMR (300 MHz, DMSO-d$_6$) δ 3.29 (s, 3H), 4.45 (s, 2H), 5.08 (d, J=8.6 Hz, 1H), 7.20-7.38 (m, 3H), 7.38-7.59 (m, 5H), 7.63-7.68 (m, 1H), 9.01 (d, J=8.6 Hz, 1H), 10.96 (s, 1H).

Example 192

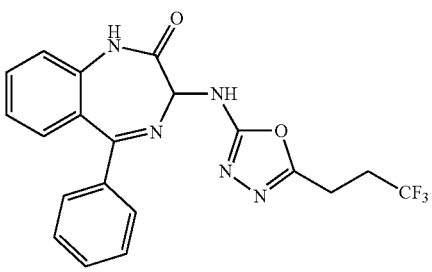 [SMILES: O=C1Nc2ccccc2C(c2ccccc2)=NC1Nc1nnc(CCC(F)(F)F)o1]

Example 192 was prepared using a procedure similar to that used to prepare Example 20 where 4,4,4-trifluorobutanoic acid was used in place of 5-chlorofuran-2-carboxylic acid. ESI-MS m/z: 416.1 [M+H]$^+$. $^1$H NMR (300 MHz, DMSO-d$_6$) δ 2.58-2.81 (m, 2H), 2.98 (dd, J=8.7, 6.5 Hz, 2H), 5.05 (d, J=8.6 Hz, 1H), 7.19-7.38 (m, 3H), 7.38-7.60 (m, 5H), 7.63-7.68 (m, 1H), 8.85 (d, J=8.7 Hz, 1H), 10.95 (s, 1H).

Example 193

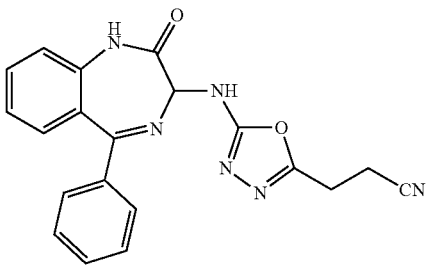 [SMILES: N#CCCc1nnc(NC2N=C(c3ccccc3)c3ccccc3NC2=O)o1]

Example 193 was prepared using a procedure similar to that used to prepare Example 20 where 3-cyanopropanoic acid was used in place of 5-chlorofuran-2-carboxylic acid. ESI-MS m/z: 373.1 [M+H]$^+$. $^1$H NMR (300 MHz, DMSO-d$_6$) δ 2.89 (t, J=6.8 Hz, 2H), 3.07 (t, J=7.2 Hz, 2H), 5.04 (s, 1H), 7.18-7.37 (m, 3H), 7.38-7.58 (m, 5H), 7.62-7.67 (m, 1H), 8.88 (d, J=4.9 Hz, 1H), 10.94 (s, 1H).

Example 194

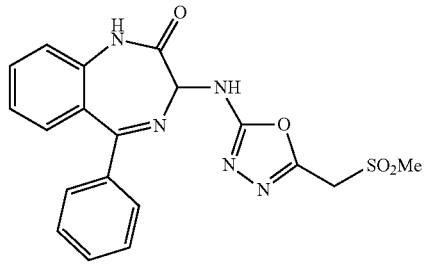 [SMILES: CS(=O)(=O)Cc1nnc(NC2N=C(c3ccccc3)c3ccccc3NC2=O)o1]

Example 194 was prepared using a procedure similar to that used to prepare Example 20 where 2-(methylsulfonyl)acetic acid was used in place of 5-chlorofuran-2-carboxylic acid. ESI-MS m/z: 412.1 [M+H]$^+$. $^1$H NMR (300 MHz, DMSO-d$_6$) δ 3.13 (s, 3H), 4.89 (s, 2H), 5.09 (d, J=8.5 Hz, 1H), 7.20-7.40 (m, 3H), 7.38-7.59 (m, 5H), 7.63-7.68 (m, 1H), 9.17 (d, J=8.5 Hz, 1H), 10.97 (s, 1H).

Example 195

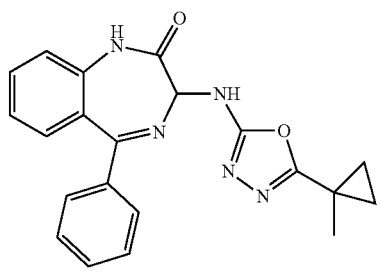 [SMILES: CC1(c2nnc(NC3N=C(c4ccccc4)c4ccccc4NC3=O)o2)CC1]

Example 195 was prepared using a procedure similar to that used to prepare Example 20 where 1-methylcyclopropane-1-carboxylic acid was used in place of 5-chlorofuran-2-carboxylic acid. ESI-MS m/z: 374.2 [M+H]+. 1H NMR (300 MHz, DMSO-d6) δ 0.77-0.92 (m, 2H), 1.00-1.10 (m, 2H), 1.39 (s, 3H), 5.00 (d, J=7.8 Hz, 1H), 7.18-7.58 (m, 8H), 7.61-7.67 (m, 1H), 8.62 (d, J=8.1 Hz, 1H), 10.94 (s, 1H).

Example 196

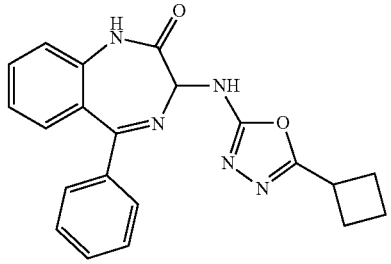 [SMILES: O=C1Nc2ccccc2C(c2ccccc2)=NC1Nc1nnc(C2CCC2)o1]

Example 196 was prepared using a procedure similar to that used to prepare Example 20 where cyclobutanecarboxylic acid was used in place of 5-chlorofuran-2-carboxylic acid. ESI-MS m/z: 374.3 [M+H]+. 1H NMR (300 MHz, DMSO-d6) δ 1.79-2.12 (m, 2H), 2.13-2.39 (m, 4H), 3.58 (m, 1H), 5.05 (d, J=8.7 Hz, 1H), 7.19-7.58 (m, 8H), 7.65 (m, 1H), 8.75 (d, J=8.7 Hz, 1H), 10.94 (s, 1H).

Example 197

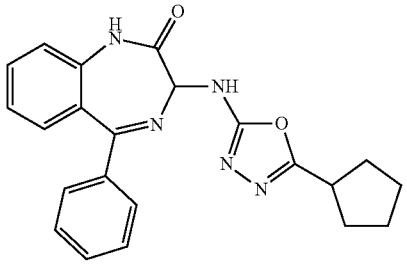 [SMILES: O=C1Nc2ccccc2C(c2ccccc2)=NC1Nc1nnc(C2CCCC2)o1]

Example 197 was prepared using a procedure similar to that used to prepare Example 20 where cyclopentanecarboxylic acid was used in place of 5-chlorofuran-2-carboxylic acid. ESI-MS m/z: 388.3 [M+H]+. 1H NMR (300 MHz, DMSO-d6) δ 1.52-1.83 (m, 6H), 1.87-2.07 (m, 2H), 3.08-3.25 (m, 1H), 5.03 (d, J=8.6 Hz, 1H), 7.19-7.37 (m, 3H), 7.38-7.58 (m, 5H), 7.65 (m, 1H), 8.69 (d, J=8.7 Hz, 1H), 10.93 (s, 1H).

Example 198

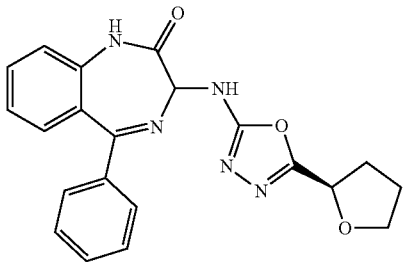 [SMILES: O=C1Nc2ccccc2C(c2ccccc2)=NC1Nc1nnc([C@H]2CCCO2)o1]

Example 198 was prepared using a procedure similar to that used to prepare Example 20 where (R)-tetrahydrofuran-2-carboxylic acid was used in place of 5-chlorofuran-2-carboxylic acid. ESI-MS m/z: 390.3 [M+H]+. 1H NMR (300 MHz, DMSO-d6) δ 1.82-2.30 (m, 4H), 3.74-3.86 (m, 2H), 4.94 (m, 1H), 5.06 (d, J=8.5 Hz, 1H), 7.18-7.38 (m, 3H), 7.38-7.71 (m, 6H), 8.93 (m, 1H), 10.96 (s, 1H).

Example 199

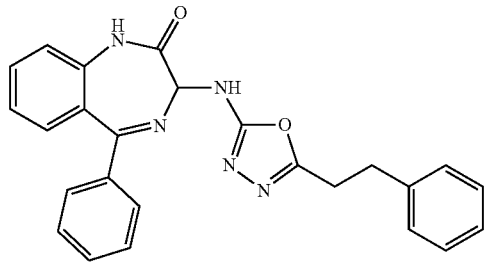 [SMILES: O=C1Nc2ccccc2C(c2ccccc2)=NC1Nc1nnc(CCc2ccccc2)o1]

Example 199 was prepared using a procedure similar to that used to prepare Example 20 where 3-phenylpropanoic acid was used in place of 5-chlorofuran-2-carboxylic acid. ESI-MS m/z: 424.4 [M+H]+. 1H NMR (300 MHz, DMSO-d6) δ 2.90-3.09 (m, 4H), 5.02 (s, 1H), 7.14-7.71 (m, 14H), 8.73 (s, 1H), 10.95 (s, 1H).

Example 200

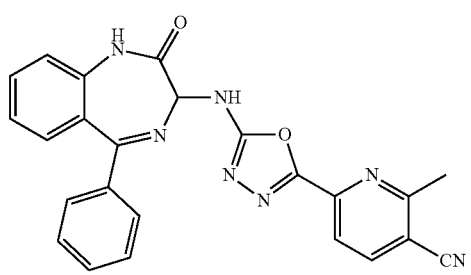 [SMILES: Cc1nc(-c2nnc(NC3N=C(c4ccccc4)c4ccccc4NC3=O)o2)ccc1C#N]

Example 200 was prepared using a procedure similar to that used to prepare Example 20 where 5-cyano-6-methylpicolinic acid was used in place of 5-chlorofuran-2-carboxylic acid. ESI-MS m/z: 436.3 [M+H]+. 1H NMR (300 MHz, DMSO-d6) δ 2.73 (s, 3H), 5.20 (d, J=7.2 Hz, 1H), 7.21-7.40 (m, 3H), 7.40-7.59 (m, 5H), 7.67 (ddd, J=8.5, 7.2, 1.8 Hz, 1H), 7.96 (d, J=8.2 Hz, 1H), 8.38 (d, J=8.2 Hz, 1H), 9.52 (d, J=8.2 Hz, 1H), 11.01 (s, 1H).

Example 201

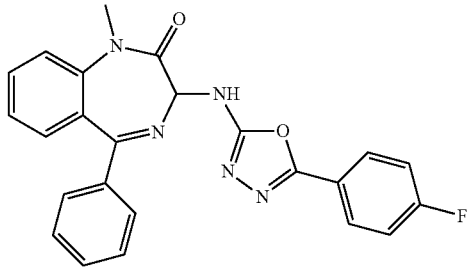 [SMILES: CN1C(=O)C(Nc2nnc(-c3ccc(F)cc3)o2)N=C(c2ccccc2)c2ccccc21]

A solution of Example 7 (0.2 g, 0.48 mmol), K₂CO₃ (0.13 g, 0.96 mmol) MeI (68 mg, 0.48 mmol) in DMF (3 mL). The mixture was stirred at r.t. for 6 hrs, It was diluted with EA and washed with brine. The organic phase was dried and concentrated. The residue was purified by Prep-HPLC to give the desired product as a white solid (31.2 mg, 15.2%). ESI-MS m/z: 428.1 [M+H]⁺. ¹H NMR (300 MHz, DMSO-d₆) δ 3.44 (s, 3H), 5.23 (d, J=8.6 Hz, 1H), 7.36-7.62 (m, 9H), 7.77 (m, 2H), 7.83-7.96 (m, 2H), 9.22 (d, J=8.7 Hz, 1H).

Example 202

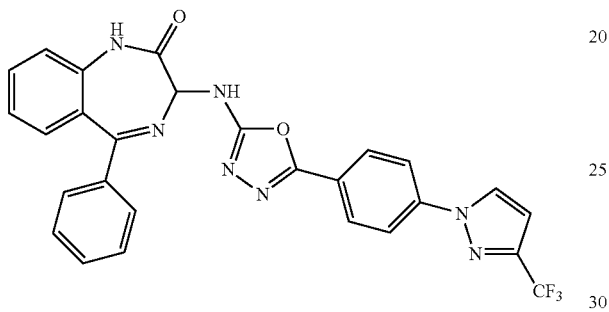

Example 202 was prepared using a procedure similar to that used to prepare Example 20 where 4-(3-(trifluoromethyl)-1H-pyrazol-1-yl)benzoic acid was used in place of 5-chlorofuran-2-carboxylic acid. ESI-MS m/z: 530.4 [M+H]⁺. ¹H NMR (300 MHz, DMSO-d₆) δ 5.19 (d, J=8.4 Hz, 1H), 7.19-7.59 (m, 9H), 7.61-7.76 (m, 3H), 7.94-8.06 (m, 3H), 9.29 (d, J=8.5 Hz, 1H), 11.01 (s, 1H).

Example 203

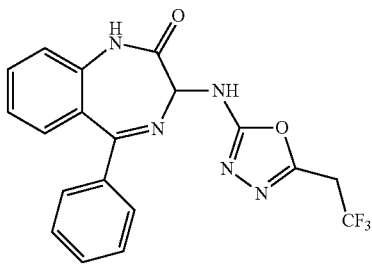 [SMILES: O=C1Nc2ccccc2C(c2ccccc2)=NC1Nc1nnc(CC(F)(F)F)o1]

Example 203 was prepared using a procedure similar to that used to prepare Example 20 where 3,3,3-trifluoropropanoic acid was used in place of 5-chlorofuran-2-carboxylic acid. ESI-MS m/z: 402.1 [M+H]⁺. ¹H NMR (300 MHz, DMSO-d₆) δ 4.11 (q, J=10.7 Hz, 2H), 5.07 (d, J=8.4 Hz, 1H), 7.20-7.59 (m, 8H), 7.65 (ddd, J=8.4, 7.0, 1.8 Hz, 1H), 9.13 (d, J=8.5 Hz, 1H), 10.96 (s, 1H).

Example 204

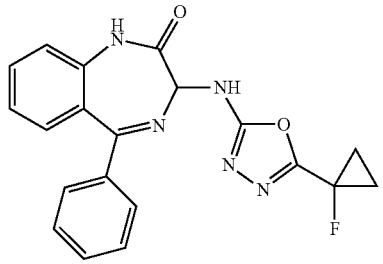 [SMILES: O=C1Nc2ccccc2C(c2ccccc2)=NC1Nc1nnc(C2(F)CC2)o1]

Example 204 was prepared using a procedure similar to that used to prepare Example 20 where 1-fluorocyclopropane-1-carboxylic acid was used in place of 5-chlorofuran-2-carboxylic acid. ESI-MS m/z: 370.3 [M+H]⁺. ¹H NMR (400 MHz, DMSO-d₆) δ 1.19-1.34 (m, 2H), 1.49-1.63 (m, 2H), 5.10 (d, J=8.4 Hz, 1H), 7.23-7.39 (m, 3H), 7.42-7.62 (m, 6H), 7.67 (m, 1H), 9.18 (d, J=8.5 Hz, 1H), 10.99 (s, 1H).

Example 205

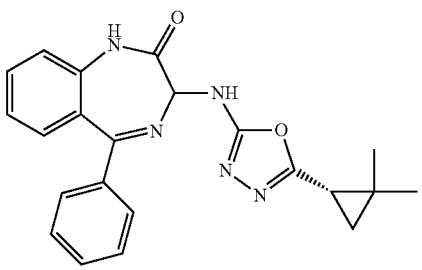 [SMILES: CC1(C)C[C@@H]1c1nnc(NC2N=C(c3ccccc3)c3ccccc3NC2=O)o1]

Example 205 was prepared using a procedure similar to that used to prepare Example 20 where (S)-2,2-dimethylcyclopropane-1-carboxylic acid was used in place of 5-chlorofuran-2-carboxylic acid. ESI-MS m/z: 388.2 [M+H]⁺. ¹H NMR (400 MHz, DMSO-d₆) δ 0.94-1.00 (m, 5H), 1.18 (s, 3H), 1.86-1.90 (m, 1H), 5.03-5.05 (d, J=8.0 Hz, 1H), 7.24-7.34 (m, 3H), 7.44-7.55 (m, 5H), 7.64-7.68 (m, 1H), 8.70-8.73 (m, 1H), 10.93 (s, 1H).

Example 206

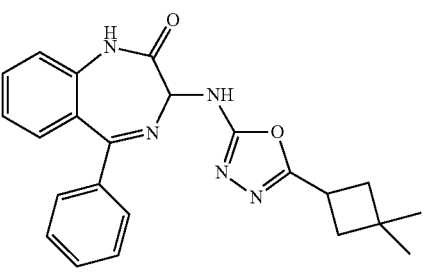 [SMILES: CC1(C)CC(c2nnc(NC3N=C(c4ccccc4)c4ccccc4NC3=O)o2)C1]

Example 206 was prepared using a procedure similar to that used to prepare Example 20 where 3,3-dimethylcyclobutane-1-carboxylic acid was used in place of 5-chlorofuran-2-carboxylic acid. ESI-MS m/z: 402.4 [M+H]⁺. ¹H NMR (400 MHz, DMSO-d$_6$) δ 1.10 (s, 3H), 1.20 (s, 3H), 1.99-2.16 (m, 4H), 3.56 (m, 1H), 5.06 (d, J=8.7 Hz, 1H), 7.22-7.38 (m, 3H), 7.41-7.58 (m, 5H), 7.66 (m, 1H), 8.75 (d, J=8.7 Hz, 1H), 10.95 (s, 1H).

Example 207

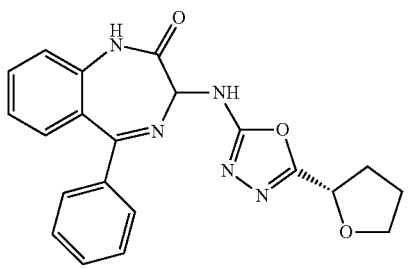 [SMILES: O=C1Nc2ccccc2C(c2ccccc2)=NC1Nc1nnc([C@@H]2CCCO2)o1]

Example 207 was prepared using a procedure similar to that used to prepare Example 20 where (S)-tetrahydrofuran-2-carboxylic acid was used in place of 5-chlorofuran-2-carboxylic acid. ESI-MS m/z: 390.2 [M+H]$^+$. $^1$H NMR (400 MHz, DMSO-d$_6$) δ 1.93-2.01 (m, 2H), 2.15-2.22 (m, 2H), 3.79-3.83 (m, 2H), 4.93-5.08 (m, 2H), 7.25-7.35 (m, 3H), 7.44-7.53 (m, 5H), 7.64-7.68 (m, 1H), 8.93-8.96 (m, 1H), 11.00 (s, 1H).

Example 208

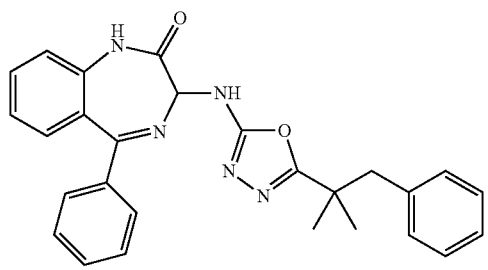 [SMILES: CC(C)(Cc1ccccc1)c1nnc(NC2N=C(c3ccccc3)c3ccccc3NC2=O)o1]

Example 208 was prepared using a procedure similar to that used to prepare Example 20 where 2,2-dimethyl-3-phenylpropanoic acid was used in place of 5-chlorofuran-2-carboxylic acid. ESI-MS m/z: 452.4 [M+H]$^+$. $^1$H NMR (400 MHz, DMSO-d$_6$) δ 1.22-1.30 (m, 6H), 2.91 (s, 2H), 5.05 (d, J=8.7 Hz, 1H), 6.95-7.02 (m, 2H), 7.15-7.38 (m, 6H), 7.42-7.60 (m, 5H), 7.67 (m, 1H), 8.73 (d, J=8.8 Hz, 1H), 10.96 (s, 1H).

Example 209

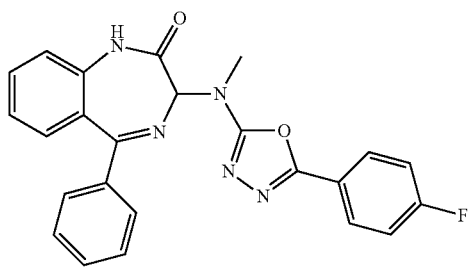 [SMILES: CN(c1nnc(-c2ccc(F)cc2)o1)C1N=C(c2ccccc2)c2ccccc2NC1=O]

Example 209 Step a

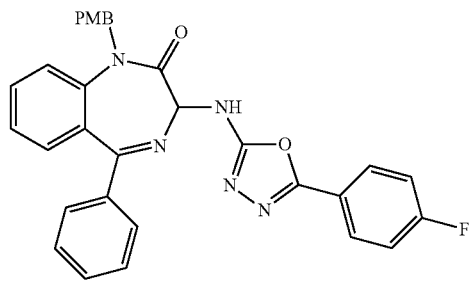

A solution of 3-amino-1-(4-methoxybenzyl)-5-phenyl-1,3-dihydro-2H-benzo[e][1,4]diazepin-2-one, from Example 91 step b, (0.37 g, 1 mmol), TCDI (196 mg, 1.1 mmol) in DMF (10 mL) was stirred for 0.5 hours. 4-fluorobenzohydrazide (169 mg, 1.1 mmol) was added and then stirred for 3 hours. EDCI (764 mg, 4 mmol) was added and then stirred for 1 hours at 60° C. Then it was purified by flash to afford product as a white solid (0.3 g, 56%). ESI-MS m/z: 534.3 [M+H]$^+$.

Example 209 Step b

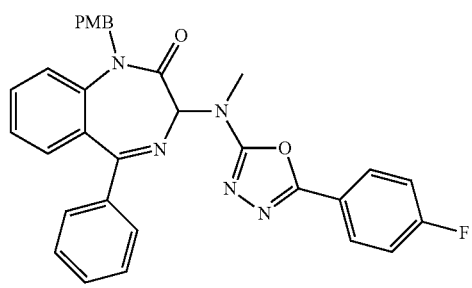

A solution of the compound from step a (0.3 g, 0.56 mmol), K$_2$CO$_3$ (0.15 g, 1.12 mmol) MeI (95 mg, 0.68 mmol) in DMF (5 mL). The mixture was stirred at r.t. for 6 hrs, It was diluted with EA and washed with brine. The organic phase was dried and concentrated to afford product as a yellow solid (0.3 g, 98%). ESI-MS m/z: 548.5 [M+H]$^+$.

Example 209 Step c

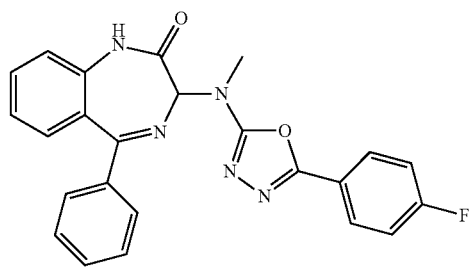 [SMILES: CN(c1nnc(-c2ccc(F)cc2)o1)C1N=C(c2ccccc2)c2ccccc2NC1=O]

A mixture of the compound from step b (200 mg, 0.37 mmol) and AlCl$_3$ (490 mg, 3.7 mmol) in anisole (5 mL) was heated to 70° C. for 3 hrs under N$_2$. Solvent was removed. The residue was purified by Prep-HPLC to afford product as light yellow solid (79.6 mg, 50.4%). ESI-MS m/z: 428.1 [M+H]$^+$. $^1$H NMR (300 MHz, DMSO-d$_6$) δ 3.55 (s, 3H), 5.49 (s, 1H), 7.25-7.45 (m, 5H), 7.46-7.64 (m, 5H), 7.65-7.77 (m, 1H), 7.93 (m, 2H), 11.06 (s, 1H).

Example 210

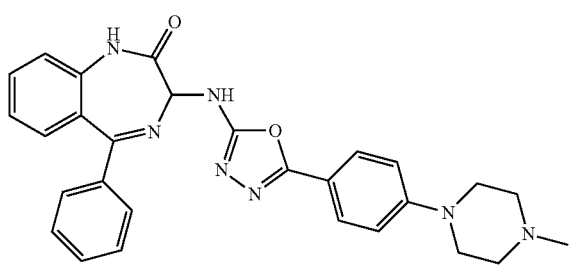 [SMILES: CN1CCN(c2ccc(-c3nnc(NC4N=C(c5ccccc5)c5ccccc5NC4=O)o3)cc2)CC1]

Example 210 was prepared using a procedure similar to that used to prepare Example 20 where 4-(4-methylpiperazin-1-yl)benzoic acid was used in place of 5-chlorofuran-2-carboxylic acid ESI-MS m/z: 494.3 [M+H]$^+$. $^1$H NMR (300 MHz, DMSO-d$_6$) δ 3.15 (t, J=4.9 Hz, 4H), 3.75 (dd, J=6.0, 3.6 Hz, 4H), 5.10-5.19 (m, 1H), 7.08-7.73 (m, 14H), 7.82 (s, 1H), 8.99-9.09 (m, 1H), 10.99 (s, 1H).

Example 211

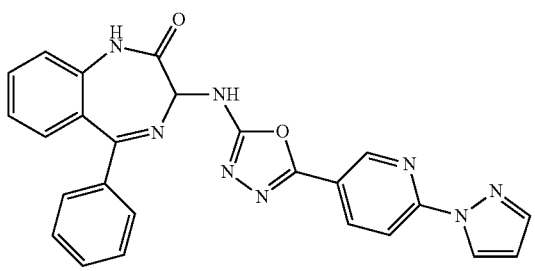 [SMILES: O=C1Nc2ccccc2C(c2ccccc2)=NC1Nc1nnc(-c2ccc(-n3cccn3)nc2)o1]

Example 211 was prepared using a procedure similar to that used to prepare Example 20 where 6-(1H-pyrazol-1-yl)nicotinic acid was used in place of 5-chlorofuran-2-carboxylic acid. ESI-MS m/z: 482.3 [M+H]$^+$. $^1$H NMR (300 MHz, DMSO-d$_6$) δ 5.18 (d, J=6.6 Hz, 1H), 6.64 (dd, J=2.7, 1.7 Hz, 1H), 7.22-7.59 (m, 8H), 7.67 (ddd, J=8.4, 7.1, 1.7 Hz, 1H), 7.90 (dd, J=1.6, 0.7 Hz, 1H), 8.09 (dd, J=8.6, 0.9 Hz, 1H), 8.36 (dd, J=8.7, 2.3 Hz, 1H), 8.68 (dd, J=2.6, 0.7 Hz, 1H), 8.86 (dd, J=2.3, 0.8 Hz, 1H), 9.28 (d, J=7.2 Hz, 1H), 11.01 (s, 1H).

Example 212

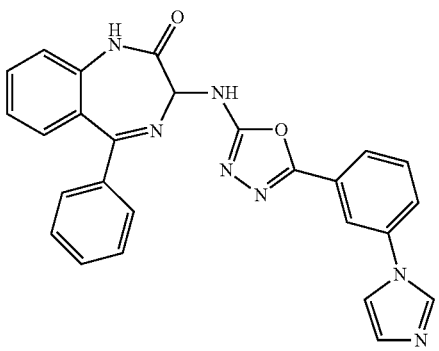 [SMILES: O=C1Nc2ccccc2C(c2ccccc2)=NC1Nc1nnc(-c2cccc(-n3ccnc3)c2)o1]

Example 212 was prepared using a procedure similar to that used to prepare Example 20 where 3-(1H-imidazol-1-yl)benzoic acid was used in place of 5-chlorofuran-2-carboxylic acid. ESI-MS m/z: 462.1 [M+H]$^+$. $^1$H NMR (300 MHz, DMSO-d6) δ 5.21 (d, J=8.4 Hz, 1H), 7.13-7.20 (m, 1H), 7.24-7.61 (m, 8H), 7.63-7.90 (m, 5H), 7.98-8.11 (m, 1H), 8.37 (s, 1H), 9.23 (d, J=8.3 Hz, 1H), 11.02 (s, 1H).

Example 213

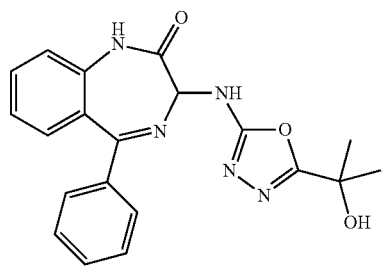 [SMILES: CC(C)(O)c1nnc(NC2N=C(c3ccccc3)c3ccccc3NC2=O)o1]

Example 213 was prepared using a procedure similar to that used to prepare Example 20 where 4-(1H-imidazol-1-yl)benzoic acid was used in place of 5-chlorofuran-2-carboxylic acid. ESI-MS m/z: 378.1 [M+H]$^+$. $^1$H NMR (300 MHz, DMSO-d6) δ 1.49 (s, 6H), 2.44 (s, 1H), 5.07 (d, J=8.6 Hz, 1H), 5.67 (s, 1H), 7.22-7.43 (m, 3H), 7.41-7.61 (m, 5H), 7.67 (m, 1H), 8.82 (d, J=8.7 Hz, 1H), 10.92-10.99 (s, 1H).

Example 214

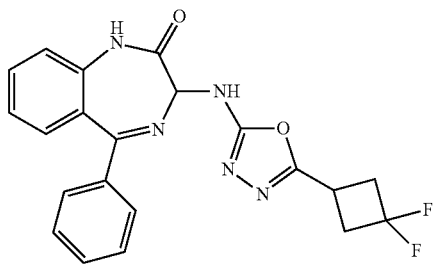 [SMILES: O=C1Nc2ccccc2C(c2ccccc2)=NC1Nc1nnc(C2CC(F)(F)C2)o1]

Example 214 was prepared using a procedure similar to that used to prepare Example 20 where 3,3-difluorocyclobutane-1-carboxylic acid was used in place of 5-chlorofuran-2-carboxylic acid. ESI-MS m/z: 410.1 [M+H]$^+$. H-NMR-PH-ETA-A1-426-0: $^1$H NMR (300 MHz, DMSO-d$_6$) δ 2.75-3.17 (m, 4H), 3.55 (dddd, J=11.1, 9.3, 5.3, 3.8 Hz, 1H), 5.06 (d, J=8.6 Hz, 1H), 7.20-7.38 (m, 3H), 7.38-7.59 (m, 5H), 7.65 (ddd, J=8.5, 7.0, 1.8 Hz, 1H), 8.89 (d, J=8.6 Hz, 1H), 10.95 (s, 1H).

Example 215

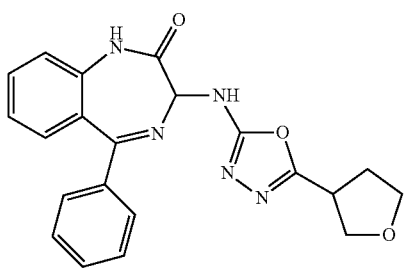 [SMILES: O=C1Nc2ccccc2C(c2ccccc2)=NC1Nc1nnc(C2CCOC2)o1]

Example 215 was prepared using a procedure similar to that used to prepare Example 20 where tetrahydrofuran-3-carboxylic acid was used in place of 5-chlorofuran-2-carboxylic acid. ESI-MS m/z: 390.1 [M+H]$^+$. $^1$H NMR (300 MHz, DMSO-d6) δ 2.03-2.31 (m, 2H), 3.60 (m, 1H), 3.70-3.91 (m, 3H), 3.97 (m, 1H), 5.07 (d, J=8.7 Hz, 1H), 7.22-7.40 (m, 3H), 7.41-7.61 (m, 5H), 7.67 (m, 1H), 8.51 (s, 0.2H), 8.83 (d, J=8.6 Hz, 1H), 10.97 (d, J=8.6 Hz, 1H).

Example 216

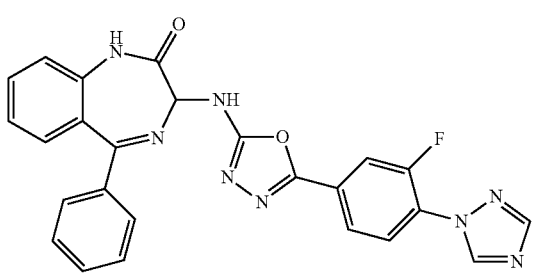 [SMILES: O=C1Nc2ccccc2C(c2ccccc2)=NC1Nc1nnc(-c2ccc(-n3cncn3)c(F)c2)o1]

Example 216 was prepared using a procedure similar to that used to prepare Example 20 where 3-fluoro-4-(1H-1,2,4-triazol-1-yl)benzoic acid was used in place of 5-chlorofuran-2-carboxylic acid. ESI-MS m/z: 481.3 [M+H]$^+$. $^1$H NMR (300 MHz, DMSO-d$_6$) δ 5.19 (d, J=7.5 Hz, 1H), 7.22-7.59 (m, 8H), 7.67 (ddd, J=8.5, 7.0, 1.7 Hz, 1H), 7.78-7.94 (m, 2H), 8.03 (t, J=8.0 Hz, 1H), 8.36 (s, 1H), 9.11 (d, J=2.5 Hz, 1H), 9.32 (d, J=8.2 Hz, 1H), 11.02 (s, 1H).

Example 217

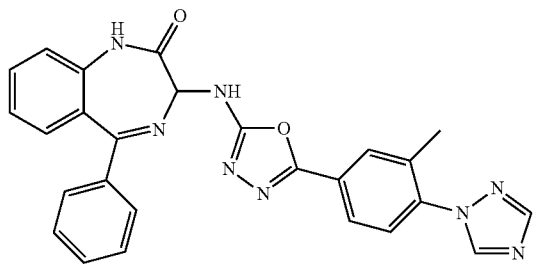 [SMILES: Cc1cc(-c2nnc(NC3N=C(c4ccccc4)c4ccccc4NC3=O)o2)ccc1-n1cncn1]

Example 217 was prepared using a procedure similar to that used to prepare Example 20 where 3-methyl-4-(1H-1,2,4-triazol-1-yl)benzoic acid was used in place of 5-chlorofuran-2-carboxylic acid. ESI-MS m/z: 477.3 [M+H]$^+$. $^1$H NMR (300 MHz, DMSO-d$_6$) δ 2.30 (s, 3H), 5.19 (d, J=8.1 Hz, 1H), 7.22-7.74 (m, 10H), 7.80 (dd, J=8.4, 1.9 Hz, 1H), 7.91 (t, J=1.2 Hz, 1H), 8.28 (s, 1H), 8.97 (s, 1H), 9.23 (d, J=8.2 Hz, 1H), 11.01 (s, 1H).

Example 218

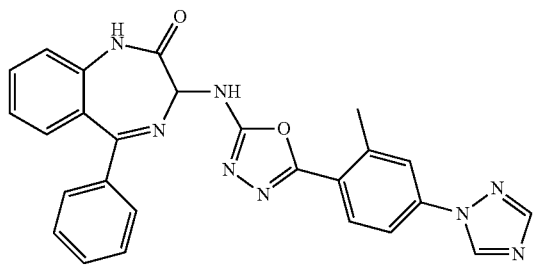 [SMILES: Cc1cc(-n2cncn2)ccc1-c1nnc(NC2N=C(c3ccccc3)c3ccccc3NC2=O)o1]

Example 218 was prepared using a procedure similar to that used to prepare Example 20 where 2-methyl-4-(1H-1,2,4-triazol-1-yl)benzoic acid was used in place of 5-chlorofuran-2-carboxylic acid. ESI-MS m/z: 477.2 [M+H]$^+$. $^1$H NMR (300 MHz, DMSO-d$_6$) δ 2.67 (s, 3H), 5.20 (d, J=7.9 Hz, 1H), 7.24-7.43 (m, 3H), 7.44-7.64 (m, 5H), 7.64-7.78 (m, 1H), 7.95 (d, J=16.1 Hz, 3H), 8.31 (s, 1H), 9.19 (d, J=8.3 Hz, 1H), 9.41 (s, 1H), 11.01 (s, 1H).

Example 219

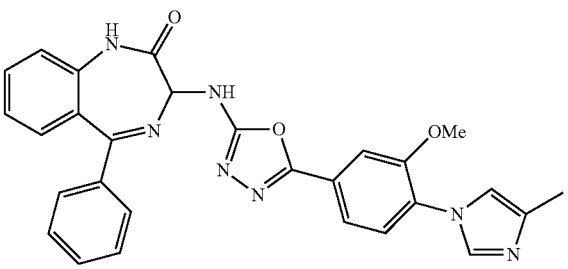 [SMILES: COc1cc(-c2nnc(NC3N=C(c4ccccc4)c4ccccc4NC3=O)o2)ccc1-n1cnc(C)c1]

Example 219 was prepared using a procedure similar to that used to prepare Example 20 where 3-methoxy-4-(4-methyl-1H-imidazol-1-yl)benzoic acid was used in place of 5-chlorofuran-2-carboxylic acid. ESI-MS m/z: 506.2 [M+H]+. 1H NMR (300 MHz, DMSO-d6) δ 2.18 (s, 3H), 3.94 (s, 3H), 5.19 (d, J=7.9 Hz, 1H), 7.19-7.81 (m, 13H), 7.89 (d, J=1.4 Hz, 1H), 9.19 (d, J=8.1 Hz, 1H), 11.03 (s, 1H).

Example 220

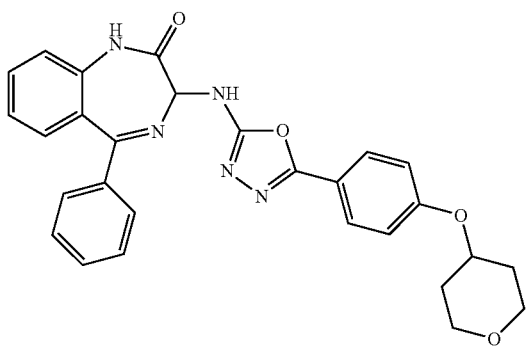 [SMILES: O=C1Nc2ccccc2C(c2ccccc2)=NC1Nc1nnc(-c2ccc(OC3CCOCC3)cc2)o1]

Example 220 was prepared using a procedure similar to that used to prepare Example 20 where 4-((tetrahydro-2H-pyran-4-yl)oxy)benzoic acid was used in place of 5-chlorofuran-2-carboxylic acid. ESI-MS m/z: 496.4 [M+H]+. 1H NMR (300 MHz, DMSO-d$_6$) δ 1.62 (dtd, J=13.3, 9.0, 4.1 Hz, 2H), 1.91-2.09 (m, 2H), 3.51 (ddd, J=11.7, 9.5, 2.8 Hz, 2H), 3.88 (dt, J=11.4, 4.6 Hz, 2H), 4.70 (td, J=8.9, 4.5 Hz, 1H), 5.16 (d, J=8.5 Hz, 1H), 7.16 (d, J=8.8 Hz, 2H), 7.24-7.43 (m, 3H), 7.42-7.62 (m, 5H), 7.63-7.84 (m, 3H), 9.02 (d, J=8.5 Hz, 1H), 10.98 (s, 1H).

Example 221

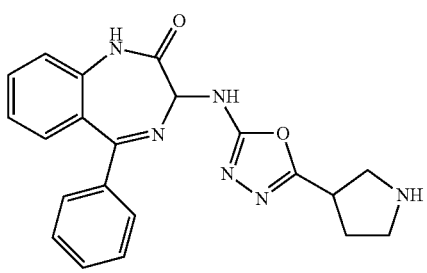 [SMILES: O=C1Nc2ccccc2C(c2ccccc2)=NC1Nc1nnc(C2CCNC2)o1]

Example 221 was prepared using a procedure similar to that used to prepare Example 20 where pyrrolidine-3-carboxylic acid was used in place of 5-chlorofuran-2-carboxylic acid. ESI-MS m/z: 489.1 [M+H]+. 1H NMR (300 MHz, DMSO-d$_6$) δ 1.98 (dt, J=12.8, 7.0 Hz, 1H), 2.12 (ddd, J=12.9, 8.7, 6.4 Hz, 1H), 2.99 (q, J=8.2, 6.8 Hz, 3H), 3.27 (dd, J=11.1, 7.8 Hz, 1H), 3.43 (q, J=7.7 Hz, 1H), 5.04-5.10 (m, 1H), 7.24-7.39 (m, 3H), 7.43-7.59 (m, 5H), 7.67 (ddd, J=8.4, 7.0, 1.8 Hz, 1H), 8.34 (s, 2H), 8.80 (d, J=8.4 Hz, 1H).

Example 222

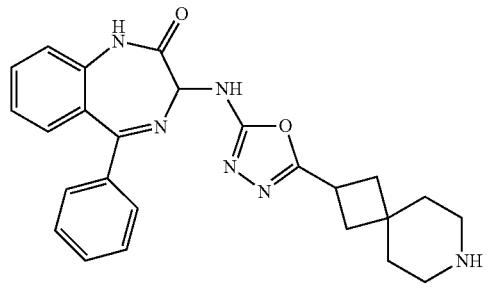 [SMILES: O=C1Nc2ccccc2C(c2ccccc2)=NC1Nc1nnc(C2CC3(CCNCC3)C2)o1]

Example 222 was prepared using a procedure similar to that used to prepare Example 20 where 7-azaspiro[3.5]nonane-2-carboxylic acid was used in place of 5-chlorofuran-2-carboxylic acid. ESI-MS m/z: 443.4 [M+H]+. 1H NMR (400 MHz, DMSO-d$_6$) δ 1.63 (q, J=5.1 Hz, 2H), 1.75 (dd, J=7.2, 3.9 Hz, 2H), 2.03 (ddd, J=12.6, 8.3, 2.2 Hz, 2H), 2.18-2.29 (m, 2H), 2.86 (dt, J=34.9, 5.5 Hz, 4H), 3.59 (d, J=8.6 Hz, 1H), 5.05 (d, J=7.8 Hz, 1H), 7.22-7.40 (m, 3H), 7.42-7.59 (m, 5H), 7.66 (ddd, J=8.5, 7.1, 1.7 Hz, 1H), 8.40 (s, 1H), 8.77 (d, J=8.7 Hz, 1H).

Example 223

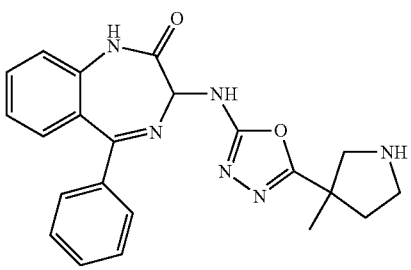 [SMILES: CC1(c2nnc(NC3N=C(c4ccccc4)c4ccccc4NC3=O)o2)CCNC1]

Example 223 was prepared using a procedure similar to that used to prepare Example 20 where 3-methylpyrrolidine-3-carboxylic acid was used in place of 5-chlorofuran-2-carboxylic acid. ESI-MS m/z: 403.3 [M+H]+. 1H NMR (300 MHz, DMSO-d6) δ 1.40 (s, 3H), 1.80 (m, 1H), 2.24 (m, 1H), 2.88 (d, J=11.2 Hz, 1H), 2.94-3.16 (m, 3H), 3.23 (d, J=11.2 Hz, 1H), 5.07 (d, J=8.4 Hz, 1H), 7.22-7.40 (m, 3H), 7.41-7.61 (m, 5H), 7.61-7.73 (m, 1H), 8.41 (s, 1H), 8.78 (d, J=8.7 Hz, 1H), 11.10 (s, 1H).

Example 224

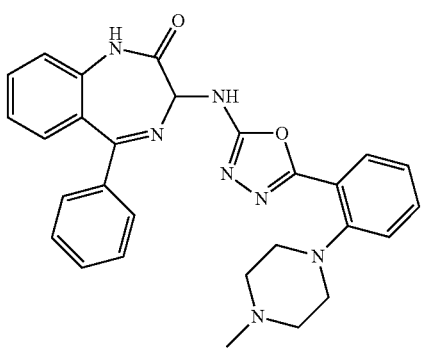 [SMILES: CN1CCN(c2ccccc2-c2nnc(NC3N=C(c4ccccc4)c4ccccc4NC3=O)o2)CC1]

Example 224 was prepared using a procedure similar to that used to prepare Example 20 where 2-(4-methylpiperazin-1-yl)benzoic acid was used in place of 5-chlorofuran-2-carboxylic acid. ESI-MS m/z: 494.4 [M+H]+. $^1$H NMR (300 MHz, DMSO-d$_6$) δ 2.18 (s, 3H), 2.38 (d, J=5.4 Hz, 4H), 2.89 (t, J=4.6 Hz, 4H), 5.18 (d, J=8.5 Hz, 1H), 7.06-7.22 (m, 2H), 7.23-7.41 (m, 3H), 7.41-7.59 (m, 6H), 7.59-7.75 (m, 2H), 9.03 (d, J=8.6 Hz, 1H), 10.99 (s, 1H).

Example 225

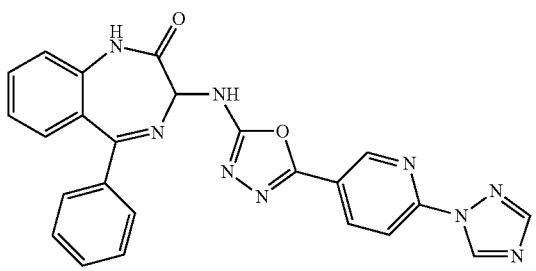 [SMILES: O=C1Nc2ccccc2C(c2ccccc2)=NC1Nc1nnc(-c2ccc(-n3cncn3)nc2)o1]

Example 225 was prepared using a procedure similar to that used to prepare Example 20 where 6-(1H-1,2,4-triazol-1-yl)nicotinic acid was used in place of 5-chlorofuran-2-carboxylic acid. ESI-MS m/z: 464.4 [M+H]+. $^1$H NMR (300 MHz, DMSO-d$_6$) δ 5.17 (s, 1H), 7.20-7.39 (m, 3H), 7.39-7.61 (m, 5H), 7.60-7.72 (m, 1H), 8.05 (d, J=8.6 Hz, 1H), 8.34-8.53 (m, 2H), 8.93 (d, J=2.3 Hz, 1H), 9.30 (s, 1H), 9.46 (s, 1H), 11.03 (s, 1H).

Example 226

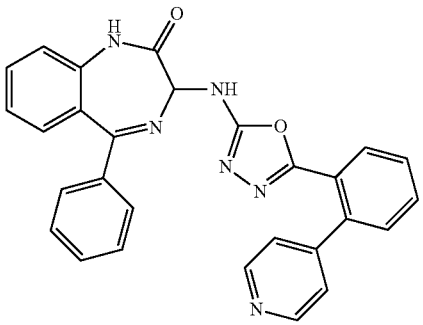 [SMILES: O=C1Nc2ccccc2C(c2ccccc2)=NC1Nc1nnc(-c2ccccc2-c2ccncc2)o1]

Example 226 was prepared using a procedure similar to that used to prepare Example 20 where 2-(pyridin-4-yl)benzoic acid was used in place of 5-chlorofuran-2-carboxylic acid. ESI-MS m/z: 473.3 [M+H]+. $^1$H NMR (300 MHz, DMSO-d$_6$) δ 4.94 (d, J=8.5 Hz, 1H), 7.21-7.37 (m, 5H), 7.38-7.58 (m, 6H), 7.66 (tdd, J=6.8, 3.6, 1.7 Hz, 3H), 7.84 (dd, J=7.3, 1.9 Hz, 1H), 8.46-8.56 (m, 2H), 8.98 (d, J=8.6 Hz, 1H), 10.93 (s, 1H).

Example 227

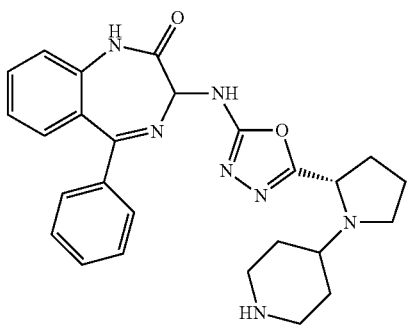 [SMILES: O=C1Nc2ccccc2C(c2ccccc2)=NC1Nc1nnc([C@@H]2CCCN2C2CCNCC2)o1]

Example 227 was prepared using a procedure similar to that used to prepare Example 20 where piperidin-4-yl-L-proline was used in place of 5-chlorofuran-2-carboxylic acid. ESI-MS m/z: 472.3 [M+H]+. $^1$H NMR (300 MHz, DMSO-d6) δ 1.42 (m, 2H), 1.82 (m, 6H), 2.09 (m, 1H), 2.62-2.79 (m, 2H), 2.85 (s, 1H), 3.00 (m, 4H), 4.06-4.16 (m, 1H), 5.07 (d, J=8.5 Hz, 1H), 7.22-7.40 (m, 3H), 7.51 (q, J=7.9, 6.9 Hz, 5H), 7.61-7.74 (m, 1H), 8.37-8.44 (s, 1H), 8.82 (d, J=8.7 Hz, 1H), 10.92 (s, 1H).

Example 228

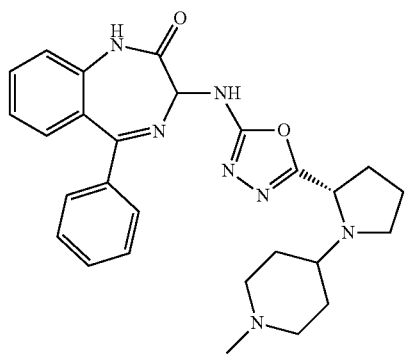 [SMILES: CN1CCC(N2CCC[C@H]2c2nnc(NC3N=C(c4ccccc4)c4ccccc4NC3=O)o2)CC1]

A solution of Example 227 (188 mg, 0.4 mmol), HCHO (0.5 mL), NaBH(OAc)$_3$ (212 mg, 1.0 mmol) in THF (20 mL) was stirred for 1 hour at 50° C. Extracted with EA (3×), dried Na$_2$SO$_4$, filtered and purified by Prep-HPLC (MeCN/H$_2$O) to give desired compound as a yellow solid (10 mg, 26%). ESI-MS m/z: 486.4 [M+H]+. $^1$H NMR (300 MHz, DMSO-d$_6$) δ 1.22-1.46 (m, 2H), 1.63-1.96 (m, 8H), 2.10 (s, 3H), 2.22 (m, 1H), 2.68 (m, 3H), 2.85 (m, 1H), 4.08 (m, 1H), 5.07 (m, 1H), 7.22-7.39 (m, 3H), 7.40-7.73 (m, 6H), 8.78 (m, 1H), 10.94 (s, 1H)

Example 229

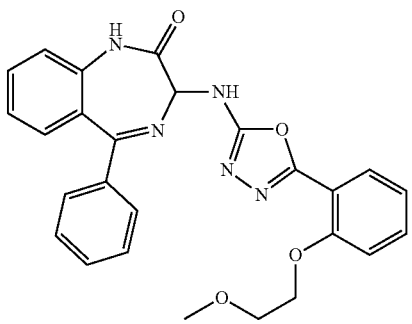 [SMILES: COCCOc1ccccc1-c1nnc(NC2N=C(c3ccccc3)c3ccccc3NC2=O)o1]

Example 229 was prepared using a procedure similar to that used to prepare Example 20 where 2-(2-methoxyethoxy)benzoic acid was used in place of 5-chlorofuran-2-carboxylic acid. ESI-MS m/z: 470.4 [M+H]+. $^1$H NMR (300 MHz, DMSO-d$_6$) δ 3.27 (s, 3H), 3.61-3.72 (m, 2H), 4.18 (dd, J=5.6, 3.8 Hz, 2H), 5.15 (d, J=8.5 Hz, 1H), 7.08 (td, J=7.5, 1.0 Hz, 1H), 7.16-7.39 (m, 4H), 7.41-7.57 (m, 6H), 7.67 (ddd, J=8.4, 5.0, 1.8 Hz, 2H), 9.00 (d, J=8.6 Hz, 1H), 10.98 (s, 1H).

Example 230

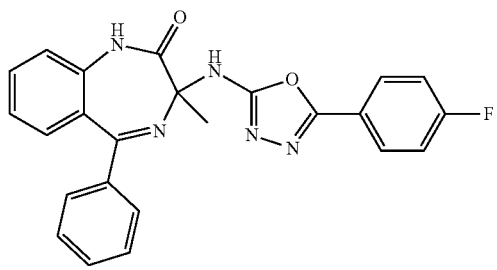 [SMILES: CC1(Nc2nnc(-c3ccc(F)cc3)o2)N=C(c2ccccc2)c2ccccc2NC1=O]

Example 230 Step a

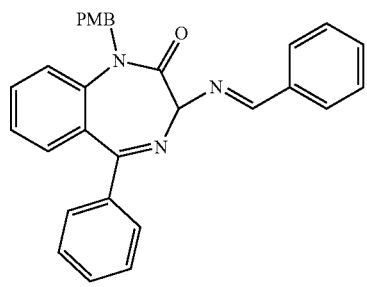

A solution of 3-amino-1-(4-methoxybenzyl)-5-phenyl-1,3-dihydro-2H-benzo[e][1,4]diazepin-2-one, from Example 91 step b, (1.0 g, 2.70 mmol), benzaldehyde (314 mg, 2.96 mmol), 4 Å molecular sieves (10 g) and MgSO$_4$ (10 g) in 50 mL DCM was stirred at room temperature overnight under N$_2$. Then the solid was filtered out and the filtrate was concentrated to afford crude product, which was used directly in the next step. ESI-MS m/z: 460.3 [M+H]+.

Example 230 Step b

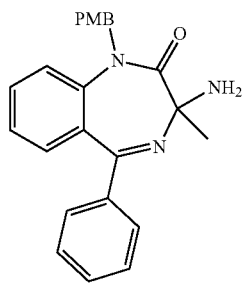

A solution of the compound from step a (1.0 g, 2.18 mmol) in THF (20 mL) was added to NaHMDS (2.4 mL) in THF (5 mL) at −70° C. under N$_2$. After stirring for 5 min, MeI (340 mg, 2.40 mmol) was added. The mixture was stirred at −70° C. for 2 hrs, then it was warmed to room temperature and stirred overnight. It was quenched by brine and solvent was removed. The residue was dissolved in 2N HCl (10 mL) and MeOH (5 mL). The mixture was stirred for 30 min, basified by 2N NaOH and extracted with EtOAc. It was purified silica gel column to afford product as tin solid (160 mg). ESI-MS m/z: 386.1 [M+H]+.

Example 230 Step c

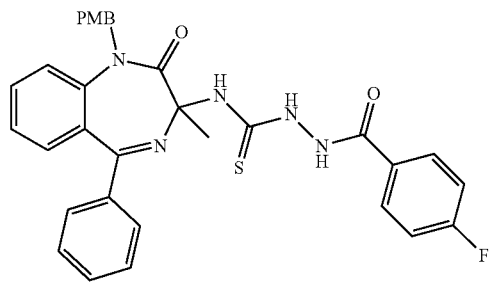

A solution of the compound from step b (150 mg, 0.39 mmol) and Et$_3$N (79 mg, 0.78 mmol) in DCM (5 mL) was added thiophosgene (49 mg, 0.43 mmol) at 0° C. After stirring for 2 hrs at 0° C., 4-fluorobenzohydrazide (200 mg, 1.3 mmol) was added. It was stirred for another one hour before concentrated. The residue was purified by reverse phase C18 column chromatography (MeCN/H$_2$O) to afford product as yellow solid (70 mg). ESI-MS m/z: 582.4 [M+H]+.

Example 230 Step d

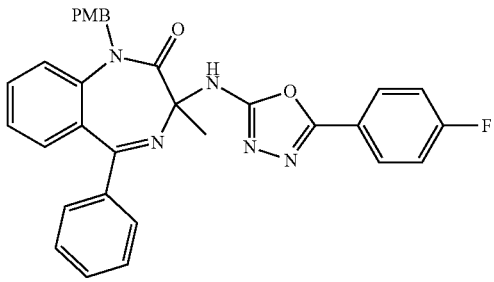

A mixture of the compound from step c (70 mg, 0.12 mmol) and EDCI (44 mg, 0.24 mmol) in DMF (2 mL) was heated to 60° C. for 1 hour. Then it was purified by reverse phase C18 column chromatography (MeCN/H₂O) to afford product as yellow solid (48 mg). ESI-MS m/z: 548.4 [M+H]⁺.

Example 230 Step g

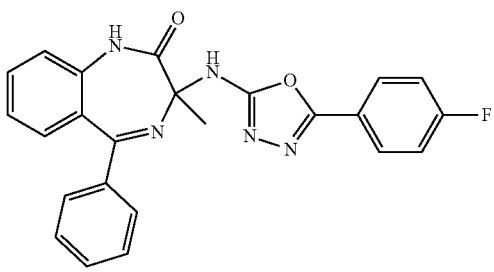 [SMILES: CC1(Nc2nnc(-c3ccc(F)cc3)o2)N=C(c2ccccc2)c2ccccc2NC1=O]

A mixture of the compound from step d (48 mg, 0.087 mmol) and AlCl₃ (200 mg, 1.5 mmol) in anisole (5 mL) was heated to 70° C. for 5 hrs under N₂. Solvent was removed. The residue was purified by prep-TLC to afford product as yellow solid (6 mg). ESI-MS m/z: 428.0 [M+H]⁺. ¹H NMR (400 MHz, DMSO-d₆) δ 1.25 (s, 3H), 7.05-7.31 (m, 3H), 7.34-7.62 (m, 8H), 7.75-7.90 (m, 2H), 8.23 (s, 1H), 11.02 (s, 1H).

Example 231

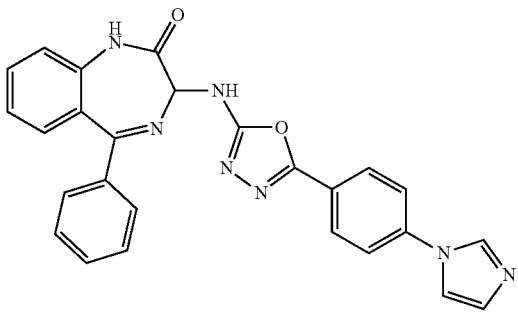 [SMILES: O=C1Nc2ccccc2C(c2ccccc2)=NC1Nc1nnc(-c2ccc(-n3ccnc3)cc2)o1]

Example 231 was prepared using a procedure similar to that used to prepare Example 20 where 4-(1H-imidazol-1-yl)benzoic acid was used in place of 5-chlorofuran-2-carboxylic acid. ESI-MS m/z: 462.2 [M+H]⁺. ¹H NMR (400 MHz, DMSO-d₆) δ 5.15 (s, 1H), 7.16 (s, 1H), 7.24-7.28 (m, 1H), 7.34-7.36 (m, 2H), 7.45-7.48 (m, 2H), 7.51-7.55 (m, 3H), 7.60-7.65 (m, 1H), 7.67-7.69 (m, 3H), 7.86-7.89 (m, 2H), 7.93-7.95 (m, 1H), 8.39 (s, 1H), 11.03-11.04 (s, 1H).

Example 232

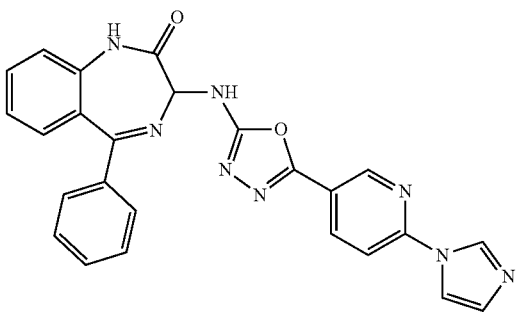 [SMILES: O=C1Nc2ccccc2C(c2ccccc2)=NC1Nc1nnc(-c2ccc(-n3ccnc3)nc2)o1]

Example 232 was prepared using a procedure similar to that used to prepare Example 20 where 6-(1H-imidazol-1-yl)nicotinic acid was used in place of 5-chlorofuran-2-carboxylic acid. ESI-MS m/z: 463.0 [M+H]⁺. ¹H NMR (300 MHz, DMSO-d₆) δ 1.23 (s, 1H), 5.19 (d, J=8.3 Hz, 1H), 7.14-7.74 (m, 11H), 7.97-8.07 (m, 2H), 8.36 (dd, J=8.6, 2.3 Hz, 1H), 8.63 (s, 1H), 8.89 (d, J=2.2 Hz, 1H), 9.28 (d, J=8.5 Hz, 1H), 11.02 (s, 1H).

Example 233

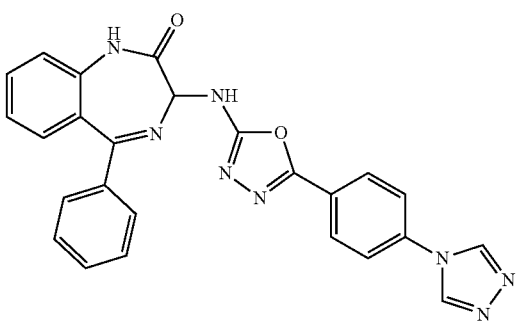 [SMILES: O=C1Nc2ccccc2C(c2ccccc2)=NC1Nc1nnc(-c2ccc(-n3cnnc3)cc2)o1]

Example 233 was prepared using a procedure similar to that used to prepare Example 20 where 4-(4H-1,2,4-triazol-4-yl)benzoic acid was used in place of 5-chlorofuran-2-carboxylic acid. ESI-MS m/z: 463.0 [M+H]⁺. H-NMR-PH-ETA-A1-433-0: ¹H NMR (300 MHz, DMSO-d₆) δ 5.18 (d, J=8.0 Hz, 1H), 7.22-7.60 (m, 8H), 7.68 (ddd, J=8.4, 7.1, 1.7 Hz, 1H), 7.86-8.04 (m, 4H), 9.23 (s, 3H), 11.01 (s, 1H).

Example 234

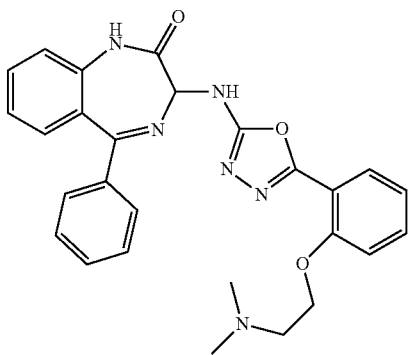 [SMILES: CN(C)CCOc1ccccc1-c1nnc(NC2N=C(c3ccccc3)c3ccccc3NC2=O)o1]

Example 234 was prepared using a procedure similar to that used to prepare Example 20 where 2-(2-(dimethylamino)ethoxy)benzoic acid was used in place of 5-chlorofuran-2-carboxylic acid. ESI-MS m/z: 483.5 [M+H]$^+$. $^1$H NMR (300 MHz, DMSO-d$_6$) δ 2.18 (s, 6H), 2.63 (t, J=5.9 Hz, 2H), 4.13 (t, J=5.9 Hz, 2H), 5.14 (d, J=8.6 Hz, 1H), 7.07 (td, J=7.5, 1.0 Hz, 1H), 7.16-7.59 (m, 10H), 7.61-7.73 (m, 2H), 8.96 (d, J=8.7 Hz, 1H), 10.97 (s, 1H).

Example 235

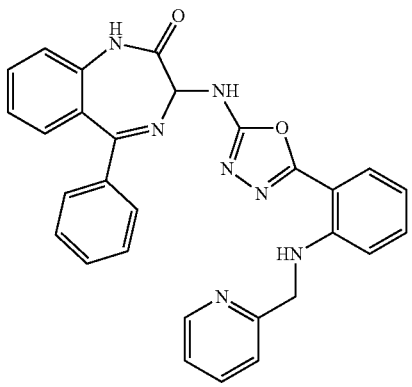 [SMILES: O=C1Nc2ccccc2C(c2ccccc2)=NC1Nc1nnc(-c2ccccc2NCc2ccccn2)o1]

Example 235 was prepared using a procedure similar to that used to prepare Example 20 where 2-((pyridin-2-ylmethyl)amino)benzoic acid was used in place of 5-chlorofuran-2-carboxylic acid. ESI-MS m/z: 496.2 [M+H]$^+$. $^1$H NMR (300 MHz, DMSO-d$_6$) δ 4.60 (d, J=5.4 Hz, 2H), 5.17 (d, J=8.5 Hz, 1H), 6.68-6.83 (m, 2H), 7.22-7.81 (m, 14H), 8.02 (t, J=5.5 Hz, 1H), 8.46 (s, 1H), 8.51-8.60 (m, 1H), 9.15 (d, J=8.5 Hz, 1H), 11.01 (s, 1H).

Example 236

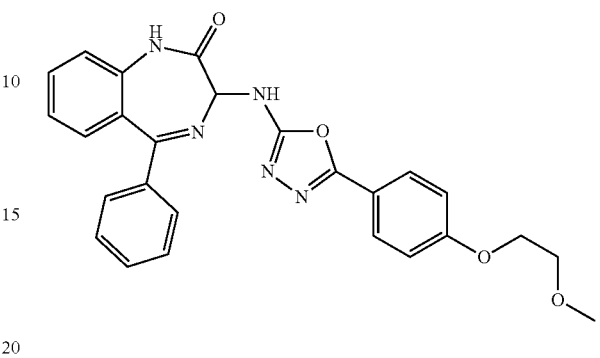

Example 236 Step a

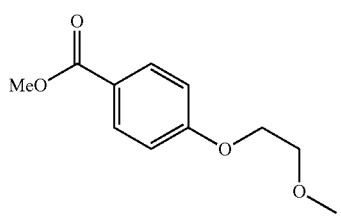

A solution of methyl 4-hydroxybenzoate (1.52 g, 10 mmol), 2-methoxyethanol (1.52 g, 20 mmol), DIAD (5 mL) and PPh$_3$ (5 mL) in THF (50 mL) was stirred for overnight at rt. It was used directly to the next step. ESI-MS m/z: 211.2 [M+H]$^+$.

Example 236 Step b

NaOH (50 mL, 3.0 M) was added to the reaction mixture in step a, and then it was stirred for 4 hours at rt. It was concentrated, and extracted with EA (×3) and washed with brine (×2). The water layers were combined and adjusted pH to 1-2 with HCl, and then extracted with EA (×3) and washed with brine (×2). The organic layers were combined concentrated to give desired compound as a white solid (900 mg, 46%). ESI-MS m/z: 196.8 [M+H]$^+$.

Example 236

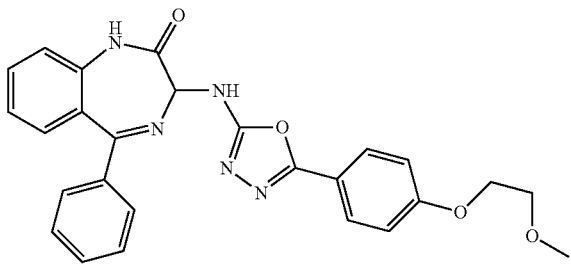 [SMILES: COCCOc1ccc(-c2nnc(NC3N=C(c4ccccc4)c4ccccc4NC3=O)o2)cc1]

Example 236 was prepared using a procedure similar to that used to prepare Example 20 where 4-(2-methoxyethoxy)benzoic acid was used in place of 5-chlorofuran-2-carboxylic acid. ESI-MS m/z: 470.1 [M+H]⁺. ¹H NMR (300 MHz, DMSO-$d_6$) δ 3.31 (s, 3H), 3.58-3.73 (m, 2H), 4.08-4.24 (m, 2H), 5.14 (d, 1H), 7.05-7.18 (d, 2H), 7.18-7.38 (m, 3H), 7.40-7.57 (m, 5H), 7.56-7.87 (m, 3H), 9.03 (d, 1H), 10.99 (s, 1H).

Example 237

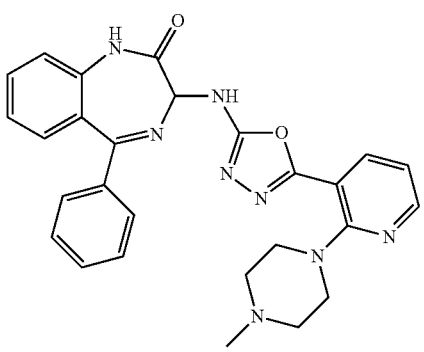 [SMILES: CN1CCN(c2ncccc2-c2nnc(NC3N=C(c4ccccc4)c4ccccc4NC3=O)o2)CC1]

Example 237 was prepared using a procedure similar to that used to prepare Example 20 where 2-(4-methylpiperazin-1-yl)nicotinic acid was used in place of 5-chlorofuran-2-carboxylic acid. ESI-MS m/z: 495.2 [M+H]⁺. ¹H NMR (300 MHz, DMSO-$d_6$) δ 2.16 (s, 6H), 2.36 (t, J=4.7 Hz, 4H), 3.15 (dd, J=5.6, 3.7 Hz, 4H), 5.15 (d, J=8.5 Hz, 1H), 6.99 (dd, J=7.6, 4.8 Hz, 1H), 7.22-7.60 (m, 8H), 7.67 (ddd, J=8.5, 7.1, 1.7 Hz, 1H), 7.91 (dd, J=7.6, 1.9 Hz, 1H), 8.32 (dd, J=4.8, 1.9 Hz, 1H), 9.12 (d, J=8.7 Hz, 1H), 10.98 (s, 1H).

Example 238

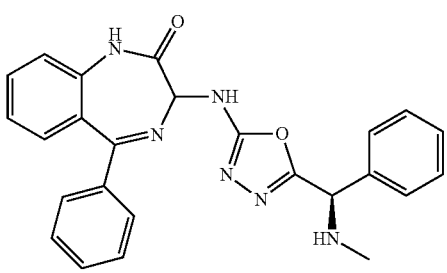 [SMILES: CN[C@H](c1ccccc1)c1nnc(NC2N=C(c3ccccc3)c3ccccc3NC2=O)o1]

Example 238 was prepared using a procedure similar to that used to prepare Example 20 where (R)-2-(methylamino)-2-phenylacetic acid was used in place of 5-chlorofuran-2-carboxylic acid. ESI-MS m/z: 439.3 [M+H]⁺. ¹H NMR (300 MHz, DMSO-$d_6$) δ 2.24 (s, 3H), 4.84 (s, 1H), 5.03 (d, J=8.6 Hz, 1H), 7.19-7.58 (m, 13H), 7.65 (ddd, J=8.4, 6.9, 1.9 Hz, 1H), 8.29 (s, 1H), 8.82 (dd, J=8.7, 2.4 Hz, 1H).

Example 239

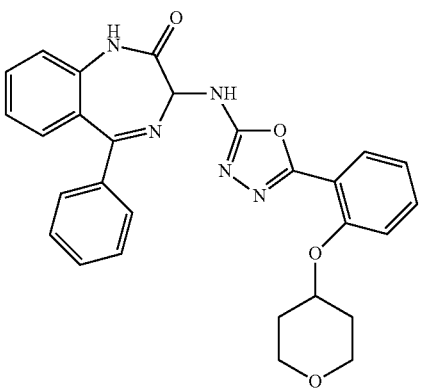 [SMILES: O=C1Nc2ccccc2C(c2ccccc2)=NC1Nc1nnc(-c2ccccc2OC2CCOCC2)o1]

Example 239 was prepared using a procedure similar to that used to prepare Example 20 where 2-((tetrahydro-2H-pyran-4-yl)oxy)benzoic acid was used in place of 5-chlorofuran-2-carboxylic acid. ESI-MS m/z: 496.2 [M+H]⁺. ¹H NMR (300 MHz, DMSO-$d_6$) δ 1.62 (ddt, J=11.6, 7.9, 4.7 Hz, 2H), 1.88 (dd, J=12.4, 6.4 Hz, 2H), 3.38-3.51 (m, 2H), 3.81 (dt, J=10.2, 4.6 Hz, 2H), 4.71 (tt, J=7.4, 3.7 Hz, 1H), 5.14 (d, J=8.6 Hz, 1H), 7.07 (t, J=7.4 Hz, 1H), 7.22-7.59 (m, 10H), 7.60-7.74 (m, 2H), 9.05 (d, J=8.6 Hz, 1H), 10.98 (s, 1H).

Example 240

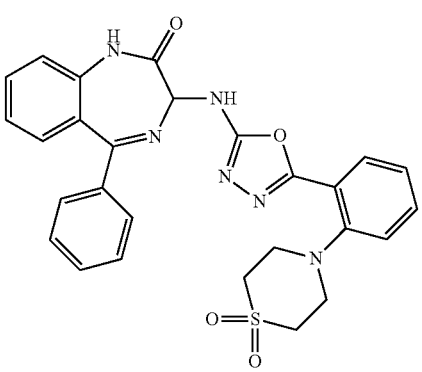 [SMILES: O=C1Nc2ccccc2C(c2ccccc2)=NC1Nc1nnc(-c2ccccc2N2CCS(=O)(=O)CC2)o1]

Example 240 was prepared using a procedure similar to that used to prepare Example 20 where 2-(1,1-dioxidothiomorpholino)benzoic acid was used in place of 5-chlorofuran-2-carboxylic acid. ESI-MS m/z: 529.3 [M+H]⁺. ¹H NMR (300 MHz, DMSO-$d_6$) δ 3.31 (s, 4H), 3.38 (d, J=4.9 Hz, 4H), 5.17 (d, J=8.7 Hz, 1H), 7.19-7.39 (m, 5H), 7.42-7.58 (m, 6H), 7.64-7.81 (m, 2H), 9.27 (d, J=8.7 Hz, 1H), 11.00 (s, 1H).

Example 241

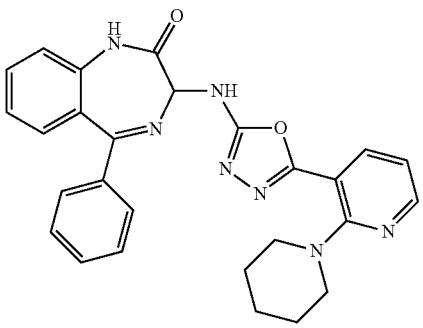 [SMILES: O=C1Nc2ccccc2C(c2ccccc2)=NC1Nc1nnc(-c2cccnc2N2CCCCC2)o1]

Example 241 was prepared using a procedure similar to that used to prepare Example 20 where 2-(piperidin-1-yl) nicotinic acid was used in place of 5-chlorofuran-2-carboxylic acid. ESI-MS m/z: 480.2 [M+H]+. 1H NMR (300 MHz, DMSO-d6) δ 1.54 (d, J=7.4 Hz, 6H), 3.10 (d, J=5.5 Hz, 4H), 5.15 (d, J=8.7 Hz, 1H), 6.94 (dd, J=7.6, 4.8 Hz, 1H), 7.21-7.39 (m, 3H), 7.40-7.59 (m, 5H), 7.67 (ddd, J=8.3, 7.0, 1.8 Hz, 1H), 7.88 (dd, J=7.6, 1.9 Hz, 1H), 8.29 (dd, J=4.8, 1.9 Hz, 1H), 9.11 (d, J=8.7 Hz, 1H), 10.98 (s, 1H).

Example 242

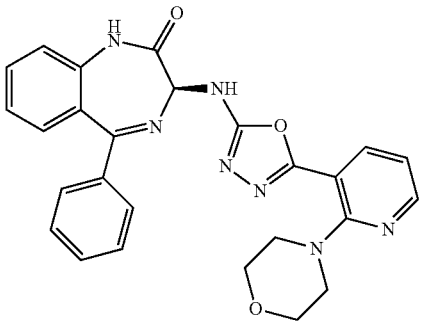 [SMILES: O=C1Nc2ccccc2C(c2ccccc2)=N[C@@H]1Nc1nnc(-c2cccnc2N2CCOCC2)o1]

Example 242 was prepared using a procedure similar to that used to prepare Example 152 where ethyl 2-morpholinonicotinate, which was prepared similarly to ethyl 3-morpholinopicolinate in Example 132 step b, was used in place of ethyl 2-morpholino-4-(trifluoromethyl)benzoate. ESI-MS m/z: 482.1980 [M+H]+.

Example 243

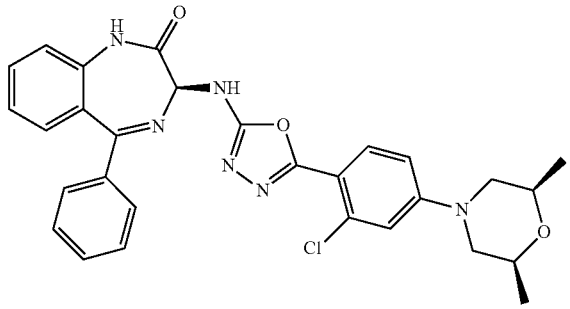 [SMILES: C[C@@H]1CN(c2ccc(-c3nnc(N[C@H]4N=C(c5ccccc5)c5ccccc5NC4=O)o3)c(Cl)c2)C[C@H](C)O1]

Example 243 was prepared using a procedure similar to that used to prepare Example 161 where cis-2,6-dimethylmorpholine and ethyl 2-chloro-4-fluorobenzoate were used in place of morpholine and methyl 5-chloropyrazine-2-carboxylate, respectively. ESI-MS m/z: 543.3 [M+H]+.

Example 244

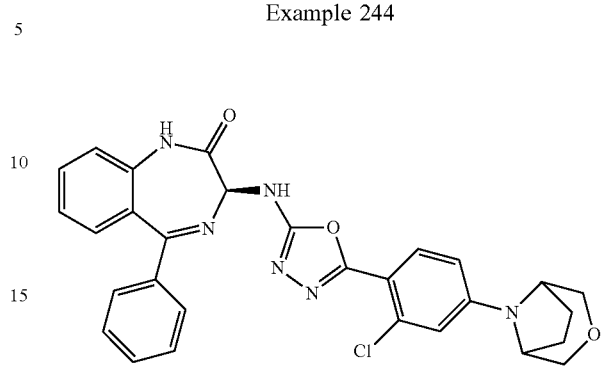

Example 244 was prepared using a procedure similar to that used to prepare Example 161 where (1R,5S)-3-oxa-8-azabicyclo[3.2.1]octane and ethyl 2-chloro-4-fluorobenzoate were used in place of morpholine and methyl 5-chloropyrazine-2-carboxylate, respectively. ESI-MS m/z: 541.3 [M+H]+.

Example 245

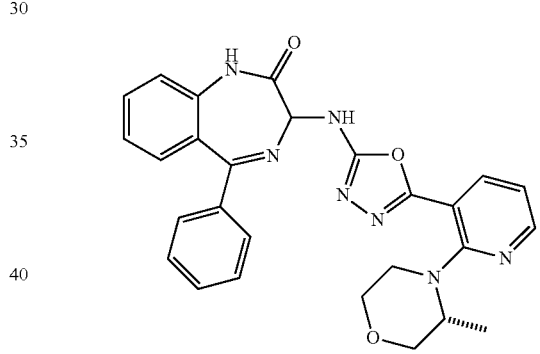

Example 245 Step a

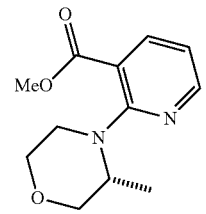 [SMILES: COC(=O)c1cccnc1N1CCOC[C@H]1C]

A solution of methyl 2-fluoronicotinate (1 g, 6.5 mmol), (R)-3-methylmorpholine (722 mg, 7.2 mmol) and K2CO3 (1.79 g, 13.0 mmol) in DMSO (5 mL) was stirred for 1 hour at 100° C. It was diluted with water, extracted with EA (×3), washed with brine (×2), the organic layers was combined, dried, concentrated to give 1.2 g (crude) of desired compound as a colourless oil, which was used directly in the next step. ESI-MS m/z: 237.1 [M+H]+.

Example 245 Step b

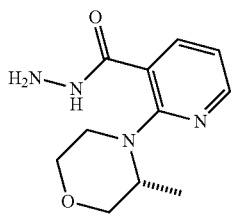 [SMILES: C[C@@H]1COCCN1c1ncccc1C(=O)NN]

A solution of the compound from step a (1.2 g, 5.0 mol) and NH$_2$NH$_2$.H$_2$O (5 mL) in EtOH (10 mL) was refluxed for 2 hours. It was concentrated and purified by Prep-HPLC (MeCN/H$_2$O) to give the desired compound as a white solid (1 g, 83%). ESI-MS m/z: 237.1 [M+H]$^+$.

Example 245 Step c

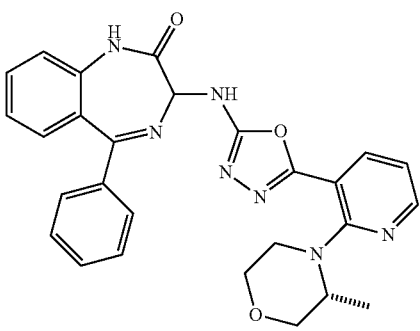 [SMILES: C[C@@H]1COCCN1c1ncccc1-c1nnc(NC2N=C(c3ccccc3)c3ccccc3NC2=O)o1]

Example 245 was prepared using a procedure similar to that used to prepare Example 21 where (R)-2-(3-methylmorpholino)nicotinohydrazide was used in place of tetrahydro-2H-pyran-4-carbohydrazide. ESI-MS m/z: 496.1 [M+H]$^+$. $^1$H NMR (300 MHz, DMSO-d$_6$) δ 1.00 (m, 3H), 3.03-3.04 (m, 1H), 3.24-3.25 (m, 1H), 3.38-3.79 (m, 5H), 5.15 (m, 1H), 7.03 (m, 1H), 7.32 (m, 3H), 7.41-7.60 (m, 5H), 7.67 (m, 1H), 7.95 (m, 1H), 8.33-8.41 (m, 1H), 9.15 (m, 1H), 10.98 (s, 1H).

Example 246

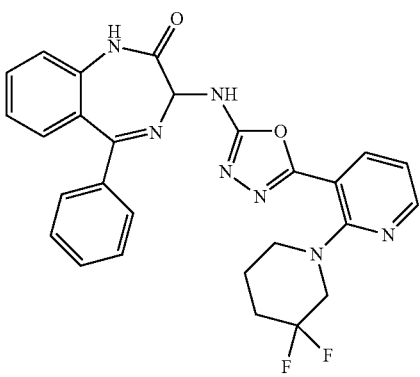 [SMILES: O=C1Nc2ccccc2C(c2ccccc2)=NC1Nc1nnc(-c2cccnc2N2CCCC(F)(F)C2)o1]

Example 246 was prepared using a procedure similar to that used to prepare Example 245 where 3,3-difluoropiperidine was used in place of (R)-3-methylmorpholine. ESI-MS m/z: 516.5 [M+H]$^+$. $^1$H NMR (300 MHz, DMSO-d6) δ 1.83 (d, J=7.3 Hz, 2H), 1.93-2.14 (m, 2H), 3.18 (d, J=6.1 Hz, 2H), 3.43-3.58 (m, 2H), 5.16 (d, J=7.7 Hz, 1H), 7.08 (m, 1H), 7.22-7.61 (m, 8H), 7.62-7.74 (m, 1H), 7.98 (m, 1H), 8.36 (m, 1H), 9.13 (d, J=8.0 Hz, 1H), 11.00 (s, 1H).

Example 247

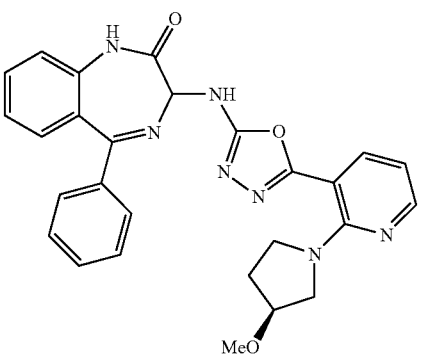 [SMILES: CO[C@H]1CCN(c2ncccc2-c2nnc(NC3N=C(c4ccccc4)c4ccccc4NC3=O)o2)C1]

Example 247 was prepared using a procedure similar to that used to prepare Example 245 where (S)-3-methoxypyrrolidine was used in place of (R)-3-methylmorpholine. ESI-MS m/z: 496.5 [M+H]$^+$. $^1$H NMR (300 MHz, DMSO-d6) δ 1.84-2.01 (m, 2H), 3.10-3.50 (m, 7H), 3.96 (m, 1H), 5.14 (m, 1H), 6.76 (m, 1H), 7.21-7.39 (m, 3H), 7.39-7.60 (m, 5H), 7.60-7.77 (m, 2H), 8.26 (m, 1H), 9.01 (m, 1H), 10.95 (s, 1H).

Example 248

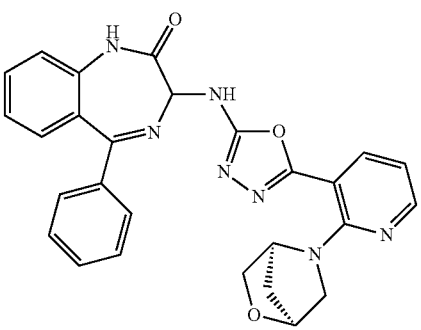 [SMILES: O=C1Nc2ccccc2C(c2ccccc2)=NC1Nc1nnc(-c2cccnc2N2C[C@@H]3C[C@H]2CO3)o1]

Example 248 was prepared using a procedure similar to that used to prepare Example 245 where (1S,4S)-2-oxa-5-azabicyclo[2.2.1]heptane was used in place of (R)-3-methylmorpholine. ESI-MS m/z: 494.5 [M+H]$^+$. $^1$H NMR (300 MHz, DMSO-d6) δ 1.78 (s, 2H), 2.68 (m, 1H), 3.27-3.40 (m, 1H), 3.70-3.83 (m, 2H), 4.53 (s, 1H), 4.70-4.80 (m, 1H), 5.13 (m, 1H), 6.84 (m, 1H), 7.21-7.39 (m, 3H), 7.49 (m, 5H), 7.66 (m, 1H), 7.78 (m, 1H), 8.27 (m, 1H), 9.03 (d, J=8.5 Hz, 1H), 10.96 (s, 1H).

Example 249

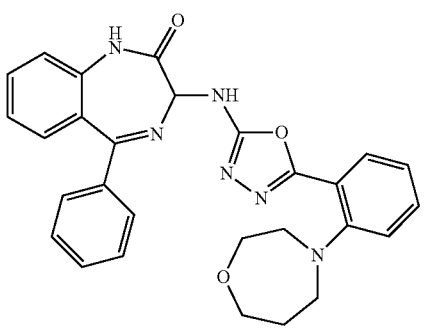 [SMILES: O=C1Nc2ccccc2C(c2ccccc2)=NC1Nc1nnc(-c2ccccc2N2CCCOCC2)o1]

Example 249 was prepared using a procedure similar to that used to prepare Example 245 where 1,4-oxazepane was used in place of (R)-3-methylmorpholine. ESI-MS m/z: 496.5 [M+H]+. ¹H NMR (300 MHz, DMSO-d$_6$) δ 1.83 (m, 2H), 3.45 (m, 4H), 3.53-3.64 (m, 2H), 3.69 (m, 2H), 5.13 (d, J=8.6 Hz, 1H), 6.83 (m, 1H), 7.21-7.39 (m, 3H), 7.40-7.59 (m, 5H), 7.66 (m, 1H), 7.77 (m, 1H), 8.27 (m, 1H), 9.02 (d, J=8.6 Hz, 1H), 10.96 (s, 1H).

Example 250

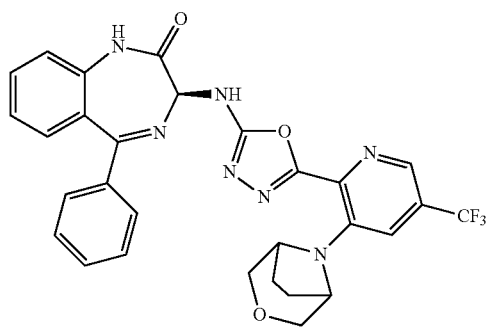 [SMILES: O=C1Nc2ccccc2C(c2ccccc2)=N[C@@H]1Nc1nnc(-c2ncc(C(F)(F)F)cc2N2C3CCC2COC3)o1]

Example 250 was prepared using a procedure similar to that used to prepare Example 160 where 3-oxa-8-azabicyclo[3.2.1]octane and ethyl 3-chloro-5-(trifluoromethyl)picolinate were used in place of morpholine and methyl 5-bromo-3-fluoropicolinate, respectively. ESI MS m/z=576.2 [M+H]+.

Example 251

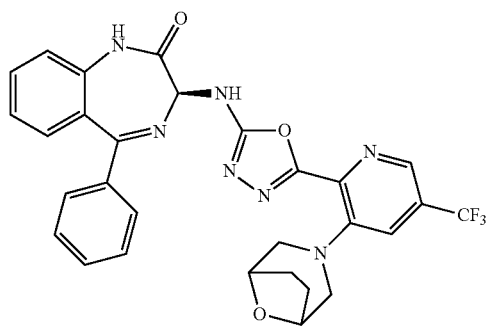 [SMILES: O=C1Nc2ccccc2C(c2ccccc2)=N[C@@H]1Nc1nnc(-c2ncc(C(F)(F)F)cc2N2CC3CCC(C2)O3)o1]

Example 251 was prepared using a procedure similar to that used to prepare Example 160 where 8-oxa-3-azabicyclo[3.2.1]octane and ethyl 3-chloro-5-(trifluoromethyl)picolinate were used in place of morpholine and methyl 5-bromo-3-fluoropicolinate, respectively. ESI MS m/z=576.2 [M+H]+.

Example 252

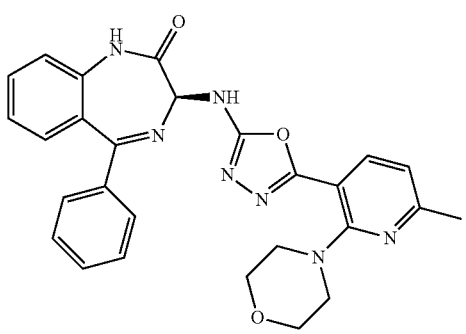 [SMILES: Cc1ccc(-c2nnc(N[C@H]3N=C(c4ccccc4)c4ccccc4NC3=O)o2)c(N2CCOCC2)n1]

Example 252 was prepared using a procedure similar to that used to prepare Example 160 where methyl 2-chloro-6-methylnicotinate was used in place of methyl 5-bromo-3-fluoropicolinate. ESI MS m/z=496.2 [M+H]+.

Example 253

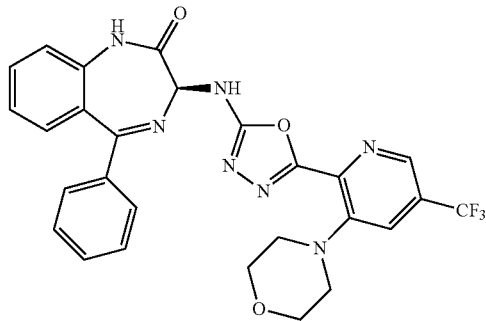 [SMILES: O=C1Nc2ccccc2C(c2ccccc2)=N[C@@H]1Nc1nnc(-c2ncc(C(F)(F)F)cc2N2CCOCC2)o1]

Example 253 was prepared using a procedure similar to that used to prepare Example 160 where ethyl 3-chloro-5-(trifluoromethyl)picolinate was used in place of methyl 5-bromo-3-fluoropicolinate. ESI-MS m/z: 550.2 [M+H]+.

Example 254

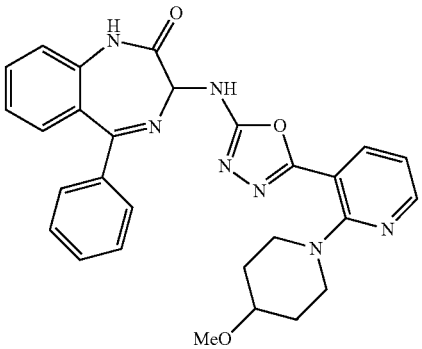 [SMILES: COC1CCN(c2ncccc2-c2nnc(NC3N=C(c4ccccc4)c4ccccc4NC3=O)o2)CC1]

Example 254 was prepared using a procedure similar to that used to prepare Example 245 where 4-methoxypiperidine was used in place of (R)-3-methylmorpholine. ESI-MS m/z: 510.5 [M+H]+. 1H NMR (300 MHz, DMSO-d6) δ 1.53 (m, 2H), 1.85 (s, 1H), 2.85-2.99 (m, 2H), 3.23 (s, 6H), 5.15 (d, J=8.5 Hz, 1H), 6.96 (m, 1H), 7.21-7.59 (m, 8H), 7.67 (m, 1H), 7.90 (m, 1H), 8.30 (m, 1H), 9.12 (d, J=8.6 Hz, 1H), 10.97 (s, 1H).

Example 255

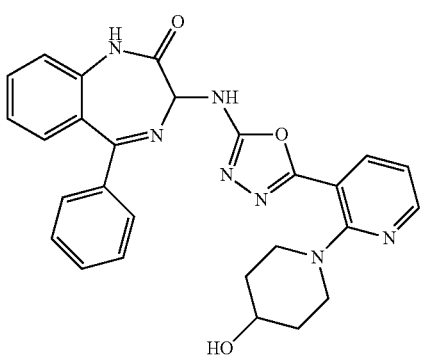

Example 255 was prepared using a procedure similar to that used to prepare Example 245 where piperidin-4-ol was used in place of (R)-3-methylmorpholine. ESI-MS m/z: 496.4 [M+H]+. 1H NMR (300 MHz, DMSO-d6) δ 1.47 (m, 2H), 1.68-1.81 (m, 2H), 2.83-2.97 (m, 2H), 3.57-3.70 (m, 1H), 4.66 (s, 1H), 5.15 (d, J=8.6 Hz, 1H), 6.94 (m, 1H), 7.21-7.40 (m, 3H), 7.39-7.59 (m, 5H), 7.67 (m, 1H), 7.88 (m, 1H), 8.30 (m, 1H), 9.10 (d, J=8.6 Hz, 1H), 10.97 (s, 1H).

Example 256

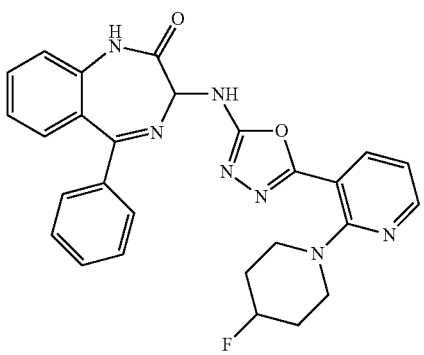 [SMILES: O=C1Nc2ccccc2C(c2ccccc2)=NC1Nc1nnc(-c2cccnc2N2CCC(F)CC2)o1]

Example 256 was prepared using a procedure similar to that used to prepare Example 245 where 4-fluoropiperidine was used in place of (R)-3-methylmorpholine. ESI-MS m/z: 498.4 [M+H]+. 1H NMR (300 MHz, DMSO-d6) δ 1.72-1.88 (m, 4H), 1.94 (d, J=19.8 Hz, 4H), 3.11 (m, 4H), 4.75 (m, 1H), 5.15 (d, J=8.6 Hz, 2H), 7.01 (m, 2H), 7.32 (m, 6H), 7.39-7.62 (m, 10H), 7.67 (m, 2H), 7.94 (m, 2H), 8.33 (m, 2H), 9.15 (d, J=8.6 Hz, 2H), 10.97 (s, 2H).

Example 257

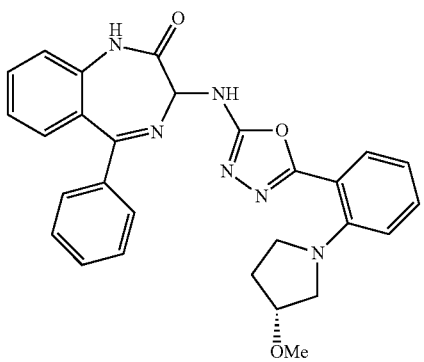 [SMILES: CO[C@@H]1CCN(c2ccccc2-c2nnc(NC3N=C(c4ccccc4)c4ccccc4NC3=O)o2)C1]

Example 257 was prepared using a procedure similar to that used to prepare Example 245 where (R)-3-methoxypyrrolidine was used in place of (R)-3-methylmorpholine. ESI-MS m/z: 496.4 [M+H]+. 1H NMR (300 MHz, DMSO-d6) δ 1.94 (m, 2H), 3.09-3.50 (m, 7H), 3.96 (m, 1H), 5.14 (m, 1H), 6.76 (m, 1H), 7.21-7.39 (m, 3H), 7.39-7.60 (m, 5H), 7.60-7.77 (m, 2H), 8.26 (m, 1H), 9.01 (m, 1H), 10.97 (s, 1H).

Example 258

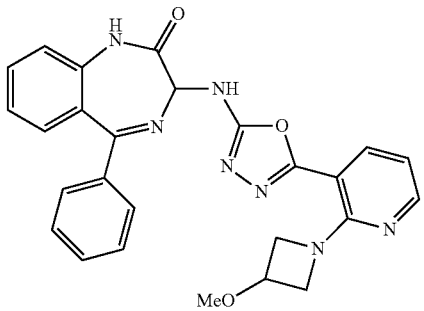 [SMILES: COC1CN(c2ncccc2-c2nnc(NC3N=C(c4ccccc4)c4ccccc4NC3=O)o2)C1]

Example 258 was prepared using a procedure similar to that used to prepare Example 245 where 3-methoxyazetidine was used in place of (R)-3-methylmorpholine. ESI-MS m/z: 482.4 [M+H]+. 1H NMR (300 MHz, DMSO-d6) δ 3.19 (s, 3H), 3.73 (m, 2H), 4.02-4.26 (m, 3H), 5.15 (d, J=8.5 Hz, 1H), 6.84 (m, 1H), 7.21-7.40 (m, 3H), 7.39-7.60 (m, 5H), 7.67 (m, 1H), 7.79 (dd, J=7.6, 1.9 Hz, 1H), 8.28 (m, 1H), 9.09 (d, J=8.5 Hz, 1H), 10.97 (s, 1H).

Example 259

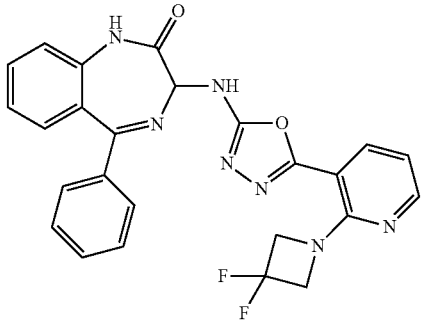 [SMILES: O=C1Nc2ccccc2C(c2ccccc2)=NC1Nc1nnc(-c2cccnc2N2CC(F)(F)C2)o1]

Example 259 was prepared using a procedure similar to that used to prepare Example 245 where 3,3-difluoroazetidine was used in place of (R)-3-methylmorpholine. ESI-MS m/z: 488.4 [M+H]+. H NMR (300 MHz, DMSO-d6) δ 4.41 (m, 4H), 5.18 (d, J=8.3 Hz, 1H), 7.05 (m, 1H), 7.21-7.78 (m, 9H), 7.97 (m, 1H), 8.37 (m, 1H), 9.20 (d, J=8.5 Hz, 1H), 11.01 (s, 1H).

Example 260

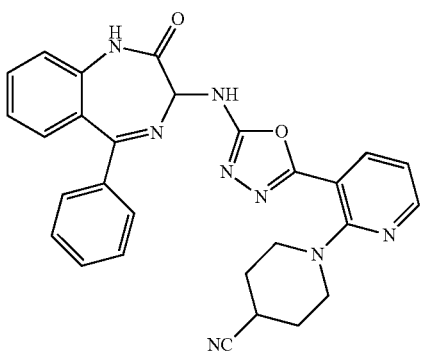 [SMILES: N#CC1CCN(c2ncccc2-c2nnc(NC3N=C(c4ccccc4)c4ccccc4NC3=O)o2)CC1]

Example 260 was prepared using a procedure similar to that used to prepare Example 245 where piperidine-4-carbonitrile was used in place of (R)-3-methylmorpholine. ESI-MS m/z: 505.3 [M+H]+. $^1$H NMR (300 MHz, DMSO-d6) δ 1.77-2.03 (m, 4H), 3.03 (m, 3H), 3.31 (d, J=6.8 Hz, 2H), 5.16 (s, 1H), 7.04 (m, 1H), 7.22-7.40 (m, 3H), 7.40-7.60 (m, 5H), 7.67 (m, 1H), 7.97 (m, 1H), 8.34 (m, 1H), 9.21 (s, 1H), 9.80 (s, 1H).

Example 261

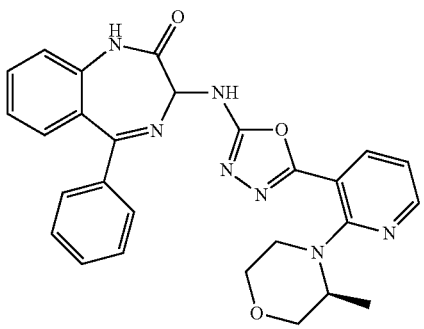 [SMILES: C[C@H]1COCCN1c1ncccc1-c1nnc(NC2N=C(c3ccccc3)c3ccccc3NC2=O)o1]

Example 261 was prepared using a procedure similar to that used to prepare Example 245 where (S)-3-methylmorpholine was used in place of (R)-3-methylmorpholine. ESI-MS m/z: 496.5 [M+H]+. $^1$H NMR (400 MHz, DMSO-d$_6$) δ 1.02 (m, 3H), 2.99-3.09 (m, 1H), 3.29 (m, 1H), 3.47 (m, 1H), 3.52-3.82 (m, 4H), 5.18 (m, 1H), 7.05 (m, 1H), 7.29 (m, 1H), 7.36 (m, 2H), 7.43-7.59 (m, 5H), 7.64-7.71 (m, 1H), 7.97 (m, 1H), 8.38 (m, 1H), 9.13-9.34 (m, 1H), 11.01 (s, 1H).

Example 262

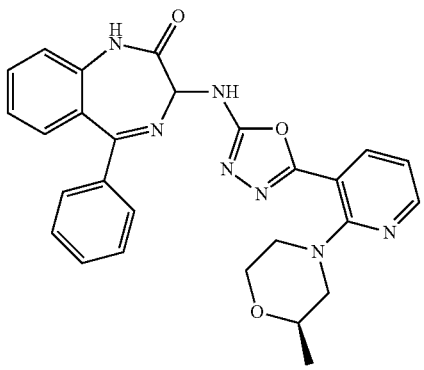 [SMILES: C[C@@H]1CN(c2ncccc2-c2nnc(NC3N=C(c4ccccc4)c4ccccc4NC3=O)o2)CCO1]

Example 262 was prepared using a procedure similar to that used to prepare Example 245 where (R)-2-methylmorpholine was used in place of (R)-3-methylmorpholine. ESI-MS m/z: 496.4 [M+H]+. $^1$H NMR (300 MHz, DMSO-d$_6$) δ 1.06 (d, J=6.1 Hz, 3H), 2.53-2.62 (m, 1H), 2.84 (m, 1H), 3.41 (m, 2H), 3.55-3.70 (m, 2H), 3.76 (s, 1H), 5.12-5.18 (m, 1H), 7.02 (m, 1H), 7.22-7.41 (m, 3H), 7.42-7.57 (m, 5H), 7.67 (m, 1H), 7.95 (m, 1H), 8.25-8.36 (m, 1H), 9.09-9.20 (m, 1H).

Example 263

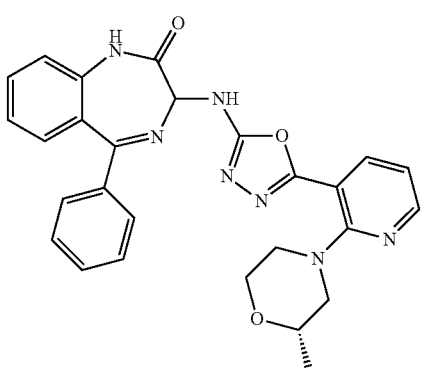

Example 263 was prepared using a procedure similar to that used to prepare Example 245 where (S)-2-methylmorpholine was used in place of (R)-3-methylmorpholine. ESI-MS m/z: 496.2 [M+H]+. $^1$H NMR (400 MHz, DMSO-d$_6$) δ 1.08 (d, J=6.2 Hz, 3H), 2.57 (d, J=10.1 Hz, 1H), 2.86 (m, 1H), 3.39 (m, 2H), 3.58-3.93 (m, 3H), 5.18 (d, J=8.2 Hz, 1H), 7.03 (m, 1H), 7.29 (m, 1H), 7.36 (m, 2H), 7.50 (m, 5H), 7.68 (m, 1H), 7.97 (d, J=7.6 Hz, 1H), 8.27-8.51 (m, 1H), 9.18 (m, 1H), 10.83-11.23 (m, 1H).

Example 264

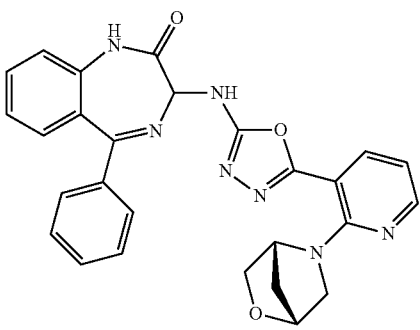 [SMILES: O=C1Nc2ccccc2C(c2ccccc2)=NC1Nc1nnc(-c2cccnc2N2C[C@H]3C[C@@H]2CO3)o1]

Example 264 was prepared using a procedure similar to that used to prepare Example 245 where (1R,4R)-2-oxa-5-azabicyclo[2.2.1]heptane was used in place of (R)-3-methylmorpholine. ESI-MS m/z: 494.5 [M+H]+. 1H NMR (400 MHz, DMSO-d6) δ 1.79 (s, 2H), 2.71 (m, 1H), 3.37 (m, 1H), 3.70-3.90 (m, 2H), 4.54 (s, 1H), 4.76 (m, 1H), 5.15 (m, 1H), 6.85 (m, 1H), 7.24-7.41 (m, 3H), 7.44-7.60 (m, 5H), 7.67 (m, 1H), 7.80 (m, 1H), 8.29 (m, 1H), 9.03 (d, J=8.5 Hz, 1H), 10.98 (s, 1H).

Example 265

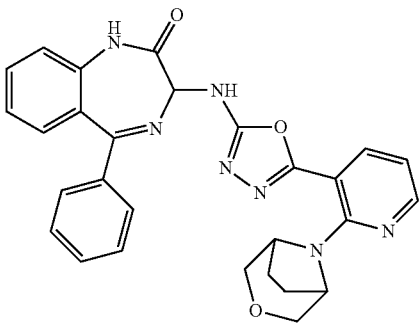 [SMILES: O=C1Nc2ccccc2C(c2ccccc2)=NC1Nc1nnc(-c2cccnc2N2C3CCC2COC3)o1]

Example 265 was prepared using a procedure similar to that used to prepare Example 245 where 3-oxa-8-azabicyclo[3.2.1]octane was used in place of (R)-3-methylmorpholine. ESI-MS m/z: 508.2 [M+H]+. 1H NMR (400 MHz, DMSO-d6) δ 1.72-1.79 (m, 2H), 1.81-1.84 (m, 2H), 3.48-3.50 (m, 2H), 3.73-3.78 (m, 2H), 3.96-4.03 (m, 2H), 5.14-5.16 (d, J=8.0, 1H), 6.94-6.98 (m, 1H), 7.26-7.29 (m, 1H), 7.33-7.35 (m, 2H), 7.44-7.53 (m, 5H), 7.54-7.55 (m, 1H), 65-7.69 (m, 1H), 7.89-7.92 (m, 1H), 8.29-8.30-9.42 (m, 1H), 9.14-9.16 (d, J=8.0, 1H), 10.97 (s, 1H).

Example 266

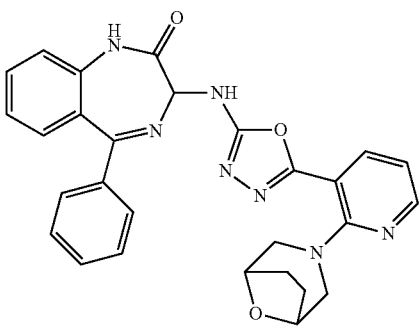 [SMILES: O=C1Nc2ccccc2C(c2ccccc2)=NC1Nc1nnc(-c2cccnc2N2CC3CCC(C2)O3)o1]

Example 266 was prepared using a procedure similar to that used to prepare Example 245 where 8-oxa-3-azabicyclo[3.2.1]octane was used in place of (R)-3-methylmorpholine. ESI-MS m/z: 508.1 [M+H]+. 1H NMR (300 MHz, DMSO-d6) δ 1.63-1.80 (m, 2H), 1.89 (dd, J=7.4, 4.6 Hz, 2H), 3.01 (dt, J=12.5, 2.2 Hz, 2H), 3.28 (dd, J=11.4, 3.3 Hz, 2H), 4.28 (dd, J=4.4, 2.3 Hz, 2H), 5.15 (d, J=8.6 Hz, 1H), 6.97 (dd, J=7.6, 4.7 Hz, 1H), 7.32 (ddd, J=18.4, 7.4, 1.3 Hz, 3H), 7.41-7.60 (m, 5H), 7.67 (ddd, J=8.4, 7.0, 1.7 Hz, 1H), 7.85 (dd, J=7.6, 1.9 Hz, 1H), 8.32 (dd, J=4.8, 1.9 Hz, 1H), 9.12 (d, J=8.6 Hz, 1H), 10.97 (s, 1H).

Example 267

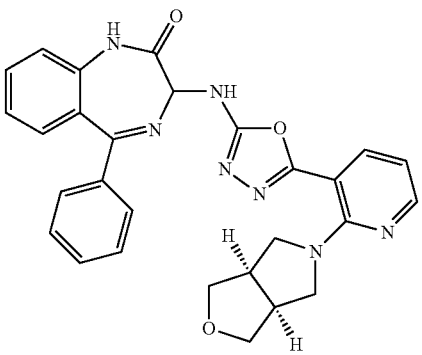 [SMILES: O=C1Nc2ccccc2C(c2ccccc2)=NC1Nc1nnc(-c2cccnc2N2C[C@H]3COC[C@H]3C2)o1]

Example 267 was prepared using a procedure similar to that used to prepare Example 245 where (3aR,6aS)-hexahydro-1H-furo[3,4-c]pyrrole was used in place of (R)-3-methylmorpholine. ESI-MS m/z: 508.5 [M+H]+. 1H NMR (300 MHz, DMSO-d6) δ 2.90 (dq, J=7.5, 4.1 Hz, 2H), 3.16 (ddd, J=10.8, 5.9, 3.1 Hz, 2H), 3.37-3.60 (m, 4H), 3.80 (dd, J=8.7, 6.2 Hz, 2H), 5.17 (d, J=8.5 Hz, 1H), 6.84 (dd, J=7.5, 4.8 Hz, 1H), 7.33 (dd, J=18.6, 7.8 Hz, 3H), 7.42-7.63 (m, 5H), 7.63-7.84 (m, 2H), 8.30 (dd, J=4.7, 1.8 Hz, 1H), 9.07 (d, J=8.6 Hz, 1H), 10.98 (s, 1H).

Example 268

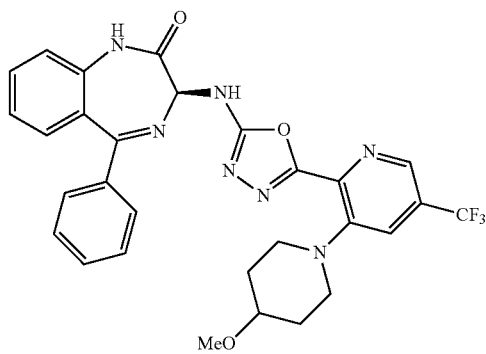 [SMILES: COC1CCN(c2cc(C(F)(F)F)cnc2-c2nnc(N[C@H]3N=C(c4ccccc4)c4ccccc4NC3=O)o2)CC1]

Example 268 was prepared using a procedure similar to that used to prepare Example 160 where 4-methoxypiperidine and ethyl 3-chloro-5-(trifluoromethyl)picolinate were used in place of morpholine and methyl 5-bromo-3-fluoropicolinate, respectively. ESI-MS m/z: 578.2 [M+H]+.

Example 269

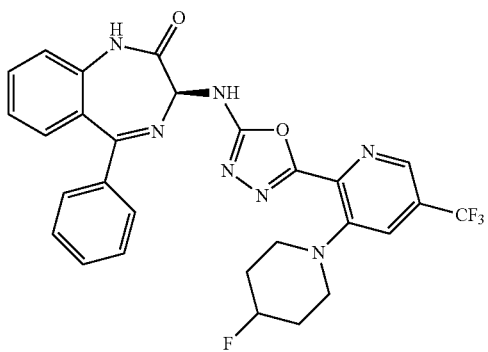 [SMILES: O=C1Nc2ccccc2C(c2ccccc2)=N[C@@H]1Nc1nnc(-c2ncc(C(F)(F)F)cc2N2CCC(F)CC2)o1]

Example 269 was prepared using a procedure similar to that used to prepare Example 160 where 4-fluoropiperidine and ethyl 3-chloro-5-(trifluoromethyl)picolinate were used in place of morpholine and methyl 5-bromo-3-fluoropicolinate, respectively. ESI-MS m/z: 566.2 [M+H]$^+$.

Example 270

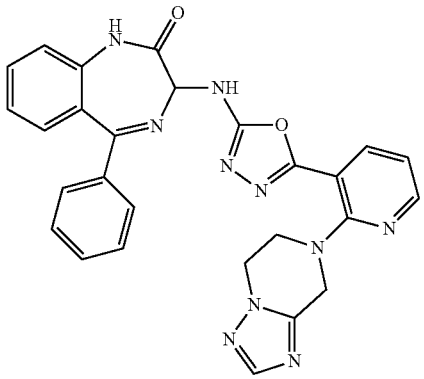 [SMILES: O=C1Nc2ccccc2C(c2ccccc2)=NC1Nc1nnc(-c2cccnc2N2CCn3ncnc3C2)o1]

Example 270 was prepared using a procedure similar to that used to prepare Example 245 where 5,6,7,8-tetrahydro-[1,2,4]triazolo[1,5-a]pyrazine was used in place of (R)-3-methylmorpholine. ESI-MS m/z: 519.2 [M+H]$^+$. $^1$H NMR (300 MHz, DMSO-d$_6$) δ 3.68 (q, J=4.6 Hz, 2H), 4.30 (t, J=5.4 Hz, 2H), 4.59 (d, J=2.6 Hz, 2H), 5.13 (s, 1H), 7.12-7.74 (m, 10H), 7.96 (s, 1H), 8.08 (dd, J=7.7, 1.9 Hz, 1H), 8.41 (dd, J=4.8, 1.9 Hz, 1H), 9.17 (s, 1H).

Example 271

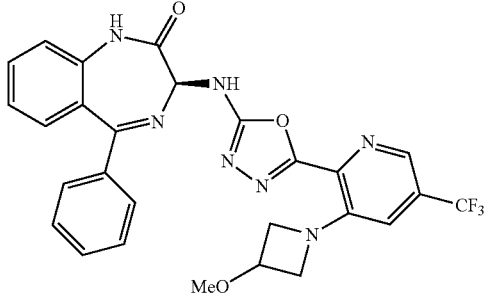 [SMILES: COC1CN(c2cc(C(F)(F)F)cnc2-c2nnc(N[C@H]3N=C(c4ccccc4)c4ccccc4NC3=O)o2)C1]

Example 271 was prepared using a procedure similar to that used to prepare Example 160 where 3-methoxyazetidine and ethyl 3-chloro-5-(trifluoromethyl)picolinate were used in place of morpholine and methyl 5-bromo-3-fluoropicolinate, respectively. ESI MS m/z=550.1830 [M+H]$^+$.

Example 272

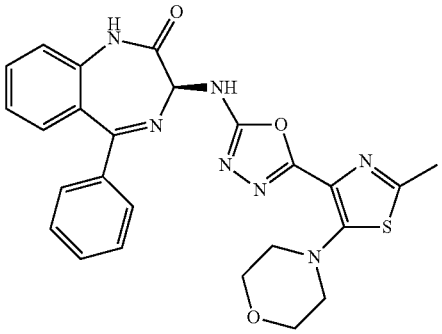 [SMILES: Cc1nc(-c2nnc(N[C@H]3N=C(c4ccccc4)c4ccccc4NC3=O)o2)c(N2CCOCC2)s1]

Example 272 Step a

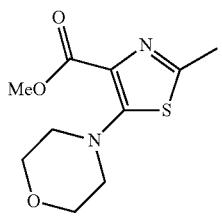 [SMILES: COC(=O)c1nc(C)sc1N1CCOCC1]

In an oven-dried vial, methyl 2-methyl-5-bromothiazole-4-carboxylate (0.5 g, 2.12 mmol) was dissolved in morpholine (4 ml, 46.4 mmol) and sealed. The reaction was heated to 60° C. and stirred overnight. The reaction mixture was concentrated, removing excess morpholine. The crude product was added to a silica gel column and was eluted with ethyl acetate/hexane 0% to 100% to give methyl 2-methyl-5-morpholinothiazole-4-carboxylate (0.126 g, 25% yield) as a white solid. ESI MS m/z=243.1 [M+H]$^+$.

Example 272 Step b

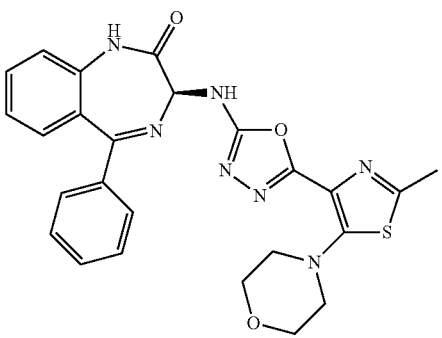 [SMILES: Cc1nc(-c2nnc(N[C@H]3N=C(c4ccccc4)c4ccccc4NC3=O)o2)c(N2CCOCC2)s1]

Example 272 was prepared using a procedure similar to that used to prepare Example 152 where methyl 2-methyl- 5-morpholinothiazole-4-carboxylate was used in place of ethyl 2-morpholino-4-(trifluoromethyl)benzoate. ESI MS m/z=502.2 [M+H]$^+$.

Example 273

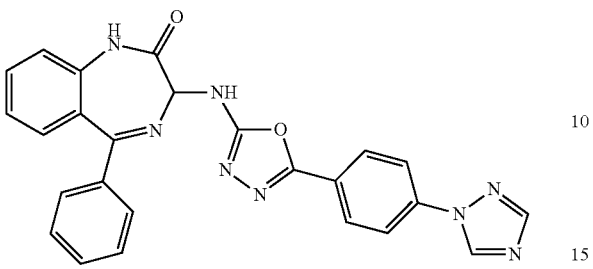

Example 273 was prepared using a procedure similar to that used to prepare Example 20 where 4-(1H-1,2,4-triazol-1-yl)benzoic acid was used in place of 5-chlorofuran-2-carboxylic acid. ESI MS m/z=463.2 [M+H]$^+$. $^1$H NMR (400 MHz, DMSO-d$_6$) δ 5.18-5.20 (d, J=8.0, 1H), 7.27-7.29 (m, 1H), 7.31-7.35 (m, 2H), 7.37-7.45 (m, 2H), 7.47-7.51 (m, 3H), 7.53-7.56 (m, 1H), 7.66-7.70 (m, 2H), 7.71-7.99 (m, 2H), 8.00-8.09 (m, 1H), 9.22-9.24 (m, 1H), 9.42 (s, 1H), 11.00 (s, 1H).

Example 274

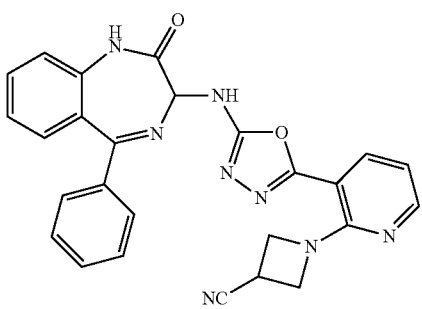 [SMILES: N#CC1CN(c2ncccc2-c2nnc(NC3N=C(c4ccccc4)c4ccccc4NC3=O)o2)C1]

Example 274 was prepared using a procedure similar to that used to prepare Example 245 where azetidine-3-carbonitrile was used in place of (R)-3-methylmorpholine. ESI-MS m/z: 477.2 [M+H]$^+$. $^1$H NMR (300 MHz, Methanol-d$_4$) δ 3.69 (tt, J=8.9, 6.0 Hz, 1H), 4.22 (ddd, J=8.4, 6.2, 1.5 Hz, 2H), 4.35 (td, J=8.8, 2.4 Hz, 2H), 5.30 (s, 1H), 6.95 (dd, J=7.7, 4.9 Hz, 1H), 7.23-7.72 (m, 10H), 7.98 (dd, J=7.7, 1.8 Hz, 1H), 8.32 (dd, J=4.9, 1.8 Hz, 1H), 8.52 (s, 2H).

Example 275

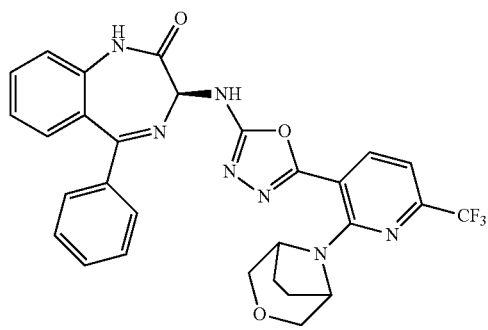 [SMILES: O=C1Nc2ccccc2C(c2ccccc2)=N[C@@H]1Nc1nnc(-c2ccc(C(F)(F)F)nc2N2C3CCC2COC3)o1]

Example 275 was prepared using a procedure similar to that used to prepare Example 160 where 3-oxa-8-azabicyclo[3.2.1]octane and ethyl 2-chloro-6-(trifluoromethyl)nicotinate were used in place of morpholine and methyl 5-bromo-3-fluoropicolinate, respectively. ESI-MS m/z: 576.3 [M+H]$^+$.

Example 276

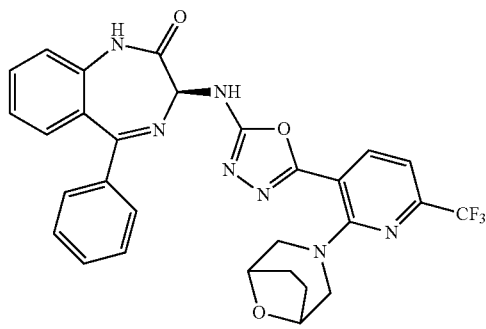 [SMILES: O=C1Nc2ccccc2C(c2ccccc2)=N[C@@H]1Nc1nnc(-c2ccc(C(F)(F)F)nc2N2CC3CCC(C2)O3)o1]

Example 276 was prepared using a procedure similar to that used to prepare Example 160 where 3-oxa-8-azabicyclo[3.2.1]octane and ethyl 2-chloro-6-(trifluoromethyl)nicotinate were used in place of morpholine and methyl 5-bromo-3-fluoropicolinate, respectively. ESI-MS m/z: 576.3 [M+H]$^+$.

Example 277

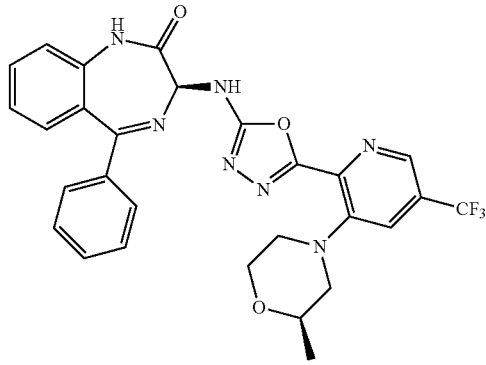 [SMILES: C[C@@H]1CN(c2cc(C(F)(F)F)cnc2-c2nnc(N[C@H]3N=C(c4ccccc4)c4ccccc4NC3=O)o2)CCO1]

Example 277 was prepared using a procedure similar to that used to prepare Example 160 where (R)-2-methylmorpholine and ethyl 3-chloro-5-(trifluoromethyl)picolinate were used in place of morpholine and methyl 5-bromo-3-fluoropicolinate, respectively. ESI-MS m/z: 564.3 [M+H]$^+$.

Example 278

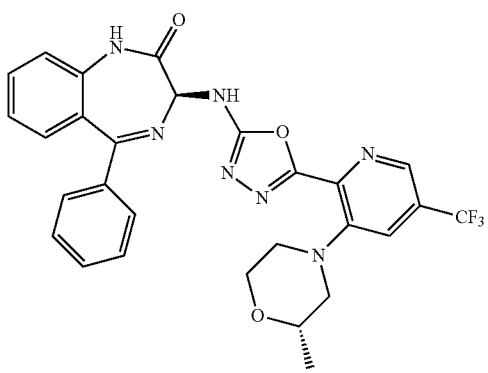 [SMILES: C[C@H]1CN(c2cc(C(F)(F)F)cnc2-c2nnc(N[C@H]3N=C(c4ccccc4)c4ccccc4NC3=O)o2)CCO1]

Example 278 was prepared using a procedure similar to that used to prepare Example 160 where (S)-2-methylmorpholine and ethyl 3-chloro-5-(trifluoromethyl)picolinate were used in place of morpholine and methyl 5-bromo-3-fluoropicolinate, respectively. ESI-MS m/z: 564.3 [M+H]+.

Example 279

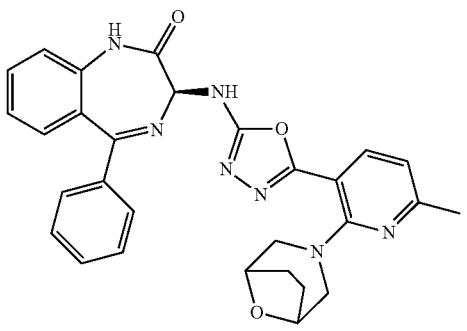 [SMILES: Cc1ccc(-c2nnc(N[C@H]3N=C(c4ccccc4)c4ccccc4NC3=O)o2)c(N2CC3CCC(C2)O3)n1]

Example 279 was prepared using a procedure similar to that used to prepare Example 160 where 3-oxa-8-azabicyclo[3.2.1]octane and methyl 2-chloro-6-methylnicotinate were used in place of morpholine and methy5-bromo-3-fluoropicolinate, respectively. ESI-MS m/z: 522.3 [M+H]+. 1H NMR (400 MHz, DMSO-d6) δ 1.62-1.81 (m, 2H), 1.90 (dd, J=7.2, 4.8 Hz, 2H), 2.41 (s, 3H), 3.00 (dt, J=12.6, 2.0 Hz, 2H), 3.28 (s, 2H), 4.18-4.38 (m, 2H), 5.15 (d, J=8.5 Hz, 1H), 6.85 (d, J=7.7 Hz, 1H), 7.29 (td, J=7.4, 1.2 Hz, 1H), 7.36 (dd, J=7.7, 1.4 Hz, 1H), 7.44-7.58 (m, 5H), 7.68 (ddd, J=8.6, 7.2, 1.7 Hz, 1H), 7.74 (d, J=7.7 Hz, 1H), 9.10 (d, J=8.7 Hz, 1H), 10.99 (s, 1H).

Example 280

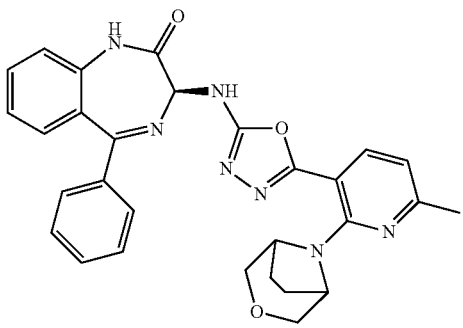 [SMILES: Cc1ccc(-c2nnc(N[C@H]3N=C(c4ccccc4)c4ccccc4NC3=O)o2)c(N2C3CCC2COC3)n1]

Example 280 was prepared using a procedure similar to that used to prepare Example 160 where 8-oxa-3-azabicyclo[3.2.1]octane and methyl 2-chloro-6-methylnicotinate were used in place of morpholine and methy5-bromo-3-fluoropicolinate, respectively. ESI-MS m/z: 522.3 [M+H]+. 1H NMR (400 MHz, DMSO-d6) δ 1.77 (m, 4H), 2.39 (s, 3H), 3.44-3.53 (d, 2H), 3.70-3.81 (m, 2H), 3.94-4.08 (d, 2H), 5.15 (d, 1H), 6.83 (d, 1H), 7.32 (d, 3H), 7.41-7.60 (m, 5H), 7.67 (m, 1H), 7.79 (d, 1H), 9.10 (d, 1H), 10.98 (s, 1H).

Example 281

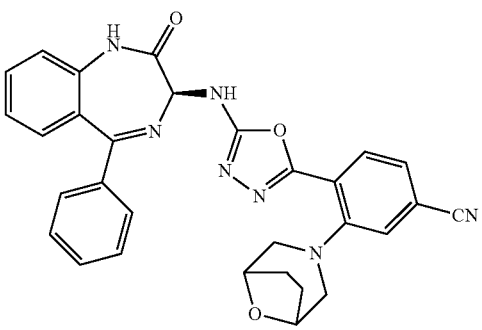 [SMILES: N#Cc1ccc(-c2nnc(N[C@H]3N=C(c4ccccc4)c4ccccc4NC3=O)o2)c(N2CC3CCC(C2)O3)c1]

Example 281 was prepared using a procedure similar to that used to prepare Example 151 where 2-(8-oxa-3-azabicyclo[3.2.1]octan-3-yl)-4-cyanobenzoic acid, which was prepared similarly to 4-cyano-2-morpholinobenzoic acid in Example 131, was used in place of 6-fluoro-2-morpholinonicotinic acid. ESI-MS m/z: 532.2 [M+H]+. 1H NMR (400 MHz, DMSO-d6) δ 1.60-1.82 (m, 2H), 1.95-2.11 (m, 2H), 2.80-2.99 (m, 4H), 4.19-4.35 (m, 2H), 5.18 (d, J=8.6 Hz, 1H), 7.26-7.74 (m, 12H), 9.27 (dd, J=8.5, 1.6 Hz, 1H), 11.00 (s, 1H).

Example 282

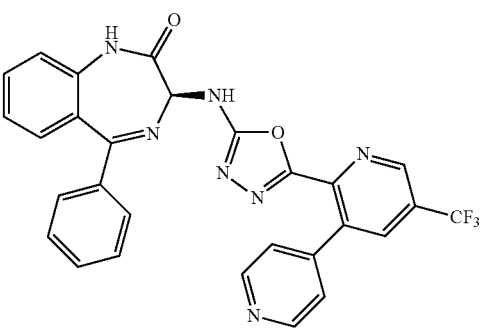 [SMILES: O=C1Nc2ccccc2C(c2ccccc2)=N[C@@H]1Nc1nnc(-c2ncc(C(F)(F)F)cc2-c2ccncc2)o1]

Example 282 Step a

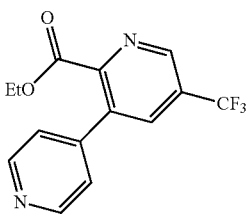

A solution of the ethyl 3-chloro-5-(trifluoromethyl)picolinate (1 g, 4.0 mmol), pyridin-4-ylboronic acid (583 mg, 4.7 mmol), Pd(dppf)Cl₂.DCM (1.8 g, 2.2 mol) and Na₂CO₃ (848 mg, 8.0 mol) in DMF (5 mL) was stirred for 1 hour at 130° C. It was purified by reverse phase C18 column chromatography (MeCN/H₂O) to give ethyl 5-(trifluoromethyl)-[3,4'-bipyridine]-2-carboxylate as a white solid (513 mg, 43%). ESI-MS m/z: 297.0 [M+H]⁺.

Example 282 Step b

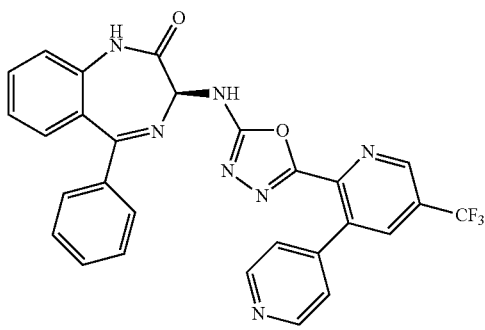 [SMILES: O=C1Nc2ccccc2C(c2ccccc2)=N[C@@H]1Nc1nnc(-c2ncc(C(F)(F)F)cc2-c2ccncc2)o1]

Example 282 was prepared using a procedure similar to that used to prepare Example 152 where ethyl 5-(trifluoromethyl)[3,4'-bipyridine]-2-carboxylate was used in place of ethyl 2-morpholino-4-(trifluoromethyl)benzoate. ESI-MS m/z: 542.2 [M+H]⁺. ¹H NMR (300 MHz, DMSO-d₆) δ 5.07 (d, J=7.8 Hz, 1H), 7.21-7.36 (m, 3H), 7.37-7.58 (m, 6H), 7.65 (m, 1H), 8.31-8.38 (m, 1H), 8.55-8.63 (m, 2H), 9.21 (m, 1H), 9.42 (d, J=8.4 Hz, 1H), 10.93 (s, 1H).

Example 283

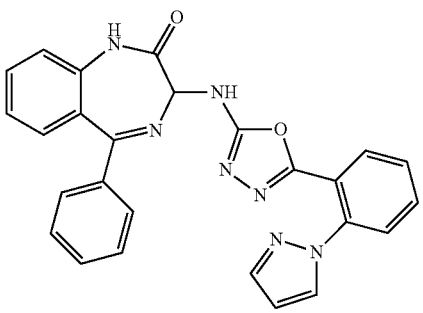 [SMILES: O=C1Nc2ccccc2C(c2ccccc2)=NC1Nc1nnc(-c2ccccc2-n2cccn2)o1]

Example 283 was prepared using a procedure similar to that used to prepare Example 20 where 2-(1H-pyrazol-1-yl)benzoic acid was used in place of 5-chlorofuran-2-carboxylic acid. ESI-MS m/z: 462.4 [M+H]⁺. ¹H NMR (400 MHz, DMSO-d₆) δ 4.89 (d, J=8.6 Hz, 1H), 6.13-6.19 (m, 1H), 7.24-7.78 (m, 13H), 7.81-7.91 (m, 1H), 7.95-8.05 (m, 1H), 8.91 (d, J=8.6 Hz, 1H), 10.94 (s, 1H).

Example 284

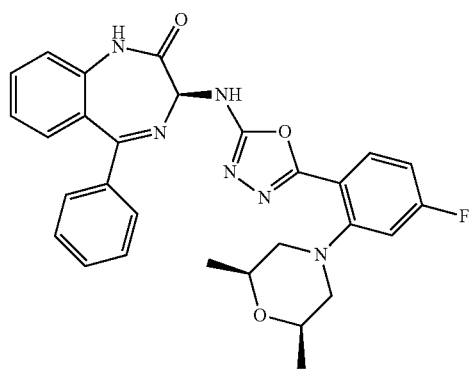 [SMILES: C[C@@H]1CN(c2cc(F)ccc2-c2nnc(N[C@H]3N=C(c4ccccc4)c4ccccc4NC3=O)o2)C[C@H](C)O1]

Example 284 was prepared using a procedure similar to that used to prepare Example 159 where ethyl 2-(cis-2,6-dimethylmorpholino)-4-fluorobenzoate was used in place of ethyl 4-fluoro-2-morpholinobenzoate. ESI-MS m/z: 527.2 [M+H]⁺.

Example 285

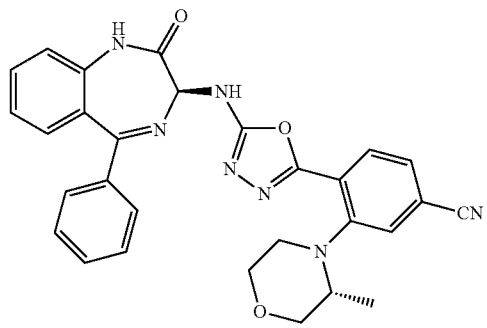 [SMILES: C[C@@H]1COCCN1c1cc(C#N)ccc1-c1nnc(N[C@H]2N=C(c3ccccc3)c3ccccc3NC2=O)o1]

Example 285 was prepared using a procedure similar to that used to prepare Example 151 where (R)-4-cyano-2-(3-methylmorpholino)benzoic acid, which was prepared similarly to 4-cyano-2-morpholinobenzoic acid in Example 131, was used in place of 6-fluoro-2-morpholinonicotinic acid. ESI-MS m/z: 520.6 [M+H]⁺.

Example 286

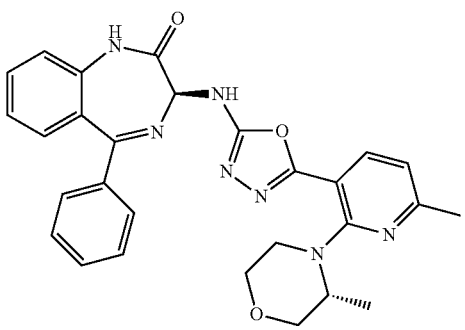 [SMILES: Cc1ccc(-c2nnc(N[C@H]3N=C(c4ccccc4)c4ccccc4NC3=O)o2)c(N2CCOC[C@H]2C)n1]

Example 286 was prepared using a procedure similar to that used to prepare Example 160 where (R)-3-methylmorpholine and methyl 2-chloro-6-methylnicotinate were used in place of morpholine and methy5-bromo-3-fluoropicolinate, respectively. ESI-MS m/z: 510.2 [M+H]+. ¹H NMR (400 MHz, DMSO-d₆) δ 0.99-1.01 (m, 3H), 2.50-2.51 (m, 3H), 3.03-3.07 (m, 1H), 3.22-3.26 (m, 1H), 3.33-3.46 (m, 1H), 3.50-3.53 (m, 1H), 3.57-3.69 (m, 1H), 3.73-3.78 (m, 2H), 5.14-5.16 (d, J=8.0, 1H), 6.89-6.91 (d, J=8.0, 1H), 7.26-7.36 (m, 3H), 7.44-7.55 (m, 5H), 7.65-7.70 (m, 1H), 7.82-7.84 (m, 1H), 9.08-9.11 (d, J=12.0, 1H), 10.98 (s, 1H).

Example 287

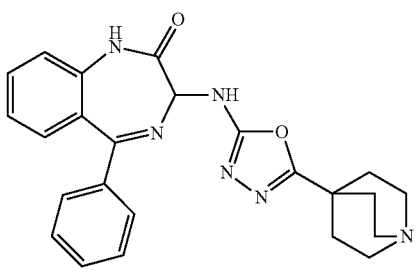 [SMILES: O=C1Nc2ccccc2C(c2ccccc2)=NC1Nc1nnc(C23CCN(CC2)CC3)o1]

Example 287 was prepared using a procedure similar to that used to prepare Example 20 where quinuclidine-4-carboxylic acid was used in place of 5-chlorofuran-2-carboxylic acid. ESI-MS m/z: 390.1 [M+H]+. H NMR (300 MHz, DMSO-d6) δ 1.69 (m, 6H), 2.76-2.88 (m, 6H), 5.03 (d, J=8.7 Hz, 1H), 7.19-7.37 (m, 3H), 7.38-7.59 (m, 5H), 7.65 (m, 1H), 8.72 (d, J=8.7 Hz, 1H), 10.88 (s, 1H).

Example 288

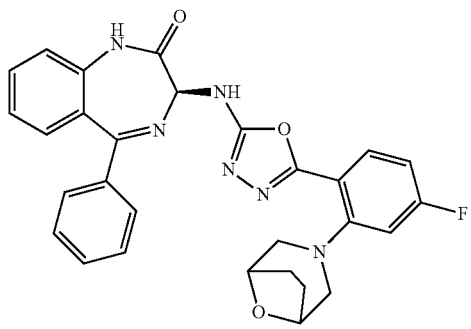 [SMILES: O=C1Nc2ccccc2C(c2ccccc2)=N[C@@H]1Nc1nnc(-c2ccc(F)cc2N2CC3CCC(C2)O3)o1]

Example 288 was prepared using a procedure similar to that used to prepare Example 159 where ethyl 2-(8-oxa-3-azabicyclo[3.2.1]octan-3-yl)-4-fluorobenzoate was used in place of ethyl 4-fluoro-2-morpholinobenzoate. ESI-MS m/z: 525.2 [M+H]+.

Example 289

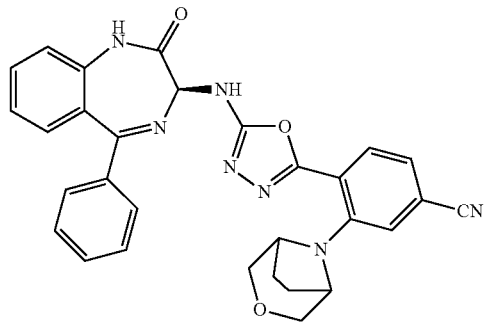 [SMILES: N#Cc1ccc(-c2nnc(N[C@H]3N=C(c4ccccc4)c4ccccc4NC3=O)o2)c(N2C3CCC2COC3)c1]

Example 289 was prepared using a procedure similar to that used to prepare Example 151 where 2-(3-oxa-8-azabicyclo[3.2.1]octan-8-yl)-4-cyanobenzoic acid, which was prepared similarly to 4-cyano-2-morpholinobenzoic acid in Example 131, was used in place of 6-fluoro-2-morpholinonicotinic acid. ESI-MS m/z: 532.3 [M+H]+. ¹H NMR (400 MHz, DMSO-d₆) δ 1.82-1.85 (m, 4H), 3.45-3.48 (m, 2H), 3.69-3.80 (m, 4H), 5.15-5.17 (m, 1H), 7.26-7.33 (m, 2H), 4.53-4.54 (m, 1H), 7.35-7.44 (m, 3H), 7.46-7.55 (m, 6H), 7.65-7.74 (m, 2H), 9.24-9.26 (d, J=8.0, 1H), 10.97 (s, 1H).

Example 290

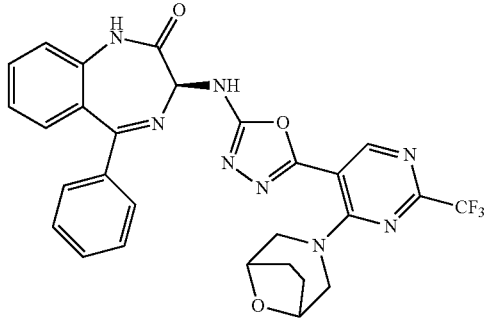 [SMILES: O=C1Nc2ccccc2C(c2ccccc2)=N[C@@H]1Nc1nnc(-c2cnc(C(F)(F)F)nc2N2CC3CCC(C2)O3)o1]

Example 290 was prepared using a procedure similar to that used to prepare Example 162 where 8-oxa-3-azabicyclo [3.2.1]octane was used in place of morpholine. ESI-MS m/z: 551.6 [M+H]+. ¹H NMR (400 MHz, DMSO-d₆) δ 1.69 (m, 4H), 3.22 (d, J=12.9 Hz, 2H), 3.67 (m, 2H), 4.35 (s, 2H), 5.15 (d, J=6.9 Hz, 1H), 7.26 (m, 1H), 7.34 (d, J=8.2 Hz, 2H), 7.48 (m, 5H), 7.65 (m, 1H), 8.66 (s, 1H), 9.24 (d, J=7.9 Hz, 1H), 10.98 (s, 1H).

Example 291

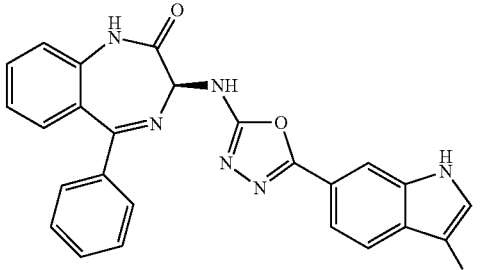

Example 291 was prepared using a procedure similar to that used to prepare Example 20 where 3-cyano-1H-indole- 6-carboxylic acid was used in place of 5-chlorofuran-2-carboxylic acid. ESI-MS m/z: 460.1 [M+H]⁺. ¹H NMR (300 MHz, DMSO-d6) δ 5.19 (d, J=8.6 Hz, 1H), 7.24-7.89 (m, 11H), 7.96-8.03 (m, 1H), 8.44 (s, 1H), 9.16 (d, J=8.6 Hz, 1H), 11.02 (s, 1H), 12.52 (s, 1H).

Example 292

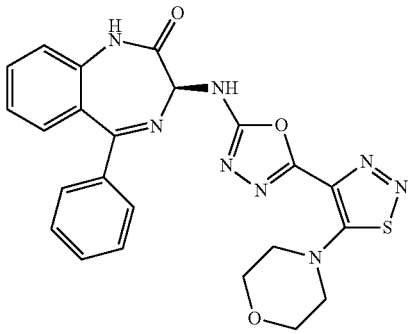 [SMILES: O=C1Nc2ccccc2C(c2ccccc2)=N[C@@H]1Nc1nnc(-c2nnsc2N2CCOCC2)o1]

Example 292 was prepared using a procedure similar to that used to prepare Example 272. ESI-MS m/z: 489.1 [M+H]⁺.

Example 293

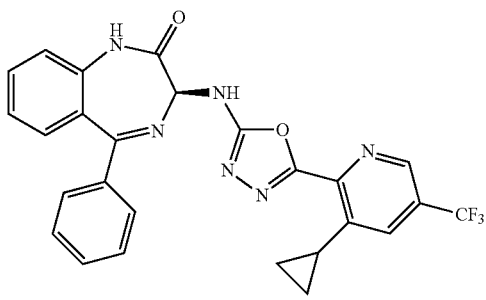 [SMILES: O=C1Nc2ccccc2C(c2ccccc2)=N[C@@H]1Nc1nnc(-c2ncc(C(F)(F)F)cc2C2CC2)o1]

Example 293 was prepared using a procedure similar to that used to prepare Example 282. ESI-MS m/z: 505.1 [M+H]⁺. ¹H NMR (300 MHz, DMSO-d₆) δ 0.92 (m, 2H), 1.10 (m, 2H), 2.90-3.00 (m, 1H), 5.20-5.23 (d, J=7.8 Hz, 1H), 7.25-7.37 (m, 3H), 7.37-7.56 (m, 5H), 7.65 (m, 1H), 7.82 (s, 1H), 8.89 (s, 1H), 9.41 (d, J=8.4 Hz, 1H), 10.98 (s, 1H).

Example 294

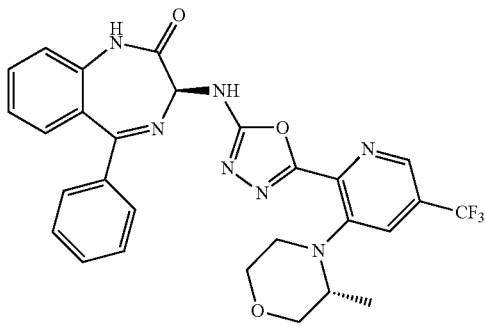 [SMILES: C[C@@H]1COCCN1c1cc(C(F)(F)F)cnc1-c1nnc(N[C@H]2N=C(c3ccccc3)c3ccccc3NC2=O)o1]

Example 294 was prepared using a procedure similar to that used to prepare Example 160 where (R)-3-methylmorpholine and ethyl 3-chloro-5-(trifluoromethyl)picolinate were used in place of morpholine and methyl 5-bromo-3-fluoropicolinate, respectively. ESI-MS m/z: 564.4 [M+H]⁺.

¹H NMR (300 MHz, DMSO-d₆) δ 0.80 (d, J=6.3 Hz, 3H), 2.71-2.83 (m, 2H), 3.35 (s, 2H), 3.50 (m, 1H), 3.58-3.68 (m, 1H), 3.78 (m, 2H), 5.20 (d, J=8.3 Hz, 1H), 7.22-7.38 (m, 3H), 7.40-7.58 (m, 5H), 7.61-7.75 (m, 1H), 8.04 (d, J=1.9 Hz, 1H), 8.45 (s, 0.29H), 8.72-8.78 (m, 1H), 9.37 (d, J=8.5 Hz, 1H), 10.97 (s, 1H).

Example 295

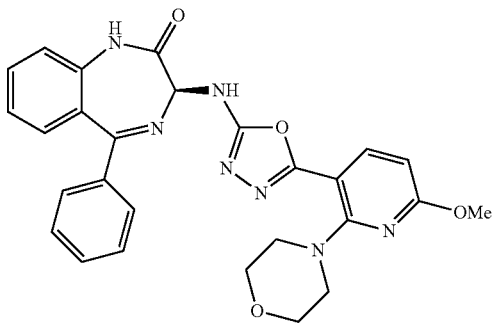 [SMILES: COc1ccc(-c2nnc(N[C@H]3N=C(c4ccccc4)c4ccccc4NC3=O)o2)c(N2CCOCC2)n1]

Example 295 was prepared using a procedure similar to that used to prepare Example 160 where methyl 2-chloro-6-methoxynicotinate was used in place of methy5-bromo-3-fluoropicolinate. ESI-MS m/z: 512.2 [M+H]⁺. ¹H NMR (300 MHz, DMSO-d₆) δ 3.11-3.27 (m, 4H), 3.62 (s, 4H), 3.87 (s, 3H), 5.13 (d, J=8.6 Hz, 1H), 6.40 (d, J=8.4 Hz, 1H), 7.18-7.40 (m, 3H), 7.40-7.58 (m, 5H), 7.61-7.74 (m, 1H), 7.83 (d, J=8.3 Hz, 1H), 9.00 (d, J=8.7 Hz, 1H), 10.88 (s, 1H).

Example 296

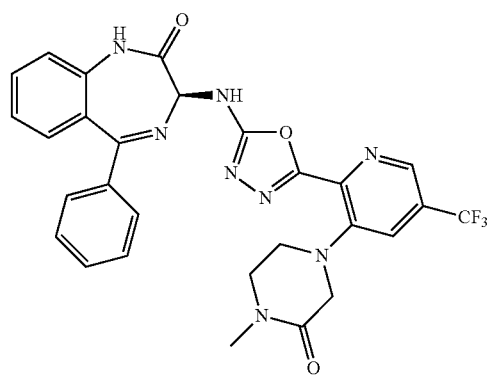 [SMILES: CN1CCN(c2cc(C(F)(F)F)cnc2-c2nnc(N[C@H]3N=C(c4ccccc4)c4ccccc4NC3=O)o2)CC1=O]

Example 296 was prepared using a procedure similar to that used to prepare Example 160 where 1-methylpiperazin-2-one and ethyl 3-chloro-5-(trifluoromethyl)picolinate were used in place of morpholine and methyl 5-bromo-3-fluoropicolinate, respectively. ESI-MS m/z: 577.3 [M+H]⁺. ¹H NMR (300 MHz, DMSO-d₆) δ 2.86 (s, 3H), 3.34 (d, J=4.6 Hz, 2H), 3.44 (m, 2H), 3.78 (s, 2H), 5.19 (d, J=8.2 Hz, 1H), 7.22-7.39 (m, 3H), 7.40-7.57 (m, 5H), 7.61-7.71 (m, 1H), 7.93 (d, J=1.9 Hz, 1H), 8.66-8.78 (m, 1H), 9.39 (d, J=8.4 Hz, 1H), 10.97 (s, 1H).

Example 297

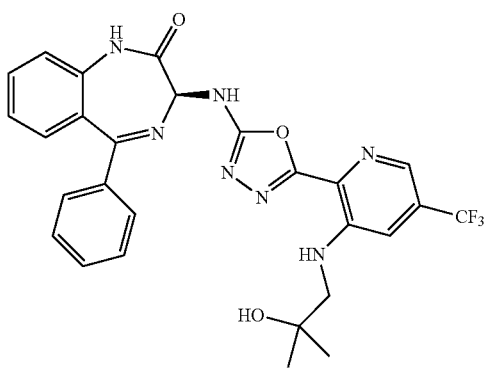 [SMILES: CC(C)(O)CNc1cc(C(F)(F)F)cnc1-c1nnc(N[C@H]2N=C(c3ccccc3)c3ccccc3NC2=O)o1]

Example 297 was prepared using a procedure similar to that used to prepare Example 151. ESI-MS m/z: 552.2 [M+H]+. $^1$H NMR (300 MHz, DMSO-d$_6$) δ 1.18 (s, 6H), 3.25 (d, J=5.2 Hz, 2H), 4.66 (s, 1H), 5.20 (d, J=8.3 Hz, 1H), 7.20-7.40 (m, 3H), 7.40-7.62 (m, 6H), 7.67 (ddd, J=8.5, 7.1, 1.7 Hz, 1H), 7.92 (t, J=5.2 Hz, 1H), 8.21 (dd, J=1.8, 0.8 Hz, 1H), 9.48 (d, J=8.4 Hz, 1H), 10.99 (s, 1H).

Example 298

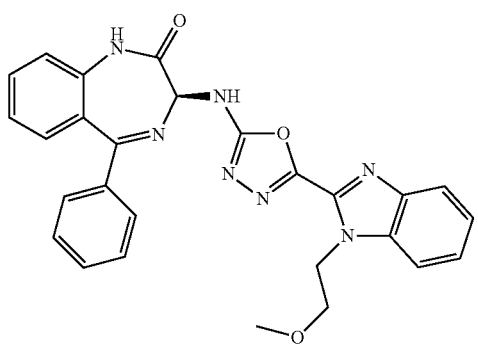 [SMILES: COCCn1c(-c2nnc(N[C@H]3N=C(c4ccccc4)c4ccccc4NC3=O)o2)nc2ccccc21]

Example 298 Step a

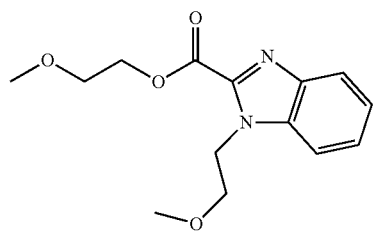 [SMILES: COCCOC(=O)c1nc2ccccc2n1CCOC]

A solution of 1H-benzo[d]imidazole-2-carboxylic acid (500 mg, 3.086 mmol), 1-bromo-2-methoxyethane (852 mg, 6.17 mmmol) and CS$_2$CO$_3$ (3.02 g, 9.258 mmol) in DMF (5 mL) was stirred for 3 hours at 60° C. It was diluted with water, extracted with EA (×3), washed with brine (×2), the organic layer was dried, concentrated to give 750 mg (crude) of desired compound as yellow oil, which was used directly in the next step. ESI-MS m/z: 279.3 [M+H]+.

Example 298 Step b

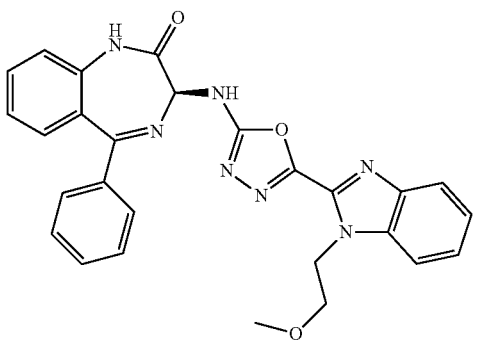 [SMILES: COCCn1c(-c2nnc(N[C@H]3N=C(c4ccccc4)c4ccccc4NC3=O)o2)nc2ccccc21]

Example 298 was prepared using a procedure similar to that used to prepare Example 152 where 2-methoxyethyl 1-(2-methoxyethyl)-1H-benzo[d]imidazole-2-carboxylate was used in place of ethyl 2-morpholino-4-(trifluoromethyl)benzoate. ESI-MS m/z: 494.4 [M+H]+. $^1$H NMR (300 MHz, DMSO-d$_6$) δ 3.16 (s, 3H), 3.72 (m, 2H), 4.85 (m, 2H), 5.23 (d, J=7.5 Hz, 1H), 7.23-7.42 (m, 5H), 7.43-7.61 (m, 3H), 7.64-7.82 (m, 3H), 9.47-9.64 (m, 1H), 11.01 (s, 1H).

Example 299

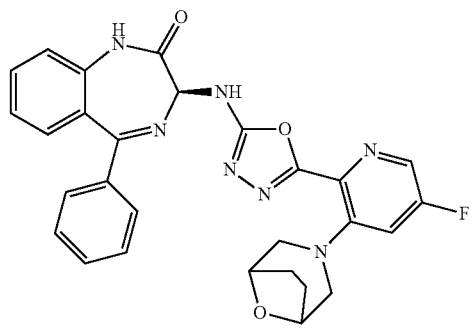 [SMILES: O=C1Nc2ccccc2C(c2ccccc2)=N[C@@H]1Nc1nnc(-c2ncc(F)cc2N2CC3CCC(C2)O3)o1]

Example 299 was prepared using a procedure similar to that used to prepare Example 151 where 3-(8-oxa-3-azabicyclo[3.2.1]octan-3-yl)-5-fluoropicolinic acid, which was prepared similarly to 5-fluoro-3-morpholinopicolinic acid in Example 136, was used in place of 6-fluoro-2-morpholinonicotinic acid. ESI-MS m/z: 526.5 [M+H]+. $^1$H NMR (300 MHz, DMSO-d6) δ 1.71 (m, 2H), 1.92-2.11 (m, 2H), 2.94 (m, 4H), 4.28 (s, 2H), 5.17 (d, 1H), 7.17-7.78 (m, 10H), 8.30 (m, 1H), 9.19 (d, 1H), 10.96 (s, 1H).

Example 300

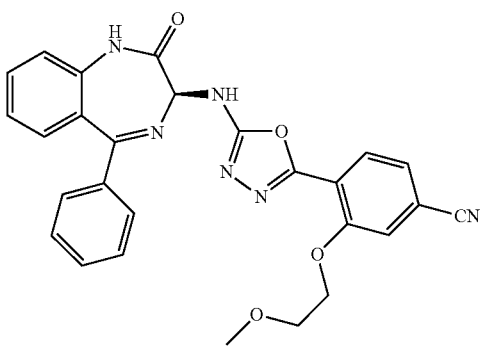 [SMILES: COCCOc1cc(C#N)ccc1-c1nnc(N[C@H]2N=C(c3ccccc3)c3ccccc3NC2=O)o1]

Example 300 Step a

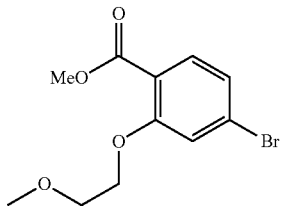 [SMILES: COCCOc1cc(Br)ccc1C(=O)OC]

To a stirred solution of methyl 4-bromo-2-hydroxybenzoate (1.5 g, 6.49 mmol), KI (108 mg, 0.65 mmol) and K$_2$CO$_3$ (2.69 g, 19.47 mmol) in DMF (30 mL) was added 1-bromo-2-methyloethane (902 mg, 6.49 mmol). The mixture was heated to 80° C. overnight and water was added (150 mL). The mixture was extracted with EA (150 mL×3) and the combined organic phase was washed with water, brine and dried over anhydrous Na$_2$SO$_4$ and concentrated. The residue was purified by silica gel chromatography (PE/EA=5/1) to give the desired compound as a yellow solid (1.7 g, 90%). ESI-MS m/z: 289.1 [M+H]$^+$.

Example 300 Step b

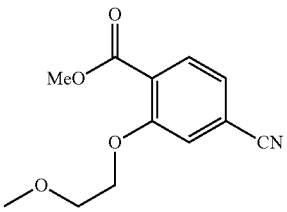 [SMILES: COCCOc1cc(C#N)ccc1C(=O)OC]

To a stirred solution of the compound from step a (1.7 g, 5.88 mmol) and Zn(CN)2 (1.36 g, 11.76 mmol) in DMF (30 mL) was added Pd(PPh$_3$)$_4$ (1.36 g, 1.18 mmol). The mixture was heated to 120° C. for 2 hours under N$_2$ Atmosphere. The mixture was cooled to rt and sat FeSO4 solution was added. The mixture was extracted with EA (100 mL×3) and the combined organic phase was washed with water, brine and dried over anhydrous Na$_2$SO4 and concentrated. The residue was purified by gel chromatography to give the title compound as a white solid (1.2 g, 78%). ESI-MS m/z: 263.0 [M+H]$^+$.

Example 300 Step c

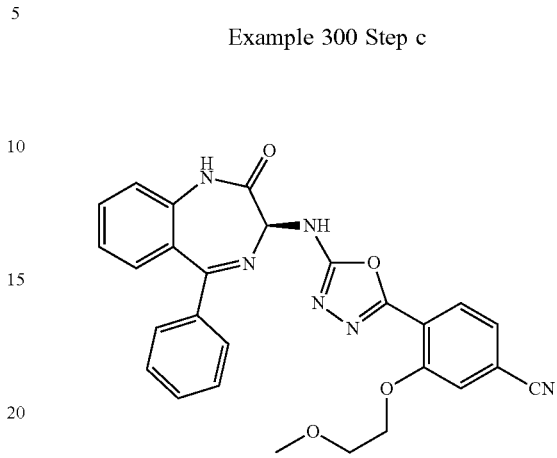

Example 300 was prepared using a procedure similar to that used to prepare Example 152 where methyl 4-cyano-2-(2-methoxyethoxy)benzoate was used in place of ethyl 2-morpholino-4-(trifluoromethyl)benzoate. ESI-MS m/z: 495.2 [M+H]$^+$. $^1$H NMR (300 MHz, DMSO-d$_6$) δ 3.27 (s, 3H), 3.67 (dd, J=5.5, 3.7 Hz, 2H), 4.28 (dd, J=5.5, 3.8 Hz, 2H), 5.17 (d, J=8.0 Hz, 1H), 7.18-7.59 (m, 9H), 7.58-7.77 (m, 2H), 7.87 (d, J=8.0 Hz, 1H), 9.20 (d, J=8.4 Hz, 1H), 10.97 (s, 1H).

Example 301

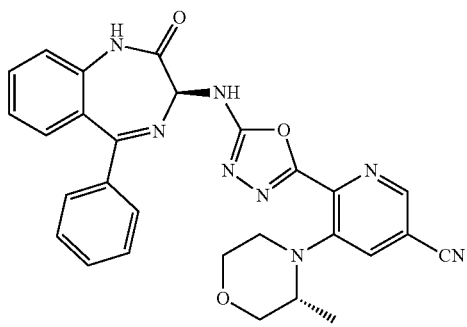 [SMILES: C[C@@H]1COCCN1c1cc(C#N)cnc1-c1nnc(N[C@H]2N=C(c3ccccc3)c3ccccc3NC2=O)o1]

Example 301 was prepared using a procedure similar to that used to prepare Example 151 where (R)-5-cyano-3-(3-methylmorpholino)picolinic acid, which was prepared similarly to 5-cyano-3-morpholinopicolinic acid in Example 140, in place of 6-fluoro-2-morpholinonicotinic acid. ESI-MS m/z: 521.4 [M+H]$^+$. $^1$H NMR (300 MHz, DMSO-d$_6$) δ 0.81 (d, J=6.3 Hz, 3H), 2.65-2.76 (m, 1H), 3.40-3.51 (m, 3H), 3.54-3.68 (m, 1H), 3.78 (m, 2H), 5.20 (d, J=8.3 Hz, 1H), 7.23-7.38 (m, 3H), 7.41-7.58 (m, 5H), 7.67 (m, 1H), 8.26 (d, J=1.8 Hz, 1H), 8.78 (d, J=1.7 Hz, 1H), 9.41 (d, J=8.5 Hz, 1H), 10.98 (s, 1H).

Example 302

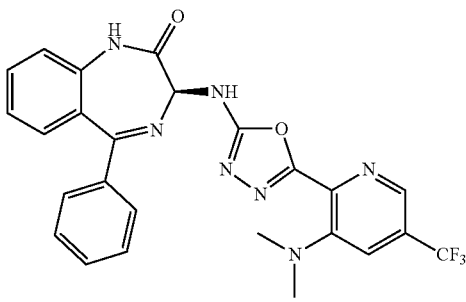 [SMILES: CN(C)c1cc(C(F)(F)F)cnc1-c1nnc(N[C@H]2N=C(c3ccccc3)c3ccccc3NC2=O)o1]

Example 302 was prepared using a procedure similar to that used to prepare Example 136 where dimethylamine and ethyl 3-chloro-5-(trifluoromethyl)picolinate were used in place of morpholine and ethyl 3,5-difluoropicolinate, respectively. ESI-MS m/z: 508.3 [M+H]$^+$.

Example 303

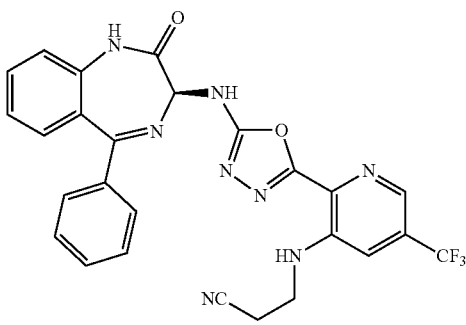 [SMILES: N#CCCNc1cc(C(F)(F)F)cnc1-c1nnc(N[C@H]2N=C(c3ccccc3)c3ccccc3NC2=O)o1]

Example 303 was prepared using a procedure similar to that used to prepare Example 136 where 3-aminopropanenitrile and ethyl 3-chloro-5-(trifluoromethyl)picolinate were used in place of morpholine and ethyl 3,5-difluoropicolinate, respectively. ESI-MS m/z: 533.2 [M+H]$^+$. $^1$H NMR (300 MHz, DMSO-d$_6$) δ 2.85 (t, J=6.5 Hz, 2H), 3.74 (q, J=6.4 Hz, 2H), 5.20 (d, J=8.3 Hz, 1H), 7.22-7.60 (m, 8H), 7.61-7.78 (m, 2H), 7.89 (t, J=6.2 Hz, 1H), 8.27-8.34 (m, 1H), 9.51 (d, J=8.4 Hz, 1H), 11.00 (s, 1H).

Example 304

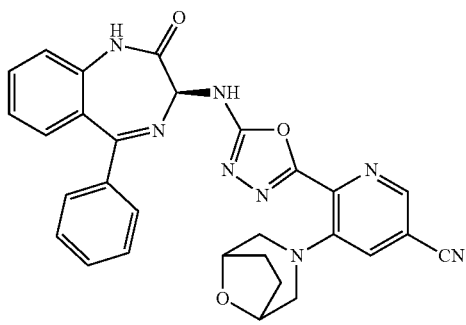 [SMILES: N#Cc1cnc(-c2nnc(N[C@H]3N=C(c4ccccc4)c4ccccc4NC3=O)o2)c(N2CC3CCC(C2)O3)c1]

Example 304 was prepared using a procedure similar to that used to prepare Example 151 where 3-(8-oxa-3-azabicyclo[3.2.1]octan-3-yl)-5-cyanopicolinic acid, which was prepared similarly to 5-cyano-3-morpholinopicolinic acid in Example 140, in place of 6-fluoro-2-morpholinonicotinic acid. ESI-MS m/z: 533.4 [M+H]$^+$. $^1$H NMR (400 MHz, DMSO-d$_6$) δ 1.71 (s, 2H), 2.07-2.11 (m, 2H), 2.94-3.05 (m, 4H), 4.30 (s, 2H), 5.19-5.21 (d, J=8.0, 1H), 7.26-7.36 (m, 3H), 7.44-7.55 (m, 5H), 7.65-7.69 (m, 1H), 8.11 (s, 1H), 8.68-8.69 (d, J=4.0, 1H), 9.40-9.42 (d, J=8.0, 1H), 11.00 (s, 1H).

Example 305

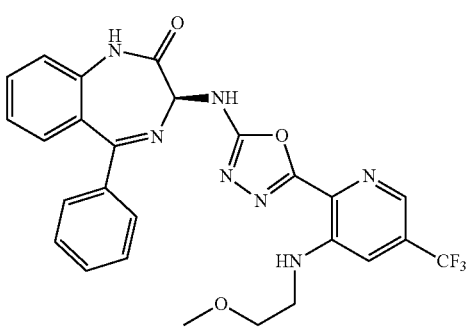 [SMILES: COCCNc1cc(C(F)(F)F)cnc1-c1nnc(N[C@H]2N=C(c3ccccc3)c3ccccc3NC2=O)o1]

Example 305 was prepared using a procedure similar to that used to prepare Example 136 where 2-methoxyethan-1-amine and ethyl 3-chloro-5-(trifluoromethyl)picolinate were used in place of morpholine and ethyl 3,5-difluoropicolinate, respectively. ESI-MS m/z: 538.5 [M+H]$^+$. $^1$H NMR (300 MHz, DMSO-d$_6$) δ 3.28 (s, 3H), 3.52 (m, 2H), 3.58 (m, 2H), 5.20 (d, 1H), 7.22-7.40 (m, 3H), 7.40-7.60 (m, 6H), 7.68 (m, 1H), 7.82 (m, 1H), 8.22-8.28 (s, 1H), 9.50 (d, 1H), 11.00 (s, 1H).

Example 306

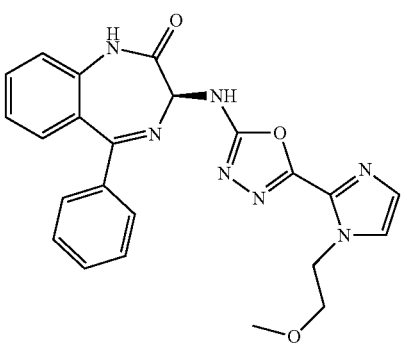 [SMILES: COCCn1ccnc1-c1nnc(N[C@H]2N=C(c3ccccc3)c3ccccc3NC2=O)o1]

Example 306 was prepared using a procedure similar to that used to prepare Example 298 where 1H-imidazole-2-carboxylic acid was used in place of 1H-benzo[d]imidazole-2-carboxylic acid. ESI-MS m/z: 444.3 [M+H]$^+$. $^1$H NMR (300 MHz, DMSO-d$_6$) δ 3.20 (s, 3H), 3.63 (m, 2H), 4.54 (m, 2H), 5.15 (d, J=8.4 Hz, 1H), 7.10 (d, J=1.1 Hz, 1H), 7.21-7.38 (m, 2H), 7.40-7.57 (m, 5H), 7.67 (m, 1H), 9.29 (d, J=8.5 Hz, 1H), 10.98 (s, 1H).

Example 307

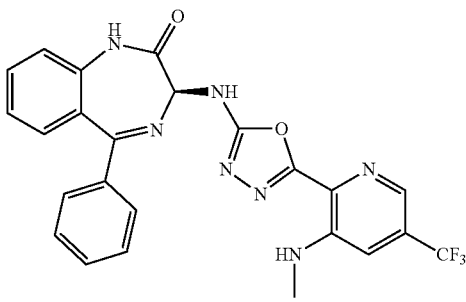 [SMILES: CNc1cc(C(F)(F)F)cnc1-c1nnc(N[C@H]2N=C(c3ccccc3)c3ccccc3NC2=O)o1]

Example 307 was prepared using a procedure similar to that used to prepare Example 136 where methylamine and ethyl 3-chloro-5-(trifluoromethyl)picolinate were used in place of morpholine and ethyl 3,5-difluoropicolinate, respectively. ESI-MS m/z: 494.3 [M+H]+. 1H NMR (300 MHz, DMSO-d6) δ 2.97 (s, 3H), 5.18 (d, J=8.3 Hz, 1H), 7.13-7.82 (m, 11H), 8.22 (d, J=1.9 Hz, 1H), 9.47 (d, J=8.4 Hz, 1H), 11.00 (s, 1H).

Example 308

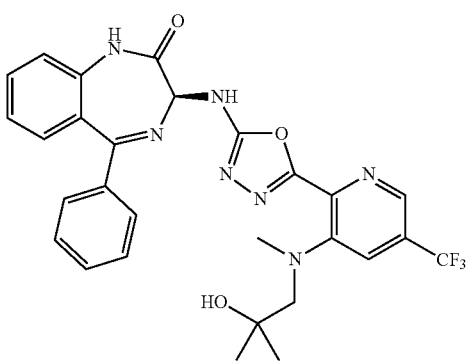 [SMILES: CN(CC(C)(C)O)c1cc(C(F)(F)F)cnc1-c1nnc(N[C@H]2N=C(c3ccccc3)c3ccccc3NC2=O)o1]

Example 308 was prepared using a procedure similar to that used to prepare Example 136 where 2-methoxy-N-methylethan-1-amine and ethyl 3-chloro-5-(trifluoromethyl)picolinate were used in place of morpholine and ethyl 3,5-difluoropicolinate, respectively. ESI-MS m/z: 566.3 [M+H]+. 1H NMR (300 MHz, DMSO-d6) δ 1.04 (s, 6H), 2.85 (s, 3H), 3.31 (d, J=2.2 Hz, 2H), 4.39 (s, 1H), 5.20 (d, J=8.5 Hz, 1H), 7.20-7.42 (m, 3H), 7.41-7.61 (m, 5H), 7.68 (ddd, J=8.4, 7.1, 1.7 Hz, 1H), 7.96-8.10 (m, 1H), 8.36-8.47 (m, 1H), 9.26 (d, J=8.6 Hz, 1H), 10.99 (s, 1H).

Example 309

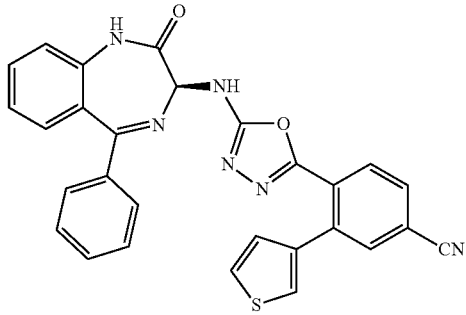

Example 309 Step a

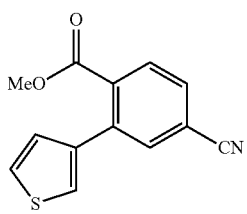 [SMILES: COC(=O)c1ccc(C#N)cc1-c1ccsc1]

A solution of methyl 2-bromo-4-cyanobenzoate (480 mg, 2.0 mmol), thiophen-3-ylboronic acid (307 mg, 2.4 mmol), Pd(dppf)Cl2 (146 mg, 0.2 mmol) and K2CO3 (552 mg, 4.0 mmol) in dioxane (10 mL) and H2O (2 mL) was stirred for 1 hour at 80° C. Extracted with EA (3×), dried Na2SO4, and filtered to give desired compound as a brown solid (389 mg, 80%). ESI-MS m/z: no signal.

Example 309 Step b

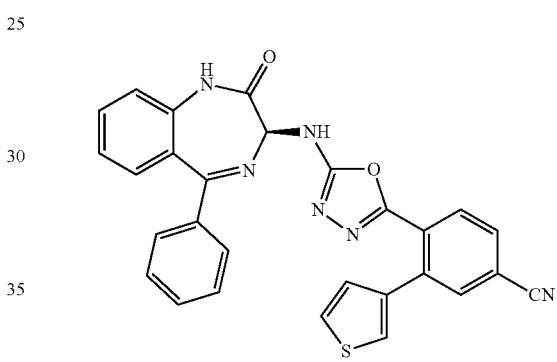

Example 309 was prepared using a procedure similar to that used to prepare Example 152 where methyl 4-cyano-2-(thiophen-3-yl)benzoate was used in place of ethyl 2-morpholino-4-(trifluoromethyl)benzoate. ESI-MS m/z: 503.3 [M+H]+. 1H NMR (300 MHz, DMSO-d6) δ 4.96 (m, 1H), 6.98-7.07 (m, 1H), 7.24-7.80 (m, 1H), 7.90-8.06 (m, 3H), 9.11 (m, 1H), 10.96 (s, 1H).

Example 310

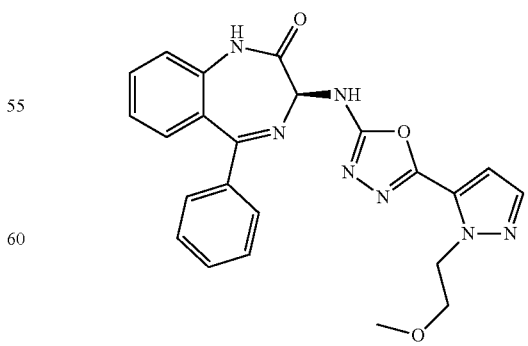

Example 310 was prepared using a procedure similar to that used to prepare Example 152 where ethyl 1-(2- methoxyethyl)-1H-pyrazole-5-carboxylate was used in place of ethyl 2-morpholino-4-(trifluoromethyl)benzoate. ESI-MS m/z: 444.3 [M+H]⁺. ¹H NMR (300 MHz, DMSO-d₆) δ 3.16 (s, 3H), 3.69 (m, 2H), 4.67 (m, 2H), 5.15 (d, J=8.4 Hz, 1H), 6.73 (d, J=2.0 Hz, 1H), 7.20-7.39 (m, 3H), 7.41-7.59 (m, 5H), 7.59-7.73 (m, 2H), 9.27 (d, J=8.4 Hz, 1H), 11.00 (s, 1H).

Example 311

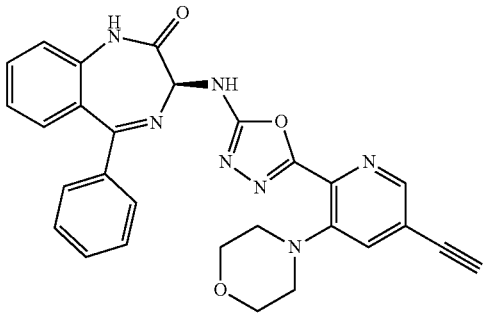 [SMILES: C#Cc1cnc(-c2nnc(N[C@H]3N=C(c4ccccc4)c4ccccc4NC3=O)o2)c(N2CCOCC2)c1]

Example 311 Step a

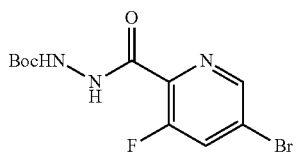

A solution of 5-bromo-3-fluoropicolinic acid (1.0 g, 4.57 mmol) was dissolved in DMF (15 mL) and BocNHNH₂ (1.2 g, 9.14 mmol) was added. HATU (1.8 g, 4.80 mmol) and Et₃N (5 mL) was added. The mixture was stirred at rt for 1 hour. Water (20 mL) was added and the mixture was extracted with EA (25 mL×3). The combined organic phase was dried over anhydrous Na₂SO₄ and concentrated. The residue was purified by silica gel chromatography (PE/EA=3/1) to give the desired product as a white solid (1.3 g, 83%).

Example 311 Step b

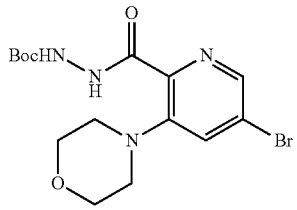 [SMILES: CC(C)(C)OC(=O)NNC(=O)c1ncc(Br)cc1N1CCOCC1]

A solution of the compound from step a (1.3 g, 3.78 mmol), morpholine (658 mg, 7.56 mmol) and K₂CO₃ (1.3 g, 9.45 mmol) in DMSO (10 mL) was stirred for overnight at 100° C. It was diluted with H₂O, and extracted with EA (×3) and washed with brine (×2). The organic layers was combined and concentrated to give 1.2 g (81%) white product. ESI-MS m/z: 401.2 [M+H]⁺.

Example 311 Step c

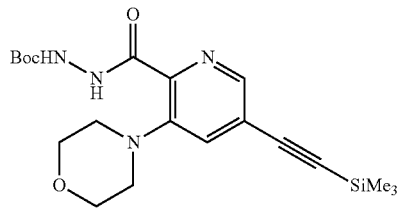 [SMILES: CC(C)(C)OC(=O)NNC(=O)c1ncc(C#C[Si](C)(C)C)cc1N1CCOCC1]

A solution of the compound from step b (500 mg, 1.25 mmol) and ethynyltrimethylsilane (368 mg, 3.75 mmol) in i-Pr₂NH (6 mL) was added Pd(PPh₃)₂Cl₂ (88 mg, 0.13 mmol) and CuI (24 mg, 0.13 mmol). The mixture was heated to 80° C. for 3 hours and then cooled to r.t. It was filtered and concentrated, then purified by reverse phase C18 column chromatography (MeCN/H₂O) to give the desired product as a yellow solid (451 mg, 86%). ESI-MS m/z: 419.4 [M+H]⁺.

Example 311 Step d

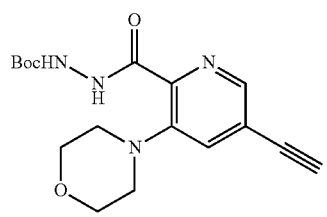 [SMILES: C#Cc1cnc(C(=O)NNC(=O)OC(C)(C)C)c(N2CCOCC2)c1]

A solution of the compound from step c (451 mg, 1.08 mmol) and K₂CO₃ (298 mg, 2.16 mmol) in MeOH (10 mL) was stirred at rt for 1 hour. It was purified by Silica gel column (PE/EA=3:1-1:1) to give tert-butyl 2-(5-ethynyl-3-morpholinopicolinoyl)hydrazine-1-carboxylate as a yellow solid (348 mg, 93%). ESI-MS m/z: 347.3 [M+H]⁺.

Example 311 Step e

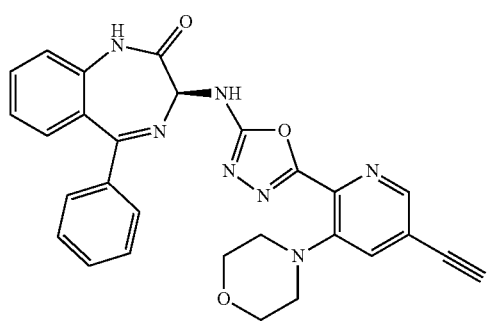 [SMILES: C#Cc1cnc(-c2nnc(N[C@H]3N=C(c4ccccc4)c4ccccc4NC3=O)o2)c(N2CCOCC2)c1]

Example 311 was prepared using a procedure similar to that used to prepare Example 151 where tert-butyl 2-(5-ethynyl-3-morpholinopicolinoyl)hydrazine-1-carboxylate was used in place of 6-fluoro-2-morpholinonicotinohydrazide. ESI-MS m/z: 506.4 [M+H]+. 1H NMR (300 MHz, DMSO-d6) δ 2.99 (d, 4H), 3.70 (d, 4H), 4.61 (s, 1H), 5.19 (d, 1H), 7.16-7.39 (m, 3H), 7.39-7.60 (m, 4H), 7.59-7.73 (m, 2H), 8.41 (d, 1H), 9.28 (d, J=8.6 Hz, 1H), 10.97 (s, 1H).

Example 312

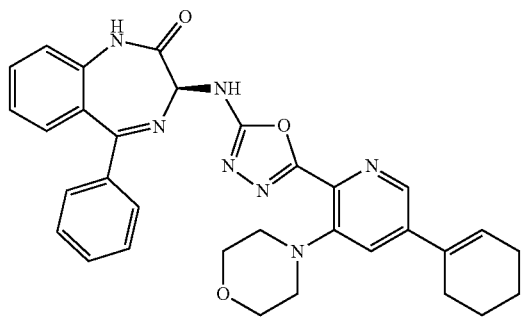 [SMILES: O=C1Nc2ccccc2C(c2ccccc2)=N[C@@H]1Nc1nnc(-c2ncc(C3=CCCCC3)cc2N2CCOCC2)o1]

Example 312 Step a

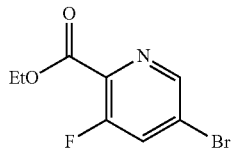 [SMILES: CCOC(=O)c1ncc(Br)cc1F]

A solution of 5-bromo-3-fluoropicolinic acid (4.0 g, 18.26 mmol) and H2SO4 (10 mL) in EtOH (25 mL) was heated to 80° C. for overnight and then cooled to rt. It was concentrated, diluted with H2O, and extracted with EA (×3) and washed with brine (×2). The organic layers was combined and concentrated to give desired compound as yellow oil (4.45 g, 95%). ESI-MS m/z: 247.8 [M+H]+.

Example 312 Step b

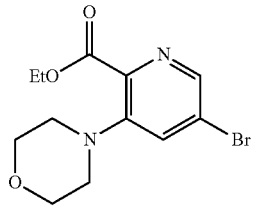 [SMILES: CCOC(=O)c1ncc(Br)cc1N1CCOCC1]

A solution of the compound from step a (4.45 g, 18.02 mmol) and K2CO3 (7.46 g, 54.06 mmol) in morpholine (20 mL) was stirred at rt for 1 hour. It was concentrated, diluted with H2O, and extracted with EA (×3) and washed with brine (×2). The organic layers was combined and concentrated, then purified by silica gel column (PE/EA=5:1) to give desired compound as a yellow solid (4.79 g, 85%). ESI-MS m/z: 315.2 [M+H]+.

Example 312 Step c

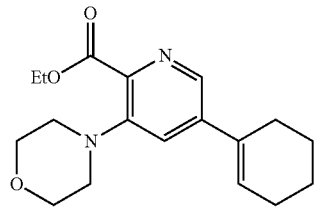 [SMILES: CCOC(=O)c1ncc(C2=CCCCC2)cc1N1CCOCC1]

A solution of the compound from step b (1.5 g, 3.18 mmol), cyclohexenylboronic acid (481 mg, 3.82 mmol), K2CO3 (878 mg, 6.36 mmol) and Pd(PPh3)4 (367 mg, 0.318 mmol) in DMF (8 mL) was stirred for overnight. It was filtered and purified by Prep-HPLC (MeCN/H2O) to give ethyl 5-(cyclohex-1-en-1-yl)-3-morpholinopicolinate as a yellow oil (440 mg, 44%). ESI-MS m/z: 317.3 [M+H]+.

Example 312 Step d

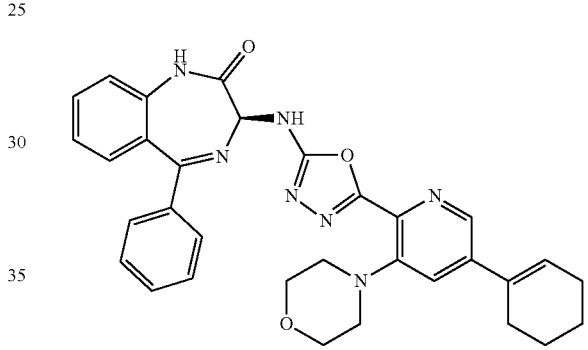

Example 312 was prepared using a procedure similar to that used to prepare Example 152 where ethyl 5-(cyclohex-1-en-1-yl)-3-morpholinopicolinate was used in place of ethyl 2-morpholino-4-(trifluoromethyl)benzoate. ESI-MS m/z: 562.3 [M+H]+. 1H NMR (300 MHz, DMSO-d6) δ 1.51-1.67 (m, 2H), 1.67-1.84 (m, 2H), 2.22 (s, 2H), 2.43 (s, 2H), 2.84-3.13 (m, 4H), 3.70 (d, 4H), 5.18 (d, 1H), 6.36-6.51 (m, 1H), 7.23-7.40 (m, 3H), 7.41-7.57 (m, 6H), 7.67 (m, 1H), 8.41 (d, 1H), 9.15 (d, 1H), 10.95 (s, 1H).

Example 313

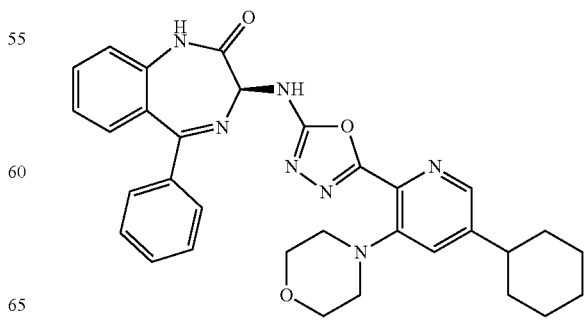

Example 313 Step a

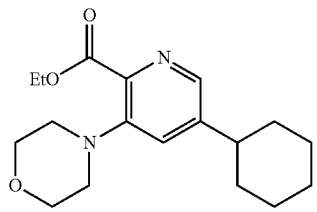 [SMILES: CCOC(=O)c1ncc(C2CCCCC2)cc1N1CCOCC1]

A solution of ethyl 5-(cyclohex-1-en-1-yl)-3-morpholinopicolinate from Example 312 step c (460 mg, 1.45 mmol) and Pd—C (100 mg) in 10 mL MeOH was stirred at room temperature for 3 hrs under Hz. Pd/C was filtered off and the filtrate was concentrated to afford ethyl 5-cyclohexyl-3-morpholinopicolinate as yellow oil (500 mg). ESI-MS m/z: 319.3 [M+H]⁺.

Example 313 Step b

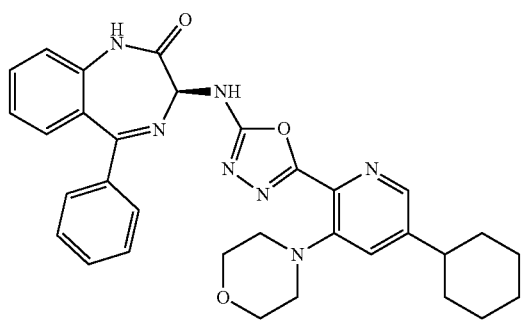 [SMILES: O=C1Nc2ccccc2C(c2ccccc2)=N[C@@H]1Nc1nnc(-c2ncc(C3CCCCC3)cc2N2CCOCC2)o1]

Example 313 was prepared using a procedure similar to that used to prepare Example 152 where ethyl 5-cyclohexyl-3-morpholinopicolinate was used in place of ethyl 2-morpholino-4-(trifluoromethyl)benzoate. ESI-MS m/z: 564.3 [M+H]⁺. ¹H NMR (300 MHz, DMSO-d₆) δ 1.39 (m, 5H), 1.76 (m, 5H), 2.52-2.71 (m, 1H), 2.97 (s, 4H), 3.69 (s, 4H), 5.17 (d, J=8.6 Hz, 1H), 7.32 (dd, J=18.4, 7.8 Hz, 3H), 7.40-7.61 (m, 6H), 7.67 (t, J=7.5 Hz, 1H), 8.23 (d, J=1.7 Hz, 1H), 9.14 (d, J=8.6 Hz, 1H), 10.96 (s, 1H).

Example 314

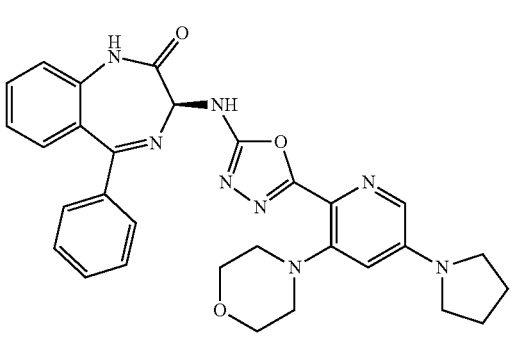 [SMILES: O=C1Nc2ccccc2C(c2ccccc2)=N[C@@H]1Nc1nnc(-c2ncc(N3CCCC3)cc2N2CCOCC2)o1]

Example 314 Step a

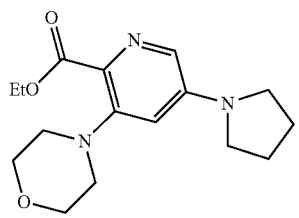 [SMILES: CCOC(=O)c1ncc(N2CCCC2)cc1N1CCOCC1]

A solution of the compound methyl 5-bromo-3-morpholinopicolinate from Example 160 step a (800 mg, 2.55 mmol), pyrrolidine (362 mg, 5.1 mmol), CuI (242 mg, 1.3 mmol), L-Proline (147 mg, 1.3 mmol) and K₂CO₃ (704 mg, 5.1 mmol) in DMSO (6 mL) was stirred at rt for 2 hours. It was filtered and then purified by Prep-HPLC (MeCN/H₂O) to give ethyl 3-morpholino-5-(pyrrolidin-1-yl)picolinate as a yellow oil (376 mg, 48%). ESI-MS m/z: 306.2 [M+H]⁺.

Example 314 Step b

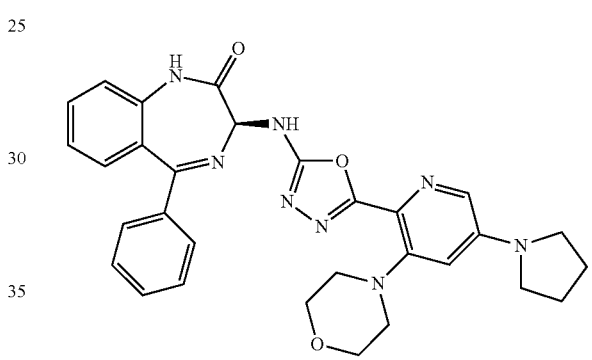

Example 314 was prepared using a procedure similar to that used to prepare Example 152 where ethyl 3-morpholino-5-(pyrrolidin-1-yl)picolinate was used in place of ethyl 2-morpholino-4-(trifluoromethyl)benzoate. ESI-MS m/z: 551.4 [M+H]⁺. ¹H NMR (400 MHz, DMSO-d₆) δ 1.87-2.10 (m, 4H), 2.79-3.14 (m, 4H), 3.25-3.52 (m, 4H), 3.70 (m, 4H), 5.16 (d, 1H), 6.52 (d, 1H), 7.24-7.32 (m, 1H), 7.36 (m, 2H), 7.42-7.59 (m, 5H), 7.68 (m, 1H), 7.73 (d, 1H), 8.94 (d, 1H), 10.96 (s, 1H).

Example 315

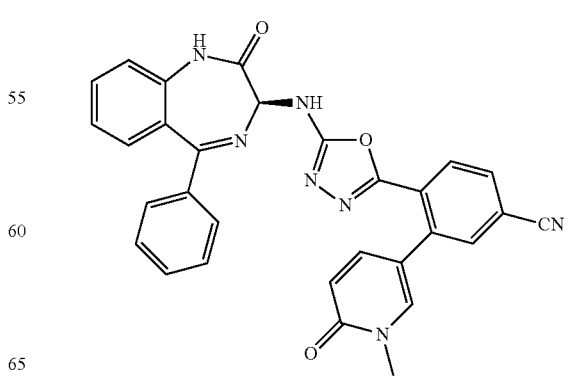

Example 315 was prepared using a procedure similar to that used to prepare Example 309 where 5-(4,4,5,5-tetramethyl-1,3,2-dioxaborolan-2-yl)pyridin-2(1H)-one was used in place of thiophen-3-ylboronic acid. ESI-MS m/z: 528.4 [M+H]⁺. ¹H NMR (400 MHz, DMSO-d₆) δ 3.47 (s, 3H), 5.12 (d, J=8.3 Hz, 1H), 6.34 (d, J=9.3 Hz, 1H), 7.23-7.40 (m, 4H), 7.50 (m, 5H), 7.67 (m, 1H), 7.90 (d, J=2.6 Hz, 1H), 7.99 (d, J=4.0 Hz, 3H), 9.27 (d, J=8.4 Hz, 1H), 10.97 (s, 1H).

Example 316

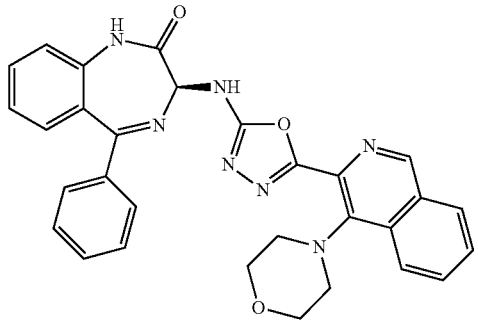 [SMILES: O=C1Nc2ccccc2C(c2ccccc2)=N[C@@H]1Nc1nnc(-c2ncc3ccccc3c2N2CCOCC2)o1]

Example 316 Step a

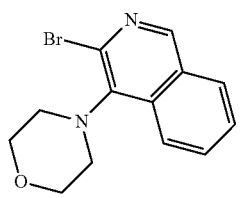 [SMILES: Brc1ncc2ccccc2c1N1CCOCC1]

A solution of 3-bromoisoquinolin-4-amine (980 mg, 4.4 mmol), Cs₂CO₃ (4.3 g, 13.2 mmol), 1-bromo-2-(2-bromoethoxy) ethane (1.5 g, 6.7 mmol) in DMA (20 mL) was stirred at 120° C. overnight. Then H₂O (20 mL) was added to the mixture and it was extracted with EA (×3). The organic layer was dried and purified by reverse phase C18 column chromatography (MeCN/H₂O) to give desired compound as brown solid (500 mg, 39%). ESI-MS m/z: 293.2 [M+H]⁺.

Example 316 Step b

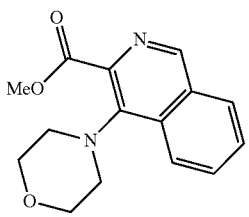 [SMILES: COC(=O)c1ncc2ccccc2c1N1CCOCC1]

A solution of the compound from step a (470 mg, 1.6 mmol), Pd(dppf)Cl₂ (200 mg, 0.245 mmol) and TEA (2 mL) in MeOH (10 mL). The solution was stirred for overnight at 100° C. in CO(g) under 20 atm. The solid was filtered out. The filtrate was concentrated under vacuum, and was purified by reverse phase C18 column chromatography (MeCN/H₂O) to give methyl 4-morpholinoisoquinoline-3-carboxylate as black solid (1.0 g). ESI-MS m/z: 273.3 [M+H]⁺.

Example 316 Step c

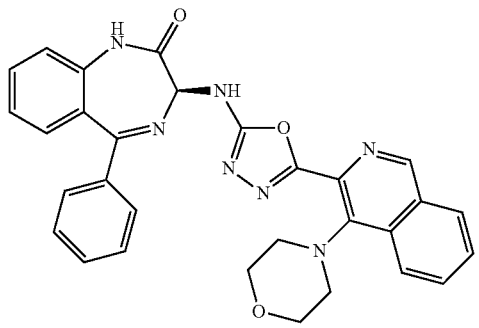 [SMILES: O=C1Nc2ccccc2C(c2ccccc2)=N[C@@H]1Nc1nnc(-c2ncc3ccccc3c2N2CCOCC2)o1]

Example 316 was prepared using a procedure similar to that used to prepare Example 152 where methyl 4-morpholinoisoquinoline-3-carboxylate was used in place of ethyl 2-morpholino-4-(trifluoromethyl)benzoate. ESI-MS m/z: 532.4 [M+H]⁺. ¹H NMR (300 MHz, DMSO-d₆) δ 3.02 (d, J=6.0 Hz, 4H), 3.78 (t, J=4.5 Hz, 4H), 5.22 (d, J=8.6 Hz, 1H), 7.22-7.60 (m, 8H), 7.68 (ddd, J=8.4, 7.1, 1.7 Hz, 1H), 7.87 (dddd, J=32.0, 8.0, 6.9, 1.2 Hz, 2H), 8.18-8.30 (m, 1H), 8.37 (d, J=8.3 Hz, 1H), 9.21 (d, J=9.6 Hz, 2H), 10.99 (s, 1H).

Example 317

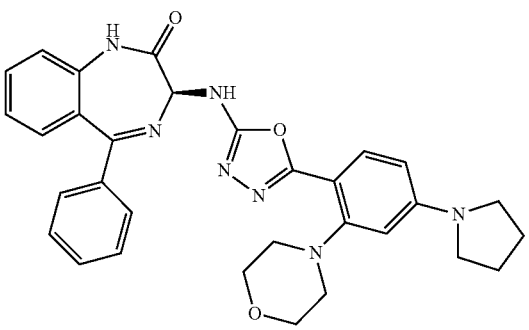

Example 317 Step a

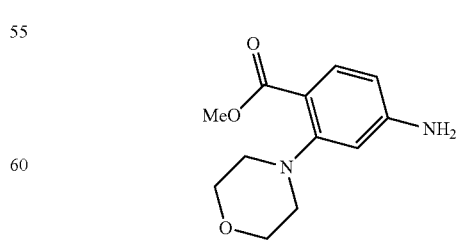

A solution of methyl 4-amino-2-fluorobenzoate (1.0 g, 5.9 mmol) and K₂CO₃ (1.6 g, 11.8 mmol) in morpholine (4 mL) was heated to 100° C. for overnight and then cooled to r.t.

Water (10 mL) was added and the mixture was extracted with EA (10 mL×3). The combined organic phase was dried over anhydrous Na$_2$SO$_4$ and concentrated. The residue was chromatographied (silica, PE:EA=2:1) to give desired compound as a pink solid (990 mg, 71%). ESI-MS m/z: 237.2 [M+H]$^+$.

Example 317 Step b

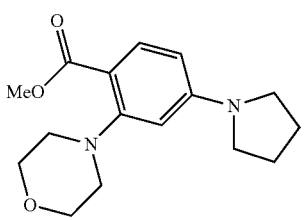 [SMILES: COC(=O)c1ccc(N2CCCC2)cc1N1CCOCC1]

A solution of the compound from step a (990 mg, 4.2 mmol) and Cs$_2$CO$_3$ (2.05 g, 6.3 mmol) in DMF (5 mL) was added 1,4-dibromobutane (898 mg, 4.2 mmol). The mixture was heated to 80° C. for 24 hours and then cooled to rt. Water (10 mL) was added and the mixture was extracted with EA (10 mL×3). The combined organic phase was washed with water (20 mL) and brine (20 mL). It was then dried over anhydrous Na$_2$SO$_4$ and concentrated. The residue was chromatographed (silica, PE:EA=5:1) to give methyl 2-morpholino-4-(pyrrolidin-1-yl)benzoate as a pink solid (200 mg, 16%). ESI-MS m/z: 291.3 [M+H]$^+$.

Example 317 Step c

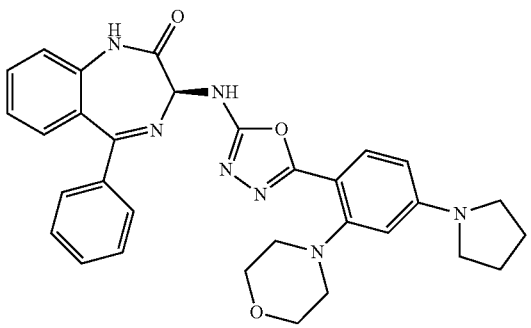 [SMILES: O=C1Nc2ccccc2C(c2ccccc2)=N[C@@H]1Nc1nnc(-c2ccc(N3CCCC3)cc2N2CCOCC2)o1]

Example 317 was prepared using a procedure similar to that used to prepare Example 152 where methyl 2-morpholino-4-(pyrrolidin-1-yl)benzoate was used in place of ethyl 2-morpholino-4-(trifluoromethyl)benzoate. ESI-MS m/z: 550.3 [M+H]$^+$. $^1$H NMR (300 MHz, DMSO-d$_6$) δ 1.91-2.01 (m, 4H), 2.88 (m, 4H), 3.24-3.30 (m, 4H), 3.68 (m, 4H), 5.12 (d, J=8.9 Hz, 1H), 6.15 (d, J=2.2 Hz, 1H), 6.29 (m, 1H), 7.24-7.41 (m, 3H), 7.41-7.57 (m, 6H), 7.66 (m, 1H), 8.80 (d, J=8.9 Hz, 1H), 10.94 (s, 1H).

Example 318

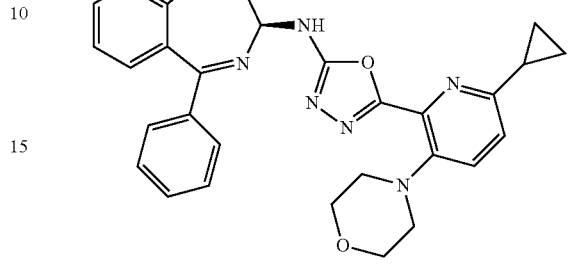

Example 318 Step a

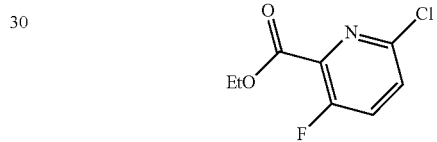

A solution of 6-chloro-3-fluoropicolinic acid (525 mg, 3.0 mmol) and H$_2$SO$_4$ (1 mL) in EtOH (20 mL) was stirred for 2 hours at 80° C. Then it was adjusted PH to 8~9, extracted with EA (3×), dried Na$_2$SO$_4$, filtered and concentrated to give desired compound as a white solid (610 mg, 100%). ESI-MS m/z: 204.2 [M+H]$^+$.

Example 318 Step b

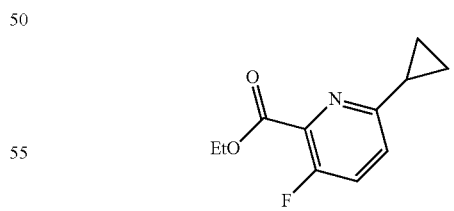

A solution of compound from step a (406 mg, 2.0 mmol), cyclopropylboronic acid (860 mg, 10.0 mmol), Pd(dppf)Cl$_2$ (146 mg, 0.2 mmol) and Cs$_2$CO$_3$ (978 mg, 3.0 mmol) in dioxane (20 mL) was heated to 120° C. for 2 hours. Then it was poured into water and extracted with EA (3×) to give desired crude compound as brown oil. (1 g). ESI-MS m/z: 209.9 [M+H]$^+$.

Example 318 Step c

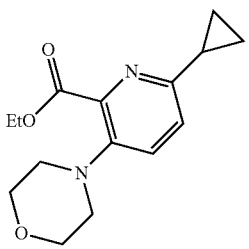 [SMILES: CCOC(=O)c1nc(C2CC2)ccc1N1CCOCC1]

A solution of compound from step b (1 g, crude) in morpholine (30 mL) was stirred for 3 hours at 110° C. The solvents were removed and extracted with EA (3×) to give desired crude ethyl 6-cyclopropyl-3-morpholinopicolinate as brown oil. (1.2 g). ESI-MS m/z: 277.3 [M+H]$^+$.

Example 318 Step d

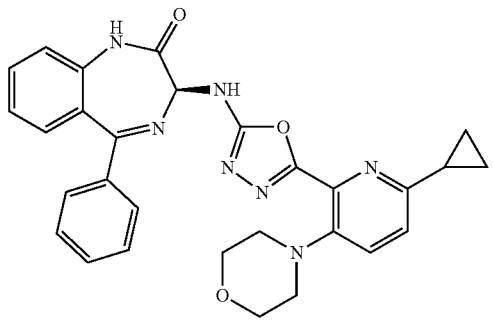 [SMILES: O=C1Nc2ccccc2C(c2ccccc2)=N[C@@H]1Nc1nnc(-c2nc(C3CC3)ccc2N2CCOCC2)o1]

Example 318 was prepared using a procedure similar to that used to prepare Example 152 where ethyl 6-cyclopropyl-3-morpholinopicolinate was used in place of ethyl 2-morpholino-4-(trifluoromethyl)benzoate. ESI-MS m/z: 522.4 [M+H]$^+$. $^1$H NMR (300 MHz, Methanol-d4) δ 1.01 (d, J=5.8 Hz, 4H), 2.14 (m, 1H), 3.08 (m, 4H), 3.86 (m, 4H), 5.39 (s, 1H), 7.26-7.79 (m, 11H).

Example 319

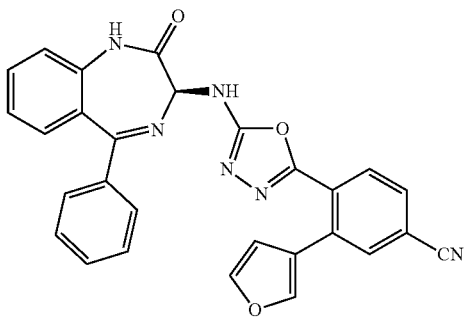 [SMILES: N#Cc1ccc(-c2nnc(N[C@H]3N=C(c4ccccc4)c4ccccc4NC3=O)o2)c(-c2ccoc2)c1]

Example 319 was prepared using a procedure similar to that used to prepare Example 309 where furan-3-ylboronic acid was used in place of thiophen-3-ylboronic acid. ESI-MS m/z: 487.3 [M+H]$^+$. $^1$H NMR (400 MHz, DMSO-d$_6$) δ 5.09 (d, J=8.4 Hz, 1H), 6.37-6.60 (m, 1H), 7.23-7.41 (m, 3H), 7.42-7.58 (m, 5H), 7.61-7.75 (m, 2H), 7.88-8.02 (m, 3H), 8.08 (d, J=1.5 Hz, 1H), 9.19 (d, J=8.4 Hz, 1H), 10.98 (s, 1H).

Example 320

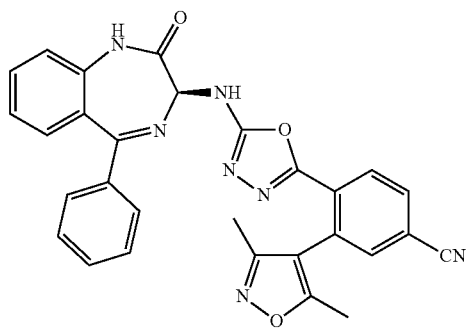 [SMILES: Cc1noc(C)c1-c1cc(C#N)ccc1-c1nnc(N[C@H]2N=C(c3ccccc3)c3ccccc3NC2=O)o1]

Example 320 was prepared using a procedure similar to that used to prepare Example 309 where (3,5-dimethylisoxazol-4-yl)boronic acid was used in place of thiophen-3-ylboronic acid. ESI-MS m/z: 516.2 [M+H]$^+$. $^1$H NMR (400 MHz, DMSO-d$_6$) δ 1.91 (d, J=3.2 Hz, 3H), 2.17 (s, 3H), 5.08 (d, J=8.1 Hz, 1H), 7.22-7.37 (m, 3H), 7.41-7.60 (m, 5H), 7.60-7.71 (m, 1H), 7.98 (d, J=1.7 Hz, 1H), 8.02-8.15 (m, 2H), 9.33 (d, J=8.4 Hz, 1H), 10.98 (s, 1H).

Example 321

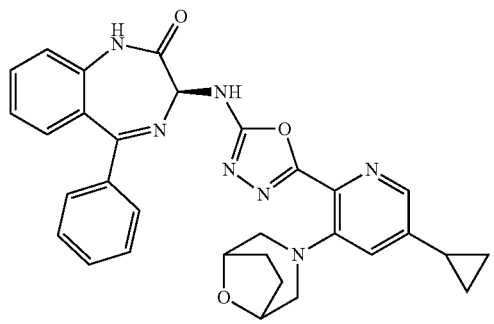 [SMILES: O=C1Nc2ccccc2C(c2ccccc2)=N[C@@H]1Nc1nnc(-c2ncc(C3CC3)cc2N2CC3CCC(C2)O3)o1]

Example 321 was prepared using a procedure similar to that used to prepare Example 169 where methyl 3-(8-oxa-3-azabicyclo[3.2.1]octan-3-yl)-5-bromopicolinate, prepared similarly to methyl 5-bromo-3-morpholinopicolinate in Example 160, was used in place of methyl 5-bromo-3-morpholinopicolinate. ESI-MS m/z: 548.2 [M+H]$^+$. $^1$H NMR (300 MHz, DMSO-d$_6$) δ 1.18 (s, 2H), 1.6 (s, 2H), 2.15 (d, 1H), 4.25-5.15 (m, 3H), 7.14-8.27 (m, 11H), 9.15 (d, 1H), 11.15 (d, 1H).

Example 322

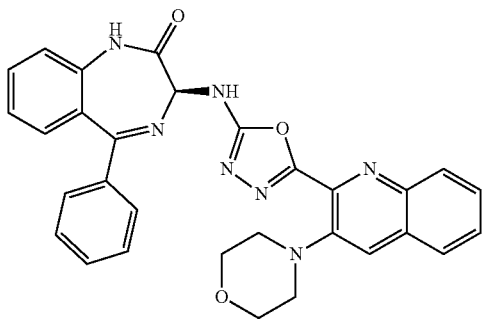 [SMILES: O=C1Nc2ccccc2C(c2ccccc2)=N[C@@H]1Nc1nnc(-c2nc3ccccc3cc2N2CCOCC2)o1]

Example 322 was prepared using a procedure similar to that used to prepare Example 316 where 2-bromoquinolin-3-amine was used in place of 3-bromoisoquinolin-4-amine. ESI-MS m/z: 532.2 [M+H]$^+$. $^1$H NMR (300 MHz, DMSO-d$_6$) δ 2.94-3.12 (m, 4H), 3.74 (m, 4H), 5.22 (d, J=7.9 Hz, 1H), 7.27 (m, 1H), 7.32-7.40 (m, 2H), 7.41-7.58 (m, 5H), 7.66 (m, 3H), 7.97 (m, 2H), 8.07 (s, 1H), 9.33 (d, J=8.5 Hz, 1H), 10.89 (s, 1H).

Example 323

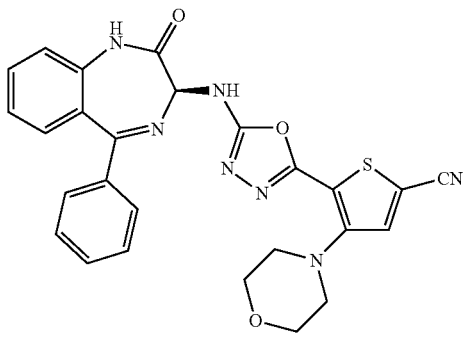 [SMILES: N#Cc1cc(N2CCOCC2)c(-c2nnc(N[C@H]3N=C(c4ccccc4)c4ccccc4NC3=O)o2)s1]

Example 323 Step a

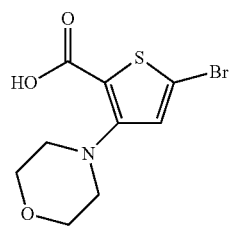 [SMILES: O=C(O)c1sc(Br)cc1N1CCOCC1]

A solution of methyl 5-bromo-3-morpholinothiophene-2-carboxylate, prepared in Example 182 step a, (900 mg, 2.9 mmol) in THF/H$_2$O (10 mL/3 mL) was added NaOH (1.18 mg, 29.4 mmol). The mixture was heated to 50° C. overnight. The mixture was cooled to room temperature and purified by reverse phase C18 column chromatography (MeCN/H$_2$O) to give the desired compound as a yellow oil (400 mg, 47%). ESI-MS m/z: 291.8 [M+H]$^+$.

Example 323 Step b

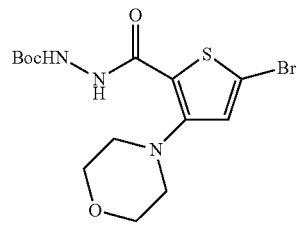 [SMILES: CC(C)(C)OC(=O)NNC(=O)c1sc(Br)cc1N1CCOCC1]

A solution of the compound from step a (400 mg, 1.37 mmol) and BocNHNH$_2$ (362.1 mg, 2.74 mmol) in DMF (5 mL) was added HATU (1.04 g, 2.74 mmol) and DIPEA (0.5 mL). The mixture was stirred at room temperature for 1 hour. Water (5 mL) was added and the mixture was extracted with EA (20 mL×3). The combined organic phase was dried over anhydrous Na$_2$SO$_4$ and concentrated. The residue was purified by silicagel chromatography (PE/EA=10/1) to give the desired compound as a yellow oil (230 mg, 41%). ESI-MS m/z: 408.1 [M+H]$^+$.

Example 323 Step c

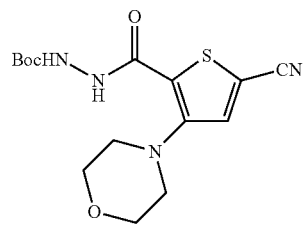 [SMILES: CC(C)(C)OC(=O)NNC(=O)c1sc(C#N)cc1N1CCOCC1]

Under N$_2$ atmosphere the compound from step b (230 mg, 0.57 mmol) was dissolved in DMF (4 mL) and Pd(PP$_3$)$_4$ (131 mg, 0.11 mmol) and Zn(CN)$_2$ (131 mg, 1.13 mmol) was added. The mixture was heated to 120° C. for 2 hours. FeSO4 solution (20 mL) was added and the mixture was extracted with EA (20 mL×3). The combined organic phase was washed with water, dried over anhydrous Na$_2$SO$_4$ and concentrated. The residue was purified by silica gel chromatography (PE/EA=5/1) to give tert-butyl 2-(5-cyano-3-morpholinothiophene-2-carbonyl)hydrazine-1-carboxylate as a yellow oil (128 mg, 64%). ESI-MS m/z: 353.1 [M+H]$^+$.

Example 323 Step d

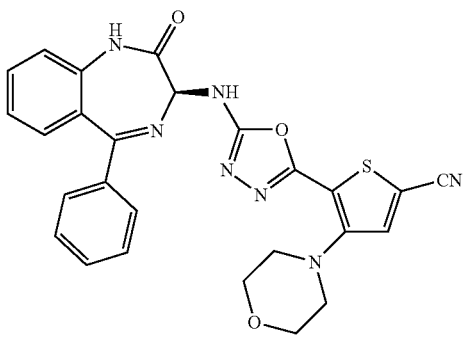 [SMILES: N#Cc1cc(N2CCOCC2)c(-c2nnc(N[C@H]3N=C(c4ccccc4)c4ccccc4NC3=O)o2)s1]

Example 323 was prepared using a procedure similar to that used to prepare Example 151 where tert-butyl 2-(5-cyano-3-morpholinothiophene-2-carbonyl)hydrazine-1-carboxylate was used in place of 6-fluoro-2-morpholinonicotinohydrazide. ESI-MS m/z: 512.2 [M+H]$^+$. $^1$H NMR (400 MHz, DMSO-d$_6$) δ 3.02-3.12 (m, 4H), 3.61-3.71 (m, 4H), 5.13 (d, J=8.3 Hz, 1H), 7.21-7.39 (m, 3H), 7.39-7.60 (m, 5H), 7.67 (ddd, J=8.5, 7.0, 1.8 Hz, 1H), 7.92 (s, 1H), 9.36 (d, J=8.4 Hz, 1H), 10.99 (s, 1H).

Example 324

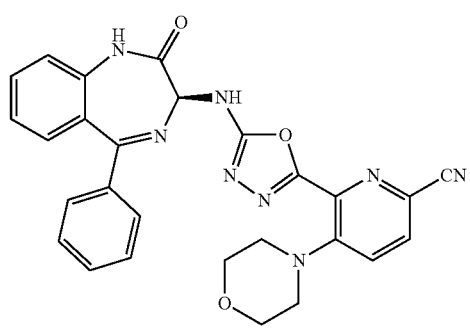 [SMILES: N#Cc1ccc(N2CCOCC2)c(-c2nnc(N[C@H]3N=C(c4ccccc4)c4ccccc4NC3=O)o2)n1]

Example 324 Step a

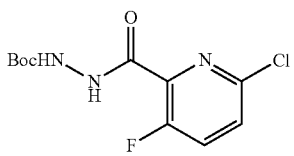 [SMILES: CC(C)(C)OC(=O)NNC(=O)c1nc(Cl)ccc1F]

A solution of 6-chloro-3-fluoropicolinic acid (1.40 g, 8 mmol), tert-butyl hydrazinecarboxylate (1.32 g, 10 mmol), DIPEA (3 mL) and HATU (3.80 g, 10 mmol) in DMF (50 mL) was stirred for 0.5 hours at 25° C. Then it was quenched with H$_2$O, extracted with EA (3×), dried Na$_2$SO$_4$, filtered and purified by reverse phase C18 column chromatography (MeCN/H$_2$O) to give desired compound as a white solid (1.74 g, 75%). ESI-MS m/z: 600.9 [2M+Na]$^+$.

Example 324 Step b

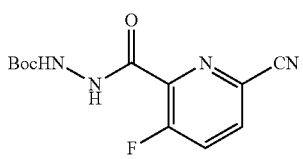 [SMILES: CC(C)(C)OC(=O)NNC(=O)c1nc(C#N)ccc1F]

A solution of compound from step a (725 mg, 2.5 mmol), Zn(CN)$_2$ (580 mg, 5 mmol) and Pd(PPh$_3$)$_4$ (580 mg, 0.5 mmol) in DMA (20 mL) was heated to 140° C. for 1 hour in the microwave. The mixture was filtered, extracted with EA (3×), the solvents were removed and purified by reverse phase C18 column chromatography (MeCN/H$_2$O) to give desired product as yellow solid. (224 mg, 32%). ESI-MS m/z: 302.9 [M+H]$^+$.

Example 324 Step c

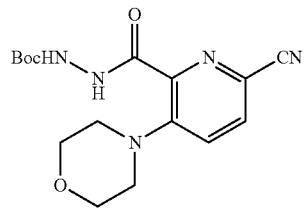 [SMILES: CC(C)(C)OC(=O)NNC(=O)c1nc(C#N)ccc1N1CCOCC1]

A solution of compound from step b (224 mg, 0.8 mmol) in morpholine (10 mL) was stirred for 1 hour at 80° C. The solvents were removed and purified by reverse phase C18 column chromatography (MeCN/H$_2$O) to give tert-butyl 2-(6-cyano-3-morpholinopicolinoyl)hydrazine-1-carboxylate as yellow solid. (208 mg, 75%). ESI-MS m/z: 348.3 [M+H]$^+$.

Example 324 Step d

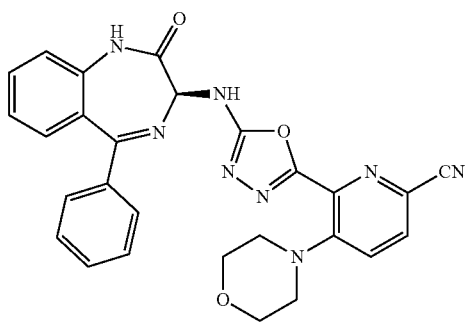 [SMILES: N#Cc1ccc(N2CCOCC2)c(-c2nnc(N[C@H]3N=C(c4ccccc4)c4ccccc4NC3=O)o2)n1]

Example 324 was prepared using a procedure similar to that used to prepare Example 151 where tert-butyl 2-(6-cyano-3-morpholinopicolinoyl)hydrazine-1-carboxylate was used in place of 6-fluoro-2-morpholinonicotinohydrazide. ESI-MS m/z: 507.3 [M+H]$^+$. H NMR (300 MHz, DMSO-d6) δ 3.08 (m, 4H), 3.70 (m, 4H), 5.18 (s, 1H), 7.20-7.58 (m, 8H), 7.67 (m, 2H), 8.01 (d, J=8.6 Hz, 1H), 9.34-9.42 (m, 1H), 10.90 (s, 1H).

Example 325

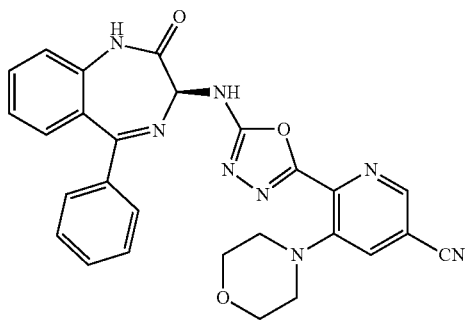 [SMILES: N#Cc1cnc(-c2nnc(N[C@H]3N=C(c4ccccc4)c4ccccc4NC3=O)o2)c(N2CCOCC2)c1]

Example 325 was prepared using a procedure similar to that used to prepare Example 151 where 5-cyano-3-morpholinopicolinic acid, prepared in Example 140, was used in place of 6-fluoro-2-morpholinonicotinic acid. ESI-MS m/z: 507.2 [M+H]+.

Example 326

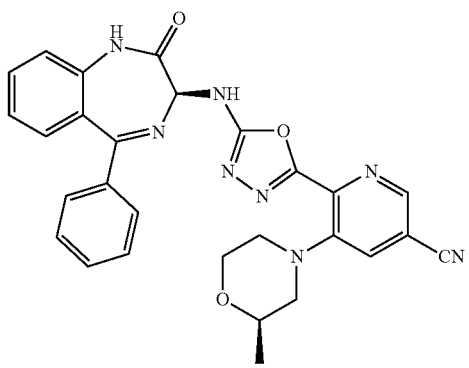 [SMILES: C[C@@H]1CN(c2cc(C#N)cnc2-c2nnc(N[C@H]3N=C(c4ccccc4)c4ccccc4NC3=O)o2)CCO1]

Example 326 was prepared using a procedure similar to that used to prepare Example 151 where (R)-5-cyano-3-(2-methylmorpholino)picolinic acid, which was prepared similarly to 5-cyano-3-morpholinopicolinic acid in Example 140, was used in place of 6-fluoro-2-morpholinonicotinic acid. ESI-MS m/z: 521.5 [M+H]+. $^1$H NMR (400 MHz, DMSO-d$_6$) δ 1.08 (d, 3H), δ 2.54-2.62 (d, 1H), 2.83 (m, 1H), 3.18 (m, 2H), 3.57-3.74 (m, 2H), 3.74-3.89 (m, 1H), 5.21 (d, 1H), 7.25-7.42 (m, 3H), 7.43-7.59 (m, 5H), 7.69 (m, 1H), 8.13 (d, 1H), 8.72 (d, 1H), 9.43 (d, 1H), 11.00 (s, 1H).

Example 327

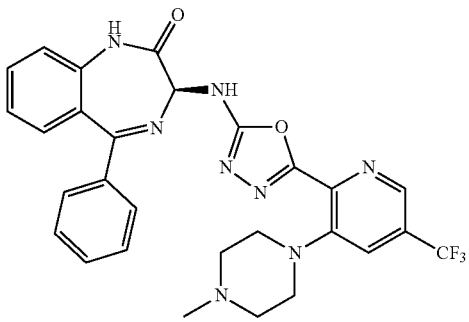 [SMILES: CN1CCN(c2cc(C(F)(F)F)cnc2-c2nnc(N[C@H]3N=C(c4ccccc4)c4ccccc4NC3=O)o2)CC1]

Example 327 was prepared using a procedure similar to that used to prepare Example 160 where 1-methylpiperazine and ethyl 3-chloro-5-(trifluoromethyl)picolinate were used in place of morpholine and methyl 5-bromo-3-fluoropicolinate, respectively. ESI-MS m/z: 563.2 [M+H]+. $^1$H NMR (400 MHz, DMSO-d$_6$) δ 2.19 (s, 3H), 2.49-2.50 (m, 4H), 3.05 (s, 4H), 5.19-5.21 (d, J=8.0, 1H), 7.28-7.37 (m, 8H), 7.44-7.54 (m, 1H), 7.66-7.85 (m, 1H), 8.65 (s, 1H), 9.35-9.37 (d, J=8.0, 1H), 10.99 (s, 1H).

Example 328

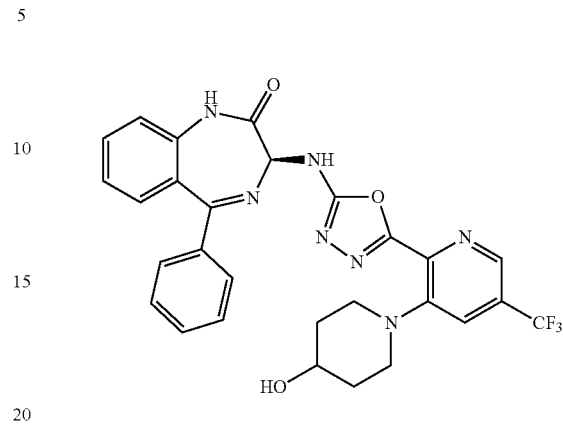

Example 328 was prepared using a procedure similar to that used to prepare Example 160 where piperidin-4-ol and ethyl 3-chloro-5-(trifluoromethyl)picolinate were used in place of morpholine and methyl 5-bromo-3-fluoropicolinate, respectively. ESI-MS m/z: 564.2 [M+H]+. $^1$H NMR (400 MHz, DMSO-d$_6$) δ 1.54-1.61 (m, 2H), 1.79-1.82 (m, 2H), 2.82-2.87 (m, 2H), 3.21-3.24 (m, 2H), 3.60-3.65 (m, 1H), 4.66-4.67 (d, J=4.0, 1H), 5.19-5.21 (d, J=4.0, 1H), 7.26-7.30 (m, 1H), 7.34-7.37 (m, 2H), 7.44-7.55 (m, 5H), 7.65-7.66 (m, 1H), 7.67-7.69 (m, 1H), 8.61 (s, 1H), 9.31-9.33 (d, J=8.0, 1H), 10.97 (s, 1H).

Example 329

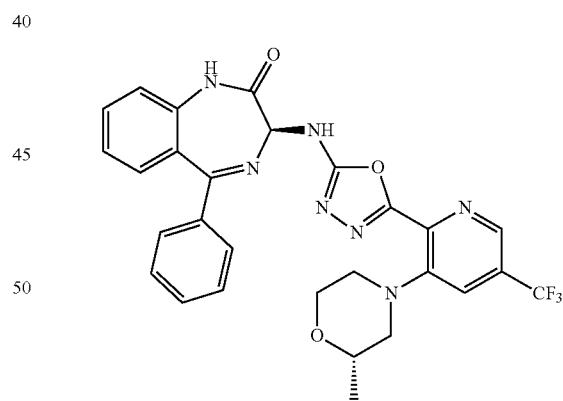

Example 329 was prepared using a procedure similar to that used to prepare Example 151 where (S)-5-cyano-3-(2-methylmorpholino)picolinic acid, which was prepared similarly to 5-cyano-3-morpholinopicolinic acid in Example 140, was used in place of 6-fluoro-2-morpholinonicotinic acid. ESI-MS m/z: 521.4 [M+H]+. $^1$H NMR (300 MHz, DMSO-d$_6$) δ 1.08 (d, 3H), 2.54-2.64 (m, 1H), 2.71-2.93 (m, 1H), 3.19 (m, 2H), 3.61-3.91 (m, 3H), 5.22 (d, 1H), 7.22-7.41 (m, 3H), 7.43-7.61 (m, 5H), 7.69 (m, 1H), 8.13 (d, 1H), 8.72 (d, 1H), 9.43 (d, 1H), 11.00 (s, 1H).

Example 330

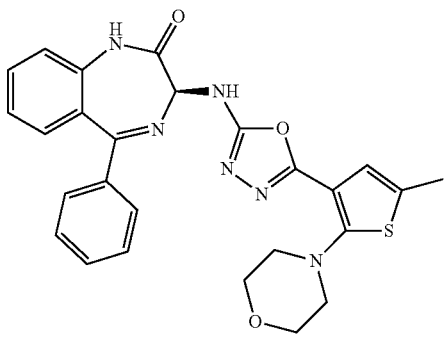 [SMILES: Cc1cc(-c2nnc(N[C@H]3N=C(c4ccccc4)c4ccccc4NC3=O)o2)c(N2CCOCC2)s1]

Example 330 Step a

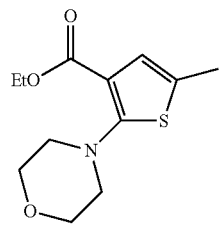

To a stirred solution of the ethyl 2-amino-5-methylthiophene-3-carboxylate (2.0 g, 10.8 mmol) in DMA (20 mL) was added 1-bromo-2-(2-bromoethoxy) ethane (5.42 g, 27.5 mmol), Cs$_2$CO$_3$ (11.4 g, 35 mmol) at rt. The mixture was refluxed overnight at 80° C. The mixture was cooled to rt, and then poured into water and extracted with EA (3*100 ml). The organic layer was dried over Na$_2$SO$_4$. The residue was purified by silica gel chromatography (PE/EA=4/1) to give the ethyl 5-methyl-2-morpholinothiophene-3-carboxylate as a white solid (700 mg, 28%). ESI-MS m/z: 256.2 [M+H]$^+$.

Example 330 Step b

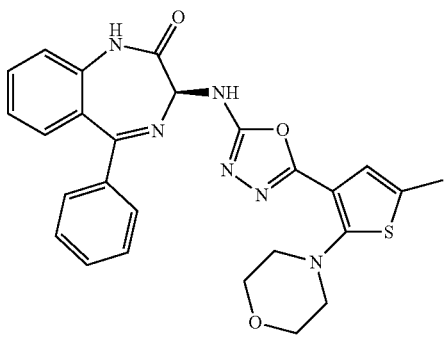 [SMILES: Cc1cc(-c2nnc(N[C@H]3N=C(c4ccccc4)c4ccccc4NC3=O)o2)c(N2CCOCC2)s1]

Example 330 was prepared using a procedure similar to that used to prepare Example 152 where ethyl 5-methyl-2-morpholinothiophene-3-carboxylate was used in place of ethyl 2-morpholino-4-(trifluoromethyl)benzoate. ESI-MS m/z: 501.0 [M+H]$^+$. $^1$H NMR (300 MHz, DMSO-d$_6$) δ2.38 (3 H, d), 2.97 (4H, dd), 3.32 (4H, m), 5.12 (1H, d), 6.90 (1H, d), 7.44 (9H, m), 8.96 (1H, d), 10.96 (1H, s).

Example 331

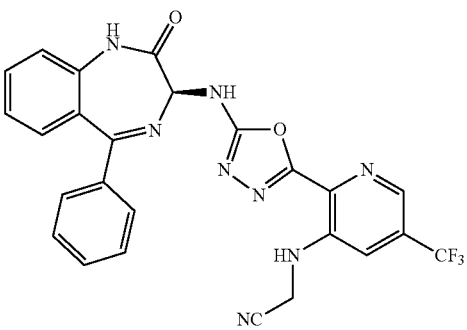 [SMILES: N#CCNc1cc(C(F)(F)F)cnc1-c1nnc(N[C@H]2N=C(c3ccccc3)c3ccccc3NC2=O)o1]

Example 331 Step a

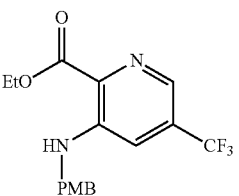

A solution of the compound ethyl 3-chloro-5-(trifluoromethyl)picolinate (3.8 g, 15 mmol) and PMBNH$_2$ (4.94 g, 36 mol) in DMSO (50 mL) was stirred for 18 hours at 110° C. It was purified by reverse phase C18 column chromatography (MeCN/H$_2$O) to give desired compound as a light yellow solid (1.4 g, 27%).

Example 331 Step b

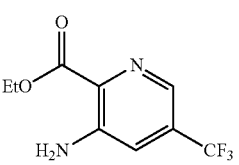

A solution of the compound from step a (1.06 g, 3 mmol) and TFA (5 mL) in DCM (20 mL) was stirred for 1 hour at rt. The crude product was purified by reverse phase C18 column chromatography (MeCN/H$_2$O) to give desired compound as a light yellow solid (585 mg, 83%). ESI-MS m/z: 235.2 [M+H]$^+$.

Example 331 Step c

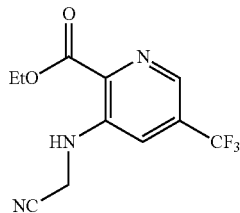 [SMILES: CCOC(=O)c1ncc(C(F)(F)F)cc1NCC#N]

A solution of the compound from step b (421 mg, 1.8 mmol), TMSCN (1.78 g, 18 mmol) and (CH₂O)ₙ (540 mg, 18 mmol) in MeCN (15 mL) was stirred for 18 hours at 90° C. The crude product was purified by reverse phase C18 column chromatography (MeCN/H₂O) to ethyl 3-((cyanomethyl)amino)-5-(trifluoromethyl)picolinate as a brown oil. (328 mg, 67%). ESI-MS m/z: 274.2 [M+H]⁺.

Example 331 d

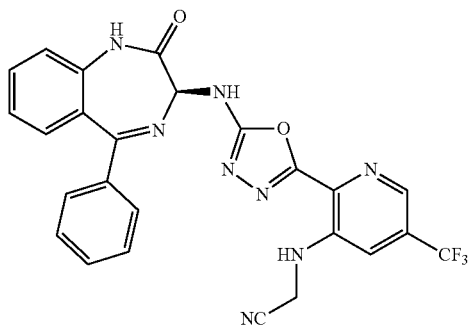 [SMILES: N#CCNc1cc(C(F)(F)F)cnc1-c1nnc(N[C@H]2N=C(c3ccccc3)c3ccccc3NC2=O)o1]

Example 331 was prepared using a procedure similar to that used to prepare Example 152 where ethyl 3-((cyanomethyl)amino)-5-(trifluoromethyl)picolinate was used in place of ethyl 2-morpholino-4-(trifluoromethyl)benzoate. ESI-MS m/z: 519.4 [M+H]⁺. H NMR (300 MHz, DMSO-d6) δ 4.76 (d, J=6.4 Hz, 2H), 5.23 (s, 1H), 7.19-7.61 (m, 8H), 7.63-7.83 (m, 2H), 8.03 (m, 1H), 8.46 (m, 1H), 9.56 (s, 1H), 10.96 (s, 1H).

Example 332

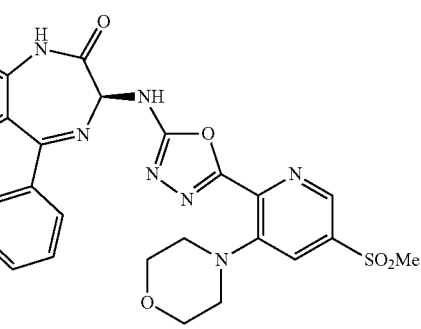

Example 332 Step a

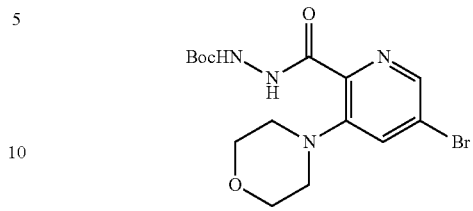

A solution of tert-butyl 2-(5-bromo-3-morpholinopicolinoyl)hydrazine-1-carboxylate, prepared in Example 311 step b, (2.0 g, 6.0 mmol) was dissolved in DMSO (20 mL), then morpholine (1.04 g, 12.0 mmol) and K₂CO₃ (2.48 g, 18.0 mmol) was added. The mixture was stirred at rt overnight. It was concentrated, diluted with H₂O, and extracted with EA (×3) and washed with brine (×2). The organic layers was combined and concentrated, then purified by reverse phase C18 column chromatography (MeCN/H₂O) to give desired compound as a light gray solid (1.96 g, 82%). ESI-MS m/z: 401.1 [M+H]⁺.

Example 332 Step b

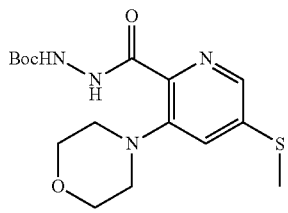

A solution of the compound from step a (700 mg, 1.8 mmol) was dissolved in 1-methylpyrrolidin-2-one (6 mL), then NaSCH₃ (245 mg, 3.5 mmol) and K₂CO₃ (725 mg, 5.3 mmol) was added. The mixture was stirred at r.t. for overnight. Water (10 mL) was added and purified by reverse phase C18 column chromatography (MeCN/H₂O) to give the desired product as a brown solid (515 mg, 80%). ESI-MS m/z: 369.1 [M+H]⁺.

Example 332 Step c

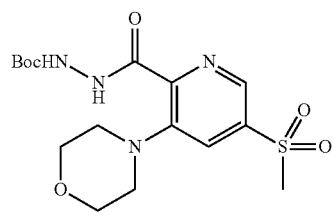 [SMILES: CC(C)(C)OC(=O)NNC(=O)c1ncc(S(C)(=O)=O)cc1N1CCOCC1]

A solution of the compound from step b (495 mg, 1.4 mmol) and Oxone (1.22 g, 2.0 mmol) in MeOH (3 mL), acetone (3 mL) and H₂O (3 mL) was stirred for three hours at rt. It was concentrated, and extracted with EA (×3) and washed with brine (×2). The organic layers were combined and concentrated to give 254 mg (47%) of tert-butyl 2-(5-

(methylsulfonyl)-3-morpholinopicolinoyl)hydrazine-1-carboxylate as a yellow product. ESI-MS m/z: 401.2 [M+H]$^+$.

Example 332

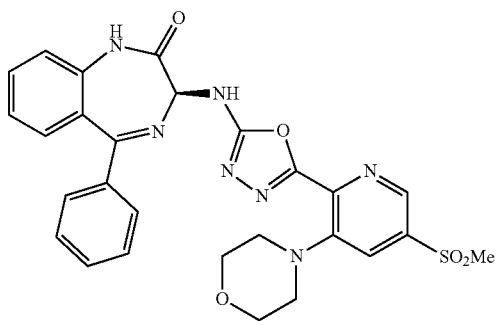 [SMILES: CS(=O)(=O)c1cnc(-c2nnc(N[C@H]3N=C(c4ccccc4)c4ccccc4NC3=O)o2)c(N2CCOCC2)c1]

Example 332 was prepared using a procedure similar to that used to prepare Example 151 where tert-butyl 2-(5-(methyl sulfonyl)-3-morpholinopicolinoyl)hydrazine-1-carboxylate was used in place of 6-fluoro-2-morpholinonicotinohydrazide. ESI-MS m/z: 560.5 [M+H]$^+$. $^1$H NMR (400 MHz, DMSO-d$_6$) δ 3.09 (s, 4H), 3.39 (s, 3H), 3.75 (s, 4H), 5.22 (d, 1H), 7.29 (d, 1H), 7.33-7.40 (m, 2H), 7.41-7.60 (m, 5H), 7.63-7.75 (m, 1H), 7.98 (d, 1H), 8.76 (d, 1H), 9.44 (d, 1H), 10.99 (s, 1H).

Example 333

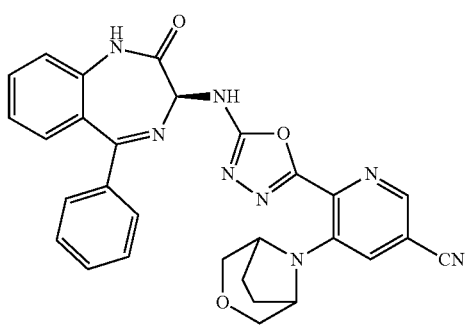 [SMILES: N#Cc1cnc(-c2nnc(N[C@H]3N=C(c4ccccc4)c4ccccc4NC3=O)o2)c(N2C3CCC2COC3)c1]

Example 333 was prepared using a procedure similar to that used to prepare Example 151 where 3-(3-oxa-8-azabicyclo[3.2.1]octan-8-yl)-5-cyanopicolinic acid, which was prepared similarly to 5-cyano-3-morpholinopicolinic acid in Example 140, was used in place of 6-fluoro-2-morpholinonicotinic acid. ESI-MS m/z: 533.5 [M+H]$^+$. $^1$H NMR (400 MHz, DMSO-d$_6$) δ 1.86 (s, 4H), 3.49 (m, 2H), 3.80 (m, 2H), 3.84-3.97 (d, 2H), 5.21 (d, 1H), 7.23-7.40 (m, 3H), 7.40-7.60 (m, 5H), 7.68 (m, 1H), 8.04 (d, 1H), 8.58 (d, 1H), 9.39 (d, 1H), 11.00 (s, 1H).

Example 334

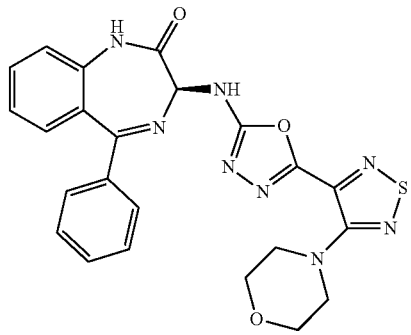 [SMILES: O=C1Nc2ccccc2C(c2ccccc2)=N[C@@H]1Nc1nnc(-c2nsnc2N2CCOCC2)o1]

Example 334 was prepared using a procedure similar to that used to prepare Example 272 where methyl 4-bromo-1,2,5-thiadiazole-3-carboxylate was used in place of methyl 2-methyl-5-bromothiazole-4-carboxylate. ESI-MS m/z: 560.5 [M+H]$^+$.

Example 335

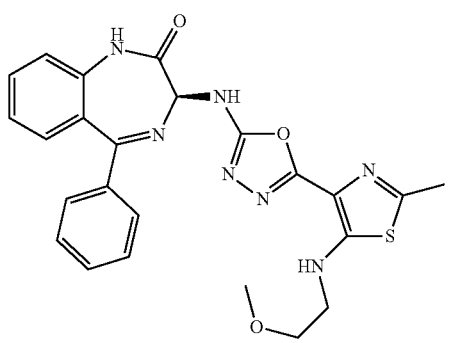 [SMILES: COCCNc1sc(C)nc1-c1nnc(N[C@H]2N=C(c3ccccc3)c3ccccc3NC2=O)o1]

Example 335 Step a

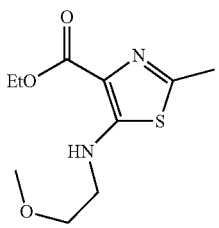

A solution of ethyl 5-amino-2-methylthiazole-4-carboxylate (1.7 g, 9.0 mmol), 1-bromo-2-methoxyethane (1.2 g, 9.0 mmol) and Cs$_2$CO$_3$ (4.4 g, 13.5 mmol) in DMF (10 mL) was heated to 50° C. for 7 hours and then cooled to r.t. The crude product was purified by reverse phase C18 column chromatography (MeCN/H$_2$O) to give ethyl 5-((2-methoxyethyl)amino)-2-methylthiazole-4-carboxylate as an orange oil (850 mg, 3.48 mmol, 39%). ESI-MS m/z: 245.2 [M+H]$^+$.

Example 335 Step b

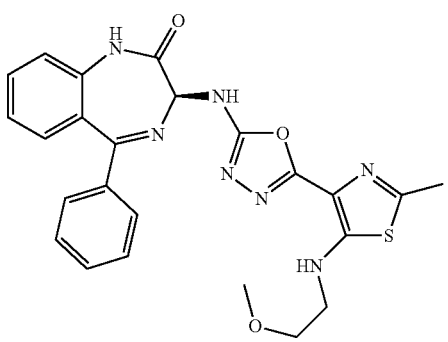 [SMILES: COCCNc1sc(C)nc1-c1nnc(N[C@H]2N=C(c3ccccc3)c3ccccc3NC2=O)o1]

Example 335 was prepared using a procedure similar to that used to prepare Example 152 where ethyl 5-((2-methoxyethyl)amino)-2-methylthiazole-4-carboxylate was used in place of ethyl 2-morpholino-4-(trifluoromethyl)benzoate. ESI-MS m/z: 490.3 [M+H]$^+$. $^1$H NMR (300 MHz, DMSO-d$_6$) δ 2.52 (s, 3H), 3.27 (s, 3H), 3.38 (d, J=5.4 Hz, 2H), 3.52 (m, 2H), 5.11 (d, J=8.7 Hz, 1H), 6.84 (m, 1H), 7.22-7.37 (m, 3H), 7.40-7.58 (m, 5H), 7.67 (m, 1H), 8.89 (d, J=8.7 Hz, 1H), 10.95 (s, 1H).

Example 336

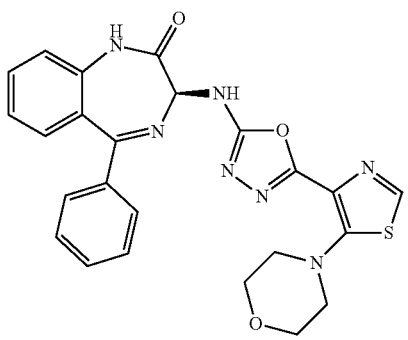 [SMILES: O=C1Nc2ccccc2C(c2ccccc2)=N[C@@H]1Nc1nnc(-c2ncsc2N2CCOCC2)o1]

Example 336 Step a

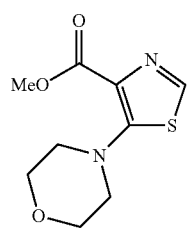

In an oven-dried vial, methyl 5-bromothiazole-4-carboxylate (200 mg, 0.90 mmol) was dissolved in MeCN (2.4 mL). Morpholine (87 uL, 0.99 mmol) and DBU (0.2 mL, 1.35 mmol) were added to the vial sequentially. The vial was sealed and heated to 80° C. for 5 hours. Cool the vial to room temperature and quench with water. Extract aqueous layer (3×) with EtOAc. The organic layer was dried with Na$_2$SO$_4$, filtered and concentrated. The crude product was purified on silica gel (hexane/EtOAc: 0% to 80%), affording methyl 5-morpholinothiazole-4-carboxylate (120 mg, 58%) as a white solid. ESI MS m/z=229.1 [M+H]$^+$.

Example 336 Step b

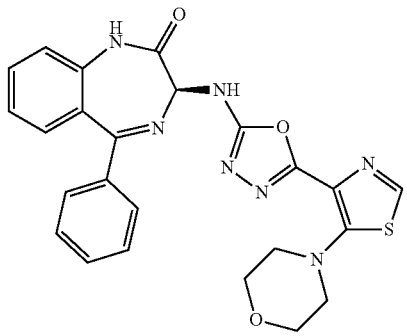 [SMILES: O=C1Nc2ccccc2C(c2ccccc2)=N[C@@H]1Nc1nnc(-c2ncsc2N2CCOCC2)o1]

Example 336 was prepared using a procedure similar to that used to prepare Example 152 where methyl 5-morpholinothiazole-4-carboxylate was used in place of ethyl 2-morpholino-4-(trifluoromethyl)benzoate. ESI MS m/z=488.1537 [M+H]$^+$.

Example 337

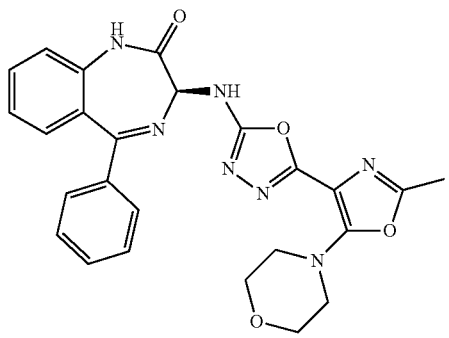 [SMILES: Cc1nc(-c2nnc(N[C@H]3N=C(c4ccccc4)c4ccccc4NC3=O)o2)c(N2CCOCC2)o1]

Example 337 was prepared using a procedure similar to that used to prepare Example 272 where ethyl 5-bromooxazole-4-carboxylate was used in place of methyl 2-methyl-5-bromothiazole-4-carboxylate. ESI MS m/z=486.2 [M+H]$^+$.

Example 338

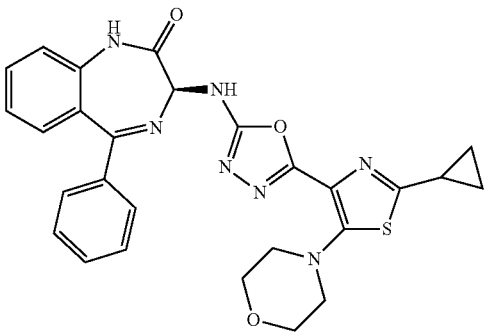 [SMILES: O=C1Nc2ccccc2C(c2ccccc2)=N[C@@H]1Nc1nnc(-c2nc(C3CC3)sc2N2CCOCC2)o1]

Example 338 Step a

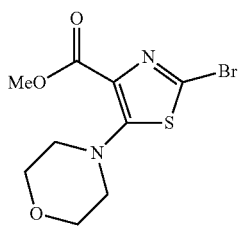

To an oven-dried vial, methyl 5-morpholinothiazole-4-carboxylate, prepared in Example 336, (247 mg, 1.08 mmol) was dissolved in MeCN (5.4 mL). NBS (208 mg, 1.17 mmol) was added to the vial in one portion at room temperature. The reaction was allowed to stir at room temperature until the starting material was consumed. The reaction mixture was concentrated and purified on silica gel (hexane/EtOAc: 0% to 80%), affording methyl 2-bromo-5-morpholinothiazole-4-carboxylate (256 mg, 77%) as a white solid. ESI MS m/z=309.0 [M+H]$^+$.

Example 338 Step b

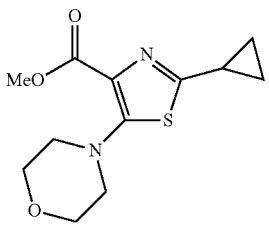 [SMILES: COC(=O)c1nc(C2CC2)sc1N1CCOCC1]

To a vial, add methyl 2-bromo-5-morpholinothiazole-4-carboxylate (212 mg, 0.69 mmol), cyclopropylboronic acid (65 mg, 0.76 mmol), K$_2$CO$_3$ (286 mg, 2.07 mmol) and Pd(PPh$_3$)$_4$ (40 mg, 0.04 mmol). The vial was sealed and evacuated with nitrogen. Toluene (2.9 mL) and water (0.6 mL) were added to the vial with a syringe. The reaction mixture was heated to 80° C. and stirred at that temperature for 20 hours. The vial was cooled to room temperature and quenched with water. The aqueous layer was extracted (3×) with EtOAc. The organic layer was dried with NaSO$_4$, filtered and concentrated. The crude product was added to a silica gel column and was eluted with ethyl acetate/hexane 0% to 100% to give methyl 2-cyclopropyl-5-morpholinothiazole-4-carboxylate (76 mg, 41%) as a solid.

Example 338 Step c

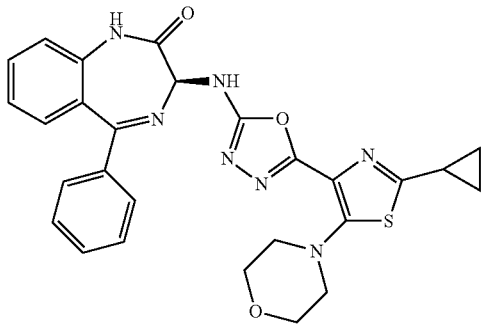 [SMILES: O=C1Nc2ccccc2C(c2ccccc2)=N[C@@H]1Nc1nnc(-c2nc(C3CC3)sc2N2CCOCC2)o1]

Example 338 was prepared using a procedure similar to that used to prepare Example 152 where methyl 2-cyclopropyl-5-morpholinothiazole-4-carboxylate was used in place of ethyl 2-morpholino-4-(trifluoromethyl)benzoate. ESI MS m/z=528.4 [M+H]$^+$. $^1$H NMR (300 MHz, DMSO-d$_6$) δ 0.72-1.00 (m, 2H), 1.08 (m, 2H), 2.33 (m, 1H), 2.82-3.16 (m, 4H), 3.54-3.90 (m, 4H), 5.14 (d, J=8.3 Hz, 1H), 7.22-7.41 (m, 3H), 7.41-7.60 (m, 5H), 7.67 (m, 1H), 9.07 (d, J=8.4 Hz, 1H), 10.97 (s, 1H).

Example 339

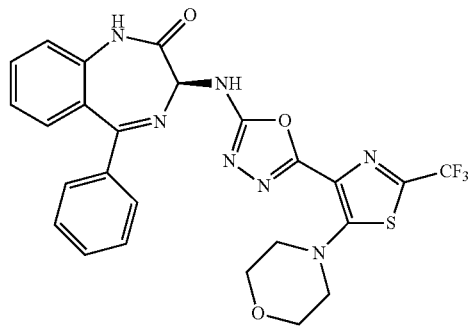 [SMILES: O=C1Nc2ccccc2C(c2ccccc2)=N[C@@H]1Nc1nnc(-c2nc(C(F)(F)F)sc2N2CCOCC2)o1]

Example 339 was prepared using a procedure similar to that used to prepare Example 272 where ethyl 5-bromo-2-(trifluoromethyl)thiazole-4-carboxylate was used in place of methyl 2-methyl-5-bromothiazole-4-carboxylate. ESI-MS m/z: 556.1 [M+H]$^+$.

Example 340

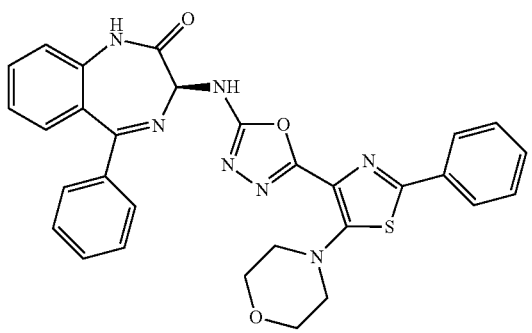 [SMILES: O=C1Nc2ccccc2C(c2ccccc2)=N[C@@H]1Nc1nnc(-c2nc(-c3ccccc3)sc2N2CCOCC2)o1]

Example 340 was prepared using a procedure similar to that used to prepare Example 338 where phenylboronic acid was used in place of cyclopropylboronic acid. ESI MS m/z=564.1823 [M+H]$^+$.

Example 341

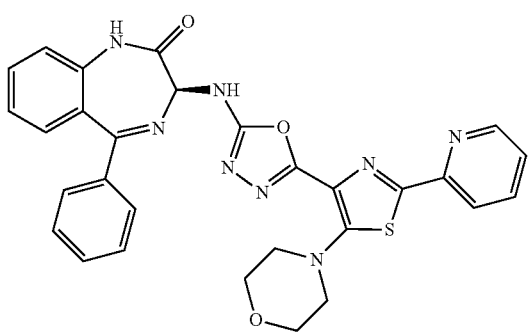

Example 341 Step a

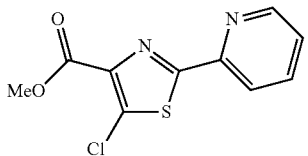 [SMILES: COC(=O)c1nc(-c2ccccn2)sc1Cl]

To an oven-dried vial, methyl 2-bromo-5-chlorothiazole-4-carboxylate (200 mg, 0.78 mmol) and Pd(Ph₃P)₄ (90 mg, 0.08 mmol) were added. The vial was sealed and evacuated and refilled with nitrogen (3×). To the sealed vial, THF (3.9 mL) and pyridin-2-ylzinc(II) bromide (1.9 mL, 0.94 mmol) were added sequentially. The vial was heated to 65° C. overnight. The reaction mixture was allowed to cool and then diluted with water and EtOAc. The aqueous layer was extracted twice with EtOAc. The organic layer was dried with Na₂SO₄, filtered and concentrated. The crude product was added to a silica gel column and was eluted with ethyl acetate/hexane 0% to 100% to give methyl 5-chloro-2-(pyridin-2-yl)thiazole-4-carboxylate (106 mg, 53% yield) as a solid. ESI MS m/z=255.0 [M+H]⁺.

Example 341 Step b

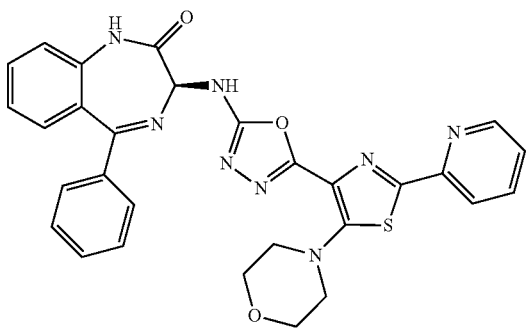

Example 341 was prepared using a procedure similar to that used to prepare Example 272 where methyl 5-chloro-2-(pyridin-2-yl)thiazole-4-carboxylate was used in place of methyl 2-methyl-5-bromothiazole-4-carboxylate. ESI MS m/z=565.3 [M+H]⁺.

Example 342

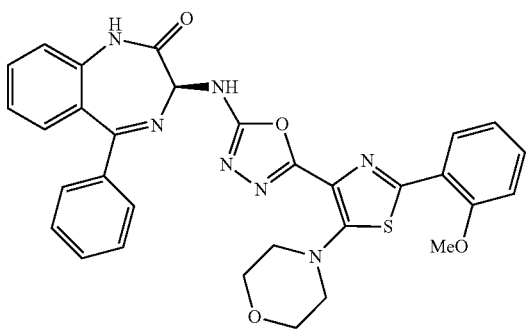 [SMILES: COc1ccccc1-c1nc(-c2nnc(N[C@H]3N=C(c4ccccc4)c4ccccc4NC3=O)o2)c(N2CCOCC2)s1]

Example 342 Step a

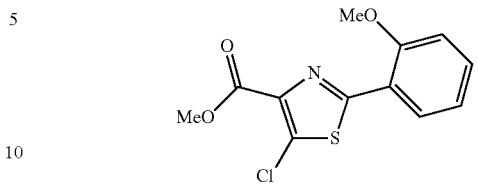

To a vial, add methyl 2-bromo-5-chlorothiazole-4-carboxylate (200 mg, 0.78 mmol), (2-methoxyphenyl)boronic acid (142 mg, 0.94 mmol), Pd(Ph₃P)₄ (90 mg, 0.08 mmol) and K₂CO₃ (323 mg, 2.34 mmol). The vial was sealed and evacuated with nitrogen (3×). Toluene (3.2 mL) and water (650 μL) were added to the sealed vial. The vial was heated to 80° C. and stirred overnight. The reaction mixture was diluted with water and EtOAc. The aqueous layer was extracted twice with EtOAc. The organic layer was dried with Na₂SO₄, filtered and concentrated. The crude product was added to a silica gel column and was eluted with ethyl acetate/hexane 0% to 50% to give methyl 5-chloro-2-(2-methoxyphenyl)thiazole-4-carboxylate (150 mg, 68% yield) as a white solid. ESI MS m/z=284.0 [M+H]⁺.

Example 342 Step b

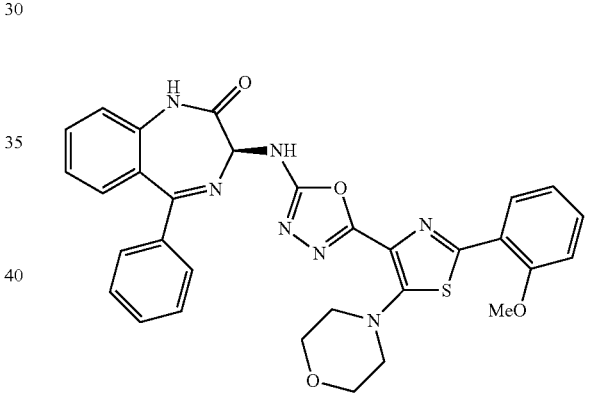

Example 342 was prepared using a procedure similar to that used to prepare Example 272 where methyl 5-chloro-2-(2-methoxyphenyl)thiazole-4-carboxylate was used in place of methyl 2-methyl-5-bromothiazole-4-carboxylate. ESI MS m/z=594.3 [M+H]⁺.

Example 343

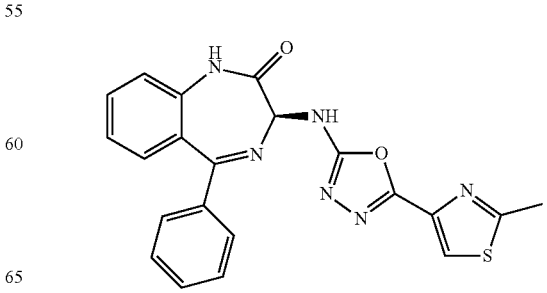

Example 343 was prepared using a procedure similar to that used to prepare Example 152 where ethyl 2-methylthiazole-4-carboxylate was used in place of ethyl 2-morpholino-4-(trifluoromethyl)benzoate. ESI MS m/z=417.1 [M+H]+.

Example 344

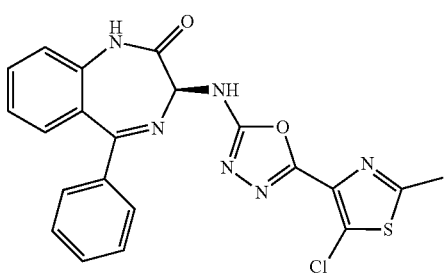 [SMILES: Cc1nc(-c2nnc(N[C@H]3N=C(c4ccccc4)c4ccccc4NC3=O)o2)c(Cl)s1]

Example 344 Step a

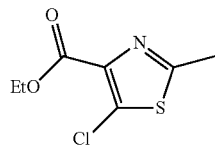

To an oven-dried vial, ethyl 2-methylthiazole-4-carboxylate (1.0 g, 5.84 mmol) was dissolved in DMF (29 mL) open to air to give a yellow solution. 1,3,5-trichloro-1,3,5-triazinane-2,4,6-trione (1.1 g, 4.67 mmol) was added to the solution and stirred overnight at room temperature. The reaction mixture was diluted with water and extracted with EtOAc. The organic layer was dried with NaSO4, filtered and concentrated. The crude product was added to a silica gel column and was eluted with ethyl acetate/hexane 0% to 20% to give ethyl 5-chloro-2-methylthiazole-4-carboxylate (257 mg, 21% yield) as an oil. ESI MS m/z=206.0 [M+H]+.

Example 344

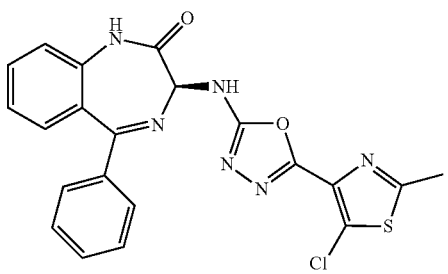 [SMILES: Cc1nc(-c2nnc(N[C@H]3N=C(c4ccccc4)c4ccccc4NC3=O)o2)c(Cl)s1]

Example 344 was prepared using a procedure similar to that used to prepare Example 152 where ethyl 5-chloro-2-methylthiazole-4-carboxylate was used in place of ethyl 2-morpholino-4-(trifluoromethyl)benzoate. ESI MS m/z=451.1 [M+H]+.

Example 345

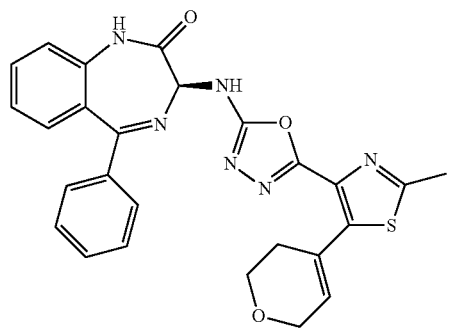 [SMILES: Cc1nc(-c2nnc(N[C@H]3N=C(c4ccccc4)c4ccccc4NC3=O)o2)c(C2=CCOCC2)s1]

Example 345 Step a

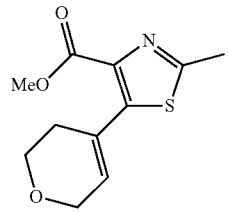

To an oven-dried vial, methyl 5-bromo-2-methylthiazole-4-carboxylate (600 mg, 2.54 mmol), 2-(3,6-dihydro-2H-pyran-4-yl)-4,4,5,5-tetramethyl-1,3,2-dioxaborolane (587 mg, 2.80 mmol), K3PO4.H2O (1.5 g, 6.61 mmol), and SPhos Pd G3 (66 mg, 0.08 mmol) were dissolved in DMF (4.4 ml) and water (436 µl) under nitrogen to give a yellow suspension. The resulting mixture was heated at 100° C. for 24 hours. The reaction mixture was cooled to room temperature and diluted with EtOAc. The aqueous layer was extracted with EtOAc (2×10 mL). The organic layer was dried with Na2SO4, filtered and concentrated. The crude product was added to a silica gel column and was eluted with ethyl acetate/hexane 0% to 40% to give methyl 5-(3,6-dihydro-2H-pyran-4-yl)-2-methylthiazole-4-carboxylate (170 mg, 28% yield) as a white solid.

Example 345 Step b

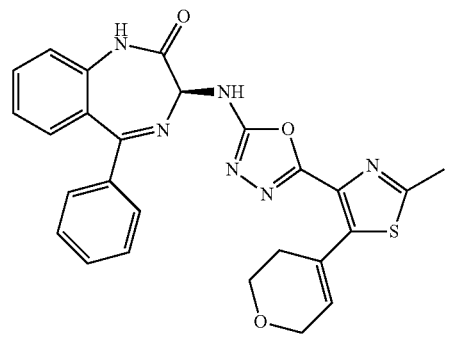 [SMILES: Cc1nc(-c2nnc(N[C@H]3N=C(c4ccccc4)c4ccccc4NC3=O)o2)c(C2=CCOCC2)s1]

Example 345 was prepared using a procedure similar to that used to prepare Example 152 where methyl 5-(3,6- dihydro-2H-pyran-4-yl)-2-methylthiazole-4-carboxylate was used in place of ethyl 2-morpholino-4-(trifluoromethyl)benzoate. ESI MS m/z=499.2 [M+H]⁺.

Example 346

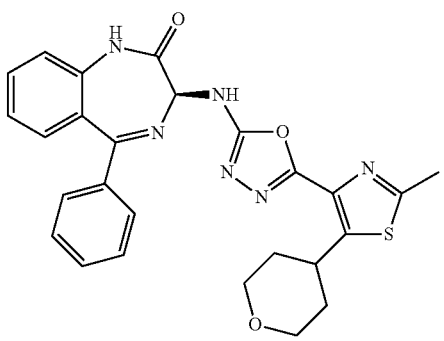 [SMILES: Cc1nc(-c2nnc(N[C@H]3N=C(c4ccccc4)c4ccccc4NC3=O)o2)c(C2CCOCC2)s1]

To a round-bottomed flask, (S)-3-((5-(5-(3,6-dihydro-2H-pyran-4-yl)-2-methylthiazol-4-yl)-1,3,4-oxadiazol-2-yl)amino)-5-phenyl-1,3-dihydro-2H-benzo[e][1,4]diazepin-2-one (Example 345) (23 mg, 0.05 mmol) was dissolved in MeOH (2 mL) to give a clear solution. Palladium on carbon (5 mg, 0.05 mmol) was added to the reaction mixture in one portion. The flask was sealed and evacuated with a hydrogen balloon. The reaction was stirred under hydrogen overnight. The reaction mixture was filtered through celite, washed with EtOAc, and concentrated, affording (S)-3-((5-(2-methyl-5-(tetrahydro-2H-pyran-4-yl)thiazol-4-yl)-1,3,4-oxadiazol-2-yl)amino)-5-phenyl-1,3-dihydro-2H-benzo[e][1,4]diazepin-2-one (17 mg, 74% yield) as a white solid. ESI MS m/z=501.2 [M+H]⁺.

Example 347

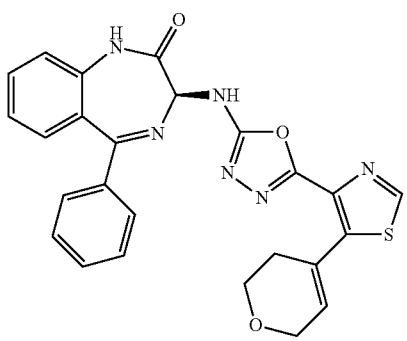 [SMILES: O=C1Nc2ccccc2C(c2ccccc2)=N[C@@H]1Nc1nnc(-c2ncsc2C2=CCOCC2)o1]

Example 347 was prepared using a procedure similar to that used to prepare Example 345 where methyl 5-bromothiazole-4-carboxylate was used in place of methyl 5-bromo-2-methylthiazole-4-carboxylate. ESI MS m/z=485.1 [M+H]⁺.

Example 348

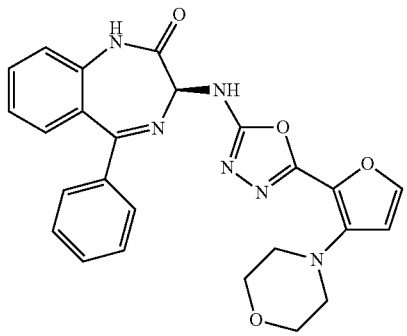 [SMILES: O=C1Nc2ccccc2C(c2ccccc2)=N[C@@H]1Nc1nnc(-c2occc2N2CCOCC2)o1]

Example 348 Step a

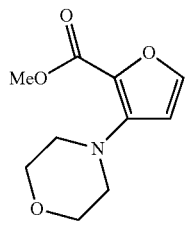

In an oven-dried round-bottomed flask, potassium iodide (706 mg, 4.25 mmol), potassium carbonate (588 mg, 4.25 mmol), and methyl 3-aminofuran-2-carboxylate (300 mg, 2.13 mmol) were dissolved in DMA (6.0 mL) under nitrogen to give a clear suspension. The flask was sealed and 1-bromo-2-(2-bromoethoxy)ethane (542 mg, 2.34 mmol) was added to the reaction mixture via syringe. The flask was heated to 120° C. and stirred overnight. The flask was cooled to room temperature and diluted with water. The aqueous layer was extracted with DCM. The organic layer was dried with Na₂SO₄, filtered and concentrated. The crude product was added to a silica gel column and was eluted with ethyl acetate/hexane 0% to 100% to give methyl 3-morpholinofuran-2-carboxylate (257 mg, 57% yield) as a white solid. ESI MS m/z=212.1 [M+H]⁺.

Example 348 Step b

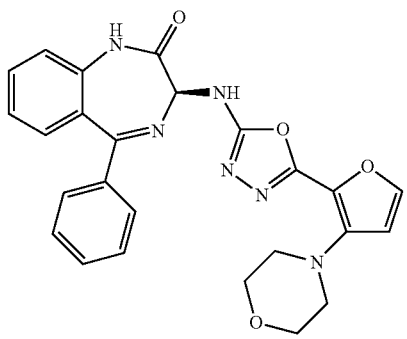 [SMILES: O=C1Nc2ccccc2C(c2ccccc2)=N[C@@H]1Nc1nnc(-c2occc2N2CCOCC2)o1]

Example 348 was prepared using a procedure similar to that used to prepare Example 152 where methyl 3-morpholinofuran-2-carboxylate was used in place of ethyl 2-morpholino-4-(trifluoromethyl)benzoate. ESI MS m/z=471.2 [M+H]+.

Example 349

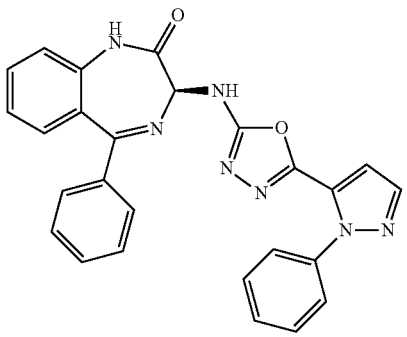 [SMILES: O=C1Nc2ccccc2C(c2ccccc2)=N[C@@H]1Nc1nnc(-c2ccnn2-c2ccccc2)o1]

Example 349 Step a

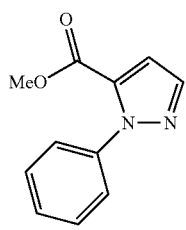 [SMILES: COC(=O)c1ccnn1-c1ccccc1]

In a round-bottomed flask fit with condenser, 1-phenyl-1H-pyrazole-5-carboxylic acid (1 g, 5.31 mmol) was dissolved in methanol (13 mL). The flask was cooled to 0° C. and SOCl₂ (1.2 mL, 16.47 mmol) was added dropwise. The flask was warmed to 60° C. and stirred overnight. The flask was cooled to room temperature and quenched with water. The aqueous layer was basified with saturated NaHCO₃ and extracted with EtOAc. The organic layer was dried with Na₂SO₄, filtered and concentrated. Methyl 1-phenyl-1H-pyrazole-5-carboxylate (0.93 g, 87% yield) was isolated as a white solid. ESI MS m/z=203.1 [M+H]+.

Example 349 Step b

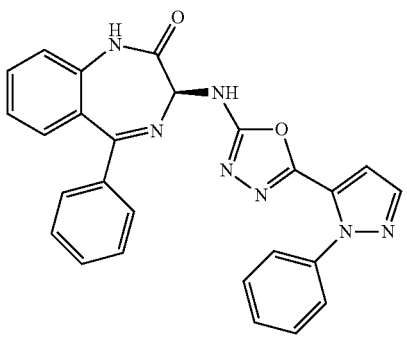 [SMILES: O=C1Nc2ccccc2C(c2ccccc2)=N[C@@H]1Nc1nnc(-c2ccnn2-c2ccccc2)o1]

Example 349 was prepared using a procedure similar to that used to prepare Example 152 where methyl 1-phenyl-1H-pyrazole-5-carboxylate was used in place of ethyl 2-morpholino-4-(trifluoromethyl)benzoate. ESI MS m/z=462.2 [M+H]+.

Example 350

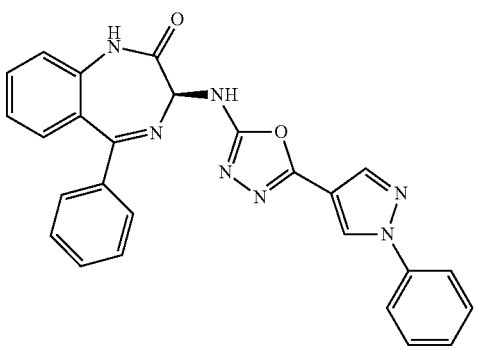 [SMILES: O=C1Nc2ccccc2C(c2ccccc2)=N[C@@H]1Nc1nnc(-c2cnn(-c3ccccc3)c2)o1]

Example 350 Step a

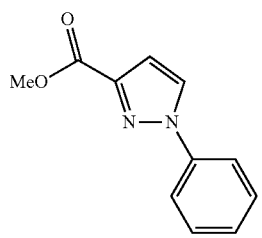 [SMILES: COC(=O)c1ccn(-c2ccccc2)n1]

In a round-bottomed flask fit with condenser, 1-phenyl-1H-pyrazole-3-carboxylic acid (0.25 g, 1.33 mmol) was dissolved in methanol (6 mL). The flask was cooled to 0° C. and trimethylsilyldiazomethane (2.7 mL, 5.32 mmol, 2M) was added dropwise to the flask. The flask was warmed to room temperature and stirred for two hours. The reaction mixture was concentrated and taken up in EtOAc and water. The aqueous layer was extracted with EtOAc (3×). The organic layer was dried with NaSO₄, filtered and concentrated. The crude product was added to a silica gel column and was eluted with ethyl acetate/hexane 0% to 50% to afford methyl 1-phenyl-1H-pyrazole-3-carboxylate (136 mg, 51% yield) as a white solid. ESI MS m/z=203.1 [M+H]+.

Example 350 Step b

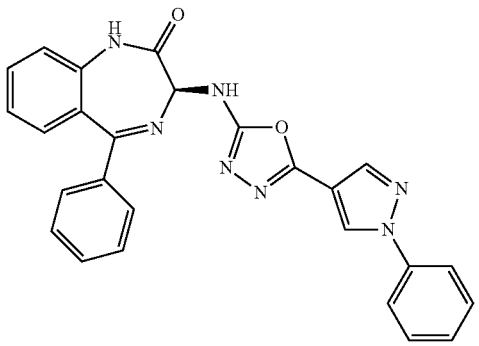 [SMILES: O=C1Nc2ccccc2C(c2ccccc2)=N[C@@H]1Nc1nnc(-c2cnn(-c3ccccc3)c2)o1]

Example 350 was prepared using a procedure similar to that used to prepare Example 152 where methyl 1-phenyl-1H-pyrazole-3-carboxylate was used in place of ethyl 2-morpholino-4-(trifluoromethyl)benzoate. ESI MS m/z=462.2 [M+H]+.

Example 351

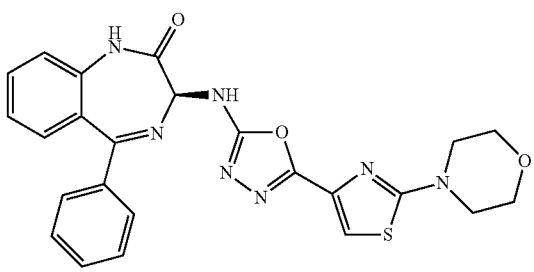 [SMILES: O=C1Nc2ccccc2C(c2ccccc2)=N[C@@H]1Nc1nnc(-c2csc(N3CCOCC3)n2)o1]

Example 351 was prepared using a procedure similar to that used to prepare Example 152 where ethyl 2-morpholinothiazole-4-carboxylate was used in place of ethyl 2-morpholino-4-(trifluoromethyl)benzoate. ESI MS m/z=488.2 [M+H]+.

Example 352

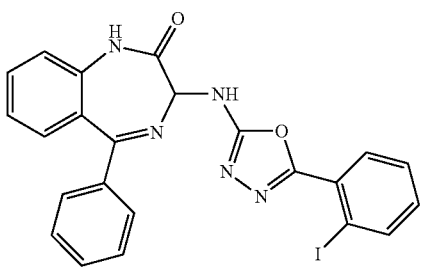 [SMILES: O=C1Nc2ccccc2C(c2ccccc2)=NC1Nc1nnc(-c2ccccc2I)o1]

Example 352 was prepared using a procedure similar to that used to prepare Example 20 where 2-iodobenzoic acid was used in place of 5-chlorofuran-2-carboxylic acid. ESI MS m/z=522.0 [M+H]+.

Example 353

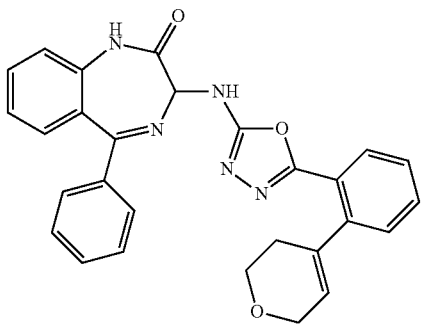 [SMILES: O=C1Nc2ccccc2C(c2ccccc2)=NC1Nc1nnc(-c2ccccc2C2CCOCC2)o1]

Example 353 was prepared using a procedure similar to that used to prepare Example 345 where 3-((5-(2-iodophenyl)-1,3,4-oxadiazol-2-yl)amino)-5-phenyl-1,3-dihydro-2H-benzo[e][1,4]diazepin-2-one was used in place of methyl 5-bromo-2-methylthiazole-4-carboxylate. ESI MS m/z=478.2 [M+H]+.

Example 354

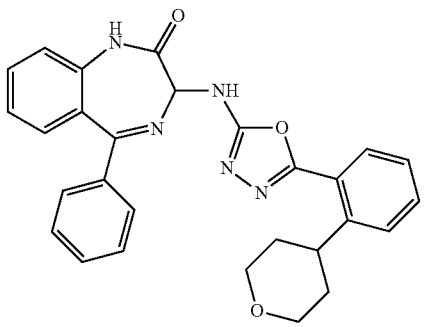

Example 354 was prepared using a procedure similar to that used to prepare Example 346 where 3-((5-(2-(3,6-dihydro-2H-pyran-4-yl)phenyl)-1,3,4-oxadiazol-2-yl)amino)-5-phenyl-1,3-dihydro-2H-benzo[e][1,4]diazepin-2-one was used in place of (S)-3-((5-(5-(3,6-dihydro-2H-pyran-4-yl)-2-methylthiazol-4-yl)-1,3,4-oxadiazol-2-yl)amino)-5-phenyl-1,3-dihydro-2H-benzo[e][1,4]diazepin-2-one. ESI MS m/z=480.3 [M+H]+.

Example 355

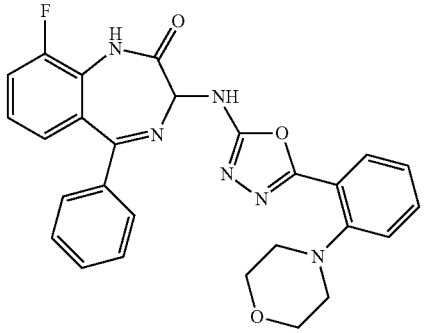 [SMILES: O=C1Nc2c(F)cccc2C(c2ccccc2)=NC1Nc1nnc(-c2ccccc2N2CCOCC2)o1]

Example 355 Step a

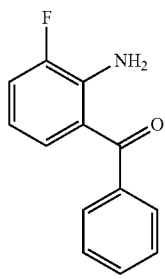 [SMILES: Nc1c(F)cccc1C(=O)c1ccccc1]

A solution of 2-amino-3-fluorobenzonitrile (25 g, 0.18 mol) in THF (400 mL) was added dropwise PhMgBr (120 mL, 3 M) at 0° C. under $N_2$ over 30 min. The reaction mixture was stirred for 2 hrs at rt. Then $HCl/H_2O$ (400 mL, 6 M) was added and the reaction mixture was stirred O/N at room temperature. LCMS showed that the reaction was complete. The organic layer was removed, the residue phase was extracted with EA (×3). The combined organic layers was washed with brine, dried over $Na_2SO_4$ and purified by silica gel chromatography (PE/EA=1/0-10/1) to give the desired compound as a yellow solid (31.5 g, 78%). ESI-MS m/z: 216.0 [M+H]+.

Example 355 Step b

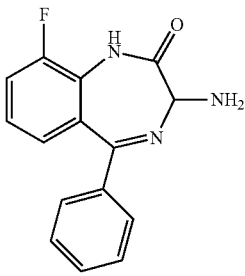 [SMILES: NC1N=C(c2ccccc2)c2cccc(F)c2NC1=O]

3-amino-9-fluoro-5-phenyl-1,3-dihydro-2H-benzo[e][1,4]diazepin-2-one was prepared using a procedure similar to that used to prepare (Z)-3-amino-5-phenyl-1H-benzo[e][1,4]diazepin-2(3H)-one in Example 1 where (2-amino-3-fluorophenyl)(phenyl)methanone was used in place of 2-benzoylaniline. ESI-MS m/z: 270.1 [M+H]+.

Example 355 Step c

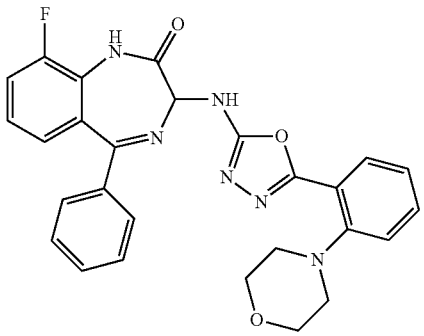 [SMILES: O=C1Nc2c(F)cccc2C(c2ccccc2)=NC1Nc1nnc(-c2ccccc2N2CCOCC2)o1]

Example 355 was prepared using a procedure similar to that used to prepare Example 21 where 3-amino-9-fluoro-5-phenyl-1,3-dihydro-2H-benzo[e][1,4]diazepin-2-one and 2-morpholinobenzohydrazide were used in place of (Z)-3-amino-5-phenyl-1H-benzo[e][1,4]diazepin-2(3H)-one and tetrahydro-2H-pyran-4-carbohydrazide, respectively. ESI-MS m/z: 499.4 [M+H]+. 1H NMR (300 MHz, DMSO-d6) δ 2.83-2.93 (m, 4H), 3.69 (dd, J=5.4, 3.4 Hz, 4H), 5.15-5.24 (m, 1H), 7.11-7.18 (m, 3H), 7.25-7.32 (m, 1H), 7.40-7.72 (m, 8H), 9.02 (d, J=7.9 Hz, 1H), 10.92 (t, J=13.9 Hz, 1H).

Example 355 (300 mg, 0.60 mmol) was purified by Chiral Separation to give the product 355a as a light yellow solid (102 mg, 33%) and 355b as an a light yellow solid (103 mg, 35%).

Example 355a

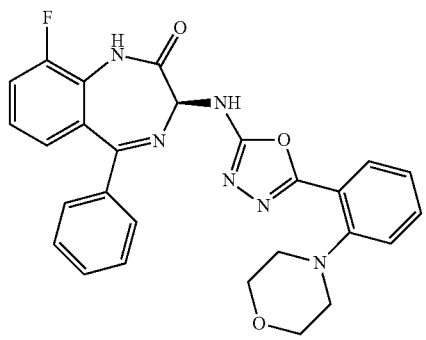

ESI-MS m/z: 499.0 [M+H]+. 1H NMR (300 MHz, DMSO-d6) δ 2.88 (dd, J=5.6, 3.5 Hz, 4H), 3.70 (dd, J=5.6, 3.5 Hz, 4H), 5.25 (d, J=8.7 Hz, 1H), 7.07-7.24 (m, 3H), 7.30-7.37 (m, 1H), 7.41-7.72 (m, 8H), 9.13 (d, J=8.7 Hz, 1H), 10.96 (s, 1H).

Example 355b

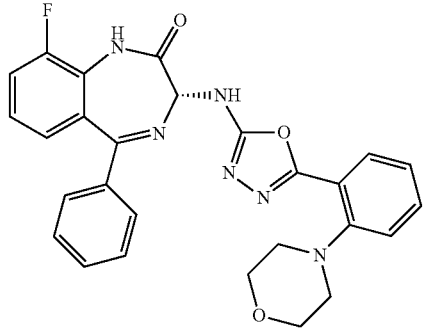 [SMILES: O=C1Nc2c(F)cccc2C(c2ccccc2)=N[C@H]1Nc1nnc(-c2ccccc2N2CCOCC2)o1]

ESI-MS m/z: 499.1 [M+H]+. 1H NMR (300 MHz, DMSO-d6) δ 2.83-2.93 (m, 4H), 3.65-3.75 (m, 4H), 5.25 (d, J=8.6 Hz, 1H), 7.07-7.24 (m, 3H), 7.30-7.37 (m, 1H), 7.41-7.72 (m, 8H), 9.13 (d, J=8.7 Hz, 1H), 10.96 (s, 1H).

Example 356

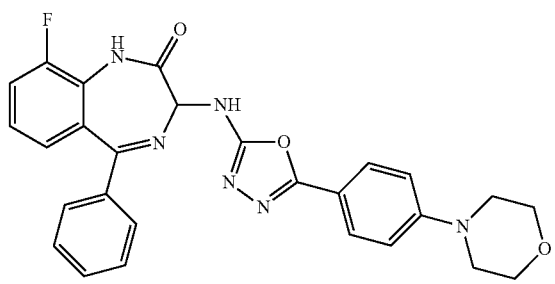 [SMILES: O=C1Nc2c(F)cccc2C(c2ccccc2)=NC1Nc1nnc(-c2ccc(N3CCOCC3)cc2)o1]

Example 355 was prepared using a procedure similar to that used to prepare Example 355 where 4-morpholinobenzohydrazide was used in place of 2-morpholinobenzohydrazide. ESI-MS m/z: 499.4 [M+H]⁺. ¹H NMR (300 MHz, DMSO-d₆) δ 3.23 (t, J=4.9 Hz, 4H), 3.74 (dd, J=6.1, 3.6 Hz, 4H), 5.21 (d, J=8.5 Hz, 1H), 7.01-7.13 (m, 2H), 7.18 (dd, J=8.0, 1.3 Hz, 1H), 7.32 (td, J=8.0, 4.9 Hz, 1H), 7.40-7.72 (m, 8H), 8.96 (d, J=8.6 Hz, 1H), 10.93 (s, 1H).

Examples 357 and 358

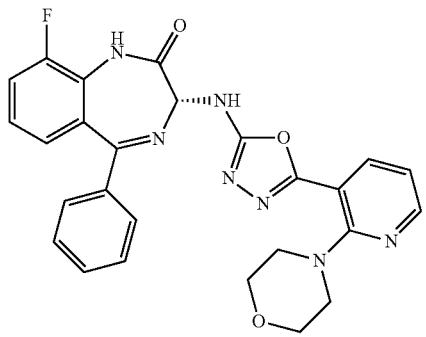

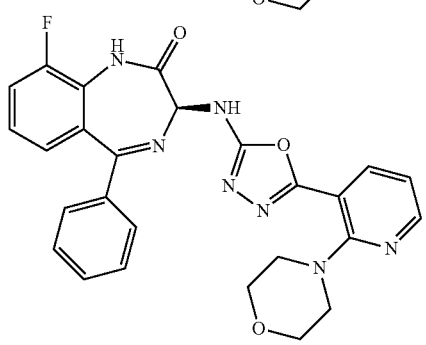

Examples 357 and 358 were prepared using a procedure similar to that used to prepare Example 355 where 2-morpholinonicotinohydrazide was used in place of 2-morpholinobenzohydrazide, followed by chiral separation.

Example 357

ESI-MS m/z: 500.2 [M+H]⁺. ¹H NMR (300 MHz, DMSO-d₆) δ 3.15 (d, J=5.0 Hz, 4H), 3.68 (d, J=4.9 Hz, 4H), 5.25 (d, J=8.5 Hz, 1H), 6.99-7.09 (m, 1H), 7.18 (d, J=8.0 Hz, 1H), 7.26-7.40 (m, 1H), 7.48-7.65 (m, 6H), 7.97 (d, J=7.5 Hz, 1H), 8.35 (d, J=4.7 Hz, 1H), 9.19 (d, J=8.5 Hz, 1H), 10.96 (s, 1H). Example 358: ESI-MS m/z: 500.2 [M+H]⁺. ¹H NMR (300 MHz, DMSO-d₆) δ 3.14 (s, 4H), 3.69 (d, J=6.5 Hz, 4H), 5.25 (d, J=8.4 Hz, 1H), 6.98-7.09 (m, 1H), 7.18 (d, J=8.0 Hz, 1H), 7.33 (q, J=7.2 Hz, 1H), 7.45-7.65 (m, 6H), 7.97 (d, J=7.5 Hz, 1H), 8.35 (d, J=5.3 Hz, 1H), 9.20 (d, J=8.5 Hz, 1H), 10.96 (s, 1H).

Examples 359 and 360

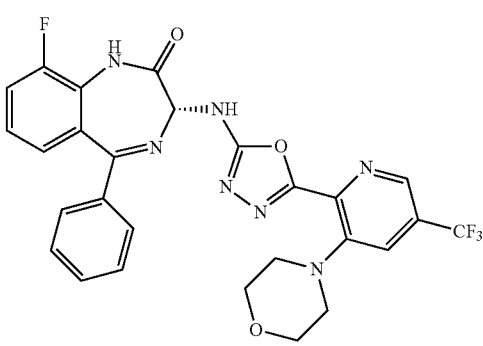

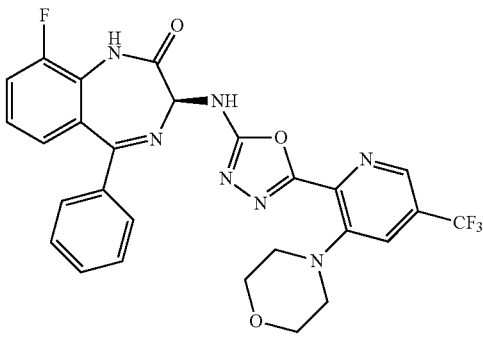

Examples 359 and 360 were prepared using a procedure similar to that used to prepare Example 355 where 3-morpholino-5-(trifluoromethyl)picolinohydrazide was used in place of 2-morpholinobenzohydrazide, followed by chiral separation.

Example 359

ESI-MS m/z: 568.4 [M+H]⁺. ¹H NMR (300 MHz, DMSO-d₆) δ 3.07 (dd, J=5.7, 3.2 Hz, 4H), 3.61-3.77 (m, 4H), 5.30 (d, J=8.2 Hz, 1H), 7.19 (d, J=7.9 Hz, 1H), 7.30-7.37 (m, 1H), 7.41-7.75 (m, 6H), 7.89 (s, 1H), 8.69 (s, 1H), 9.43 (d, J=8.4 Hz, 1H), 10.90 (s, 1H).

Example 360

ESI-MS m/z: 568.4 [M+H]⁺. ¹H NMR (300 MHz, DMSO-d₆) δ 3.02-3.12 (m, 4H), 3.72 (dd, J=5.9, 3.2 Hz, 4H), 5.29 (d, J=8.3 Hz, 1H), 7.19 (dd, J=7.9, 1.4 Hz, 1H), 7.30-7.37 (m, 1H), 7.41-7.70 (m, 6H), 7.89 (s, 1H), 8.69 (s, 1H), 9.43 (d, J=8.5 Hz, 1H), 10.92 (s, 1H).

Example 361

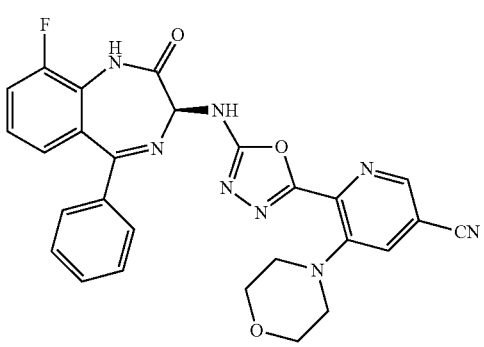 [SMILES: N#Cc1cnc(-c2nnc(N[C@H]3N=C(c4ccccc4)c4cccc(F)c4NC3=O)o2)c(N2CCOCC2)c1]

Example 361 was prepared using a procedure similar to that used to prepare Example 325, except that (S)-3-amino-9-fluoro-5-phenyl-1,3-dihydro-2H-benzo[e][1,4]diazepin-2-one was used in place of (S)-3-amino-5-phenyl-1,3-dihydro-2H-benzo[e][1,4]diazepin-2-one (A). The (S)-3-amino-9-fluoro-5-phenyl-1,3-dihydro-2H-benzo[e][1,4]diazepin-2-one was prepared in a similar way as (S)-3-amino-5-phenyl-1,3-dihydro-2H-benzo[e][1,4]diazepin-2-one (A). ESI-MS m/z: 525.3 [M+H]$^+$. $^1$H NMR (300 MHz, DMSO-d$_6$) δ 3.03 (s, 4H), 3.72-3.80 (m, 4H), 5.23-5.31 (m, 1H), 7.18-7.20 (m, 1H), 7.30-7.37 (m, 1H), 7.45-7.66 (m, 6H), 8.13-8.14 (m, 1H), 8.73 (m, 1H), 9.41-9.49 (m, 1H), 10.96 (s, 1H).

Example 362

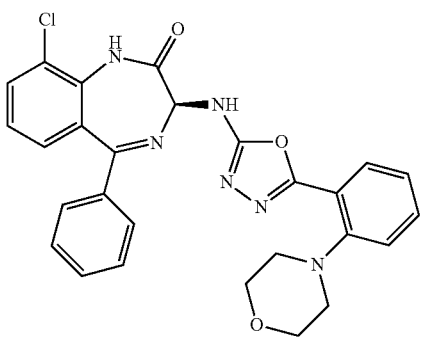

Example 355 was prepared using a procedure similar to that used to prepare Example 355 where 2-amino-3-chlorobenzonitrile were used in place of 2-amino-3-fluorobenzonitrile. ESI-MS m/z: 499.4 [M+H]$^+$. $^1$H NMR (300 MHz, DMSO-d$_6$) δ 2.83-2.93 (m, 4H), 3.62-3.77 (m, 4H), 5.18 (d, J=8.5 Hz, 1H), 7.07-7.22 (m, 2H), 7.33 (d, J=4.6 Hz, 2H), 7.41-7.61 (m, 6H), 7.67 (dd, J=7.7, 1.6 Hz, 1H), 7.85 (q, J=4.2 Hz, 1H), 9.13 (d, J=8.7 Hz, 1H), 10.64 (s, 1H).

Example 363

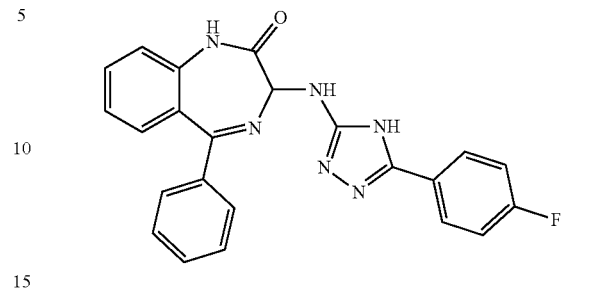

Example 363 was prepared using a procedure similar to that used to prepare Example 86 where 4-fluorobenzoyl isothiocyanate was used in place of benzoyl isothiocyanate. ESI-MS m/z: 413.3 [M+H]$^+$. $^1$H NMR (300 MHz, DMSO-d$_6$) δ 5.19 (d, J=8.8 Hz, 1H), 7.15-7.72 (m, 12H), 7.79-7.93 (m, 2H), 10.97 (s, 1H), 12.26 (s, 1H).

Example 364

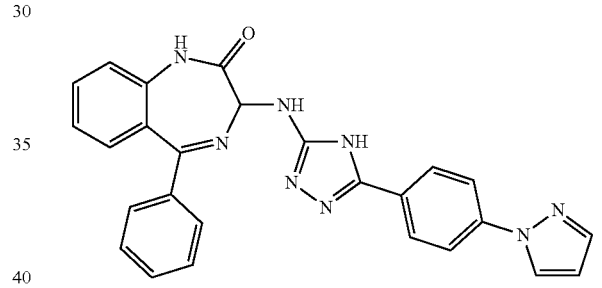

Example 364 Step a

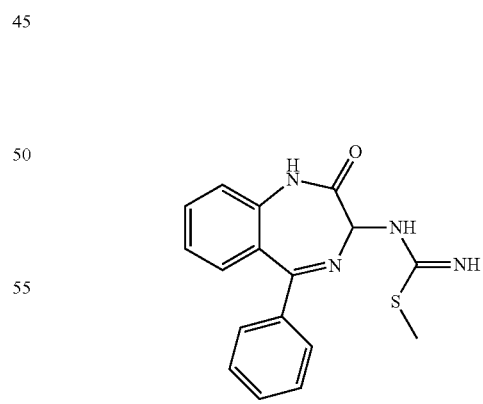

A solution of the 1-(2-oxo-5-phenyl-2,3-dihydro-1H-benzo[e][1,4]diazepin-3-yl)thiourea from Example 90 Step a (1.2 g, 3.9 mol) and MeI (577 mg, 4.1 mmol) in MeOH (20 mL) was refluxed for 1 hour. It was concentrated to give 1.4 g (crude) of desired compound as orange solid, which was used directly in the next step. ESI-MS m/z: 325.0 [M+H]$^+$.

Example 364 Step b

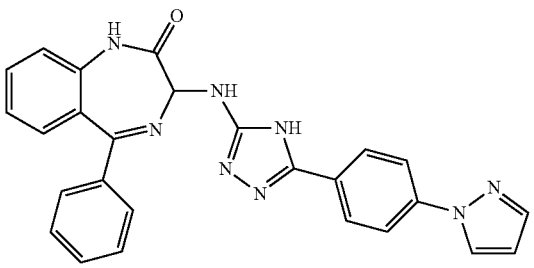

A solution of the compound from step a (150 mg, 0.463 mmol), 4-(1H-pyrazol-1-yl)benzohydrazide (103 mg, 0.51 mmol) in pyridine (5 mL) was refluxed for 1 hour in an oil bath. The crude product was purified by Prep-HPLC (MeCN/H$_2$O) to give the title compound as a white solid (27 mg, 13%). ESI-MS m/z: 461.4 [M+H]$^+$. $^1$H NMR (300 MHz, DMSO-d$_6$) δ 5.21 (d, J=8.8 Hz, 1H), 6.55 (m, 1H), 7.22-7.58 (m, 9H), 7.57-7.82 (m, 2H), 7.90 (m, 4H), 8.51 (d, J=2.5 Hz, 1H), 10.97 (s, 1H), 12.40 (s, 1H).

Example 365

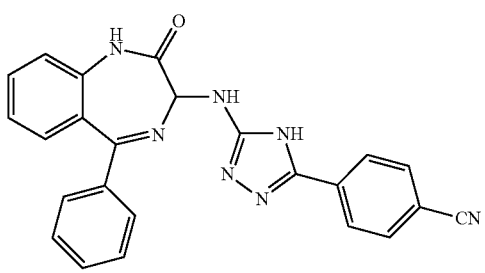

Example 365 was prepared using a procedure similar to that used to prepare Example 364 where 4-cyanobenzohydrazide was used in place of 4-(1H-pyrazol-1-yl)benzohydrazide. ESI-MS m/z: 420.3 [M+H]$^+$. $^1$H NMR (300 MHz, DMSO-d$_6$) δ 5.21 (d, J=8.6 Hz, 1H), 7.20-7.37 (m, 3H), 7.38-7.55 (m, 5H), 7.66 (m, 2H), 7.84 (d, J=8.3 Hz, 2H), 7.93-8.08 (m, 2H), 10.97 (s, 1H), 12.66 (s, 1H).

Example 366

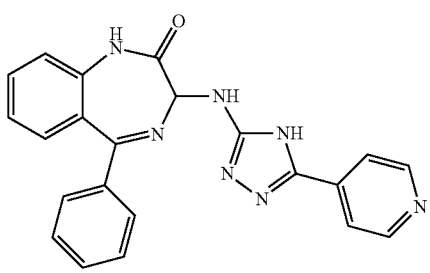 [SMILES: O=C1Nc2ccccc2C(c2ccccc2)=NC1Nc1nnc(-c2ccncc2)[nH]1]

Example 366 was prepared using a procedure similar to that used to prepare Example 364 where isonicotinohydrazide was used in place of 4-(1H-pyrazol-1-yl)benzohydrazide. ESI-MS m/z: 396.3 [M+H]$^+$. $^1$H NMR (300 MHz, DMSO-d$_6$) δ 5.23 (d, J=8.6 Hz, 1H), 7.20-7.54 (m, 8H), 7.57-7.84 (m, 4H), 8.51-8.69 (m, 2H), 10.98 (d, J=11.8 Hz, 1H), 12.62 (s, 1H).

Example 367

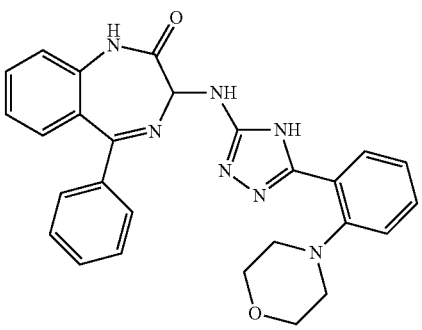 [SMILES: O=C1Nc2ccccc2C(c2ccccc2)=NC1Nc1nnc(-c2ccccc2N2CCOCC2)[nH]1]

Example 367 was prepared using a procedure similar to that used to prepare Example 364 where 2-morpholinobenzohydrazide was used in place of 4-(1H-pyrazol-1-yl)benzohydrazide. ESI-MS m/z: 480.4 [M+H]$^+$. $^1$H NMR (300 MHz, DMSO-d$_6$) δ 2.77 (m, 4H), 3.62 (s, 4H), 5.21 (d, J=8.8 Hz, 1H), 7.10 (s, 2H), 7.21-7.29 (m, 2H), 7.29-7.36 (m, 2H), 7.46 (m, 5H), 7.59-7.68 (m, 2H), 10.89 (s, 1H), 12.80 (s, 1H).

Example 368

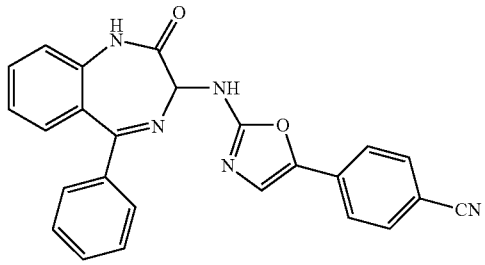

Example 368 was prepared using a procedure similar to that used to prepare Example 84 where 4-(2-azidoacetyl)benzonitrile was used in place of 2-azido-1-phenylethanone. ESI-MS m/z: 410.1 [M+H]$^+$. $^1$H NMR (400 MHz, DMSO-d$_6$) δ5.20 (s, 1H), 7.25-7.28 (m, 1H), 7.33-7.35 (m, 2H), 7.43-7.49 (m, 6H), 7.51-7.55 (m, 3H), 7.64-7.86 (m, 2H), 9.00 (s, 1H), 10.95 (s, 1H).

Example 369

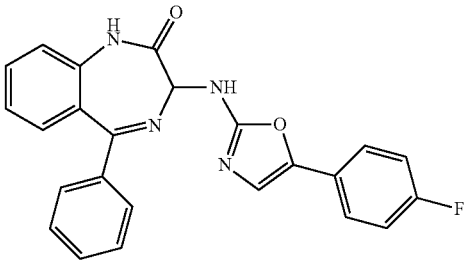 [SMILES: O=C1Nc2ccccc2C(c2ccccc2)=NC1Nc1ncc(-c2ccc(F)cc2)o1]

Example 369 was prepared using a procedure similar to that used to prepare Example 84 where 2-azido-1-(4-fluorophenyl)ethan-1-one was used in place of 2-azido-1-phenylethanone. ESI-MS m/z: 413.1 [M+H]+. 1H NMR (400 MHz, DMSO-d6) δ 5.17-5.19 (d, J=8.0, 1H), 7.10-7.14 (m, 1H), 7.19-7.26 (m, 3H), 7.27-7.36 (m, 3H), 7.44-7.49 (m, 2H), 7.51-7.57 (m, 7H), 7.65-7.69 (m, 1H), 8.70-8.73 (m, 1H), 10.95 (s, 1H).

Example 370

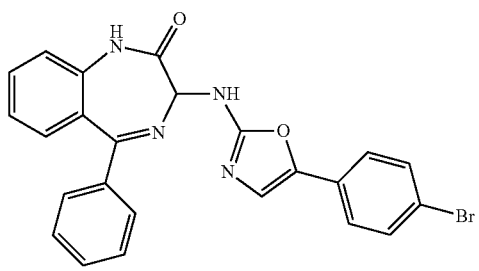 [SMILES: O=C1Nc2ccccc2C(c2ccccc2)=NC1Nc1ncc(-c2ccc(Br)cc2)o1]

Example 370 was prepared using a procedure similar to that used to prepare Example 84 where 2-azido-1-(4-bromophenyl)ethan-1-one was used in place of 2-azido-1-phenylethanone. ESI-MS m/z: 475.0 [M+H]+. 1H NMR (400 MHz, DMSO-d6) δ 5.17-5.19 (d, J=8.0 Hz, 1H), 7.25-7.29 (m, 2H), 7.33-7.35 (m, 2H), 7.44-7.49 (m, 7H), 7.51-7.59 (m, 2H), 7.61-7.68 (m, 1H), 8.75-8.77 (d, J=8.0 Hz, 1H), 10.93 (s, 1H).

Example 371

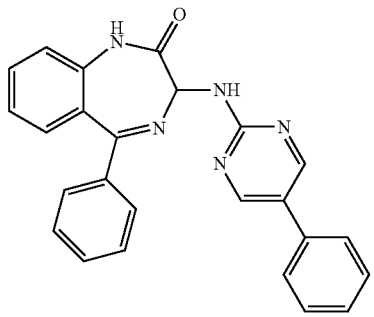 [SMILES: O=C1Nc2ccccc2C(c2ccccc2)=NC1Nc1ncc(-c2ccccc2)cn1]

Example 371 was prepared using a procedure similar to that used to prepare Example 95 where 2-chloro-5-phenylpyrimidine was used in place of 3-chloro-6-phenylpyridazine. ESI-MS m/z: 406.3 [M+H]+. 1H NMR (300 MHz, DMSO-d6) δ 5.56 (d, J=7.6 Hz, 1H), 7.30 (m, 2H), 7.47 (m, 10H), 7.62-7.77 (m, 2H), 7.95 (s, 1H), 8.20 (d, J=7.7 Hz, 1H), 8.37 (s, 1H), 10.95 (s, 1H).

Example 372

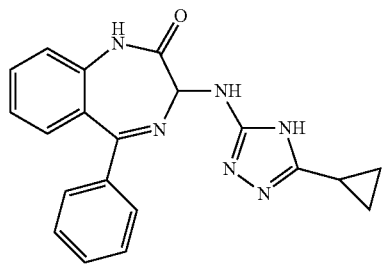

Example 372 was prepared using a procedure similar to that used to prepare Example 86 where cyclopropanecarbonyl isothiocyanate was used in place of benzoyl isothiocyanate. ESI-MS m/z: 359.3 [M+H]+. 1H NMR (300 MHz, DMSO-d6) δ 0.77 (d, J=35.3 Hz, 4H), 1.77 (m, 1H), 5.03 (d, J=9.0 Hz, 1H), 7.19-7.37 (m, 3H), 7.39-7.55 (m, 5H), 7.63 (m, 1H), 8.19 (s, 1H), 10.86 (s, 1H).

Example 373

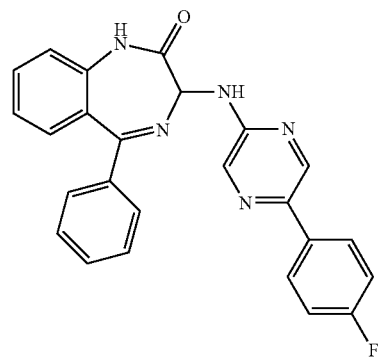 [SMILES: O=C1Nc2ccccc2C(c2ccccc2)=NC1Nc1cnc(-c2ccc(F)cc2)cn1]

Example 373 was prepared using a procedure similar to that used to prepare Example 95 where 2-chloro-5-(4-fluorophenyl)pyrazine was used in place of 3-chloro-6-phenylpyridazine. ESI-MS m/z: 424.3 [M+H]+. 1H NMR (300 MHz, DMSO-d6) δ 5.52 (d, J=7.7 Hz, 1H), 7.27 (m, 3H), 7.33-7.41 (m, 2H), 7.42-7.60 (m, 5H), 7.67 (m, 1H), 7.90-8.03 (m, 2H), 8.30-8.46 (m, 2H), 8.48-8.58 (m, 1H), 10.76-11.18 (m, 1H).

Example 374

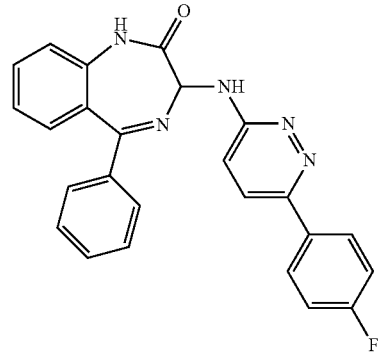 [SMILES: O=C1Nc2ccccc2C(c2ccccc2)=NC1Nc1ccc(-c2ccc(F)cc2)nn1]

Example 374 was prepared using a procedure similar to that used to prepare Example 95 where 3-chloro-6-(4- fluorophenyl)pyridazine was used in place of 3-chloro-6-phenylpyridazine. ESI-MS m/z: 424.3 [M+H]+. 1H NMR (300 MHz, DMSO-d6) δ 5.64 (d, J=6.2 Hz, 1H), 7.23-7.40 (m, 5H), 7.41-7.61 (m, 6H), 7.68 (m, 1H), 7.94-8.18 (m, 3H), 8.79 (s, 1H), 11.02 (s, 1H).

Example 375

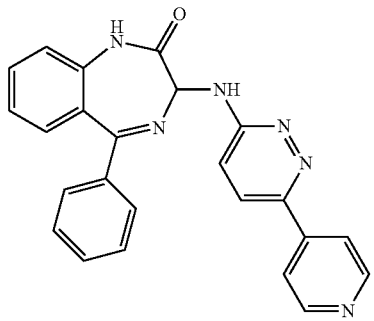 [SMILES: O=C1Nc2ccccc2C(c2ccccc2)=NC1Nc1ccc(-c2ccncc2)nn1]

Example 375 was prepared using a procedure similar to that used to prepare Example 95 where 3-chloro-6-(pyridin-4-yl)pyridazine was used in place of 3-chloro-6-phenylpyridazine. ESI-MS m/z: 407.3 [M+H]+. 1H NMR (300 MHz, DMSO-d6) δ 5.73 (d, J=7.5 Hz, 1H), 7.24-7.43 (m, 4H), 7.43-7.62 (m, 5H), 7.69 (m, 1H), 7.93-8.02 (m, 2H), 8.06 (d, J=9.4 Hz, 1H), 8.38 (d, J=7.6 Hz, 1H), 8.62-8.72 (m, 2H), 10.93 (s, 1H).

Example 376

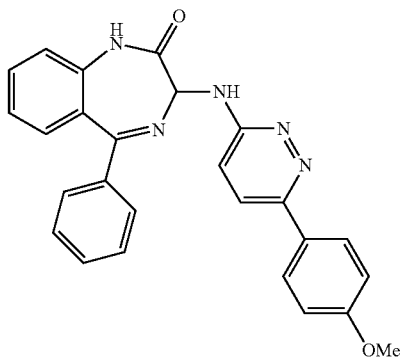 [SMILES: COc1ccc(-c2ccc(NC3N=C(c4ccccc4)c4ccccc4NC3=O)nn2)cc1]

Example 376 was prepared using a procedure similar to that used to prepare Example 95 where 3-chloro-6-(4-methoxyphenyl)pyridazine was used in place of 3-chloro-6-phenylpyridazine. ESI-MS m/z: 436.4 [M+H]+. 1H NMR (300 MHz, DMSO-d6) δ 3.79 (s, 3H), 5.68 (d, J=7.8 Hz, 1H), 6.96-7.07 (m, 2H), 7.28 (m, 2H), 7.36 (m, 2H), 7.43-7.53 (m, 4H), 7.67 (m, 1H), 7.83-7.95 (m, 3H), 8.03 (d, J=7.9 Hz, 1H), 8.44 (s, 1H), 10.92 (s, 1H).

Example 377

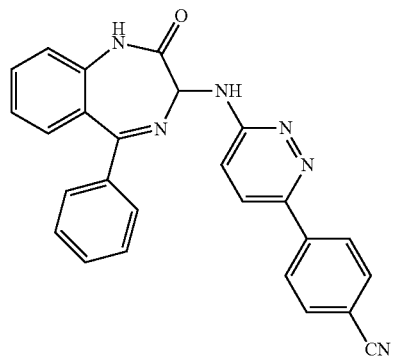 [SMILES: N#Cc1ccc(-c2ccc(NC3N=C(c4ccccc4)c4ccccc4NC3=O)nn2)cc1]

Example 377 was prepared using a procedure similar to that used to prepare Example 95 where 4-(6-chloropyridazin-3-yl)benzonitrile was used in place of 3-chloro-6-phenylpyridazine. ESI-MS m/z: 431.4 [M+H]+. 1H NMR (400 MHz, DMSO-d6) δ 5.74 (d, J=7.4 Hz, 1H), 7.27-7.43 (m, 4H), 7.44-7.59 (m, 5H), 7.66-7.75 (m, 1H), 7.92-8.01 (m, 2H), 8.03-8.12 (m, 1H), 8.16-8.26 (m, 2H), 8.37 (d, J=7.4 Hz, 1H), 10.96 (s, 1H).

Example 378

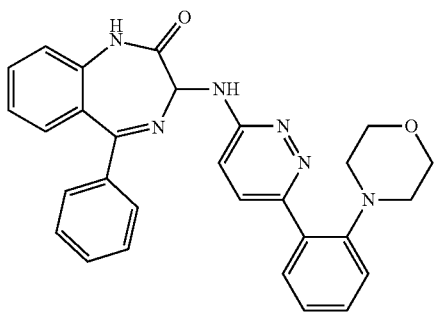 [SMILES: O=C1Nc2ccccc2C(c2ccccc2)=NC1Nc1ccc(-c2ccccc2N2CCOCC2)nn1]

Example 378 was prepared using a procedure similar to that used to prepare Example 95 where 4-(2-(6-chloropyridazin-3-yl)phenyl)morpholine was used in place of 3-chloro-6-phenylpyridazine. ESI-MS m/z: 491.1 [M+H]+. 1H NMR (400 MHz, DMSO-d6) δ 2.66-2.84 (m, 4H), 3.49-3.66 (m, 4H), 5.70 (m, 1H), 7.07-7.19 (m, 2H), 7.19-7.31 (m, 2H), 7.35 (m, 3H), 7.43-7.57 (m, 6H), 7.67 (m, 1H), 7.96 (m, 1H), 8.08 (d, J=7.9 Hz, 1H), 10.68 (s, 1H).

Example 379

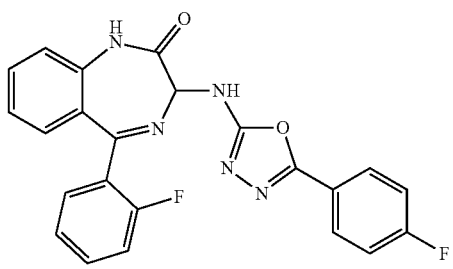 [SMILES: O=C1Nc2ccccc2C(c2ccccc2F)=NC1Nc1nnc(-c2ccc(F)cc2)o1]

Example 379 Step a

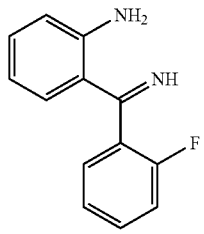 [SMILES: N=C(c1ccccc1N)c1ccccc1F]

A solution of aniline (4.65 g, 50 mmol) in DCE (100 mL) was stirred for 10 minutes at 0° C. Then BCl$_3$ (55 ml, 55 mmol, 1M in DCM) was added slowly before it was stirred for 30 minutes at 0° C. 2-fluorobenzonitrile (12 g, 100 mmol) and AlCl$_3$ (7.38 g, 55 mmol) were added and the mixture was heated to 80° C. overnight. Solid was filtered out and the filtrate was concentrated under vacuum, it was diluted with water (100 mL) and extracted with EA (3×100 mL). The organic phase was concentrated under vacuum. The crude product was used directly in the next step. ESI-MS m/z: 215.1 [M+H]$^+$.

Example 379 Step b

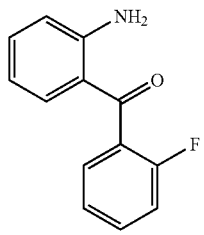 [SMILES: Nc1ccccc1C(=O)c1ccccc1F]

A solution of the compound from step a (8.79 g, 41.8 mmol) in HCl (60 mL) was stirred for 40 minutes at 0° C. The solution was heated up to 80° C. for an hour. The crude product was purified by Flash (MeCN/H$_2$O) to give desired compound as a yellow solid (2.3 g, 27%). ESI-MS m/z: 216.1 [M+H]$^+$.

Example 379 Step c

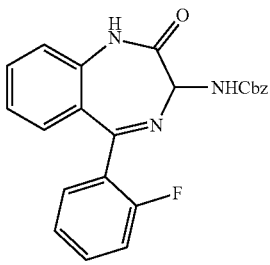 [SMILES: O=C(NC1N=C(c2ccccc2F)c2ccccc2NC1=O)OCc1ccccc1]

A solution of (COCl)$_2$ (1.85 g, 14.2 mmol) was added dropwise to 2-(1H-benzo[d][1,2,3]triazol-1-yl)-2-(benzyloxycarbonylamino)acetic acid, prepared in Example 1 step a, (3.6 g, 11 mmol) and DMF (0.5 mL) in THF (100 mL) at 0° C. and stirred for 1 h, then (2-aminophenyl)(2-fluorophenyl)methanone (1.08 g, 5.0 mmol) and NMM (1.01 g, 10.0 mmol) was added to the mixture at 0° C. and stirred for 1 h at rt. Filtered and NH$_3$.H$_2$O (7N) in MeOH (50 mL) was added and stirred for 2 h, extracted with EA (100 mL×3), washed with aq. NaOH (1N, 200 mL), dried (Na$_2$SO$_4$), concentrated and dissolved by HOAc (50 mL), then NH$_4$OAc (4.37 g, 31.0 mmol) was added and stirred for 18 h at rt. The solvents were removed and it was adjusted PH to 9~10, washed with Et$_2$O (50 mL) to afford the desired compound as an off-white solid (940 mg, 47%). ESI-MS m/z: 404.1 [M+H]$^+$.

Example 379 Step d

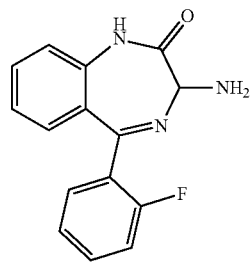 [SMILES: NC1N=C(c2ccccc2F)c2ccccc2NC1=O]

The compound from step c (940 mg, 2.3 mmol) was dissolved in HBr/HOAc (3 mL) and stirred for 30 min at 70° C. The reaction mixture was cooled at 0° C. and Et$_2$O (30 mL) was added, filtered to afford the desired compound as a yellow solid (142 mg, 23%). ESI-MS m/z: 270.1 [M+H]$^+$.

Example 379 Step e

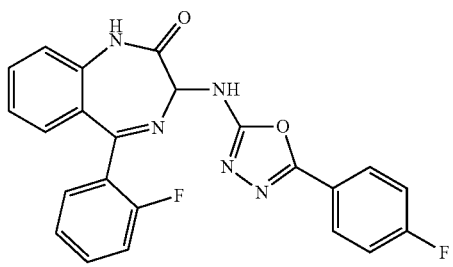 [SMILES: O=C1Nc2ccccc2C(c2ccccc2F)=NC1Nc1nnc(-c2ccc(F)cc2)o1]

A solution of the compound from step d (142 mg, 0.53 mmol), TEA (1 mL) and TCDI (140 mg, 0.79 mmol) in DMF (20 mL) and stirred for 1 h at 25° C. Then 4-fluorobenzohydrazide (120 mg, 0.78 mmol) and EDCI (764 mg, 4 mmol) was added to the mixture and stirred for 2 h at 60° C. The mixture was cooled to 0° C. and H$_2$O (60 mL) was added. Solid was collected and purified by Prep-HPLC (MeCN/H$_2$O) to afford the title compound as a light yellow solid (21 mg, 9%). ESI-MS m/z: 432.3 [M+H]$^+$. $^1$H NMR (300 MHz, DMSO-d$_6$) δ 5.17 (d, J=8.6 Hz, 1H), 7.15-7.48 (m, 7H), 7.50-7.71 (m, 3H), 7.80-7.94 (m, 2H), 9.17 (d, J=8.6 Hz, 1H), 11.08 (s, 1H).

Example 380

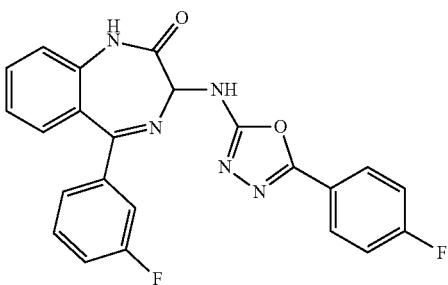 [SMILES: O=C1Nc2ccccc2C(c2cccc(F)c2)=NC1Nc1nnc(-c2ccc(F)cc2)o1]

Example 380 was prepared using a procedure similar to that used to prepare Example 379 where 3-fluorobenzonitrile was used in place of 2-fluorobenzonitrile. ESI-MS m/z: 432.1 [M+H]+. 1H NMR (300 MHz, DMSO-d6) δ 5.18 (d, J=8.3 Hz, 1H), 7.22-7.48 (m, 8H), 7.49-7.58 (m, 1H), 7.70 (t, J=7.4 Hz, 1H), 7.81-7.96 (m, 2H), 9.18 (d, J=8.4 Hz, 1H), 11.06 (s, 1H).

Example 381

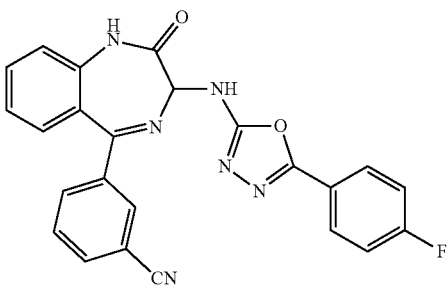 [SMILES: N#Cc1cccc(C2=NC(Nc3nnc(-c4ccc(F)cc4)o3)C(=O)Nc3ccccc32)c1]

Example 381 was prepared using a procedure similar to that used to prepare Example 379 where isophthalonitrile was used in place of 2-fluorobenzonitrile. ESI-MS m/z: 439.3 [M+H]+. 1H NMR (300 MHz, DMSO-d6) δ 5.18 (d, J=8.3 Hz, 1H), 7.22-7.48 (m, 8H), 7.49-7.58 (m, 1H), 7.70 (t, J=7.4 Hz, 1H), 7.81-7.96 (m, 2H), 9.18 (d, J=8.4 Hz, 1H), 11.06 (s, 1H).

Example 382

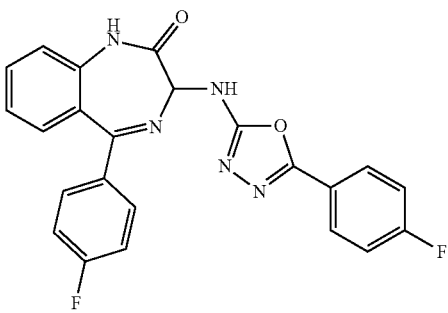 [SMILES: O=C1Nc2ccccc2C(c2ccc(F)cc2)=NC1Nc1nnc(-c2ccc(F)cc2)o1]

Example 382 was prepared using a procedure similar to that used to prepare Example 379 where 4-fluorobenzonitrile was used in place of 2-fluorobenzonitrile. ESI-MS m/z: 432.3 [M+H]+. 1H NMR (300 MHz, DMSO-d6) δ 5.16 (d, J=8.5 Hz, 1H), 7.24-7.50 (m, 7H), 7.51-7.64 (m, 2H), 7.70 (m, 1H), 7.82-7.95 (m, 2H), 9.16 (d, J=8.5 Hz, 1H), 11.02 (s, 1H).

Example 383

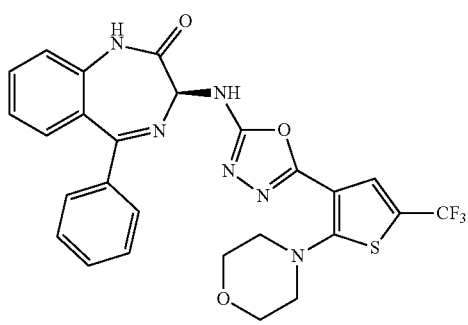 [SMILES: O=C1Nc2ccccc2C(c2ccccc2)=N[C@@H]1Nc1nnc(-c2cc(C(F)(F)F)sc2N2CCOCC2)o1]

Example 383 Step a

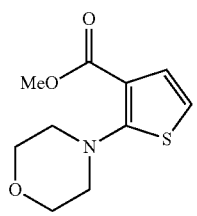 [SMILES: COC(=O)c1ccsc1N1CCOCC1]

A solution of methyl 2-aminothiophene-3-carboxylate (6.0 g, 38.4 mmol) was dissolved in DMA (40 mL), then 1-bromo-2-(2-bromoethoxy)ethane (26.5 g, 115 mmol) and Cs2CO3 (37.5 g, 115.0 mmol) was added. The mixture was stirred at 80° C. for 5 hours. It was diluted with H2O, and extracted with EA (×3) and washed with brine (×2). The organic layers was combined and concentrated, then purified by reverse phase C18 column chromatography (MeCN/H2O) to give desired compound as brown liquid (8.0 g). ESI MS m/z=227.9 [M+H]+.

Example 383 Step b

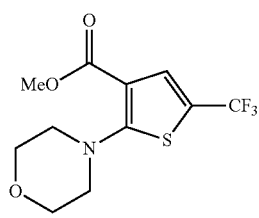 [SMILES: COC(=O)c1cc(C(F)(F)F)sc1N1CCOCC1]

A solution of iodosobenzene diacetate (4.83 g, 15 mmol) was added to the compound from step a (1.14 g, 5 mmol), TMSCF3 (2.13 g, 15 mmol) and KF (870 mg) in DMSO (40 mL) was stirred for 0.5 hour at r.t. It was quenched by H2O (50 mL) and extracted with DCM (3×), dried Na2SO4, filtered to give crude methyl 2-morpholino-5-(trifluoromethyl)thiophene-3-carboxylate as a brown oil. (5 g). ESI MS m/z=296.2 [M+H]⁺.

Example 383 Step c

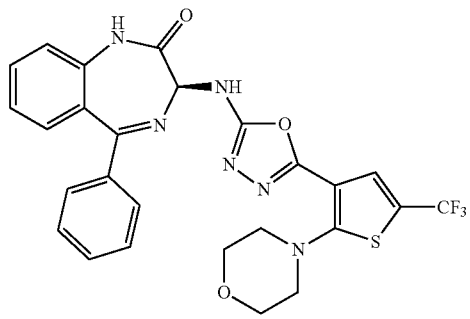 [SMILES: O=C1Nc2ccccc2C(c2ccccc2)=N[C@@H]1Nc1nnc(-c2cc(C(F)(F)F)sc2N2CCOCC2)o1]

Example 404 was prepared using a procedure similar to that used to prepare Example 152 where methyl 2-morpholino-5-(trifluoromethyl)thiophene-3-carboxylate was used in place of ethyl 2-morpholino-4-(trifluoromethyl)benzoate. ESI MS m/z=555.4 [M+H]⁺. ¹H NMR (300 MHz, DMSO-d6) δ 3.11-3.21 (m, 4H), 3.67-3.77 (m, 4H), 5.12 (d, J=8.5 Hz, 1H), 7.20-7.38 (m, 3H), 7.38-7.58 (m, 5H), 7.59-7.72 (m, 2H), 9.06 (d, J=8.6 Hz, 1H), 10.97 (s, 1H).

Example 384

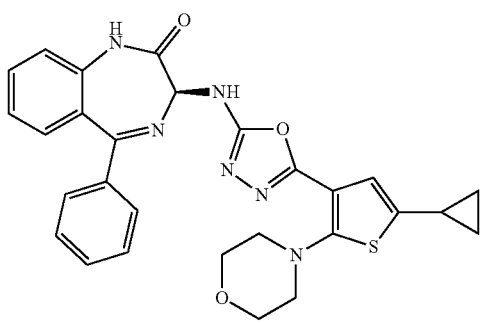 [SMILES: O=C1Nc2ccccc2C(c2ccccc2)=N[C@@H]1Nc1nnc(-c2cc(C3CC3)sc2N2CCOCC2)o1]

Example 384 Step

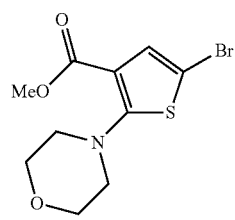 [SMILES: COC(=O)c1cc(Br)sc1N1CCOCC1]

A solution of methyl 2-morpholinothiophene-3-carboxylate, from 383 step a, (5.0 g, 22 mmol), HBr (2 mL) and DMSO (2 mL) in EA (4 mL) was stirred at rt for 1 hour. The resulting solution was diluted with water and extracted with EA (×3). The organic phase was concentrated and purified by reverse phase C18 column chromatography (MeCN/H₂O) to give the desired product as a brown solid (1.6 g, 24%). ESI MS m/z=306.2 [M+H]⁺.

Example 384 Step b

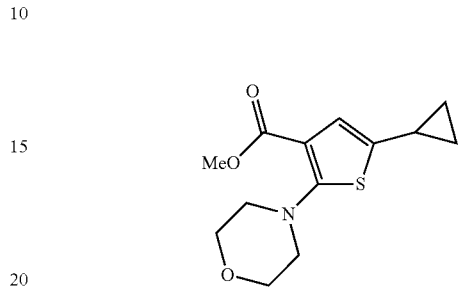

A solution of the compound from step a (488 mg, 1.6 mmol), cyclopropylboronic acid (276 mg, 3.2 mmol), Pd(OAc)₂ (72 mg, 0.32 mmol), Pcy₃.HBF₄ (118 mg, 0.32 mmol) and K₃PO₄ (680 mg, 3.2 mmol) in H₂O (2 mL) and toluene (10 mL) was stirred for one hour at 100° C. It was concentrated, and diluted with EA. The solid was filtered out. The filtrate was washed with brine (×2). The organic layers was combined and concentrated and purified by reverse phase C18 column chromatography (MeCN/H₂O) to give methyl 5-cyclopropyl-2-morpholinothiophene-3-carboxylate as brown oil 660 mg. ESI MS m/z=268.3 [M+H]⁺.

Example 384 Step c

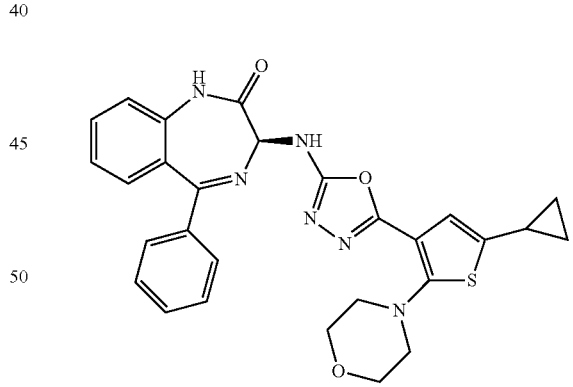

Example 384 was prepared using a procedure similar to that used to prepare Example 152 where methyl 5-cyclopropyl-2-morpholinothiophene-3-carboxylate was used in place of ethyl 2-morpholino-4-(trifluoromethyl)benzoate. ESI MS m/z=527.2 [M+H]⁺. ¹H NMR (300 MHz, DMSO-d₆) δ 0.60-0.75 (m, 2H), 0.84-1.02 (m, 2H), 2.01-2.16 (ddt, J=13.3, 8.5, 4.8 Hz, 1H), 2.93-3.02 (m, 4H), 3.65-3.74 (m, 4H), 5.08-5.18 (d, J=8.6 Hz, 1H), 6.86-6.93 (d, J=0.9 Hz, 1H), 7.23-7.40 (m, 3H), 7.41-7.60 (m, 5H), 7.62-7.74 (ddd, J=8.5, 7.0, 1.8 Hz, 1H), 8.92-9.01 (d, J=8.6 Hz, 1H), 10.95-11.02 (s, 1H).

Example 385

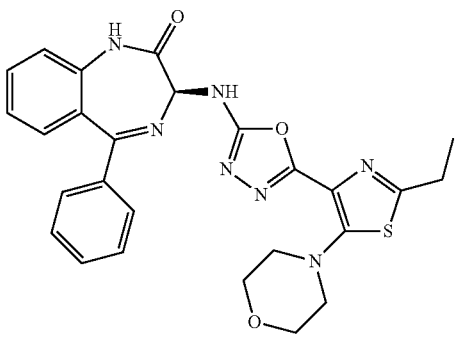 [SMILES: CCc1nc(-c2nnc(N[C@H]3N=C(c4ccccc4)c4ccccc4NC3=O)o2)c(N2CCOCC2)s1]

Example 385 Step a

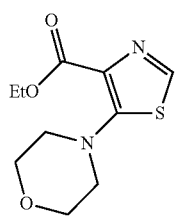 [SMILES: CCOC(=O)c1ncsc1N1CCOCC1]

A solution of ethyl 2-bromo-5-morpholinothiazole-4-carboxylate (10.0 g, 42.6 mmol) and morpholine (4.076 g, 46.86 mmol) was dissolved in MeCN (100 mL), and then DBU (9.712 g, 63.9 mmol) was added. The mixture was stirred at 80° C. for 1 hour. It was concentrated, and purified by silica gel column with PE:EA=1:1 to give the target compound as a yellow green solid (6.17 g, 60%). ESI MS m/z=243.2 [M+H]⁺.

Example 385 Step b

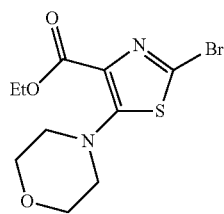 [SMILES: CCOC(=O)c1nc(Br)sc1N1CCOCC1]

A solution of the compound from step a (6.17 g, 25.51 mmol) and NBS (4.9 g, 27.55 mmol) was dissolved in MeCN (100 mL), the mixture was stirred at RT for 1 hour. It was concentrated, and purified by silica gel chromatography with PE:EA=3:1 to give ethyl 2-bromo-5-morpholinothiazole-4-carboxylate as a light yellow solid (7.53 g, 92%). ESI MS m/z=320.9 [M+H]⁺.

Example 385 Step c

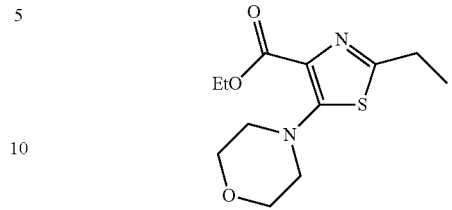

To a stirred solution of the ethyl 2-bromo-5-morpholinothiazole-4-carboxylate (300 mg, 0.97 mmol) and ZnEt₂ (229 mg, 1.87 mmol) in THF (10 mL) was added Pd(PPh₃)₄ (30 mg, 0.010 mmol) under the nitrogen. The mixture was refluxed overnight and then concentrated. The reaction mixture was poured into saturated ice water extracted with EA (3*100 ml). The organic layer was dried over Na₂SO₄. The residue was purified by flash chromatography (MeCN/H₂O) to give ethyl 2-ethyl-5-morpholinothiazole-4-carboxylate as a yellow solid (320 mg). ESI MS m/z=271.2 [M+H]⁺.

Example 385 Step d

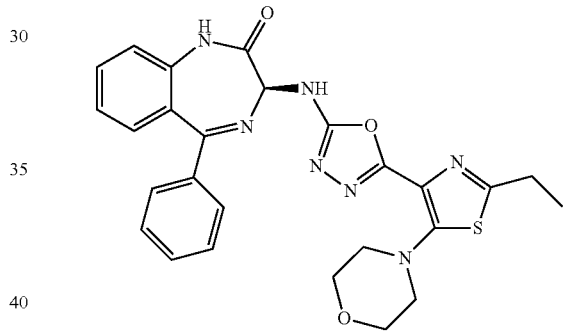

Example 385 was prepared using a procedure similar to that used to prepare Example 152 where ethyl 2-ethyl-5-morpholinothiazole-4-carboxylate was used in place of ethyl 2-morpholino-4-(trifluoromethyl)benzoate. ESI MS m/z=548.2 [M+H]⁺. ¹H NMR (300 MHz, DMSO-d₆) δ1.30 (3H, t), 2.95 (2H, t), 3.07 (4H, m), 3.72 (4H, dd), 5.15 (1H, d), 7.34 (3H, m), 7.52 (5H, m), 7.68 (1H, m), 9.07 (1H, d), 10.96 (1H, s).

Example 386

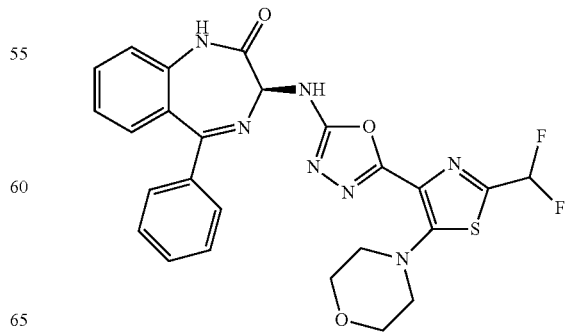

Example 387

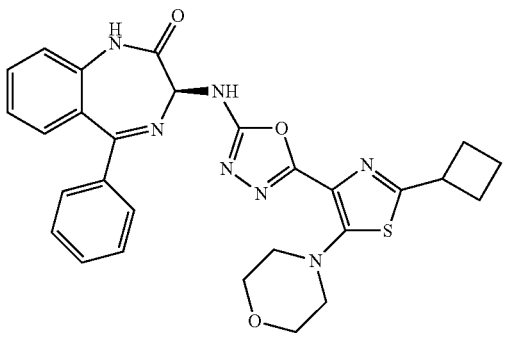 [SMILES: O=C1Nc2ccccc2C(c2ccccc2)=N[C@@H]1Nc1nnc(-c2nc(C3CCC3)sc2N2CCOCC2)o1]

Example 387 Step a

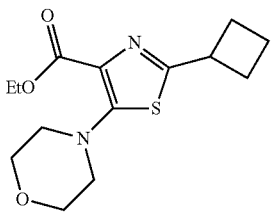

Cyclobutylzinc(II) bromide (7.6 mL, 3.8 mmol) was dropwised to a solution of ethyl 2-bromo-5-morpholinothiazole-4-carboxylate, prepared in Example 385, (1 g, 3.1 mmol) and Pd(PPh$_3$)$_4$ (361 mg, 0.031 mmol) in THF (10 mL) at 0° C. under N$_2$. The mixture was stirred for 16 hours at reflux. The solution was quenched with water, concentrated, extracted with EA (×3). The organic layers were combined, dried, concentrated. The crude product was purified by silica gel chromatography (PE-EA) to give ethyl 2-cyclobutyl-5-morpholinothiazole-4-carboxylate as yellow oil (740 mg, 81%). ESI MS m/z=297.3 [M+H]$^+$.

Example 387 Step b

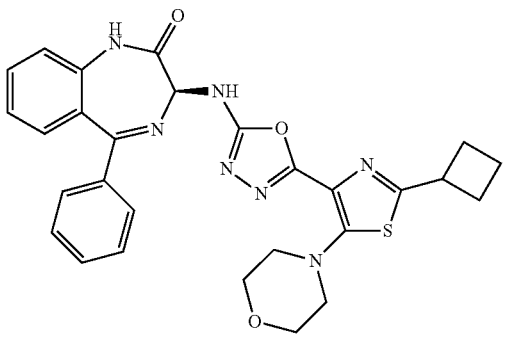 [SMILES: O=C1Nc2ccccc2C(c2ccccc2)=N[C@@H]1Nc1nnc(-c2nc(C3CCC3)sc2N2CCOCC2)o1]

Example 387 was prepared using a procedure similar to that used to prepare Example 152 where ethyl 2-cyclobutyl-5-morpholinothiazole-4-carboxylate was used in place of ethyl 2-morpholino-4-(trifluoromethyl)benzoate. ESI MS m/z=542.4 [M+H]$^+$. $^1$H NMR (400 MHz, DMSO-d$_6$) δ 1.89 (m, 1H), 1.97-2.07 (m, 1H), 2.20-2.31 (m, 2H), 2.38 (m, 2H), 3.07 (m, 4H), 3.66-3.75 (m, 4H), 3.75-3.83 (m, 1H), 5.15 (d, J=8.6 Hz, 1H), 7.25-7.40 (m, 3H), 7.51 (m, 5H), 7.68 (m, 1H), 9.07 (d, J=8.7 Hz, 1H), 10.88-11.03 (m, 1H).

Example 388

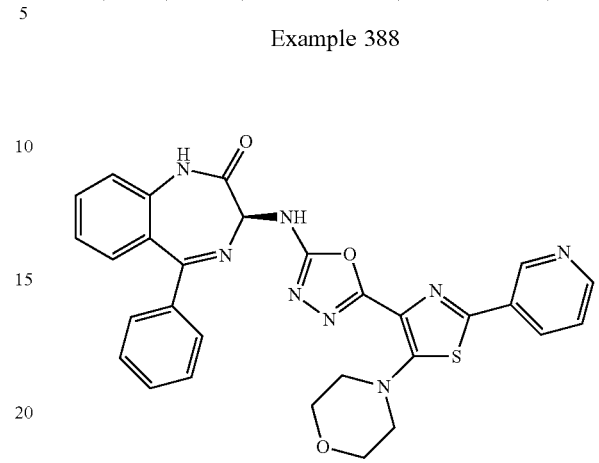

Example 388 was prepared using a procedure similar to that used to prepare Example 338 where 3-pyridylboronic acid was used in place of cyclopropylboronic acid. ESI MS m/z=565.3 [M+H]$^+$. $^1$H NMR (400 MHz, DMSO-d$_6$) δ 3.19-3.21 (m, 4H), 3.74-3.76 (m, 4H), 5.15-5.17 (d, J=8.0, 1H), 7.27-7.37 (m, 5H), 7.45-7.57 (m, 6H), 7.66-7.69 (m, 1H), 8.21-8.24 (m, 1H), 8.65-8.67 (m, 1H), 9.06-9.77 (m, 1H), 9.18-9.20 (m, 1H), 10.98 (s, 1H).

Example 389

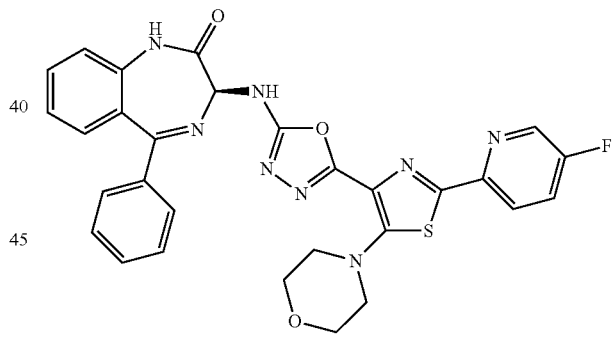

Example 389 Step a

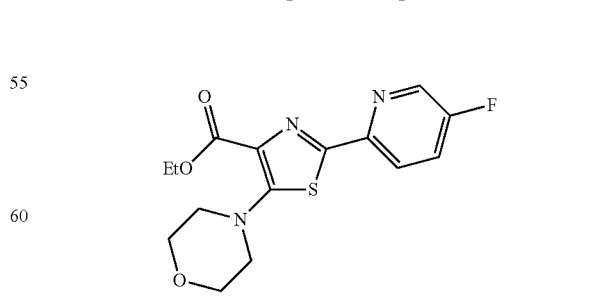

A solution of ethyl 2-bromo-5-morpholinothiazole-4-carboxylate, prepared in Example 385, (1.0 g, 3.10 mmol), (5-fluoropyridin-2-yl) zinc (II) bromide (1488 mg, 6.20 mmol), Pd (PPh₃)₄ (340 mg, 0.31 mmol) in THF (25 mL) was stirred at 65° C. for 5 hrs. Then H₂O (20 mL) was added to the mixture and extracted with EA (×3). The organic layer was dried and purified by reverse phase C18 column chromatography to give ethyl 2-(5-fluoropyridin-2-yl)-5-morpholinothiazole-4-carboxylate as yellow solid (110 mg, 11%).

Example 389 Step b

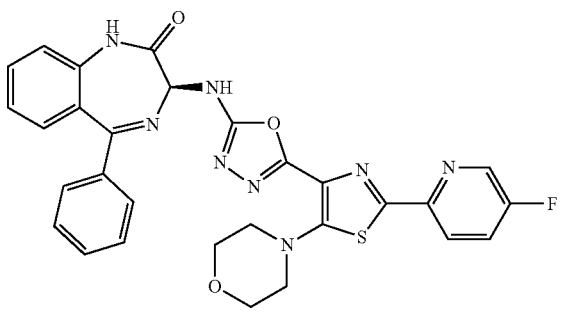 [SMILES: O=C1Nc2ccccc2C(c2ccccc2)=N[C@@H]1Nc1nnc(-c2nc(-c3ccc(F)cn3)sc2N2CCOCC2)o1]

Example 389 was prepared using a procedure similar to that used to prepare Example 152 where ethyl 2-(5-fluoropyridin-2-yl)-5-morpholinothiazole-4-carboxylate was used in place of ethyl 2-morpholino-4-(trifluoromethyl)benzoate. ESI MS m/z=583.2 [M+H]⁺. ¹H NMR (400 MHz, DMSO-d₆) δ 3.32-3.34 (m, 4H), 3.74-3.75 (m, 4H), 5.16-5.18 (d, J=8.0, 1H), 7.27-7.29 (m, 1H), 7.31-7.37 (m, 2H), 7.46-7.54 (m, 5H), 7.67-7.69 (m, 1H), 7.93-7.94 (m, 1H), 8.07-8.11 (m, 1H), 8.65-8.66 (m, 1H), 9.17-9.18 (d, J=8.0, 1H), 10.99 (s, 1H).

Example 390

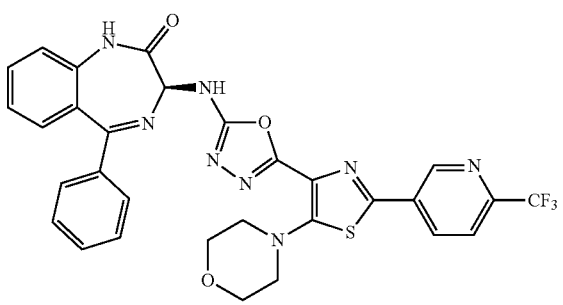 [SMILES: O=C1Nc2ccccc2C(c2ccccc2)=N[C@@H]1Nc1nnc(-c2nc(-c3ccc(C(F)(F)F)nc3)sc2N2CCOCC2)o1]

Example 390 Step a

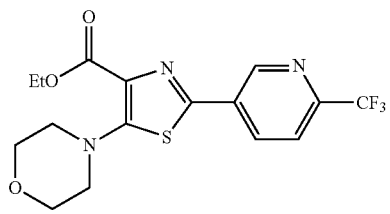 [SMILES: CCOC(=O)c1nc(-c2ccc(C(F)(F)F)nc2)sc1N1CCOCC1]

A solution of ethyl 2-bromo-5-morpholinothiazole-4-carboxylate, prepared in Example 385, (700 mg, 2.18 mmol), 6-(trifluoromethyl)pyridin-3-ylboronic acid (460 mg, 2.40 mmol), Pd(dppf)Cl₂ (320 mg, 0.43 mmol) and Cs₂CO₃ (1.42 g, 4.37 mmol) was stirred for 2 hrs at 90° C. in DMF (30 mL). It was purified by silica gel chromatography (PE:EA=5:1) to give ethyl 5-morpholino-2-(6-(trifluoromethyl)pyridin-3-yl)thiazole-4-carboxylate as a yellow solid (460 mg, 54%). ESI MS m/z=388.2 [M+H]⁺.

Example 390 Step b

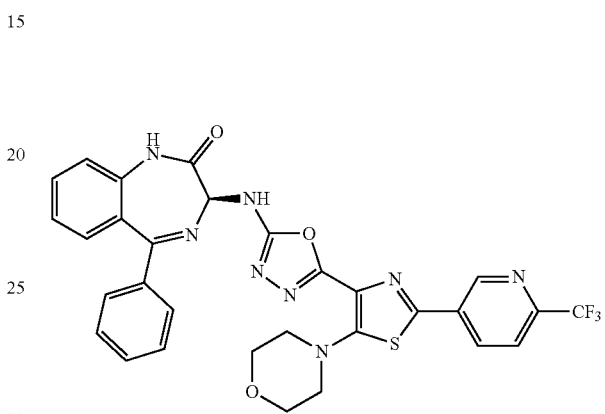

Example 390 was prepared using a procedure similar to that used to prepare Example 152 where ethyl 5-morpholino-2-(6-(trifluoromethyl)pyridin-3-yl)thiazole-4-carboxylate was used in place of ethyl 2-morpholino-4-(trifluoromethyl)benzoate. ESI MS m/z=633.4 [M+H]⁺. ¹H NMR (300 MHz, DMSO-d6) δ 3.26 (d, J=4.6 Hz, 4H), 3.77 (t, J=4.3 Hz, 4H), 5.18 (d, J=8.5 Hz, 1H), 7.34 (m, J=18.2, 7.8 Hz, 3H), 7.43-7.58 (m, 5H), 7.63-7.75 (m, 1H), 8.06 (d, J=8.3 Hz, 1H), 8.45-8.53 (m, 1H), 9.19-9.27 (m, 2H), 10.99 (s, 1H).

Example 391

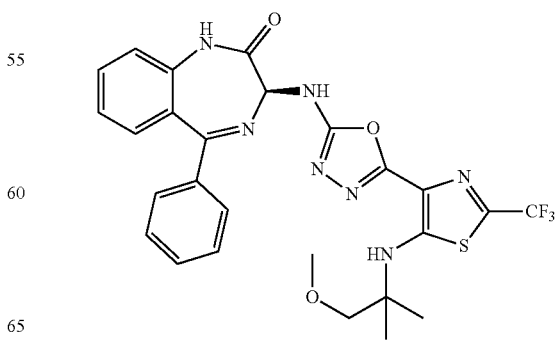

Example 392

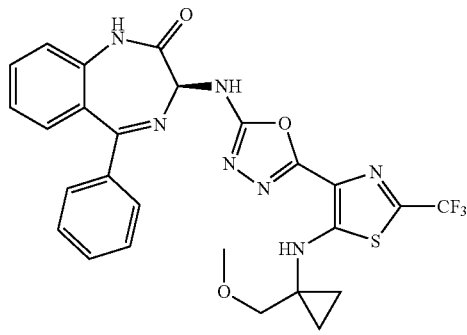 [SMILES: COCC1(Nc2sc(C(F)(F)F)nc2-c2nnc(N[C@H]3N=C(c4ccccc4)c4ccccc4NC3=O)o2)CC1]

Example 393

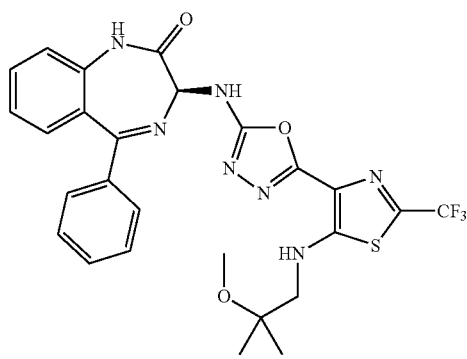 [SMILES: COC(C)(C)CNc1sc(C(F)(F)F)nc1-c1nnc(N[C@H]2N=C(c3ccccc3)c3ccccc3NC2=O)o1]

Examples 394 and 395

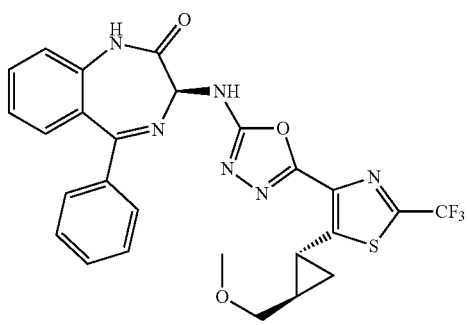
394

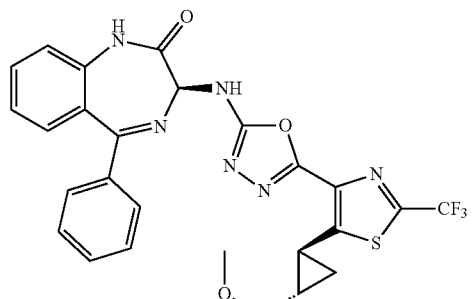
395 relative trans stereochemistry mixture of isomers 394 and 395

Examples 394 and 395 Step a

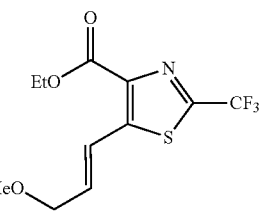

To a vial, add ethyl 5-bromo-2-(trifluoromethyl)thiazole-4-carboxylate (516 mg, 1.70 mmol), K$_2$CO$_3$ (352 mg, 2.55 mmol) and Pd(Ph$_3$P)$_4$ (392 mg, 0.34 mmol). Evacuate and refill with N$_2$ and seal. Add toluene (8 mL), ethanol (8 mL) and water (4 mL) via syringe. Add (E)-2-(3-methoxyprop-1-en-1-yl)-4,4,5,5-tetramethyl-1,3,2-dioxaborolane (0.432 mL, 2.036 mmol) via syringe. Heat vial to 80° C. and stir overnight. Dilute with water and extract with EtOAc (3×). Dry, filter and concentrate the organic layer. The crude product was added to a silica gel column and was eluted with ethyl acetate/hexane 0% to 50% to give ethyl (E)-5-(3-methoxyprop-1-en-1-yl)-2-(trifluoromethyl)thiazole-4-carboxylate (264 mg, 53% yield) as an oil.

Examples 394 and 395 Step b

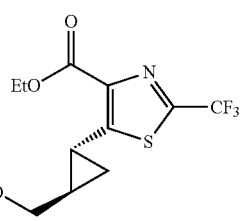

relative stereochemistry

To a oven dried vial, add ethyl (E)-4-(3-methoxyprop-1-en-1-yl)-2-(trifluoromethyl)thiazole-5-carboxylate (264 mg, 0.894 mmol) and DCM (12.8 mL). Cool to −10° C. Diethylzinc (4.5 mL, 4.47 mmol) and diiodomethane (0.721 mL, 8.94 mmol), sequentially. Allow reaction mixture to warm to room temperature and stir for 2 days. Add diethylzinc (4.5 mL, 4.47 mmol) and diiodomethane (0.72 mL, 8.94 mmol)

at 0° C. Allow reaction mixture to warm to room temperature and stir for 3 days. After 5 days, the reaction mixture was quenched with 10% HCl aq. and extracted with DCM (3×). Dry, filter and concentrate the organic layer. The crude product was added to a silica gel column and was eluted with ethyl acetate/hexane 0% to 50% to give ethyl 4-(2-(methoxymethyl)cyclopropyl)-2-(trifluoromethyl)thiazole-5-carboxylate (51 mg, 18% yield) as an oil.

Examples 394 and 395 Step c

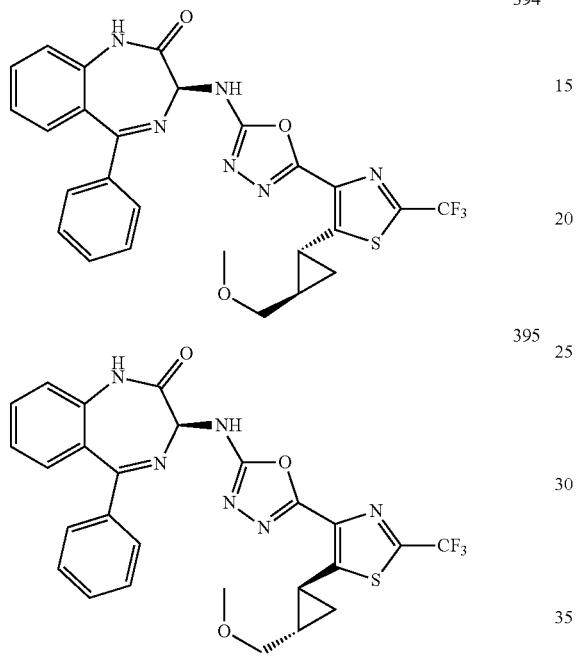

relative trans stereochemistry mixture of isomers 394 and 395

Examples 394 and 395 was prepared using a procedure similar to that used to prepare Example 21 where ethyl 4-(2-(methoxymethyl)cyclopropyl)-2-(trifluoromethyl)thiazole-5-carboxylate was converted to it's corresponding hydrazide, similar to that described in Example 152 step b, and was used in place of tetrahydro-2H-pyran-4-carbohydrazide. The racemic mixture was purified by chiral separation to give the desired compound as a mixture of trans isomers with respect to the cyclopropane. (Column=YMC CHIRAL Cellulose-SB, 250*20 mm (5 uM); Mobile Phase=50% EtOH/50% hexanes; Flow rate=20 mL/min). ESI MS m/z=555.1 [M+H]$^+$.

Example 396

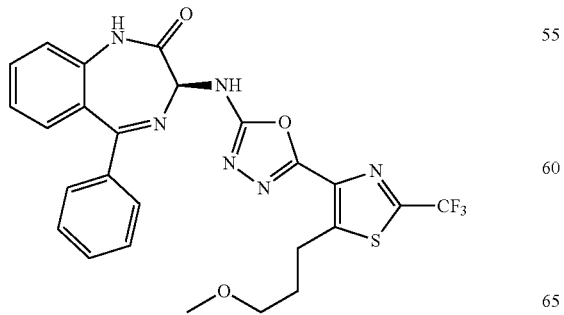

Example 397

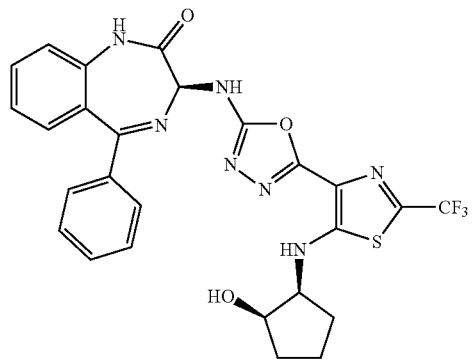 [SMILES: O=C1Nc2ccccc2C(c2ccccc2)=N[C@@H]1Nc1nnc(-c2nc(C(F)(F)F)sc2N[C@H]2CCC[C@H]2O)o1]

Example 398

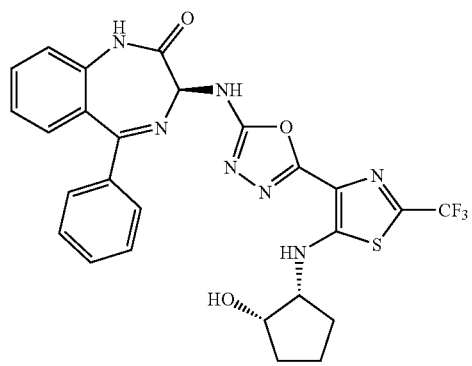 [SMILES: O=C1Nc2ccccc2C(c2ccccc2)=N[C@@H]1Nc1nnc(-c2nc(C(F)(F)F)sc2N[C@@H]2CCC[C@@H]2O)o1]

Example 399

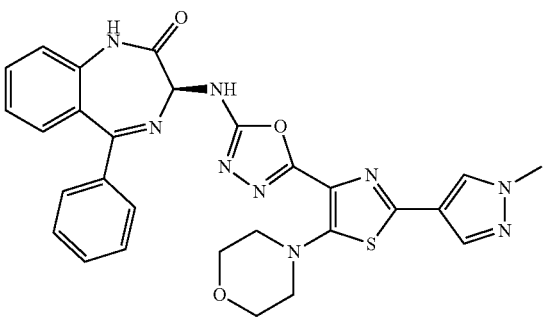 [SMILES: Cn1cc(-c2nc(-c3nnc(N[C@H]4N=C(c5ccccc5)c5ccccc5NC4=O)o3)c(N3CCOCC3)s2)cn1]

Example 399 Step a

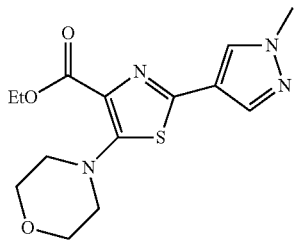 [SMILES: CCOC(=O)c1nc(-c2cnn(C)c2)sc1N1CCOCC1]

A solution of ethyl 2-bromo-5-morpholinothiazole-4-carboxylate, prepared in Example 385, (1.0 g, 3.13 mmol), 1-methyl-1H-pyrazol-4-ylboronic acid (976 mg, 4.69 mmol), Cs$_2$CO$_3$ (863 mg, 6.25 mmol) and Pd(dppf)Cl$_2$ (511 mg, 0.63 mmol) was dissolved in DMF (20 mL), then the mixture was stirred at 90° C. overnight. It was concentrated, and purified by silica gel chromatography with PE:EA=1:1 to obtain ethyl 2-(1-methyl-1H-pyrazol-4-yl)-5-morpholinothiazole-4-carboxylate as a light yellow solid (211 mg, 21%). ESI MS m/z=323.3 [M+H]$^+$.

Example 399 Step b

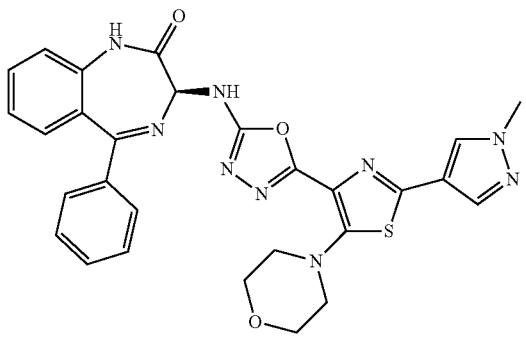 [SMILES: Cn1cc(-c2nc(-c3nnc(N[C@H]4N=C(c5ccccc5)c5ccccc5NC4=O)o3)c(N3CCOCC3)s2)cn1]

Example 399 was prepared using a procedure similar to that used to prepare Example 152 where ethyl 2-(1-methyl-1H-pyrazol-4-yl)-5-morpholinothiazole-4-carboxylate was used in place of ethyl 2-morpholino-4-(trifluoromethyl)benzoate. ESI MS m/z=568.5 [M+H]$^+$. $^1$H NMR (300 MHz, DMSO-d$_6$) δ 3.17-3.02 (m, 4H), 3.77-3.67 (m, 4H), 3.91 (s, 3H), 5.16 (d, 1H), 7.40-7.23 (m, 3H), 7.59-7.40 (m, 5H), 7.69 (m, 1H), 7.87 (d, 1H), 8.29 (s, 1H), 9.13 (d, 1H), 10.98 (s, 1H).

Example 400

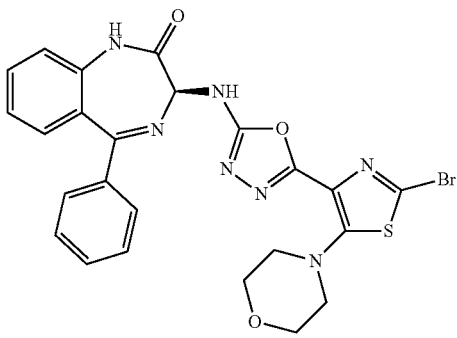 [SMILES: O=C1Nc2ccccc2C(c2ccccc2)=N[C@@H]1Nc1nnc(-c2nc(Br)sc2N2CCOCC2)o1]

Example 400 was prepared using a procedure similar to that used to prepare Example 21 where ethyl 2-bromo-5-morpholinothiazole-4-carboxylate was converted to the corresponding hydrazide, similar to that described in Example 152 step b, and used in place of tetrahydro-2H-pyran-4-carbohydrazide. ESI MS m/z=568.3 [M+H]$^+$. $^1$H NMR (400 MHz, DMSO-d$_6$) δ 3.13 (m, 4H), 3.71 (d, 4H), 5.15 (d, 1H), 7.28 (m, 1H), 7.41-7.32 (m, 2H), 7.59-7.42 (m, 5H), 7.68 (m, 1H), 9.16 (d, 1H), 10.97 (s, 1H).

Example 401

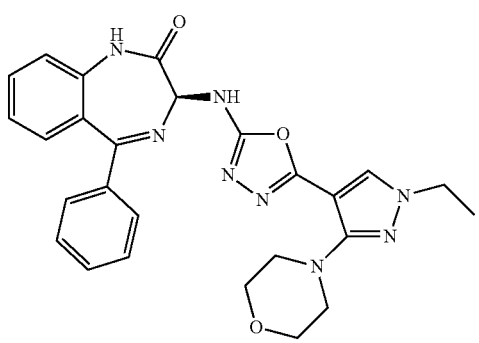 [SMILES: CCn1cc(-c2nnc(N[C@H]3N=C(c4ccccc4)c4ccccc4NC3=O)o2)c(N2CCOCC2)n1]

Example 401 Step a

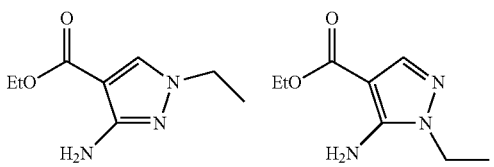

NaH (360 mg, 0.015 mol) was added to the solution of ethyl 3-amino-1H-pyrazole-4-carboxylate (2 g, 0.013 mol) in MeCN (30 mL) at 0° C. The mixture was stirred for 20 minutes at 0° C. Bromoethane (1.67 g, 0.015 mol) was added and the mixture was stirred overnight. The solution was quenched with water, concentrated. The crude product was purified via silica gel chromatography (DCM-MeOH) to give the mixture as yellow oil (1.25 g, 53%). ESI MS m/z=184.3 [M+H]$^+$.

Example 401 Step b

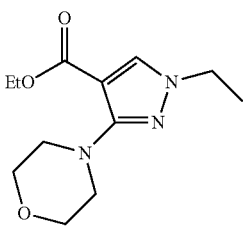

A solution of the mixture from step 1 (1.25 g, 6.8 mmol), 1-bromo-2-(2-bromoethoxy)ethane (3.1 g, 13.6 mmol), Cs$_2$CO$_3$ (4.44 g, 13.6 mmol) in DMA (20 mL) was stirred overnight at 100° C. The mixture was diluted with water, extracted with EA (×3). The organic layers were combined and washed with brine (×2), dried and concentrated. The residue was purified by reverse phase C18 column chromatography (MeCN/H₂O) to give ethyl 1-ethyl-3-morpholino-1H-pyrazole-4-carboxylate as white solid (580 mg, 34%). ESI MS m/z=254.3 [M+H]⁺.

Example 401 Step c

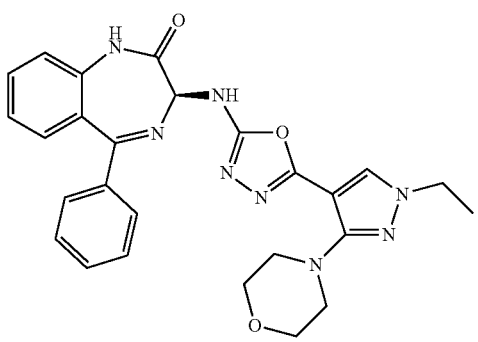 [SMILES: CCn1cc(-c2nnc(N[C@H]3N=C(c4ccccc4)c4ccccc4NC3=O)o2)c(N2CCOCC2)n1]

Example 401 was prepared using a procedure similar to that used to prepare Example 152 where ethyl 1-ethyl-3-morpholino-1H-pyrazole-4-carboxylate was used in place of ethyl 2-morpholino-4-(trifluoromethyl)benzoate. ESI MS m/z=499.4 [M+H]⁺. ¹H NMR (400 MHz, DMSO-d₆) δ 1.36 (m, 3H), 3.17 (d, J=5.3 Hz, 4H), 3.61-3.74 (m, 4H), 4.07 (m, 2H), 5.07-5.14 (m, 1H), 7.32 (m, 3H), 7.50 (m, 5H), 7.68 (m, 1H), 8.09 (d, J=2.3 Hz, 1H), 8.91 (m, 1H), 10.98 (s, 1H).

Example 402

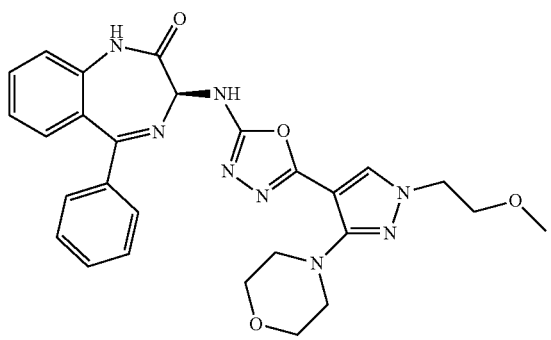 [SMILES: COCCn1cc(-c2nnc(N[C@H]3N=C(c4ccccc4)c4ccccc4NC3=O)o2)c(N2CCOCC2)n1]

Example 402 was prepared using a procedure similar to that used to prepare Example 401 where 1-bromo-2-methoxyethane was used in place of bromoethane. ESI MS m/z=529.5 [M+H]⁺. ¹H NMR (400 MHz, DMSO-d₆) δ 3.17 (m, 4H), 3.25 (s, 3H), 3.67 (m, 6H), 4.20 (m, 2H), 5.10 (d, J=8.7 Hz, 1H), 7.25-7.39 (m, 3H), 7.42-7.58 (m, 5H), 7.68 (m, 1H), 8.04 (s, 1H), 8.91 (d, J=8.7 Hz, 1H), 10.96 (s, 1H).

Example 403

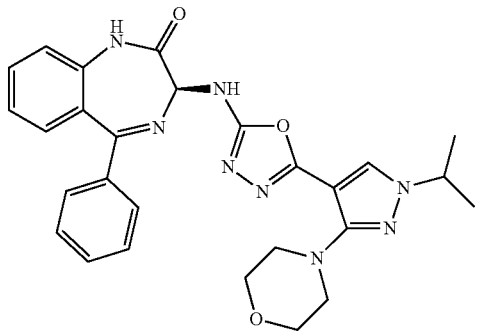 [SMILES: CC(C)n1cc(-c2nnc(N[C@H]3N=C(c4ccccc4)c4ccccc4NC3=O)o2)c(N2CCOCC2)n1]

Example 403 Step a

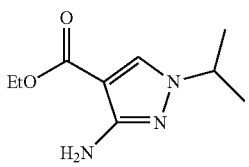

A solution of 3-amino-1-isopropyl-1H-pyrazole-4-carboxylic acid (1 g, 6 mmol) and H₂SO₄ (2 mL) in EtOH (5 mL) was refluxed for 5 hours. The solution was concentrated, adjusted pH=8 with saturated aqueous Na₂CO₃, extracted with EA (×3). The organic layers were combined, dried, concentrated to give desired 1.09 g (crude) as orange oil, that was used directly in the next step. ESI MS m/z=198.3 [M+H]⁺.

Example 403 Step b

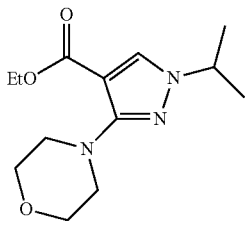 [SMILES: CCOC(=O)c1cn(C(C)C)nc1N1CCOCC1]

A solution of the compound from step a (1.09 g, 5.5 mmol), 1-bromo-2-(2-bromoethoxy)ethane (2.5 g, 11 mmol) and Cs₂CO₃ (3.6 g, 11 mmol) in DMA (10 mL) was stirred overnight at 100° C. The solution was diluted with water, extracted with EA (×3), washed with brine (×2). The organic layer was dried, concentrated. The residue was purified via silica gel chromatography (PE-EA) to give ethyl 1-isopropyl-3-morpholino-1H-pyrazole-4-carboxylate as orange oil (1 g, 67%). ESI MS m/z=268.4 [M+H]⁺.

Example 403 Step c

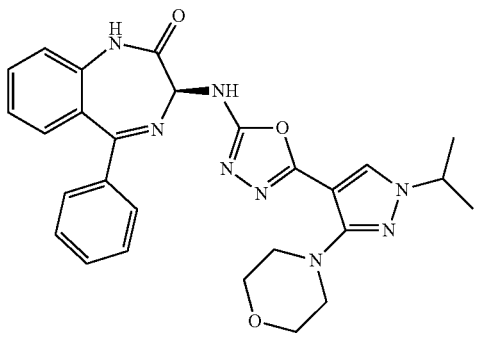 [SMILES: CC(C)n1cc(-c2nnc(N[C@H]3N=C(c4ccccc4)c4ccccc4NC3=O)o2)c(N2CCOCC2)n1]

Example 403 was prepared using a procedure similar to that used to prepare Example 152 where ethyl 1-isopropyl-3-morpholino-1H-pyrazole-4-carboxylate was used in place of ethyl 2-morpholino-4-(trifluoromethyl)benzoate. ESI MS m/z=513.4 [M+H]$^+$. $^1$H NMR (400 MHz, DMSO-d$_6$) δ 1.41 (d, J=6.6 Hz, 6H), 3.10-3.19 (m, 4H), 3.67 (m, 4H), 4.43 (m, 1H), 5.10 (d, J=8.7 Hz, 1H), 7.25-7.37 (m, 3H), 7.43-7.56 (m, 5H), 7.67 (m, 1H), 8.07 (s, 1H), 8.87 (d, J=8.7 Hz, 1H), 10.96 (s, 1H).

Example 404

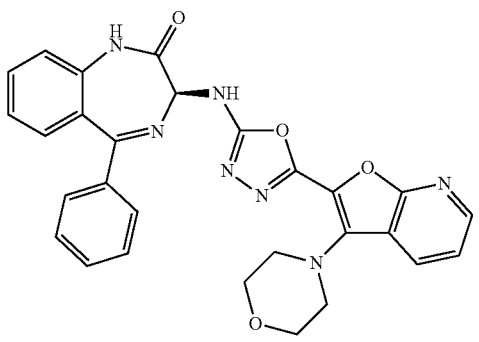 [SMILES: O=C1Nc2ccccc2C(c2ccccc2)=N[C@@H]1Nc1nnc(-c2oc3ncccc3c2N2CCOCC2)o1]

Example 404 Step a

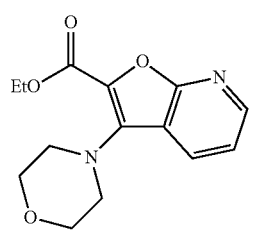 [SMILES: CCOC(=O)c1oc2ncccc2c1N1CCOCC1]

A solution of the ethyl 3-aminofuro [2, 3-b] pyridine-2-carboxylate (500 mg, 2.42 mmol) in DMF (10 mL) was added NaH (387 mg, 9.68 mmol). It was stirred at rt for 10 mins and then the 1-bromo-2-(2-bromoethoxy)ethane (1.67 g, 7.28 mmol) was added. The solution was stirred at rt for 2 hours. Then H$_2$O (20 mL) was added to the mixture and extracted with EA (×3). The organic layer was dried and purified by reverse phase C18 column chromatography to give ethyl 3-morpholinofuro[2,3-b]pyridine-2-carboxylate as yellow solid (310 mg, 46%). ESI MS m/z=276.9 [M+H]$^+$.

Example 404 Step b

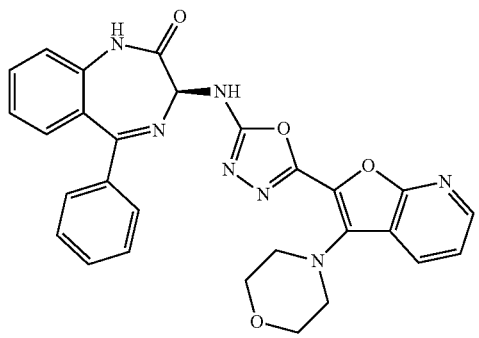 [SMILES: O=C1Nc2ccccc2C(c2ccccc2)=N[C@@H]1Nc1nnc(-c2oc3ncccc3c2N2CCOCC2)o1]

Example 404 was prepared using a procedure similar to that used to prepare Example 152 where ethyl 3-morpholinofuro[2,3-b]pyridine-2-carboxylate was used in place of ethyl 2-morpholino-4-(trifluoromethyl)benzoate. ESI MS m/z=522.2 [M+H]$^+$. $^1$H NMR (400 MHz, DMSO-d$_6$) δ 3.36-3.39 (m, 4H), 3.73-3.76 (m, 4H), 5.18-5.20 (d, J=8.0, 1H), 7.27-7.31 (m, 1H), 7.36-7.38 (m, 2H), 7.40-7.43 (m, 1H), 7.45-7.49 (m, 2H), 7.52-7.56 (m, 3H), 7.67-7.71 (m, 1H), 8.42-8.46 (m, 2H), 9.39-9.41 (d, J=8.0, 1H), 11.02 (s, 1H).

Example 405

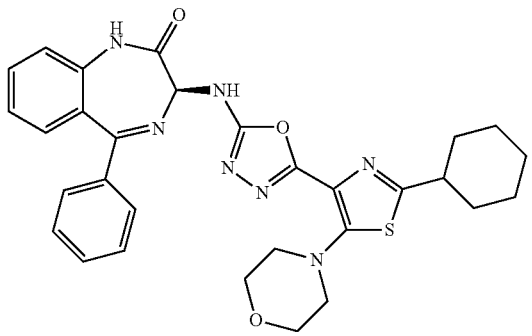 [SMILES: O=C1Nc2ccccc2C(c2ccccc2)=N[C@@H]1Nc1nnc(-c2nc(C3CCCCC3)sc2N2CCOCC2)o1]

Example 405 Step a

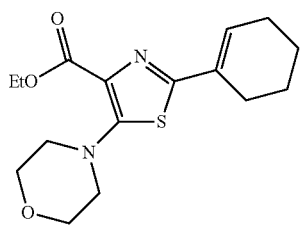 [SMILES: CCOC(=O)c1nc(C2=CCCCC2)sc1N1CCOCC1]

A solution of ethyl 2-bromo-5-morpholinothiazole-4-carboxylate, prepared in Example 385, (700 mg, 2.19 mmol), cyclohexenylboronic acid (303 mg, 2.41 mmol), K$_2$CO$_3$ (604 mg, 4.38 mmol) and Pd(dppf)Cl$_2$ (160 mg, 0.219 mmol) was dissolved in DMF (5 mL), then the mixture was stirred at 100° C. overnight. It was concentrated, and purified by silica gel chromatography with PE:EA=5:1 to obtain a yellow oil (571 mg, 81%). ESI MS m/z=322.6 [M+H]$^+$.

Example 405 Step b

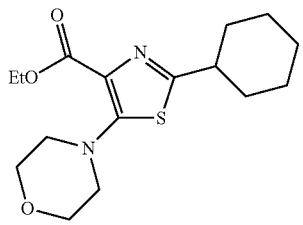 [SMILES: CCOC(=O)c1nc(C2CCCCC2)sc1N1CCOCC1]

A solution of the compound from step a (700 mg, 2.19 mmol), cyclohexenylboronic acid (303 mg, 2.41 mmol), K$_2$CO$_3$ (604 mg, 4.38 mmol) and Pd(dppf)Cl$_2$ (160 mg, 0.22 mmol) was dissolved in DMF (5 mL), then the mixture was stirred at 100° C. overnight. It was concentrated, and purified by silica gel column with PE:EA=5:1 to obtain ethyl 2-cyclohexyl-5-morpholinothiazole-4-carboxylate as a yellow oil (571 mg, 81%). ESI MS m/z=324.6 [M+H]$^+$.

Example 405 Step c

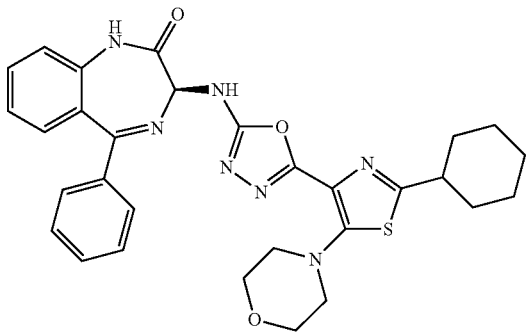 [SMILES: O=C1Nc2ccccc2C(c2ccccc2)=N[C@@H]1Nc1nnc(-c2nc(C3CCCCC3)sc2N2CCOCC2)o1]

Example 405 was prepared using a procedure similar to that used to prepare Example 152 where ethyl 2-cyclohexyl-5-morpholinothiazole-4-carboxylate was used in place of ethyl 2-morpholino-4-(trifluoromethyl)benzoate. ESI MS m/z=570.5 [M+H]$^+$. $^1$H NMR (300 MHz, DMSO-d$_6$) δ 1.55-1.16 (m, 5H), 1.90-1.63 (m, 3H), 2.04 (d, 2H), 3.15-3.00 (m, 4H), 3.82-3.61 (m, 4H), 5.15 (d, 1H), 7.43-7.23 (m, 3H), 7.62-7.43 (m, 5H), 7.68 (m, 1H), 9.08 (d, 1H), 10.97 (s, 1H).

Example 406

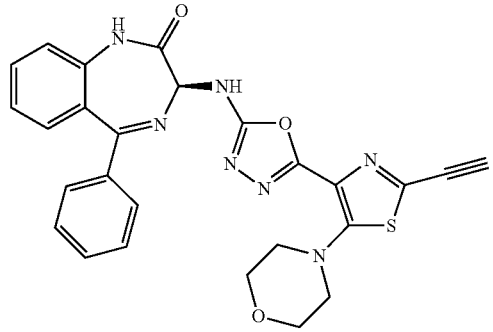 [SMILES: C#Cc1nc(-c2nnc(N[C@H]3N=C(c4ccccc4)c4ccccc4NC3=O)o2)c(N2CCOCC2)s1]

Example 406 Step a

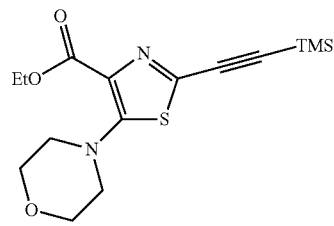 [SMILES: CCOC(=O)c1nc(C#C[Si](C)(C)C)sc1N1CCOCC1]

A solution of the compound from step a (2.0 g, 6.25 mmol), ethynyltrimethylsilane (1420 mg, 12.50 mmol), Pd(PPh$_3$)Cl$_2$ (439 mg, 0.62 mmol), PPh$_3$ (3.28 g, 12.50 mmol) and TEA (5 mL) in THF (50 mL) was stirred at rt for 20 mins. Then CuI (2.4 g, 12.50 mmol) was added to the solution and stirred at 65° C. for 2 hours. Then H$_2$O (20 mL) was added to the mixture and extracted with EA (×3). The organic layer was dried and purified by reverse phase C18 column chromatography to give desired compound as yellow oil (1.25 g, 59%). ESI MS m/z=339.0 [M+H]$^+$.

Example 406 Step b

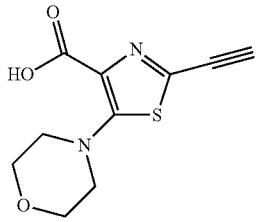 [SMILES: C#Cc1nc(C(=O)O)c(N2CCOCC2)s1]

A solution of the compound from step a (1.25 g, 3.70 mmol), LiOH (444 mg, 18.49 mmol) in H$_2$O (10 mL), THF (10 mL) was stirred at rt for 5 hours and the solution was adjusted pH value to 10. It was purified by reverse phase C18 column chromatography to give the desired compound as yellow solid (580 mg, 66%). ESI MS m/z=238.9 [M+H]$^+$.

Example 406 Step c

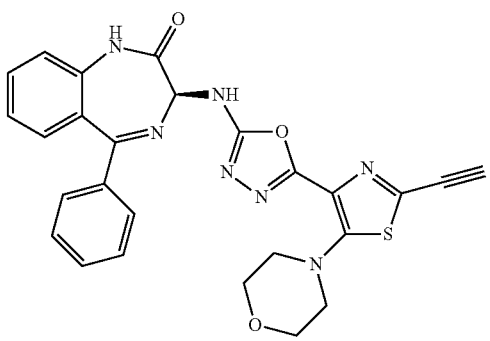 [SMILES: C#Cc1nc(-c2nnc(N[C@H]3N=C(c4ccccc4)c4ccccc4NC3=O)o2)c(N2CCOCC2)s1]

Example 406 was prepared using a procedure similar to that used to prepare Example 151 where 2-ethynyl-5-morpholinothiazole-4-carboxylic acid was used in place of 6-fluoro-2-morpholinonicotinic acid. ESI MS m/z=512.1 [M+H]+. 1H NMR (400 MHz, DMSO-d6) δ 3.17-3.20 (m, 4H), 3.71-3.73 (m, 4H), 4.91 (s, 1H), 5.14-5.16 (d, J=8.0, 1H), 7.26-7.28 (m, 1H), 7.30-7.36 (m, 2H), 7.45-7.48 (m, 2H), 7.51-7.55 (m, 3H), 7.65-7.69 (m, 1H) 9.17-9.19 (d, J=8.0, 1H), 10.97 (s, 1H).

Example 407

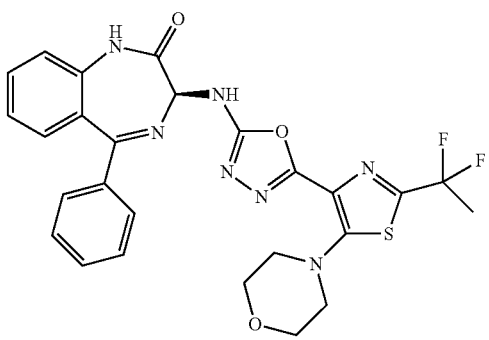 [SMILES: CC(F)(F)c1nc(-c2nnc(N[C@H]3N=C(c4ccccc4)c4ccccc4NC3=O)o2)c(N2CCOCC2)s1]

Example 407 Step a

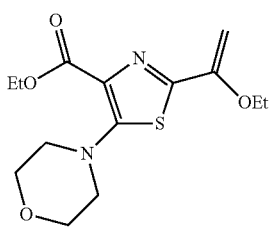 [SMILES: C=C(OCC)c1nc(C(=O)OCC)c(N2CCOCC2)s1]

To a stirring solution of ethyl 2-bromo-5-morpholinothiazole-4-carboxylate, prepared in Example 385, (400 mg, 1.25 mmol) in toluene (10 mL) was added tributyl(1-ethoxyvinyl)stannane (905 mg, 2.5 mmol) and Pd(PPh3)4 (40 mg, 0.001 mmol) at rt under the nitrogen. The mixture was refluxed for 2.5 hours at 110° C. under the nitrogen and then concentrated. The reaction mixture was poured into water and extracted with EA (3*100 ml). The organic was dried over Na2SO4. The residue was purified by silica gel chromatography (PE/EA=3/1) to give the desired compound as a white solid (300 mg, 77%). ESI MS m/z=313.2 [M+H]+.

Example 407 Step b

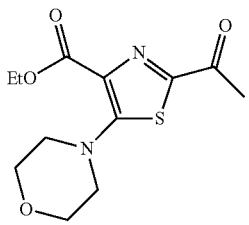 [SMILES: CCOC(=O)c1nc(C(C)=O)sc1N1CCOCC1]

The solution of compound from step a (300 mg, 0.96 mmol) was added to the HCl (5 mL) in the dioxane (8 ml) at r.t. The resulting solution was stirred at rt for 5 hrs. The reaction mixture was poured into saturated NaHCO3 liquid and extracted with EA (3*100 mL). The organic layer was dried over Na2SO4 and purified to give the desired compound product as a white solid (150 mg, 54%). ESI MS m/z=285.4 [M+H]+.

Example 407 Step c

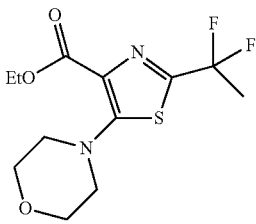 [SMILES: CCOC(=O)c1nc(C(C)(F)F)sc1N1CCOCC1]

To a stirring solution of the BAST (2 mL, 1.04 mmol) in DCM (5 mL) was added compound from step b (150 mg, 0.52 mmol) at rt. The resulting solution was stirred at rt for 3 days. During the period, additional BAST (5 mL) was added. The reaction mixture was poured into ice water and extracted with DCM (3*100 mL). The organic layer was dried over Na2SO4 and purified by silica gel chromatography (PE/EA=1/1) to give ethyl 2-(1,1-difluoroethyl)-5-morpholinothiazole-4-carboxylate as a yellow solid (160 mg, 100%). ESI MS m/z=307.1 [M+H]+.

Example 407 Step d

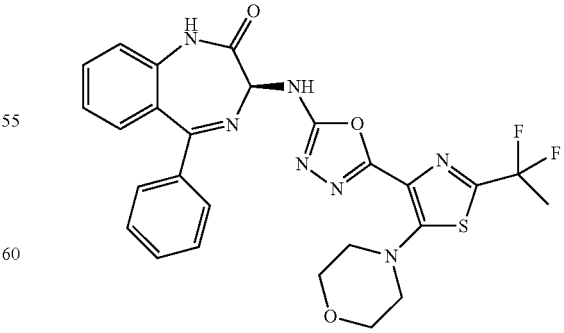

Example 407 was prepared using a procedure similar to that used to prepare Example 152 where ethyl 2-(1,1-difluoroethyl)-5-morpholinothiazole-4-carboxylate was used in place of ethyl 2-morpholino-4-(trifluoromethyl)benzoate. ESI MS m/z=552.2 [M+H]⁺. ¹H NMR (300 MHz, DMSO-d₆) δ1.24 (1H, s), 2.12 (3H, t), 3.20 (4H, m), 3.74 (4H, m), 5.15 (1H, d), 7.32 (3H, m), 7.50 (5H, m), 7.67 (1H, m), 9.20 (1H, d), 10.98 (1H, s)

Example 408

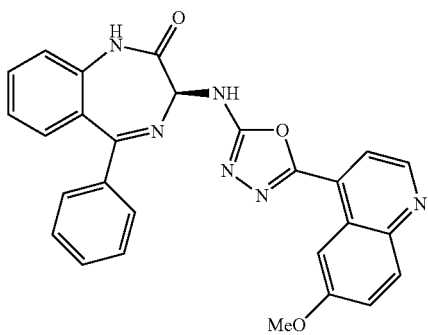 [SMILES: COc1ccc2nccc(-c3nnc(N[C@H]4N=C(c5ccccc5)c5ccccc5NC4=O)o3)c2c1]

Example 408 Step a

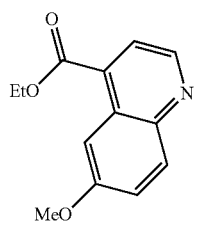 [SMILES: CCOC(=O)c1ccnc2ccc(OC)cc12]

A solution of 6-methoxyquinoline-4-carboxylic acid (500 mg, 2.46 mmol) and H₂SO₄ (2 mL) in EtOH (10 mL) was stirred at 80° C. for 2 hours. Then H₂O (20 mL) was added to the mixture and extracted with EA (×3). The organic layer was washed with NaHCO₃, brine and dried over Na₂SO₄ to give ethyl 6-methoxyquinoline-4-carboxylate as yellow solid (450 mg, 79%). ESI MS m/z=231.9 [M+H]⁺.

Example 408 Step b

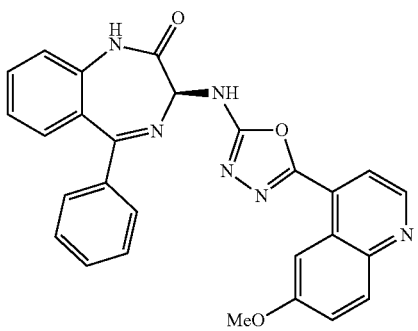 [SMILES: COc1ccc2nccc(-c3nnc(N[C@H]4N=C(c5ccccc5)c5ccccc5NC4=O)o3)c2c1]

Example 408 was prepared using a procedure similar to that used to prepare Example 152 where ethyl 6-methoxyquinoline-4-carboxylate was used in place of ethyl 2-morpholino-4-(trifluoromethyl)benzoate. ESI MS m/z=477.1 [M+H]⁺. ¹H NMR (400 MHz, DMSO-d₆) δ 3.91 (s, 3H), 5.26 (s, 1H), 7.29-7.32 (m, 1H), 7.37-7.39 (m, 2H), 7.45-7.49 (m, 2H), 7.51-7.54 (m, 4H), 7.68-7.72 (m, 1H), 7.85-7.86 (m, 1H), 8.04-8.06 (m, 1H), 8.56-8.57 (m, 1H), 8.91-8.93 (m, 1H), 9.52 (m, 1H), 10.93-10.94 (s, 1H).

Example 409

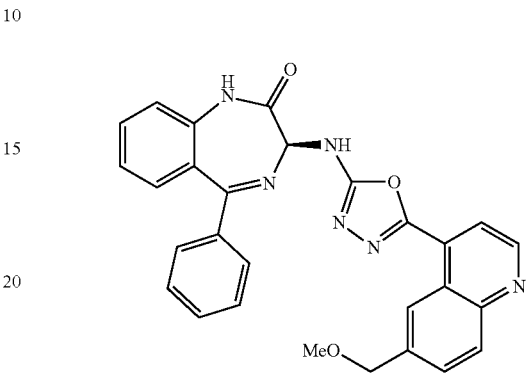

Example 409 Step a

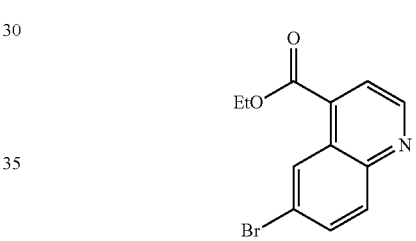

A solution of 6-bromoquinoline-4-carboxylic acid (500 mg, 2.0 mmol), EtOH (10 mL) and H₂SO₄ (2 mL) was stirred for 4 hours at 80° C. It was diluted with H₂O, and extracted with EA (×3) and washed with brine (×2). The organic layers was combined and concentrated to give a brown solid product (420 mg, 75%) that was used without further purification. ESI MS m/z=280.2 [M+H]⁺.

Example 409 Step b

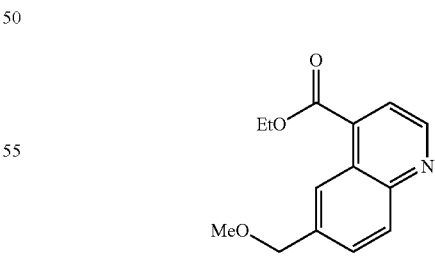

A solution of from step a (767 mg, 2.75 mmol), potassium trifluoro(methoxymethyl)borate (1.25 g, 8.25 mmol), Pd(OAc)₂ (123 mg, 0.55 mmol), RuPhos (513 mg, 1.1 mmol), and Cs₂CO₃ (2.68 g, 8.25 mmol) was dissolved in degassed CPME (4.0 mL) and H₂O (1.0 mL), then the mixture was stirred at 100° C. overnight under N₂. It was concentrated, and purified by silica gel chromatography with PE:EA=5:1 to obtain ethyl 6-(methoxymethyl)quinoline-4-carboxylate as an orange oil (206 mg, 30%). ESI MS m/z=245.5 [M+H]+.

Example 409 Step c

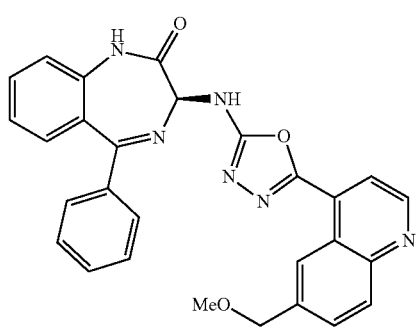 [SMILES: COCc1ccc2nccc(-c3nnc(N[C@H]4N=C(c5ccccc5)c5ccccc5NC4=O)o3)c2c1]

Example 409 was prepared using a procedure similar to that used to prepare Example 152 where ethyl 6-(methoxymethyl)quinoline-4-carboxylate was used in place of ethyl 2-morpholino-4-(trifluoromethyl)benzoate. ESI MS m/z=491.4 [M+H]+. $^1$H NMR (300 MHz, DMSO-$d_6$) δ 3.33 (s, 3H), 4.67 (s, 2H), 5.28 (d, 1H), 7.28-7.44 (m, 2H), 7.44-7.60 (m, 6H), 7.71 (m, 1H), 7.82-7.90 (m, 2H), 8.13 (d, 1H), 9.01-9.14 (m, 2H), 9.54 (d, 1H), 11.06 (s, 1H).

Example 410

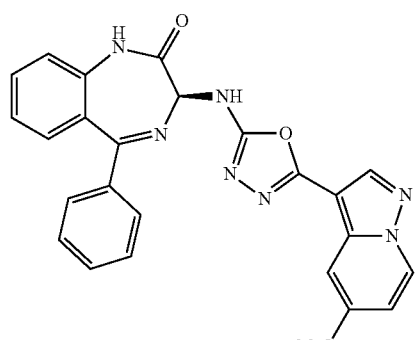

Example 410 was prepared using a procedure similar to that used to prepare Example 152 where ethyl 5-methoxypyrazolo[1,5-a]pyridine-3-carboxylate was used in place of ethyl 2-morpholino-4-(trifluoromethyl)benzoate. ESI MS m/z=466.2 [M+H]+. $^1$H NMR (300 MHz, DMSO-$d_6$) δ 3.92 (s, 3H), 5.16 (d, J=8.7 Hz, 1H), 6.80 (dd, J=7.6, 2.7 Hz, 1H), 7.29 (t, J=7.6 Hz, 1H), 7.33-7.40 (m, 3H), 7.44-7.58 (m, 5H), 7.66-7.70 (m, 1H), 8.33 (s, 1H), 8.73 (d, J=7.6 Hz, 1H), 8.94 (d, J=8.7 Hz, 1H), 11.01 (s, 1H).

Example 411

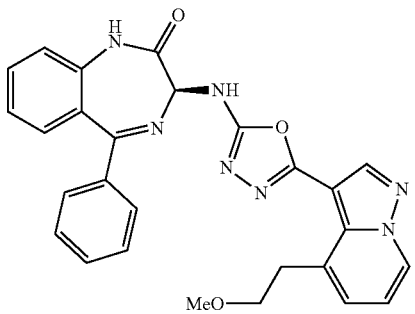 [SMILES: COCCc1cccn2ncc(-c3nnc(N[C@H]4N=C(c5ccccc5)c5ccccc5NC4=O)o3)c12]

Example 411 Step a

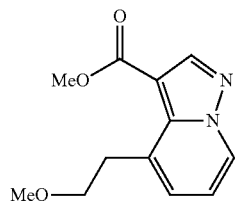 [SMILES: COCCc1cccn2ncc(C(=O)OC)c12]

A solution of methyl 4-bromopyrazolo[1,5-a]pyridine-3-carboxylate (500 mg, 1.97 mmol), potassium trifluoro(2-methoxyethyl)borate (490 mg, 1.28 mmol), RuPhos (734 mg, 1.58 mmol), Pd(OAc)$_2$ (177 mg, 0.79 mmol) and Cs$_2$CO$_3$ (1.92 g, 5.91 mmol) in CPME (8 mL) and water (2 mL) was stirred for 5 hours at 100° C. under N$_2$. The mixture was diluted with water, extracted with EA (×3), the organic layer was dried, concentrated. The crude product was purified via silica gel chromatography (PE-EA) to give desired compound as yellow solid (140 mg, 30%). ESI MS m/z=235.3 [M+H]+.

Example 411 Step b

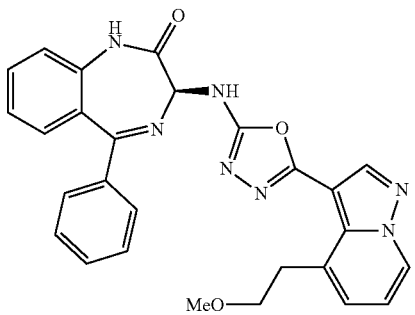 [SMILES: COCCc1cccn2ncc(-c3nnc(N[C@H]4N=C(c5ccccc5)c5ccccc5NC4=O)o3)c12]

Example 411 was prepared using a procedure similar to that used to prepare Example 152 where methyl 4-(2-methoxyethyl)pyrazolo[1,5-a]pyridine-3-carboxylate was used in place of ethyl 2-morpholino-4-(trifluoromethyl)benzoate. ESI MS m/z=494.4 [M+H]+. $^1$H NMR (400 MHz, DMSO-$d_6$) δ 3.15 (s, 2H), 3.41 (m, 2H), 3.47 (m, 2H), 5.16 (d, J=8.6 Hz, 1H), 7.06 (m, 1H), 7.26-7.34 (m, 2H), 7.36 (m, 2H), 7.43-7.63 (m, 5H), 7.68 (m, 1H), 8.36 (s, 1H), 8.74 (m, 1H), 8.94-9.06 (m, 1H), 10.99 (s, 1H).

Examples 412 and 413

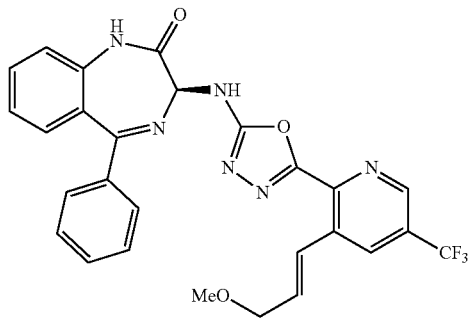
412

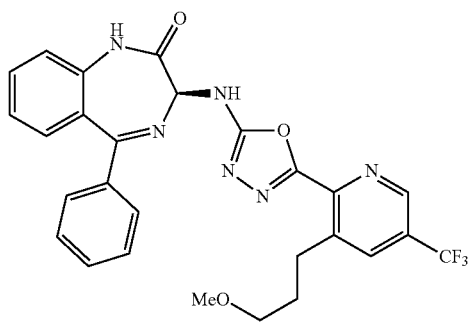
413

Examples 412 and 413 Step a

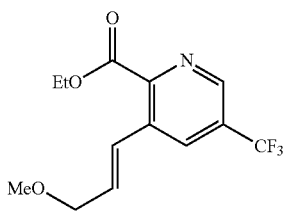 [SMILES: CCOC(=O)c1ncc(C(F)(F)F)cc1/C=C/COC]

Pd(dppf)Cl$_2$ (0.7 g, 2.15 mmol) was added to the ethyl 3-chloro-5-(trifluoromethyl)picolinate (1.64 g, 6.47 mmol), Cs$_2$CO$_3$ (2.7 g, 8.6 mmol) and (E)-3-methoxyprop-1-enyl-boronic acid (0.5 g, 4.3 mmol) in DMF (30 mL) at rt under N$_2$. The mixture was stirred for 2 hours at 100° C. The solution was diluted with EA, washed by brine. The organic phase was dried over anhydrous Na$_2$SO$_4$ and concentrated. The crude product was purified via silica gel chromatography (PE-EA) to give desired compound as yellow solid (0.53 g, 43%). ESI MS m/z=290.0 [M+H]$^+$.

Examples 412 and 413 Step b

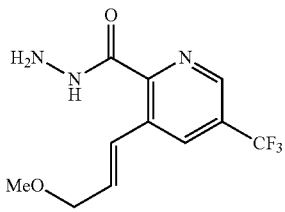
A

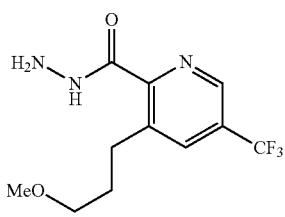
B

A solution of the compound from step a (300 mg, 1.0 mmol) and NH$_2$NH$_2$.H$_2$O (2 mL) in EtOH (5 mL) was refluxed for 2 hours. The crude product was purified by reverse phase C18 column chromatography (MeCN/H$_2$O) to give a mixture of A and B as a yellow solid (~20% of the olefin was reduced as A) (200 mg, 70%). A ESI MS m/z=276.3 [M+H]$^+$. B ESI MS m/z=278.3 [M+H]$^+$.

Examples 412 and 413 Step c

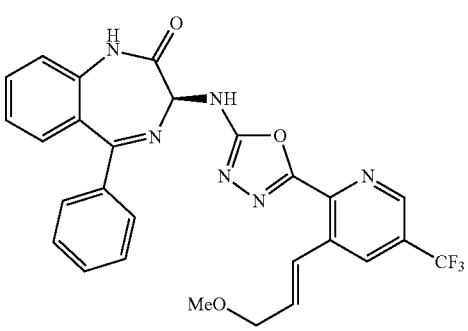
412

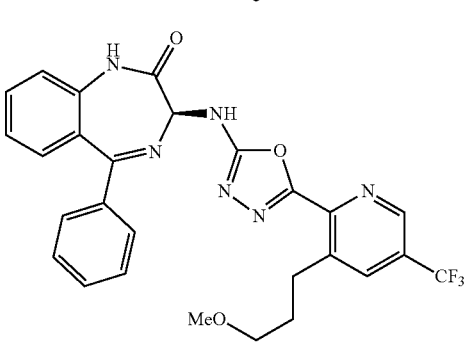
413

Examples 412 and 413 were prepared using a procedure similar to that used to prepare Example 152 where (E)-3-(3-methoxyprop-1-en-1-yl)-5-(trifluoromethyl)picolinohydrazide and 3-(3-methoxypropyl)-5-(trifluoromethyl)picolinohydrazide were used in place of 2-morpholino-4-

(trifluoromethyl)benzohydrazide. Example 418 ESI MS m/z=535.4 [M+H]+. 1H NMR (400 MHz, DMSO-d6) δ 3.32 (s, 3H), 4.11 (m, 2H), 5.22 (d, J=8.4 Hz, 1H), 6.75 (m, 1H), 7.27-7.33 (m, 1H), 7.36 (m, 2H), 7.44-7.50 (m, 2H), 7.50-7.63 (m, 4H), 7.69 (m, 1H), 8.57 (d, J=2.1 Hz, 1H), 8.95-9.10 (m, 1H), 9.50 (d, J=8.4 Hz, 1H), 11.01 (s, 1H). Example 419 ESI MS m/z=537.1 [M+H]+. 1H NMR (400 MHz, DMSO-d6) δ 1.72-1.96 (m, 2H), 3.11-3.25 (m, 4H), 3.33 (s, 3H), 5.22 (d, J=7.9 Hz, 1H), 7.25-7.32 (m, 1H), 7.33-7.41 (m, 2H), 7.43-7.50 (m, 2H), 7.50-7.60 (m, 3H), 7.68 (m, 1H), 8.27 (d, J=2.1 Hz, 1H), 8.88-9.10 (m, 1H), 9.47 (d, J=8.4 Hz, 1H), 10.99 (s, 1H).

Example 414

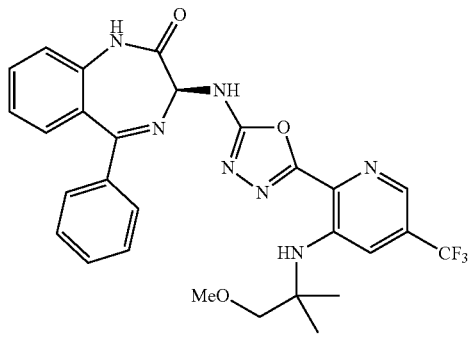 [SMILES: COCC(C)(C)Nc1cc(C(F)(F)F)cnc1-c1nnc(N[C@H]2N=C(c3ccccc3)c3ccccc3NC2=O)o1]

Examples 414 Step a

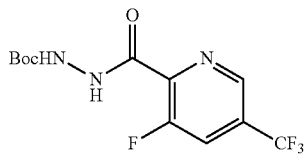

The compound 3-fluoro-5-(trifluoromethyl)picolinic acid (2.0 g, 9.56 mmol) was dissolved in DMF (8 mL) and BocNHNH2 (2.5 g, 19.12 mmol) was added, and then DIPEA (2.5 g, 19.12 mmol) and HATU (3.8 g, 10.04 mmol) were added. The mixture was stirred at rt for 1 hour. Water (30 mL) was added and the mixture was extracted with EA (50 mL×3). The combined organic phase was dried over anhydrous Na2SO4 and concentrated. The residue was purified by reverse phase C18 column chromatography to give the desired product as a yellow solid (2.0 g, 65%).

Example 414 Step b

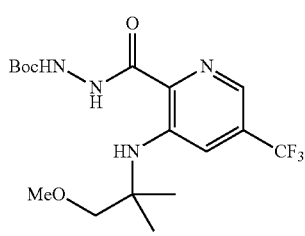 [SMILES: COCC(C)(C)Nc1cc(C(F)(F)F)cnc1C(=O)NNC(=O)OC(C)(C)C]

A solution of tert-butyl 2-(3-fluoro-5-(trifluoromethyl)picolinoyl)hydrazinecarboxylate, prepared in step a, (400 mg, 1.24 mmol) and 1-methoxy-2-methylpropan-2-amine (191 mg, 1.8 mmol) was dissolved in DMSO (10 mL). The mixture was stirred at 100° C. for 4 hours. Water (10 mL) was added and it was purified by reverse phase C18 column chromatography (MeCN/H2O) to give the desired product as a yellow solid (340 mg, 68%). ESI MS m/z=406.6 [M+H]+.

Example 414 Step c

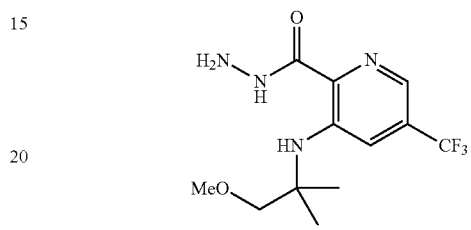

A solution of the compound from step b (340 mg, 0.84 mmol) and ZnBr2 (371 mg, 1.67 mmol) in DCM (10 mL) was stirred for one hour at RT. It was concentrated, diluted with 150 ml of EA and washed with water (×3). The organic layer was concentrated to give 1.65 g as a yellow oil. It was purified by reverse phase C18 column chromatography (MeCN/H2O) to give 200 mg of 3-((1-methoxy-2-methylpropan-2-yl)amino)-5-(trifluoromethyl)picolinohydrazide. ESI MS m/z=306.5 [M+H]+.

Example 414 Step d

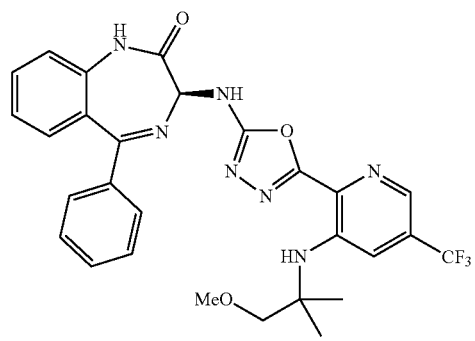 [SMILES: COCC(C)(C)Nc1cc(C(F)(F)F)cnc1-c1nnc(N[C@H]2N=C(c3ccccc3)c3ccccc3NC2=O)o1]

Example 414 was prepared using a procedure similar to that used to prepare Example 152 where 3-((1-methoxy-2-methylpropan-2-yl)amino)-5-(trifluoromethyl)picolinohydrazide was used in place of 2-morpholino-4-(trifluoromethyl)benzohydrazide. ESI MS m/z=566.5 [M+H]+. 1H NMR (300 MHz, DMSO-d6) δ 1.29-1.47 (s, 6H), 3.30-3.32 (s, 3H), 3.43-3.53 (s, 2H), 5.18-5.26 (d, J=8.2 Hz, 1H), 7.27-7.42 (m, 3H), 7.45-7.64 (m, 5H), 7.66-7.77 (m, 2H), 8.00-8.09 (s, 1H), 8.23-8.33 (d, J=1.7 Hz, 1H), 9.48-9.57 (d, J=8.4 Hz, 1H), 10.96-11.11 (s, 1H).

Example 415

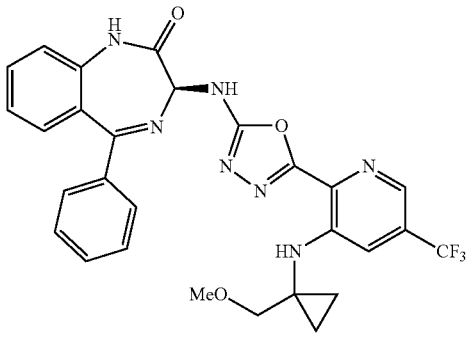 [SMILES: COCC1(Nc2cc(C(F)(F)F)cnc2-c2nnc(N[C@H]3N=C(c4ccccc4)c4ccccc4NC3=O)o2)CC1]

Example 415 was prepared using a procedure similar to that used to prepare Example 414 where 1-(methoxymethyl)cyclopropan-1-amine was used in place of 1-methoxy-2-methylpropan-2-amine. ESI MS m/z=564.2 [M+H]$^+$. $^1$H NMR (300 MHz, DMSO-d$_6$) δ 2.38 (3H, d), 2.97 (4H, dd), 3.69 (4H, t), 5.12 (1H, d), 6.90 (1H, d), 7.41 (3H, m), 7.67 (5H, m), 8.96 (1H, d), 10.96 (1H, s).

Example 416

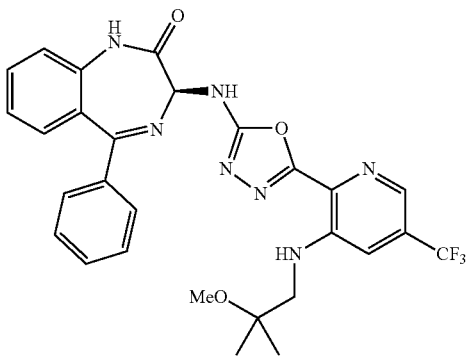 [SMILES: COC(C)(C)CNc1cc(C(F)(F)F)cnc1-c1nnc(N[C@H]2N=C(c3ccccc3)c3ccccc3NC2=O)o1]

Example 416 was prepared using a procedure similar to that used to prepare Example 414 where 2-methoxy-2-methylpropan-1-amine was used in place of 1-methoxy-2-methylpropan-2-amine. ESI MS m/z=555.4 [M+H]$^+$. H NMR (300 MHz, DMSO-d$_6$) δ 1.18 (s, 6H), 3.09 (s, 2H), 3.34 (d, J=4.7 Hz, 2H), 5.19 (d, J=8.4 Hz, 1H), 7.21-7.59 (m, 9H), 7.60-7.85 (m, 2H), 8.22 (d, J=1.8 Hz, 1H), 9.49 (d, J=8.4 Hz, 1H), 10.99 (s, 1H).

Examples 417 and 418

417

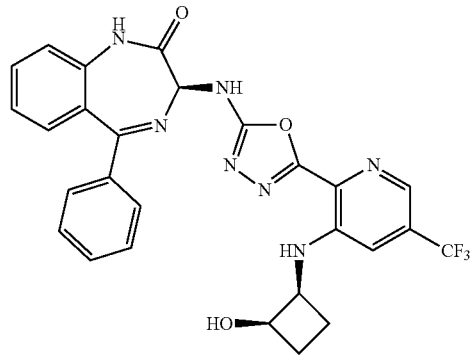

418

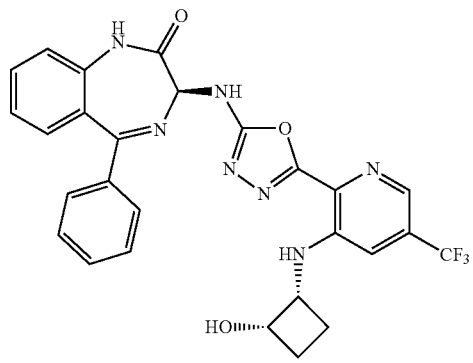

Examples 417 and 418 were prepared using a procedure similar to that used to prepare Example 414 where (cis)-2-aminocyclobutanol hydrochloride was used in place of 1-methoxy-2-methylpropan-2-amine. The crude product was purified by reverse phase C18 column chromatography and Prep-HPLC to give 417 as a yellow solid, 14 mg) and 418 as a yellow solid, 14 mg). Example 417 ESI MS m/z=550.4 [M+H]$^+$. $^1$H NMR (300 MHz, DMSO-d$_6$) δ 1.60-1.82 (m, 1H), 1.91 (m, 1H), 2.16 (d, 2H), 4.19 (s, 1H), 4.46 (s, 1H), 5.22 (d, 1H), 5.51 (d, 1H), 7.26-7.34 (m, 2H), 7.38 (m, 2H), 7.43-7.61 (m, 5H), 7.69 (m, 1H), 8.21-8.38 (m, 2H), 9.49 (d, 1H), 11.02 (s, 1H). Example 418 ESI MS m/z=550.4 [M+H]$^+$. $^1$H NMR (300 MHz, DMSO-d$_6$) δ 1.72 (m, 1H), 1.91 (m, 1H), 2.05-2.27 (m, 2H), 4.20 (s, 1H), 4.46 (s, 1H), 5.22 (d, 1H), 5.51 (d, 1H), 7.25-7.34 (m, 1H), 7.34-7.43 (m, 1H), 7.43-7.62 (m, 7H), 7.70 (m, 1H), 8.13-8.55 (m, 2H), 9.50 (d, 1H), 11.00 (s, 1H).

Example 419

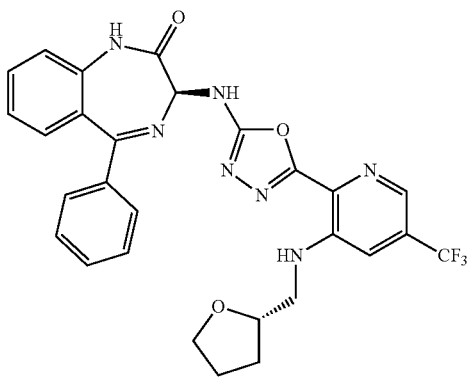 [SMILES: O=C1Nc2ccccc2C(c2ccccc2)=N[C@@H]1Nc1nnc(-c2ncc(C(F)(F)F)cc2NC[C@@H]2CCCO2)o1]

Example 419 was prepared using a procedure similar to that used to prepare Example 414 where (S)-(tetrahydrofuran-2-yl)methanamine was used in place of 1-methoxy-2-methylpropan-2-amine. ESI MS m/z=564.2 [M+H]$^+$. $^1$H NMR (400 MHz, DMSO-d$_6$) δ 1.60-1.64 (m, 1H), 1.81-1.88 (m, 2H), 1.97-2.01 (m, 1H), 3.33-3.37 (m, 1H), 3.51-3.54 (m, 1H), 3.65-3.70 (m, 1H), 3.75-3.80 (m, 1H), 4.06-4.09 (m, 1H), 5.20-5.22 (d, J=8.0, 1H), 7.27-7.29 (m, 3H), 7.32-7.38 (m, 5H), 7.45-7.49 (m, 1H), 7.51-7.54 (m, 1H), 7.61-7.86 (m, 1H), 8.25 (s, 1H), 9.51-9.54 (d, J=12.0, 1H), 10.99 (s, 1H).

Example 420

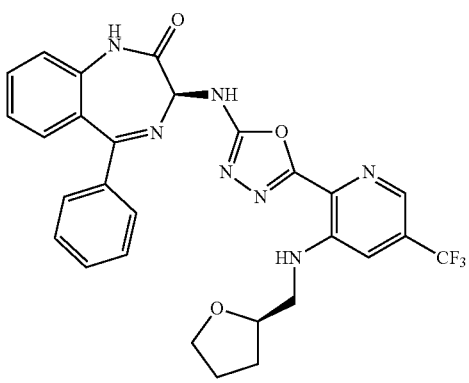 [SMILES: O=C1Nc2ccccc2C(c2ccccc2)=N[C@@H]1Nc1nnc(-c2ncc(C(F)(F)F)cc2NC[C@H]2CCCO2)o1]

Example 420 was prepared using a procedure similar to that used to prepare Example 414 where (R)-(tetrahydrofuran-2-yl)methanamine was used in place of 1-methoxy-2-methylpropan-2-amine. ESI MS m/z=564.3 [M+H]+. 1H NMR (400 MHz, DMSO-d6) δ 1.60-1.64 (m, 1H), 1.81-1.88 (m, 2H), 1.97-2.01 (m, 1H), 3.34-3.37 (m, 1H), 3.52-3.55 (m, 1H), 3.65-3.70 (m, 1H), 3.74-3.79 (m, 1H), 4.06-4.09 (m, 1H), 5.20-5.22 (d, J=8.0, 1H), 7.27-7.29 (m, 3H), 7.32-7.38 (m, 5H), 7.45-7.50 (m, 1H), 7.52-7.54 (m, 1H), 7.61-7.86 (m, 1H), 8.26 (s, 1H), 9.51-9.53 (d, J=8.0, 1H), 11.02 (s, 1H).

Example 421

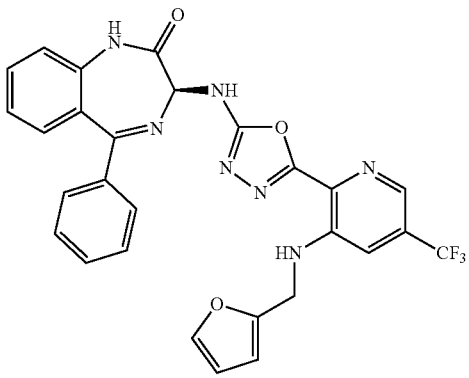 [SMILES: O=C1Nc2ccccc2C(c2ccccc2)=N[C@@H]1Nc1nnc(-c2ncc(C(F)(F)F)cc2NCc2ccco2)o1]

Example 421 was prepared using a procedure similar to that used to prepare Example 414 where furan-2-ylmethanamine was used in place of 1-methoxy-2-methylpropan-2-amine. ESI MS m/z=560.2 [M+H]+. 1H NMR (400 MHz, DMSO-d6) δ 4.66-4.68 (d, J=8.0, 1H), 5.18-5.20 (d, J=8.0, 1H), 6.40-6.42 (m, 2H), 7.25-7.28 (m, 3H), 7.30-7.36 (m, 5H), 7.43-7.70 (m, 3H), 7.99-7.02 (m, 1H), 8.30 (s, 1H), 9.51-9.54 (d, J=12.0, 1H), 11.01 (s, 1H).

Example 422

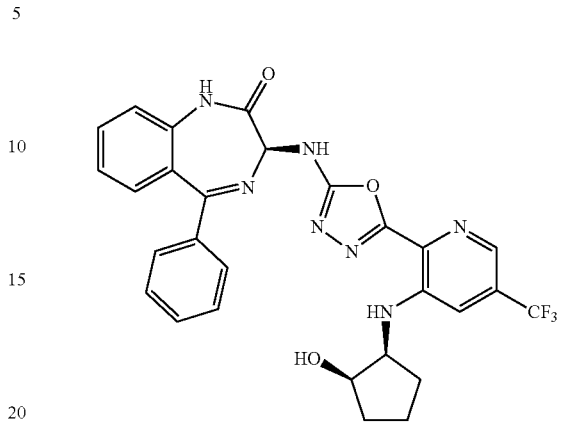

Example 422 was prepared using a procedure similar to that used to prepare Example 414 where (1R,2S)-2-aminocyclopentan-1-ol was used in place of 1-methoxy-2-methylpropan-2-amine. ESI MS m/z=564.4 [M+H]+. 1H NMR (300 MHz, DMSO-d6) δ 1.37-1.94 (m, 5H), 1.99-2.16 (m, 1H), 3.84-4.00 (m, 1H), 4.06-4.18 (dt, J=7.6, 3.6 Hz, 1H), 4.94-5.03 (d, J=4.5 Hz, 1H), 5.16-5.25 (d, J=8.4 Hz, 1H), 7.23-7.44 (m, 3H), 7.41-7.61 (m, 6H), 7.63-7.75 (ddd, J=8.3, 7.1, 1.7 Hz, 1H), 8.03-8.12 (d, J=7.4 Hz, 1H), 8.18-8.25 (m, 1H), 9.43-9.52 (d, J=8.5 Hz, 1H), 10.99-11.05 (s, 1H).

Example 423

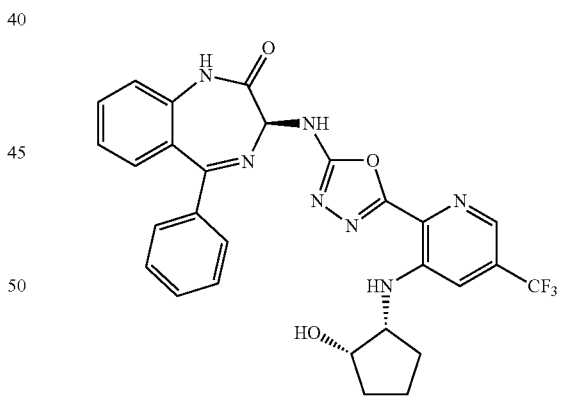

Example 423 was prepared using a procedure similar to that used to prepare Example 414 where (1S,2R)-2-aminocyclopentan-1-ol was used in place of 1-methoxy-2-methylpropan-2-amine. ESI MS m/z=564.4 [M+H]+. 1H NMR (300 MHz, DMSO-d6) δ 1.40-1.70 (m, 3H), 1.74-1.80 (s, 1H), 1.80-1.87 (s, 1H), 2.03-2.13 (m, 1H), 3.86-3.97 (t, J=6.3 Hz, 1H), 4.07-4.16 (d, J=5.4 Hz, 1H), 4.94-5.03 (d, J=4.5 Hz, 1H), 5.16-5.25 (d, J=8.4 Hz, 1H), 7.24-7.42 (m, 3H), 7.42-7.61 (m, 6H), 7.63-7.76 (ddd, J=8.6, 7.0, 1.7 Hz, 1H), 8.04-8.13 (d, J=7.5 Hz, 1H), 8.18-8.25 (d, J=1.7 Hz, 1H), 9.42-9.51 (d, J=8.4 Hz, 1H), 10.98-11.04 (s, 1H).

Example 424

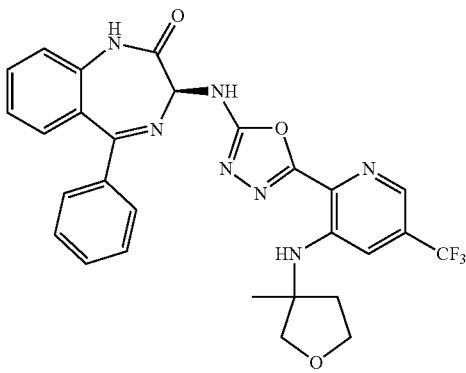 [SMILES: CC1(Nc2cc(C(F)(F)F)cnc2-c2nnc(N[C@H]3N=C(c4ccccc4)c4ccccc4NC3=O)o2)CCOC1]

Example 424 was prepared using a procedure similar to that used to prepare Example 414 where 3-methyltetrahydrofuran-3-amine was used in place of 1-methoxy-2-methylpropan-2-amine. ESI MS m/z=564.2 [M+H]⁺. H NMR (400 MHz, DMSO-d$_6$) δ 1.54 (s, 3H), 2.08 (m, 1H), 2.26 (m, 1H), 3.68 (d, J=9.3 Hz, 1H), 3.82 (m, 1H), 3.94 (m, 2H), 5.20 (d, J=8.3 Hz, 1H), 7.25-7.40 (m, 3H), 7.43-7.63 (m, 6H), 7.69 (m, 1H), 8.10 (s, 1H), 8.32 (d, J=1.8 Hz, 1H), 9.58 (d, J=8.4 Hz, 1H), 11.02 (s, 1H).

Example 425

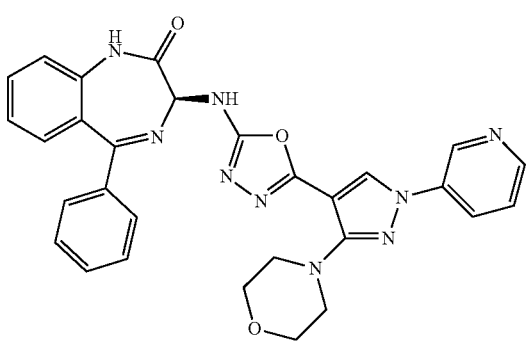 [SMILES: O=C1Nc2ccccc2C(c2ccccc2)=N[C@@H]1Nc1nnc(-c2cn(-c3cccnc3)nc2N2CCOCC2)o1]

Example 425 Step a

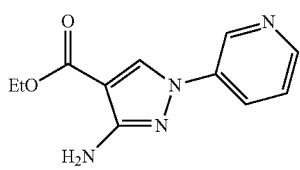 [SMILES: CCOC(=O)c1cn(-c2cccnc2)nc1N]

(E)-ethyl 2-cyano-3-ethoxyacrylate (1.37 g, 8.1 mmol) in THF (10 mL) was dropwised to the solution of 3-hydrazinylpyridine dihydrochloride (1.5 g, 8.2 mmol) and NaOEt-EtOH (10.5 g, 32.4 mmol) at 0° C. The mixture was stirred for 90 minutes at 0° C. 4 M HCl in 1,4-dioxane (8.1 mL, 32.4 mmol) was added and the solution was refluxed for 2 hours. The solution was concentrated, adjusted pH=10-13 with 1 M NaOH, extracted with EA (×3). The organic layers were combined, dried and concentrated. The crude product was purified by reverse phase C18 column chromatography (MeCN/H$_2$O) to give desired compound as an orange solid (360 mg, 19%). ESI MS m/z=233.3 [M+H]⁺. ¹H NMR (300 MHz, DMSO-d$_6$) δ 1.31 (m, 3H), 4.27 (m, 2H), 5.80 (s, 2H), 7.51 (m, 1H), 8.20 (m, 1H), 8.48 (m, 1H), 8.88 (s, 1H), 9.07 (d, J=2.6 Hz, 1H).

Example 425 Step b

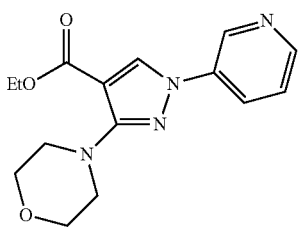 [SMILES: CCOC(=O)c1cn(-c2cccnc2)nc1N1CCOCC1]

NaH (88 mg, 2.21 mmol) was added to the solution of the compound from step a (340 mg, 1.47 mmol) in DMF (10 mL) at 0° C. The mixture was stirred for 40 minutes at 0° C. 1-bromo-2-(2-bromoethoxy)ethane (674 mg, 2.93 mmol) was added and then the solution was stirred for 3 hours at rt. The solution was quenched with water, extracted with EA (×3), washed with brine (×2). The organic layer was dried, concentrated. The residue was purified via silica gel chromatography (PE-EA) to give ethyl 3-morpholino-1-(pyridin-3-yl)-1H-pyrazole-4-carboxylate as yellow solid (180 mg, 41%). ESI MS m/z=303.3 [M+H]⁺.

Example 425 Step c

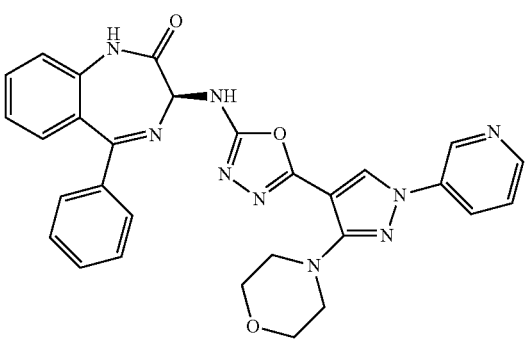 [SMILES: O=C1Nc2ccccc2C(c2ccccc2)=N[C@@H]1Nc1nnc(-c2cn(-c3cccnc3)nc2N2CCOCC2)o1]

Example 425 was prepared using a procedure similar to that used to prepare Example 152 where ethyl 3-morpholino-1-(pyridin-3-yl)-1H-pyrazole-4-carboxylate was used in place of ethyl 2-morpholino-4-(trifluoromethyl)benzoate. ESI MS m/z=548.4 [M+H]⁺. ¹H NMR (400 MHz, DMSO-d$_6$) δ 3.25-3.34 (m, 4H), 3.72 (m, 4H), 5.14 (d, J=8.6 Hz, 1H), 7.26-7.44 (m, 3H), 7.45-7.62 (m, 6H), 7.69 (m, 1H), 8.26 (m, 1H), 8.52 (m, 1H), 8.97 (s, 1H), 9.03-9.17 (m, 2H), 10.99 (s, 1H).

Example 426

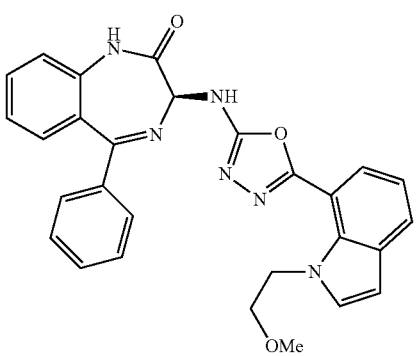 [SMILES: COCCn1ccc2cccc(-c3nnc(N[C@H]4N=C(c5ccccc5)c5ccccc5NC4=O)o3)c21]

Example 426 Step a

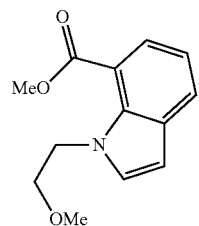 [SMILES: COCCn1ccc2cccc(C(=O)OC)c21]

A solution of methyl 1H-indole-7-carboxylate (1 g, 5.71 mmol) in DMF (30 mL) was added NaH (274 mg, 6.86 mmol) at 0° C. After stirring for 45 minutes, 1-bromo-2-methoxyethane (946 mg, 6.86 mmol) was added and stirred for 16 hours at rt. It was quenched with water, extracted with EA (×3), washed with brine (×2). The organic layer was dried, and concentrated to give the crude methyl 1-(2-methoxyethyl)-1H-indole-7-carboxylate as a yellow oil (680 mg, 51%). ESI MS m/z=233.9 [M+H]+.

Example 426 Step b

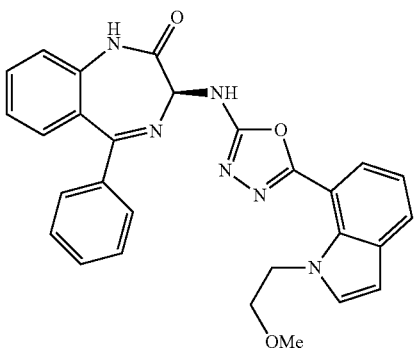 [SMILES: COCCn1ccc2cccc(-c3nnc(N[C@H]4N=C(c5ccccc5)c5ccccc5NC4=O)o3)c21]

Example 426 was prepared using a procedure similar to that used to prepare Example 152 where methyl 1-(2-methoxyethyl)-1H-indole-7-carboxylate was used in place of ethyl 2-morpholino-4-(trifluoromethyl)benzoate. ESI MS m/z=493.4 [M+H]+. 1H NMR (300 MHz, DMSO-d6) δ 3.08 (s, 3H), 3.37 (d, J=5.2 Hz, 2H), 4.54 (t, J=5.3 Hz, 2H), 5.20 (d, J=8.6 Hz, 1H), 6.61 (d, J=3.2 Hz, 1H), 7.19 (t, J=7.6 Hz, 1H), 7.26-7.33 (m, 1H), 7.34-7.57 (m, 9H), 7.69 (m, J=8.4, 7.1, 1.7 Hz, 1H), 7.80 (m, J=7.9, 1.2 Hz, 1H), 9.14 (d, J=8.6 Hz, 1H), 11.01 (s, 1H).

Example 427

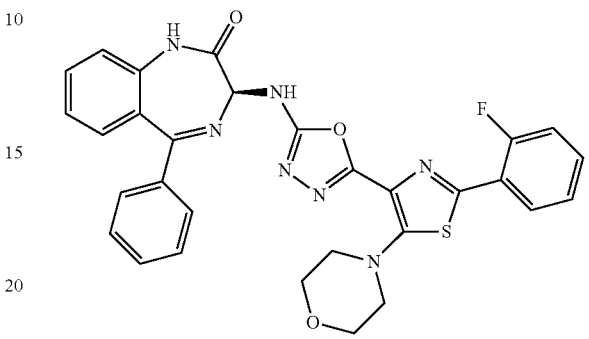

Example 427 Step a

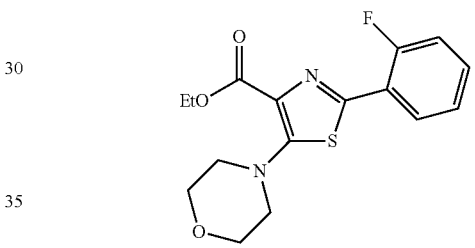

A solution of the compound from ethyl 2-bromo-5-morpholinothiazole-4-carboxylate, prepared in Example 385, (750 mg, 2.34 mmol), 2-fluorophenylboronic acid (530 mg, 3.51 mmol), Pd (dppf) Cl2 (188 mg, 0.23 mmol) and Cs2CO3 (1395 mg, 4.68 mmol) in DMF (10 mL) was stirred at 80° C. for 4 hrs. Then H2O (20 mL) was added to the mixture and extracted with EA (×3). The organic layer was dried and purified by reverse phase C18 column chromatography to give ethyl 2-(2-fluorophenyl)-5-morpholinothiazole-4-carboxylate as yellow oil (680 mg, 87%). ESI MS m/z=358.5 [M+H]+.

Example 427 Step b

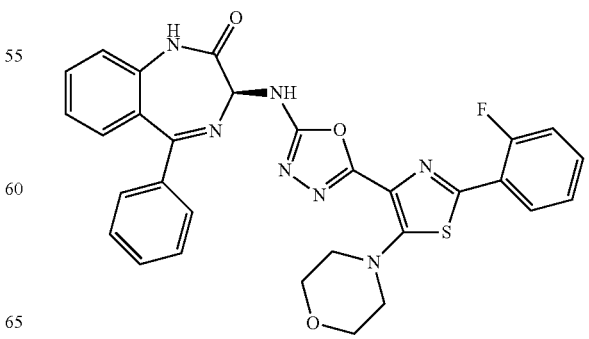

359

Example 427 was prepared using a procedure similar to that used to prepare Example 152 where ethyl 2-(2-fluorophenyl)-5-morpholinothiazole-4-carboxylate was used in place of ethyl 2-morpholino-4-(trifluoromethyl)benzoate. ESI MS m/z=582.3 [M+H]$^+$. $^1$H NMR (400 MHz, DMSO-d$_6$) δ 3.21-3.23 (m, 4H), 3.73-3.75 (m, 4H), 5.16-5.18 (d, J=8.0, 1H), 7.34-7.39 (m, 11H), 7.46-7.53 (m, 1H), 8.10-8.20 (m, 1H), 9.16-9.18 (d, J=8.0, 1H), 10.99 (s, 1H).

Example 428

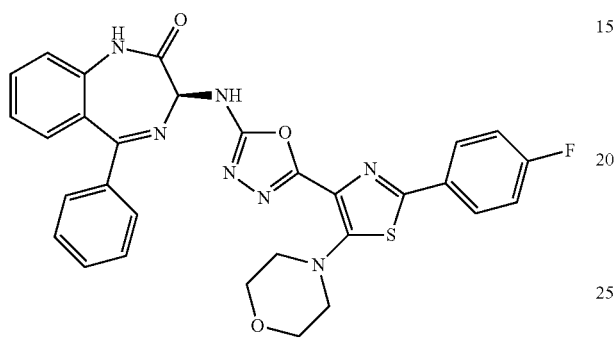

Example 428 was prepared using a procedure similar to that used to prepare Example 390 where 4-fluorophenylboronic acid was used in place of 6-(trifluoromethyl)pyridin-3-ylboronic acid. ESI MS m/z=582.2 [M+H]$^+$. $^1$H NMR (400 MHz, DMSO-d$_6$) δ 3.16-3.18 (m, 4H), 3.73-3.75 (m, 4H), 5.15-5.17 (d, J=8.0, 1H), 7.34-7.38 (m, 5H), 7.46-7.48 (m, 6H), 7.51-7.53 (m, 1H), 7.90-7.94 (m, 2H), 9.15-9.17 (d, J=8.0, 1H), 10.99 (s, 1H).

Example 429

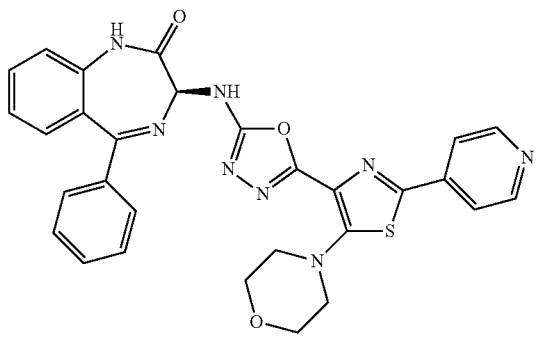 [SMILES: O=C1Nc2ccccc2C(c2ccccc2)=N[C@@H]1Nc1nnc(-c2nc(-c3ccncc3)sc2N2CCOCC2)o1]

Example 429 was prepared using a procedure similar to that used to prepare Example 390 where 4-pyridylboronic acid was used in place of 6-(trifluoromethyl)pyridin-3-ylboronic acid. ESI MS m/z=565.2 [M+H]$^+$. $^1$H NMR (400 MHz, DMSO-d$_6$) δ 3.23-3.26 (m, 4H), 3.75-3.76 (m, 4H), 5.16-5.19 (d, J=12.0, 1H), 7.35-7.38 (m, 1H), 7.47-7.50 (m, 2H), 7.52-7.54 (m, 5H), 7.80 (m, 1H), 7.82 (m, 2H), 8.70-8.72 (m, 2H), 9.20-9.30 (m, 1H), 10.99 (s, 1H).

360

Example 430

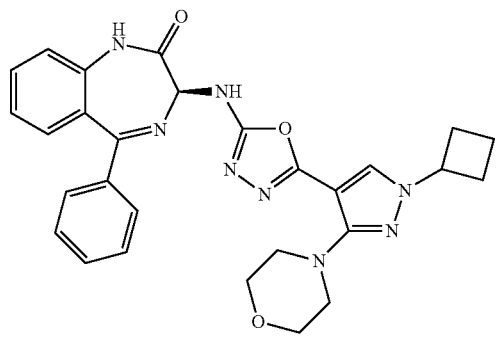 [SMILES: O=C1Nc2ccccc2C(c2ccccc2)=N[C@@H]1Nc1nnc(-c2cn(C3CCC3)nc2N2CCOCC2)o1]

Example 430 Step a

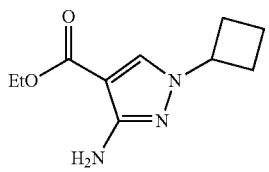 [SMILES: CCOC(=O)c1cn(C2CCC2)nc1N]

NaH (421 mg, 0.011 mol) was added to the solution of ethyl 3-amino-1H-pyrazole-4-carboxylate (1.25 g, 0.009 mol) in DMF (5 mL) at 0° C. The mixture was stirred for 1 hour at 0° C. Bromocyclobutane (2.16 g, 0.016 mol) was added and the mixture was stirred overnight at 50° C. The solution was quenched with water, extracted with EA (×3), washed with brine (×2), the organic layer was dried, concentrated. The crude product was purified via silica gel chromatography (PE-EA) to give desired compound as colourless oil (600 mg, 33%). ESI MS m/z=210.3 [M+H]$^+$. $^1$H NMR (400 MHz, DMSO-d$_6$) δ 1.24 (m, 3H), 1.73 (m, 2H), 2.27 (m, 2H), 2.34-2.50 (m, 2H), 4.16 (m, 2H), 4.61 (m, 1H), 5.38 (s, 2H), 7.95 (s, 1H).

Example 430 Step b

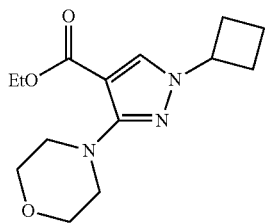 [SMILES: CCOC(=O)c1cn(C2CCC2)nc1N1CCOCC1]

A solution of the compound from step a (600 mg, 2.87 mmol), 1-bromo-2-(2-bromoethoxy)ethane (1.32 g, 5.74 mmol), Cs$_2$CO$_3$ (1.87 g, 5.74 mmol) in DMA (10 mL) was stirred overnight at 100° C. The mixture was diluted with water, extracted with EA (×3). The organic layers were combined and washed with brine (×2), dried and concentrated. The residue was purified via silica gel chromatography (PE-EA) to give ethyl 1-cyclobutyl-3-morpholino-1H-pyrazole-4-carboxylate as yellow oil (590 mg, 74%). ESI MS m/z=280.3 [M+H]⁺.

Example 430 Step c

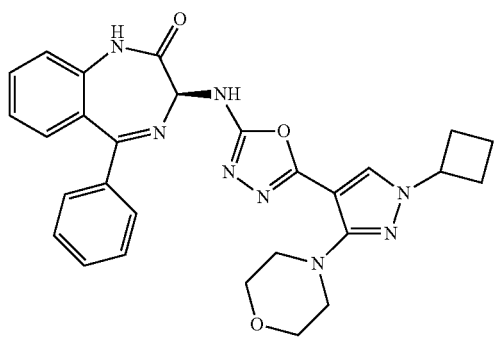 [SMILES: O=C1Nc2ccccc2C(c2ccccc2)=N[C@@H]1Nc1nnc(-c2cn(C3CCC3)nc2N2CCOCC2)o1]

Example 430 was prepared using a procedure similar to that used to prepare Example 152 where ethyl 1-cyclobutyl-3-morpholino-1H-pyrazole-4-carboxylate was used in place of ethyl 2-morpholino-4-(trifluoromethyl)benzoate. ESI MS m/z=525.5 [M+H]⁺. ¹H NMR (400 MHz, DMSO-d₆) δ 1.75 (m, 2H), 2.28-2.37 (m, 2H), 2.42-2.48 (m, 2H), 3.13-3.21 (m, 4H), 3.67 (m, 4H), 4.79 (m, 1H), 5.10 (d, J=8.7 Hz, 1H), 7.25-7.31 (m, 1H), 7.32-7.37 (m, 2H), 7.44-7.56 (m, 5H), 7.67 (m, 1H), 8.13 (s, 1H), 8.89 (d, J=8.7 Hz, 1H), 10.96 (s, 1H).

Example 431

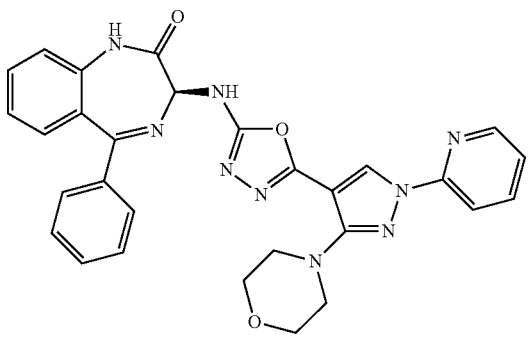 [SMILES: O=C1Nc2ccccc2C(c2ccccc2)=N[C@@H]1Nc1nnc(-c2cn(-c3ccccn3)nc2N2CCOCC2)o1]

Example 431 was prepared using a procedure similar to that used to prepare Example 430 where 2-hydrazinylpyridine dihydrochloride was used in place of 3-hydrazinylpyridine dihydrochloride. ESI MS m/z=548.3 [M+H]⁺. ¹H NMR (300 MHz, DMSO-d₆) δ 3.32-3.40 (m, 4H), 5.14 (d, J=8.5 Hz, 1H), 7.24-7.39 (m, 4H), 7.42-7.57 (m, 5H), 7.67 (m, 1H), 7.84 (m, 1H), 8.00 (m, 1H), 8.45-8.51 (m, 1H), 8.79 (s, 1H), 9.02 (d, J=8.5 Hz, 1H), 10.98 (s, 1H).

Example 432

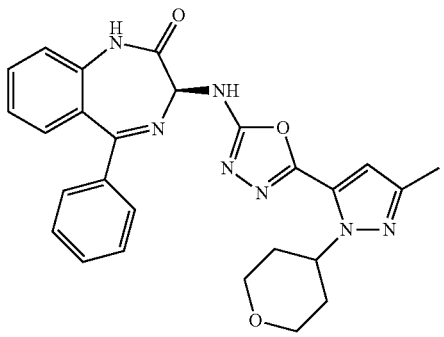 [SMILES: Cc1cc(-c2nnc(N[C@H]3N=C(c4ccccc4)c4ccccc4NC3=O)o2)n(C2CCOCC2)n1]

Example 432 Step a

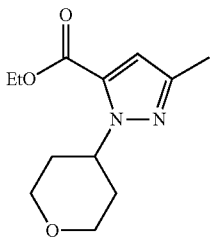

A solution of the compound 4-iodo-tetrahydro-2H-pyran (3.18 g, 15 mmol) was added to ethyl 3-methyl-1H-pyrazole-5-carboxylate (770 mg, 5 mmol) and Cs₂CO₃ in DMF (30 mL) was stirred for 18 hours at 60° C. It was quenched by H₂O (50 mL) and extracted with EA (3×), dried Na₂SO₄, filtered and purified by reverse phase C18 column chromatography (MeCN/H₂O) to give ethyl 3-methyl-1-(tetrahydro-2H-pyran-4-yl)-1H-pyrazole-5-carboxylate as a brown oil. (143 mg, 12%).

Example 432 Step b

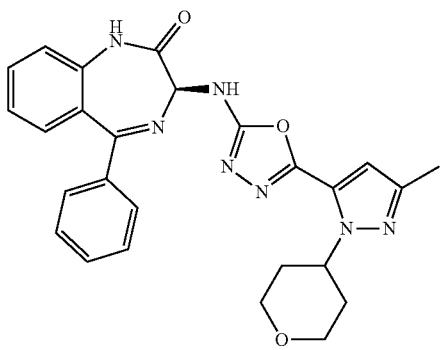 [SMILES: Cc1cc(-c2nnc(N[C@H]3N=C(c4ccccc4)c4ccccc4NC3=O)o2)n(C2CCOCC2)n1]

Example 432 was prepared using a procedure similar to that used to prepare Example 152 where ethyl 3-methyl-1-(tetrahydro-2H-pyran-4-yl)-1H-pyrazole-5-carboxylate was used in place of ethyl 2-morpholino-4-(trifluoromethyl)benzoate. ESI MS m/z=484.2 [M+H]⁺. ¹H NMR (300 MHz, Methanol-d4) δ 1.88-2.02 (m, 2H), 2.14-2.35 (m, 5H), 3.58 (m, 2H), 4.08 (m, 2H), 5.19-5.36 (m, 2H), 6.63 (s, 1H), 7.25-7.62 (m, 8H), 7.68 (m, 1H).

Example 433

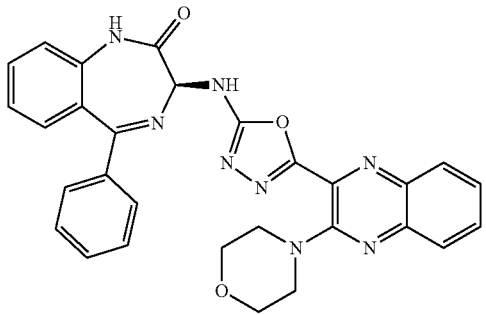 [SMILES: O=C1Nc2ccccc2C(c2ccccc2)=N[C@@H]1Nc1nnc(-c2nc3ccccc3nc2N2CCOCC2)o1]

Example 433 Step a

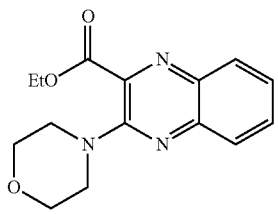 [SMILES: CCOC(=O)c1nc2ccccc2nc1N1CCOCC1]

A solution of ethyl 3-chloroquinoxaline-2-carboxylate (500 mg, 2.12 mmol) in morpholine (5 mL was stirred for 1 hour at 100° C. It was diluted with water, extracted with EA (×3), washed with brine (×2). The organic layer was dried and concentrated to give 450 mg (crude) of desired compound as yellow oil, which was used directly in the next step without further purification. ESI MS m/z=287.5 [M+H]$^+$.

Example 433 Step b

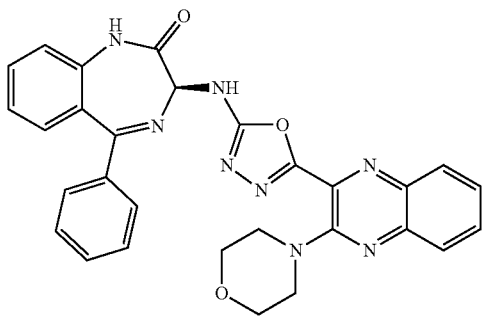 [SMILES: O=C1Nc2ccccc2C(c2ccccc2)=N[C@@H]1Nc1nnc(-c2nc3ccccc3nc2N2CCOCC2)o1]

Example 433 was prepared using a procedure similar to that used to prepare Example 152 where ethyl 3-morpholinoquinoxaline-2-carboxylate was used in place of ethyl 2-morpholino-4-(trifluoromethyl)benzoate. ESI MS m/z=533.4 [M+H]$^+$. $^1$H NMR (300 MHz, DMSO-d$_6$) δ 3.33-3.49 (m, 4H), 3.76 (t, J=4.6 Hz, 4H), 5.25 (d, J=8.4 Hz, 1H), 7.25-7.43 (m, 3H), 7.44-7.63 (m, 5H), 7.63-7.77 (m, 2H), 7.77-7.91 (m, 2H), 7.98-8.06 (m, 1H), 9.54 (d, J=8.5 Hz, 1H), 11.02 (s, 1H).

Example 434

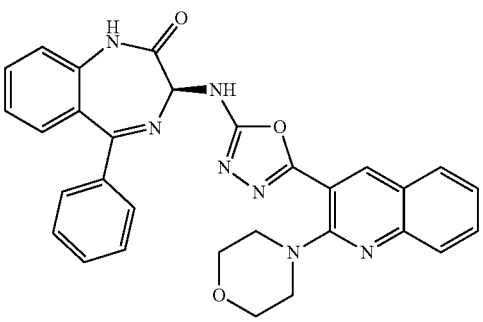 [SMILES: O=C1Nc2ccccc2C(c2ccccc2)=N[C@@H]1Nc1nnc(-c2cc3ccccc3nc2N2CCOCC2)o1]

Example 434 Step a

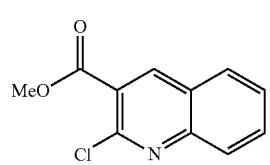 [SMILES: COC(=O)c1cc2ccccc2nc1Cl]

A solution of the compound 2-chloroquinoline-3-carboxylic acid (414 mg, 2 mmol) in MeOH (20 mL) and H$_2$SO$_4$ (1 mL) was stirred for 2 hours at 60° C. It was quenched by H$_2$O (30 mL) at 0° C. and adjusted pH to 8-9, extracted with EA (×3), dried Na$_2$SO$_4$, filtered to give desired compound as a yellow solid (354 mg, 80%). ESI MS m/z=222.2 [M+H]$^+$.

Example 435 Step b

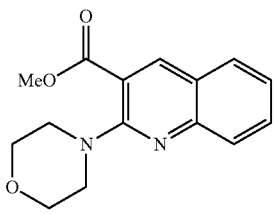 [SMILES: COC(=O)c1cc2ccccc2nc1N1CCOCC1]

A solution of the compound from step a (1.06 g, 3 mmol) in morpholine (20 mL) was stirred for 1 hour at 100° C. Extracted with EA (×3), dried Na$_2$SO$_4$, filtered to give desired compound as a light yellow solid (326 mg, 75%). ESI MS m/z=273.3 [M+H]$^+$.

Example 434 Step c

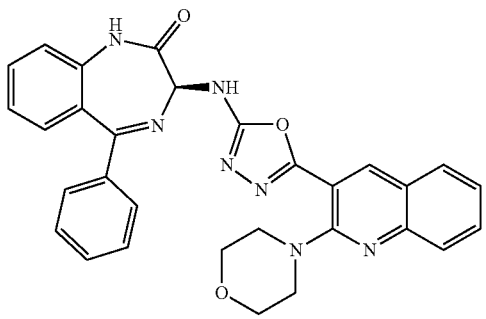

Example 434 was prepared using a procedure similar to that used to prepare Example 152 where methyl 2-morpholinoquinoline-3-carboxylate was used in place of ethyl 2-morpholino-4-(trifluoromethyl)benzoate. ESI MS m/z=532.3 [M+H]$^+$. $^1$H NMR (300 MHz, DMSO-d6) δ 3.12-3.30 (m, 4H), 3.73 (m, 4H), 5.18 (d, J=8.5 Hz, 1H), 7.21-7.59 (m, 9H), 7.60-7.80 (m, 3H), 7.94 (d, J=8.0 Hz, 1H), 8.58 (s, 1H), 9.24 (d, J=8.7 Hz, 1H), 10.98 (s, 1H).

Example 435

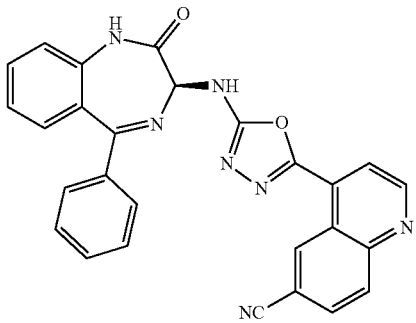 [SMILES: N#Cc1ccc2nccc(-c3nnc(N[C@H]4N=C(c5ccccc5)c5ccccc5NC4=O)o3)c2c1]

Example 435 Step a

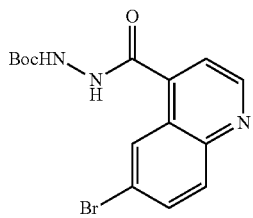 [SMILES: CC(C)(C)OC(=O)NNC(=O)c1ccnc2ccc(C#N)cc12]

6-bromoquinoline-4-carboxylic acid (502 mg, 2.0 mmol), tert-butyl hydrazinecarboxylate (528 mg, 4.0 mmol), HATU (836 mg, 2.2 mmol), DIPEA (774 mg, 6.0 mmol) in DMF (5 mL) was stirred for 6 hours at rt. The solution was quenched with water, extracted with EA (×3), washed with brine (×2), the organic layer was dried, concentrated. The crude product was purified via silica gel chromatography (PE-EA) to give the desired compound as yellow solid (680 mg, 93%). ESI MS m/z=367.9 [M+H]$^+$.

Example 435 Step b

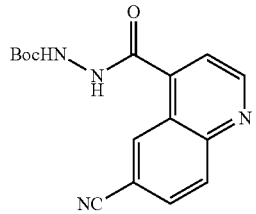

A solution of the compound from step a (680 mg, 1.86 mmol), Zn(CN)$_2$ (432 mg, 3.72 mmol), Pd(PPh$_3$)$_4$ (215 mg, 0.18 mmol) in DMF (5 mL) was stirred for 2 hours at 120° C. The mixture was diluted with water, extracted with EA (×3). The organic layers were combined and washed with brine (×2), dried and concentrated. The residue was purified via silica gel chromatography (PE-EA) to give tert-butyl 2-(6-cyanoquinoline-4-carbonyl)hydrazine-1-carboxylate as yellow oil (435 mg, 75%). ESI MS m/z=313.0 [M+H]$^+$.

Example 435 Step c

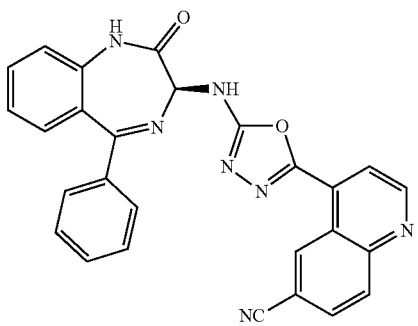 [SMILES: N#Cc1ccc2nccc(-c3nnc(N[C@H]4N=C(c5ccccc5)c5ccccc5NC4=O)o3)c2c1]

Example 435 was prepared using a procedure similar to that used to prepare Example 151 where tert-butyl 2-(6-cyanoquinoline-4-carbonyl)hydrazine-1-carboxylate was used in place of tert-butyl 2-(6-fluoro-2-morpholinonicotinoyl)hydrazine-1-carboxylate. ESI MS m/z=472.3 [M+H]$^+$. $^1$H NMR (300 MHz, DMSO-d$_6$) δ5.26-5.29 (d, J=9.0 Hz, 1H), 7.28-7.39 (m, 3H), 7.44-7.56 (m, 5H), 7.67-7.72 (m, 1H), 8.01-8.03 (m, 1H), 8.17-8.20 (m, 1H), 8.28-8.31 (m, 1H), 9.24-9.26 (d, J=6.0 Hz, 1H), 9.61-9.66 (m, 2H), 11.06 (s, 1H).

Example 436

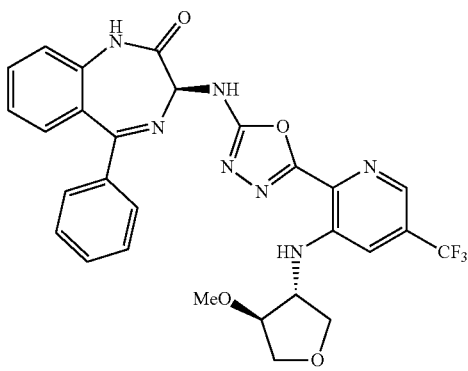

trans relative stereochemistry

Example 436 was prepared using a procedure similar to that used to prepare Example 420 where trans-4-methoxytetrahydrofuran-3-amine was used in place of 1-methoxy-2-methylpropan-2-amine. ESI MS m/z=580.1 [M+H]+. 1H NMR (300 MHz, DMSO-d6) δ 3.35 (3H, s), 3.69 (2H, m), 3.88 (2H, m), 4.05 (1H, dd), 4.33 (1H, d), 5.20 (1H, d), 7.32 (3H, m), 7.51 (5H, m), 7.67 (2H, d), 7.80 (1H, d), 8.35 (1H, d), 9.58 (1H, d), 11.02 (1H, s).

Example 437

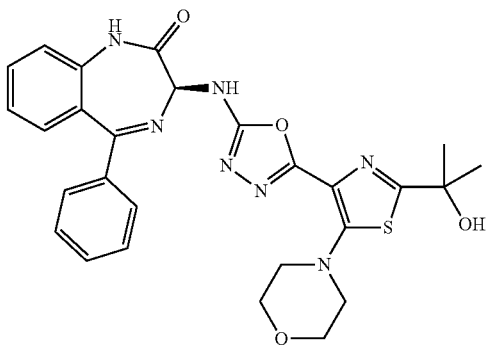 [SMILES: CC(C)(O)c1nc(-c2nnc(N[C@H]3N=C(c4ccccc4)c4ccccc4NC3=O)o2)c(N2CCOCC2)s1]

Example 437 Step a

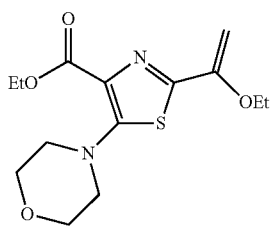 [SMILES: C=C(OCC)c1nc(C(=O)OCC)c(N2CCOCC2)s1]

To a stirring solution of ethyl 2-bromo-5-morpholinothiazole-4-carboxylate, prepared in Example 385, (400 mg, 1.25 mmol) in toluene (10 mL) was added tributyl(1-ethoxyvinyl)stannane (905 mg, 2.5 mmol) and Pd(PPh3)4 (40 mg, 0.001 mmol) at rt under the nitrogen. The mixture was refluxed for 2.5 hours at 110° C. under the nitrogen and then concentrated. The reaction mixture was poured into water and extracted with EA (3×100 mL). The organic was dried over Na2SO4. The residue was purified by silica gel chromatography (PE/EA=3/1) to give the desired compound as a white solid (300 mg, 77%). ESI MS m/z=313.2 [M+H]+.

Example 437 Step b

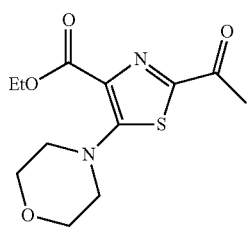 [SMILES: CCOC(=O)c1nc(C(C)=O)sc1N1CCOCC1]

The solution of compound from step a (300 mg, 0.96 mmol) was added to the HCl (5 mL) in the dioxane (8 mL) at rt. The resulting solution was stirred at rt for 5 hrs. The reaction mixture was poured into saturated NaHCO3 liquid and extracted with EA (3×100 mL). The organic layer was dried over Na2SO4 and purified to give the desired compound product as a white solid (150 mg, 55%). ESI MS m/z=285.4 [M+H]+.

Example 437 Step c

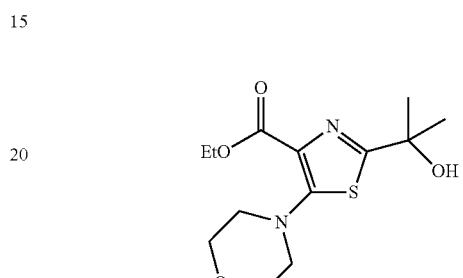

To a stirred solution of the compound from step b (200 mg, 0.7 mmol) in THF (6 mL) was added MeMgCl (0.27 ml, 0.77 mmol). The mixture was stirred at rt for 2.5 hours under the nitrogen and then concentrated. The reaction mixture was poured into ice water and extracted with EA (3×60 mL). The organic layer was dried over Na2SO4 and purified by reverse phase C18 column chromatography (ACN/H2O=1/5) to give the desired compound as a off white solid (175 mg, 83%). ESI MS m/z=301.1 [M+H]+.

Example 437 Step d

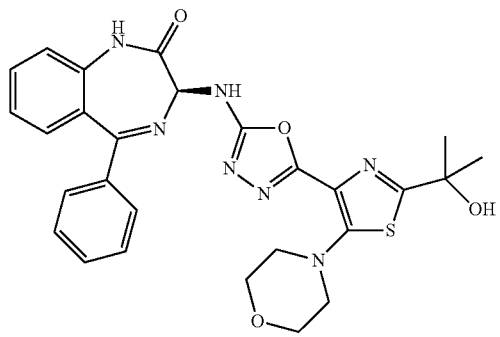 [SMILES: CC(C)(O)c1nc(-c2nnc(N[C@H]3N=C(c4ccccc4)c4ccccc4NC3=O)o2)c(N2CCOCC2)s1]

Example 437 was prepared using a procedure similar to that used to prepare Example 152 where ethyl 2-(2-hydroxypropan-2-yl)-5-morpholinothiazole-4-carboxylate was used in place of ethyl 2-morpholino-4-(trifluoromethyl)benzoate. ESI MS m/z=456.2 [M+H]+. 1H NMR (300 MHz, DMSO-d6) δ 1.48 (4H, s), 3.02 (3H, d), 3.67 (3H, d), 5.12 (1H, s), 7.32 (2H, d), 7.49 (5H, d), 8.35 (1H, d).

Example 438

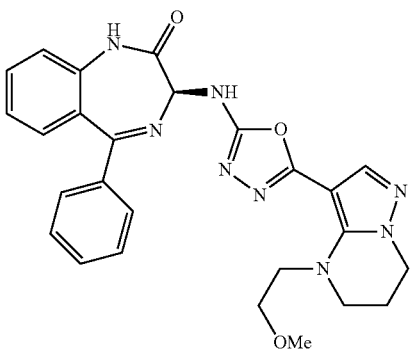 [SMILES: COCCN1CCCn2ncc(-c3nnc(N[C@H]4N=C(c5ccccc5)c5ccccc5NC4=O)o3)c21]

Example 438 Step a

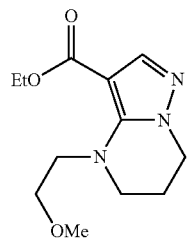 [SMILES: CCOC(=O)c1cnn2c1N(CCOC)CCC2]

NaH (61.5 mg, 1.54 mol) was added to the solution of ethyl 4,5,6,7-tetrahydropyrazolo[1,5-a]pyrimidine-3-carboxylate (250 mg, 1.28 mmol) in DMF (5 mL) at 0° C. The mixture was stirred for 1 hour at 0°. 1-Bromo-2-methoxyethane (353 mg, 2.56 mmol) was added and the mixture was stirred overnight. The solution was quenched with water, extracted with EA (×3), washed with brine (×2), the organic layer was dried, concentrated. The crude product was purified via silica gel chromatography (PE-EA) to give desired compound as yellow oil (260 mg, 80%). ESI MS m/z=254.3 [M+H]+.

Example 438 Step b

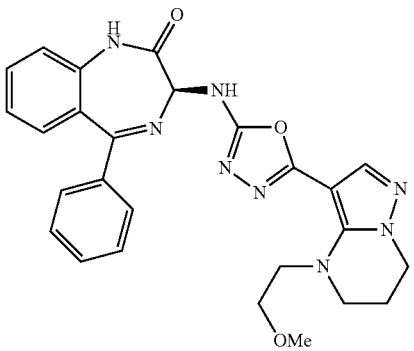 [SMILES: COCCN1CCCn2ncc(-c3nnc(N[C@H]4N=C(c5ccccc5)c5ccccc5NC4=O)o3)c21]

Example 438 was prepared using a procedure similar to that used to prepare Example 152 where ethyl 4-(2-methoxyethyl)-4,5,6,7-tetrahydropyrazolo[1,5-a]pyrimidine-3-carboxylate was used in place of ethyl 2-morpholino-4-(trifluoromethyl)benzoate. ESI MS m/z=499.5 [M+H]+. $^1$H NMR (400 MHz, DMSO-d$_6$) δ 2.03 (m, 2H), 3.18 (s, 3H), 3.37 (s, 2H), 3.41 (m, 2H), 3.79 (m, 2H), 4.02 (m, 2H), 5.09 (d, J=8.7 Hz, 1H), 7.24-7.32 (m, 1H), 7.34 (m, 2H), 7.43-7.58 (m, 6H), 7.67 (m, 1H), 8.76 (d, J=8.7 Hz, 1H), 10.95 (s, 1H).

Example 439

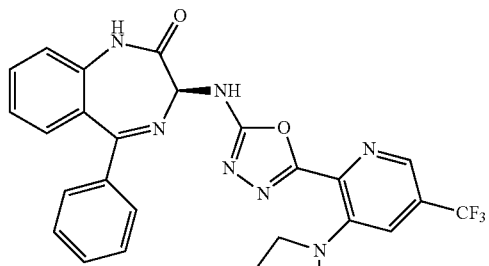

Example 439 Step a

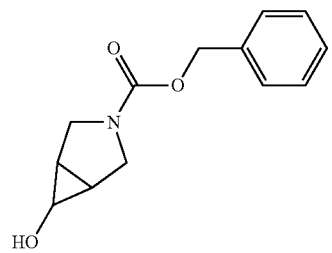 [SMILES: O=C(OCc1ccccc1)N1CC2C(O)C2C1]

3-Azabicyclo[3.1.0]hexan-6-ol (220 mg, 1.62 mmol) was dissolved in THF (5 mL) and K$_2$CO$_3$ (289.8 mg, 2.1 mmol) was added. CbzCl (360 mg, 2.1 mmol) was then added and the mixture was stirred at rt overnight. Water was added and the mixture was extracted with EA. The combined organic phase was dried over anhydrous Na$_2$SO$_4$ and concentrated. The residue was purified by silica gel chromatography (PE:EA=10:1) to give the desired product as a white solid (250 mg, 66%). ESI MS m/z=234.2 [M+H]+.

Example 439 Step b

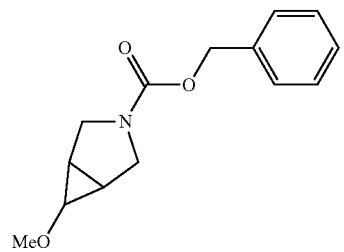 [SMILES: COC1C2CN(C(=O)OCc3ccccc3)CC21]

The compound from step a (250 mg, 1.07 mmol) was dissolved in DCM (8 mL) and cooled with ice bath. The proton sponge (689 mg, 3.21 mmol) was added and then trimethyloxonium tetrafluoroborate (238 mg, 1.6 mmol) was added. The mixture was warmed to rt and stirred overnight. Water was added and the mixture was extracted with EA. The combined organic phase was dried over anhydrous Na₂SO₄ and concentrated. The residue was purified by Prep-TLC (PE:EA=2:1) to give the desired product as a yellow oil (121 mg, 46%) and the starting material (50 mg, 0.21 mmol). ESI MS m/z=248.3 [M+H]⁺.

Example 439 Step c

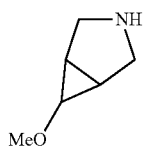

The compound from step b (121 mg, 0.49 mmol) was dissolved in MeOH (10 mL) and Pd/C (20 mg) was added. The mixture was exchanged with H₂ three times and then stirred overnight. The mixture was filtered and the filtrate was concentrated to give 6-methoxy-3-azabicyclo[3.1.0]hexane as a white solid (30 mg, 55%). There was no signal on LCMS of the product.

Example 439 Step d

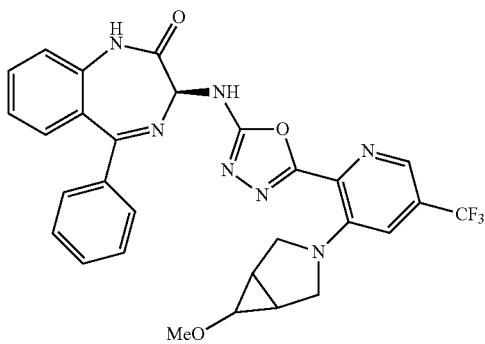 [SMILES: COC1C2CN(c3cc(C(F)(F)F)cnc3-c3nnc(N[C@H]4N=C(c5ccccc5)c5ccccc5NC4=O)o3)CC21]

Example 439 was prepared using a procedure similar to that used to prepare Example 414 where 6-methoxy-3-azabicyclo[3.1.0]hexane was used in place of 1-methoxy-2-methylpropan-2-amine. ESI MS m/z=576.5 [M+H]⁺. ¹H NMR (300 MHz, DMSO-d₆) δ ¹H NMR (300 MHz, DMSO-d₆) δ 3.24 (s, 3H), 3.26-3.31 (m, 2H), 5.20 (d, J=8.4 Hz, 1H), 7.18-7.40 (m, 3H), 7.40-7.61 (m, 6H), 7.68 (t, J=7.9 Hz, 1H), 8.37 (s, 1H), 9.26 (d, J=8.5 Hz, 1H), 11.00 (s, 1H).

Example 440

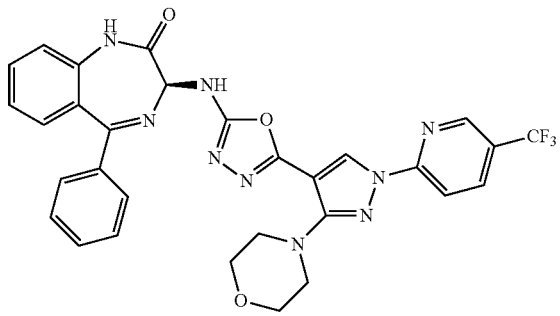 [SMILES: O=C1Nc2ccccc2C(c2ccccc2)=N[C@@H]1Nc1nnc(-c2cn(-c3ccc(C(F)(F)F)cn3)nc2N2CCOCC2)o1]

Example 440 Step a

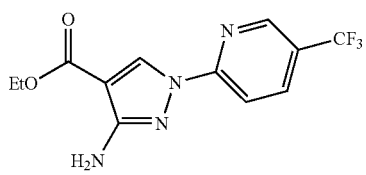 [SMILES: CCOC(=O)c1cn(-c2ccc(C(F)(F)F)cn2)nc1N]

A solution of ethyl 3-amino-1H-pyrazole-4-carboxylate (1.55 g, 0.01 mol), 2-bromo-5-(trifluoromethyl)pyridine (2.25 g, 0.01 mol), Cs₂CO₃ (6.52 g, 0.02 mol) in DMF (20 mL) was stirred for 1 hour at 100° C. The mixture was diluted with water, extracted with EA (×3). The organic layers were combined and washed with brine (×2), dried, concentrated. The crude product was purified via silica gel chromatography (PE-EA) to give desired compound as yellow solid (1.95 g, 65%). ESI MS m/z=301.2 [M+H]⁺. ¹H NMR (300 MHz, DMSO-d₆) δ 1.31 (m, 3H), 4.14-4.40 (m, 2H), 5.96 (d, J=4.0 Hz, 2H), 7.86 (m, 1H), 8.36 (m, 1H), 8.74 (d, J=3.7 Hz, 1H), 8.83 (d, J=2.8 Hz, 1H).

Example 440 Step b

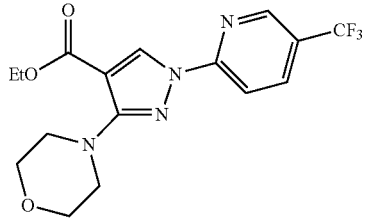 [SMILES: CCOC(=O)c1cn(-c2ccc(C(F)(F)F)cn2)nc1N1CCOCC1]

NaH (360 mg, 0.015 mol) was added to the solution of the compound from step a (1.95 g, 6.5 mmol) and 1-bromo-2-(2-bromoethoxy)ethane (1.645 g, 7.2 mmol) in DMF (20 mL) at 0° C. The mixture was stirred overnight at r.t. The mixture was quenched with water, extracted with EA (×3). The organic layers were combined and washed with brine (×2), dried and concentrated. The crude product was purified via silica gel chromatography (PE-EA) to give desired compound as yellow solid (350 mg, 15%). ESI MS m/z=371.2 [M+H]⁺.

Example 440 Step c

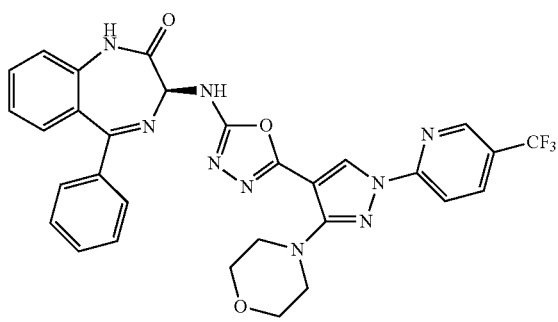 [SMILES: O=C1Nc2ccccc2C(c2ccccc2)=N[C@@H]1Nc1nnc(-c2cn(-c3ccc(C(F)(F)F)cn3)nc2N2CCOCC2)o1]

Example 440 was prepared using a procedure similar to that used to prepare Example 152 where ethyl 3-morpholino-1-(5-(trifluoromethyl)pyridin-2-yl)-1H-pyrazole-4-carboxylate was used in place of ethyl 2-morpholino-4-(trifluoromethyl)benzoate. ESI MS m/z=616.4 [M+H]$^+$. $^1$H NMR (300 MHz, DMSO-d$_6$) δ 3.39 (m, 4H), 3.67-3.85 (m, 4H), 5.16 (d, J=8.5 Hz, 1H), 7.25-7.40 (m, 3H), 7.45-7.62 (m, 5H), 7.65-7.73 (m, 1H), 8.01 (d, J=8.7 Hz, 1H), 8.41 (m, 1H), 8.87 (s, 1H), 8.88-8.96 (m, 1H), 9.10 (d, J=8.5 Hz, 1H), 11.01 (s, 1H).

Example 441

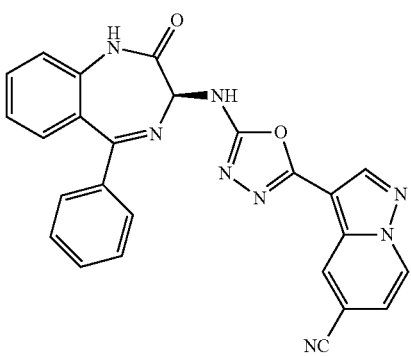 [SMILES: N#Cc1ccn2ncc(-c3nnc(N[C@H]4N=C(c5ccccc5)c5ccccc5NC4=O)o3)c2c1]

Example 441 was prepared using a procedure similar to that used to prepare Example 435 where 5-bromopyrazolo[1,5-a]pyridine-3-carboxylic acid was used in place of 6-bromoquinoline-4-carboxylic acid. ESI MS m/z=461.3 [M+H]$^+$. $^1$H NMR (300 MHz, DMSO-d$_6$) δ5.18-5.20 (d, J=6.0 Hz, 1H), 7.27-7.39 (m, 1H), 7.43-7.46 (m, 2H), 7.49-7.54 (m, 6H), 7.66-7.71 (m, 1H), 8.64-8.70 (m, 2H), 9.01-9.11 (m, 2H), 10.70 (s, 1H). 5-bromopyrazolo[1,5-a]pyridine-3-carboxylic acid.

Examples 442 and 443

442

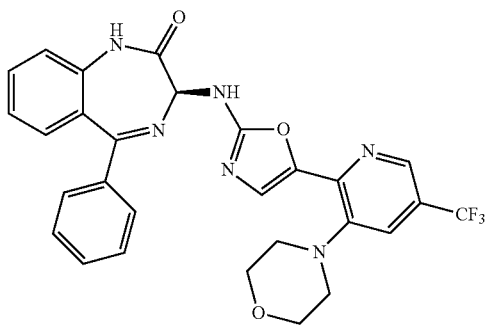

-continued

443

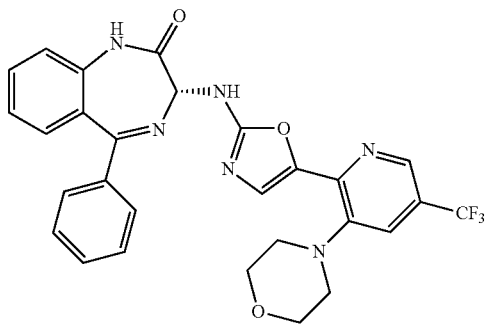

Examples 442 and 443 Step a

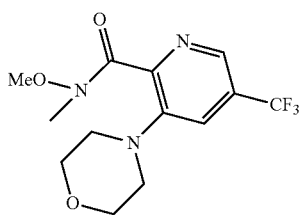 [SMILES: CON(C)C(=O)c1ncc(C(F)(F)F)cc1N1CCOCC1]

A 2M solution of trimethylaluminum in hexanes (23 mL, 44.40 mmol) was added to a mixture of N,O-dimethylhydroxylamine hydrochloride (4.3 g, 44.40 mmol) in DCM (30 mL) and the reaction was stirred at 0° C. for 40 mins. A solution of 3-morpholino-5-(trifluoromethyl)picolinic acid (9 g, 29.60 mmol) in DCM (20 mL) was added and the reaction mixture was stirred at 40° C. for 2 hours. After cooling to r.t., the mixture was carefully quenched with 1N HCl and diluted with DCM. After 30 min stirring layers were separated and the organic layers were washed with brine, dried over anhydrous Na$_2$SO$_4$ and concentrated to give the desired compound as a yellow solid (9 g, 95%). ESI MS m/z=320.3[M+H]$^+$.

Examples 442 and 443 Step b

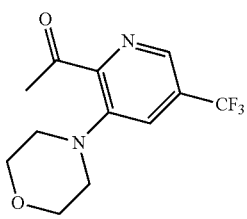 [SMILES: CC(=O)c1ncc(C(F)(F)F)cc1N1CCOCC1]

A solution of the (3 M) MeMgCl (10.3 mL, 31 mmol) in hexane was dropwise to the compound from step a (9 g, 28.20 mmol) in THF at 0° C. under N$_2$. It was stirred for 2 hours at 0° C. The mixture was diluted with EA and quenched with sat. NH$_4$C$_1$, the organic layers were washed with brine, dried over anhydrous Na$_2$SO$_4$ and concentrated to give the desired compound as a yellow oil (7.2 g, 93%). ESI MS m/z=275.2 [M+H]$^+$.

Examples 442 and 443 Step c

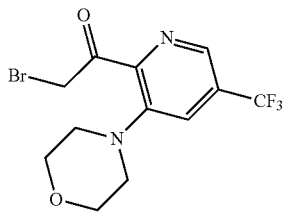

HBr—AcOH was added to a solution of the compound from step b (7.20 g, 26.3 mmol) in AcOH (20 mL), Then pyridinium tribromide (9.20 g, 28.9 mmol) was added at rt. It was stirred for 2 hours at rt and filtered. The solid was washed with AcOH and partitioned between EA/sat NaHCO$_3$, the organic layers were washed with brine, dried over anhydrous Na$_2$SO$_4$ and concentrated to give the desired compound as a yellow solid (6.1 g, 66%). ESI MS m/z=355.1 [M+H]$^+$.

Examples 442 and 443 Step d

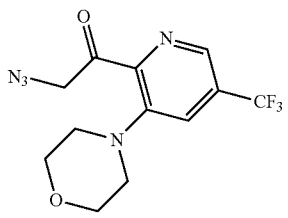 [SMILES: [N-]=[N+]=NCC(=O)c1ncc(C(F)(F)F)cc1N1CCOCC1]

A solution of the compound from step 3 (3 g, 8.52 mmol), NaN$_3$ (0.61 g, 9.38 mmol) in acetone/H$_2$O=2/1 (15 mL) was stirred for 1 hour at rt. The mixture was diluted with EA, washed by brine. The organic phase was dried over anhydrous Na$_2$SO$_4$ and concentrated to 10 ml in EA. It was used for next step directly. ESI MS m/z=316.1 [M+H]$^+$.

Examples 442 and 443 Step e

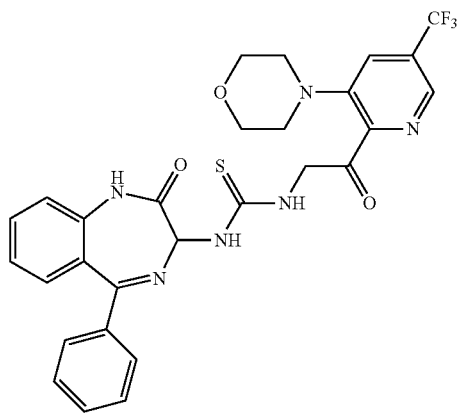 [SMILES: O=C(CNC(=S)NC1N=C(c2ccccc2)c2ccccc2NC1=O)c1ncc(C(F)(F)F)cc1N1CCOCC1]

TCDI (1.97 g, 11.08 mmol) was added to a solution of the compound (Z)-3-amino-5-phenyl-1H-benzo[e][1,4]diaz- epin-2(3H)-one (2.14 g, 8.52 mmol) in DCM (10 mL). It was stirred for 20 mins. The mixture was diluted with DCM, washed by brine. The organic phase was dried over anhydrous Na$_2$SO$_4$ and concentrated to give the isothiocyanate intermediate. A solution of the compound from step d in EA was added to the isothiocyanate and PPh$_3$ (2.70 g, 10.20 mmol) in dioxane under N$_2$. The mixture was stirred at 90° C. for 40 mins then at rt overnight. The solvents were removed and purified by reverse phase C18 column chromatography (MeCN/H$_2$O) to give desired compound as yellow solid. (230 mg, 4%). ESI MS m/z=583.4 [M+H]$^+$.

Examples 442 and 443 Step f

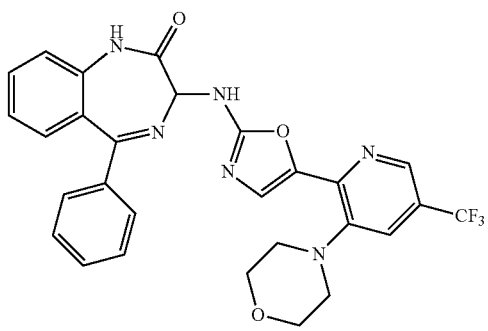 [SMILES: O=C1Nc2ccccc2C(c2ccccc2)=NC1Nc1ncc(-c2ncc(C(F)(F)F)cc2N2CCOCC2)o1]

EDCI (260 mg, 1.37 mmol) was added to a solution of the compound from step e (230 mg, 0.34 mmol) in DMF. It was stirred for 5 hours at 90° C. The crude product was purified by Prep-HPLC (MeCN/H$_2$O) to give desired compound as yellow solid (70 mg, 38%). ESI MS m/z=549.4 [M+H]$^+$.

Examples 442 and 443 Step g

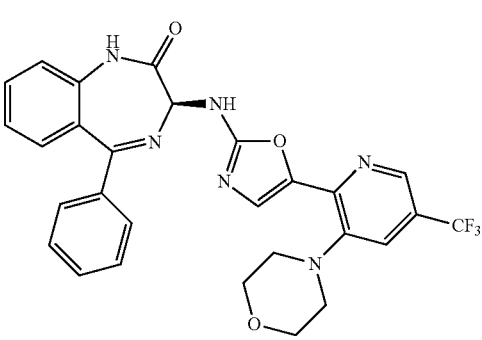

442

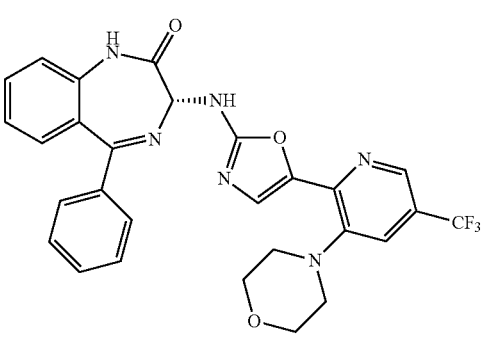

443

The compound from step f (70 mg, 0.13 mmol) was purified by Prep-Chiral-HPLC to give the title compound 442 (21 mg, 29%) as yellow solid and 443 (22 mg, 31%) as yellow solid. Example 442 ESI MS m/z=549.4 [M+H]$^+$. $^1$H NMR (400 MHz, DMSO-d$_6$) δ 2.94 (m, 4H), 3.77 (m, 4H), 5.26 (d, J=8.5 Hz, 1H), 7.25-7.31 (m, 1H), 7.34 (m, 2H), 7.42-7.60 (m, 5H), 7.67 (m, 1H), 7.84 (d, J=2.1 Hz, 2H), 8.58-8.71 (m, 1H), 9.20 (d, J=8.6 Hz, 1H), 10.93 (s, 1H). Example 443 ESI MS m/z=549.4 [M+H]$^+$. $^1$H NMR (400 MHz, DMSO-d$_6$) δ 2.94 (m, 4H), 3.77 (m, 4H), 5.26 (d, J=8.5 Hz, 1H), 7.23-7.32 (m, 1H), 7.34 (m, 2H), 7.41-7.58 (m, 5H), 7.67 (m, 1H), 7.84 (d, J=2.0 Hz, 2H), 8.63 (m, 1H), 9.20 (d, J=8.6 Hz, 1H), 10.93 (s, 1H).

Examples 444 and 445

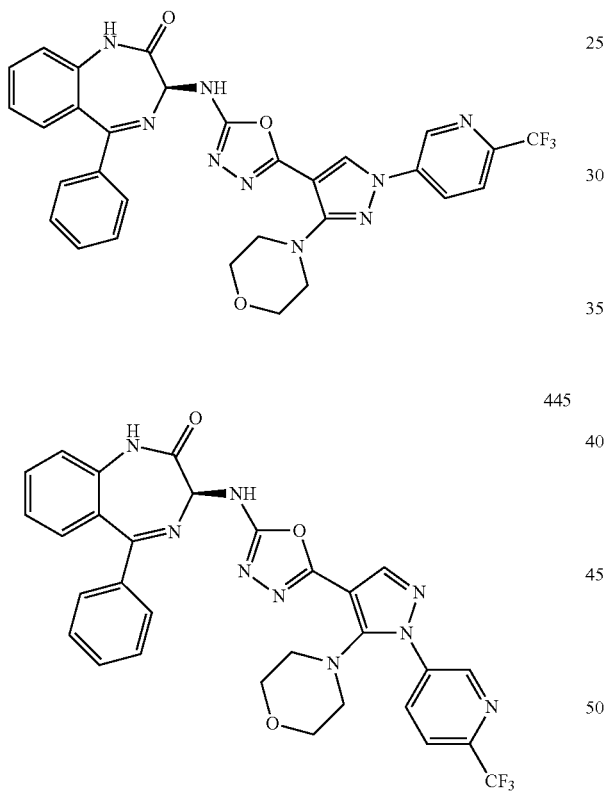

Examples 444 and 445 Step a

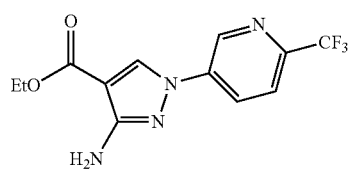

-continued

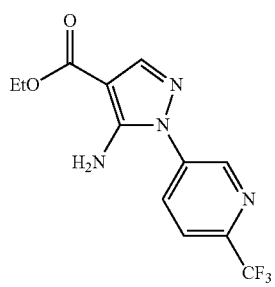

A solution of ethyl 3-amino-1H-pyrazole-4-carboxylate (1.55 g, 0.01 mol), 5-fluoro-2-(trifluoromethyl)pyridine (1.65 g, 0.01 mol), Cs$_2$CO$_3$ (4.89 g, 0.015 mol) in DMF (8 mL) was stirred for 1 hour at 100° C. The mixture was diluted with water, extracted with EA (×3). The organic layers were combined and washed with brine (×2), dried, concentrated. The crude product was purified via silica gel chromatography (PE-EA) to give the mixture of desired compounds as a yellow solid (1.04 g, 35%). ESI MS m/z=301.1[M+H]$^+$.

Examples 444 and 445 Step b

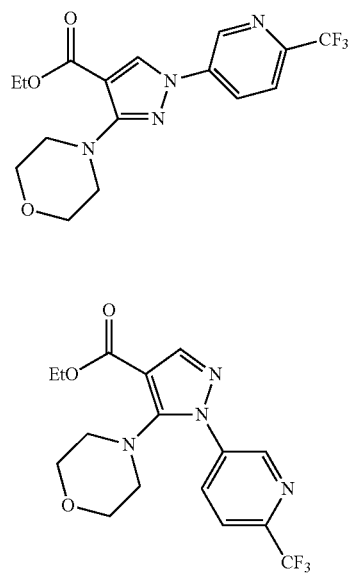

NaH (168 mg, 4.2 mmol) was added to the solution of the compound from step a (1.04 g, 3.5 mmol) and 1-bromo-2-(2-bromoethoxy)ethane (966 mg, 4.2 mmol) in DMF (20 mL) at 0° C. The mixture was stirred overnight. The mixture was quenched with water, extracted with EA (×3). The organic layers were combined and washed with brine (×2), dried, concentrated. The crude product was purified via silica gel chromatography (PE-EA) to give the mixture of desired compounds as a white solid (280 mg, 22%). ESI MS m/z=371.2 [M+H]$^+$.

Examples 444 and 445 Step c

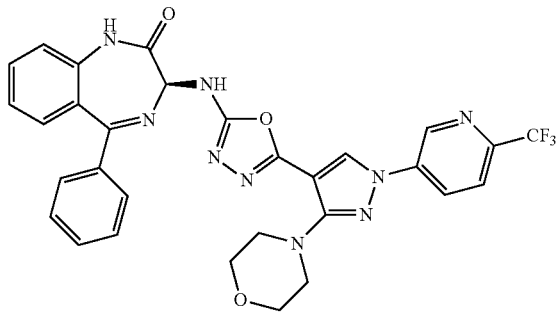

444

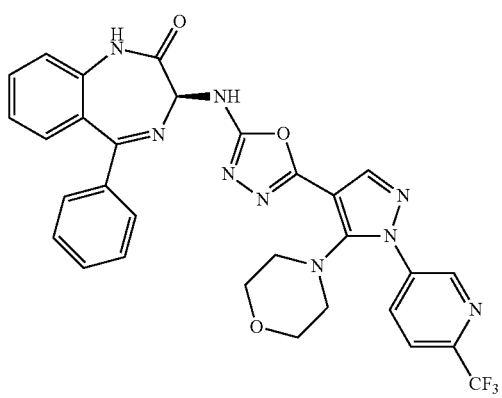

445

Examples 444 and 445 were prepared using a procedure similar to that used to prepare Example 152 where ethyl 3-morpholino-1-(6-(trifluoromethyl)pyridin-3-yl)-1H-pyrazole-4-carboxylate and ethyl 5-morpholino-1-(6-(trifluoromethyl)pyridin-3-yl)-1H-pyrazole-4-carboxylate were used in place of ethyl 2-morpholino-4-(trifluoromethyl)benzoate. The isomers were separated by prep HPLC (MeCN/H2O/0.1% FA). Example 444 ESI MS m/z=616.5 [M+H]⁺. ¹H NMR (300 MHz, DMSO-d₆) δ 3.31 (m, 4H), 3.74 (m, 4H), 5.16 (d, J=8.5 Hz, 1H), 7.25-7.42 (m, 3H), 7.51 (m, J=5H), 7.65-7.74 (m, 1H), 8.07 (d, J=8.7 Hz, 1H), 8.51 (m, 1H), 9.09-9.16 (m, 2H), 9.32 (d, J=2.5 Hz, 1H), 11.00 (s, 1H). Example 445 ESI MS m/z=616.5 [M+H]⁺. ¹H NMR (300 MHz, DMSO-d₆) δ 3.14 (m, 4H), 3.59 (m, 4H), 5.17 (d, J=8.4 Hz, 1H), 7.26-7.41 (m, 3H), 7.44-7.61 (m, 5H), 7.64-7.73 (m, 1H), 8.11-8.20 (m, 2H), 8.50 (m, 1H), 9.12-9.21 (m, 2H), 11.01 (s, 1H).

Examples 446 and 447

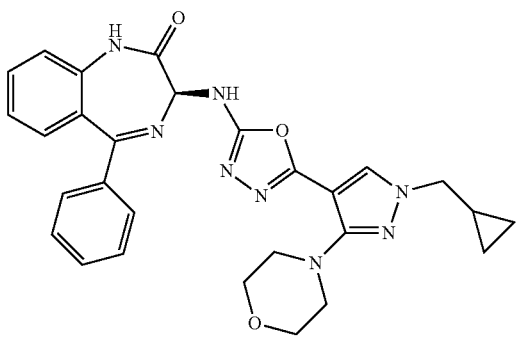

446

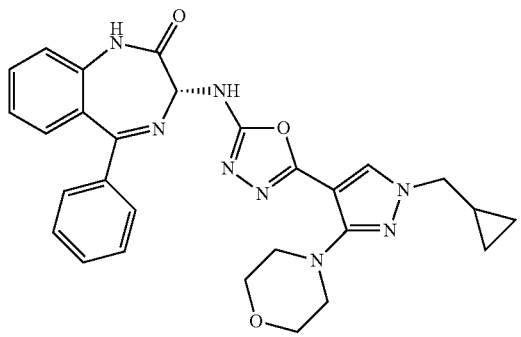

447

Examples 446 and 447 Step a

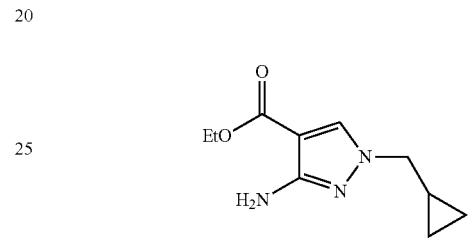

NaH (1.6 g, 0.04 mol) was added to the solution of ethyl 3-amino-1H-pyrazole-4-carboxylate (3.10 g, 0.02 mol) in DMF (25 mL) at 0° C. Then (bromomethyl)cyclopropane (2.68 g, 0.02 mol) was added. The mixture was stirred for 3 hours at rt. The solution was quenched with water, extracted with EA (×3), washed with brine (×2), the organic layer was dried, concentrated. The crude product was purified via silica gel chromatography (PE-EA) to give desired compound as a yellow oil (1.81 g, 43%). ESI MS m/z=209.9 [M+H]⁺.

Examples 446 and 447 Step b

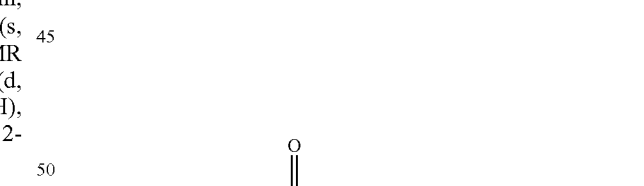

A solution of the compound from step a (1.81 g, 8.66 mmol), 1-bromo-2-(2-bromoethoxy)ethane (6.0 g, 25.98 mmol) and Cs₂CO₃ (5.64 g, 17.32 mmol) in DMA (20 mL) was stirred for 4 hours at 100° C. The mixture was diluted with water, extracted with EA (×3). The organic layers were combined and washed with brine (×2), dried, and concentrated. The residue was purified via silica gel chromatography (PE-EA) to give desired compound as off-white solid (1.08 g, 45%). ESI MS m/z=280.0 [M+H]⁺.

Examples 446 and 447 Step c

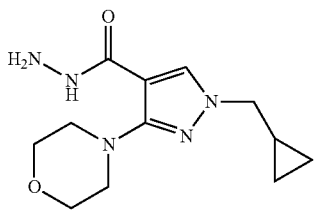 [SMILES: NNC(=O)c1cn(CC2CC2)nc1N1CCOCC1]

A solution of the compound from step b (1.08 g, 3.87 mmol) and NH$_2$NH$_2$.H$_2$O (10 mL) in EtOH (20 mL) was refluxed for 3 hours. The crude product was purified by Prep-HPLC (MeCN/H$_2$O) to give desired compound as yellow oil (810 mg, 79%). ESI MS m/z=260.0 [M+H]$^+$.

Examples 446 and 447 Step d

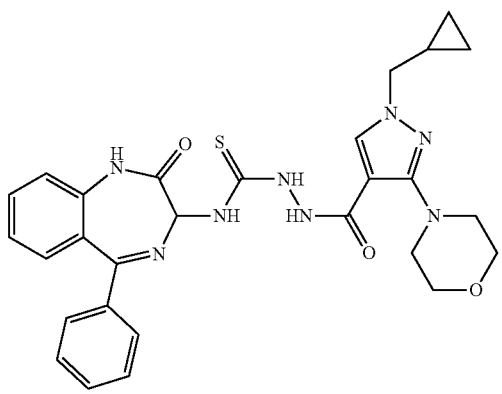 [SMILES: O=C(NNC(=S)NC1N=C(c2ccccc2)c2ccccc2NC1=O)c1cn(CC2CC2)nc1N1CCOCC1]

A solution of (Z)-3-amino-5-phenyl-1H-benzo[e][1,4]diazepin-2(3H)-one (753 mg, 3.0 mmol), and di(1H-imidazol-1-yl)methanethione (1.6 g, 9.0 mmol) in DMF (10 mL) was stirred for 1 hour at 0° C. and the compound from step c (810 mg, 3.05 mmol) was added to the solution and stirred at rt for 2 hours. The residue was purified by Prep-HPLC (MeCN/H$_2$O) to give desired compound as a yellow solid (950 mg, 57%). ESI MS m/z=559.3 [M+H]$^+$.

Examples 446 and 447 Step e

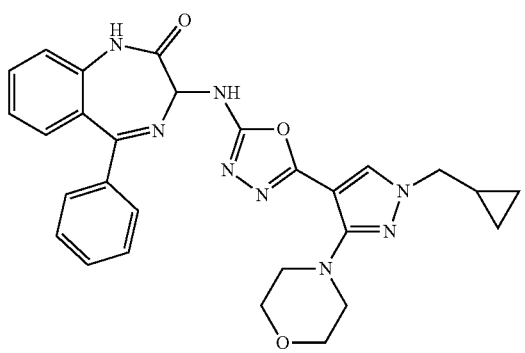 [SMILES: O=C1Nc2ccccc2C(c2ccccc2)=NC1Nc1nnc(-c2cn(CC3CC3)nc2N2CCOCC2)o1]

EDCI (980 mg, 5.10 mmol) was added to the solution of the compound from step d (950 mg, 1.70 mmol) in DMF (5 mL). The mixture was stirred at 60° C. for 2 hours. The mixture was diluted with water, extracted with DCM (×3). The organic layers were combined and dried, concentrated. The residue was then purified by preparative TLC (EA) and Prep-HPLC (MeCN/H2O/0.1% FA) to give the desired compound as a yellow solid (500 mg, 56%). ESI MS m/z=525.3 [M+H]$^+$.

Examples 446 and 447 Step f

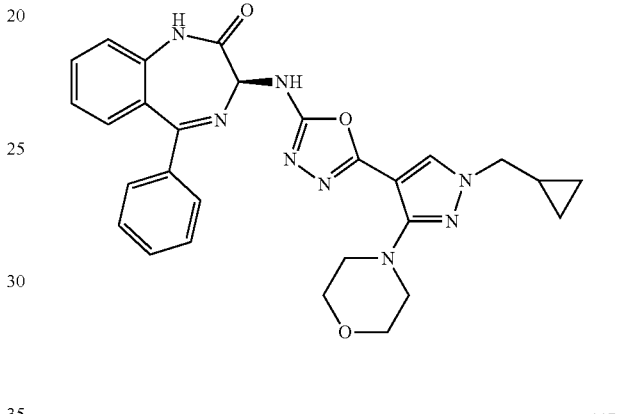

446

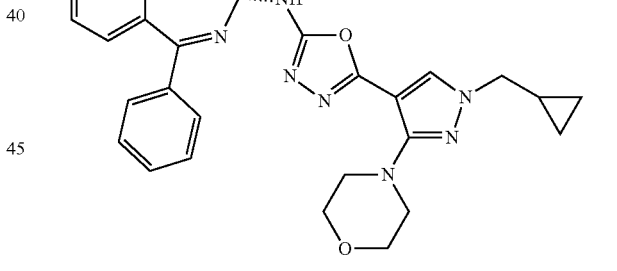

447

The compound from step e (500 mg, 0.95 mmol) was separated by chiral-HPLC to give 446 as a off-white solid (101 mg) and 447 as a yellow solid (162 mg). Example 446: ESI MS m/z=525.5 [M+H]$^+$. $^1$H NMR (300 MHz, DMSO-d$_6$) δ 0.35-0.39 (m, 2H), 0.51-0.57 (m, 2H), 1.24-1.28 (m, 1H), 3.17-3.18 (m, 4H), 3.66-3.67 (m, 4H), 3.89-3.91 (m, 2H), 5.08-5.11 (d, J=9.0 Hz, 1H), 7.26-7.36 (m, 3H), 7.44-7.54 (m, 5H), 7.65-7.70 (m, 1H), 8.10 (s, 1H), 8.88-8.91 (d, J=9.0 Hz, 1H), 10.96 (s, 1H). Example 447: ESI MS m/z=525.4 [M+H]$^+$. $^1$H NMR (300 MHz, DMSO-d$_6$) δ 0.36-0.38 (m, 2H), 0.52-0.55 (m, 2H), 1.08-1.40 (m, 1H), 3.17-3.18 (m, 4H), 3.66-3.68 (m, 4H), 3.89-3.91 (m, 2H), 5.08-5.11 (d, J=9.0 Hz, 1H), 7.28 (m, 3H), 7.33-7.36 (m, 5H), 7.46-7.52 (m, 1H), 8.10 (s, 1H), 8.88-8.91 (d, J=9.0 Hz, 1H), 10.96 (s, 1H).

Example 448

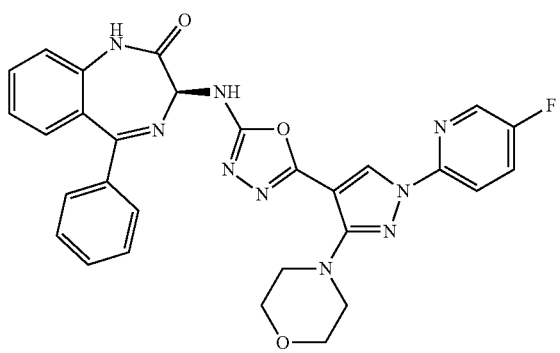 [SMILES: O=C1Nc2ccccc2C(c2ccccc2)=N[C@@H]1Nc1nnc(-c2cn(-c3ccc(F)cn3)nc2N2CCOCC2)o1]

Example 448 was prepared using a procedure similar to that used to prepare Example 448 where 2,5-difluoropyridine was used in place of 2-bromo-5-(trifluoromethyl)pyridine. ESI MS m/z=566.3 [M+H]$^+$. $^1$H NMR (400 MHz, DMSO-d$_6$) δ 3.31 (m, 4H), 3.73 (m, 4H), 5.14 (d, J=8.0 Hz, 1H), 7.25-7.38 (m, 3H), 7.42-7.61 (m, 5H), 7.68 (m, 1H), 7.89 (m, 1H), 7.97 (m, 1H), 8.52 (d, J=2.9 Hz, 1H), 8.74 (s, 1H), 9.06 (d, J=8.6 Hz, 1H).

Example 449

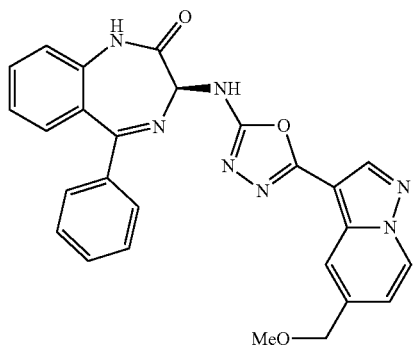 [SMILES: COCc1ccn2ncc(-c3nnc(N[C@H]4N=C(c5ccccc5)c5ccccc5NC4=O)o3)c2c1]

Example 449 Step a

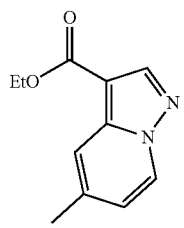

A solution of ethyl 5-bromopyrazolo[1,5-a]pyridine-3-carboxylate (1.0 g, 3.73 mmol), methylboronic acid (448 mg, 7.46 mmol), Pd(dppf)Cl$_2$ (545 mg, 0.746 mmol) and Cs$_2$CO$_3$ (2.42 g, 7.46 mmol) was dissolved in DMF (5.0 mL), then the mixture was stirred at 100° C. for two hours. It was concentrated, and purified by silica gel chromatography with PE:EA=5:1 to obtain the desired compound as an orange solid (589 mg, 77%). ESI MS m/z=204.5 [M+H]$^+$.

Example 449 Step b

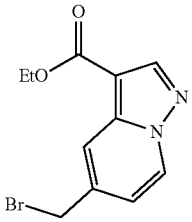 [SMILES: CCOC(=O)c1cnn2ccc(CBr)cc12]

A solution of the compound from step a (434 mg, 2.13 mmol), BPO (515 mg, 2.13 mmol), and NBS (398 mg, 2.24 mmol) was dissolved in CCl$_4$ (6 mL) at rt, then the mixture was stirred at 78° C. for one hour. After completion, the mixture was quenched with water, and extracted with EA (20 mL×2), the organic layer was combined, washed with water, saturated solution of NaHCO$_3$ (15 mL) and brine (15 mL) in turn, then dried with anhydrous Na$_2$SO$_4$ and concentrated to obtain a yellow solid (415 mg, 69%) that was used without further purification. ESI MS m/z=282.3 [M+H]$^+$.

Example 449 Step c

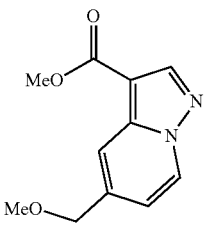 [SMILES: COCc1ccn2ncc(C(=O)OC)c2c1]

A mixture of NaH (96 mg, 3.99 mmol) in MeOH (5 mL) was stirred at 0° C. for 5 minutes, then the compound from step b (375 mg, 1.33 mmol) was added to the mixture. It was heated to 50° C. for one hour. After completion, the mixture was poured into ice-water solution of glacial acetic acid, and extracted with EA (25 mL×2), the organic layer was combined, washed with brine (15 mL), then dried with anhydrous Na$_2$SO$_4$ and concentrated to obtain methyl 5-(methoxymethyl)pyrazolo[1,5-a]pyridine-3-carboxylate as a light yellow solid that was used without further purification. ESI MS m/z=220.5 [M+H]$^+$.

Example 449 Step d

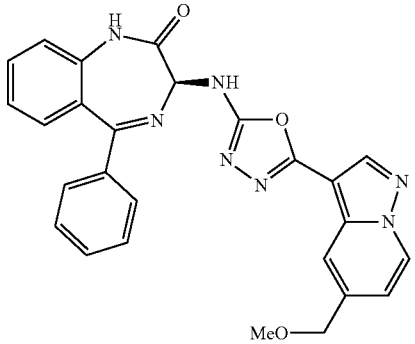 [SMILES: COCc1ccn2ncc(-c3nnc(N[C@H]4N=C(c5ccccc5)c5ccccc5NC4=O)o3)c2c1]

Example 449 was prepared using a procedure similar to that used to prepare Example 152 where methyl 5-(methoxymethyl)pyrazolo[1,5-a]pyridine-3-carboxylate was used in place of ethyl 2-morpholino-4-(trifluoromethyl)

benzoate. ESI MS m/z=480.3[M+H]⁺. ¹H NMR (400 MHz, DMSO-d₆) δ 3.38 (s, 3H), 4.56 (s, 2H), 5.17 (d, 1H), 7.04 (m, 1H), 7.25-7.33 (m, 1H), 7.37 (m, 2H), 7.42-7.58 (m, 5H), 7.69 (m, 1H), 7.95-8.04 (m, 1H), 8.42 (s, 1H), 8.84 (d, 1H), 8.98 (d, 1H), 10.90 (s, 1H).

Example 450

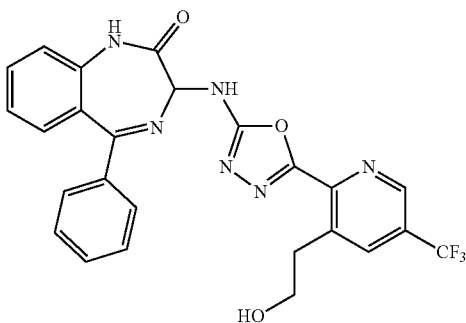 [SMILES: O=C1Nc2ccccc2C(c2ccccc2)=NC1Nc1nnc(-c2ncc(C(F)(F)F)cc2CCO)o1]

Example 450 Step a

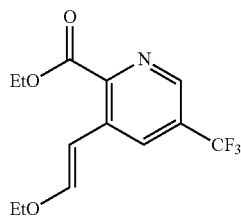 [SMILES: CCO/C=C/c1cc(C(F)(F)F)cnc1C(=O)OCC]

A solution of ethyl 3-chloro-5-(trifluoromethyl)pyridine-2-carboxylate (700 mg, 2.76 mmol), 2-[(E)-2-ethoxyethenyl]-4,4,5,5-tetramethyl-1,3,2-dioxaborolane (545 mg, 2.75 mmol), Pd(dppf)Cl₂ (197 mg, 0.27 mmol) and Cs₂CO₃ (2.7 g, 8.29 mmol) in 1,4-dioxane (15 mL) and water (5 mL) was stirred for 1 hour at 80° C. The reaction was then diluted by the addition of water. The resulting solution was extracted with EA. The crude product was purified by reverse phase C18 column chromatography to give the desired compound (550 mg, 69%) as off-white oil. ESI MS m/z=290.1 [M+H]⁺.

Example 450 Step b

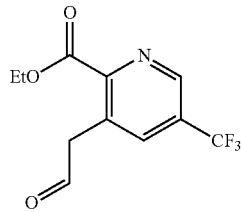 [SMILES: CCOC(=O)c1ncc(C(F)(F)F)cc1CC=O]

A solution of compound from step a (400 mg, 1.38 mmol), HCl-dioxane (2 mL, 4N) in dioxane (2 mL) was stirred for 2 hours at rt. The reaction was then quenched by the addition of NaHCO₃ and extracted with of DCM. The organic layers combined and dried over anhydrous sodium sulfate and concentrated under vacuum to give the desired compound (388 mg, 107%) as a yellow oil that was used without further purification. ESI MS m/z=262.0 [M+H]⁺.

Example 450 Step c

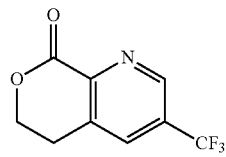

A solution of compound from step b (380 mg, 1.45 mmol) in THF (6 mL) was added BH₃.THF (2.9 mL, 2.9 mmol) dropwise at 0° C. It was stirred for 30 min at 0° C. The reaction was then quenched by the addition of water and extracted with DCM. The organic layers combined and concentrated under vacuum. The organic layer was purified by silica gel column to give the desired compound 160 mg as off-white oil. ESI MS m/z=264.1 [M+H]⁺.

Example 450 Step d

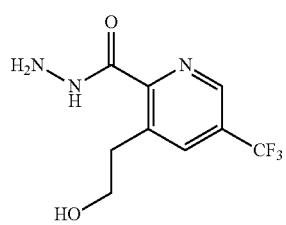 [SMILES: NNC(=O)c1ncc(C(F)(F)F)cc1CCO]

A solution of compound from step c (160 mg, 0.61 mmol), NH₂NH₂.H₂O (2 mL) in EtOH (2 mL) was stirred for 1 hour at 80° C. The reaction was then washed by the addition of water and extracted with of DCM. The organic layers combined and concentrated under vacuum to give 3-(2-hydroxyethyl)-5-(trifluoromethyl)picolinohydrazide (100 mg, 66%) as off-white oil. ESI MS m/z=250.0 [M+H]⁺.

Example 450 Step e

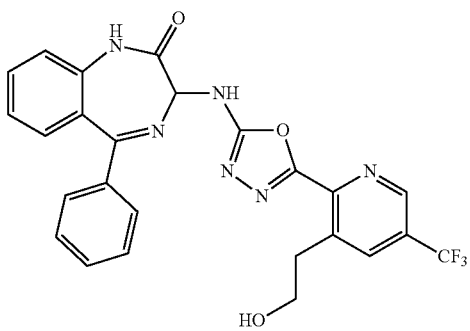 [SMILES: O=C1Nc2ccccc2C(c2ccccc2)=NC1Nc1nnc(-c2ncc(C(F)(F)F)cc2CCO)o1]

Example 450 was prepared using a procedure similar to that used to prepare Example 21 where 3-(2-hydroxyethyl)-5-(trifluoromethyl)picolinohydrazide was used in place of tetrahydro-2H-pyran-4-carbohydrazide. ESI MS m/z=509.2

[M+H]+. 1H NMR (400 MHz, DMSO-d6) δ 3.30 (d, J=6.1 Hz, 2H), 3.70 (q, J=5.8, 5.8, 5.6 Hz, 2H), 4.69 (t, J=5.3, 5.3 Hz, 1H), 5.21 (d, J=6.5 Hz, 1H), 7.23-7.41 (m, 3H), 7.43-7.59 (m, 5H), 7.63-7.79 (m, 1H), 8.25 (d, J=2.2 Hz, 1H), 8.92-9.05 (m, 1H), 9.38-9.56 (m, 1H), 10.98 (s, 1H).

Example 451

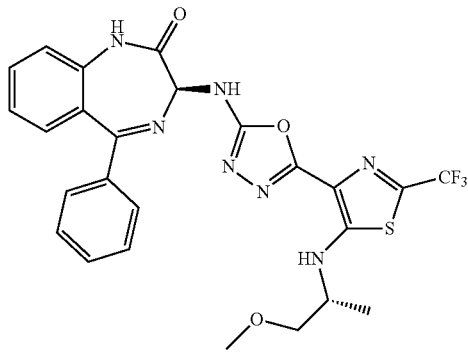 [SMILES: COC[C@@H](C)Nc1sc(C(F)(F)F)nc1-c1nnc(N[C@H]2N=C(c3ccccc3)c3ccccc3NC2=O)o1]

Example 451 was prepared using a procedure similar to that used in Example 339 where (R)-1-methoxypropan-2-amine was used in place of morpholine. ESI MS m/z=558.2 [M+H]+.

Example 452

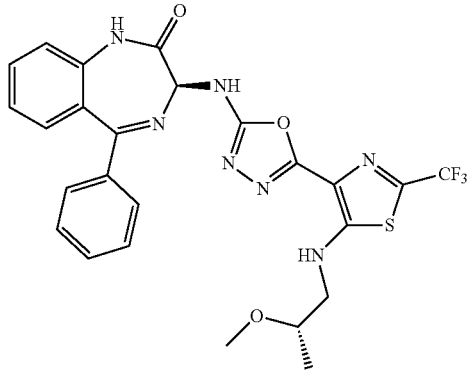 [SMILES: CO[C@@H](C)CNc1sc(C(F)(F)F)nc1-c1nnc(N[C@H]2N=C(c3ccccc3)c3ccccc3NC2=O)o1]

Example 452 was prepared using a procedure similar to that used in Example 339 where (S)-2-methoxypropan-1-amine was used in place of morpholine. ESI MS m/z=558.2 [M+H]+.

Example 453

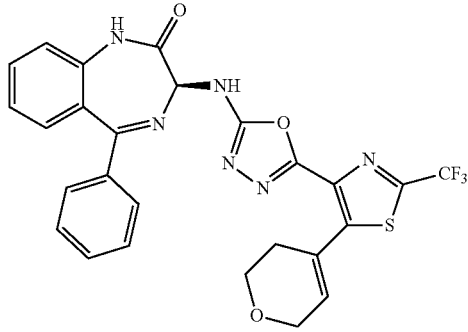 [SMILES: O=C1Nc2ccccc2C(c2ccccc2)=N[C@@H]1Nc1nnc(-c2nc(C(F)(F)F)sc2C2=CCOCC2)o1]

Example 453 Step a

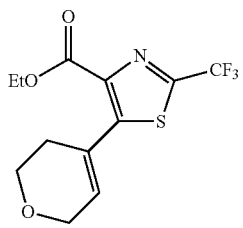 [SMILES: CCOC(=O)c1nc(C(F)(F)F)sc1C1=CCOCC1]

Example 453 step a was prepared using a procedure similar to that used to prepare Example 345 where ethyl 5-bromo-2-(trifluoromethyl)thiazole-4-carboxylate was used in place of methyl 5-bromo-2-methylthiazole-4-carboxylate.

Example 453 Step b

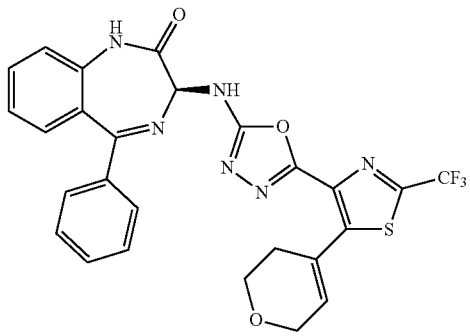 [SMILES: O=C1Nc2ccccc2C(c2ccccc2)=N[C@@H]1Nc1nnc(-c2nc(C(F)(F)F)sc2C2=CCOCC2)o1]

Example 453 step b was prepared using a procedure similar to that used to prepare Example 152 where ethyl 5-(3,6-dihydro-2H-pyran-4-yl)-2-(trifluoromethyl)thiazole-4-carboxylate was used in place of ethyl 2-morpholino-4-(trifluoromethyl)benzoate. ESI MS m/z=553.1 [M+H]+.

Example 454

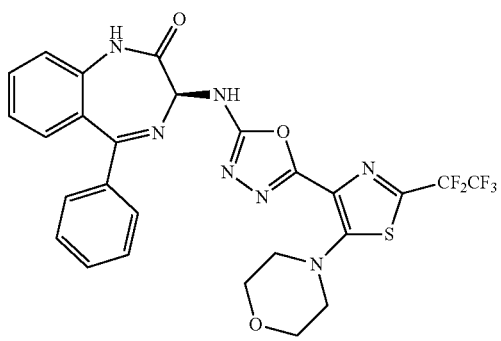

Example 454 Step a

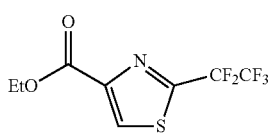

To a oven-dried round-bottomed flask, 2,2,3,3,3-pentafluoropropanamide (2 g, 12.27 mmol) was dissolved in THF (29.9 mL) under nitrogen to give a color solution. Lawesson's reagent (2.98 g, 7.36 mmol) was added to the reaction mixture. Stir reaction vessel at 80° C. overnight. The reaction mixture was cooled and ethyl 3-bromo-2-oxopropanoate (1.92 mL, 15.33 mmol) was added. The flask was again heated to 80° C. and stirred overnight. The mixture was poured into water and the aqueous layer was extracted with EtOAc. The organic layer was dried, filtered and concentrated. The crude product was added to a silica gel column and was eluted with ethyl acetate/hexane 0% to 50% to give ethyl 2-(perfluoroethyl)thiazole-4-carboxylate (1.29 g, 38% yield) as a white solid.

Example 454 Step b

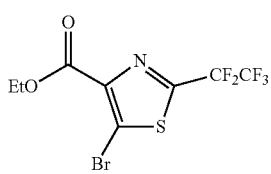

A solution of ethyl 2-(perfluoroethyl)thiazole-4-carboxylate (1.29 g, 4.69 mmol) in THF (10.7 mL) was added to LDA (2.93 mL, 5.86 mmol) in THF (32.0 mL) at −78° C. under N$_2$. The mixture was stirred for 45 minutes at same temperature. To this, a solution of 1,2-dibromotetrachloroethane (2.29 g, 7.03 mmol) in THF (10.7 mL) was dropwised and warmed to room temperature over 2 hours. The reaction was quenched with saturated ammonium chloride solution. Water was added and the mixture was extracted with ethyl acetate (3×). The organic layer was combined, dried and concentrated. The crude product was added to a silica gel column and was eluted with ethyl acetate/hexane 0% to 50% to give ethyl 5-bromo-2-(perfluoroethyl)thiazole-4-carboxylate (0.894 g, 54% yield) as a white solid.

Example 454 Step c

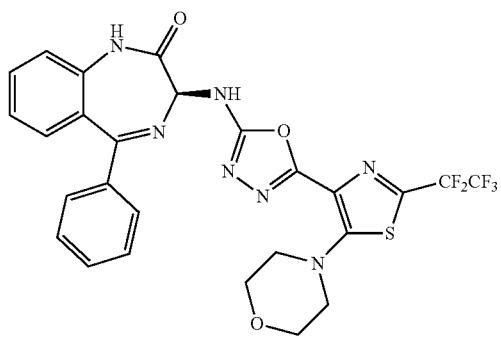

Example 454 was prepared using a procedure similar to that used to prepare Example 272 where ethyl 5-bromo-2-(perfluoroethyl)thiazole-4-carboxylate was used in place of methyl 2-methyl-5-bromothiazole-4-carboxylate. ESI-MS m/z: 606.1 [M+H]$^+$.

Example 455

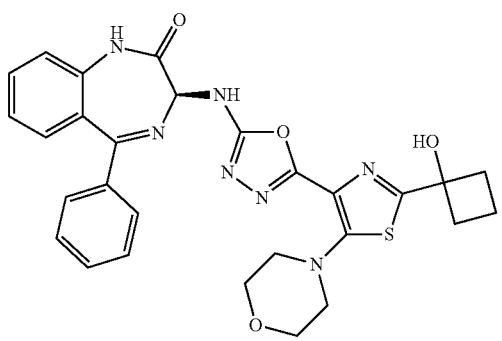 [SMILES: O=C1Nc2ccccc2C(c2ccccc2)=N[C@@H]1Nc1nnc(-c2nc(C3(O)CCC3)sc2N2CCOCC2)o1]

Example 455 Step a

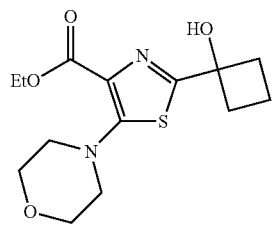 [SMILES: CCOC(=O)c1nc(C2(O)CCC2)sc1N1CCOCC1]

To a cold (−78° C.) solution of ethyl 5-morpholinothiazole-4-carboxylate (0.5 g, 2.06 mmol) in THF (5.2 mL) was added n-BuLi (1.29 mL, 2.06 mmol) dropwise. The reaction was stirred for 15 minutes and cyclobutanone (0.15 mL, 2.06 mmol) was added via syringe. The reaction was stirred for 1 hour and was then quenched by the addition of saturated aqueous bicarbonate solution. The cold bath was removed and the reaction was warmed to room temperature. Ethyl acetate was added and the layers were separated. The aqueous layer was extracted with additional ethyl acetate (2×). The combined organics were dried with anhydrous sodium sulfate, filtered and concentrated under reduced pressure to give the crude title compound. The crude product was added to a silica gel column and was eluted with ethyl acetate/hexane 0% to 50% to give ethyl 2-(1-hydroxycyclobutyl)-5-morpholinothiazole-4-carboxylate (427 mg, 66% yield) as a yellow solid.

Example 455 Step b

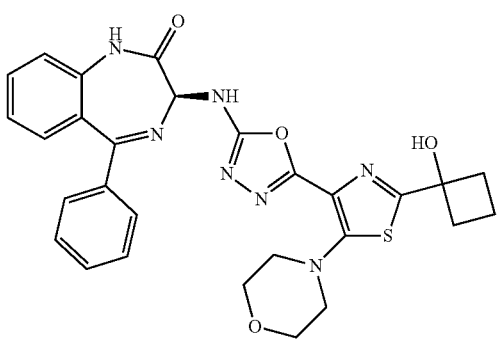 [SMILES: O=C1Nc2ccccc2C(c2ccccc2)=N[C@@H]1Nc1nnc(-c2nc(C3(O)CCC3)sc2N2CCOCC2)o1]

Example 455 was prepared using a procedure similar to that used to prepare Example 152 where ethyl 2-(1-hydroxy-cyclobutyl)-5-morpholinothiazole-4-carboxylate was used in place of ethyl 2-morpholino-4-(trifluoromethyl)benzoate. ESI MS m/z=558.2 [M+H]$^+$.

Example 456

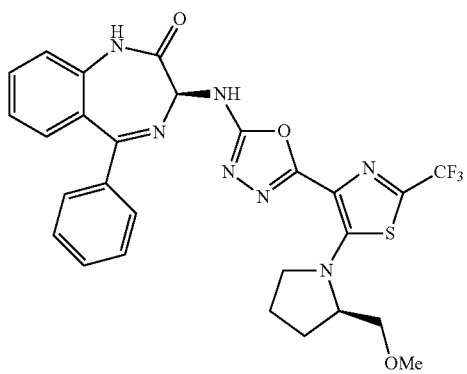 [SMILES: COC[C@H]1CCCN1c1sc(C(F)(F)F)nc1-c1nnc(N[C@H]2N=C(c3ccccc3)c3ccccc3NC2=O)o1]

Example 456 was prepared using a procedure similar to that used to prepare Example 21 where ethyl (R)-5-(2-(methoxymethyl)pyrrolidin-1-yl)-2-(trifluoromethyl)thiazole-4-carboxylate, which was prepared similarly to ethyl 5-morpholino-2-(trifluoromethyl)thiazole-4-carboxylate in Example 339, was converted to the corresponding hydrazide and used in of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=584.2 [M+H]$^+$.

Example 457

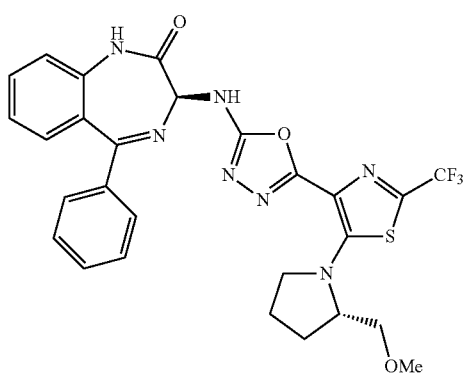 [SMILES: COC[C@@H]1CCCN1c1sc(C(F)(F)F)nc1-c1nnc(N[C@H]2N=C(c3ccccc3)c3ccccc3NC2=O)o1]

Example 457 was prepared using a procedure similar to that used to prepare Example 21 where ethyl (S)-5-(2-(methoxymethyl)pyrrolidin-1-yl)-2-(trifluoromethyl)thiazole-4-carboxylate, which was prepared similarly to ethyl 5-morpholino-2-(trifluoromethyl)thiazole-4-carboxylate in Example 339, was converted to the corresponding hydrazide and used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=584.2 [M+H]$^+$.

Example 458

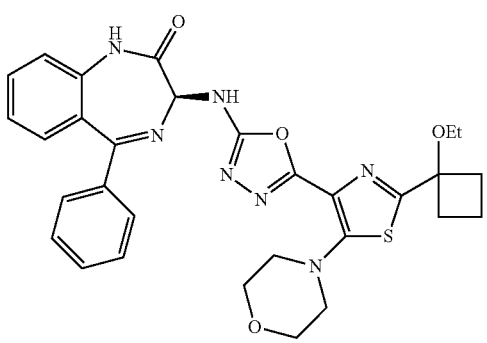 [SMILES: CCOC1(c2nc(-c3nnc(N[C@H]4N=C(c5ccccc5)c5ccccc5NC4=O)o3)c(N3CCOCC3)s2)CCC1]

Example 458 Step a

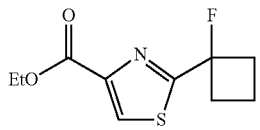

Example 458 step a was prepared using a procedure similar to that used to prepare Example 454 where 1-fluorocyclobutane-1-carboxamide was used in place of 2,2,3,3,3-pentafluoropropanamide to give ethyl 2-(1-fluorocyclobutyl)thiazole-4-carboxylate.

Example 458 Step b

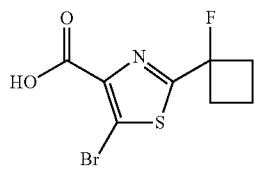 [SMILES: O=C(O)c1nc(C2(F)CCC2)sc1Br]

Ethyl 2-(1-fluorocyclobutyl)thiazole-4-carboxylate (230 mg, 1.0 mmol) was taken up in MeOH (2 mL) and 1M NaOH (2 mL) and stirred at room temperature for 30 mins. The reaction mixture was concentrated and the aqueous layer was extracted 3× with EtOAc. The organic layer was dried, filtered and concentrated. 2-(1-fluorocyclobutyl)thiazole-4-carboxylic acid (197 mg, 98% yield) was isolated as a white solid.

A solution of 2-(1-fluorocyclobutyl)thiazole-4-carboxylic acid (197 mg, 0.98 mmol) in Tetrahydrofuran (11.5 mL) was cooled to −78° C. under argon and treated with a n-butyl-lithium (1.29 mL, 2.06 mmol). The reaction mixture was left to warm to room temperature over 15 minutes, then cooled again to −78° C. A solution of bromine (55 µL, 1.08 mmol) in hexane (0.5 mL) was added. The reaction mixture was left to warm to room temperature, then quenched by addition of 1N HCl. The mixture was extracted three times with methylene chloride, and the combined organic layers were dried over sodium sulphate and evaporated. The crude product was added to a silica gel column and was eluted with methanol/dichloromethane 0% to 10% to give 5-bromo-2-(1-fluorocyclobutyl)thiazole-4-carboxylic acid (219 mg, 80% yield) as a white solid.

Example 458 Step c

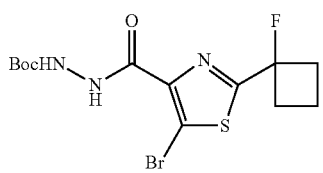 [SMILES: CC(C)(C)OC(=O)NNC(=O)c1nc(C2(F)CCC2)sc1Br]

To a vial, 5-bromo-2-(1-fluorocyclobutyl)thiazole-4-carboxylic acid (218 mg, 0.78 mmol), HATU (355 mg, 0.93 mmol) and tert-butyl hydrazinecarboxylate (123 mg, 0.93 mmol) was dissolved in DMF (7.2 mL) open to air to give a yellow solution. DIPEA (272 µL, 1.56 mmol) was added to the reaction mixture in one portion. Stir at room temperature for 2 hours. Concentrate reaction mixture and load crude reaction mixture on to silica gel plug. The crude product was added to a silica gel column and was eluted with ethyl acetate/hexane 0% to 50% to give tert-butyl 2-(5-bromo-2-(1-fluorocyclobutyl)thiazole-4-carbonyl)hydrazine-1-carboxylate (270 mg, 88% yield) as a white solid.

Example 458 Step d

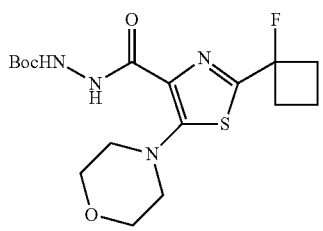 [SMILES: CC(C)(C)OC(=O)NNC(=O)c1nc(C2(F)CCC2)sc1N1CCOCC1]

To a oven-dried vial, tert-butyl 2-(5-bromo-2-(1-fluorocyclobutyl)thiazole-4-carbonyl)hydrazine-1-carboxylate (270 mg, 0.69 mmol) was dissolved in morpholine (1370 µL) open to air to give a color suspension. K₂CO₃ (189 mg, 1.37 mmol) was added to the reaction mixture. Stir at 80° C. for 3 hours. Filtered and washed with DCM and concentrate the organic layer. The crude product was added to a silica gel column and was eluted with ethyl acetate/hexane 0% to 50% to give ethyl tert-butyl 2-(2-(1-fluorocyclobutyl)-5-morpholinothiazole-4-carbonyl)hydrazine-1-carboxylate (198 mg, 72% yield) as a white solid.

Example 458 Step e

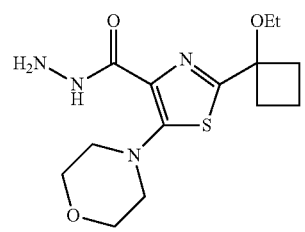 [SMILES: CCOC1(c2nc(C(=O)NN)c(N3CCOCC3)s2)CCC1]

A solution of tert-butyl 2-(2-(1-fluorocyclobutyl)-5-morpholinothiazole-4-carbonyl)hydrazine-1-carboxylate (198 mg, 0.49 mmol) and hydrochloric acid, 37% (1.12 mL) in EtOH (11.2 mL) was stirred at room temperature for 1 hour. It was adjusted to pH=7-8 with saturated aqueous NaHCO₃. Extract with DCM (3×). Dry and concentrate organic layer. The crude product was added to a silica gel column and was eluted with methanol/dichloromethane 0% to 10% to give 2-(1-ethoxycyclobutyl)-5-morpholinothiazole-4-carbohydrazide (51 mg, 32% yield) as a white solid.

Example 458 Step f

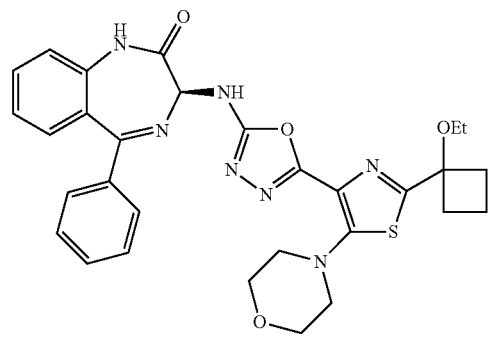 [SMILES: CCOC1(c2nc(-c3nnc(N[C@H]4N=C(c5ccccc5)c5ccccc5NC4=O)o3)c(N3CCOCC3)s2)CCC1]

Example 458 was prepared using a procedure similar to that used to prepare Example 21 where 2-(1-ethoxycyclobutyl)-5-morpholinothiazole-4-carbohydrazide was used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% i-PrOH/50% hexanes; Flow rate=20 mL/min). ESI MS m/z=586.2 [M+H]⁺.

Example 459

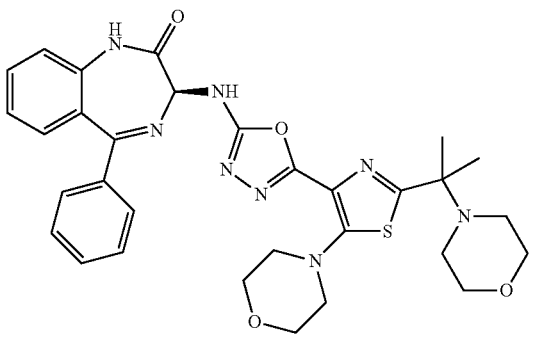 [SMILES: CC(C)(c1nc(-c2nnc(N[C@H]3N=C(c4ccccc4)c4ccccc4NC3=O)o2)c(N2CCOCC2)s1)N1CCOCC1]

Example 459 Step a

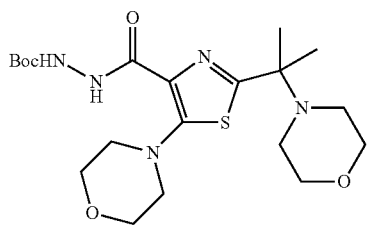 [SMILES: CC(C)(C)OC(=O)NNC(=O)c1nc(C(C)(C)N2CCOCC2)sc1N1CCOCC1]

To a oven-dried vial, tert-butyl 2-(5-bromo-2-(2-fluoropropan-2-yl)thiazole-4-carbonyl)hydrazine-1-carboxylate (166 mg, 0.43 mmol) was dissolved in Morpholine (0.87 mL) open to air to give a yellow suspension. K₂CO₃ (120 mg, 0.87 mmol) was added to the reaction mixture and allowed to stir at 90° C. for four hours. The reaction mixture was filtered and washed with DCM. The filtrate was concentrated. The crude product was added to a silica gel column and was eluted with ethyl acetate/hexane 0% to 50% to give ethyl tert-butyl 2-(5-morpholino-2-(2-morpholinopropan-2-yl)thiazole-4-carbonyl)hydrazine-1-carboxylate (180 mg, 91% yield) as a white solid.

Example 459 Step b

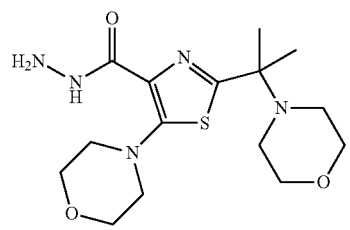 [SMILES: CC(C)(c1nc(C(=O)NN)c(N2CCOCC2)s1)N1CCOCC1]

To a vial, tert-butyl 2-(5-morpholino-2-(2-morpholinopropan-2-yl)thiazole-4-carbonyl)hydrazine-1-carboxylate (180 mg, 0.395 mmol) was taken up in DCM (0.6 mL) and TFA (0.6 mL). Stir reaction at room temperature for 1 hour. Reaction mixture was concentrated and taken up in DCM and sat. aq. NaHCO₃ (aq). The aqueous layer was extracted with DCM (2×). The organic layer was dried, filtered and concentrated. 5-morpholino-2-(2-morpholinopropan-2-yl)thiazole-4-carbohydrazide (135 mg, 96% yield) was taken forward without purification.

Example 459 Step c

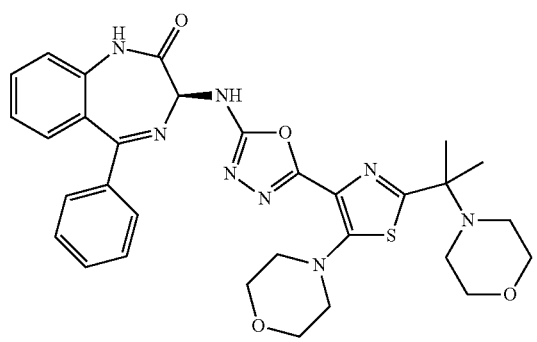 [SMILES: CC(C)(c1nc(-c2nnc(N[C@H]3N=C(c4ccccc4)c4ccccc4NC3=O)o2)c(N2CCOCC2)s1)N1CCOCC1]

Example 459 was prepared using a procedure similar to that used to prepare Example 21 where 5-morpholino-2-(2-morpholinopropan-2-yl)thiazole-4-carbohydrazide was used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% i-PrOH/50% hexanes; Flow rate=20 mL/min). ESI MS m/z=528.2 [M-C₄H₉NO]⁺

Example 460

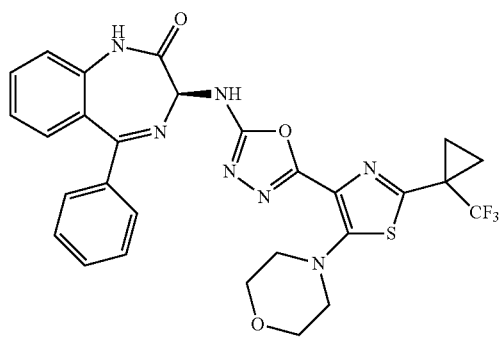 [SMILES: O=C1Nc2ccccc2C(c2ccccc2)=N[C@@H]1Nc1nnc(-c2nc(C3(C(F)(F)F)CC3)sc2N2CCOCC2)o1]

Example 460 step a was prepared using a procedure similar to 458 where 1-(trifluoromethyl)cyclopropane-1-carb oxamide was used in place of 1-fluorocyclobutane-1-carboxamide. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=596.2 [M+H]⁺.

Example 461

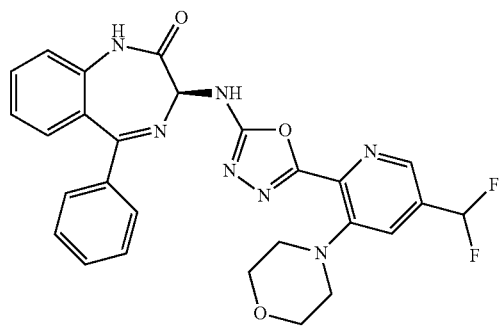 [SMILES: O=C1Nc2ccccc2C(c2ccccc2)=N[C@@H]1Nc1nnc(-c2ncc(C(F)F)cc2N2CCOCC2)o1]

Example 461 Step a

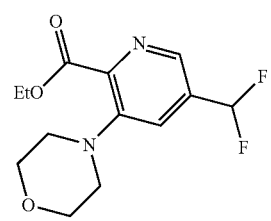 [SMILES: CCOC(=O)c1ncc(C(F)F)cc1N1CCOCC1]

An oven dried vial was charged with methyl 5-bromo-3-morpholinopicolinate (340 mg, 1.13 mmol), cesium fluoride (858 mg, 5.65 mmol), and copper (I) iodide (1402 mg, 11.29 mmol). The vial was purged with nitrogen gas, then NMP (20 mL) was added via syringe. To this mixture was added (difluoromethyl)trimethylsilane (1402 mg, 11.29 mmol). The reaction mixture was heated at 120° C. for 24 hours. After cooling to rt, the reaction mixture was filtered through a pad of silica gel and washed with EtOAc (50 mL). The filtrate was concentrated and purified by RP-HPLC (30-95% MeCN:water) to provide methyl 5-(difluoromethyl)-3-morpholinopicolinate (30 mg, 10% yield) as a yellow oil. ESI MS m/z=273.1 [M+H]$^+$.

Example 461 Step b

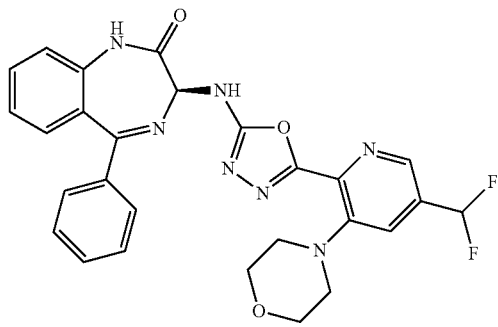 [SMILES: O=C1Nc2ccccc2C(c2ccccc2)=N[C@@H]1Nc1nnc(-c2ncc(C(F)F)cc2N2CCOCC2)o1]

Example 461 was prepared using a procedure similar to that used to prepare Example 152 where methyl 5-(difluoromethyl)-3-morpholinopicolinate was used in place of ethyl 2-morpholino-4-(trifluoromethyl)benzoate. ESI MS m/z=596.2 [M+H]$^+$.

Example 462

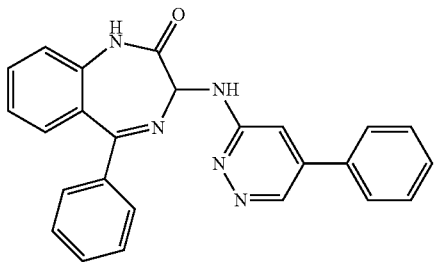 [SMILES: O=C1Nc2ccccc2C(c2ccccc2)=NC1Nc1cc(-c2ccccc2)cnn1]

Example 462 Step a

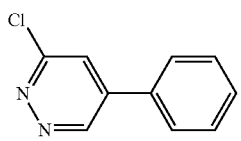 [SMILES: Clc1cc(-c2ccccc2)cnn1]

An oven dried vial was charged with 3,5-dichloropyridazine (100 mg, 0.67 mmol), phenylboronic acid (82 mg, 0.671 mmol), potassium fluoride (97 mg, 1.68 mmol), palladium acetate (8 mg, 0.034 mmol), and Q-Phos (24 mg, 0.034 mmol). The vial was purged with nitrogen gas, then toluene (5 mL) and water (1.2 mL) were added via syringe. The reaction mixture was heated at 70° C. for 22 hours. After cooling to rt, the reaction mixture was diluted with EtOAc (4 mL). The reaction mixture was filtered through a pad of celite and concentrated. The residue was purified on silica gel (0-100% EtOAc:hexanes) to provide 3-chloro-5-phenylpyridazine (110 mg, 86% yield) as a tan solid. ESI MS m/z=191.1 [M+H]$^+$.

Example 462 Step b

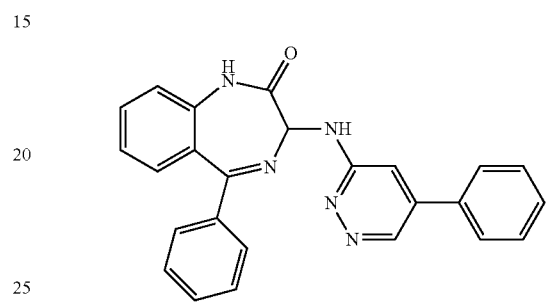

An oven dried vial was charged with 3-chloro-5-phenylpyridazine (80 mg, 0.420 mmol), 3-amino-5-phenyl-1,3-dihydro-2H-benzo[e][1,4]diazepin-2-one (158 mg, 0.629 mmol), potassium tert-butoxide (141 mg, 1.259 mmol), SPhos (17 mg, 0.042 mmol), and SPhos-palladium G3 (33 mg, 0.042 mmol). The vial was purged with nitrogen gas, then tert-butanol was added (10 mL). The reaction mixture was heated at 60° C. for 90 min. After cooling to rt, the reaction mixture was filtered through a pad of silica gel and concentrated. The residue was purified on silica gel (0-10% MeOH:DCM) to provide the product as a tan solid (25 mg, 15% yield). ESI MS m/z=406.1 [M+H]$^+$.

Example 463

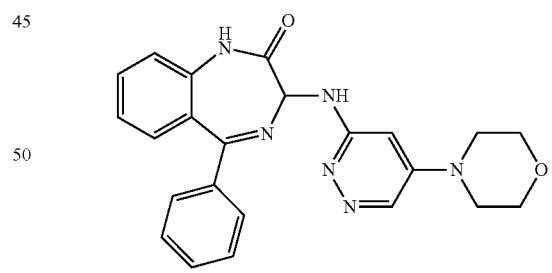

Example 463 Step a

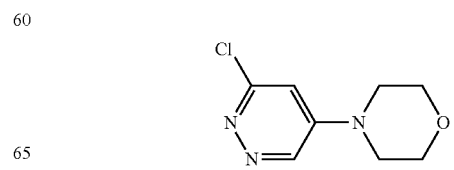

An oven dried vial was charged with 3,5-dichloropyridazine (115 mg, 0.772 mmol). The vial was purged with nitrogen gas, then MeCN (5 mL) was added via syringe. Morpholine (0.22 mL, 2.57 mmol) was added dropwise at 0° C. The reaction mixture was stirred at rt for 1 h, then concentrated. The residue was purified by RP-HPLC (60-100% MeCN:water) to provide 4-(6-chloropyridazin-4-yl)morpholine as a yellow oil (115 mg, 75% yield). ESI MS m/z=200.2 [M+H]$^+$.

Example 463 Step b

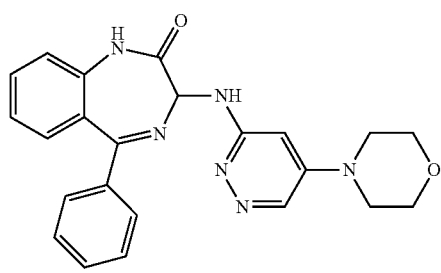 [SMILES: O=C1Nc2ccccc2C(c2ccccc2)=NC1Nc1cc(N2CCOCC2)cnn1]

An oven dried vial was charged with 4-(6-chloropyridazin-4-yl)morpholine (120 mg, 0.601 mmol), 3-amino-5-phenyl-1,3-dihydro-2H-benzo[e][1,4]diazepin-2-one (76 mg, 0.301 mmol), potassium tert-butoxide (101 mg, 0.902 mmol), and SPhos-palladium G3 (12 mg, 0.015 mmol). The vial was purged with nitrogen gas, then tert-butanol was added (5 mL). The reaction mixture was heated at 80 C for 20 hours. After cooling to rt, the reaction mixture was filtered through a pad of silica gel and concentrated. The residue was purified by RP-HPLC (30-100% MeCN:water) to provide the product as a tan solid (20 mg, 16% yield). ESI MS m/z=415.1 [M+H]$^+$.

Example 464

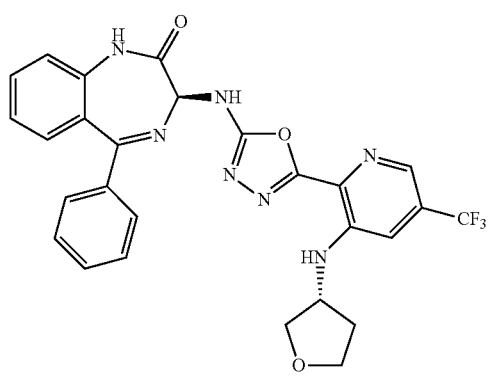 [SMILES: O=C1Nc2ccccc2C(c2ccccc2)=N[C@@H]1Nc1nnc(-c2ncc(C(F)(F)F)cc2N[C@@H]2CCOC2)o1]

Example 464 was prepared using a procedure similar to that used to Example 160 where (R)-tetrahydrofuran-3-amine and ethyl 3-chloro-5-(trifluoromethyl)picolinate were used in place of morpholine and methyl 5-bromo-3-fluoropicolinate, respectively. ESI MS m/z=550.1 M+H]$^+$.

Example 465

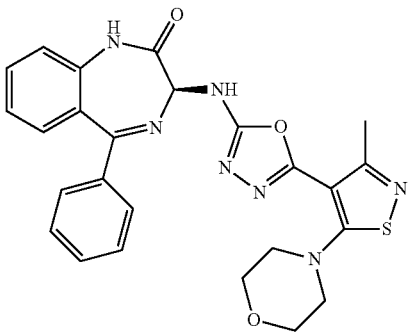

Example 465 was prepared using a procedure similar to that used to prepare Example 430 where ethyl 5-amino-3-methylisothiazole-4-carboxylate was used in place of ethyl 3-amino-1-cyclobutyl-1H-pyrazole-4-carboxylate. ESI MS m/z=502.1 [M+H]$^+$.

Example 466

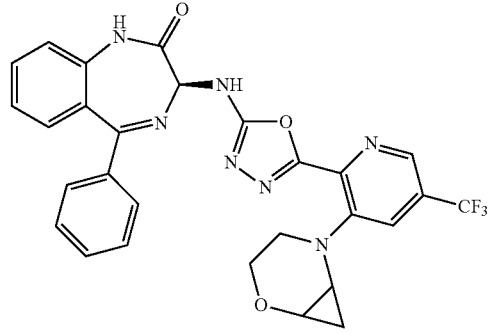

mixture of diastereomers

Example 466 was prepared using a procedure similar to that used to Example 160 where 2-oxa-5-azabicyclo[4.1.0]heptane and ethyl 3-chloro-5-(trifluoromethyl)picolinate were used in place of morpholine and methyl 5-bromo-3-fluoropicolinate, respectively. ESI MS m/z=562.1 [M+H]$^+$.

Example 467

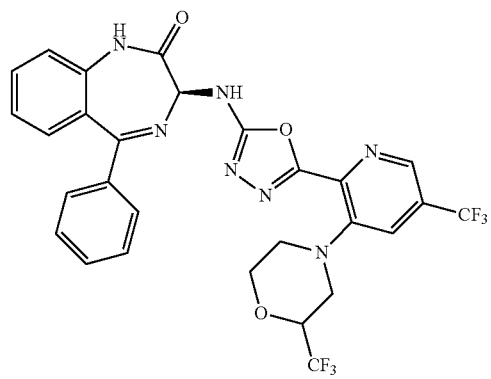

mixture of diastereomers

Example 467 was prepared using a procedure similar to that used to Example 160 where 2-(trifluoromethyl)morpholine and ethyl 3-chloro-5-(trifluoromethyl)picolinate were used in place of morpholine and methyl 5-bromo-3-fluoropicolinate, respectively. ESI MS m/z=618.1 [M+H]+.

Example 468

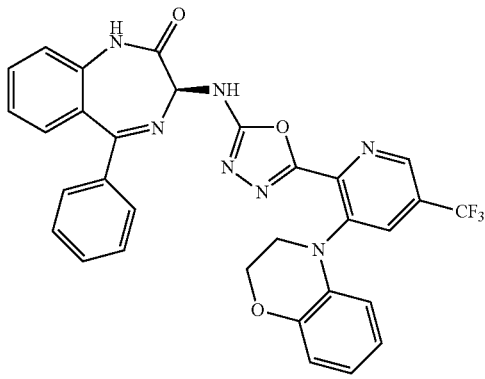 [SMILES: O=C1Nc2ccccc2C(c2ccccc2)=N[C@@H]1Nc1nnc(-c2ncc(C(F)(F)F)cc2N2CCOc3ccccc32)o1]

Example 468 was prepared using a procedure similar to that used to Example 160 where 3,4-dihydro-2H-benzo[b][1,4]oxazine and ethyl 3-chloro-5-(trifluoromethyl)picolinate were used in place of morpholine and methyl 5-bromo-3-fluoropicolinate, respectively. ESI MS m/z=598.1 [M+H]+.

Example 469

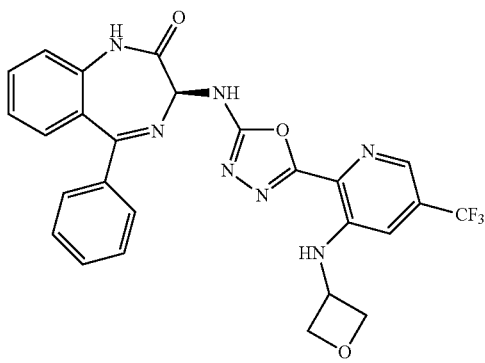 [SMILES: O=C1Nc2ccccc2C(c2ccccc2)=N[C@@H]1Nc1nnc(-c2ncc(C(F)(F)F)cc2NC2COC2)o1]

Example 469 was prepared using a procedure similar to that used to Example 160 where oxetan-3-amine and ethyl 3-chloro-5-(trifluoromethyl)picolinate were used in place of morpholine and methyl 5-bromo-3-fluoropicolinate, respectively. ESI MS m/z=536.1 [M+H]+.

Example 470

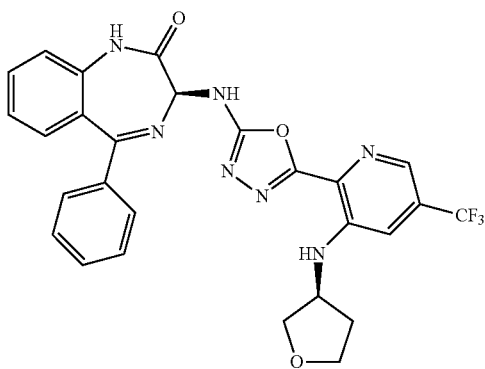 [SMILES: O=C1Nc2ccccc2C(c2ccccc2)=N[C@@H]1Nc1nnc(-c2ncc(C(F)(F)F)cc2N[C@H]2CCOC2)o1]

Example 470 was prepared using a procedure similar to that used to Example 160 where (S)-tetrahydrofuran-3-amine and ethyl 3-chloro-5-(trifluoromethyl)picolinate were used in place of morpholine and methyl 5-bromo-3-fluoropicolinate, respectively. ESI MS m/z=550.1 [M+H]+.

Example 471

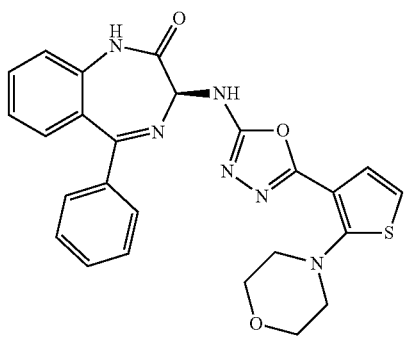 [SMILES: O=C1Nc2ccccc2C(c2ccccc2)=N[C@@H]1Nc1nnc(-c2ccsc2N2CCOCC2)o1]

Example 471 was prepared using a procedure similar to that used to prepare Example 430 where ethyl 2-aminothiophene-3-carboxylate was used in place of ethyl 3-amino-1-cyclobutyl-1H-pyrazole-4-carboxylate. ESI MS m/z=487.1 [M+H]+.

Example 472

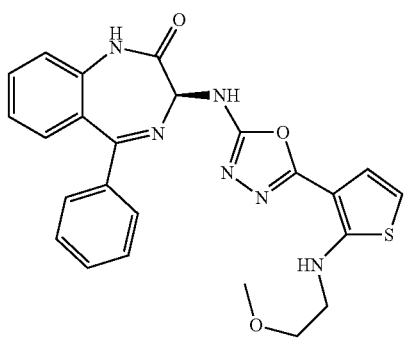 [SMILES: COCCNc1sccc1-c1nnc(N[C@H]2N=C(c3ccccc3)c3ccccc3NC2=O)o1]

Example 472 was prepared using a procedure similar to that used to prepare Example 471 where 1-bromo-2-methoxyethane was used in place of 1-bromo-2-(2-bromoethoxy)ethane. ESI MS m/z=475.1 [M+H]+.

Example 473

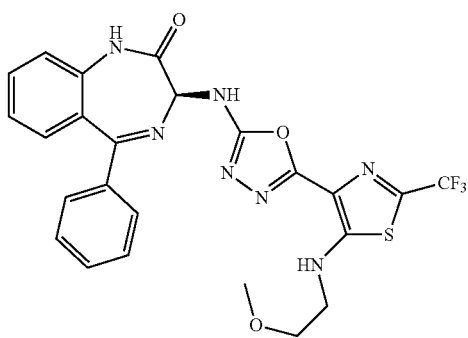 [SMILES: COCCNc1sc(C(F)(F)F)nc1-c1nnc(N[C@H]2N=C(c3ccccc3)c3ccccc3NC2=O)o1]

Example 473 was prepared using a procedure similar to that used in Example 339 where 2-methoxyethan-1-amine was used in place of morpholine. ESI MS m/z=544.1[M+H]⁺.

Example 474

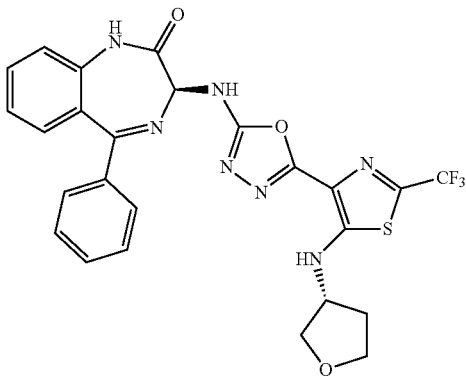 [SMILES: O=C1Nc2ccccc2C(c2ccccc2)=N[C@@H]1Nc1nnc(-c2nc(C(F)(F)F)sc2N[C@@H]2CCOC2)o1]

Example 474 was prepared using a procedure similar to that used in Example 339 where (R)-tetrahydrofuran-3-amine was used in place of morpholine. ESI MS m/z=556.1 [M+H]⁺.

Example 475

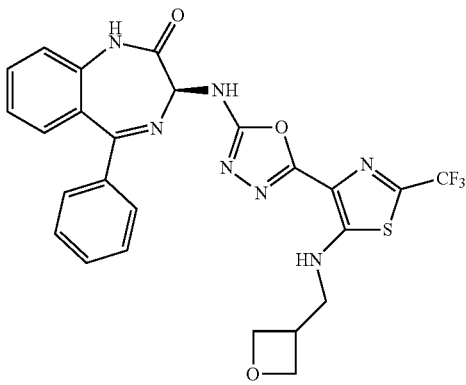 [SMILES: O=C1Nc2ccccc2C(c2ccccc2)=N[C@@H]1Nc1nnc(-c2nc(C(F)(F)F)sc2NCC2COC2)o1]

Example 475 was prepared using a procedure similar to that used in Example 339 where oxetan-3-ylmethanamine was used in place of morpholine. ESI MS m/z=556.1 [M+H]⁺.

Example 476

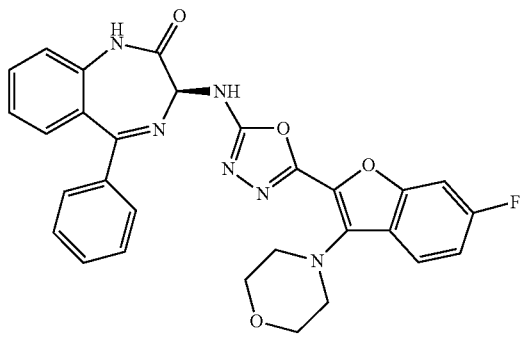 [SMILES: O=C1Nc2ccccc2C(c2ccccc2)=N[C@@H]1Nc1nnc(-c2oc3cc(F)ccc3c2N2CCOCC2)o1]

Example 476 Step a

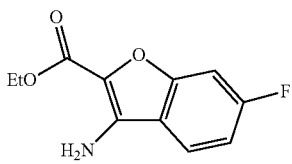 [SMILES: CCOC(=O)c1oc2cc(F)ccc2c1N]

To an 8 mL vial 4-fluoro-2-hydroxybenzonitrile (150 mg, 1.094 mmol) was dissolved in acetone (2188 µL). To the solution was added ethyl 2-bromoacetate (121 µL, 1.094 mmol) followed by potassium carbonate (151 mg, 1.094 mmol). The vial was sealed with electrical tape and heated to 40° C. for 12 h. The reaction was allowed to cool to room temperature and water (2 mL) and EtOAc (2 mL) were added. The organic layer was separated and the aqueous layer was washed with EtOAc (2×2 mL). The combined organic layer was dried over MgSO$_4$ and concentrated. The crude reaction mixture was purified by silica gel chromatography (80:20 Hex/EtOAc). The desired product, ethyl 3-amino-6-fluorobenzofuran-2-carboxylate, was obtained as a white solid (186 mg, 76% yield).

Example 476 Step b

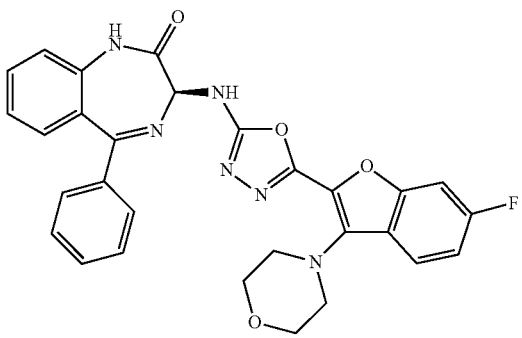 [SMILES: O=C1Nc2ccccc2C(c2ccccc2)=N[C@@H]1Nc1nnc(-c2oc3cc(F)ccc3c2N2CCOCC2)o1]

Example 476 was prepared using a procedure similar to that used to prepare Example 430 where ethyl 3-amino-6-fluorobenzofuran-2-carboxylate was used in place of ethyl 3-amino-1-cyclobutyl-1H-pyrazole-4-carboxylate. ESI MS m/z=539.2 [M+H]⁺.

Example 477

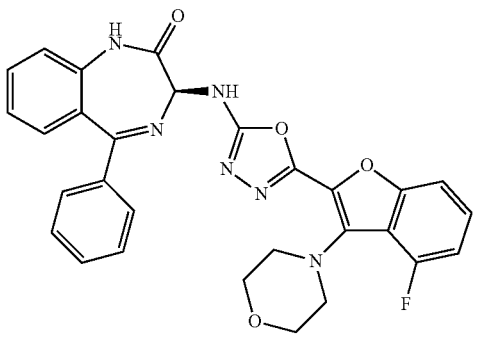 [SMILES: O=C1Nc2ccccc2C(c2ccccc2)=N[C@@H]1Nc1nnc(-c2oc3cccc(F)c3c2N2CCOCC2)o1]

Example 477 was prepared using a procedure similar to that used to prepare Example 476 where 2-fluoro-6-hydroxybenzonitrile was used in place of 4-fluoro-2-hydroxybenzonitrile. ESI MS m/z=539.2 [M+H]⁺.

Example 478

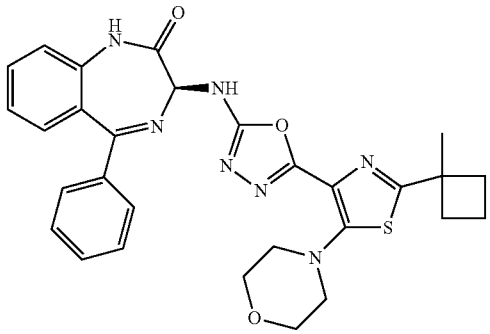 [SMILES: CC1(c2nc(-c3nnc(N[C@H]4N=C(c5ccccc5)c5ccccc5NC4=O)o3)c(N3CCOCC3)s2)CCC1]

Example 478 was prepared using a procedure similar to 458 where 1-methylcyclobutane-1-carboxamide was used in place of 1-fluorocyclobutane-1-carboxamide. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=556.3 [M+H]⁺.

Example 479

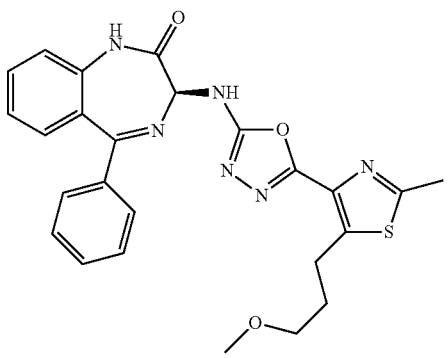 [SMILES: COCCCc1sc(C)nc1-c1nnc(N[C@H]2N=C(c3ccccc3)c3ccccc3NC2=O)o1]

Example 479 Step a

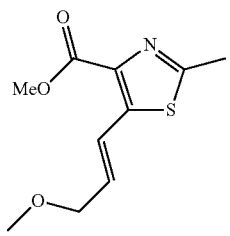

To an nitrogen-sparged solution of methyl methyl 5-bromo-2-methylthiazole-4-carboxylate (0.5 g, 2.012 mmol), (E)-2-(3-methoxyprop-1-en-1-yl)-4,4,5,5-tetramethyl-1,3,2-dioxaborolane (1.068 ml, 5.03 mmol), and potassium phosphate (1.525 g, 7.04 mmol) in dry THF (20 mL) was added tetrakis(triphenylphosphine)palladium(0) (0.470 g, 0.402 mmol). After an additional 2 min sparging, the mixture was stirred at 66° C. for 16 h at which time it was diluted with water (20 mL) and extracted 3× with ethyl acetate. The combined organics were washed with brine, dried over anhydrous MgSO₄, filtered, and concentrated in vacuo. The resulting residue was flash chromatographed on silica gel to afford methyl (E)-5-(3-methoxyprop-1-en-1-yl)-2-methylthiazole-4-carboxylate (310.1 mg, 1.364 mmol, 67.8% yield) (TLC 30% EtOAc in hexanes, rf~0.2) as a yellowish oil.

Example 479 Step b

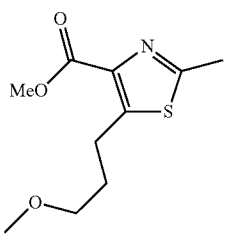

An oven dried 20 mL vial was charged with methyl (E)-5-(3-methoxyprop-1-en-1-yl)-2-methylthiazole-4-carboxylate (257 mg, 1.131 mmol), palladium on carbon (120 mg, 0.113 mmol) and anhydrous MeOH (11.308 mL). The flask was then purged with hydrogen and then stirred under hydrogen atm at rt overnight. The solvent was evaporated and the crude residue filtered through a plug of silica gel using 1:1 EtOAc:hexanes as the eluent. Then the crude residue was purified through column chromatography to yield methyl 5-(3-methoxypropyl)-2-methylthiazole-4-carboxylate (195.1 mg, 0.851 mmol, 75% yield) as a colorless oil.

Example 479 Step c

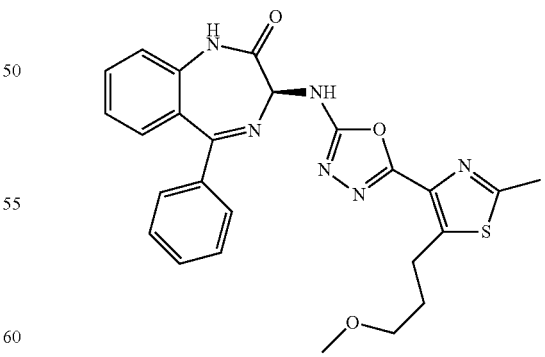

Example 479 was prepared using a procedure similar to that used to prepare Example 152 where methyl 5-(3-methoxypropyl)-2-methylthiazole-4-carboxylate was used in place of ethyl 2-morpholino-4-(trifluoromethyl)benzoate. ESI MS m/z=489.2 [M+H]⁺.

Examples 480, 481, 482, and 483

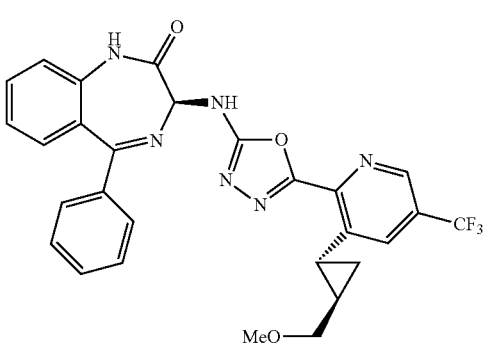
480

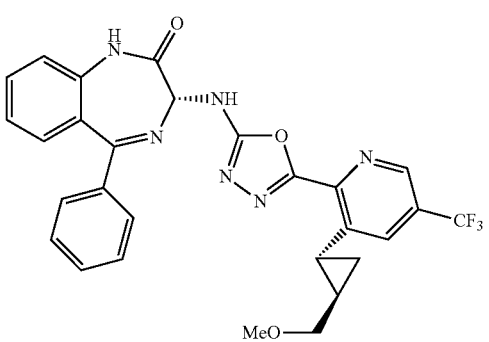
481

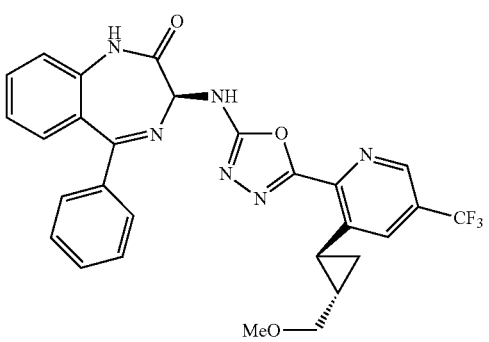
482

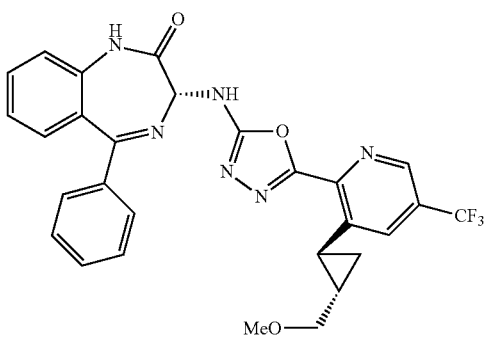
483

Examples 480, 481, 482, and 483 Step a

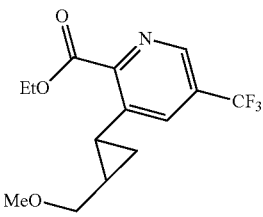 [SMILES: CCOC(=O)c1ncc(C(F)(F)F)cc1C1CC1COC]

Et$_2$Zn (1 M in Hexane) (10.4 mL, 10.4 mmol) was added to the PH-ETA-A1-770-1 (0.3 g, 1.04 mmol) at 0° C., then CH$_2$I$_2$ (5.6 g, 20.8 mmol) was added under N$_2$. The mixture was stirred for 1 day at rt. The reaction mixture was quenched with saturated aqueous ammonium chloride solution and extracted with EtOAc. The organic layer was washed with brine, dried over sodium sulfate and concentrated. The crude product was purified by silica gel chromatography (PE-EA) and chiral-Prep-HPLC to give desired compound as yellow oil (0.23 g, 73%). ESI MS m/z=304.3 [M+H]$^+$.

Examples 480, 481, 482, and 483 Step b

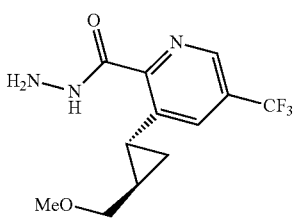
A

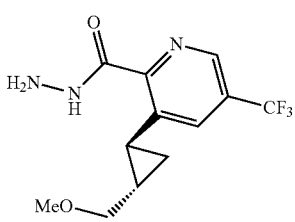
B

A solution of the compound from step a (230 mg, 0.76 mmol) and NH$_2$NH$_2$.H$_2$O (2 mL) in EtOH (5 mL) was stirred for 1 hour at r.t. The crude product was purified by Flash-Prep-HPLC (MeCN/H$_2$O) to give desired mixture of compounds as a yellow oil (150 mg, 68%). The mixture was separated by chiral-Prep-HPLC to give A (67 mg, 45%) and B (70 mg, 47%). A: ESI MS m/z=290.3 [M+H]$^+$. B: ESI MS m/z=290.3 [M+H]$^+$.

Examples 480, 481, 482, and 483 Step c

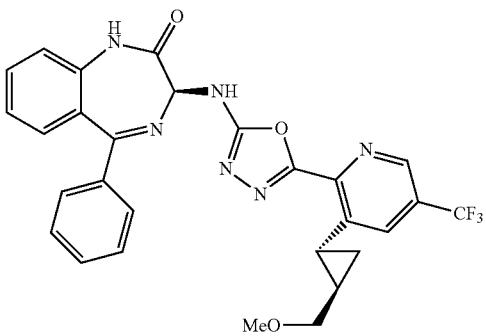

480

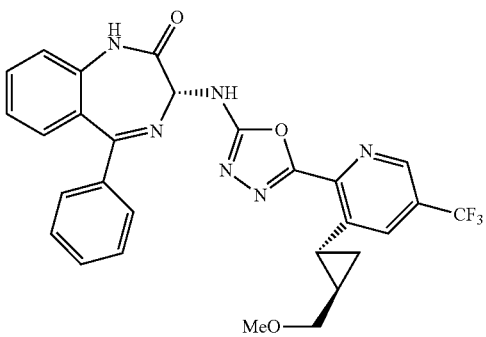

481

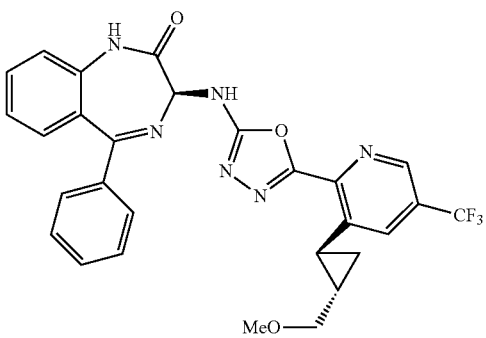

482

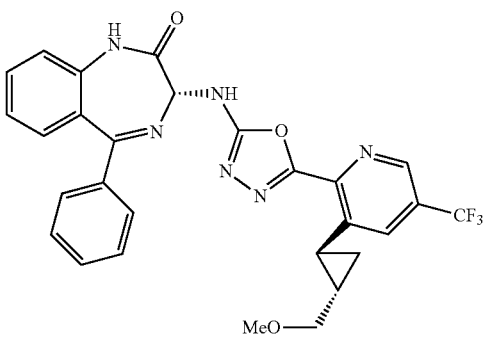

483

Examples 480 and 481 (with hydrazide A from step b), and 482 and 483 (with hydrazide B from step b), were prepared using a procedure similar to that used to prepare Example 21 where hydrazide A and hydrazide B were used in place of tetrahydro-2H-pyran-4-carbohydrazide. Compounds 481 and 482 were separated by chiral-Prep-HPLC. Compounds 483 and 484 were separated by chiral-Prep-HPLC. Example 480: ESI MS m/z=549.5 [M+H]+. $^1$H NMR (300 MHz, DMSO-$d_6$) δ 1.05 (m, 1H), 1.19 (m, 1H), 1.58 (m, 1H), 2.90 (m, 1H), 3.23 (s, 3H), 3.28 (d, J=6.5 Hz, 1H), 3.46 (m, 1H), 5.22 (d, J=8.2 Hz, 1H), 7.24-7.42 (m, 3H), 7.41-7.61 (m, 5H), 7.68 (m, 1H), 7.83-7.93 (m, 1H), 8.83-9.04 (m, 1H), 9.44 (d, J=8.4 Hz, 1H), 11.00 (s, 1H). Example 481: ESI MS m/z=549.4 [M+H]+. $^1$H NMR (300 MHz, DMSO-$d_6$) δ 1.05 (m, 1H), 1.13-1.28 (m, 1H), 1.51-1.67 (m, 1H), 2.90 (m, 1H), 3.23 (s, 3H), 3.26-3.31 (m, 1H), 3.46 (m, 1H), 5.22 (d, J=8.3 Hz, 1H), 7.24-7.41 (m, 3H), 7.42-7.60 (m, 5H), 7.68 (m, 1H), 7.88 (d, J=2.2 Hz, 1H), 8.84-9.08 (m, 1H), 9.44 (d, J=8.3 Hz, 1H), 11.00 (s, 1H). Example 482: ESI MS m/z=549.4 [M+H]+. $^1$H NMR (300 MHz, DMSO-$d_6$) δ 1.05 (m, 1H), 1.13-1.27 (m, 1H), 1.50-1.67 (m, 1H), 2.89 (m, 1H), 3.23 (s, 3H), 3.25-3.31 (m, 1H), 3.45 (m, 1H), 5.22 (d, J=8.4 Hz, 1H), 7.25-7.40 (m, 3H), 7.43-7.58 (m, 5H), 7.68 (m, 1H), 7.82-7.94 (m, 1H), 8.91 (m, 1H), 9.45 (d, J=8.4 Hz, 1H), 11.01 (s, 1H). Example 483: ESI MS m/z=549.5 [M+H]+. $^1$H NMR (300 MHz, DMSO-$d_6$) δ 0.98-1.10 (m, 1H), 1.19 (m, 1H), 1.50-1.65 (m, 1H), 2.90 (m, 1H), 3.23 (s, 3H), 3.28 (m, 1H), 3.45 (m, 1H), 5.22 (d, J=8.4 Hz, 1H), 7.24-7.40 (m, 3H), 7.42-7.58 (m, 5H), 7.68 (m, 1H), 7.84-7.89 (m, 1H), 8.91 (m, 1H), 9.45 (d, J=8.4 Hz, 1H), 11.00 (s, 1H).

Examples 484, 485, 486, and 487

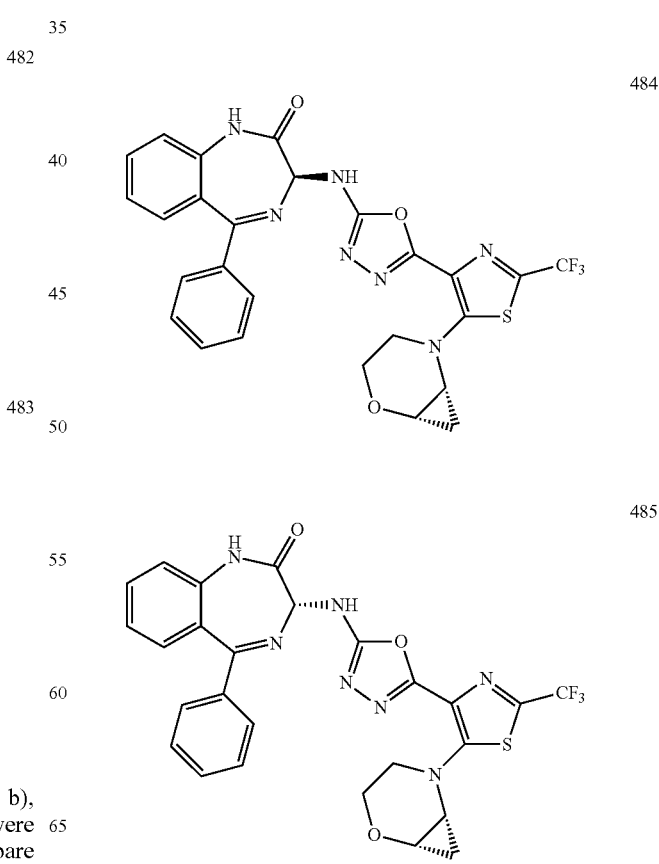

411
-continued

486

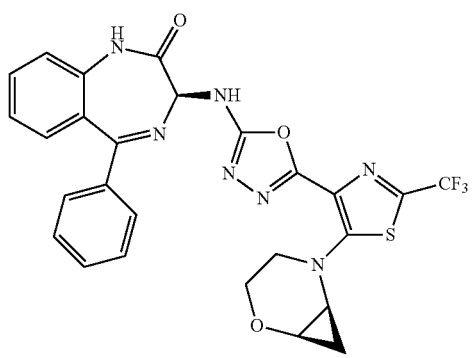

487

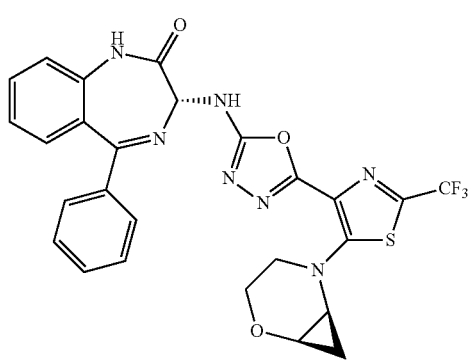

Examples 484, 485, 486, and 487 Step a

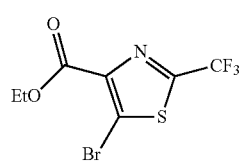 [SMILES: CCOC(=O)c1nc(C(F)(F)F)sc1Br]

A solution of ethyl 2-(trifluoromethyl)thiazole-4-carboxylate (1.3 g, 5.78 mmol) in THF (5 mL) was dropwised to the solution of LDA (5.8 mL, 11.56 mmol) in THF (10 mL) at −78° C. under $N_2$. The mixture was stirred for 45 minutes at same temperature. To this, a solution of 1,2-dibromo-1,1,2,2-tetrachloroethane (5.58 g, 17.34 mmol) in THF (5 mL) was dropwised and warmed to room temperature, stirred for 2 hours. The reaction was quenched with saturated ammonium chloride solution. Water was added and the mixture was extracted with EA (×3). The organic layer was combined, dried and concentrated. The residue was purified via silica gel chromatography (petroleum ether-ethyl acetate) to give the desired compound as yellow oil (900 mg, 51%). ESI MS m/z=549.5 [M+H]⁺.

412
Examples 484, 485, 486, and 487 Step b

A

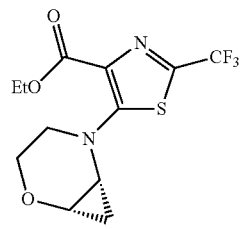

B

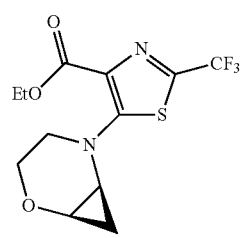

A solution of the compound from step a (800 mg, 2.64 mmol), 2-oxa-5-azabicyclo[4.1.0]heptane hydrochloride (535 mg, 3.96 mmol) and DIPEA (0.8 mL) in DMSO (4 mL) was stirred overnight at 80° C. It was extracted with EA (25 mL×2), combined the organic layer, and dried with anhydrous $Na_2SO_4$, then concentrated and purified by silica gel column to give the mixture of enantiomers as an orange oil (443 mg, 52%). The mixture was purified by chiral-Prep-HPLC to give A (200 mg, 42%) and B (210 mg, 44%). ESI MS m/z=549.5 [M+H]⁺.

Examples 484, 485, 486, and 487 Step c

484

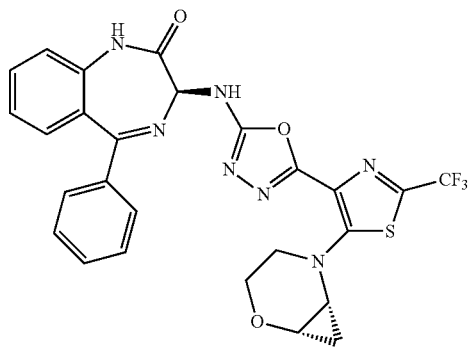

485

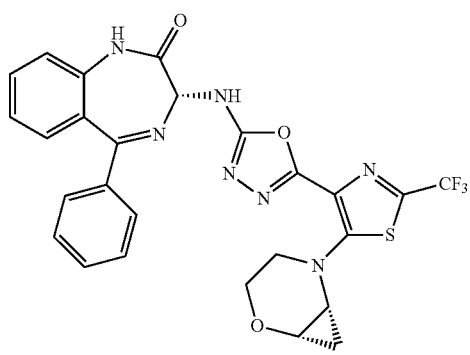

-continued

486

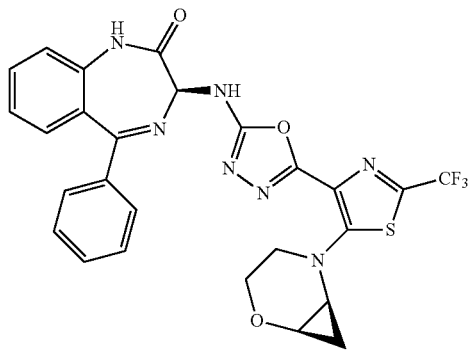

487

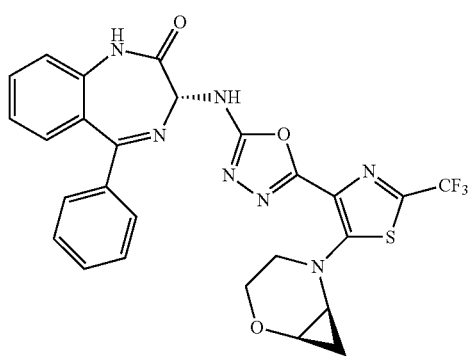

Examples 484 and 485 (with ester A from step b), and 486 and 487 (with ester B from step b), were prepared using a procedure similar to that used to prepare Examples 480, 481, 482, and 483. Example 484: ESI MS m/z=568.4 [M+H]$^+$. $^1$H NMR (300 MHz, DMSO-d$_6$) δ 0.81 (m, 2H), 2.94 (m, 2H), 3.56-3.83 (m, 3H), 3.88 (m, 1H), 5.15 (d, 1H), 7.13-7.41 (m, 3H), 7.41-7.61 (m, 5H), 7.61-7.83 (m, 1H), 9.14 (d, 1H), 10.97 (s, 1H). Example 485: ESI MS m/z=568.4 [M+H]$^+$. $^1$H NMR (300 MHz, DMSO-d$_6$) δ 0.82 (s, 2H), 2.92 (m, 2H), 3.57-4.02 (m, 4H), 5.15 (d, 1H), 7.32 (m, 3H), 7.51 (m, 5H), 7.67 (m, 1H), 9.14 (d, 1H), 10.97 (s, 1H). Example 486: ESI MS m/z=568.4 [M+H]$^+$. $^1$H NMR (300 MHz, DMSO-d$_6$) δ 0.73-0.92 (m, 2H), 2.92 (m, 2H), 3.64 (m, 1H), 3.67-3.82 (m, 2H), 3.89 (m, 1H), 5.15 (d, 1H), 7.19-7.39 (m, 3H), 7.39-7.59 (m, 5H), 7.68 (m, 1H), 9.14 (d, 1H), 10.97 (s, 1H). Example 487: ESI MS m/z=568.4 [M+H]$^+$. $^1$H NMR (300 MHz, DMSO-d$_6$) δ 0.82 (m, 2H), 2.93 (m, 2H), 3.65 (m, 1H), 3.68-3.81 (m, 2H), 3.89 (m, 1H), 5.15 (d, 1H), 7.14-7.40 (m, 3H), 7.40-7.59 (m, 5H), 7.68 (m, 1H), 9.14 (d, 1H), 10.97 (s, 1H).

Examples 488 and 489

488

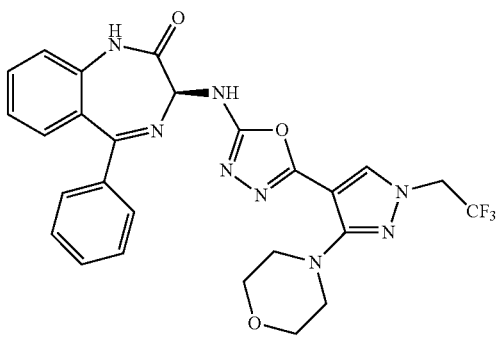

489

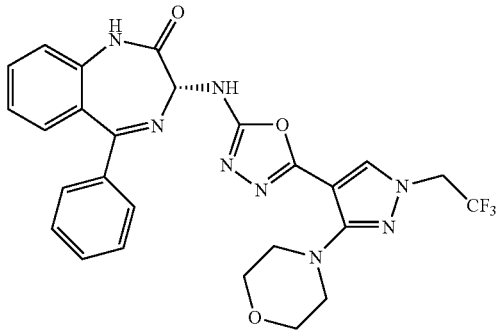

Examples 488 and 489 Step a

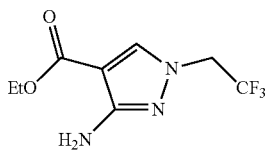 [SMILES: CCOC(=O)c1cn(CC(F)(F)F)nc1N]

To a stirred solution of the ethyl 3-amino-1H-pyrazole-4-carboxylate (4 g, 0.025 mol) in DMF (50 mL) was added Cs$_2$CO$_3$ (8.2 g, 0.025 mol) and 1,1,1-trifluoro-2-iodoethane (10.5 g, 0.055 mol) at rt. The mixture was stirred at 70° C. over the night and then concentrated. The reaction mixture was filtered and the filtrate was poured into water and extracted with EA (3×150 mL). The organic layer was dried over Na$_2$SO$_4$. The residue was purified via silica gel chromatography (petroleum ether-ethyl acetate) to give the desired compound as a yellow solid (2.5 g, 44%). ESI MS m/z=238.2 [M+H]$^+$.

Examples 488 and 489 Step b

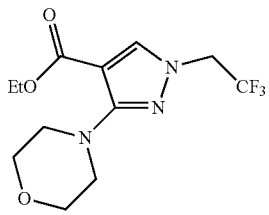 [SMILES: CCOC(=O)c1cn(CC(F)(F)F)nc1N1CCOCC1]

To a stirred solution of the compound from step 1 (2.5 g, 0.011 mol) in the DMA (30 mL) was added to 1-bromo-2-(2-bromoethoxy) ethane (5.82 g, 0.025 mol) and Cs$_2$CO$_3$ (5.5 g, 0.017 mol) at rt. The resulting solution was stirred at 100° C. for 6 hours and then concentrated. The reaction mixture was poured into water and extracted with EA (3×150 ml). The organic layer was dried over Na$_2$SO$_4$. The residue was purified via silica gel chromatography (petroleum ether-ethyl acetate) to give the desired product as a yellow solid (700 mg, 21%). ESI MS m/z=308.4 [M+H]$^+$.

Examples 488 and 489 Step c

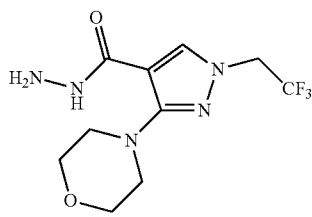 [SMILES: NNC(=O)c1cn(CC(F)(F)F)nc1N1CCOCC1]

To a stirring solution of the compound from step 2 (700 mg, 3.74 mmol) in EtOH (5 mL) was added NH$_2$NH$_2$.H$_2$O (4 mL) at rt. The resulting solution was stirred at rt for 5 hours. The reaction mixture was purified by reverse phase C18 column chromatography (MeCN:H$_2$O) (MeCN/H$_2$O) to give the desired product as a yellow solid (300 mg, 27%). ESI MS m/z=294.1 [M+H]$^+$.

Examples 488 and 489 Step d

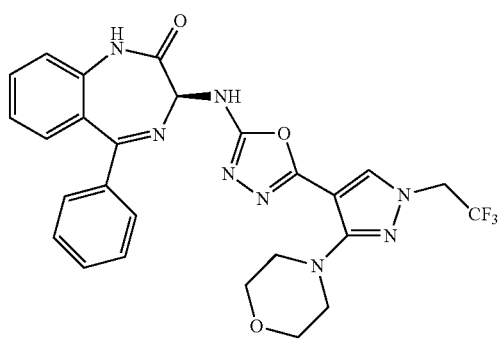
488

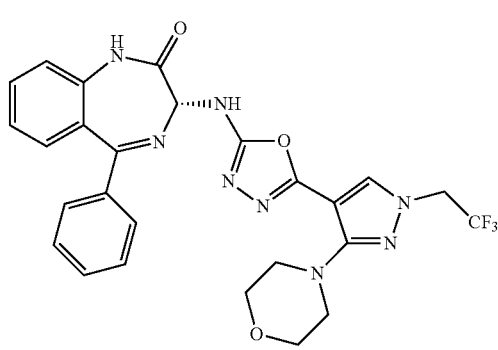
489

Examples 488 and 489 were prepared using a procedure similar to that used to prepare Example 21 where 3-morpholino-1-(2,2,2-trifluoroethyl)-1H-pyrazole-4-carbohydrazide was used in place of tetrahydro-2H-pyran-4-carbohydrazide. Examples 488 and 489 were separated by chiral-Prep-HPLC. Example 488: ESI MS m/z=553.0 [M+H]$^+$. $^1$H NMR (300 MHz, DMSO-d$_6$) δ3.12-3.23 (dd, J=6.1, 3.4 Hz, 4H), 3.61-3.82 (m, 4H), 5.00-5.23 (m, 3H), 7.26-7.39 (m, 3H), 7.39-7.59 (m, 5H), 7.64-7.76 (m, J=8.5, 7.0, 1.8 Hz, 1H), 8.16-8.32 (s, 1H), 8.93-9.12 (d, J=8.7 Hz, 1H), 10.90-11.12 (s, 1H). Example 489: ESI MS m/z=553.0 [M+H]$^+$. $^1$H NMR (300 MHz, DMSO-d6) δ3.10-3.26 (dd, J=6.1, 3.4 Hz, 4H), 3.61-3.78 (m, 4H), 5.00-5.18 (dd, J=8.8, 3.4 Hz, 3H), 7.13-7.38 (m, 3H), 7.39-7.62 (m, 5H), 7.65-7.76 (m, J=8.5, 7.0, 1.8 Hz, 1H), 8.16-8.29 (s, 1H), 8.95-9.10 (d, J=8.6 Hz, 1H), 10.83-11.10 (s, 1H).

Example 490

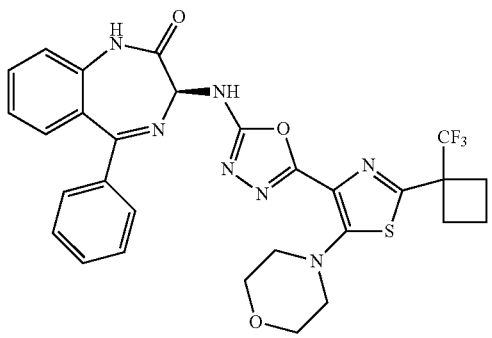

Example 490 was prepared using a procedure similar to 458 where 1-(trifluoromethyl)cyclobutane-1-carboxamide was used in place of 1-fluorocyclobutane-1-carboxamide. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=610.2 [M+H]$^+$.

Example 491

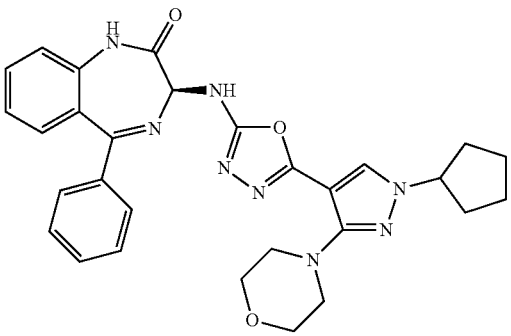 [SMILES: O=C1Nc2ccccc2C(c2ccccc2)=N[C@@H]1Nc1nnc(-c2cn(C3CCCC3)nc2N2CCOCC2)o1]

Example 491 was prepared using a procedure similar to 430 where bromocyclopentane was used in place of bromocyclobutane. ESI MS m/z=539.5 [M+H]$^+$. $^1$H NMR (300 MHz, DMSO-d$_6$) δ 1.55-1.69 (m, 2H), 1.77 (m, 2H), 1.84-1.96 (m, 2H), 1.96-2.10 (m, 2H), 3.02-3.26 (m, 4H), 3.66 (m, 4H), 4.63 (m, 1H), 5.10 (d, J=8.7 Hz, 1H), 7.23-7.39 (m, 3H), 7.41-7.58 (m, 5H), 7.67 (m, 1H), 8.06 (s, 1H), 8.85 (d, J=8.7 Hz, 1H), 10.96 (s, 1H).

Example 492

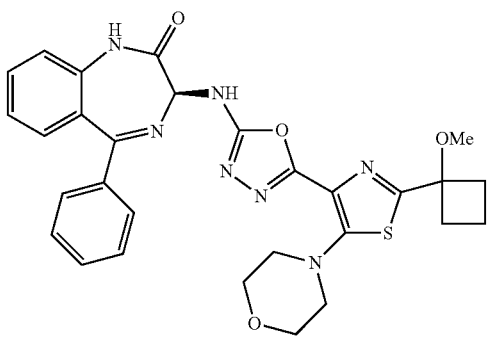 [SMILES: COC1(c2nc(-c3nnc(N[C@H]4N=C(c5ccccc5)c5ccccc5NC4=O)o3)c(N3CCOCC3)s2)CCC1]

Example 492 was prepared using a procedure similar to 458 where MeOH was used in place of EtOH in step e. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=572.2 [M+H]$^+$.

Example 493

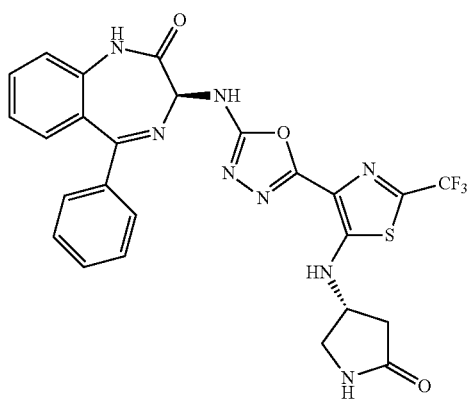 [SMILES: O=C1C[C@@H](Nc2sc(C(F)(F)F)nc2-c2nnc(N[C@H]3N=C(c4ccccc4)c4ccccc4NC3=O)o2)CN1]

Example 493 was prepared using a procedure similar to that used to prepare Example 21 where ethyl (R)-5-((5-oxopyrrolidin-3-yl)amino)-2-(trifluoromethyl)thiazole-4-carboxylate, which was prepared similarly to ethyl 5-morpholino-2-(trifluoromethyl)thiazole-4-carboxylate in Example 339, was converted to the corresponding hydrazide and used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=569.1 [M+H]$^+$. $^1$H NMR (300 MHz, DMSO-d$_6$) δ 2.33 (dd, J=16.7, 5.3 Hz, 1H), 2.69 (dd, J=16.7, 7.9 Hz, 1H), 3.28 (dd, J=10.2, 4.5 Hz, 1H), 3.70 (dd, J=10.1, 7.0 Hz, 1H), 4.23 (q, J=6.1, 6.1, 6.0 Hz, 1H), 5.15 (d, J=8.4 Hz, 1H), 7.24-7.39 (m, 3H), 7.42-7.58 (m, 5H), 7.68 (ddd, J=8.4, 7.0, 1.8 Hz, 1H), 7.81 (s, 1H), 9.15 (d, J=8.6 Hz, 1H), 10.95 (s, 1H).

Example 494

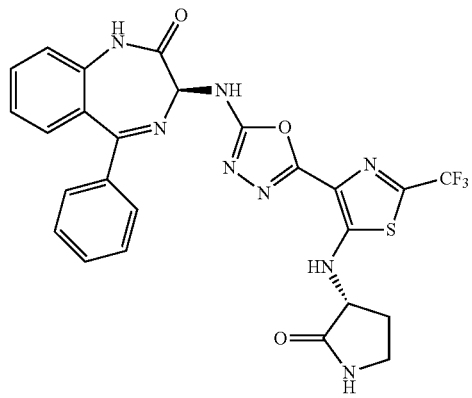 [SMILES: O=C1Nc2ccccc2C(c2ccccc2)=N[C@@H]1Nc1nnc(-c2nc(C(F)(F)F)sc2N[C@@H]2CCNC2=O)o1]

Example 494 was prepared using a procedure similar to that used to prepare Example 21 where ethyl (R)-5-((2-oxopyrrolidin-3-yl)amino)-2-(trifluoromethyl)thiazole-4-carboxylate, which was prepared similarly to ethyl 5-morpholino-2-(trifluoromethyl)thiazole-4-carboxylate in Example 339, was converted to the corresponding hydrazide and used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=569.1 [M+H]$^+$. $^1$H NMR (300 MHz, DMSO-d$_6$) δ 2.03 (dq, J=12.2, 9.6, 9.6, 9.6 Hz, 1H), 2.62 (dt, J=12.6, 6.6, 6.6 Hz, 1H), 3.30 (d, J=3.4 Hz, 2H), 4.26 (t, J=9.3, 9.3 Hz, 1H), 5.16 (d, J=8.4 Hz, 1H), 7.19-7.43 (m, 3H), 7.40-7.76 (m, 7H), 8.21 (s, 1H), 9.14 (d, J=8.5 Hz, 1H), 10.98 (s, 1H).

Example 495

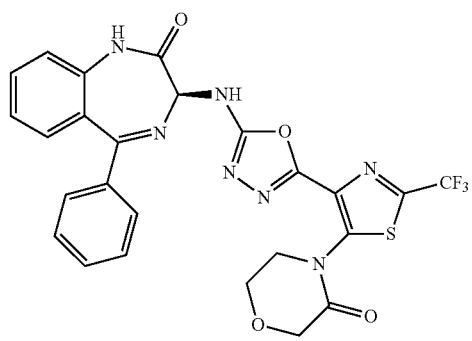 [SMILES: O=C1Nc2ccccc2C(c2ccccc2)=N[C@@H]1Nc1nnc(-c2nc(C(F)(F)F)sc2N2CCOCC2=O)o1]

Example 495 Step a

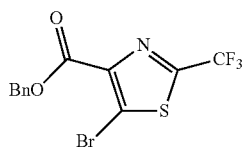 [SMILES: O=C(OCc1ccccc1)c1nc(C(F)(F)F)sc1Br]

A solution of ethyl 5-bromo-2-(trifluoromethyl)thiazole-4-carboxylate (500 mg, 1.65 mmol), LiOH (198 mg, 8.25 mmol) in THF (5 mL) and H$_2$O (2 mL) was stirred for 1 hour at RT. It was adjusted pH value to 4 with 3 N HCl and purified by Flash (MeCN/H$_2$O) to give the desired acid as yellow solid (410 mg, 90.3%). The acid (410 mg, 1.49 mmol), K$_2$CO$_3$ (411 mg, 2.98 mmol), BnBr (507 mg, 2.98 mmol) in DMF (5 mL) was stirred for 1 hour at RT and purified by Flash (MeCN/H$_2$O) to give the desired compound as yellow solid (505 mg, 92.8%). The compound had no signal on LCMS.

Example 495 Step b

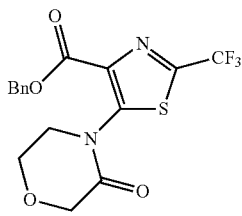 [SMILES: O=C(OCc1ccccc1)c1nc(C(F)(F)F)sc1N1CCOCC1=O]

A solution of the compound from step 1 (580 mg, 1.59 mmol), morpholin-3-one (481 mg, 4.76 mmol), Pd$_2$(dba)$_3$ (164 mg, 0.15 mmol), Xantphos (184 mg, 0.31 mmol), Cs$_2$CO$_3$ (1.03 g, 3.18 mmol) in 1,4-dioxane (10 mL) was stirred at 100° C. for 2 hours. The solution was concentrated and purified by TLC give the desired product as yellow solid (140 mg, 22.81%). ESI MS m/z=409.1 [M+H]$^+$.

Example 495 Step c

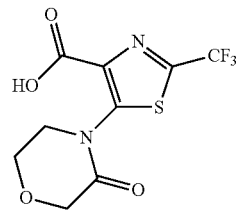 [SMILES: O=C(O)c1nc(C(F)(F)F)sc1N1CCOCC1=O]

A solution of the compound from step 2 (140 mg, 0.36 mmol), Pd/C (50 mg) in MeOH (10 mL) under H$_2$ was stirred at RT for 2 hours. The solid was filtered out and concentrated to give 5-(3-oxomorpholino)-2-(trifluoromethyl)thiazole-4-carboxylic acid as yellow solid (70 mg, 65.69%). ESI MS m/z=297.2 [M+H]$^+$.

Example 495 Step d

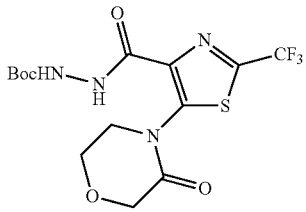 [SMILES: CC(C)(C)OC(=O)NNC(=O)c1nc(C(F)(F)F)sc1N1CCOCC1=O]

A solution of the compound from step 3 (70 mg, 0.23 mmol), tert-butyl hydrazinecarboxylate (62 mg, 0.46 mmol), HATU (131 mg, 0.34 mmol), DIPEA (0.5 mL) in DMF (2 mL) was stirred at RT for 2 hours. The solution was purified by Flash (MeCN/H$_2$O) to give the desired product as yellow oil (50 mg, 53.02%). ESI MS m/z=354.9 [M-t-Bu]$^+$.

Example 495 Step e

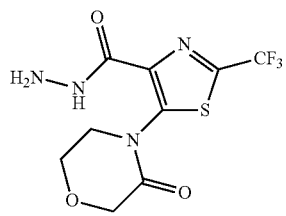 [SMILES: NNC(=O)c1nc(C(F)(F)F)sc1N1CCOCC1=O]

A solution of the compound from step 4 (50 mg, 0.12 mmol), TFA (2 mL) in DCM (16 mL) was stirred at RT for 1 hour. The solution was adjusted pH value to 10 with Sat. NaHCO$_3$ solution and purified by Flash (MeCN/H$_2$O) to give 5-(3-oxomorpholino)-2-(trifluoromethyl)thiazole-4-carbohydrazide as yellow solid (25 mg, 67.56%). ESI MS m/z=310.5 [M+H]$^+$.

Example 495 Step f

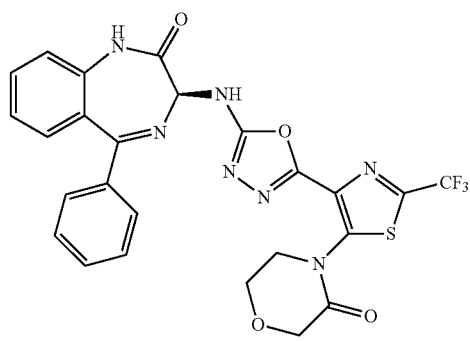 [SMILES: O=C1Nc2ccccc2C(c2ccccc2)=N[C@@H]1Nc1nnc(-c2nc(C(F)(F)F)sc2N2CCOCC2=O)o1]

Example 495 was prepared using a procedure similar to that used to prepare Example 21 where 5-(3-oxomorpholino)-2-(trifluoromethyl)thiazole-4-carbohydrazide was used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=570.1 [M+H]$^+$. $^1$H NMR (300 MHz, DMSO-d$_6$) δ 3.82-3.84 (m, 2H), 3.99-4.03 (m, 2H), 4.32 (s, 2H), 5.16-5.19 (d, J=9.0 Hz, 1H), 7.27-7.36 (m, 3H), 7.43-7.53 (m, 5H), 7.64-7.67 (m, 1H), 9.43-9.46 (d, J=9.0 Hz, 1H), 10.98 (s, 1H).

Example 496

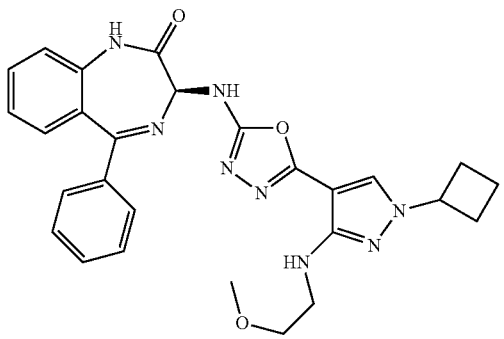 [SMILES: COCCNc1nn(C2CCC2)cc1-c1nnc(N[C@H]2N=C(c3ccccc3)c3ccccc3NC2=O)o1]

Example 496 was prepared using a procedure similar to that used to prepare Example 430 where 1-bromo-2-methoxyethane was used in place of 1-bromo-2-(2-bromoethoxy)ethane. ESI MS m/z=513.4 [M+H]$^+$. $^1$H NMR (400 MHz, DMSO-d$_6$) δ 1.65-1.84 (m, 2H), 2.31 (m, 2H), 2.40-2.48 (m, 2H), 3.27 (s, 3H), 3.39 (m, 2H), 3.51 (m, 2H), 4.72 (m, 1H), 5.10 (d, J=8.6 Hz, 1H), 5.40 (s, 1H), 7.24-7.31 (m, 1H), 7.32-7.38 (m, 2H), 7.43-7.57 (m, 5H), 7.67 (m, 1H), 7.99 (s, 1H), 8.85 (d, J=8.7 Hz, 1H), 10.97 (s, 1H).

Example 497

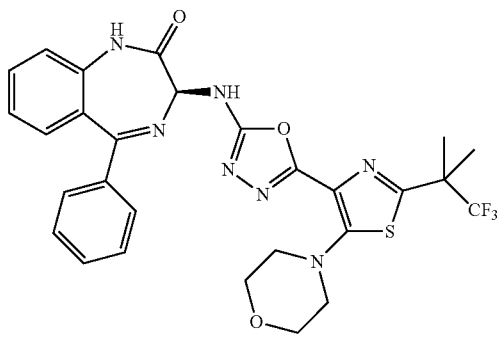 [SMILES: CC(C)(c1nc(-c2nnc(N[C@H]3N=C(c4ccccc4)c4ccccc4NC3=O)o2)c(N2CCOCC2)s1)C(F)(F)F]

Example 497 was prepared using a procedure similar to 458 where 3,3,3-trifluoro-2,2-dimethylpropanamide was used in place of 1-fluorocyclobutane-1-carboxamide. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=598.2 [M+H]$^+$.

Example 498

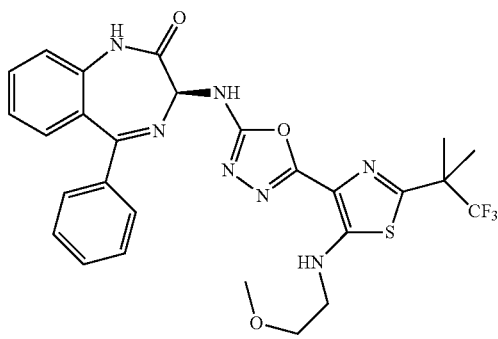 [SMILES: COCCNc1sc(C(C)(C)C(F)(F)F)nc1-c1nnc(N[C@H]2N=C(c3ccccc3)c3ccccc3NC2=O)o1]

Example 498 was prepared using a procedure similar to 458 where 3,3,3-trifluoro-2,2-dimethylpropanamide and 2-methoxyethan-1-amine were used in place of 1-fluorocyclobutane-1-carboxamide and morpholine, respectively. The racemic mixture was purified by chiral separation. (Column=YMC CHIRAL Cellulose-SB, 250*20 mm (5 uM); Mobile Phase=50% EtOH/50% hexanes; Flow rate=20 mL/min). ESI MS m/z=586.2 [M+H]$^+$.

Example 499

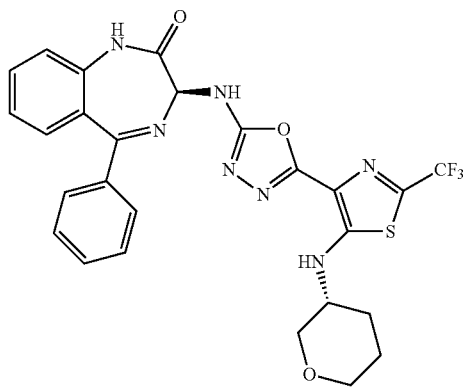 [SMILES: O=C1Nc2ccccc2C(c2ccccc2)=N[C@@H]1Nc1nnc(-c2nc(C(F)(F)F)sc2N[C@@H]2CCCOC2)o1]

Example 499 was prepared using a procedure similar to that used to prepare Example 21 where ethyl (R)-5-((tetrahydro-2H-pyran-3-yl)amino)-2-(trifluoromethyl)thiazole-4-carboxylate, which was prepared similarly to ethyl 5-morpholino-2-(trifluoromethyl)thiazole-4-carboxylate in Example 339, was converted to the corresponding hydrazide and used in place of tetrahydro-2H-pyran-4-carbohydrazide. The racemic mixture was purified by chiral separation. (Column=YMC CHIRAL Cellulose-SB, 250*20 mm (5 uM); Mobile Phase=50% iPrOH/50% hexanes; Flow rate=20 mL/min). ESI MS m/z=570.1 [M+H]$^+$.

Examples 500-518

The following compounds are prepared according to the general method described in Examples 430, 458 and 499.

Example 500

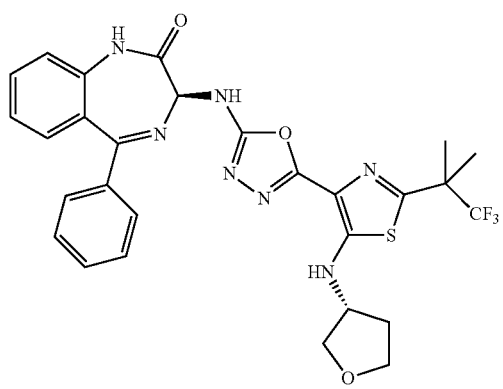 [SMILES: CC(C)(c1nc(-c2nnc(N[C@H]3N=C(c4ccccc4)c4ccccc4NC3=O)o2)c(N[C@@H]2CCOC2)s1)C(F)(F)F]

423
Example 501
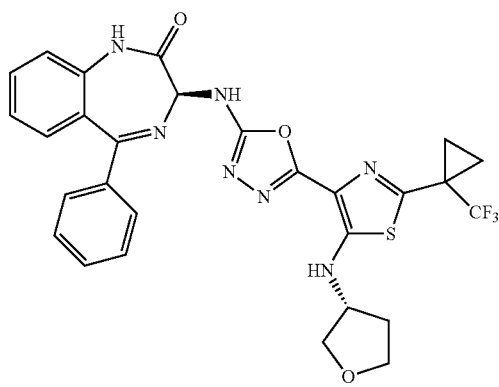 [SMILES: O=C1Nc2ccccc2C(c2ccccc2)=N[C@@H]1Nc1nnc(-c2nc(C3(C(F)(F)F)CC3)sc2N[C@@H]2CCOC2)o1]
Example 502
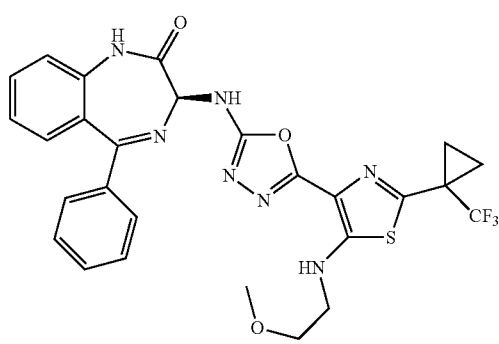 [SMILES: COCCNc1sc(C2(C(F)(F)F)CC2)nc1-c1nnc(N[C@H]2N=C(c3ccccc3)c3ccccc3NC2=O)o1]
Example 503
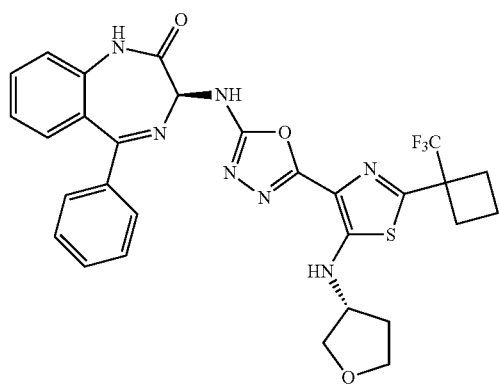 [SMILES: O=C1Nc2ccccc2C(c2ccccc2)=N[C@@H]1Nc1nnc(-c2nc(C3(C(F)(F)F)CCC3)sc2N[C@@H]2CCOC2)o1]
424
Example 504
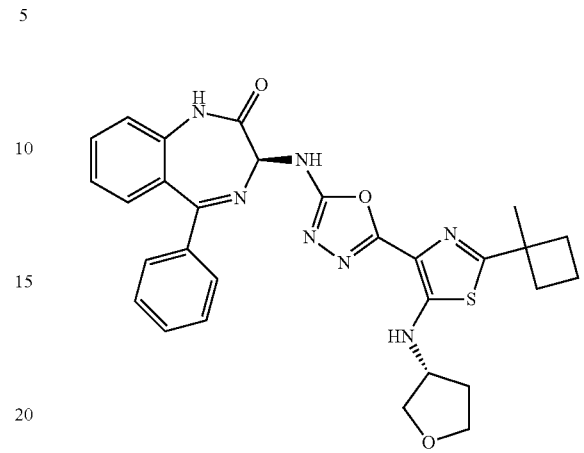
Example 505
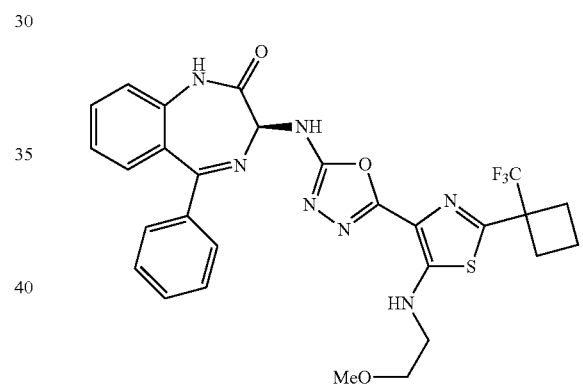
Example 506
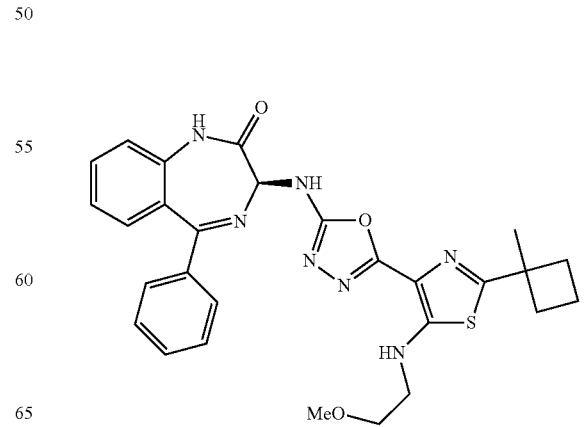

425
Example 507
426
Example 510
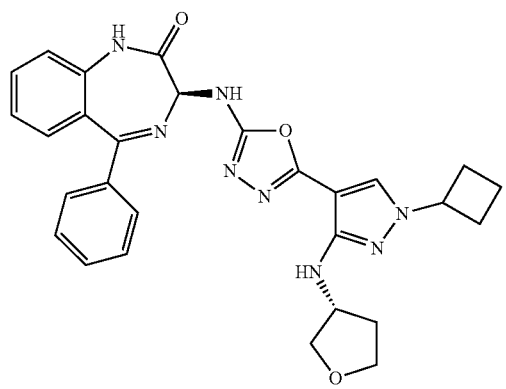 [SMILES: O=C1Nc2ccccc2C(c2ccccc2)=N[C@@H]1Nc1nnc(-c2cn(C3CCC3)nc2N[C@@H]2CCOC2)o1]
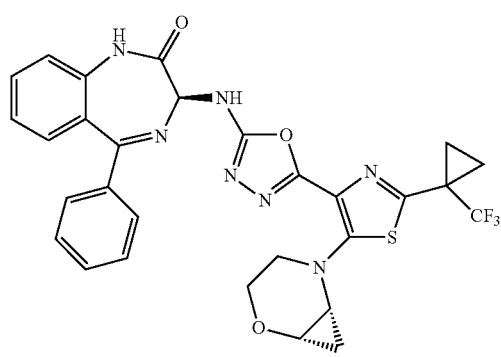
Example 508
Example 511
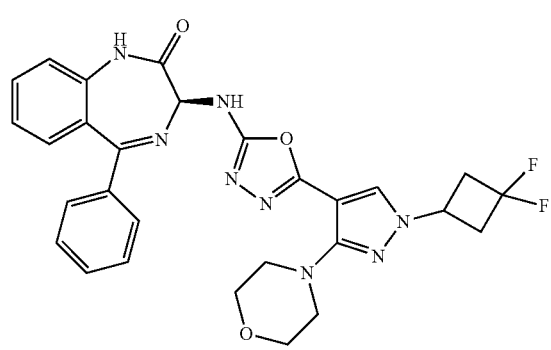 [SMILES: O=C1Nc2ccccc2C(c2ccccc2)=N[C@@H]1Nc1nnc(-c2cn(C3CC(F)(F)C3)nc2N2CCOCC2)o1]
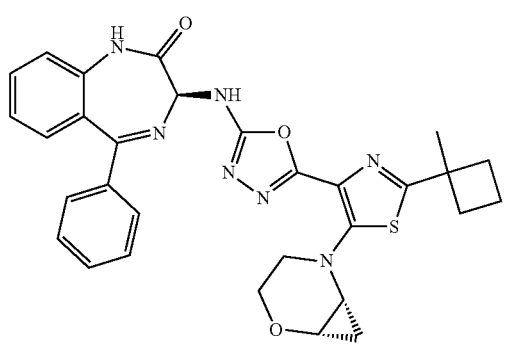
Example 509
Example 512
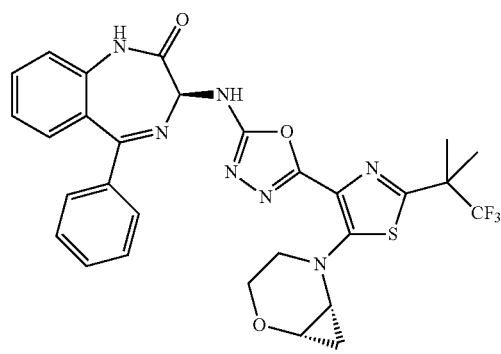 [SMILES: CC(C)(c1nc(-c2nnc(N[C@H]3N=C(c4ccccc4)c4ccccc4NC3=O)o2)c(N2CCO[C@H]3C[C@H]32)s1)C(F)(F)F]
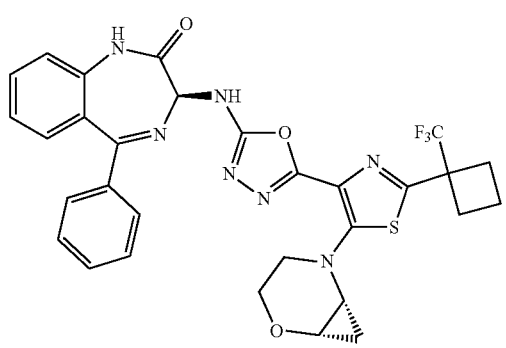 [SMILES: O=C1Nc2ccccc2C(c2ccccc2)=N[C@@H]1Nc1nnc(-c2nc(C3(C(F)(F)F)CCC3)sc2N2CCO[C@H]3C[C@H]32)o1]

427

Example 513

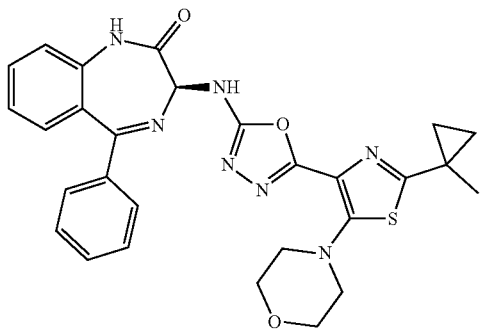 [SMILES: CC1(c2nc(-c3nnc(N[C@H]4N=C(c5ccccc5)c5ccccc5NC4=O)o3)c(N3CCOCC3)s2)CC1]

Example 514

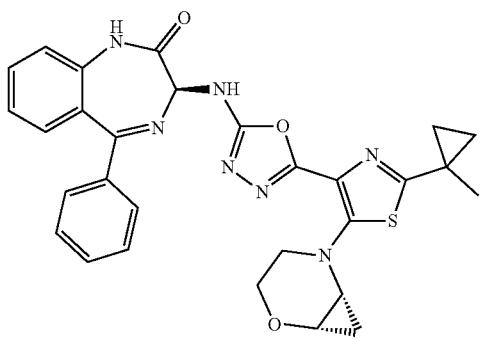 [SMILES: CC1(c2nc(-c3nnc(N[C@H]4N=C(c5ccccc5)c5ccccc5NC4=O)o3)c(N3CCO[C@H]4C[C@H]43)s2)CC1]

Example 515

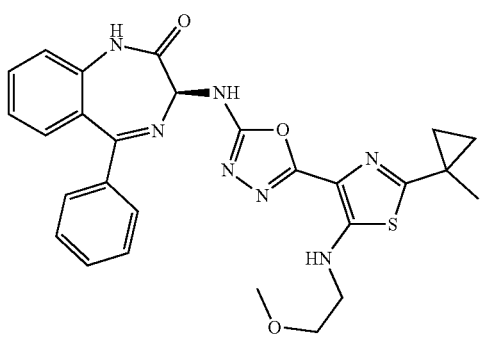 [SMILES: COCCNc1sc(C2(C)CC2)nc1-c1nnc(N[C@H]2N=C(c3ccccc3)c3ccccc3NC2=O)o1]

428

Example 516

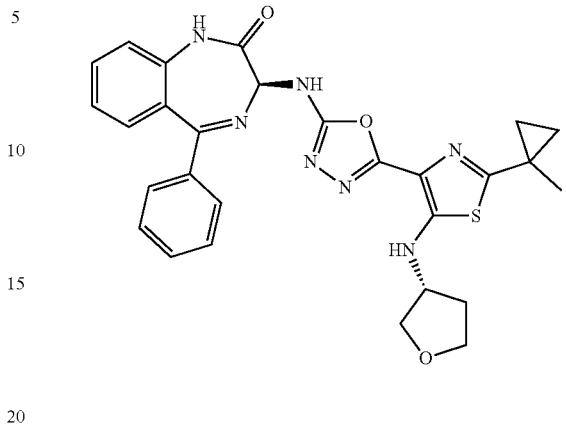

Example 517

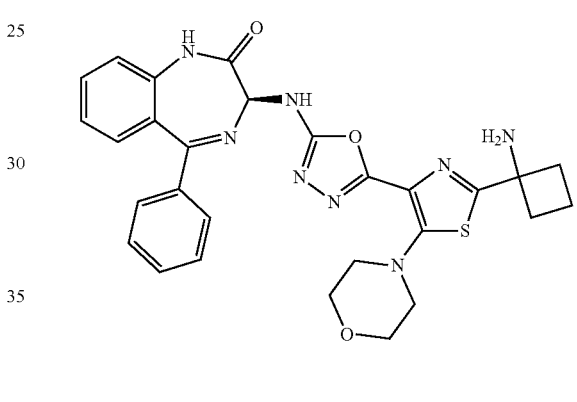

Example 518

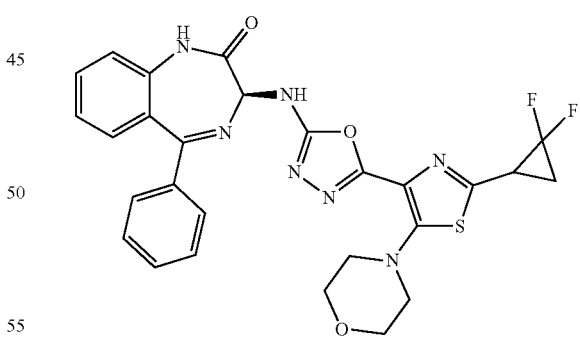

Assays
Methods for RSV-A Assay

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% (TCID$_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: HEp-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 µL. Viral stock is then added to the wells at a multiplicity of infection (MOI) of 0.1 in a volume of 25 µL, bringing the total volume of each well to 100 µL. The MOI is calculated using the PFU/mL, or TCID$_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 µL of growth media containing an equal quantity of sucrose as those wells receiving the viral stock in order to keep consistent in media and volume conditions. The outer wells of the plate are filled with 125 µL of moat media (DMEM, 1% Penn/Strep) to act as a thermal and evaporative moat around the test wells. Following a 5-day incubation period, the plates are read using ATPlite (50 µL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 µL of viral stock for 25 µL of growth media. These data are used to calculate the EC$_{50}$ and CC$_{50}$ of each compound (Table 2). EC$_{50}$ ranges are as follows: A<0.4 µM; B 0.4-0.8 µM; C>0.8 µM and CC$_{50}$ ranges are as follows: A>50 µM; B 10-50 µM; C<10 µM.

TABLE 2

Summary of Activities for RSV-A

| Example | Human RSV-A ("Long" strain) EC$_{50}$ | CC$_{50}$ ATPlite | Example | Human RSV-A ("Long" strain) EC$_{50}$ | CC$_{50}$ ATPlite |
|---|---|---|---|---|---|
| 1 | C | A | 2 | C | A |
| 3 | C | A | 4 | C | A |
| 5 | C | A | 6 | C | A |
| 7a | B | A | 7b | C | B |
| 8 | C | A | 9 | C | A |
| 10a | B | A | 10b | C | C |
| 11 | B | A | 12 | B | A |
| 13 | A | A | 14 | A | B |
| 15 | B | A | 16 | B | A |
| 17 | C | A | 18 | C | A |
| 19 | C | A | 20 | C | A |
| 21 | C | A | 22 | C | A |
| 23 | C | A | 24 | B | — |
| 25 | C | A | 26 | C | A |
| 27 | C | A | 28 | C | A |
| 29 | C | A | 30 | C | A |
| 31 | B | A | 32 | B | A |
| 33 | C | A | 34 | B | A |
| 35 | C | A | 36 | B | B |
| 37 | C | A | 38 | C | A |
| 39 | C | A | 40 | C | A |
| 41 | C | A | 42 | B | A |
| 43 | C | A | 44 | C | A |
| 45 | C | A | 46 | C | A |
| 47 | C | A | 48 | C | A |
| 49 | C | A | 50 | C | A |
| 51 | B | A | 52 | A | A |
| 53 | B | A | 54 | A | A |
| 55 | A | A | 56 | C | — |
| 57 | C | A | 58 | C | A |
| 59 | C | A | 60 | C | A |
| 61 | B | A | 62 | C | A |
| 63 | C | A | 64 | C | A |
| 65 | C | A | 66 | B | A |
| 67 | C | A | 68 | C | A |
| 69 | C | A | 70 | C | A |
| 71 | C | A | 72 | C | A |
| 73 | C | A | 74 | C | A |
| 75 | C | A | 76 | C | A |
| 77 | B | A | 78 | C | — |
| 79 | C | A | 80 | C | A |
| 81 | C | A | 82 | B | A |
| 83 | C | A | 84 | C | B |
| 85 | C | — | 86 | C | A |
| 87 | C | B | 88 | C | B |
| 89 | C | B | 90 | C | C |
| 91 | C | — | 92 | C | B |
| 93 | C | B | 94 | C | B |
| 95 | B | — | 96 | C | B |
| 97 | C | A | 98 | C | A |
| 99 | C | B | 100 | C | B |
| 101 | C | B | 102 | C | — |
| 103 | C | B | 104 | C | B |
| 105 | C | A | 106 | C | C |
| 107 | C | — | 108 | C | — |
| 109 | C | — | 110 | C | — |
| 111 | C | — | 112 | C | — |
| 113 | B | — | 114 | C | — |
| 115 | A | — | 116 | C | — |
| 117 | C | — | 118 | C | — |
| 119 | B | — | 120 | A | — |
| 121 | C | — | 122 | C | — |
| 123 | A | — | 124a | A | — |
| 124b | C | — | 125a | A | — |
| 125b | C | — | 126a | A | — |
| 126b | C | — | 127 | A | — |
| 128 | B | — | 129 | A | — |
| 130 | B | — | 131 | A | — |
| 132 | A | — | 133 | B | — |
| 134 | C | — | 135 | C | — |
| 136 | A | — | 137 | C | — |
| 138 | A | — | 139 | A | — |
| 140 | A | — | 141 | C | — |
| 142 | B | — | 143 | A | — |
| 144 | A | — | 145 | B | — |
| 146 | C | — | 147 | C | — |
| 148 | C | — | 149 | B | — |
| 150 | A | — | 151 | A | — |
| 152 | A | — | 153 | A | — |
| 154 | A | — | 155 | A | — |
| 156 | C | — | 157 | A | — |
| 158 | A | — | 159 | A | — |
| 160 | A | — | 161 | C | — |
| 162 | A | — | 163 | C | — |
| 164 | A | — | 165 | B | — |
| 166 | C | — | 167 | A | — |
| 168 | A | — | 169 | A | — |
| 170 | C | — | 171 | C | — |
| 172 | C | — | 173 | C | — |
| 174 | A | — | 175 | A | — |
| 176 | A | — | 177 | C | — |
| 178 | B | — | 179 | A | — |
| 180 | A | — | 181 | A | — |
| 182 | A | — | 183 | A | — |
| 184 | B | — | 185 | C | — |
| 186 | C | — | 187 | B | — |
| 188 | C | — | 189 | C | — |
| 190 | C | — | 191 | C | — |

TABLE 2-continued

Summary of Activities for RSV-A

| Example | Human RSV-A ("Long" strain) EC$_{50}$ | CC$_{50}$ ATPlite | Example | Human RSV-A ("Long" strain) EC$_{50}$ | CC$_{50}$ ATPlite | Example | Human RSV-A ("Long" strain) EC$_{50}$ | CC$_{50}$ ATPlite | Example | Human RSV-A ("Long" strain) EC$_{50}$ | CC$_{50}$ ATPlite |
|---|---|---|---|---|---|---|---|---|---|---|---|
| 192 | C | — | 193 | C | — | 340 | A | — | 341 | A | — |
| 194 | C | — | 195 | C | — | 342 | A | — | 343 | C | — |
| 196 | C | — | 197 | C | — | 344 | C | — | 345 | A | — |
| 198 | C | — | 199 | C | — | 346 | A | — | 347 | A | — |
| 200 | B | — | 201 | C | — | 348 | A | — | 349 | C | — |
| 202 | C | — | 203 | C | — | 350 | B | — | 351 | B | — |
| 204 | C | — | 205 | C | — | 352 | — | — | 353 | C | — |
| 206 | C | — | 207 | C | — | 354 | C | — | 355a | A | — |
| 208 | C | — | 209 | C | — | 355b | C | — | 356 | B | — |
| 210 | C | — | 211 | C | — | 357 | C | — | 358 | A | — |
| 212 | C | — | 213 | C | — | 359 | A | — | 360 | A | — |
| 214 | C | — | 215 | C | — | 361 | A | — | 362 | C | — |
| 216 | B | — | 217 | B | — | 363 | C | — | 364 | A | — |
| 218 | C | — | 219 | C | — | 365 | B | — | 366 | C | — |
| 220 | C | — | 221 | C | — | 367 | C | — | 368 | B | — |
| 222 | C | — | 223 | C | — | 369 | C | — | 370 | C | — |
| 224 | C | — | 225 | C | — | 371 | C | — | 372 | C | — |
| 226 | C | — | 227 | C | — | 373 | C | — | 374 | C | — |
| 228 | C | — | 229 | C | — | 375 | C | — | 376 | C | — |
| 230 | C | — | 231 | A | — | 377 | A | — | 378 | C | — |
| 232 | C | — | 233 | C | — | 379 | C | — | 380 | B | — |
| 234 | C | — | 235 | C | — | 381 | C | — | 382 | C | — |
| 236 | C | — | 237 | C | — | 383 | A | — | 384 | A | — |
| 238 | C | — | 239 | C | — | 385 | A | — | 387 | A | — |
| 240 | C | — | 241 | C | — | 388 | A | — | 389 | A | — |
| 242 | A | — | 243 | C | — | 390 | A | — | 393 | — | — |
| 244 | C | — | 245 | A | — | 394 | C | — | 395 | C | — |
| 246 | C | — | 247 | C | — | 396 | C | — | 399 | A | — |
| 248 | C | — | 249 | C | — | 400 | A | — | 401 | A | — |
| 250 | A | — | 251 | A | — | 402 | A | — | 403 | A | — |
| 252 | A | — | 253 | A | — | 404 | A | — | 405 | A | — |
| 254 | C | — | 255 | C | — | 406 | A | — | 407 | A | — |
| 256 | C | — | 257 | C | — | 408 | C | — | 409 | C | — |
| 258 | C | — | 259 | C | — | 410 | C | — | 411 | C | — |
| 260 | C | — | 261 | C | — | 412 | C | — | 413 | C | — |
| 262 | C | — | 263 | B | — | 414 | C | — | 415 | C | — |
| 264 | C | — | 265 | C | — | 416 | C | — | 417 | C | — |
| 266 | B | — | 267 | C | — | 418 | C | — | 419 | B | — |
| 268 | C | — | 269 | C | — | 420 | A | — | 421 | C | — |
| 270 | C | — | 271 | C | — | 422 | B | — | 423 | B | — |
| 272 | A | — | 273 | B | — | 424 | C | — | 425 | A | — |
| 274 | C | — | 275 | C | — | 426 | C | — | 427 | A | — |
| 276 | B | — | 277 | A | — | 428 | A | — | 429 | A | — |
| 278 | A | — | 279 | A | — | 430 | A | — | 431 | A | — |
| 280 | A | — | 281 | A | — | 432 | C | — | 433 | A | — |
| 282 | C | — | 283 | C | — | 434 | A | — | 435 | C | — |
| 284 | C | — | 285 | A | — | 436 | A | — | 437 | A | — |
| 286 | A | — | 287 | C | — | 438 | B | — | 439 | C | — |
| 288 | B | — | 289 | A | — | 440 | B | — | 441 | C | — |
| 290 | C | — | 291 | C | — | 442 | A | — | 443 | C | — |
| 292 | A | — | 293 | C | — | 444 | A | — | 445 | B | — |
| 294 | A | — | 295 | A | — | 446 | A | — | 447 | B | — |
| 296 | C | — | 297 | A | — | 448 | A | — | 449 | C | — |
| 298 | C | — | 299 | A | — | 450 | C | — | 451 | B | — |
| 300 | A | — | 301 | A | — | 452 | A | — | 453 | A | — |
| 302 | C | — | 303 | A | — | 454 | A | — | 455 | A | — |
| 304 | A | — | 305 | A | — | 456 | C | — | 457 | C | — |
| 306 | C | — | 307 | C | — | 458 | A | — | 459 | A | — |
| 308 | C | — | 309 | C | — | 460 | A | — | 461 | A | — |
| 310 | C | — | 311 | A | — | 462 | C | — | 463 | C | — |
| 312 | B | — | 313 | A | — | 464 | A | — | 465 | B | — |
| 314 | A | — | 315 | C | — | 466 | A | — | 467 | A | — |
| 316 | C | — | 317 | A | — | 468 | C | — | 469 | A | — |
| 318 | A | — | 319 | C | — | 470 | C | — | 471 | A | — |
| 320 | C | — | 321 | A | — | 472 | C | — | 473 | A | — |
| 322 | A | — | 323 | A | — | 474 | A | — | 475 | B | — |
| 324 | A | — | 325 | A | — | 476 | B | — | 477 | A | — |
| 326 | B | — | 327 | B | — | 478 | A | — | 479 | C | — |
| 328 | C | — | 329 | A | — | 480 | C | — | 481 | C | — |
| 330 | A | — | 331 | C | — | 482 | C | — | 483 | C | — |
| 332 | C | — | 333 | B | — | 484 | A | — | 485 | C | — |
| 334 | A | — | 335 | A | — | 486 | C | — | 487 | C | — |
| 336 | A | — | 337 | A | — | | | | | | |
| 338 | A | — | 339 | A | — | | | | | | |

TABLE 2-continued

Summary of Activities for RSV-A

| Example | Human RSV-A ("Long") strain) $EC_{50}$ | $CC_{50}$ ATPlite | Example | Human RSV-A ("Long") strain) $EC_{50}$ | $CC_{50}$ ATPlite |
|---|---|---|---|---|---|
| 488 | A | — | 489 | C | — |
| 490 | A | — | | | |

Methods for RSV-B Assay

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype B, strain 9320. Flasks were inoculated with RSV-B and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 5-fold viral dilutions across a 96-well plate, cultured for 4 days. Viral stock titers were also quantified by a plaque forming unit assay, as described elsewhere.

The assay is run as follows: A549 cells (originally derived through explant culture from a 58 year old male's carcinomatous lung tissue) are seeded into the inner 60 wells of a 96-well plate at 3,000 cells per well in a volume of 50 µL using A549 growth media (F-12K Media, 1% Penn/Strep, 1% nonessential amino acids, 10% heat-inactivated FBS). 2-fold serial dilutions of control and test compounds are added to the wells in duplicate in a total volume of 25 µL. Viral stock is then added to the wells at a multiplicity of infection (MOI) of 0.5 in a volume of 25 µL, bringing the total volume of each well to 100 µL. The MOI is calculated using the PFU/mL, or TCID50 if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 µL of moat media (DMEM, 1% Penn/Strep) to act as a thermal and evaporative moat around the test wells. 6 days post infection, the plates are read using qPCR or ATP lite (50 uL added per well), which quantifies the amount of ATP (a measure of cell health) present in each well. Assay plates treated with APTlite are read using the Envision luminometer. These data are used to calculate the $EC_{50}$ of each compound (Table 3). $EC_{50}$ ranges are as follows: A<0.4 µM; B 0.4-0.8 µM; C>0.8 µM.

TABLE 3

Summary of Activities for RSV-B

| Example | Human RSV-B $EC_{50}$ | Example | Human RSV-B $EC_{50}$ |
|---|---|---|---|
| 7a | C | 95 | C |
| 108 | C | 120 | B |
| 123 | B | 124 | A |
| 125 | B | 127 | A |
| 129 | A | 131 | A |
| 136 | A | 139 | A |

TABLE 3-continued

Summary of Activities for RSV-B

| Example | Human RSV-B $EC_{50}$ | Example | Human RSV-B $EC_{50}$ |
|---|---|---|---|
| 144 | A | 153 | A |
| 155 | A | 158 | A |
| 160 | A | 168 | A |
| 169 | A | 175 | B |
| 179 | A | 224 | A |
| 242 | A | 245 | B |
| 250 | A | 251 | A |
| 252 | A | 253 | A |
| 263 | B | 268 | B |
| 269 | B | 272 | A |
| 276 | C | 277 | A |
| 278 | A | 300 | A |
| 303 | A | 304 | A |
| 322 | A | 334 | A |
| 336 | A | 338 | A |
| 339 | A | 340 | A |
| 341 | A | 351 | B |
| 355a | A | 358 | A |
| 364 | B | 377 | A |
| 385 | A | 387 | A |
| 388 | A | 403 | A |
| 407 | A | 429 | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

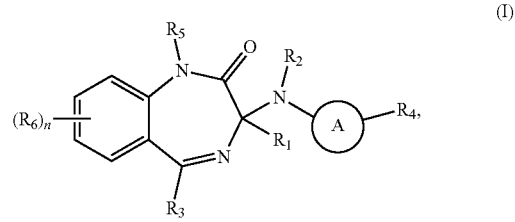

or a pharmaceutically acceptable salt thereof, wherein:
  $R_1$ is selected from the group consisting of:
   1) Hydrogen;
   2) Halogen;
   3) CN;
   4) Optionally substituted —$C_1$-$C_8$ alkyl; and
   5) Optionally substituted —$C_1$-$C_8$ alkyl —O—$R_{11}$;
  $R_2$ and $R_5$ are each independently selected from the group consisting of:
   1) Hydrogen; and
   2) Optionally substituted —$C_1$-$C_8$ alkyl;
  A is selected from the group consisting of:
   1) Optionally substituted —$C_3$-$C_{12}$ cycloalkyl;
   2) Optionally substituted —$C_3$-$C_{12}$ cycloalkenyl;
   3) Optionally substituted aryl; and
   4) Optionally substituted heteroaryl
  $R_3$ is hydrogen or $R_{11}$;
  $R_4$ is selected from the group consisting of:
   1) Optionally substituted —$C_3$-$C_{12}$ cycloalkyl;
   2) Optionally substituted —$C_3$-$C_{12}$ cycloalkenyl;
   3) Optionally substituted 3- to 12-membered heterocyclic;
   4) Optionally substituted aryl;

5) Optionally substituted heteroaryl;
6) Optionally substituted aryl-O—;
7) Optionally substituted heteroaryl-O;
8) Optionally substituted aryl-$C_1$-$C_4$-alkyl; and
9) Optionally substituted heteroaryl-$C_1$-$C_4$-alkyl;

wherein $R_4$ is optionally substituted with 1 to 3 substituents independently selected from halo, —$CH_3$, —$CF_3$, —$OCF_3$, —CN, —$NH_2$, —OH, —$CH_2N(CH_3)_2$, —$C(O)CH_3$, —NH—($C_1$-$C_6$)alkyl, —NH—($C_1$-$C_6$)alkyl-($C_1$-$C_6$)alkoxy, —$SO_2$—($C_1$-$C_6$)alkyl, —$SO_2$—NH—($C_1$-$C_6$)alkyl, —NH—$SO_2$—($C_1$-$C_6$)alkyl, 3- to 12-membered heterocyclic, aryl, heteroaryl, $C_1$-$C_8$-alkyl, $C_2$-$C_8$-alkenyl, $C_3$-$C_8$-cycloalkyl, $C_3$-$C_8$-cycloalkenyl, $C_1$-$C_8$-alkoxy, $CH_3OCH_2$—, $CH_3OCH_2CH_2O$—,

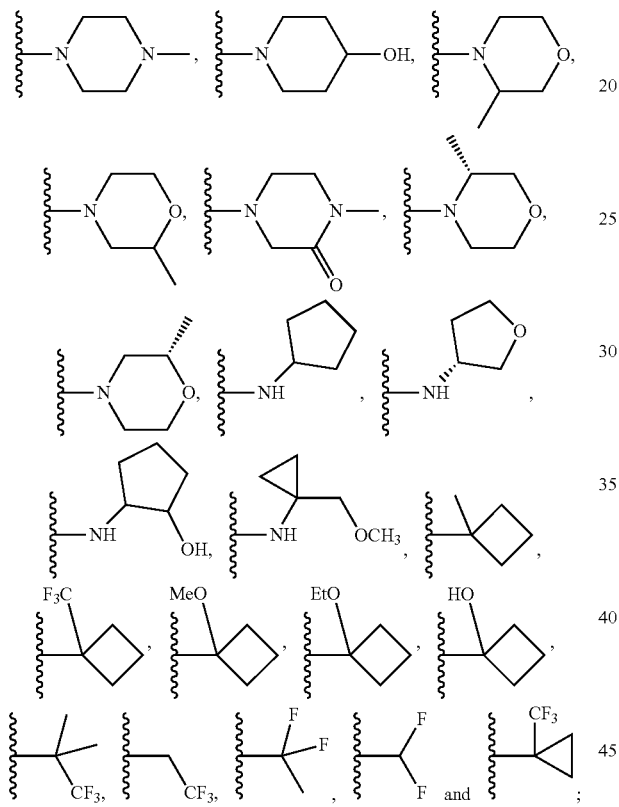

each $R_6$ is independently selected from hydrogen, halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —NH$C_1$-$C_8$ alkyl, optionally substituted —S—(—$C_1$-$C_8$ alkyl), optionally substituted —$SO_2$—(—$C_1$-$C_8$ alkyl), optionally substituted —$SO_2$—NH—(—$C_1$-$C_8$ alkyl), optionally substituted —NH—$SO_2$—(—$C_1$-$C_8$ alkyl), —$CO_2R_{12}$, —$NR_{13}R_{14}$, and —CO—$NR_{13}R_{14}$;

$R_{11}$ and $R_{12}$ are each independently selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocyclic;
7) Optionally substituted aryl; and
8) Optionally substituted heteroaryl;

$R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, —C(O)$R_{12}$, —S(O)$_2R_{12}$, and —S(O)$_2$NH$R_{12}$, and optionally substituted —$C_1$-$C_8$-alkoxy; alternatively, $R_{13}$ and $R_{14}$ are taken together with the nitrogen atom to which they are attached to form a heterocyclic ring; and n is 0, 1, 2, 3 or 4; and wherein each substituted $R_1$, $R_2$, $R_5$, $R_6$, $R_{11}$, $R_{12}$, $R_{13}$, $R_{14}$ and A is substituted by one or more substituents selected from deuterium, tritium, —F, —Cl, —Br, —I, —OH, protected hydroxy, —$NO_2$, —CN, —$NH_2$, —$N_3$, protected amino, alkoxy, thioalkoxy, oxo, thioxo, —$C_1$-$C_{12}$-alkyl, —$C_2$-$C_{12}$-alkenyl, —$C_2$-$C_{12}$-alkynyl, —$C_3$-$C_{12}$-cycloalkyl-halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocyclic, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocyclic, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocyclic, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocyclic, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocyclic, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocyclic, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocyclic, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocyclic, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocyclic, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocyclic, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocyclic, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocyclic, —C(NH)NH—$C_1$-$C_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocyclic, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocyclic —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocyclic, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocyclic, —CH$_2$NH$_2$, —CH$_2$SO$_2$CH$_3$, -aryl, -arylalkyl, -heteroaryl, -heteroarylalkyl, -heterocyclic, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocyclic, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl.

2. The compound of claim 1, wherein the compound is represented by Formula (Ia) or Formula (Ib):

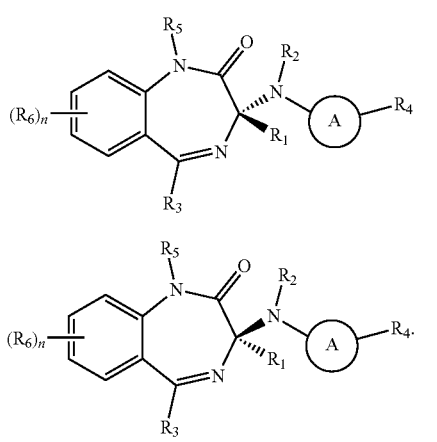

3. The compound of claim 1, wherein A is selected from one of the following by removal of two hydrogen atoms:

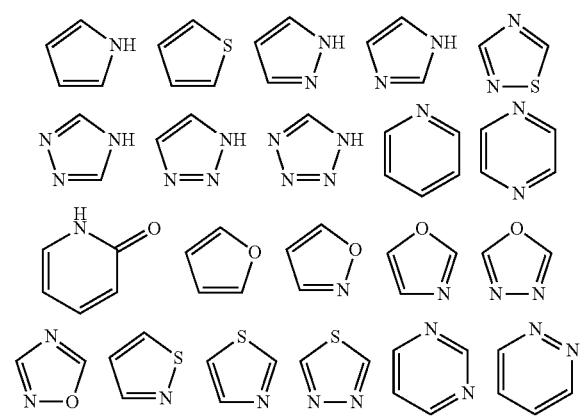

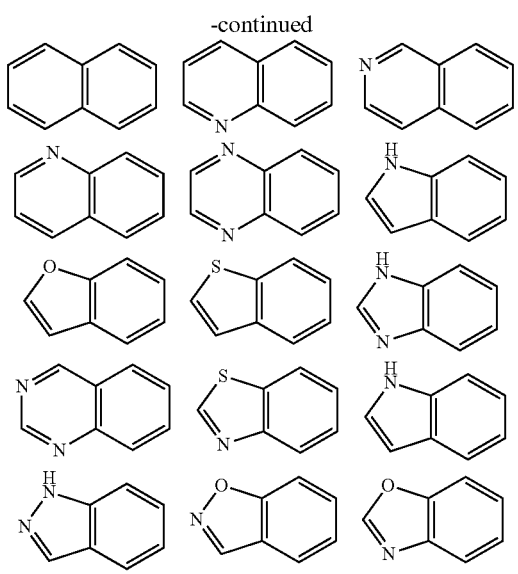

wherein each of the above shown is optionally substituted when possible.

4. The compound of claim 1, wherein R$_4$ is selected from one of the following by removal of one hydrogen atom:

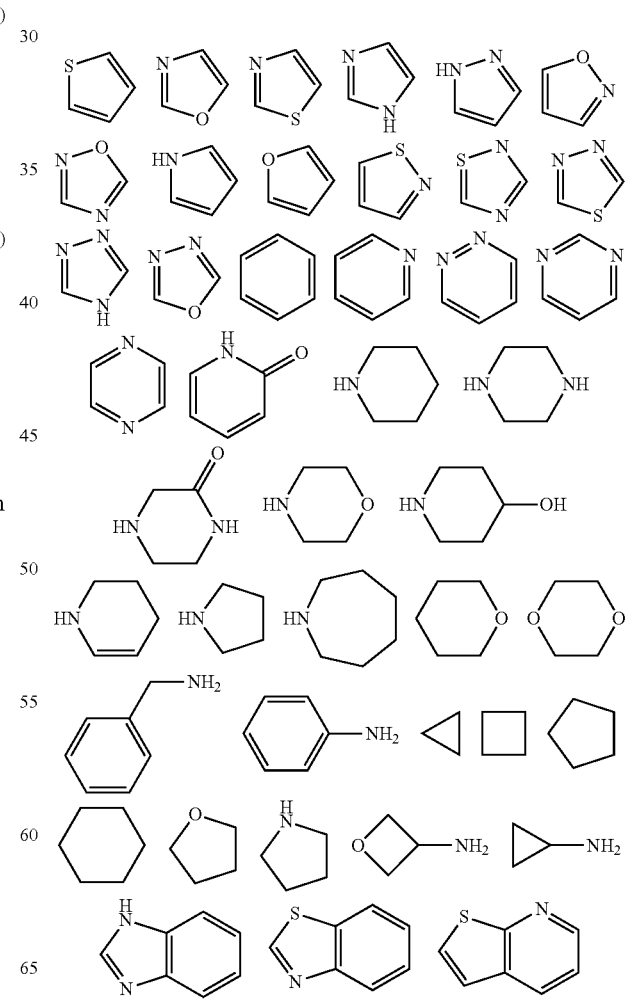

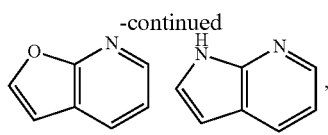

wherein each of the above shown is optionally substituted.

5. The compound of claim 1, wherein $R_4$ is substituted by one to three substituents independently selected from:

halo, —CH₃, —CF₃, —OCF₃, —CN, —NH₂, —OH, —CH₂N(CH₃)₂, —C(O)CH₃, —NH(C₁-C₆)alkyl, —NH—(C₁-C₆)alkyl-(C₁-C₆)alkoxy, —SO₂—(C₁-C₆)alkyl, —SO₂—NH—(C₁-C₆)alkyl, —NH—SO₂—(C₁-C₆)alkyl, 3 to 12-membered heterocyclic, aryl, heteroaryl, —C₁-C₈-alkyl, —C₁-C₈-alkenyl, —C₃-C₈-cycloalkyl, —C₃-C₈-cycloalkenyl, and —C₁-C₈-alkoxy.

6. The compound of claim 1 wherein $R_4$ is substituted by one, two or three substituents selected from: CH₃, CN, fluoro, chloro, CH₃O—, CH₃C(O)—, CH₃OCH₂—, CH₃OCH₂CH₂O—, —CF₃, CF₃O—,

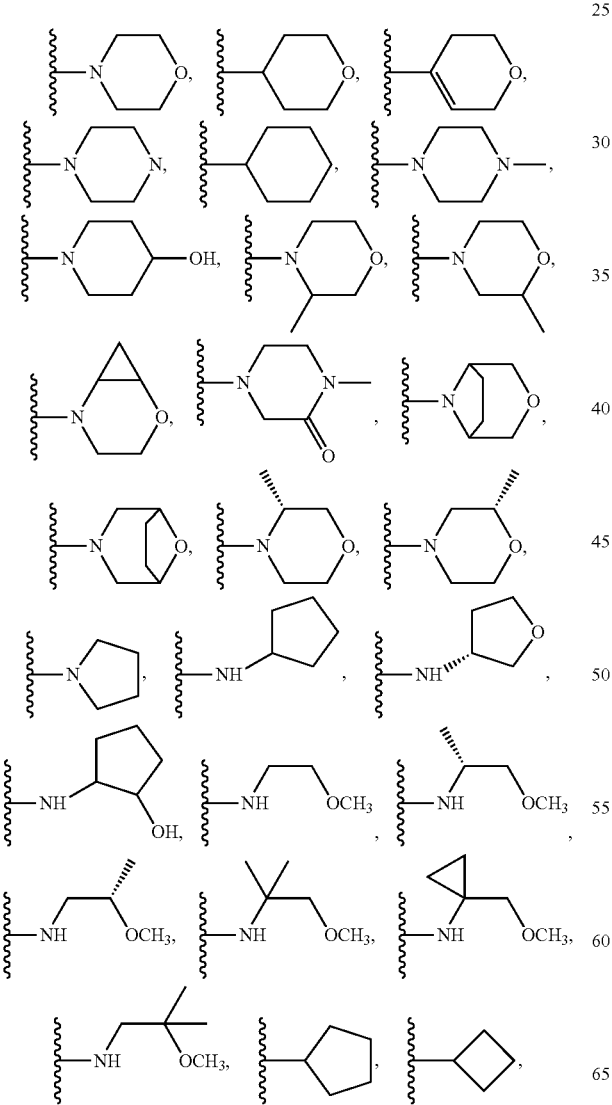

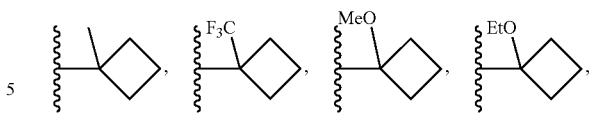

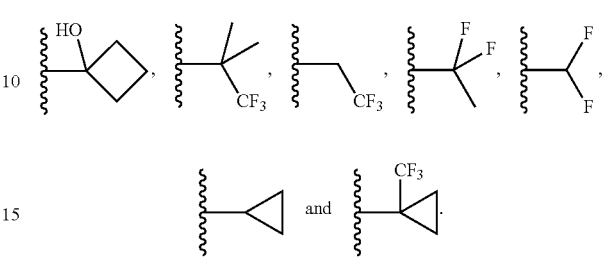

7. The compound of claim 1, represented by Formula IIa-1, IIa-2, IIb-1, or IIb-2,

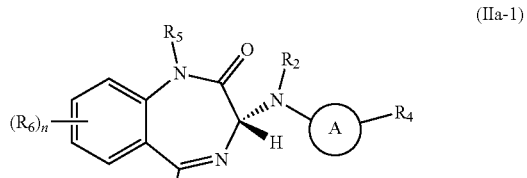

(IIa-1)

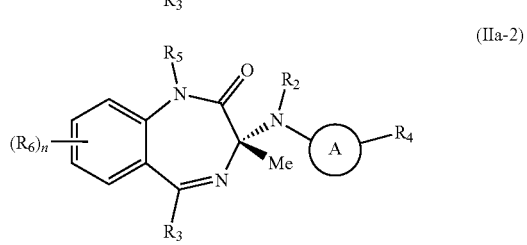

(IIa-2)

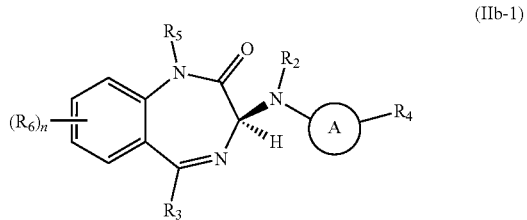

(IIb-1)

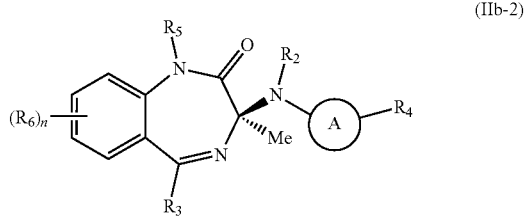

(IIb-2)

or a pharmaceutically acceptable salt thereof.

8. The compound of claim 1, represented by Formula IV-1, IV-2, IV-3, or IV-4,

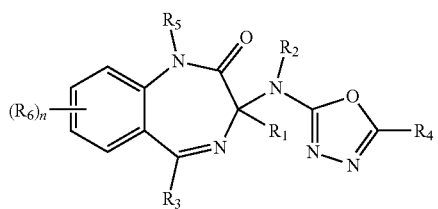 (IV-1)
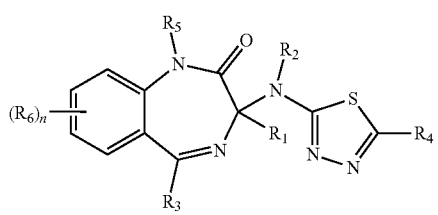 (IV-2)
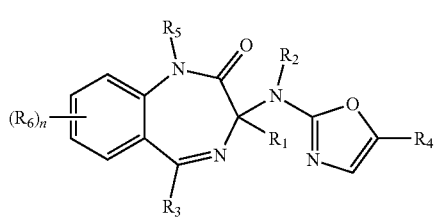 (IV-3)
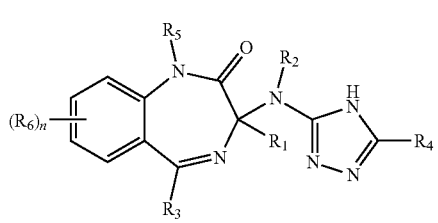 (IV-4)
or a pharmaceutically acceptable salt thereof.
9. The compound of claim 1, represented by Formula V-1, V-2, V-3, or V-4,
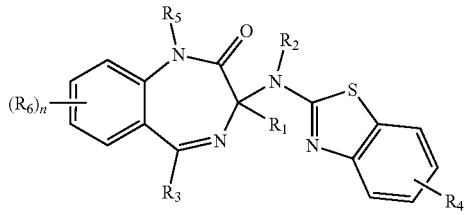 (V-1)
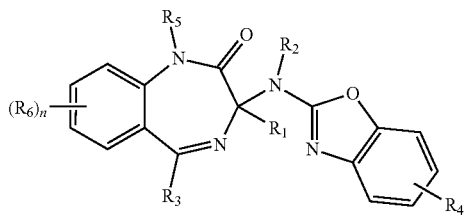 (V-2)
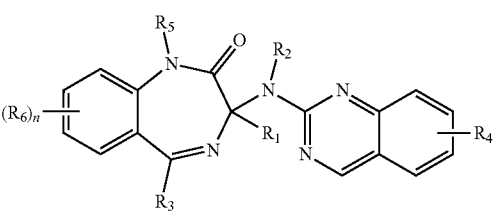 (V-3)
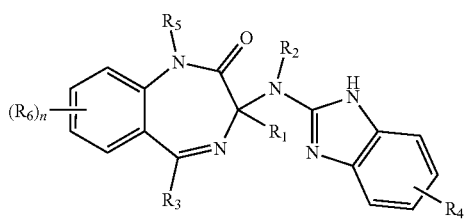 (V-4)
or a pharmaceutically acceptable salt thereof.
10. A compound selected from the compounds set forth below or a pharmaceutically acceptable salt thereof:
| Compound | Structure |
|---|---|
| 1 | 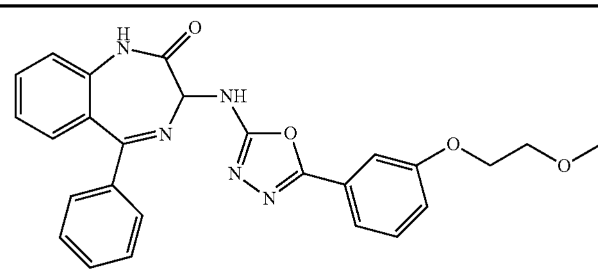 |
| 2 | 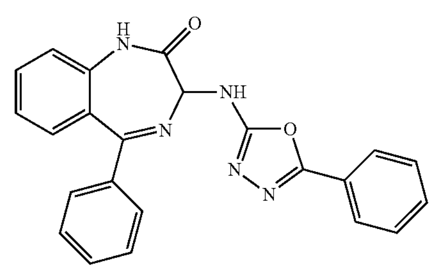 [SMILES: O=C1Nc2ccccc2C(c2ccccc2)=NC1Nc1nnc(-c2ccccc2)o1] |

-continued

| Compound | Structure |
|---|---|
| 3 | 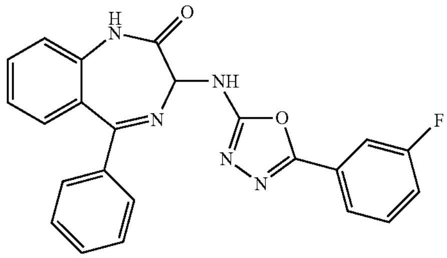 [SMILES: O=C1Nc2ccccc2C(c2ccccc2)=NC1Nc1nnc(-c2cccc(F)c2)o1] |
| 4 | 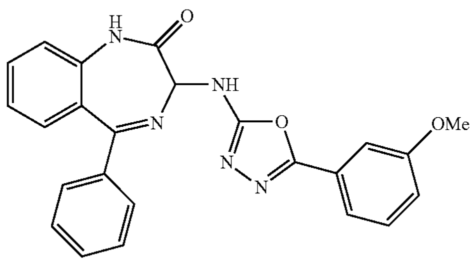 [SMILES: COc1cccc(-c2nnc(NC3N=C(c4ccccc4)c4ccccc4NC3=O)o2)c1] |
| 5 | 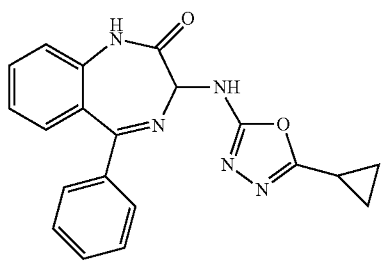 [SMILES: O=C1Nc2ccccc2C(c2ccccc2)=NC1Nc1nnc(C2CC2)o1] |
| 6 | 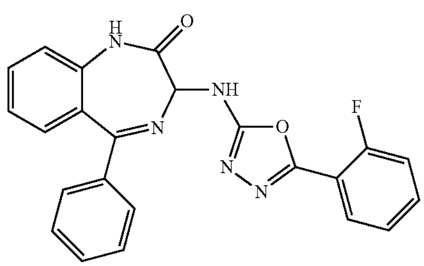 [SMILES: O=C1Nc2ccccc2C(c2ccccc2)=NC1Nc1nnc(-c2ccccc2F)o1] |
| 7a | 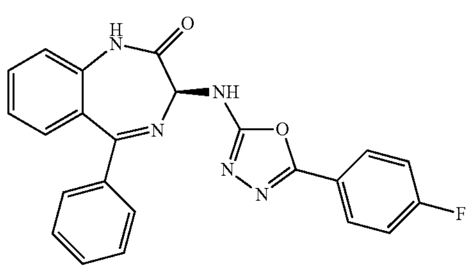 [SMILES: O=C1Nc2ccccc2C(c2ccccc2)=N[C@@H]1Nc1nnc(-c2ccc(F)cc2)o1] |
| 7b | 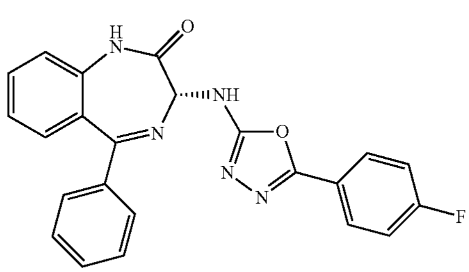 |

| Compound | Structure |
|---|---|
| 8 | 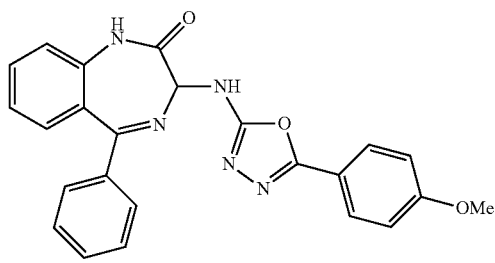 [SMILES: COc1ccc(-c2nnc(NC3N=C(c4ccccc4)c4ccccc4NC3=O)o2)cc1] |
| 9 | 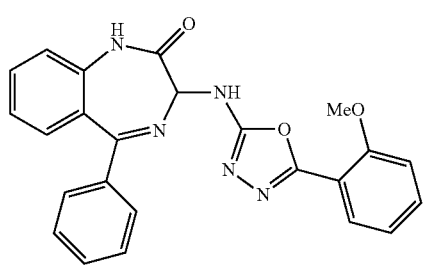 [SMILES: COc1ccccc1-c1nnc(NC2N=C(c3ccccc3)c3ccccc3NC2=O)o1] |
| 10a | 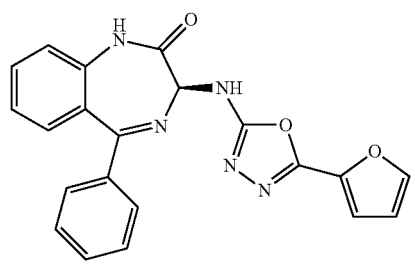 [SMILES: O=C1Nc2ccccc2C(c2ccccc2)=N[C@@H]1Nc1nnc(-c2ccco2)o1] |
| 10b | 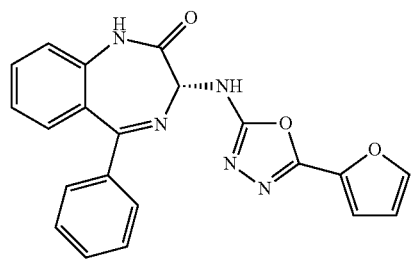 |
| 11 | 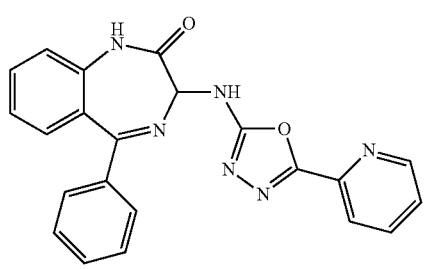 |

-continued

| Compound | Structure |
|---|---|
| 12 | 3-({5-[4-cyanophenyl]-1,3,4-oxadiazol-2-yl}amino)-5-phenyl-1,3-dihydro-2H-1,4-benzodiazepin-2-one |
| 13 | 3-({5-[4-chlorophenyl]-1,3,4-oxadiazol-2-yl}amino)-5-phenyl-1,3-dihydro-2H-1,4-benzodiazepin-2-one |
| 14 | 3-({5-[4-fluoro-3-methoxyphenyl]-1,3,4-oxadiazol-2-yl}amino)-5-phenyl-1,3-dihydro-2H-1,4-benzodiazepin-2-one |
| 15 | 3-({5-[3-isopropoxyphenyl]-1,3,4-oxadiazol-2-yl}amino)-5-phenyl-1,3-dihydro-2H-1,4-benzodiazepin-2-one |
| 16 | 3-({5-(naphthalen-2-yl)-1,3,4-oxadiazol-2-yl}amino)-5-phenyl-1,3-dihydro-2H-1,4-benzodiazepin-2-one |
| 17 | 3-({5-(naphthalen-1-yl)-1,3,4-oxadiazol-2-yl}amino)-5-phenyl-1,3-dihydro-2H-1,4-benzodiazepin-2-one |

-continued
| Compound | Structure |
|---|---|
| 19 | 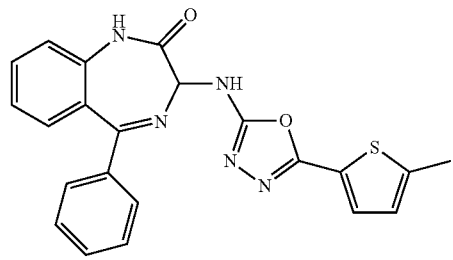 [SMILES: Cc1ccc(-c2nnc(NC3N=C(c4ccccc4)c4ccccc4NC3=O)o2)s1] |
| 20 | 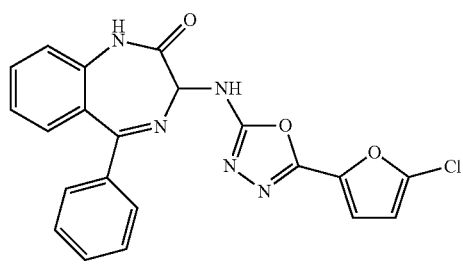 [SMILES: O=C1Nc2ccccc2C(c2ccccc2)=NC1Nc1nnc(-c2ccc(Cl)o2)o1] |
| 21 | 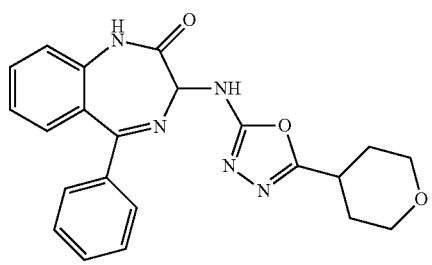 [SMILES: O=C1Nc2ccccc2C(c2ccccc2)=NC1Nc1nnc(C2CCOCC2)o1] |
| 22 | 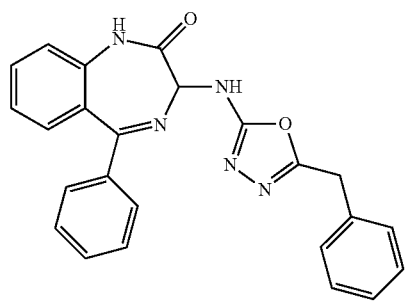 [SMILES: O=C1Nc2ccccc2C(c2ccccc2)=NC1Nc1nnc(Cc2ccccc2)o1] |
| 23 | 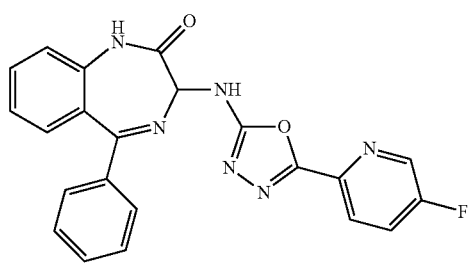 [SMILES: O=C1Nc2ccccc2C(c2ccccc2)=NC1Nc1nnc(-c2ccc(F)cn2)o1] |

-continued
| Compound | Structure |
|---|---|
| 24 | 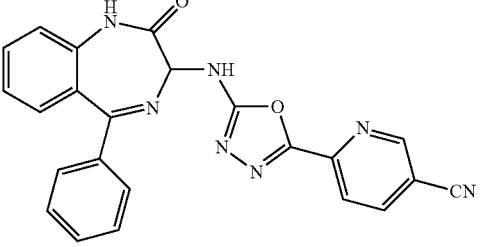 |
| 25 | 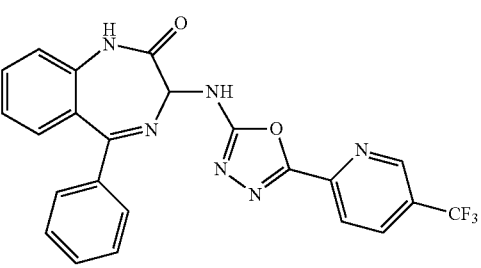 [SMILES: O=C1Nc2ccccc2C(c2ccccc2)=NC1Nc1nnc(-c2ccc(C(F)(F)F)cn2)o1] |
| 26 | 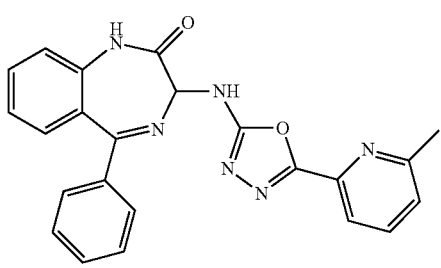 [SMILES: Cc1cccc(-c2nnc(NC3N=C(c4ccccc4)c4ccccc4NC3=O)o2)n1] |
| 27 | 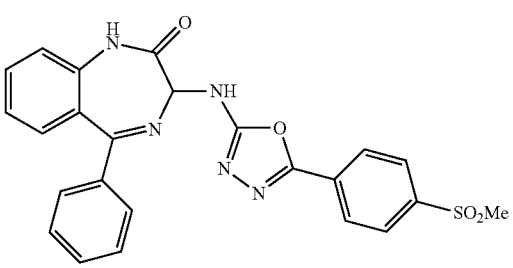 [SMILES: CS(=O)(=O)c1ccc(-c2nnc(NC3N=C(c4ccccc4)c4ccccc4NC3=O)o2)cc1] |
| 28 | 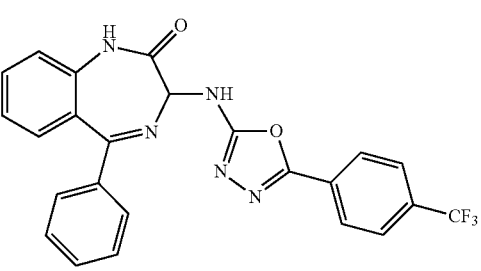 |
| 29 | 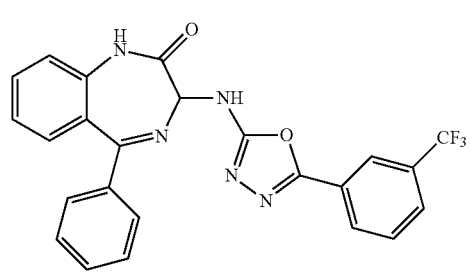 [SMILES: O=C1Nc2ccccc2C(c2ccccc2)=NC1Nc1nnc(-c2cccc(C(F)(F)F)c2)o1] |

-continued

| Compound | Structure |
|---|---|
| 30 | 1,4-benzodiazepin-2-one linked via NH to 1,3,4-oxadiazole bearing 4-(trifluoromethoxy)phenyl |
| 31 | 1,4-benzodiazepin-2-one linked via NH to 1,3,4-oxadiazole bearing 4-(sulfamoyl)phenyl (SO₂NH₂) |
| 32 | 1,4-benzodiazepin-2-one linked via NH to 1,3,4-oxadiazole bearing 3-cyano-4-fluorophenyl |
| 33 | 1,4-benzodiazepin-2-one linked via NH to 1,3,4-oxadiazole bearing 3-fluoro-4-cyanophenyl |
| 34 | 1,4-benzodiazepin-2-one linked via NH to 1,3,4-oxadiazole bearing 3-methyl-4-cyanophenyl |
| 35 | 1,4-benzodiazepin-2-one linked via NH to 1,3,4-oxadiazole bearing 3-cyanophenyl |

-continued

| Compound | Structure |
|---|---|
| 36 | 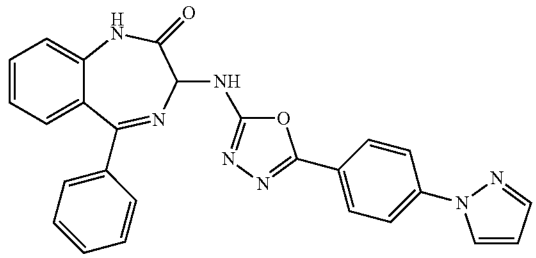 |
| 37 | 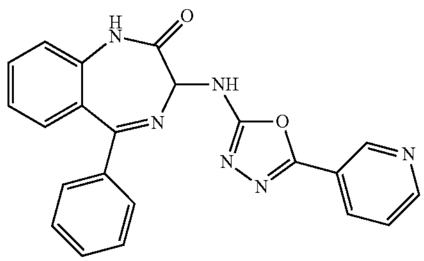 [SMILES: O=C1Nc2ccccc2C(c2ccccc2)=NC1Nc1nnc(-c2cccnc2)o1] |
| 38 | 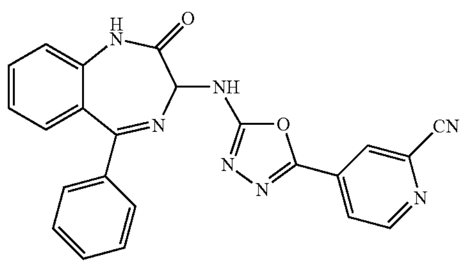 [SMILES: N#Cc1cc(-c2nnc(NC3N=C(c4ccccc4)c4ccccc4NC3=O)o2)ccn1] |
| 39 | 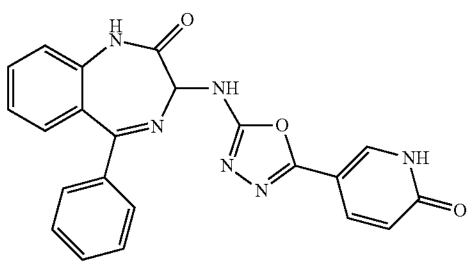 [SMILES: O=C1Nc2ccccc2C(c2ccccc2)=NC1Nc1nnc(-c2ccc(=O)[nH]c2)o1] |
| 40 | 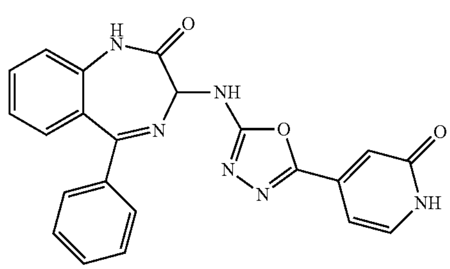 [SMILES: O=C1Nc2ccccc2C(c2ccccc2)=NC1Nc1nnc(-c2cc[nH]c(=O)c2)o1] |
| 41 | 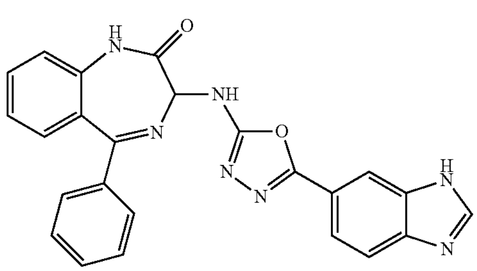 [SMILES: O=C1Nc2ccccc2C(c2ccccc2)=NC1Nc1nnc(-c2ccc3nc[nH]c3c2)o1] |

-continued
| Compound | Structure |
|---|---|
| 42 | 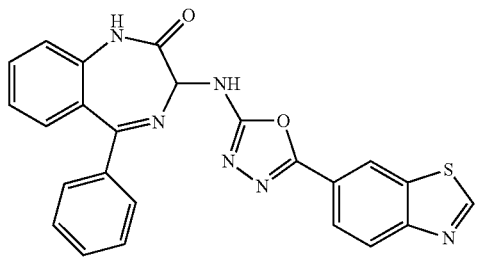 [SMILES: O=C1Nc2ccccc2C(c2ccccc2)=NC1Nc1nnc(-c2ccc3ncsc3c2)o1] |
| 43 | 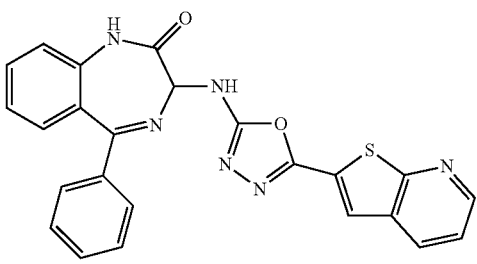 [SMILES: O=C1Nc2ccccc2C(c2ccccc2)=NC1Nc1nnc(-c2cc3cccnc3s2)o1] |
| 44 | 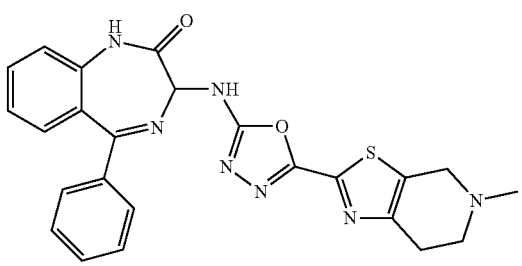 [SMILES: CN1CCc2nc(-c3nnc(NC4N=C(c5ccccc5)c5ccccc5NC4=O)o3)sc2C1] |
| 45 | 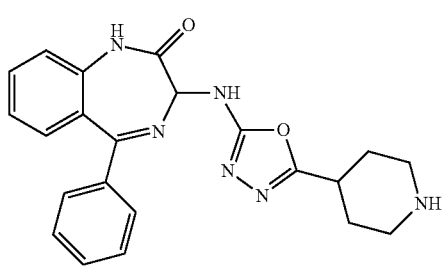 [SMILES: O=C1Nc2ccccc2C(c2ccccc2)=NC1Nc1nnc(C2CCNCC2)o1] |
| 46 | 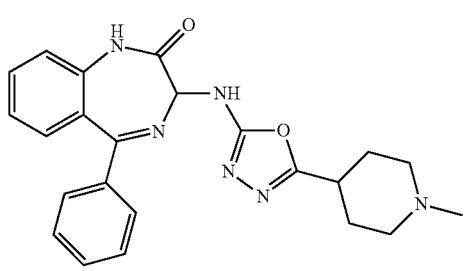 [SMILES: CN1CCC(c2nnc(NC3N=C(c4ccccc4)c4ccccc4NC3=O)o2)CC1] |
| 47 | 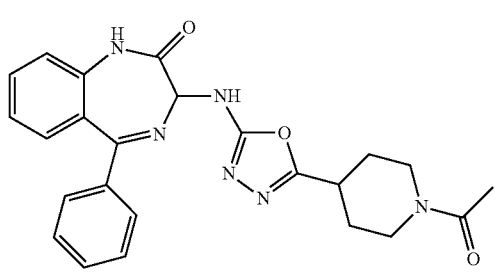 [SMILES: CC(=O)N1CCC(c2nnc(NC3N=C(c4ccccc4)c4ccccc4NC3=O)o2)CC1] |

| Compound | Structure |
|---|---|
| 48 | 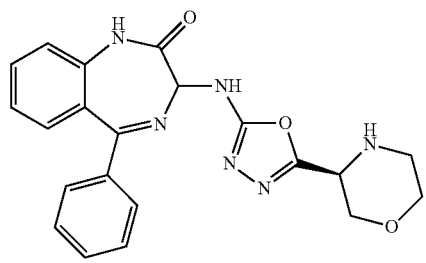 [SMILES: O=C1Nc2ccccc2C(c2ccccc2)=NC1Nc1nnc([C@@H]2COCCN2)o1] |
| 49 | 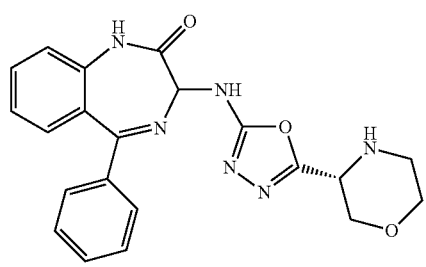 [SMILES: O=C1Nc2ccccc2C(c2ccccc2)=NC1Nc1nnc([C@H]2COCCN2)o1] |
| 50 | 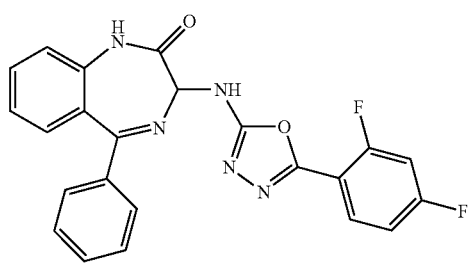 [SMILES: O=C1Nc2ccccc2C(c2ccccc2)=NC1Nc1nnc(-c2ccc(F)cc2F)o1] |
| 51 | 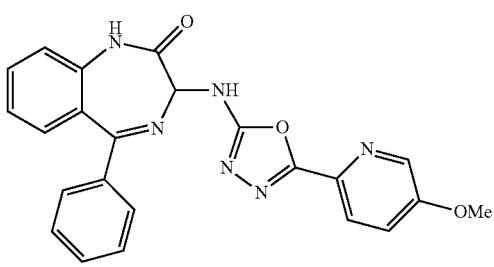 [SMILES: COc1ccc(-c2nnc(NC3N=C(c4ccccc4)c4ccccc4NC3=O)o2)nc1] |
| 52 | 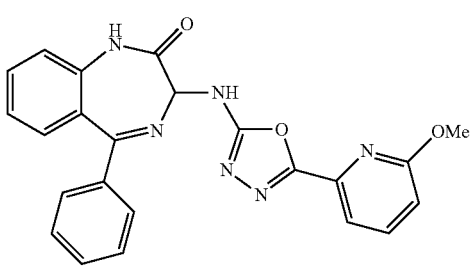 [SMILES: COc1cccc(-c2nnc(NC3N=C(c4ccccc4)c4ccccc4NC3=O)o2)n1] |
| 53 | 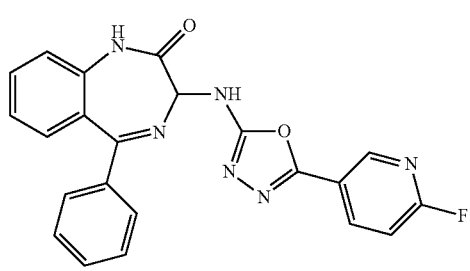 [SMILES: O=C1Nc2ccccc2C(c2ccccc2)=NC1Nc1nnc(-c2ccc(F)nc2)o1] |

| Compound | Structure |
|---|---|
| 54 | 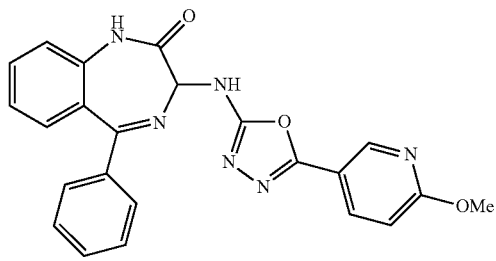 [SMILES: COc1ccc(-c2nnc(NC3N=C(c4ccccc4)c4ccccc4NC3=O)o2)cn1] |
| 55 | 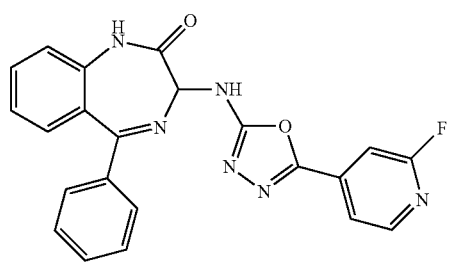 [SMILES: O=C1Nc2ccccc2C(c2ccccc2)=NC1Nc1nnc(-c2ccnc(F)c2)o1] |
| 56 | 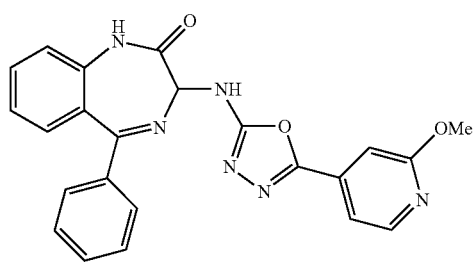 [SMILES: COc1cc(-c2nnc(NC3N=C(c4ccccc4)c4ccccc4NC3=O)o2)ccn1] |
| 57 | 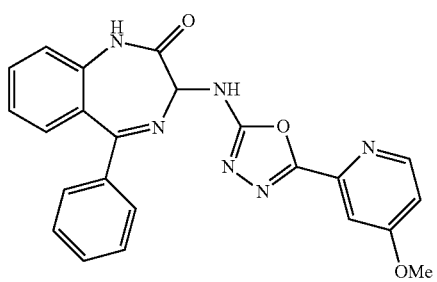 [SMILES: COc1ccnc(-c2nnc(NC3N=C(c4ccccc4)c4ccccc4NC3=O)o2)c1] |
| 58 | 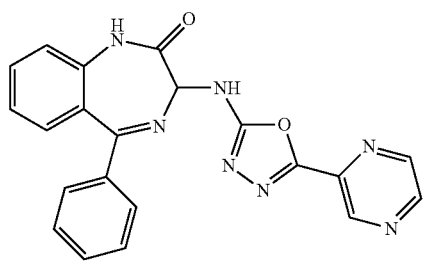 [SMILES: O=C1Nc2ccccc2C(c2ccccc2)=NC1Nc1nnc(-c2cnccn2)o1] |

-continued

| Compound | Structure |
|---|---|
| 59 | 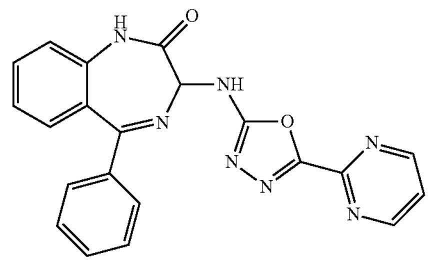 [SMILES: O=C1Nc2ccccc2C(c2ccccc2)=NC1Nc1nnc(-c2ncccn2)o1] |
| 60 | 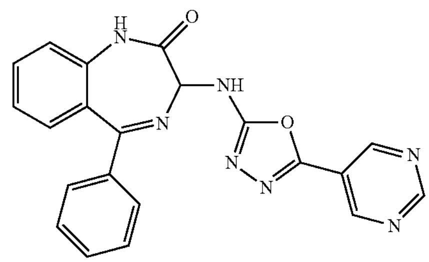 |
| 61 | 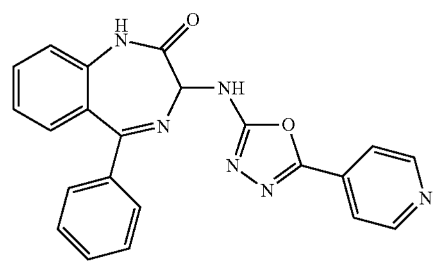 |
| 62 | 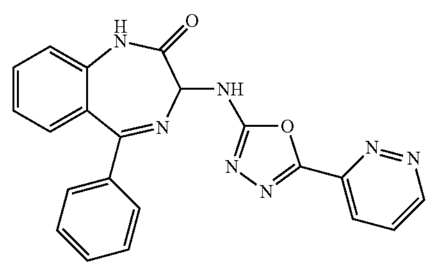 [SMILES: O=C1Nc2ccccc2C(c2ccccc2)=NC1Nc1nnc(-c2cccnn2)o1] |
| 63 | 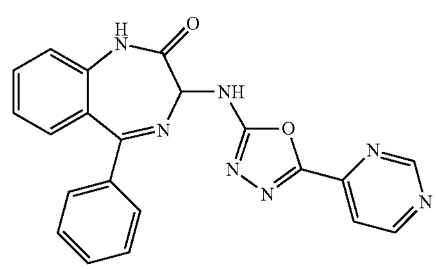 |
| 64 | 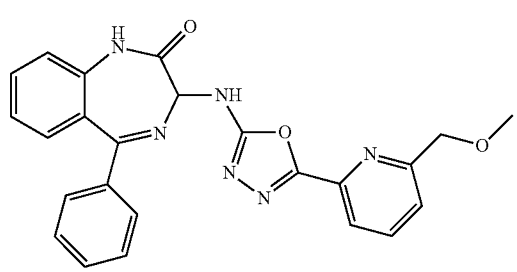 [SMILES: COCc1cccc(-c2nnc(NC3N=C(c4ccccc4)c4ccccc4NC3=O)o2)n1] |

-continued
| Compound | Structure |
|---|---|
| 65 | 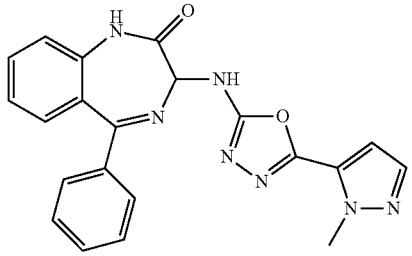 [SMILES: Cn1nccc1-c1nnc(NC2N=C(c3ccccc3)c3ccccc3NC2=O)o1] |
| 66 | 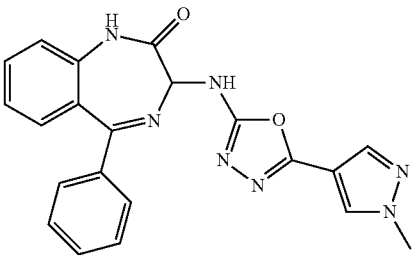 [SMILES: Cn1cc(-c2nnc(NC3N=C(c4ccccc4)c4ccccc4NC3=O)o2)cn1] |
| 67 | 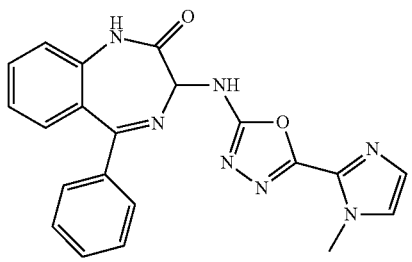 [SMILES: Cn1ccnc1-c1nnc(NC2N=C(c3ccccc3)c3ccccc3NC2=O)o1] |
| 68 | 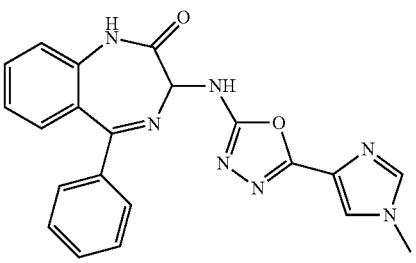 [SMILES: Cn1cnc(-c2nnc(NC3N=C(c4ccccc4)c4ccccc4NC3=O)o2)c1] |
| 69 | 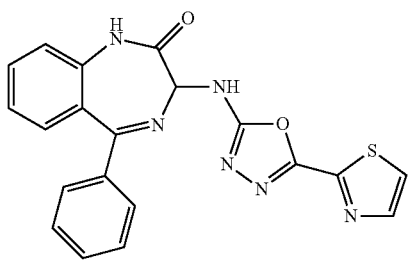 |
| 70 | 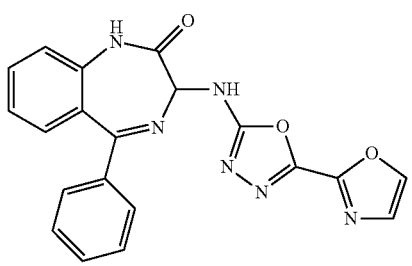 [SMILES: O=C1Nc2ccccc2C(c2ccccc2)=NC1Nc1nnc(-c2ncco2)o1] |

| Compound | Structure |
|---|---|
| 71 | 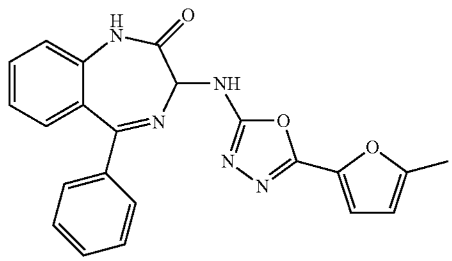 |
| 72 | 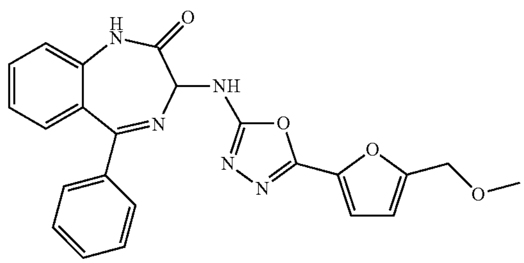 [SMILES: COCc1ccc(-c2nnc(NC3N=C(c4ccccc4)c4ccccc4NC3=O)o2)o1] |
| 73 | 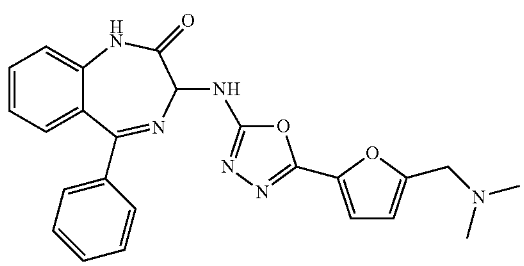 [SMILES: CN(C)Cc1ccc(-c2nnc(NC3N=C(c4ccccc4)c4ccccc4NC3=O)o2)o1] |
| 74 | 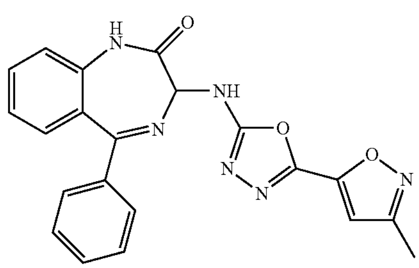 [SMILES: Cc1cc(-c2nnc(NC3N=C(c4ccccc4)c4ccccc4NC3=O)o2)on1] |
| 75 | 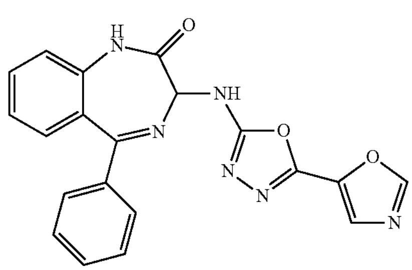 [SMILES: O=C1Nc2ccccc2C(c2ccccc2)=NC1Nc1nnc(-c2cnco2)o1] |
| 76 | 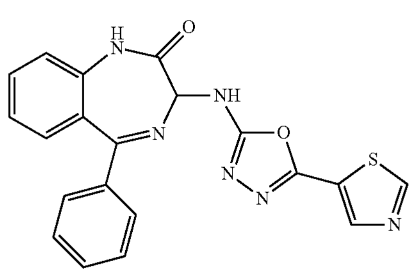 [SMILES: O=C1Nc2ccccc2C(c2ccccc2)=NC1Nc1nnc(-c2cncs2)o1] |

| Compound | Structure |
|---|---|
| 77 | (1H-benzo[e][1,4]diazepin-2(3H)-one with 3-NH linked to 1,3,4-oxadiazole bearing thiazol-4-yl; 5-phenyl) |
| 80 | (benzodiazepinone with 3-NH linked to 1,3,4-thiadiazole bearing 4-fluorophenyl; 5-phenyl) |
| 81 | (benzodiazepinone with 3-NH linked to 5-phenyl-1,3,4-thiadiazole; 5-phenyl) |
| 82 | (benzodiazepinone with 3-NH linked to 1,3,4-thiadiazole bearing 4-cyanophenyl; 5-phenyl) |
| 83 | (benzodiazepinone with 3-NH linked to 1,3,4-thiadiazole bearing pyridin-4-yl; 5-phenyl) |
| 84 | (benzodiazepinone with 3-NH linked to 5-phenyloxazol-2-yl; 5-phenyl) |

-continued

| Compound | Structure |
|---|---|
| 85 | 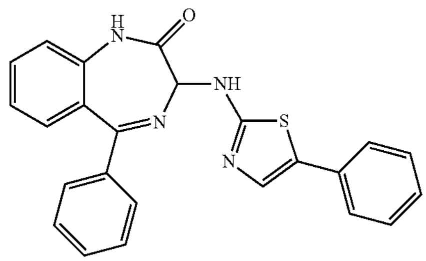 [SMILES: O=C1Nc2ccccc2C(c2ccccc2)=NC1Nc1ncc(-c2ccccc2)s1] |
| 86 | 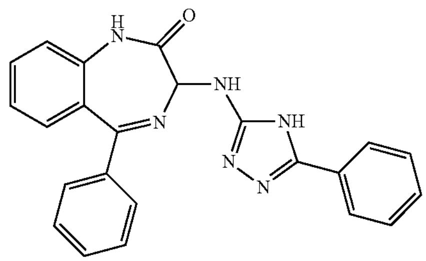 [SMILES: O=C1Nc2ccccc2C(c2ccccc2)=NC1Nc1nnc(-c2ccccc2)[nH]1] |
| 87 | 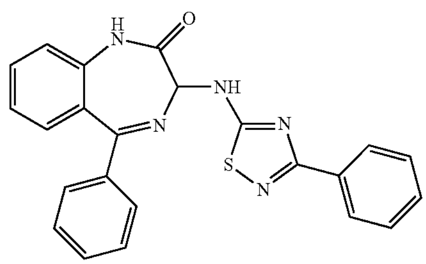 [SMILES: O=C1Nc2ccccc2C(c2ccccc2)=NC1Nc1nc(-c2ccccc2)ns1] |
| 88 | 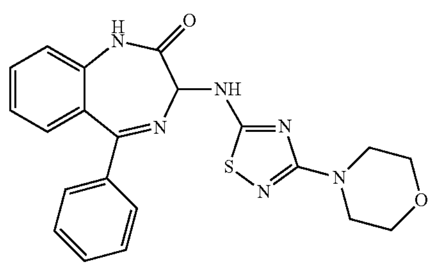 [SMILES: O=C1Nc2ccccc2C(c2ccccc2)=NC1Nc1nc(N2CCOCC2)ns1] |
| 89 | 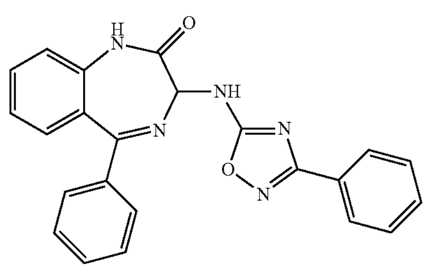 [SMILES: O=C1Nc2ccccc2C(c2ccccc2)=NC1Nc1nc(-c2ccccc2)no1] |
| 90 | 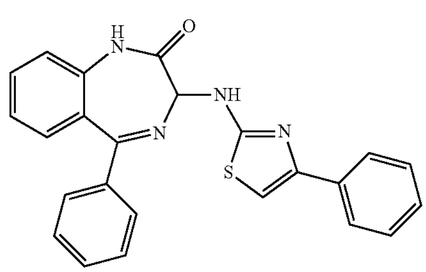 [SMILES: O=C1Nc2ccccc2C(c2ccccc2)=NC1Nc1nc(-c2ccccc2)cs1] |

-continued
| Compound | Structure |
|---|---|
| 91 | 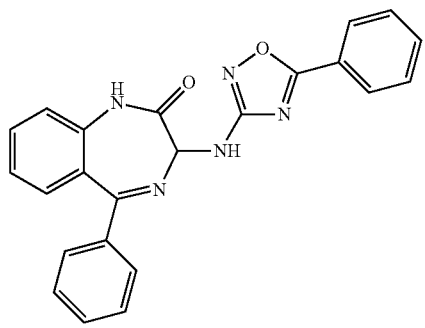 [SMILES: O=C1Nc2ccccc2C(c2ccccc2)=NC1Nc1noc(-c2ccccc2)n1] |
| 92 | 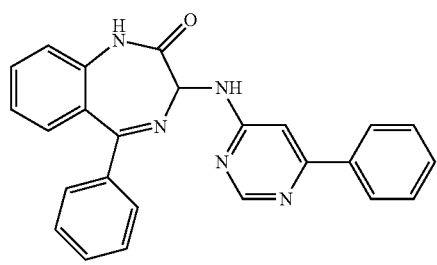 [SMILES: O=C1Nc2ccccc2C(c2ccccc2)=NC1Nc1cc(-c2ccccc2)ncn1] |
| 93 | 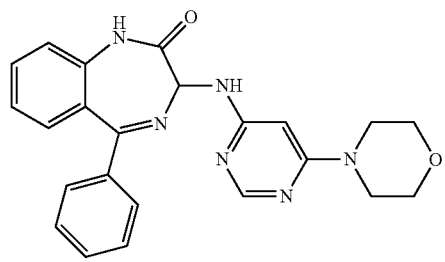 |
| 94 | 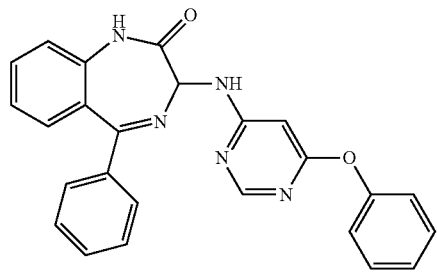 [SMILES: O=C1Nc2ccccc2C(c2ccccc2)=NC1Nc1cc(Oc2ccccc2)ncn1] |
| 95 | 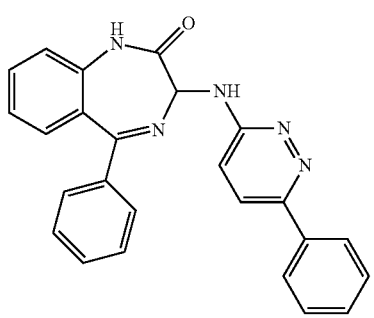 [SMILES: O=C1Nc2ccccc2C(c2ccccc2)=NC1Nc1ccc(-c2ccccc2)nn1] |

-continued

| Compound | Structure |
|---|---|
| 96 | 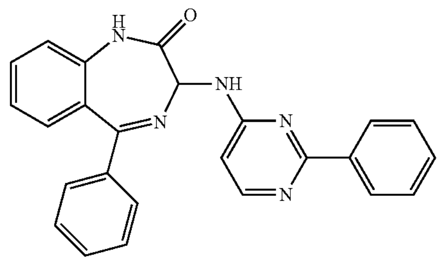 [SMILES: O=C1Nc2ccccc2C(c2ccccc2)=NC1Nc1ccnc(-c2ccccc2)n1] |
| 97 | 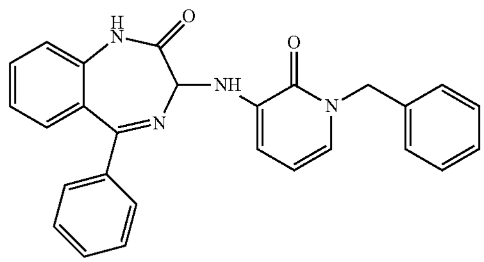 [SMILES: O=C1Nc2ccccc2C(c2ccccc2)=NC1Nc1cccn(Cc2ccccc2)c1=O] |
| 107 | 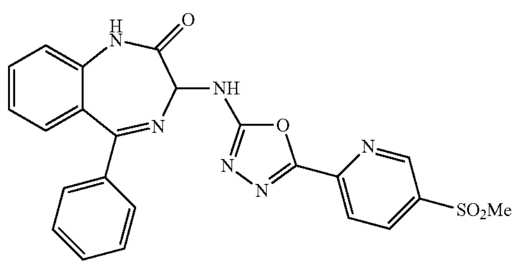 [SMILES: CS(=O)(=O)c1ccc(-c2nnc(NC3N=C(c4ccccc4)c4ccccc4NC3=O)o2)nc1] |
| 108 | 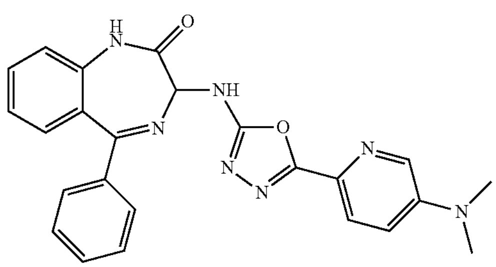 [SMILES: CN(C)c1ccc(-c2nnc(NC3N=C(c4ccccc4)c4ccccc4NC3=O)o2)nc1] |
| 109 | 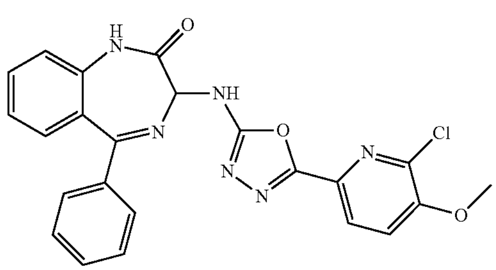 [SMILES: COc1ccc(-c2nnc(NC3N=C(c4ccccc4)c4ccccc4NC3=O)o2)nc1Cl] |
| 110 | 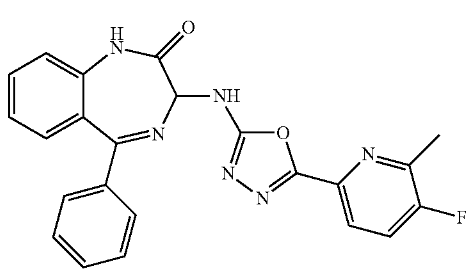 [SMILES: Cc1nc(-c2nnc(NC3N=C(c4ccccc4)c4ccccc4NC3=O)o2)ccc1F] |

-continued

| Compound | Structure |
|---|---|
| 111 | 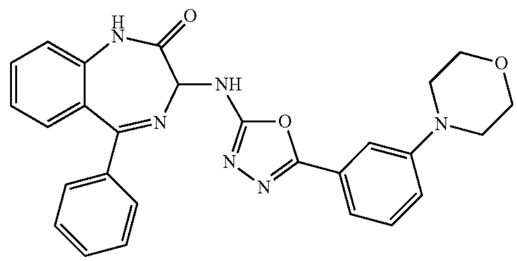 [SMILES: O=C1Nc2ccccc2C(c2ccccc2)=NC1Nc1nnc(-c2cccc(N3CCOCC3)c2)o1] |
| 112 | 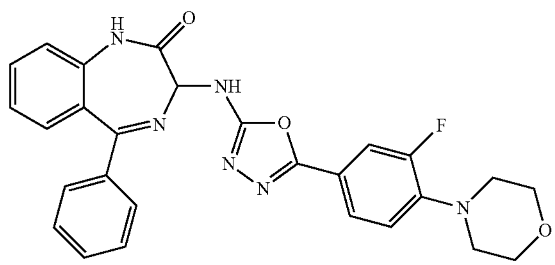 [SMILES: O=C1Nc2ccccc2C(c2ccccc2)=NC1Nc1nnc(-c2ccc(N3CCOCC3)c(F)c2)o1] |
| 113 | 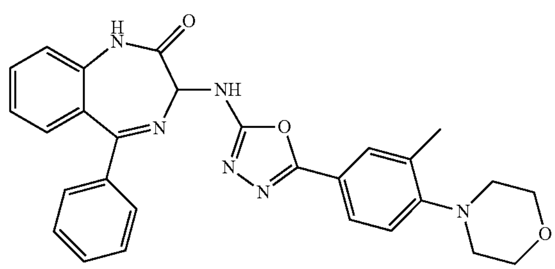 |
| 114 | 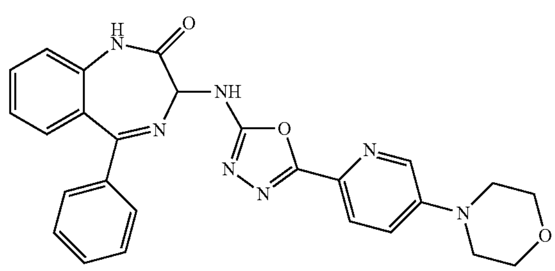 [SMILES: O=C1Nc2ccccc2C(c2ccccc2)=NC1Nc1nnc(-c2ccc(N3CCOCC3)cn2)o1] |
| 115 | 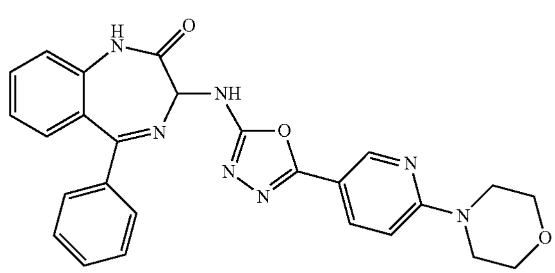 |
| 116 | 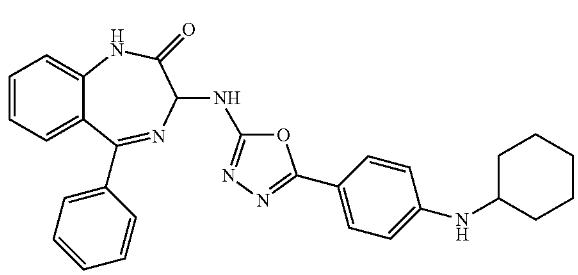 [SMILES: O=C1Nc2ccccc2C(c2ccccc2)=NC1Nc1nnc(-c2ccc(NC3CCCCC3)cc2)o1] |

| Compound | Structure |
|---|---|
| 117 | 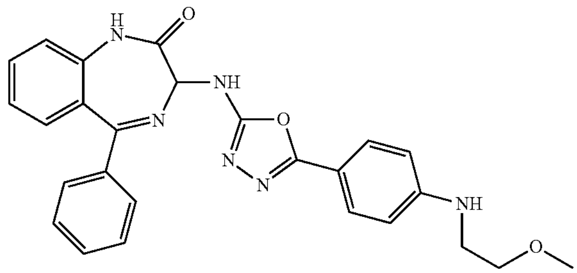 [SMILES: COCCNc1ccc(-c2nnc(NC3N=C(c4ccccc4)c4ccccc4NC3=O)o2)cc1] |
| 118 | 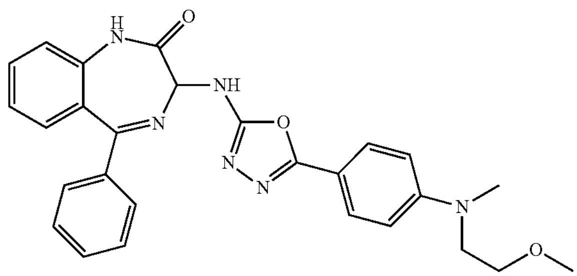 [SMILES: COCCN(C)c1ccc(-c2nnc(NC3N=C(c4ccccc4)c4ccccc4NC3=O)o2)cc1] |
| 119 | 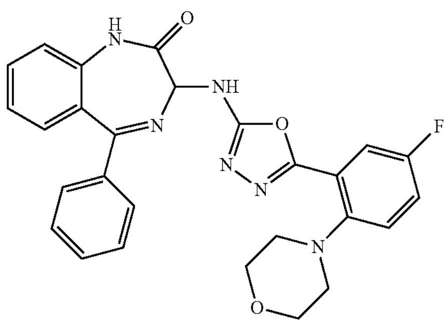 [SMILES: O=C1Nc2ccccc2C(c2ccccc2)=NC1Nc1nnc(-c2cc(F)ccc2N2CCOCC2)o1] |
| 120 | 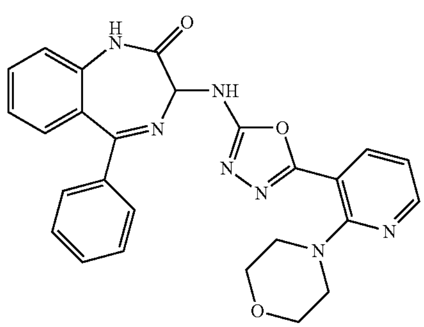 |
| 121 | 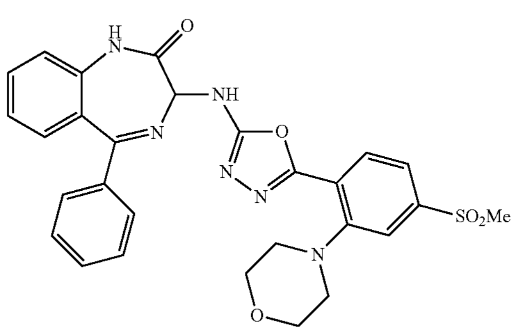 [SMILES: CS(=O)(=O)c1ccc(-c2nnc(NC3N=C(c4ccccc4)c4ccccc4NC3=O)o2)c(N2CCOCC2)c1] |

| Compound | Structure |
|---|---|
| 122 | 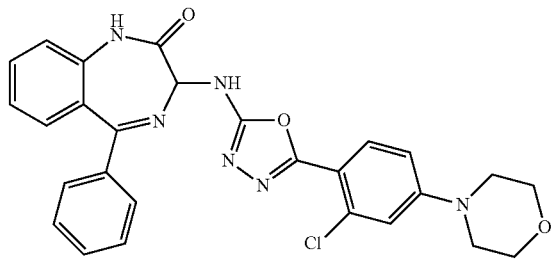 [SMILES: O=C1Nc2ccccc2C(c2ccccc2)=NC1Nc1nnc(-c2ccc(N3CCOCC3)cc2Cl)o1] |
| 123 | 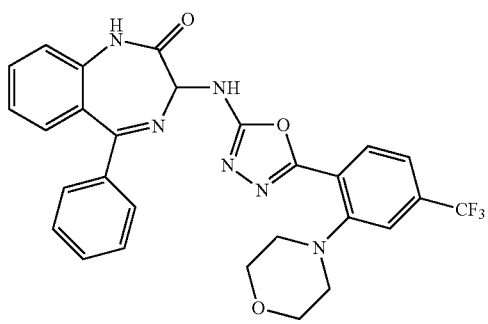 [SMILES: O=C1Nc2ccccc2C(c2ccccc2)=NC1Nc1nnc(-c2ccc(C(F)(F)F)cc2N2CCOCC2)o1] |
| 124a | 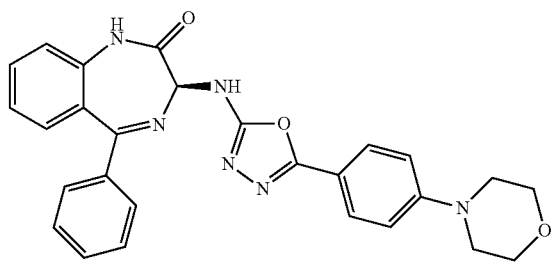 [SMILES: O=C1Nc2ccccc2C(c2ccccc2)=N[C@@H]1Nc1nnc(-c2ccc(N3CCOCC3)cc2)o1] |
| 124b | 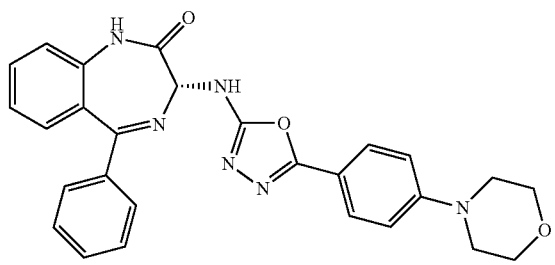 [SMILES: O=C1Nc2ccccc2C(c2ccccc2)=N[C@H]1Nc1nnc(-c2ccc(N3CCOCC3)cc2)o1] |
| 125a | 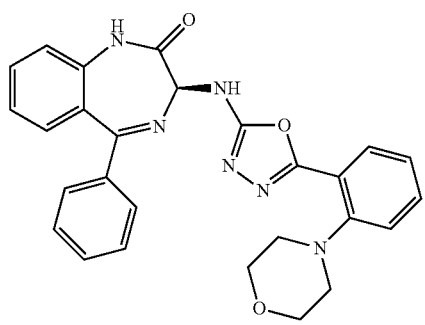 [SMILES: O=C1Nc2ccccc2C(c2ccccc2)=N[C@@H]1Nc1nnc(-c2ccccc2N2CCOCC2)o1] |

-continued

| Compound | Structure |
|---|---|
| 125b | (structure) |
| 126a | (structure) |
| 126b | (structure) |
| 127 | (structure) |
| 128 | (structure) |

-continued

| Compound | Structure |
|---|---|
| 129 | 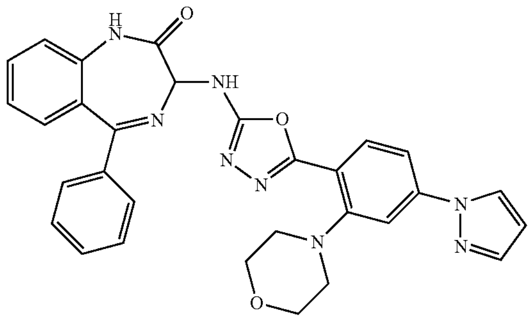 [SMILES: O=C1Nc2ccccc2C(c2ccccc2)=NC1Nc1nnc(-c2ccc(-n3cccn3)cc2N2CCOCC2)o1] |
| 130 | 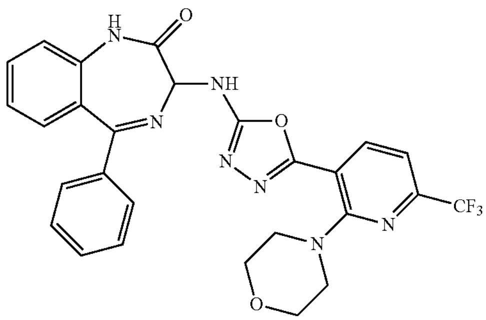 [SMILES: O=C1Nc2ccccc2C(c2ccccc2)=NC1Nc1nnc(-c2ccc(C(F)(F)F)nc2N2CCOCC2)o1] |
| 131 | 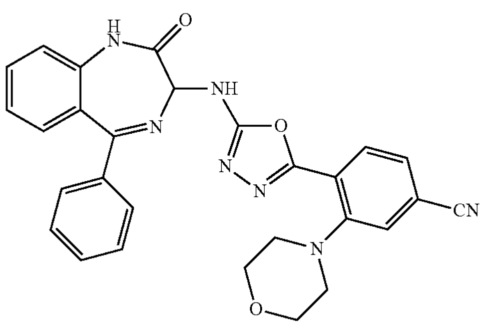 [SMILES: N#Cc1ccc(-c2nnc(NC3N=C(c4ccccc4)c4ccccc4NC3=O)o2)c(N2CCOCC2)c1] |
| 132 | 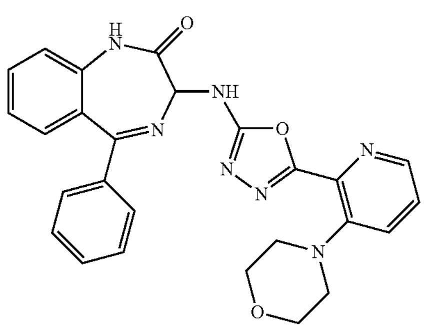 |
| 133 | 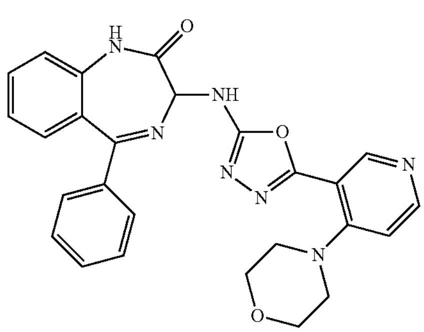 |

-continued
| Compound | Structure |
|---|---|
| 134 | 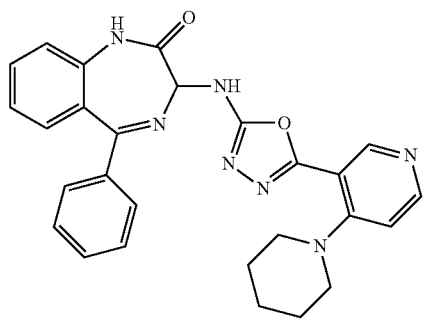 |
| 135 | 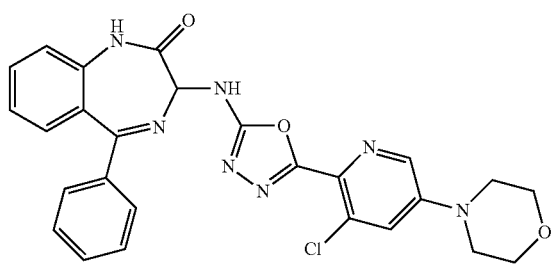 [SMILES: O=C1Nc2ccccc2C(c2ccccc2)=NC1Nc1nnc(-c2ncc(N3CCOCC3)cc2Cl)o1] |
| 136 | 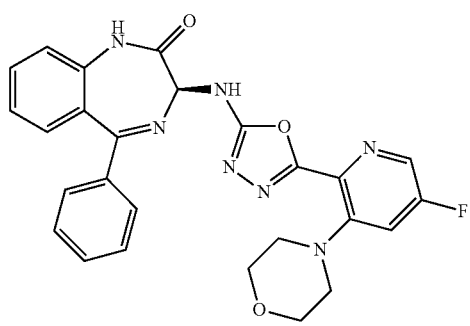 [SMILES: O=C1Nc2ccccc2C(c2ccccc2)=N[C@@H]1Nc1nnc(-c2ncc(F)cc2N2CCOCC2)o1] |
| 137 | 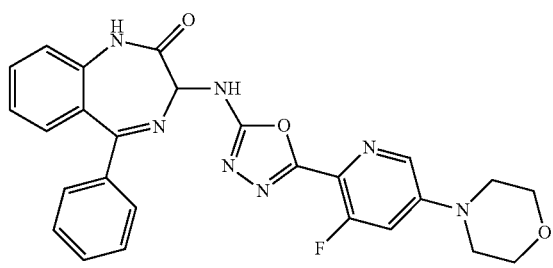 |
| 138 | 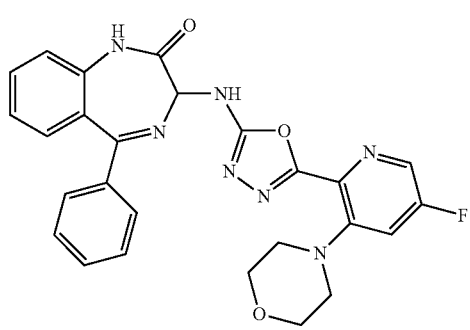 [SMILES: O=C1Nc2ccccc2C(c2ccccc2)=NC1Nc1nnc(-c2ncc(F)cc2N2CCOCC2)o1] |

-continued

| Compound | Structure |
|---|---|
| 139 | 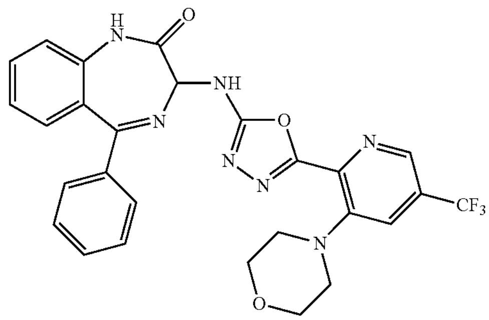 [SMILES: O=C1Nc2ccccc2C(c2ccccc2)=NC1Nc1nnc(-c2ncc(C(F)(F)F)cc2N2CCOCC2)o1] |
| 140 | 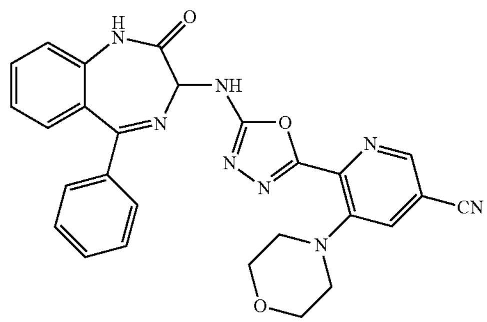 |
| 141 | 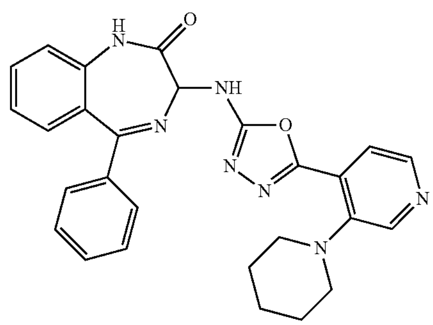 [SMILES: O=C1Nc2ccccc2C(c2ccccc2)=NC1Nc1nnc(-c2ccncc2N2CCCCC2)o1] |
| 142 | 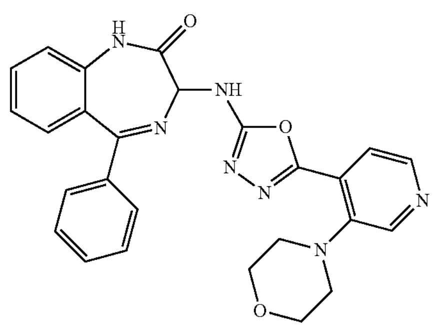 [SMILES: O=C1Nc2ccccc2C(c2ccccc2)=NC1Nc1nnc(-c2ccncc2N2CCOCC2)o1] |
| 143 | 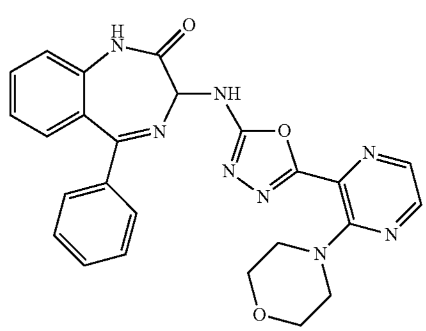 |

-continued
| Compound | Structure |
|---|---|
| 144 | 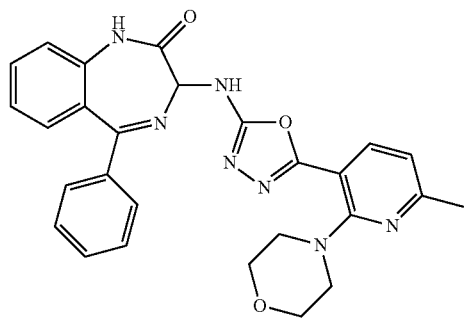 [SMILES: Cc1ccc(-c2nnc(NC3N=C(c4ccccc4)c4ccccc4NC3=O)o2)c(N2CCOCC2)n1] |
| 145 | 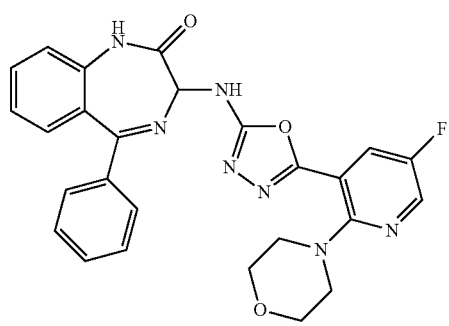 [SMILES: O=C1Nc2ccccc2C(c2ccccc2)=NC1Nc1nnc(-c2cc(F)cnc2N2CCOCC2)o1] |
| 146 | 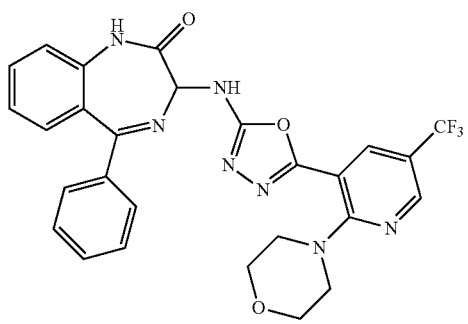 [SMILES: O=C1Nc2ccccc2C(c2ccccc2)=NC1Nc1nnc(-c2cc(C(F)(F)F)cnc2N2CCOCC2)o1] |
| 147 | 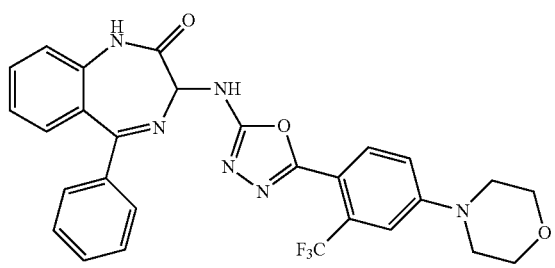 |
| 148 | 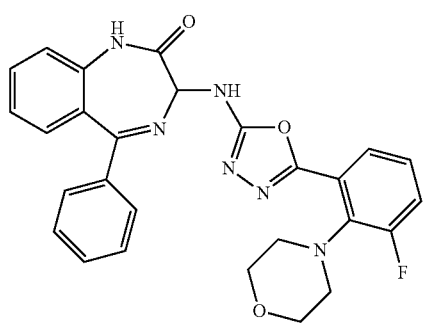 [SMILES: O=C1Nc2ccccc2C(c2ccccc2)=NC1Nc1nnc(-c2cccc(F)c2N2CCOCC2)o1] |

| Compound | Structure |
|---|---|
| 149 | 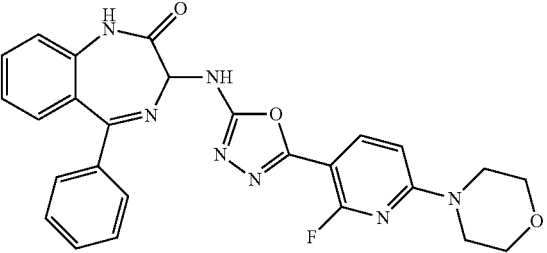 [SMILES: O=C1Nc2ccccc2C(c2ccccc2)=NC1Nc1nnc(-c2ccc(N3CCOCC3)nc2F)o1] |
| 150 | 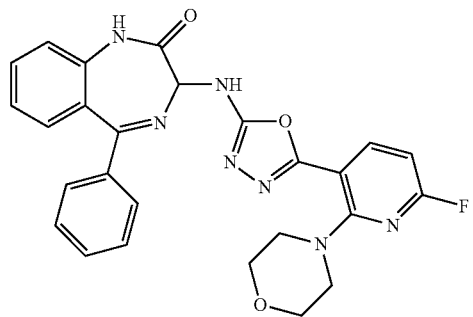 [SMILES: O=C1Nc2ccccc2C(c2ccccc2)=NC1Nc1nnc(-c2ccc(F)nc2N2CCOCC2)o1] |
| 151 | 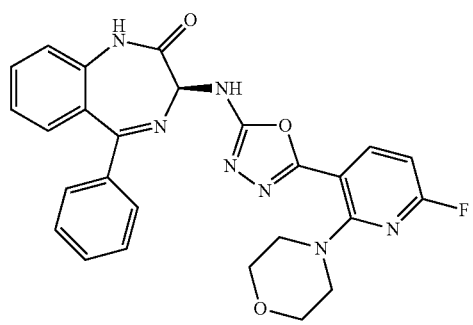 [SMILES: O=C1Nc2ccccc2C(c2ccccc2)=N[C@@H]1Nc1nnc(-c2ccc(F)nc2N2CCOCC2)o1] |
| 152 | 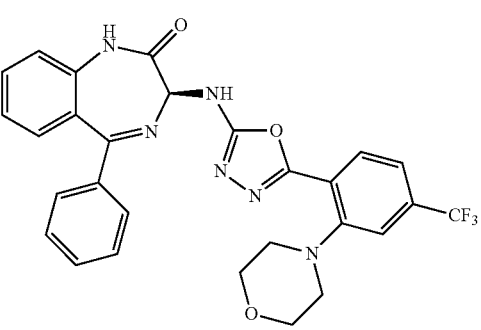 |
| 153 | 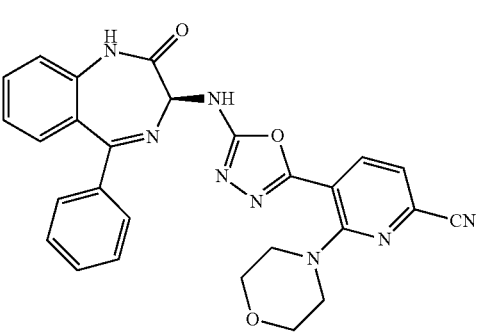 [SMILES: N#Cc1ccc(-c2nnc(N[C@H]3N=C(c4ccccc4)c4ccccc4NC3=O)o2)c(N2CCOCC2)n1] |

-continued

| Compound | Structure |
|---|---|
| 154 | 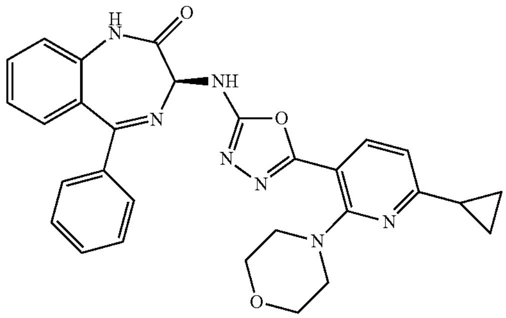 [SMILES: O=C1Nc2ccccc2C(c2ccccc2)=N[C@@H]1Nc1nnc(-c2ccc(C3CC3)nc2N2CCOCC2)o1] |
| 155 | 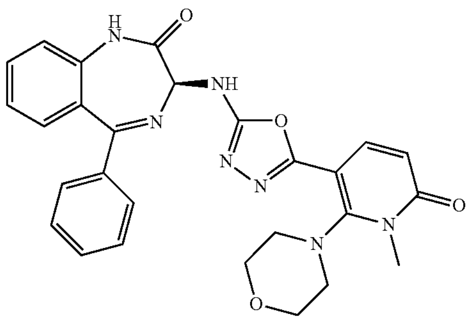 [SMILES: Cn1c(N2CCOCC2)c(-c2nnc(N[C@H]3N=C(c4ccccc4)c4ccccc4NC3=O)o2)ccc1=O] |
| 156 | 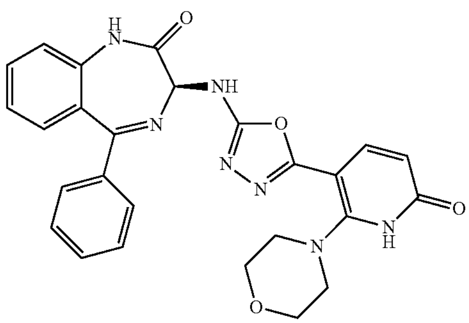 [SMILES: O=C1Nc2ccccc2C(c2ccccc2)=N[C@@H]1Nc1nnc(-c2ccc(=O)[nH]c2N2CCOCC2)o1] |
| 157 | 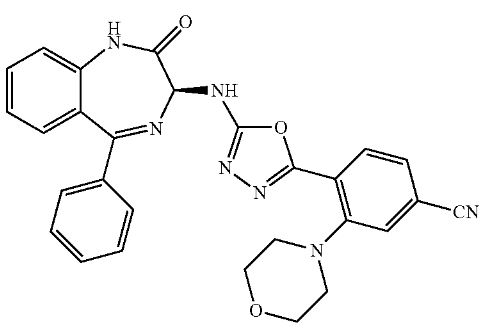 [SMILES: N#Cc1ccc(-c2nnc(N[C@H]3N=C(c4ccccc4)c4ccccc4NC3=O)o2)c(N2CCOCC2)c1] |
| 158 | 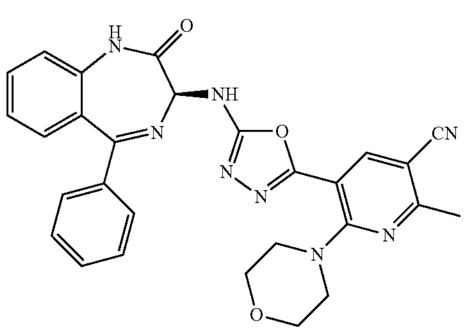 [SMILES: Cc1nc(N2CCOCC2)c(-c2nnc(N[C@H]3N=C(c4ccccc4)c4ccccc4NC3=O)o2)cc1C#N] |

-continued

| Compound | Structure |
|---|---|
| 159 | 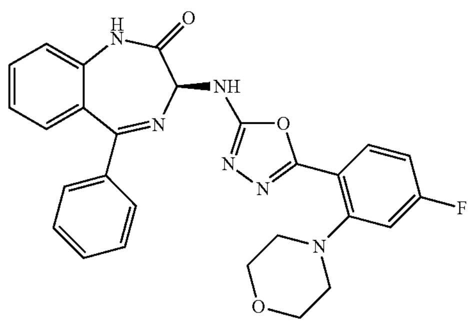 [SMILES: O=C1Nc2ccccc2C(c2ccccc2)=N[C@@H]1Nc1nnc(-c2ccc(F)cc2N2CCOCC2)o1] |
| 160 | 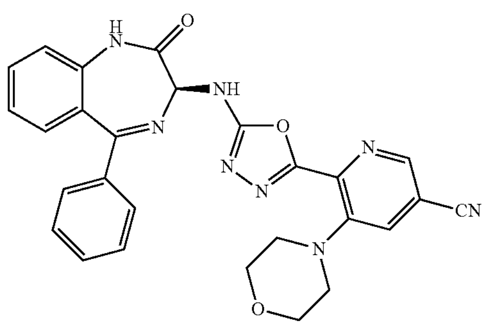 [SMILES: N#Cc1cnc(-c2nnc(N[C@H]3N=C(c4ccccc4)c4ccccc4NC3=O)o2)c(N2CCOCC2)c1] |
| 161 | 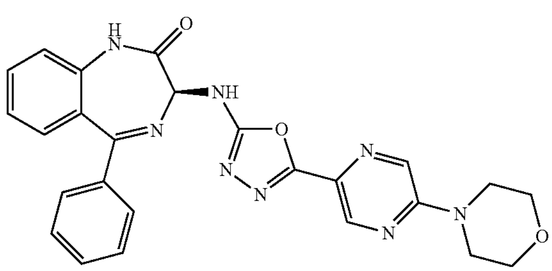 [SMILES: O=C1Nc2ccccc2C(c2ccccc2)=N[C@@H]1Nc1nnc(-c2cnc(N3CCOCC3)cn2)o1] |
| 162 | 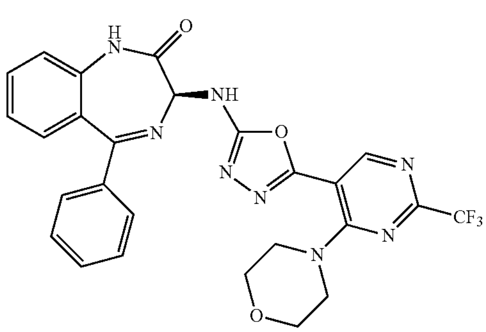 [SMILES: O=C1Nc2ccccc2C(c2ccccc2)=N[C@@H]1Nc1nnc(-c2cnc(C(F)(F)F)nc2N2CCOCC2)o1] |
| 163 | 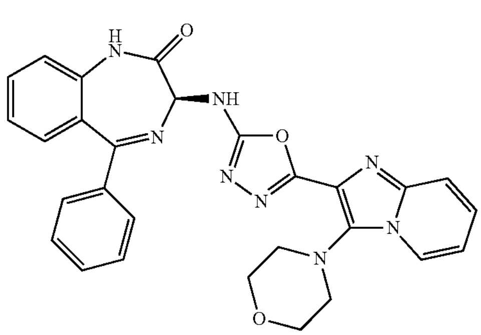 [SMILES: O=C1Nc2ccccc2C(c2ccccc2)=N[C@@H]1Nc1nnc(-c2nc3ccccn3c2N2CCOCC2)o1] |

| Compound | Structure |
|---|---|
| 164 | 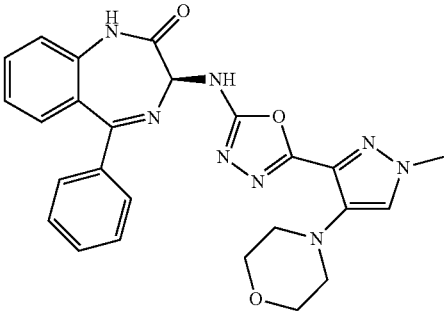 [SMILES: Cn1cc(N2CCOCC2)c(-c2nnc(N[C@H]3N=C(c4ccccc4)c4ccccc4NC3=O)o2)n1] |
| 165 | 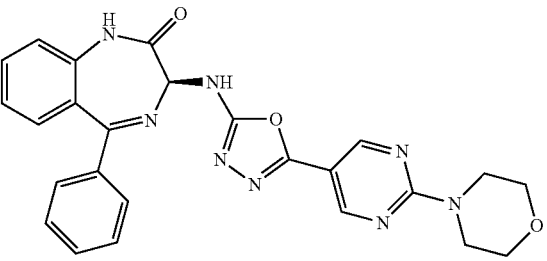 [SMILES: O=C1Nc2ccccc2C(c2ccccc2)=N[C@@H]1Nc1nnc(-c2cnc(N3CCOCC3)nc2)o1] |
| 166 | 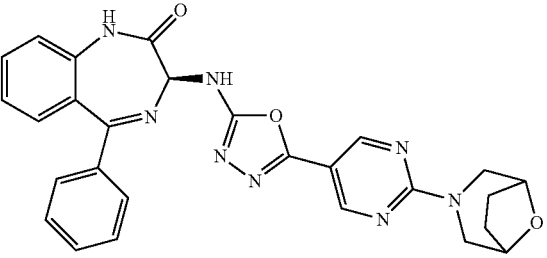 [SMILES: O=C1Nc2ccccc2C(c2ccccc2)=N[C@@H]1Nc1nnc(-c2cnc(N3CC4CCC(C3)O4)nc2)o1] |
| 167 | 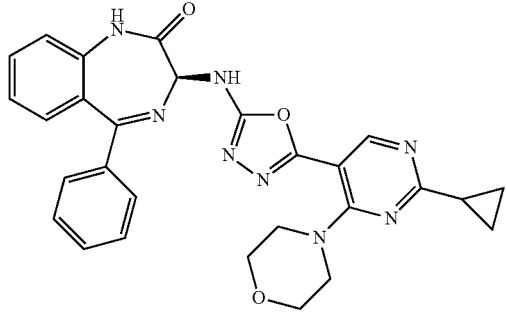 [SMILES: O=C1Nc2ccccc2C(c2ccccc2)=N[C@@H]1Nc1nnc(-c2cnc(C3CC3)nc2N2CCOCC2)o1] |
| 168 | 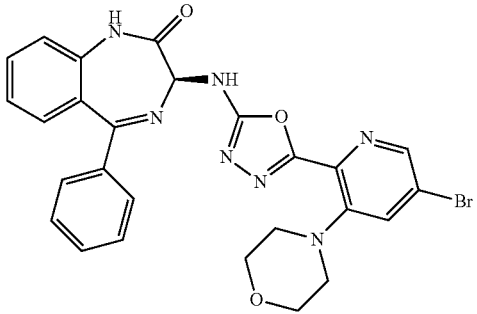 [SMILES: O=C1Nc2ccccc2C(c2ccccc2)=N[C@@H]1Nc1nnc(-c2ncc(Br)cc2N2CCOCC2)o1] |

-continued
| Compound | Structure |
|---|---|
| 169 | 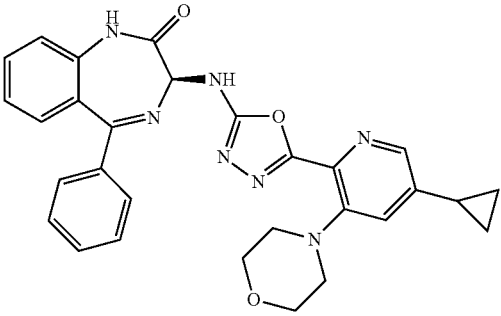 [SMILES: O=C1Nc2ccccc2C(c2ccccc2)=N[C@@H]1Nc1nnc(-c2ncc(C3CC3)cc2N2CCOCC2)o1] |
| 170 | 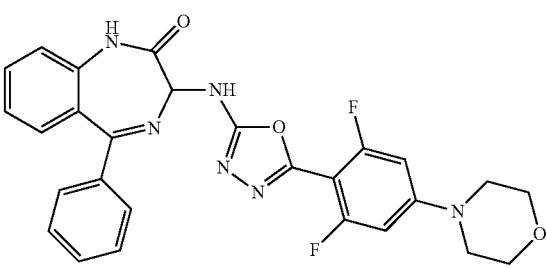 [SMILES: O=C1Nc2ccccc2C(c2ccccc2)=NC1Nc1nnc(-c2c(F)cc(N3CCOCC3)cc2F)o1] |
| 171 | 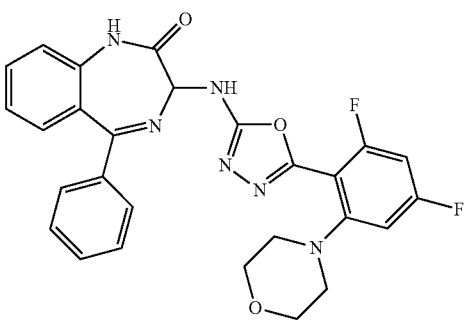 [SMILES: O=C1Nc2ccccc2C(c2ccccc2)=NC1Nc1nnc(-c2c(F)cc(F)cc2N2CCOCC2)o1] |
| 172 | 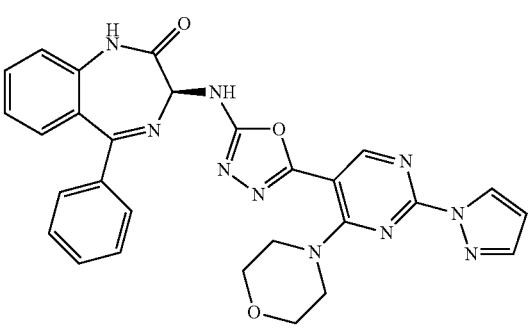 [SMILES: O=C1Nc2ccccc2C(c2ccccc2)=N[C@@H]1Nc1nnc(-c2cnc(-n3cccn3)nc2N2CCOCC2)o1] |
| 173 | 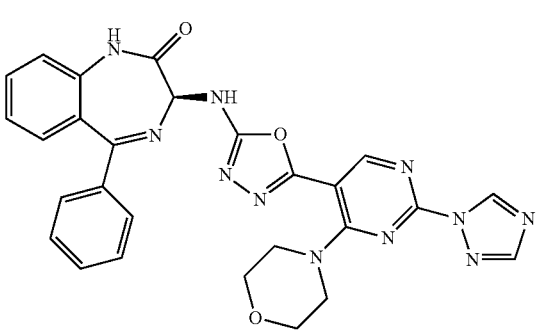 [SMILES: O=C1Nc2ccccc2C(c2ccccc2)=N[C@@H]1Nc1nnc(-c2cnc(-n3cncn3)nc2N2CCOCC2)o1] |

-continued

| Compound | Structure |
|---|---|
| 174 | 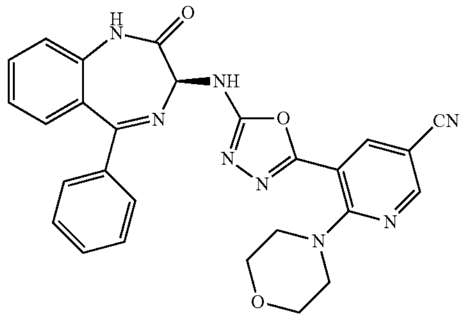 [SMILES: N#Cc1cnc(N2CCOCC2)c(-c2nnc(N[C@H]3N=C(c4ccccc4)c4ccccc4NC3=O)o2)c1] |
| 175 | 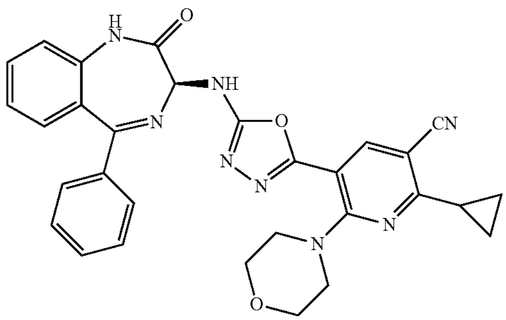 [SMILES: N#Cc1cc(-c2nnc(N[C@H]3N=C(c4ccccc4)c4ccccc4NC3=O)o2)c(N2CCOCC2)nc1C1CC1] |
| 176 | 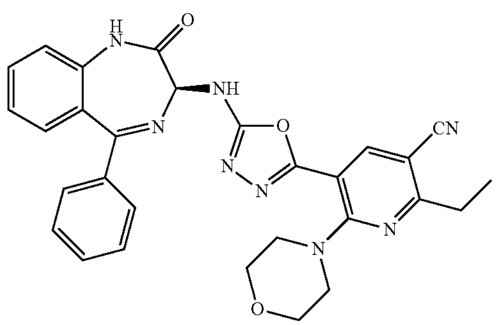 [SMILES: CCc1nc(N2CCOCC2)c(-c2nnc(N[C@H]3N=C(c4ccccc4)c4ccccc4NC3=O)o2)cc1C#N] |
| 177 | 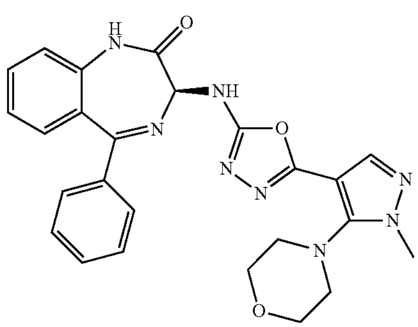 [SMILES: Cn1ncc(-c2nnc(N[C@H]3N=C(c4ccccc4)c4ccccc4NC3=O)o2)c1N1CCOCC1] |
| 178 | 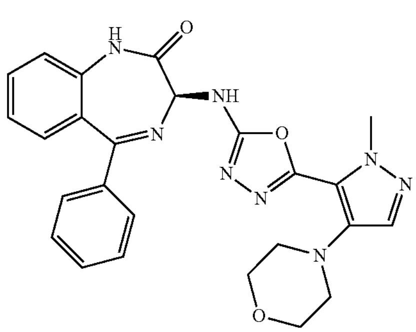 [SMILES: Cn1ncc(N2CCOCC2)c1-c1nnc(N[C@H]2N=C(c3ccccc3)c3ccccc3NC2=O)o1] |

| Compound | Structure |
|---|---|
| 179 | 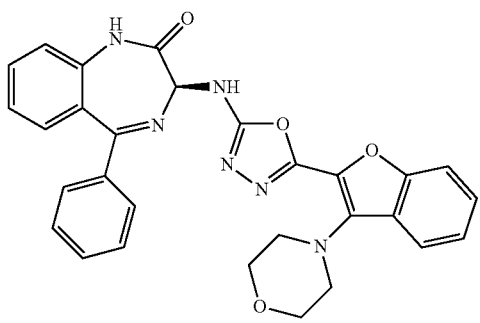 [SMILES: O=C1Nc2ccccc2C(c2ccccc2)=N[C@@H]1Nc1nnc(-c2oc3ccccc3c2N2CCOCC2)o1] |
| 180 | 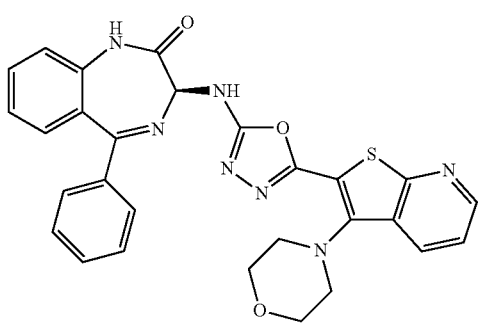 [SMILES: O=C1Nc2ccccc2C(c2ccccc2)=N[C@@H]1Nc1nnc(-c2sc3ncccc3c2N2CCOCC2)o1] |
| 181 | 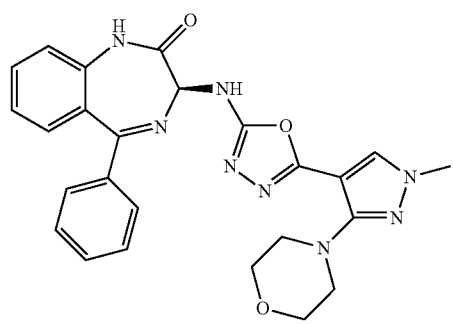 [SMILES: Cn1cc(-c2nnc(N[C@H]3N=C(c4ccccc4)c4ccccc4NC3=O)o2)c(N2CCOCC2)n1] |
| 182 | 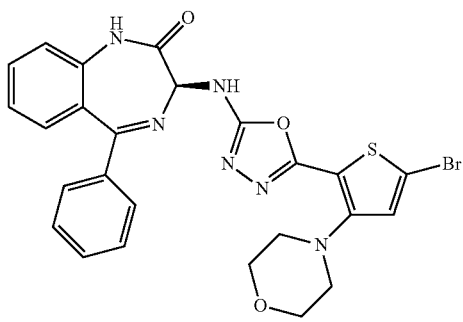 [SMILES: O=C1Nc2ccccc2C(c2ccccc2)=N[C@@H]1Nc1nnc(-c2sc(Br)cc2N2CCOCC2)o1] |
| 183 | 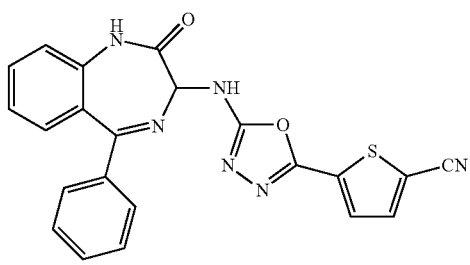 [SMILES: N#Cc1ccc(-c2nnc(NC3N=C(c4ccccc4)c4ccccc4NC3=O)o2)s1] |

-continued

| Compound | Structure |
|---|---|
| 184 | 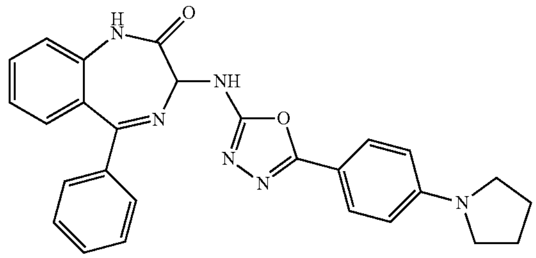 [SMILES: O=C1Nc2ccccc2C(c2ccccc2)=NC1Nc1nnc(-c2ccc(N3CCCC3)cc2)o1] |
| 185 | 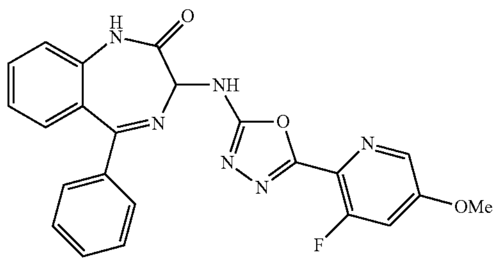 [SMILES: COc1cnc(-c2nnc(NC3N=C(c4ccccc4)c4ccccc4NC3=O)o2)c(F)c1] |
| 186 | 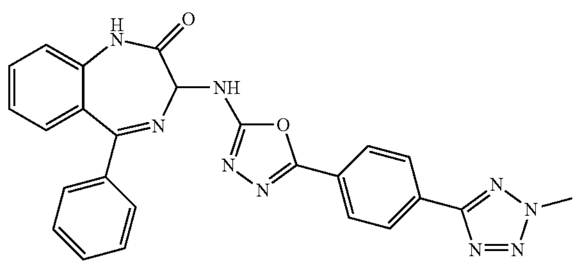 [SMILES: Cn1nnc(-c2ccc(-c3nnc(NC4N=C(c5ccccc5)c5ccccc5NC4=O)o3)cc2)n1] |
| 187 | 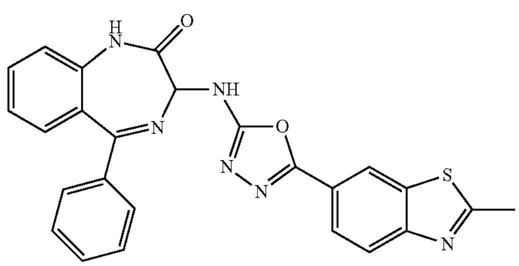 [SMILES: Cc1nc2ccc(-c3nnc(NC4N=C(c5ccccc5)c5ccccc5NC4=O)o3)cc2s1] |
| 195 | 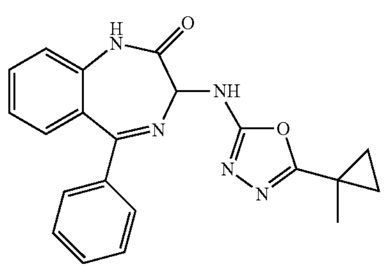 [SMILES: CC1(c2nnc(NC3N=C(c4ccccc4)c4ccccc4NC3=O)o2)CC1] |
| 196 | 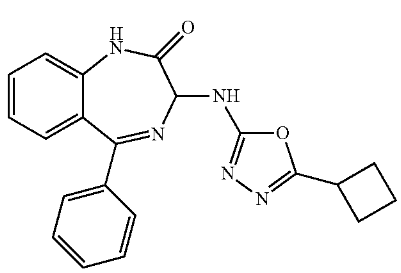 [SMILES: O=C1Nc2ccccc2C(c2ccccc2)=NC1Nc1nnc(C2CCC2)o1] |

-continued
| Compound | Structure |
|---|---|
| 197 | 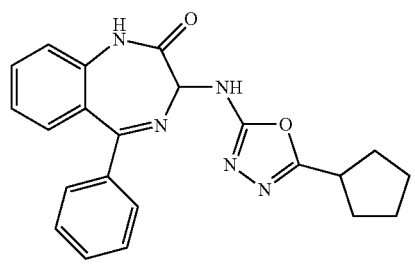 |
| 198 | 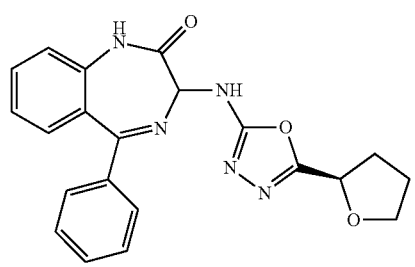 [SMILES: O=C1Nc2ccccc2C(c2ccccc2)=NC1Nc1nnc([C@H]2CCCO2)o1] |
| 199 | 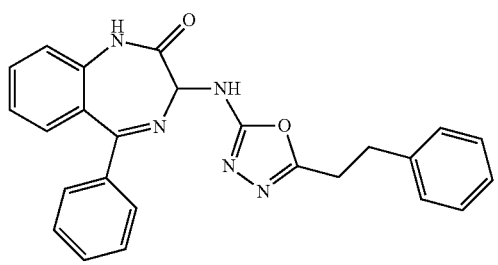 [SMILES: O=C1Nc2ccccc2C(c2ccccc2)=NC1Nc1nnc(CCc2ccccc2)o1] |
| 200 | 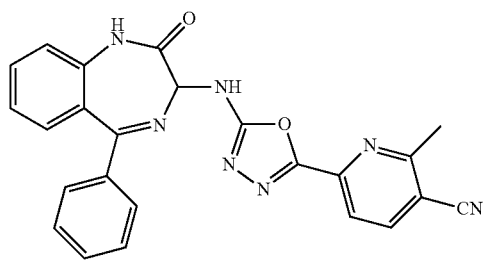 [SMILES: Cc1nc(-c2nnc(NC3N=C(c4ccccc4)c4ccccc4NC3=O)o2)ccc1C#N] |
| 201 | 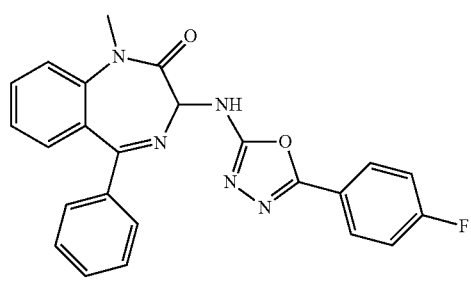 [SMILES: CN1C(=O)C(Nc2nnc(-c3ccc(F)cc3)o2)N=C(c2ccccc2)c2ccccc21] |

-continued
| Compound | Structure |
|---|---|
| 202 | 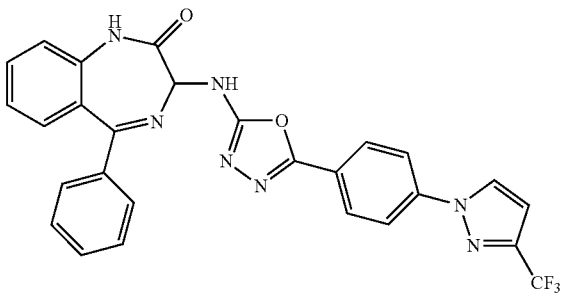 [SMILES: O=C1Nc2ccccc2C(c2ccccc2)=NC1Nc1nnc(-c2ccc(-n3ccc(C(F)(F)F)n3)cc2)o1] |
| 204 | 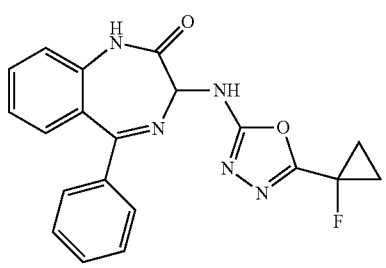 [SMILES: O=C1Nc2ccccc2C(c2ccccc2)=NC1Nc1nnc(C2(F)CC2)o1] |
| 205 | 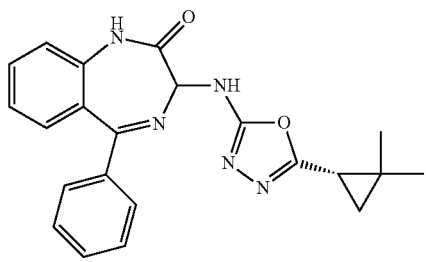 [SMILES: CC1(C)C[C@@H]1c1nnc(NC2N=C(c3ccccc3)c3ccccc3NC2=O)o1] |
| 206 | 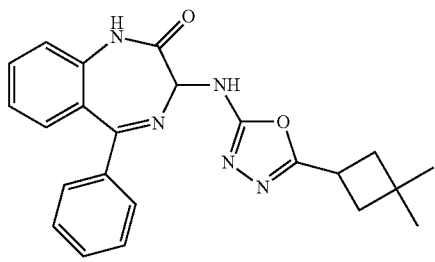 [SMILES: CC1(C)CC(c2nnc(NC3N=C(c4ccccc4)c4ccccc4NC3=O)o2)C1] |
| 207 | 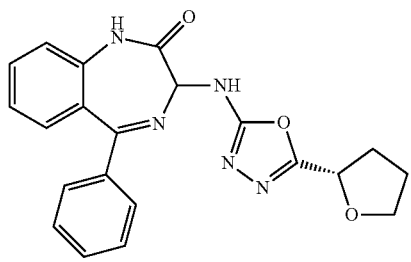 [SMILES: O=C1Nc2ccccc2C(c2ccccc2)=NC1Nc1nnc([C@@H]2CCCO2)o1] |

-continued
| Compound | Structure |
|---|---|
| 208 | 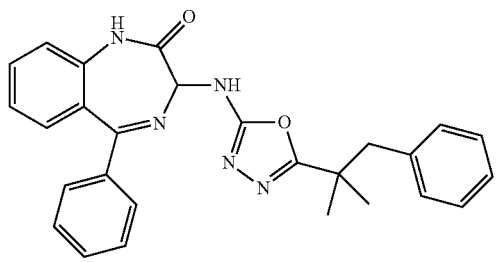 [SMILES: CC(C)(Cc1ccccc1)c1nnc(NC2N=C(c3ccccc3)c3ccccc3NC2=O)o1] |
| 209 | 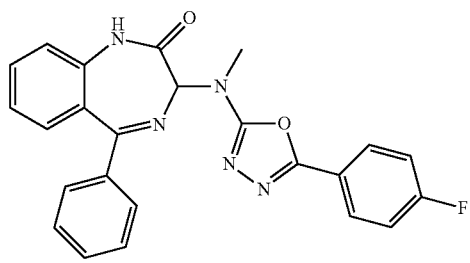 [SMILES: CN(c1nnc(-c2ccc(F)cc2)o1)C1N=C(c2ccccc2)c2ccccc2NC1=O] |
| 210 | 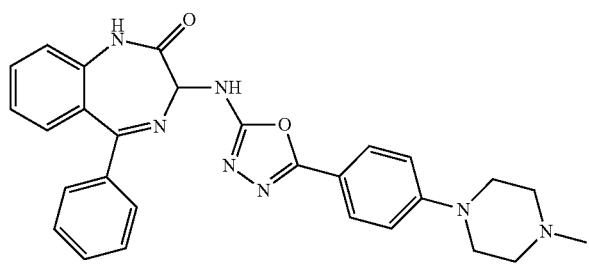 [SMILES: CN1CCN(c2ccc(-c3nnc(NC4N=C(c5ccccc5)c5ccccc5NC4=O)o3)cc2)CC1] |
| 211 | 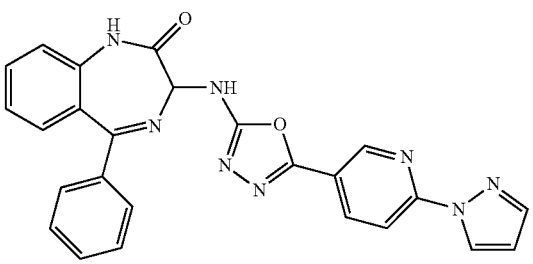 [SMILES: O=C1Nc2ccccc2C(c2ccccc2)=NC1Nc1nnc(-c2ccc(-n3cccn3)nc2)o1] |
| 212 | 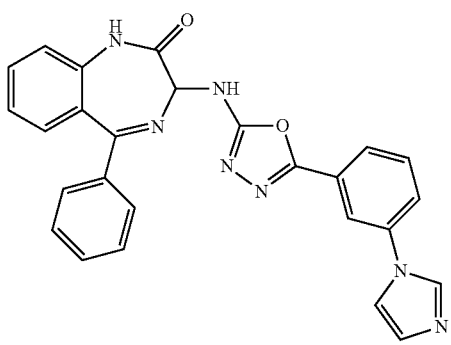 [SMILES: O=C1Nc2ccccc2C(c2ccccc2)=NC1Nc1nnc(-c2cccc(-n3ccnc3)c2)o1] |

-continued

| Compound | Structure |
|---|---|
| 214 | 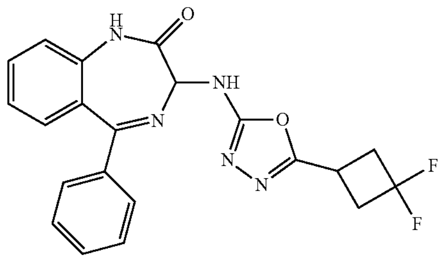 [SMILES: O=C1Nc2ccccc2C(c2ccccc2)=NC1Nc1nnc(C2CC(F)(F)C2)o1] |
| 215 | 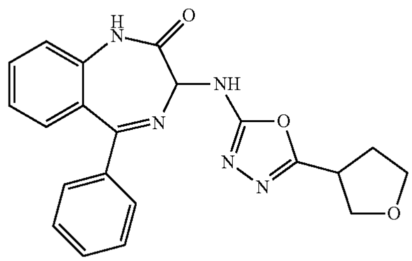 [SMILES: O=C1Nc2ccccc2C(c2ccccc2)=NC1Nc1nnc(C2CCOC2)o1] |
| 216 | 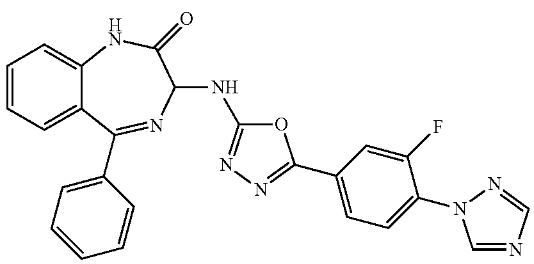 [SMILES: Cc1cc(-c2nnc(NC3N=C(c4ccccc4)c4ccccc4NC3=O)o2)ccc1-n1cncn1] |
| 217 | 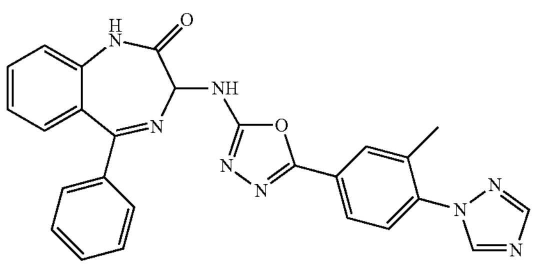 |
| 218 | 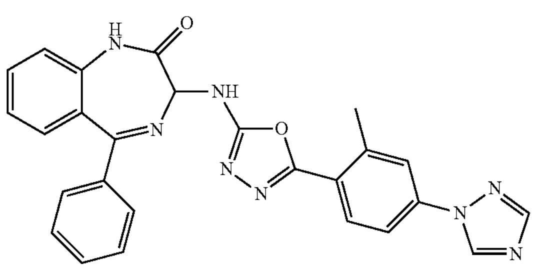 [SMILES: Cc1cc(-n2cncn2)ccc1-c1nnc(NC2N=C(c3ccccc3)c3ccccc3NC2=O)o1] |
| 219 | 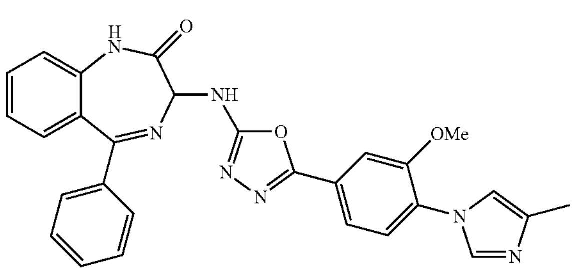 [SMILES: COc1cc(-c2nnc(NC3N=C(c4ccccc4)c4ccccc4NC3=O)o2)ccc1-n1cnc(C)c1] |

-continued
| Compound | Structure |
|---|---|
| 220 | 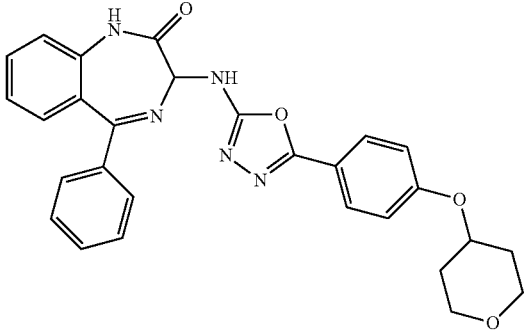 [SMILES: O=C1Nc2ccccc2C(c2ccccc2)=NC1Nc1nnc(-c2ccc(OC3CCOCC3)cc2)o1] |
| 221 | 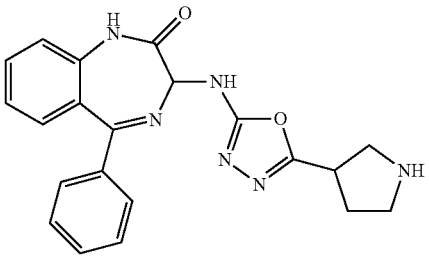 [SMILES: O=C1Nc2ccccc2C(c2ccccc2)=NC1Nc1nnc(C2CCNC2)o1] |
| 222 | 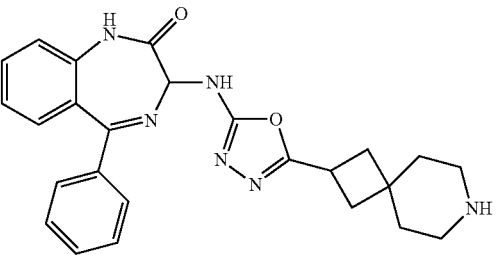 [SMILES: O=C1Nc2ccccc2C(c2ccccc2)=NC1Nc1nnc(C2CC3(CCNCC3)C2)o1] |
| 223 | 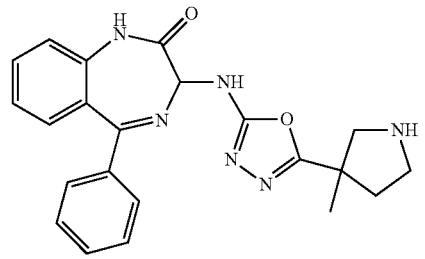 [SMILES: CC1(c2nnc(NC3N=C(c4ccccc4)c4ccccc4NC3=O)o2)CCNC1] |
| 224 | 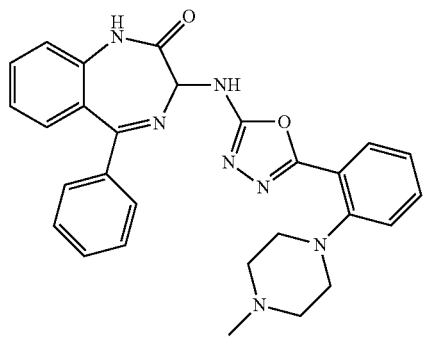 [SMILES: CN1CCN(c2ccccc2-c2nnc(NC3N=C(c4ccccc4)c4ccccc4NC3=O)o2)CC1] |

-continued

| Compound | Structure |
|---|---|
| 225 | 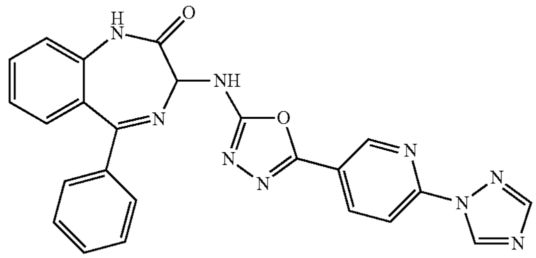 [SMILES: O=C1Nc2ccccc2C(c2ccccc2)=NC1Nc1nnc(-c2ccc(-n3cncn3)nc2)o1] |
| 226 | 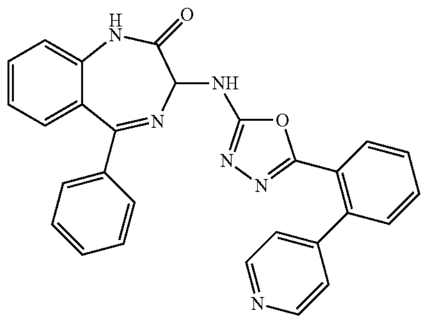 [SMILES: O=C1Nc2ccccc2C(c2ccccc2)=NC1Nc1nnc(-c2ccccc2-c2ccncc2)o1] |
| 227 | 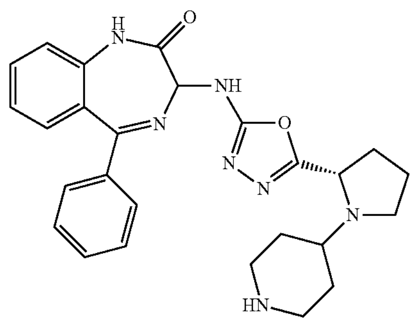 [SMILES: O=C1Nc2ccccc2C(c2ccccc2)=NC1Nc1nnc([C@@H]2CCCN2C2CCNCC2)o1] |
| 228 | 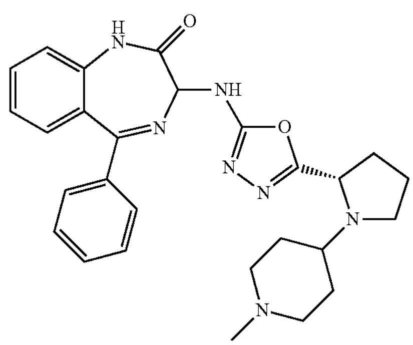 [SMILES: CN1CCC(N2CCC[C@H]2c2nnc(NC3N=C(c4ccccc4)c4ccccc4NC3=O)o2)CC1] |
| 229 | 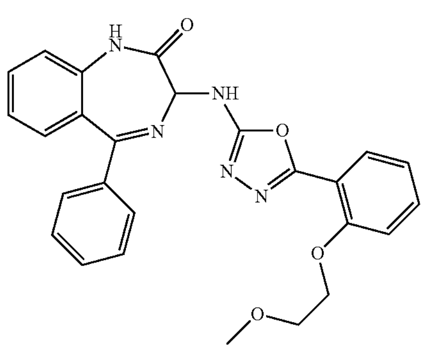 [SMILES: COCCOc1ccccc1-c1nnc(NC2N=C(c3ccccc3)c3ccccc3NC2=O)o1] |

-continued
| Compound | Structure |
|---|---|
| 230 | 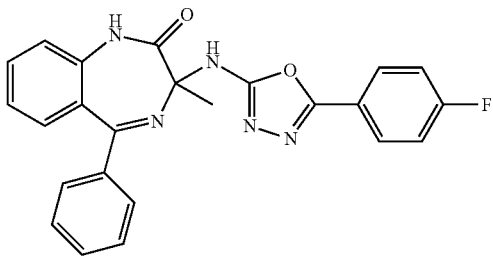 [SMILES: CC1(Nc2nnc(-c3ccc(F)cc3)o2)N=C(c2ccccc2)c2ccccc2NC1=O] |
| 231 | 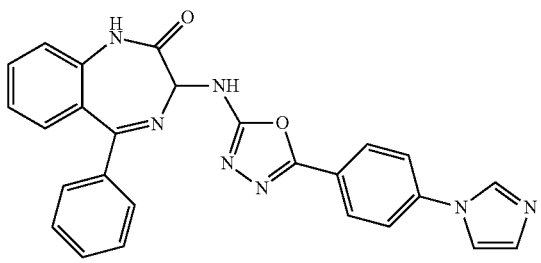 [SMILES: O=C1Nc2ccccc2C(c2ccccc2)=NC1Nc1nnc(-c2ccc(-n3ccnc3)cc2)o1] |
| 232 | 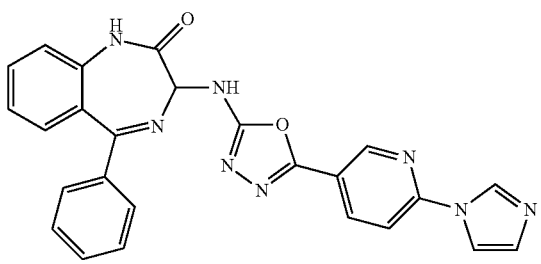 [SMILES: O=C1Nc2ccccc2C(c2ccccc2)=NC1Nc1nnc(-c2ccc(-n3ccnc3)nc2)o1] |
| 233 | 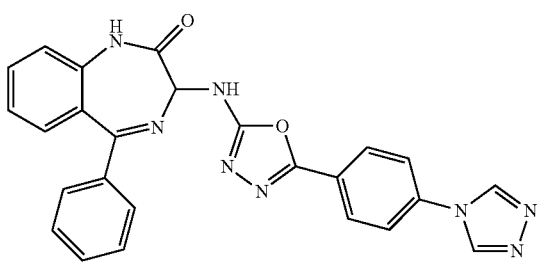 [SMILES: O=C1Nc2ccccc2C(c2ccccc2)=NC1Nc1nnc(-c2ccc(-n3cnnc3)cc2)o1] |
| 234 | 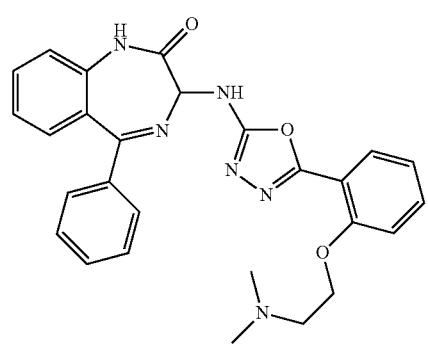 [SMILES: CN(C)CCOc1ccccc1-c1nnc(NC2N=C(c3ccccc3)c3ccccc3NC2=O)o1] |

| Compound | Structure |
|---|---|
| 235 | 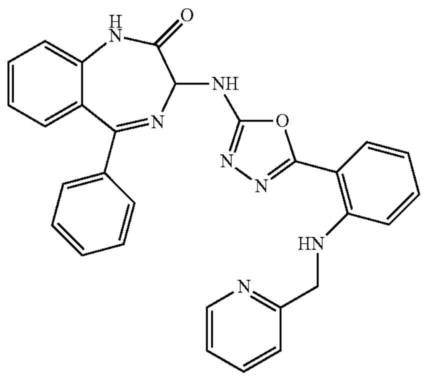 [SMILES: O=C1Nc2ccccc2C(c2ccccc2)=NC1Nc1nnc(-c2ccccc2NCc2ccccn2)o1] |
| 236 | 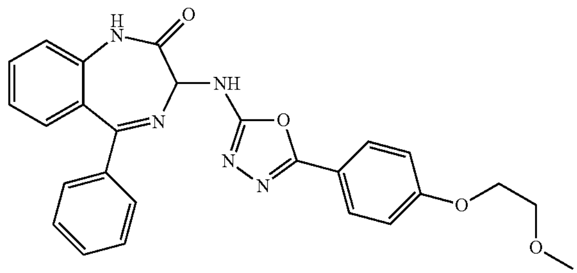 [SMILES: COCCOc1ccc(-c2nnc(NC3N=C(c4ccccc4)c4ccccc4NC3=O)o2)cc1] |
| 237 | 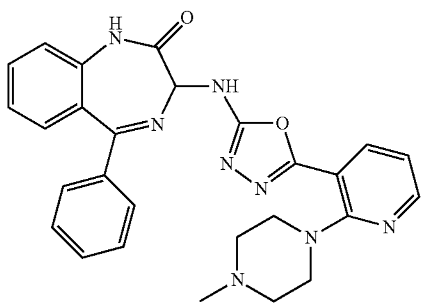 [SMILES: CN1CCN(c2ncccc2-c2nnc(NC3N=C(c4ccccc4)c4ccccc4NC3=O)o2)CC1] |
| 238 | 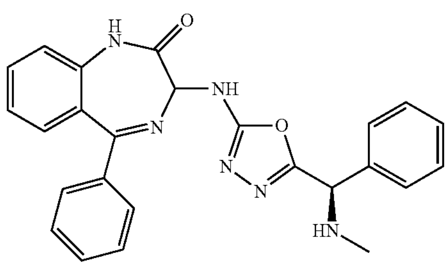 [SMILES: CN[C@H](c1ccccc1)c1nnc(NC2N=C(c3ccccc3)c3ccccc3NC2=O)o1] |
| 239 | 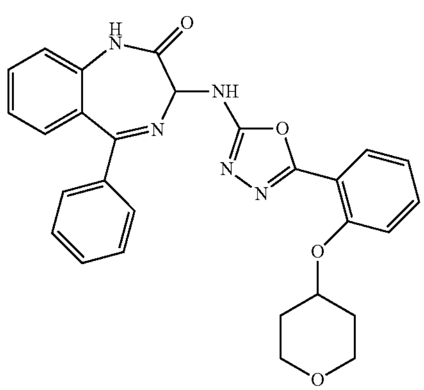 [SMILES: O=C1Nc2ccccc2C(c2ccccc2)=NC1Nc1nnc(-c2ccccc2OC2CCOCC2)o1] |

-continued
| Compound | Structure |
|---|---|
| 240 | 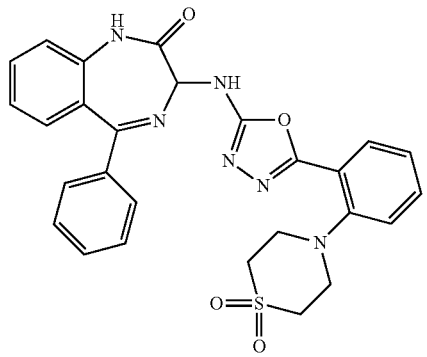 [SMILES: O=C1Nc2ccccc2C(c2ccccc2)=NC1Nc1nnc(-c2ccccc2N2CCS(=O)(=O)CC2)o1] |
| 241 | 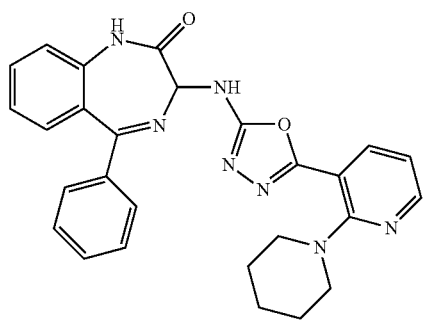 |
| 242 | 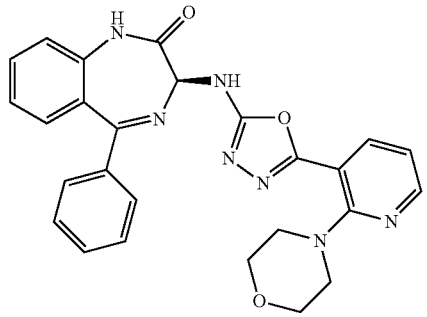 [SMILES: O=C1Nc2ccccc2C(c2ccccc2)=N[C@@H]1Nc1nnc(-c2cccnc2N2CCOCC2)o1] |
| 243 | 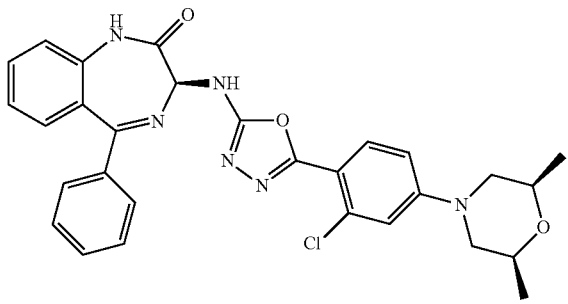 [SMILES: C[C@@H]1CN(c2ccc(-c3nnc(N[C@H]4N=C(c5ccccc5)c5ccccc5NC4=O)o3)c(Cl)c2)C[C@H](C)O1] |
| 244 | 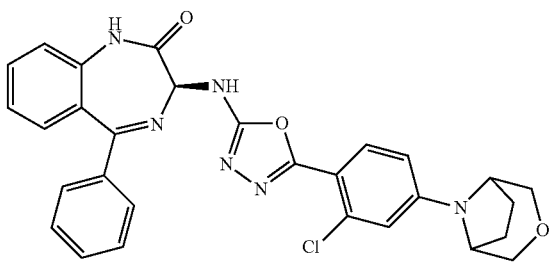 [SMILES: O=C1Nc2ccccc2C(c2ccccc2)=N[C@@H]1Nc1nnc(-c2ccc(N3C4CCC3COC4)cc2Cl)o1] |

| Compound | Structure |
|---|---|
| 245 | 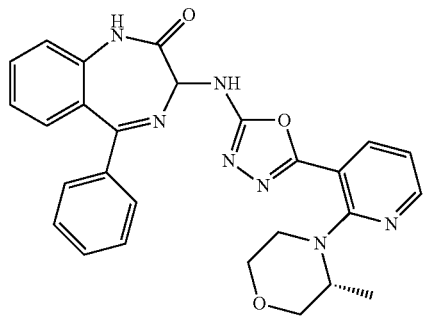 [SMILES: C[C@@H]1COCCN1c1ncccc1-c1nnc(NC2N=C(c3ccccc3)c3ccccc3NC2=O)o1] |
| 246 | 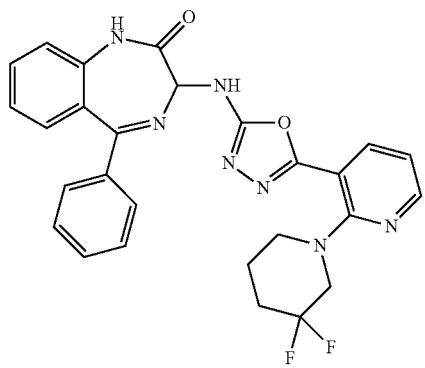 [SMILES: O=C1Nc2ccccc2C(c2ccccc2)=NC1Nc1nnc(-c2cccnc2N2CCCC(F)(F)C2)o1] |
| 247 | 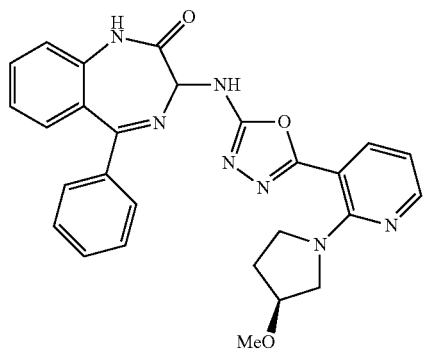 [SMILES: CO[C@H]1CCN(c2ncccc2-c2nnc(NC3N=C(c4ccccc4)c4ccccc4NC3=O)o2)C1] |
| 248 | 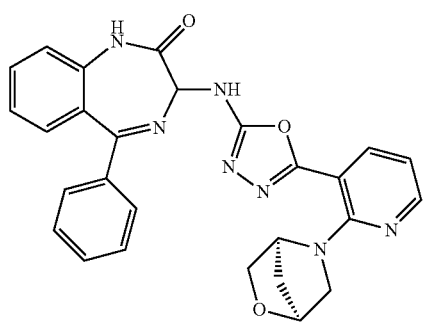 [SMILES: O=C1Nc2ccccc2C(c2ccccc2)=NC1Nc1nnc(-c2cccnc2N2C[C@@H]3C[C@H]2CO3)o1] |

-continued

| Compound | Structure |
|---|---|
| 249 | 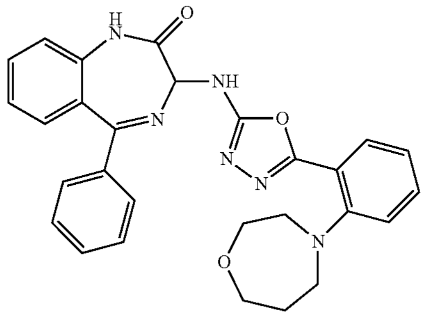 [SMILES: O=C1Nc2ccccc2C(c2ccccc2)=NC1Nc1nnc(-c2ccccc2N2CCCOCC2)o1] |
| 250 | 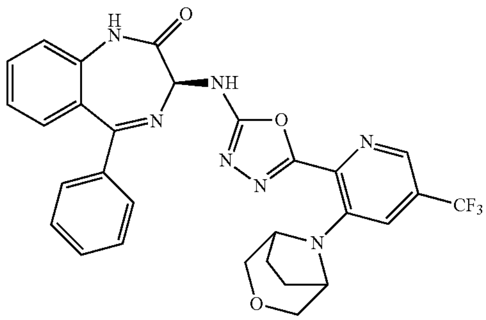 [SMILES: O=C1Nc2ccccc2C(c2ccccc2)=N[C@@H]1Nc1nnc(-c2ncc(C(F)(F)F)cc2N2C3CCC2COC3)o1] |
| 251 | 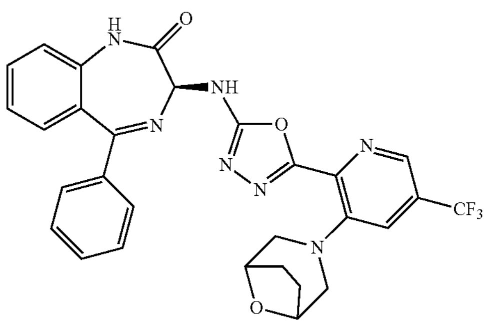 [SMILES: O=C1Nc2ccccc2C(c2ccccc2)=N[C@@H]1Nc1nnc(-c2ncc(C(F)(F)F)cc2N2CC3CCC(C2)O3)o1] |
| 252 | 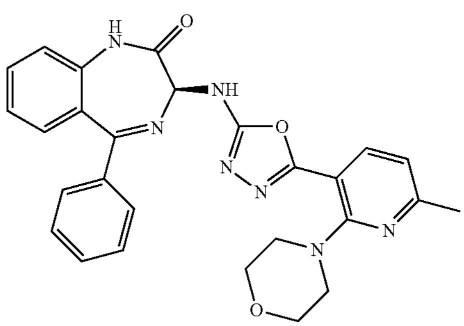 [SMILES: Cc1ccc(-c2nnc(N[C@H]3N=C(c4ccccc4)c4ccccc4NC3=O)o2)c(N2CCOCC2)n1] |
| 253 | 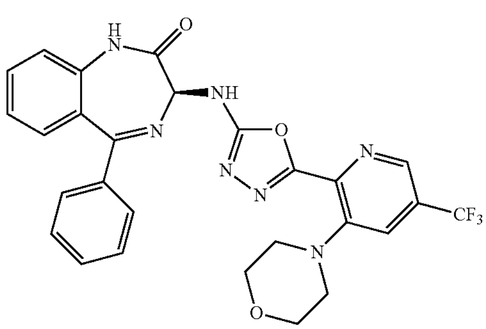 [SMILES: O=C1Nc2ccccc2C(c2ccccc2)=N[C@@H]1Nc1nnc(-c2ncc(C(F)(F)F)cc2N2CCOCC2)o1] |

| Compound | Structure |
|---|---|
| 254 | 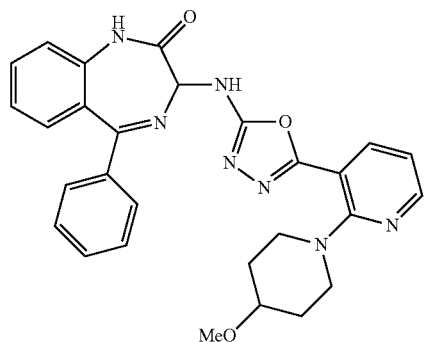 [SMILES: COC1CCN(c2ncccc2-c2nnc(NC3N=C(c4ccccc4)c4ccccc4NC3=O)o2)CC1] |
| 255 | 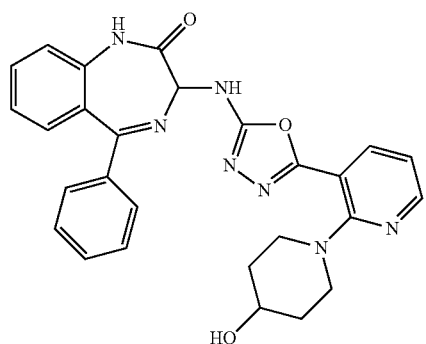 [SMILES: O=C1Nc2ccccc2C(c2ccccc2)=NC1Nc1nnc(-c2cccnc2N2CCC(O)CC2)o1] |
| 256 | 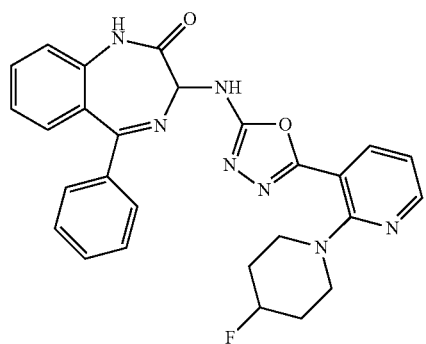 [SMILES: O=C1Nc2ccccc2C(c2ccccc2)=NC1Nc1nnc(-c2cccnc2N2CCC(F)CC2)o1] |
| 257 | 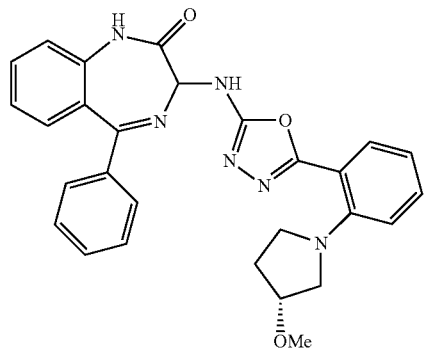 [SMILES: CO[C@@H]1CCN(c2ccccc2-c2nnc(NC3N=C(c4ccccc4)c4ccccc4NC3=O)o2)C1] |

-continued
| Compound | Structure |
|---|---|
| 258 | 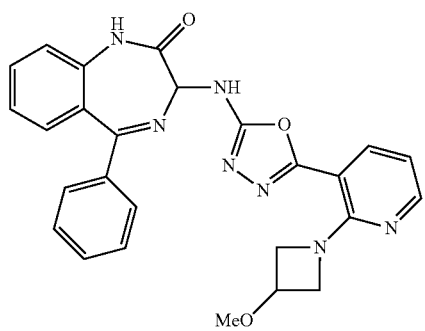 [SMILES: COC1CN(c2ncccc2-c2nnc(NC3N=C(c4ccccc4)c4ccccc4NC3=O)o2)C1] |
| 259 | 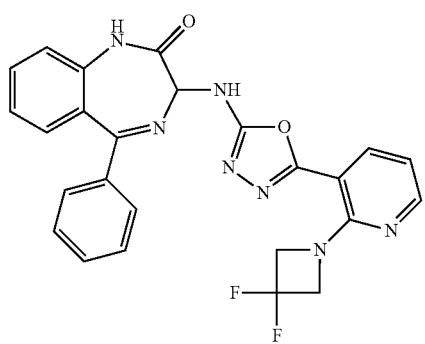 [SMILES: O=C1Nc2ccccc2C(c2ccccc2)=NC1Nc1nnc(-c2cccnc2N2CC(F)(F)C2)o1] |
| 260 | 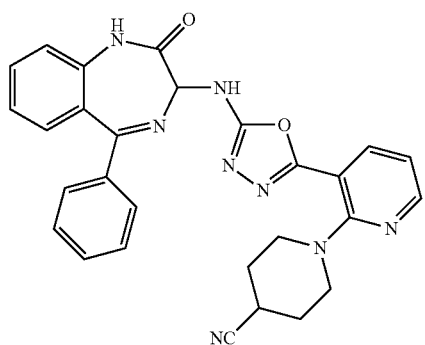 [SMILES: N#CC1CCN(c2ncccc2-c2nnc(NC3N=C(c4ccccc4)c4ccccc4NC3=O)o2)CC1] |
| 261 | 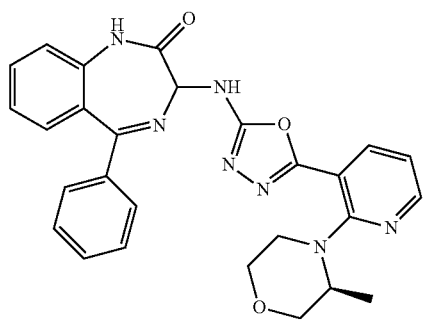 [SMILES: C[C@H]1COCCN1c1ncccc1-c1nnc(NC2N=C(c3ccccc3)c3ccccc3NC2=O)o1] |

| Compound | Structure |
|---|---|
| 262 | 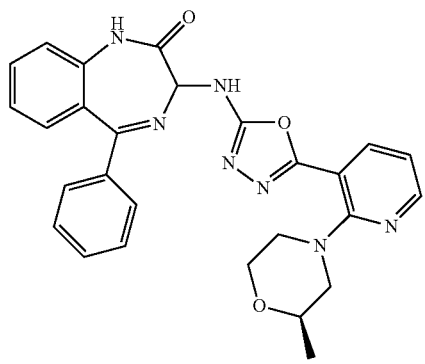 [SMILES: C[C@@H]1CN(c2ncccc2-c2nnc(NC3N=C(c4ccccc4)c4ccccc4NC3=O)o2)CCO1] |
| 263 | 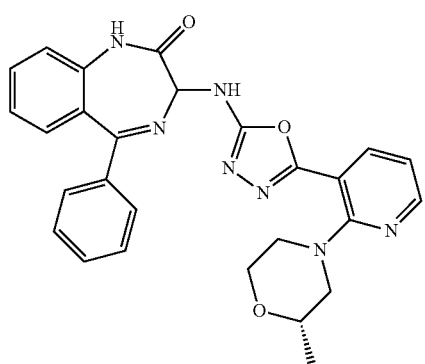 [SMILES: C[C@H]1CN(c2ncccc2-c2nnc(NC3N=C(c4ccccc4)c4ccccc4NC3=O)o2)CCO1] |
| 264 | 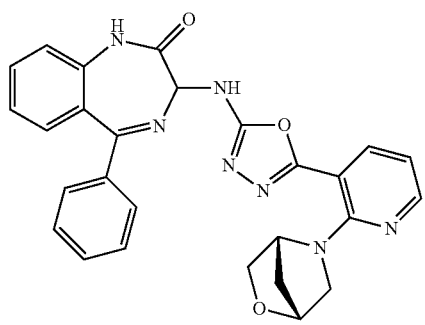 [SMILES: O=C1Nc2ccccc2C(c2ccccc2)=NC1Nc1nnc(-c2cccnc2N2C[C@H]3C[C@@H]2CO3)o1] |
| 265 | 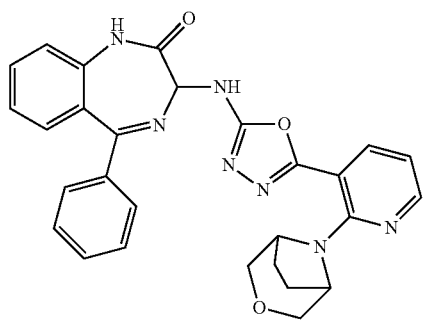 [SMILES: O=C1Nc2ccccc2C(c2ccccc2)=NC1Nc1nnc(-c2cccnc2N2C3CCC2COC3)o1] |

| Compound | Structure |
|---|---|
| 266 | 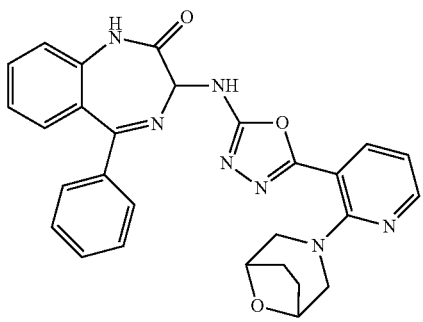 [SMILES: O=C1Nc2ccccc2C(c2ccccc2)=NC1Nc1nnc(-c2cccnc2N2CC3CCC(C2)O3)o1] |
| 267 | 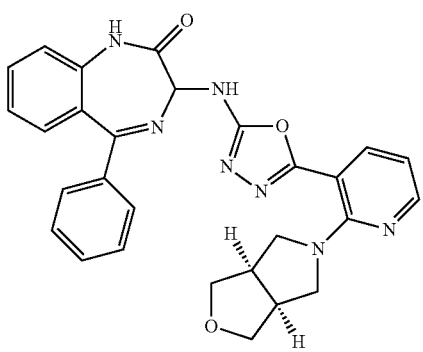 [SMILES: O=C1Nc2ccccc2C(c2ccccc2)=NC1Nc1nnc(-c2cccnc2N2C[C@H]3COC[C@H]3C2)o1] |
| 268 | 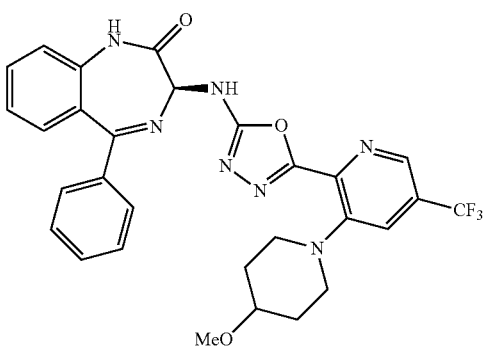 [SMILES: COC1CCN(c2cc(C(F)(F)F)cnc2-c2nnc(N[C@H]3N=C(c4ccccc4)c4ccccc4NC3=O)o2)CC1] |
| 269 | 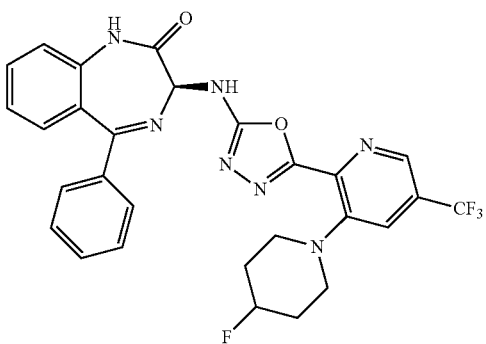 [SMILES: O=C1Nc2ccccc2C(c2ccccc2)=N[C@@H]1Nc1nnc(-c2ncc(C(F)(F)F)cc2N2CCC(F)CC2)o1] |

| Compound | Structure |
|---|---|
| 270 | 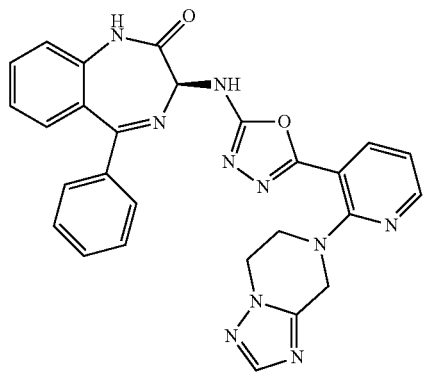 [SMILES: O=C1Nc2ccccc2C(c2ccccc2)=N[C@@H]1Nc1nnc(-c2cccnc2N2CCn3ncnc3C2)o1] |
| 271 | 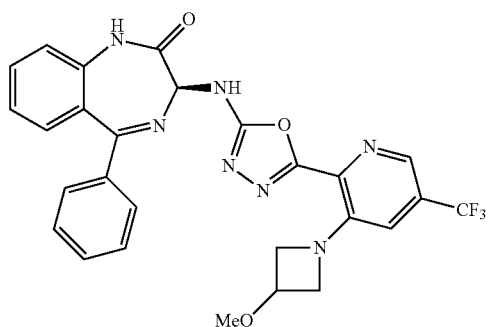 [SMILES: COC1CN(c2cc(C(F)(F)F)cnc2-c2nnc(N[C@H]3N=C(c4ccccc4)c4ccccc4NC3=O)o2)C1] |
| 272 | 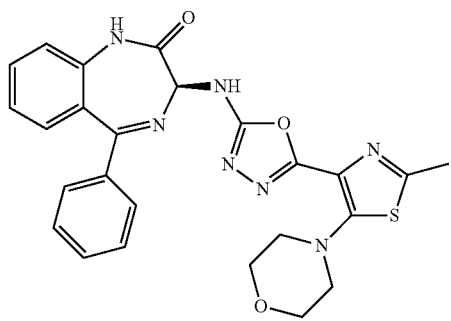 |
| 273 | 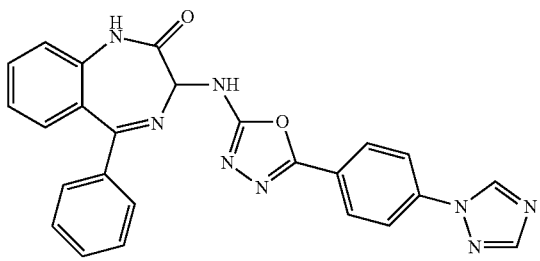 [SMILES: O=C1Nc2ccccc2C(c2ccccc2)=NC1Nc1nnc(-c2ccc(-n3cncn3)cc2)o1] |

| Compound | Structure |
|---|---|
| 274 | 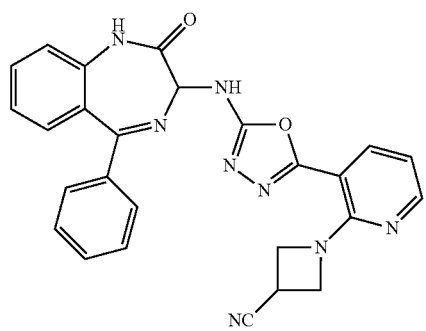 [SMILES: N#CC1CN(c2ncccc2-c2nnc(NC3N=C(c4ccccc4)c4ccccc4NC3=O)o2)C1] |
| 275 | 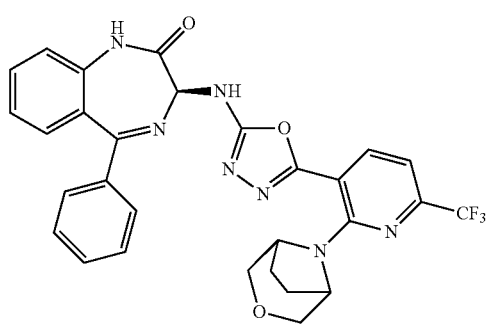 [SMILES: O=C1Nc2ccccc2C(c2ccccc2)=N[C@@H]1Nc1nnc(-c2ccc(C(F)(F)F)nc2N2C3CCC2COC3)o1] |
| 276 | 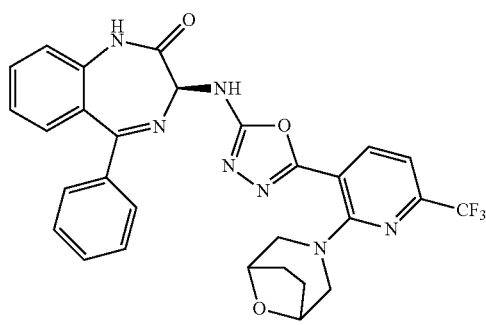 [SMILES: O=C1Nc2ccccc2C(c2ccccc2)=N[C@@H]1Nc1nnc(-c2ccc(C(F)(F)F)nc2N2CC3CCC(C2)O3)o1] |
| 277 | 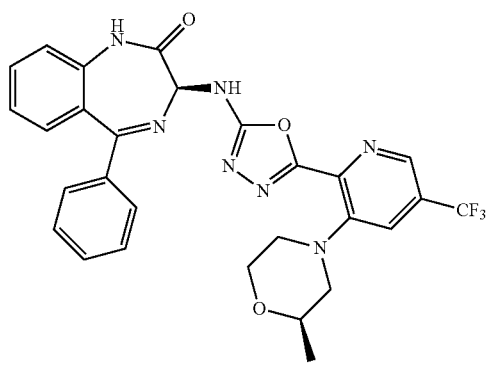 [SMILES: C[C@@H]1CN(c2cc(C(F)(F)F)cnc2-c2nnc(N[C@H]3N=C(c4ccccc4)c4ccccc4NC3=O)o2)CCO1] |

| Compound | Structure |
|---|---|
| 278 | 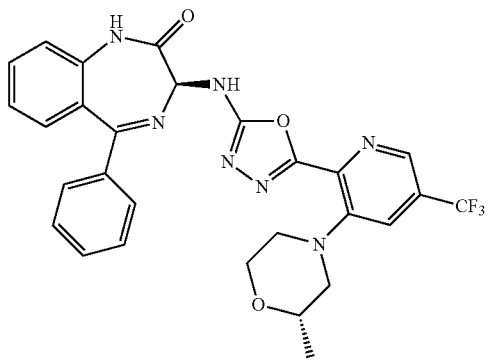 [SMILES: C[C@H]1CN(c2cc(C(F)(F)F)cnc2-c2nnc(N[C@H]3N=C(c4ccccc4)c4ccccc4NC3=O)o2)CCO1] |
| 279 | 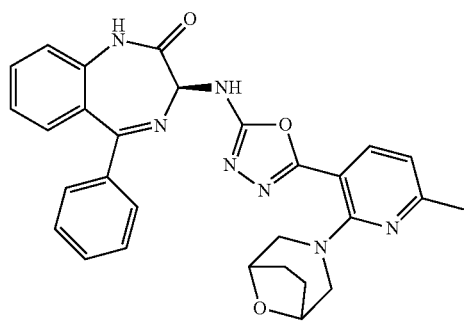 [SMILES: Cc1ccc(-c2nnc(N[C@H]3N=C(c4ccccc4)c4ccccc4NC3=O)o2)c(N2CC3CCC(C2)O3)n1] |
| 280 | 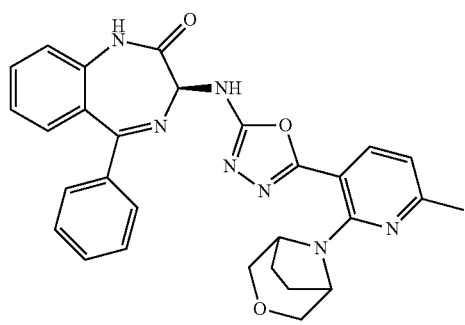 [SMILES: Cc1ccc(-c2nnc(N[C@H]3N=C(c4ccccc4)c4ccccc4NC3=O)o2)c(N2C3CCC2COC3)n1] |
| 281 | 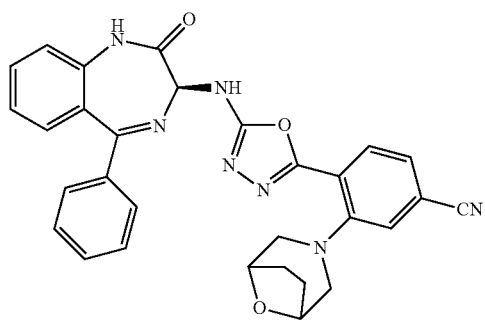 [SMILES: N#Cc1ccc(-c2nnc(N[C@H]3N=C(c4ccccc4)c4ccccc4NC3=O)o2)c(N2CC3CCC(C2)O3)c1] |

| Compound | Structure |
|---|---|
| 282 | 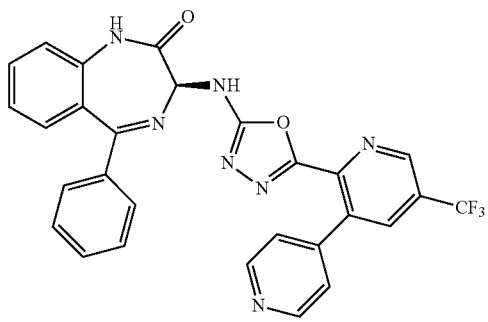 [SMILES: O=C1Nc2ccccc2C(c2ccccc2)=N[C@@H]1Nc1nnc(-c2ncc(C(F)(F)F)cc2-c2ccncc2)o1] |
| 283 | 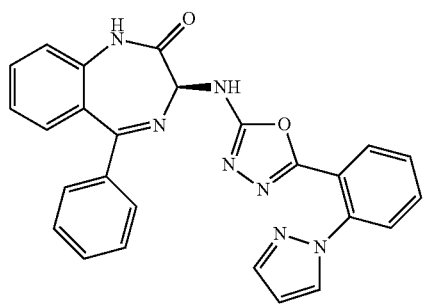 [SMILES: O=C1Nc2ccccc2C(c2ccccc2)=N[C@@H]1Nc1nnc(-c2ccccc2-n2cccn2)o1] |
| 284 | 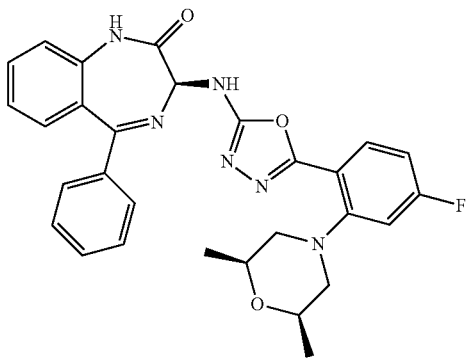 [SMILES: C[C@@H]1CN(c2cc(F)ccc2-c2nnc(N[C@H]3N=C(c4ccccc4)c4ccccc4NC3=O)o2)C[C@H](C)O1] |
| 285 | 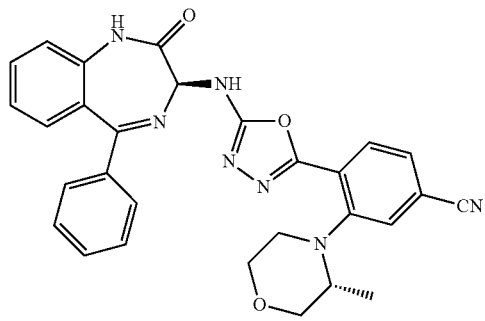 [SMILES: C[C@@H]1COCCN1c1cc(C#N)ccc1-c1nnc(N[C@H]2N=C(c3ccccc3)c3ccccc3NC2=O)o1] |

| Compound | Structure |
|---|---|
| 286 | 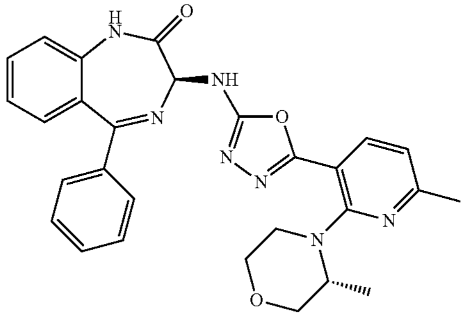 [SMILES: Cc1ccc(-c2nnc(N[C@H]3N=C(c4ccccc4)c4ccccc4NC3=O)o2)c(N2CCOC[C@H]2C)n1] |
| 287 | 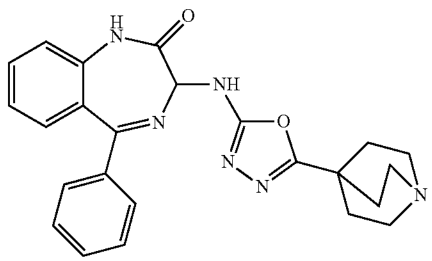 [SMILES: O=C1Nc2ccccc2C(c2ccccc2)=NC1Nc1nnc(C23CCN(CC2)CC3)o1] |
| 288 | 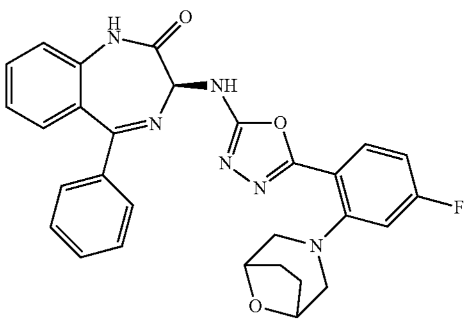 [SMILES: O=C1Nc2ccccc2C(c2ccccc2)=N[C@@H]1Nc1nnc(-c2ccc(F)cc2N2CC3CCC(C2)O3)o1] |
| 289 | 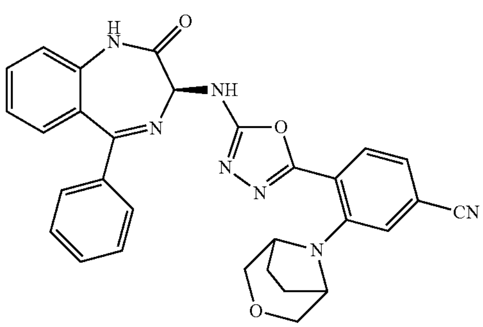 [SMILES: N#Cc1ccc(-c2nnc(N[C@H]3N=C(c4ccccc4)c4ccccc4NC3=O)o2)c(N2C3CCC2COC3)c1] |
| 290 | 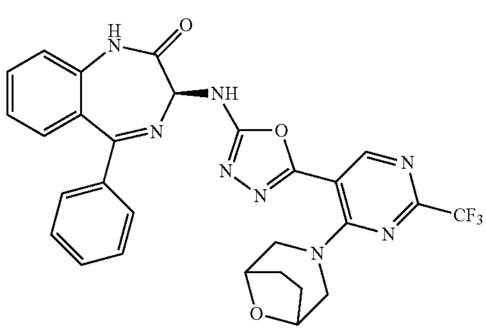 |

-continued

| Compound | Structure |
|---|---|
| 291 | (structure) |
| 292 | (structure) |
| 293 | (structure) |
| 294 | (structure) |
| 295 | (structure) |

-continued
| Compound | Structure |
|---|---|
| 296 | 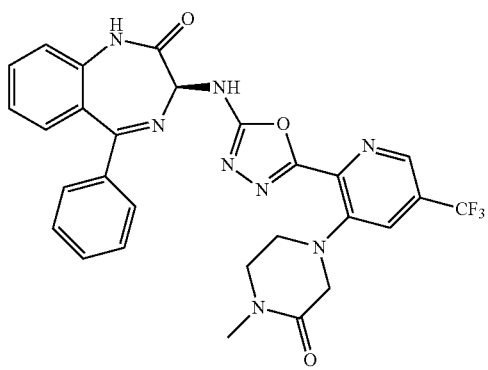 [SMILES: CN1CCN(c2cc(C(F)(F)F)cnc2-c2nnc(N[C@H]3N=C(c4ccccc4)c4ccccc4NC3=O)o2)CC1=O] |
| 297 | 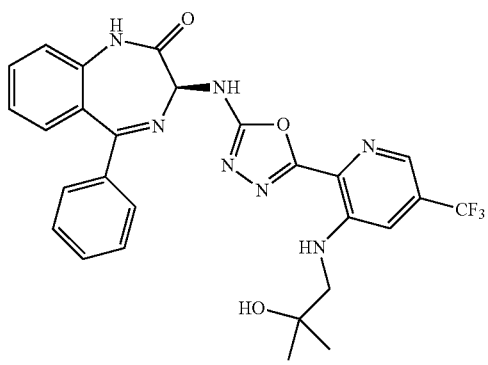 [SMILES: CC(C)(O)CNc1cc(C(F)(F)F)cnc1-c1nnc(N[C@H]2N=C(c3ccccc3)c3ccccc3NC2=O)o1] |
| 298 | 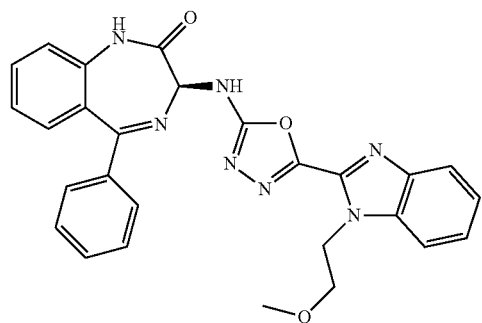 [SMILES: COCCn1c(-c2nnc(N[C@H]3N=C(c4ccccc4)c4ccccc4NC3=O)o2)nc2ccccc21] |
| 299 | 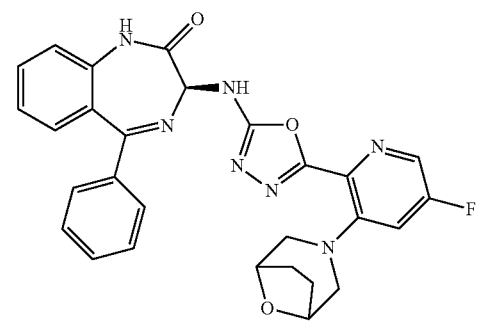 [SMILES: O=C1Nc2ccccc2C(c2ccccc2)=N[C@@H]1Nc1nnc(-c2ncc(F)cc2N2CC3CCC(C2)O3)o1] |

-continued
| Compound | Structure |
|---|---|
| 300 | 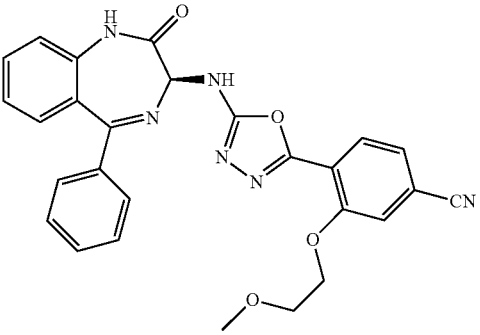 [SMILES: COCCOc1cc(C#N)ccc1-c1nnc(N[C@H]2N=C(c3ccccc3)c3ccccc3NC2=O)o1] |
| 301 | 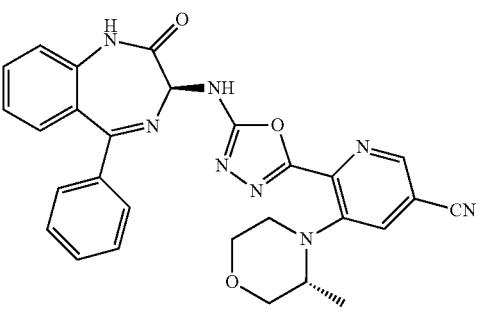 [SMILES: C[C@@H]1COCCN1c1cc(C#N)cnc1-c1nnc(N[C@H]2N=C(c3ccccc3)c3ccccc3NC2=O)o1] |
| 302 | 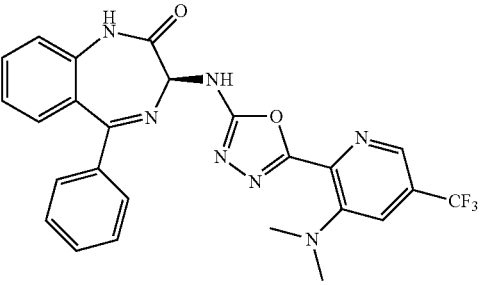 [SMILES: CN(C)c1cc(C(F)(F)F)cnc1-c1nnc(N[C@H]2N=C(c3ccccc3)c3ccccc3NC2=O)o1] |
| 303 | 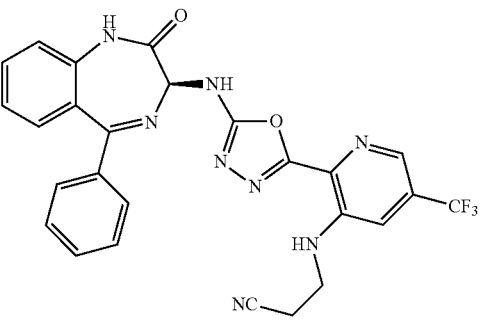 [SMILES: N#CCCNc1cc(C(F)(F)F)cnc1-c1nnc(N[C@H]2N=C(c3ccccc3)c3ccccc3NC2=O)o1] |
| 304 | 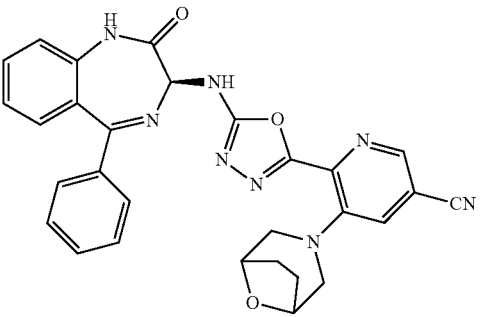 [SMILES: N#Cc1cnc(-c2nnc(N[C@H]3N=C(c4ccccc4)c4ccccc4NC3=O)o2)c(N2CC3CCC(C2)O3)c1] |

| Compound | Structure |
|---|---|
| 305 | 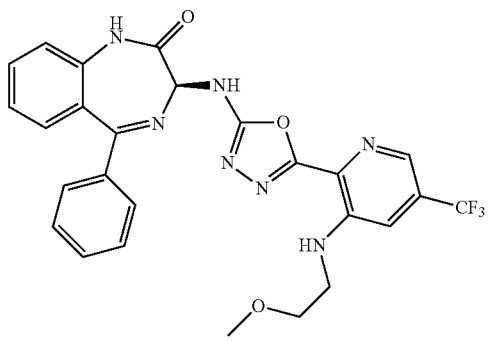 [SMILES: COCCNc1cc(C(F)(F)F)cnc1-c1nnc(N[C@H]2N=C(c3ccccc3)c3ccccc3NC2=O)o1] |
| 306 | 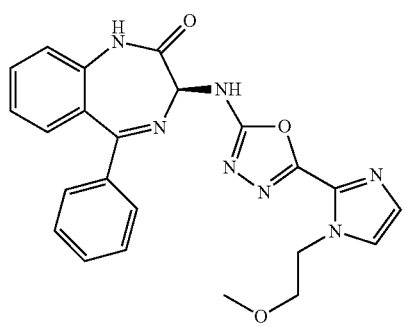 [SMILES: COCCn1ccnc1-c1nnc(N[C@H]2N=C(c3ccccc3)c3ccccc3NC2=O)o1] |
| 307 | 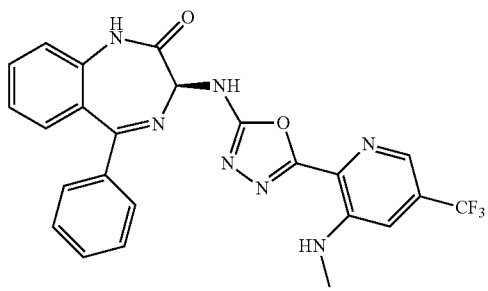 |
| 308 | 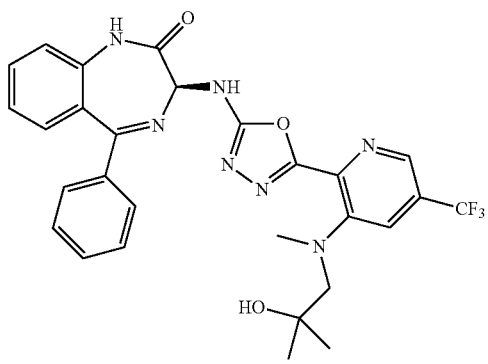 [SMILES: CN(CC(C)(C)O)c1cc(C(F)(F)F)cnc1-c1nnc(N[C@H]2N=C(c3ccccc3)c3ccccc3NC2=O)o1] |

-continued

| Compound | Structure |
|---|---|
| 309 | 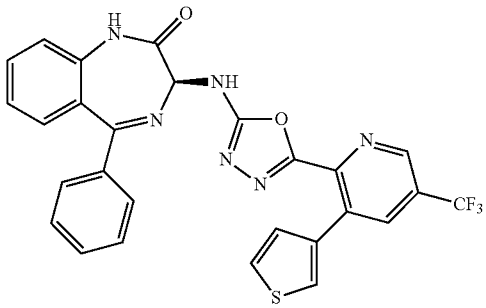 [SMILES: O=C1Nc2ccccc2C(c2ccccc2)=N[C@@H]1Nc1nnc(-c2ncc(C(F)(F)F)cc2-c2ccsc2)o1] |
| 310 | 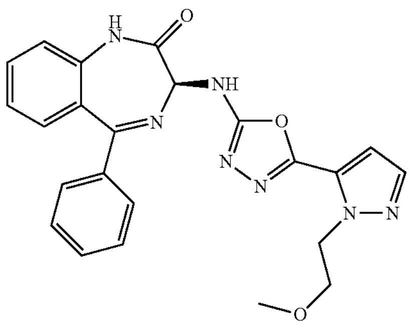 [SMILES: COCCn1nccc1-c1nnc(N[C@H]2N=C(c3ccccc3)c3ccccc3NC2=O)o1] |
| 311 | 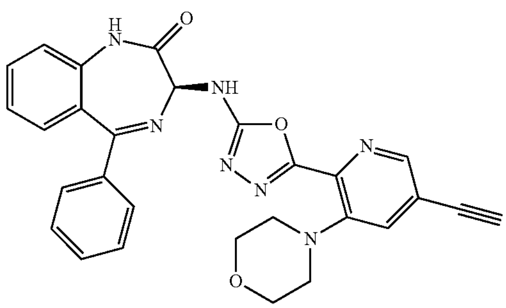 [SMILES: C#Cc1cnc(-c2nnc(N[C@H]3N=C(c4ccccc4)c4ccccc4NC3=O)o2)c(N2CCOCC2)c1] |
| 312 | 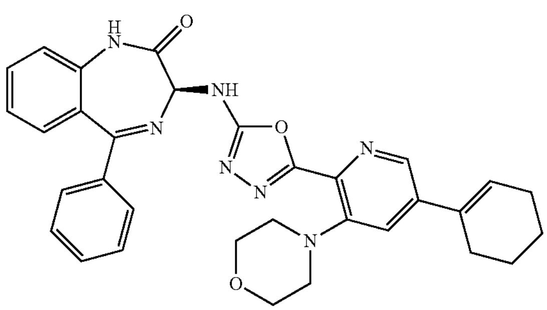 [SMILES: O=C1Nc2ccccc2C(c2ccccc2)=N[C@@H]1Nc1nnc(-c2ncc(C3=CCCCC3)cc2N2CCOCC2)o1] |
| 313 | 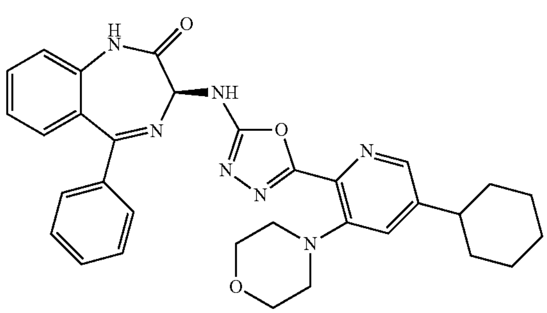 [SMILES: O=C1Nc2ccccc2C(c2ccccc2)=N[C@@H]1Nc1nnc(-c2ncc(C3CCCCC3)cc2N2CCOCC2)o1] |

| Compound | Structure |
|---|---|
| 314 | 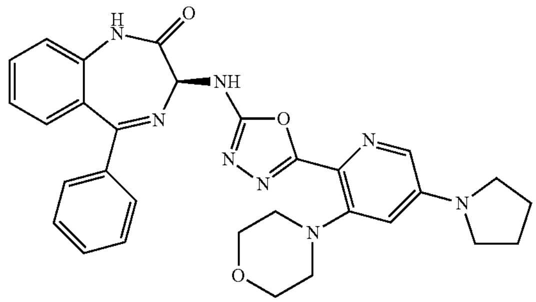 [SMILES: O=C1Nc2ccccc2C(c2ccccc2)=N[C@@H]1Nc1nnc(-c2ncc(N3CCCC3)cc2N2CCOCC2)o1] |
| 315 | 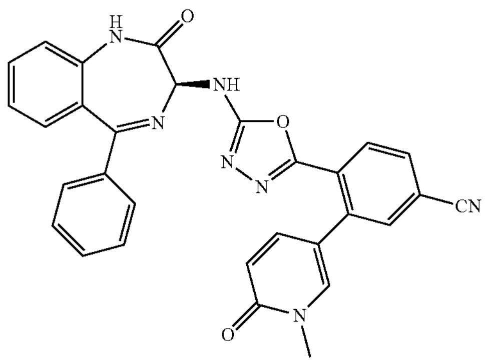 [SMILES: Cn1cc(-c2cc(C#N)ccc2-c2nnc(N[C@H]3N=C(c4ccccc4)c4ccccc4NC3=O)o2)ccc1=O] |
| 316 | 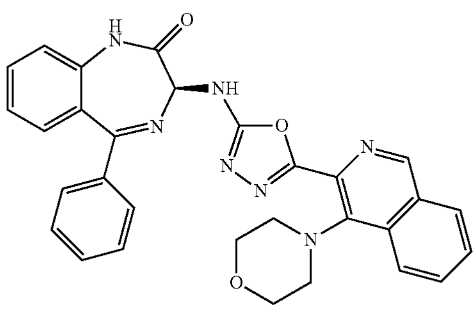 [SMILES: O=C1Nc2ccccc2C(c2ccccc2)=N[C@@H]1Nc1nnc(-c2ncc3ccccc3c2N2CCOCC2)o1] |
| 317 | 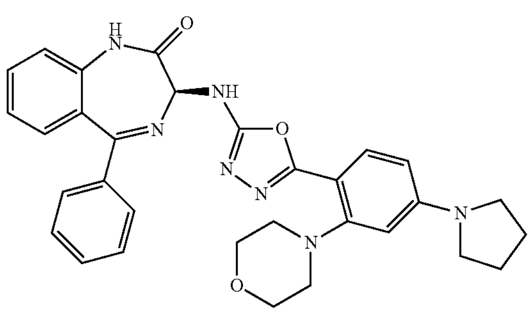 [SMILES: O=C1Nc2ccccc2C(c2ccccc2)=N[C@@H]1Nc1nnc(-c2ccc(N3CCCC3)cc2N2CCOCC2)o1] |
| 318 | 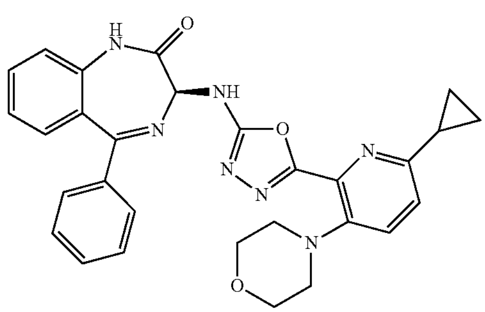 [SMILES: O=C1Nc2ccccc2C(c2ccccc2)=N[C@@H]1Nc1nnc(-c2nc(C3CC3)ccc2N2CCOCC2)o1] |

-continued

| Compound | Structure |
|---|---|
| 319 | 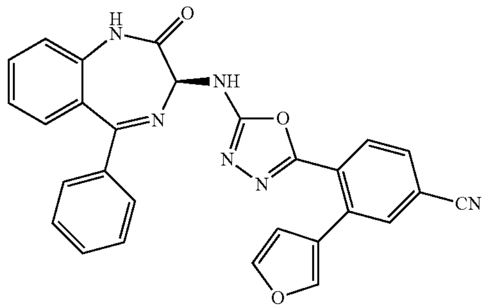 [SMILES: N#Cc1ccc(-c2nnc(N[C@H]3N=C(c4ccccc4)c4ccccc4NC3=O)o2)c(-c2ccoc2)c1] |
| 320 | 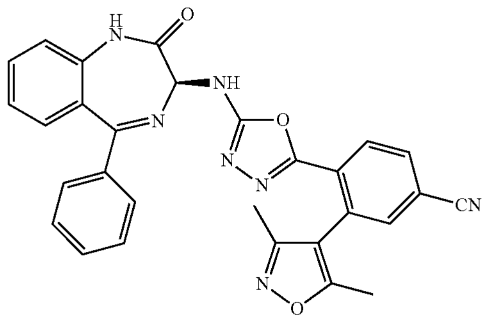 [SMILES: Cc1noc(C)c1-c1cc(C#N)ccc1-c1nnc(N[C@H]2N=C(c3ccccc3)c3ccccc3NC2=O)o1] |
| 321 | 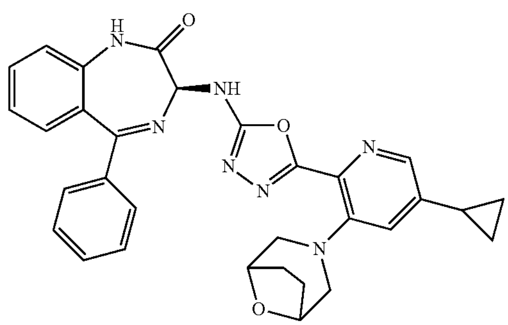 [SMILES: O=C1Nc2ccccc2C(c2ccccc2)=N[C@@H]1Nc1nnc(-c2ncc(C3CC3)cc2N2CC3CCC(C2)O3)o1] |
| 322 | 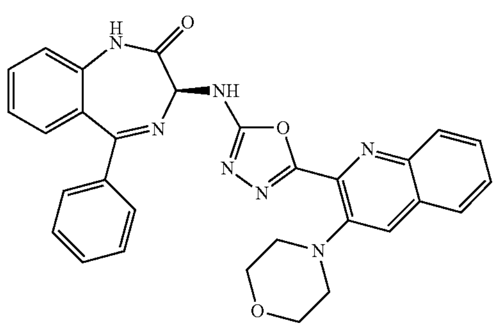 |
| 323 | 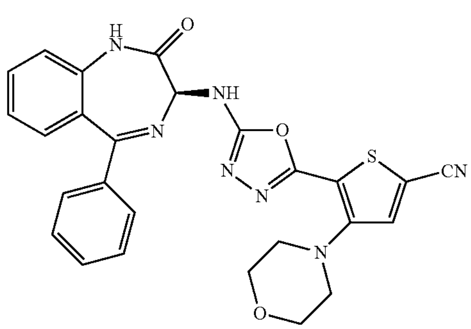 [SMILES: N#Cc1cc(N2CCOCC2)c(-c2nnc(N[C@H]3N=C(c4ccccc4)c4ccccc4NC3=O)o2)s1] |

| Compound | Structure |
|---|---|
| 324 | 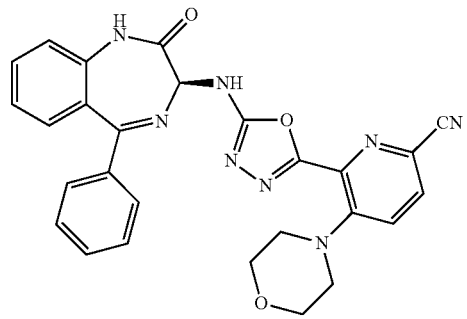 [SMILES: N#Cc1ccc(N2CCOCC2)c(-c2nnc(N[C@H]3N=C(c4ccccc4)c4ccccc4NC3=O)o2)n1] |
| 325 | 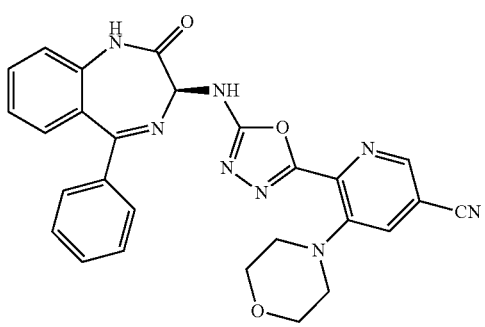 [SMILES: N#Cc1cnc(-c2nnc(N[C@H]3N=C(c4ccccc4)c4ccccc4NC3=O)o2)c(N2CCOCC2)c1] |
| 326 | 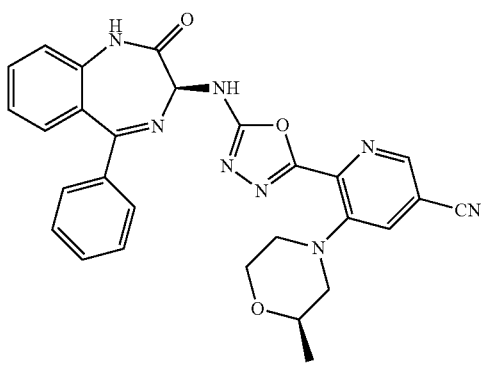 [SMILES: C[C@@H]1CN(c2cc(C#N)cnc2-c2nnc(N[C@H]3N=C(c4ccccc4)c4ccccc4NC3=O)o2)CCO1] |
| 327 | 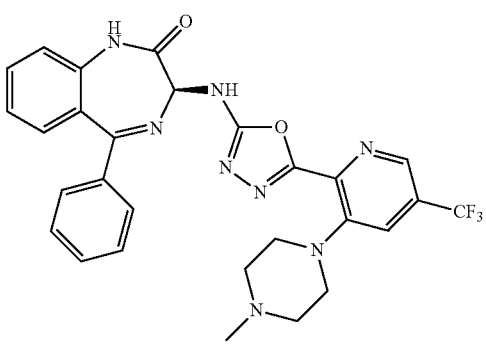 [SMILES: CN1CCN(c2cc(C(F)(F)F)cnc2-c2nnc(N[C@H]3N=C(c4ccccc4)c4ccccc4NC3=O)o2)CC1] |

| Compound | Structure |
|---|---|
| 328 | 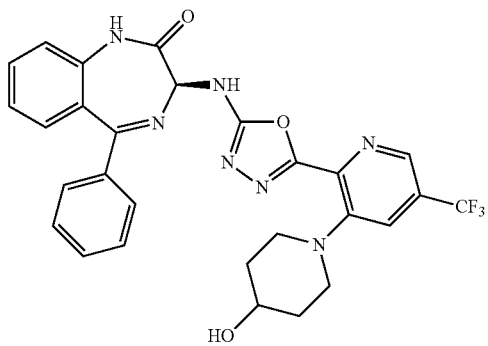 [SMILES: O=C1Nc2ccccc2C(c2ccccc2)=N[C@@H]1Nc1nnc(-c2ncc(C(F)(F)F)cc2N2CCC(O)CC2)o1] |
| 329 | 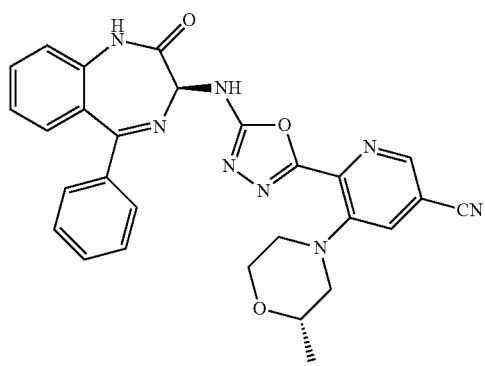 [SMILES: C[C@H]1CN(c2cc(C#N)cnc2-c2nnc(N[C@H]3N=C(c4ccccc4)c4ccccc4NC3=O)o2)CCO1] |
| 330 | 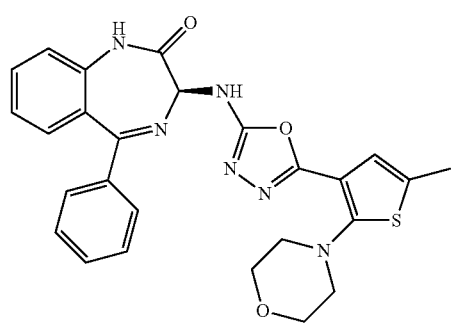 [SMILES: Cc1cc(-c2nnc(N[C@H]3N=C(c4ccccc4)c4ccccc4NC3=O)o2)c(N2CCOCC2)s1] |
| 331 | 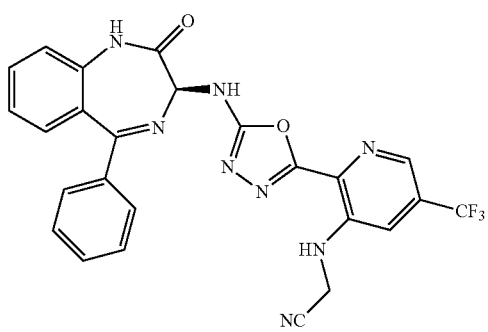 [SMILES: N#CCNc1cc(C(F)(F)F)cnc1-c1nnc(N[C@H]2N=C(c3ccccc3)c3ccccc3NC2=O)o1] |

| Compound | Structure |
|---|---|
| 332 | 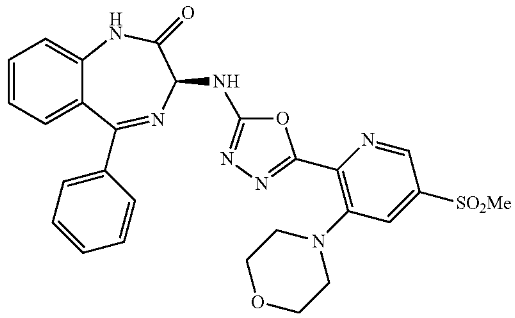 [SMILES: CS(=O)(=O)c1cnc(-c2nnc(N[C@H]3N=C(c4ccccc4)c4ccccc4NC3=O)o2)c(N2CCOCC2)c1] |
| 333 | 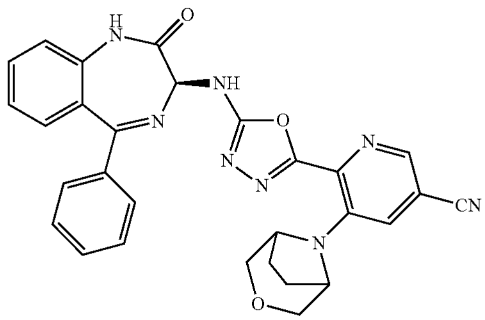 [SMILES: N#Cc1cnc(-c2nnc(N[C@H]3N=C(c4ccccc4)c4ccccc4NC3=O)o2)c(N2C3CCC2COC3)c1] |
| 334 | 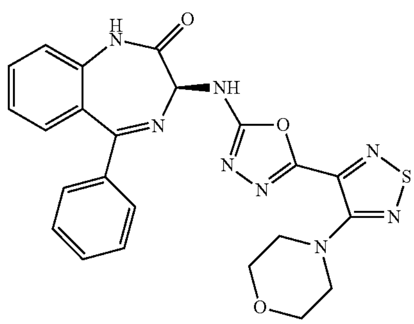 [SMILES: O=C1Nc2ccccc2C(c2ccccc2)=N[C@@H]1Nc1nnc(-c2nsnc2N2CCOCC2)o1] |
| 335 | 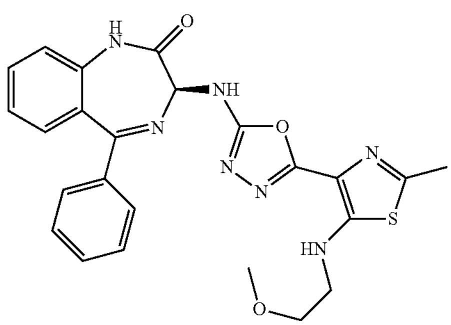 [SMILES: COCCNc1sc(C)nc1-c1nnc(N[C@H]2N=C(c3ccccc3)c3ccccc3NC2=O)o1] |
| 336 | 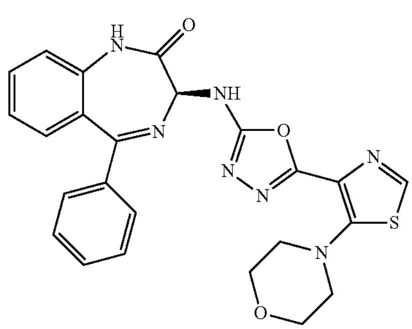 [SMILES: O=C1Nc2ccccc2C(c2ccccc2)=N[C@@H]1Nc1nnc(-c2ncsc2N2CCOCC2)o1] |

| Compound | Structure |
|---|---|
| 337 | 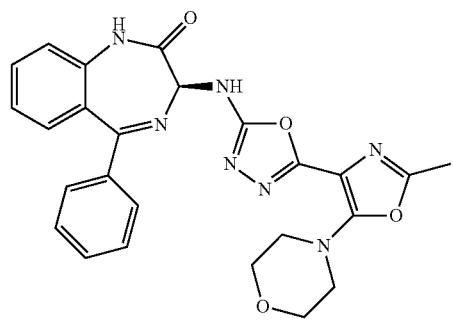 |
| 338 | 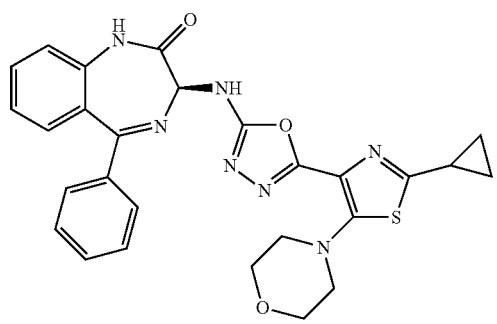 [SMILES: O=C1Nc2ccccc2C(c2ccccc2)=N[C@@H]1Nc1nnc(-c2nc(C3CC3)sc2N2CCOCC2)o1] |
| 339 | 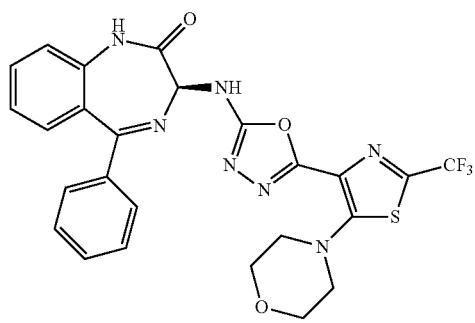 [SMILES: O=C1Nc2ccccc2C(c2ccccc2)=N[C@@H]1Nc1nnc(-c2nc(C(F)(F)F)sc2N2CCOCC2)o1] |
| 340 | 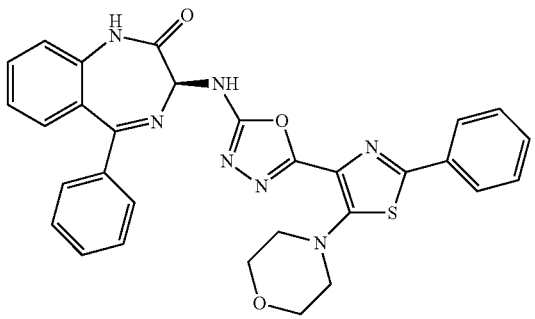 [SMILES: O=C1Nc2ccccc2C(c2ccccc2)=N[C@@H]1Nc1nnc(-c2nc(-c3ccccc3)sc2N2CCOCC2)o1] |

-continued
| Compound | Structure |
|---|---|
| 341 | 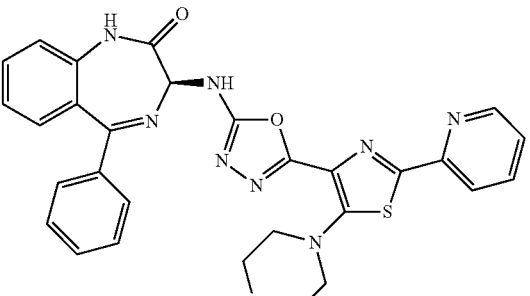 |
| 342 | 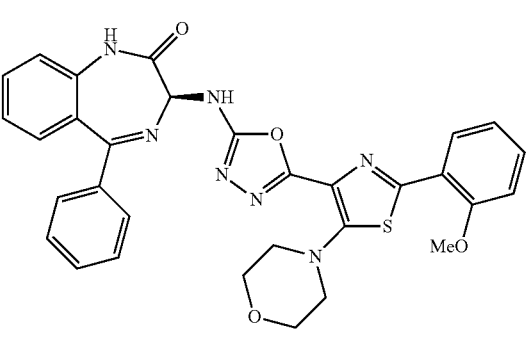 [SMILES: COc1ccccc1-c1nc(-c2nnc(N[C@H]3N=C(c4ccccc4)c4ccccc4NC3=O)o2)c(N2CCOCC2)s1] |
| 343 | 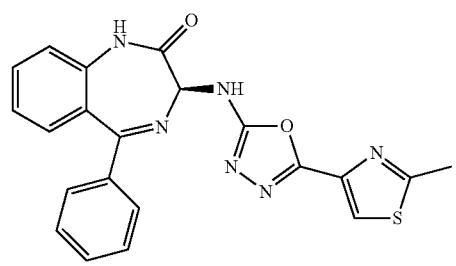 [SMILES: Cc1nc(-c2nnc(N[C@H]3N=C(c4ccccc4)c4ccccc4NC3=O)o2)cs1] |
| 344 | 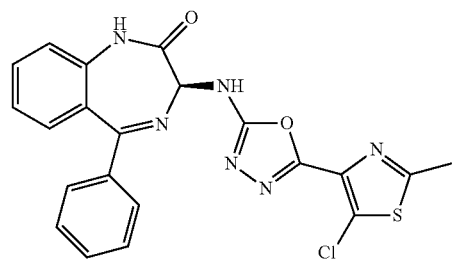 [SMILES: Cc1nc(-c2nnc(N[C@H]3N=C(c4ccccc4)c4ccccc4NC3=O)o2)c(Cl)s1] |
| 345 | 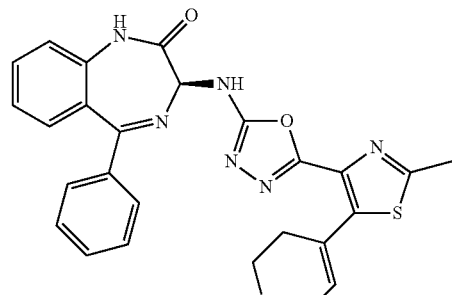 |

-continued

| Compound | Structure |
|---|---|
| 346 | 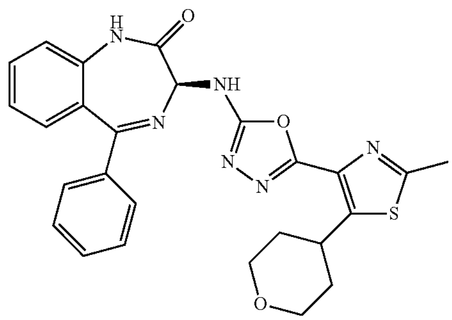 [SMILES: Cc1nc(-c2nnc(N[C@H]3N=C(c4ccccc4)c4ccccc4NC3=O)o2)c(C2CCOCC2)s1] |
| 347 | 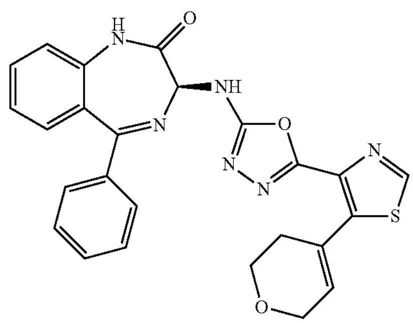 [SMILES: O=C1Nc2ccccc2C(c2ccccc2)=N[C@@H]1Nc1nnc(-c2ncsc2C2=CCOCC2)o1] |
| 348 | 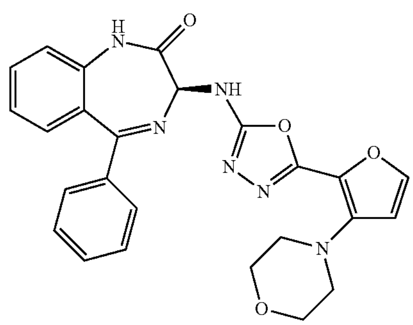 [SMILES: O=C1Nc2ccccc2C(c2ccccc2)=N[C@@H]1Nc1nnc(-c2occc2N2CCOCC2)o1] |
| 349 | 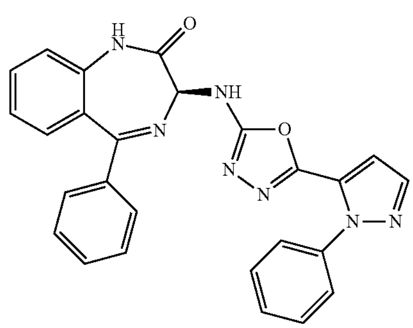 [SMILES: O=C1Nc2ccccc2C(c2ccccc2)=N[C@@H]1Nc1nnc(-c2ccnn2-c2ccccc2)o1] |
| 350 | 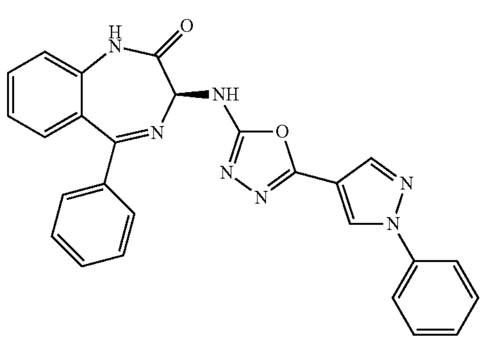 [SMILES: O=C1Nc2ccccc2C(c2ccccc2)=N[C@@H]1Nc1nnc(-c2cnn(-c3ccccc3)c2)o1] |

| Compound | Structure |
|---|---|
| 351 | 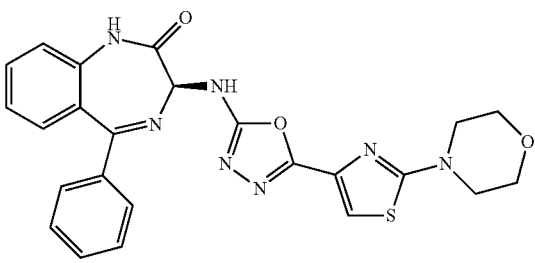 [SMILES: O=C1Nc2ccccc2C(c2ccccc2)=N[C@@H]1Nc1nnc(-c2csc(N3CCOCC3)n2)o1] |
| 352 | 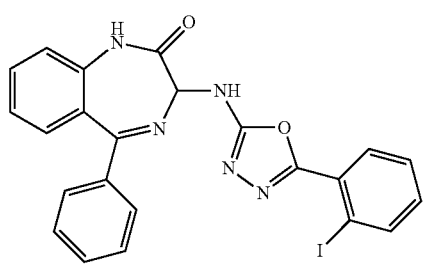 [SMILES: O=C1Nc2ccccc2C(c2ccccc2)=NC1Nc1nnc(-c2ccccc2I)o1] |
| 353 | 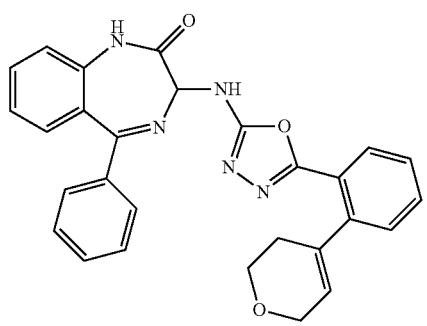 [SMILES: O=C1Nc2ccccc2C(c2ccccc2)=NC1Nc1nnc(-c2ccccc2C2=CCOCC2)o1] |
| 354 | 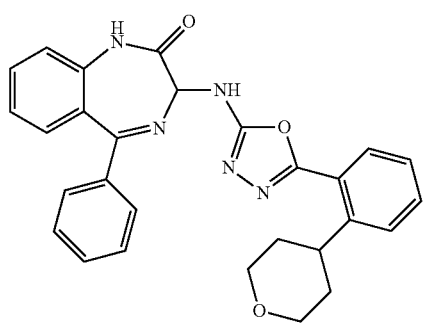 |
| 355a | 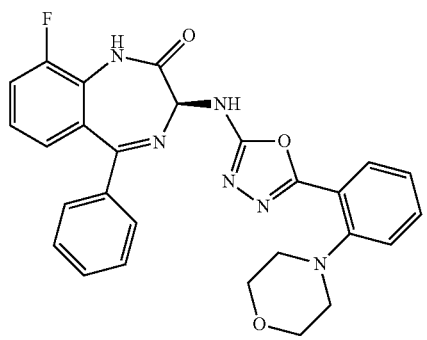 [SMILES: O=C1Nc2c(F)cccc2C(c2ccccc2)=N[C@@H]1Nc1nnc(-c2ccccc2N2CCOCC2)o1] |

-continued
| Compound | Structure |
|---|---|
| 355b | 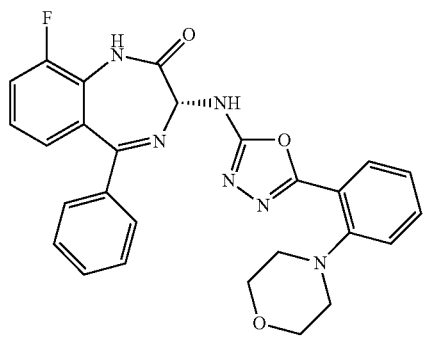 [SMILES: O=C1Nc2c(F)cccc2C(c2ccccc2)=N[C@H]1Nc1nnc(-c2ccccc2N2CCOCC2)o1] |
| 356 | 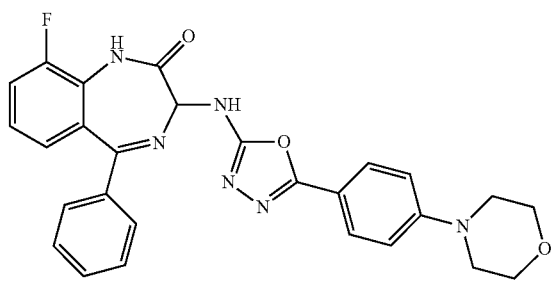 [SMILES: O=C1Nc2c(F)cccc2C(c2ccccc2)=NC1Nc1nnc(-c2ccc(N3CCOCC3)cc2)o1] |
| 357 | 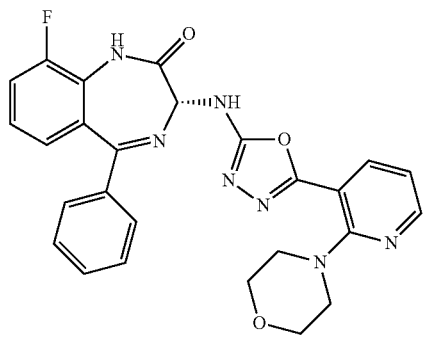 [SMILES: O=C1Nc2c(F)cccc2C(c2ccccc2)=N[C@H]1Nc1nnc(-c2cccnc2N2CCOCC2)o1] |
| 358 | 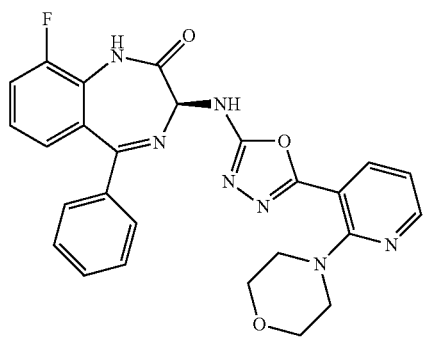 |

-continued
| Compound | Structure |
|---|---|
| 359 | 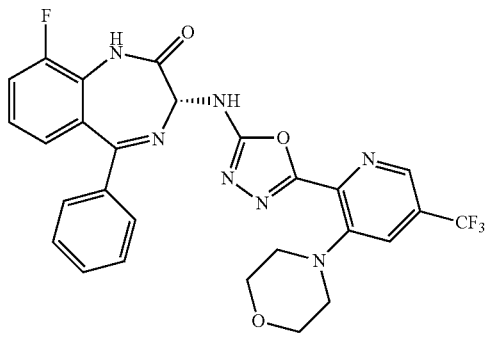 [SMILES: O=C1Nc2c(F)cccc2C(c2ccccc2)=N[C@H]1Nc1nnc(-c2ncc(C(F)(F)F)cc2N2CCOCC2)o1] |
| 360 | 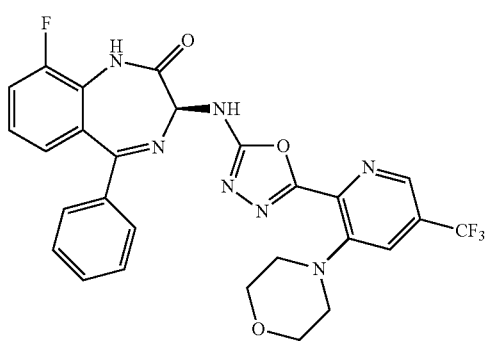 [SMILES: O=C1Nc2c(F)cccc2C(c2ccccc2)=N[C@@H]1Nc1nnc(-c2ncc(C(F)(F)F)cc2N2CCOCC2)o1] |
| 361 | 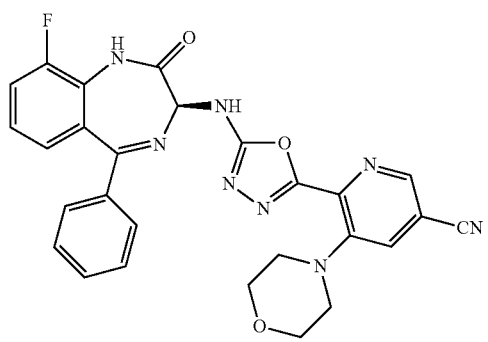 [SMILES: N#Cc1cnc(-c2nnc(N[C@H]3N=C(c4ccccc4)c4cccc(F)c4NC3=O)o2)c(N2CCOCC2)c1] |
| 362 | 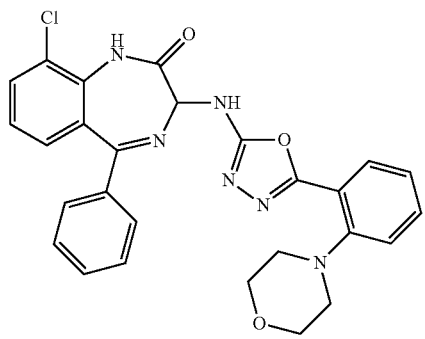 |

| Compound | Structure |
|---|---|
| 363 | 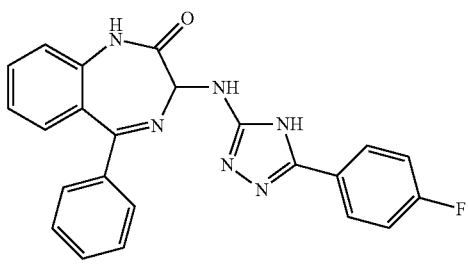 [SMILES: O=C1Nc2ccccc2C(c2ccccc2)=NC1Nc1nnc(-c2ccc(F)cc2)[nH]1] |
| 364 | 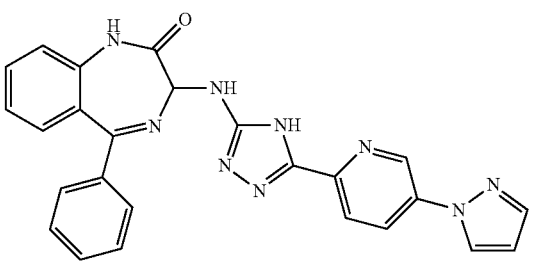 [SMILES: O=C1Nc2ccccc2C(c2ccccc2)=NC1Nc1nnc(-c2ccc(-n3cccn3)cn2)[nH]1] |
| 365 | 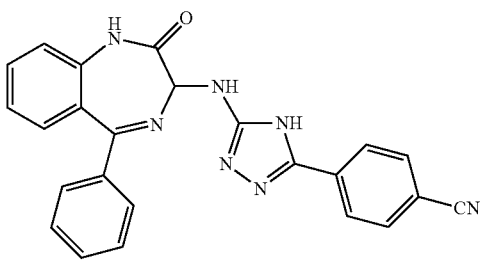 [SMILES: N#Cc1ccc(-c2nnc(NC3N=C(c4ccccc4)c4ccccc4NC3=O)[nH]2)cc1] |
| 366 | 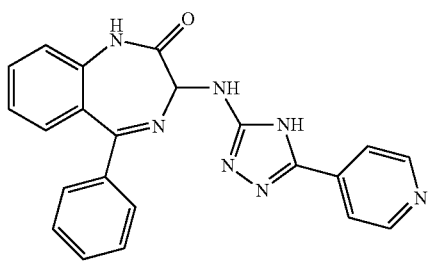 [SMILES: O=C1Nc2ccccc2C(c2ccccc2)=NC1Nc1nnc(-c2ccncc2)[nH]1] |
| 367 | 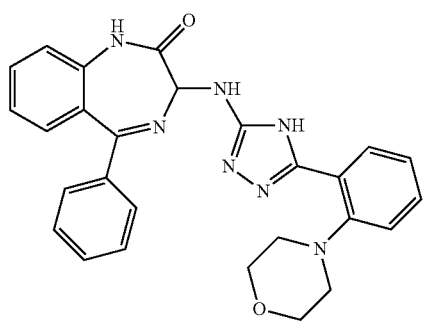 |

| Compound | Structure |
|---|---|
| 368 | (structure: 1,4-benzodiazepin-2-one with phenyl substituent, NH-linked to oxazole bearing 4-cyanophenyl) |
| 369 | (structure: 1,4-benzodiazepin-2-one with phenyl substituent, NH-linked to oxazole bearing 4-fluorophenyl) |
| 370 | (structure: 1,4-benzodiazepin-2-one with phenyl substituent, NH-linked to oxazole bearing 4-bromophenyl) |
| 371 | (structure: 1,4-benzodiazepin-2-one with phenyl substituent, NH-linked to 5-phenylpyrimidin-2-yl) |
| 372 | (structure: 1,4-benzodiazepin-2-one with phenyl substituent, NH-linked to 4-cyclopropyl-1H-imidazol-2-yl) |

-continued
| Compound | Structure |
|---|---|
| 373 | 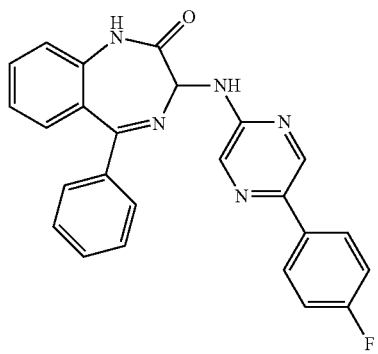 [SMILES: O=C1Nc2ccccc2C(c2ccccc2)=NC1Nc1cnc(-c2ccc(F)cc2)cn1] |
| 374 | 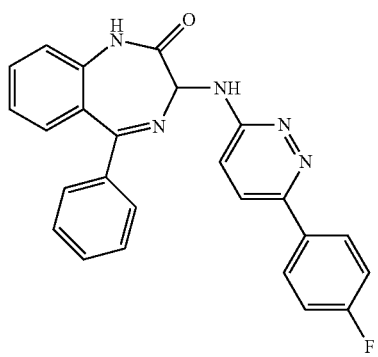 [SMILES: O=C1Nc2ccccc2C(c2ccccc2)=NC1Nc1ccc(-c2ccc(F)cc2)nn1] |
| 375 | 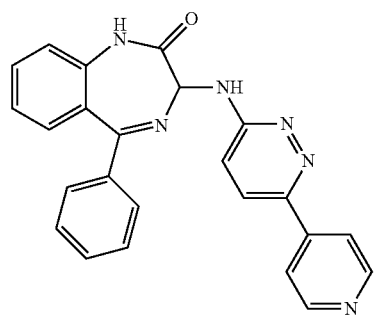 [SMILES: O=C1Nc2ccccc2C(c2ccccc2)=NC1Nc1ccc(-c2ccncc2)nn1] |
| 376 | 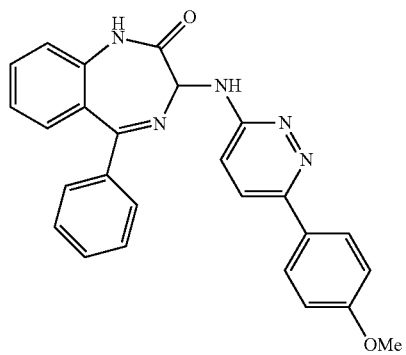 [SMILES: COc1ccc(-c2ccc(NC3N=C(c4ccccc4)c4ccccc4NC3=O)nn2)cc1] |

| Compound | Structure |
|---|---|
| 377 | 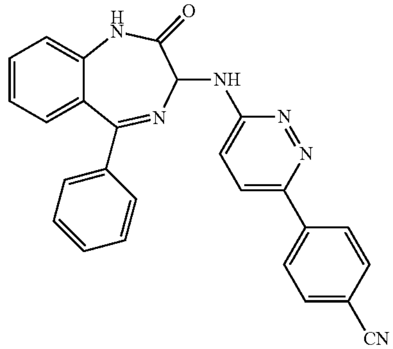 [SMILES: N#Cc1ccc(-c2ccc(NC3N=C(c4ccccc4)c4ccccc4NC3=O)nn2)cc1] |
| 378 | 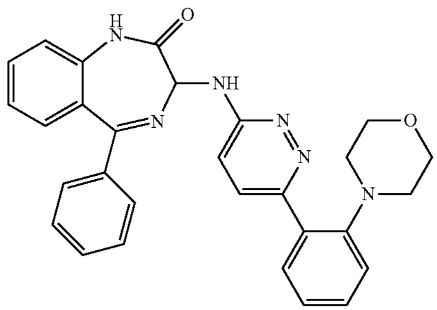 [SMILES: O=C1Nc2ccccc2C(c2ccccc2)=NC1Nc1ccc(-c2ccccc2N2CCOCC2)nn1] |
| 379 | 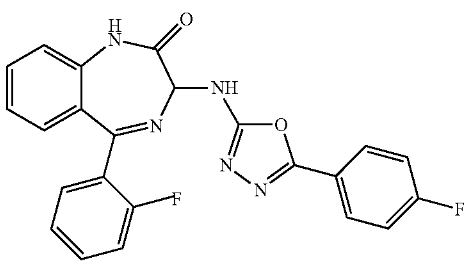 |
| 380 | 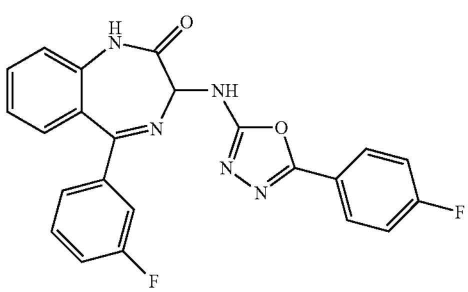 [SMILES: O=C1Nc2ccccc2C(c2cccc(F)c2)=NC1Nc1nnc(-c2ccc(F)cc2)o1] |
| 381 | 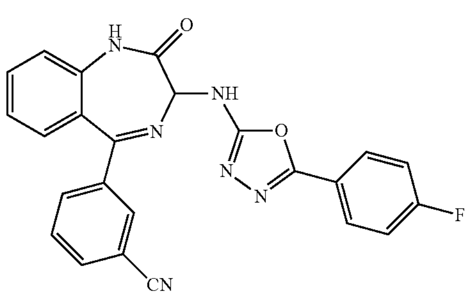 [SMILES: N#Cc1cccc(C2=NC(Nc3nnc(-c4ccc(F)cc4)o3)C(=O)Nc3ccccc32)c1] |

| Compound | Structure |
|---|---|
| 382 | 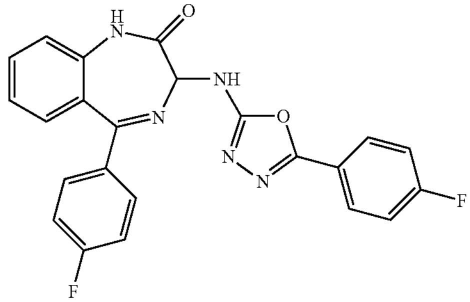 [SMILES: O=C1Nc2ccccc2C(c2ccc(F)cc2)=NC1Nc1nnc(-c2ccc(F)cc2)o1] |
| 383 | 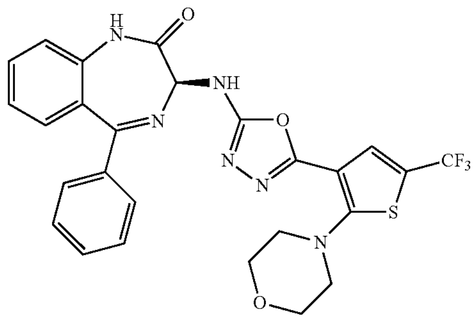 |
| 384 | 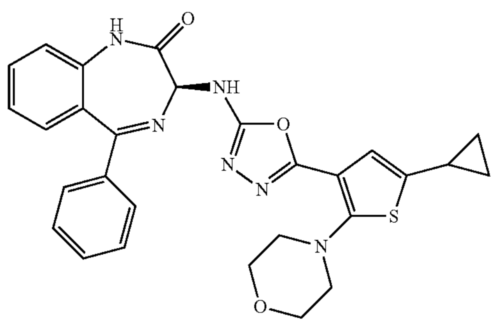 |
| 385 | 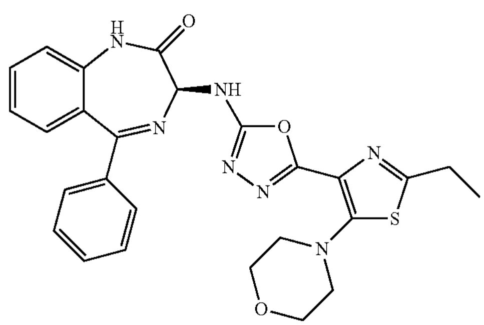 [SMILES: CCc1nc(-c2nnc(N[C@H]3N=C(c4ccccc4)c4ccccc4NC3=O)o2)c(N2CCOCC2)s1] |
| 386 | 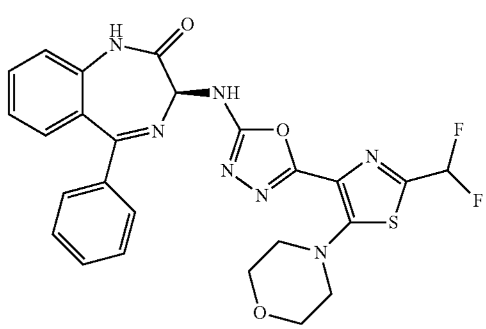 [SMILES: O=C1Nc2ccccc2C(c2ccccc2)=N[C@@H]1Nc1nnc(-c2nc(C(F)F)sc2N2CCOCC2)o1] |

| Compound | Structure |
|---|---|
| 387 | 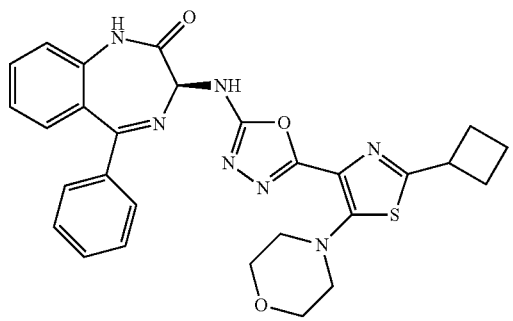 [SMILES: O=C1Nc2ccccc2C(c2ccccc2)=N[C@@H]1Nc1nnc(-c2nc(C3CCC3)sc2N2CCOCC2)o1] |
| 388 | 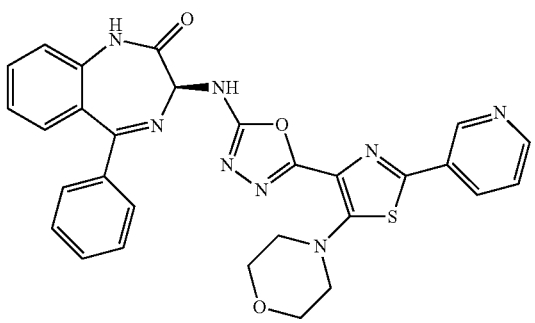 |
| 389 | 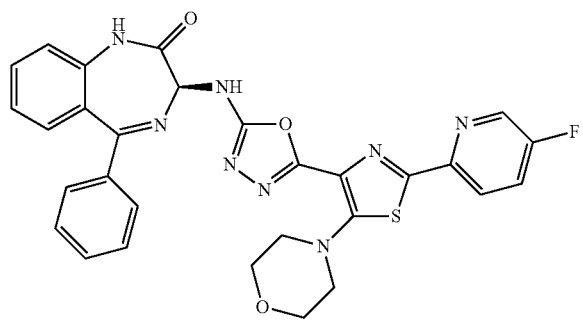 |
| 390 | 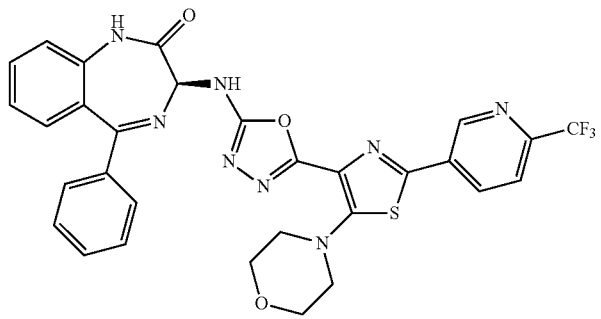 [SMILES: O=C1Nc2ccccc2C(c2ccccc2)=N[C@@H]1Nc1nnc(-c2nc(-c3ccc(C(F)(F)F)nc3)sc2N2CCOCC2)o1] |

| Compound | Structure |
|---|---|
| 391 | 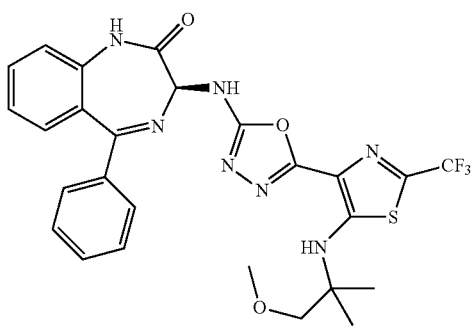 [SMILES: COCC(C)(C)Nc1sc(C(F)(F)F)nc1-c1nnc(N[C@H]2N=C(c3ccccc3)c3ccccc3NC2=O)o1] |
| 392 | 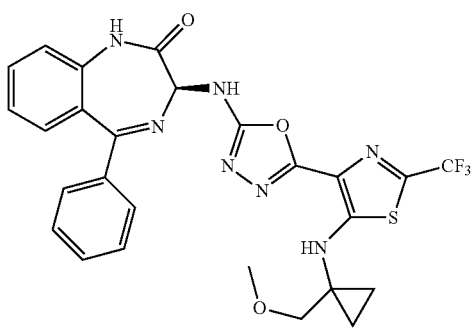 [SMILES: COCC1(Nc2sc(C(F)(F)F)nc2-c2nnc(N[C@H]3N=C(c4ccccc4)c4ccccc4NC3=O)o2)CC1] |
| 393 | 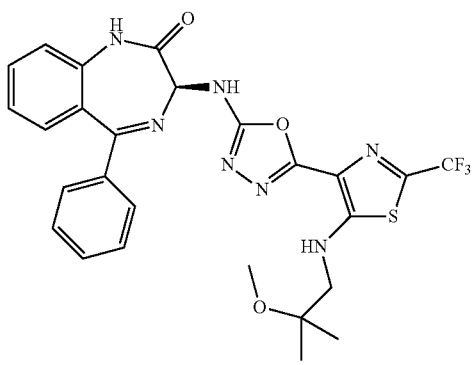 [SMILES: COC(C)(C)CNc1sc(C(F)(F)F)nc1-c1nnc(N[C@H]2N=C(c3ccccc3)c3ccccc3NC2=O)o1] |
| 394 | 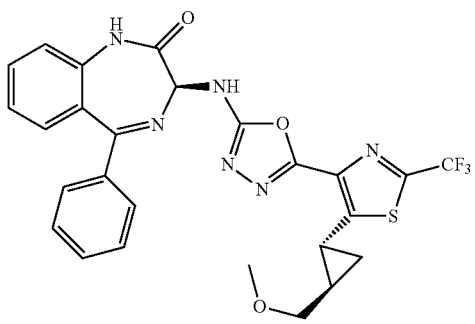 [SMILES: COC[C@@H]1C[C@H]1c1sc(C(F)(F)F)nc1-c1nnc(N[C@H]2N=C(c3ccccc3)c3ccccc3NC2=O)o1] |

-continued

| Compound | Structure |
|---|---|
| 395 | 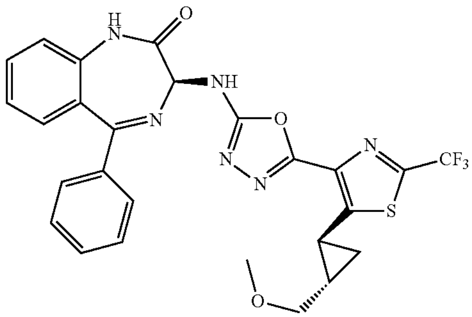 [SMILES: COC[C@H]1C[C@@H]1c1sc(C(F)(F)F)nc1-c1nnc(N[C@H]2N=C(c3ccccc3)c3ccccc3NC2=O)o1] |
| 396 | 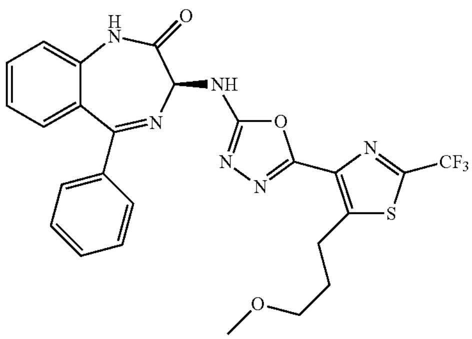 [SMILES: COCCCc1sc(C(F)(F)F)nc1-c1nnc(N[C@H]2N=C(c3ccccc3)c3ccccc3NC2=O)o1] |
| 397 | 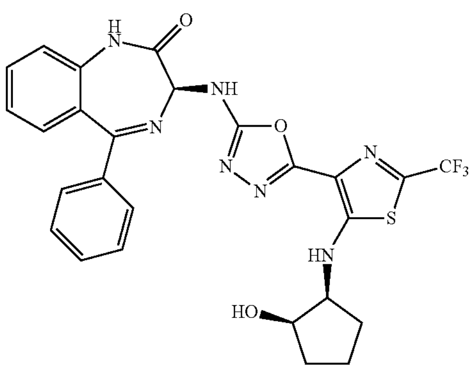 [SMILES: O=C1Nc2ccccc2C(c2ccccc2)=N[C@@H]1Nc1nnc(-c2nc(C(F)(F)F)sc2N[C@H]2CCC[C@H]2O)o1] |
| 398 | 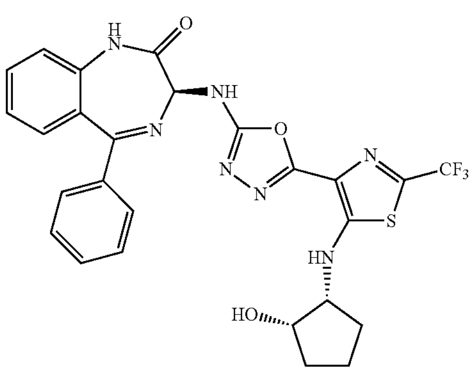 [SMILES: O=C1Nc2ccccc2C(c2ccccc2)=N[C@@H]1Nc1nnc(-c2nc(C(F)(F)F)sc2N[C@@H]2CCC[C@@H]2O)o1] |

| Compound | Structure |
|---|---|
| 399 | 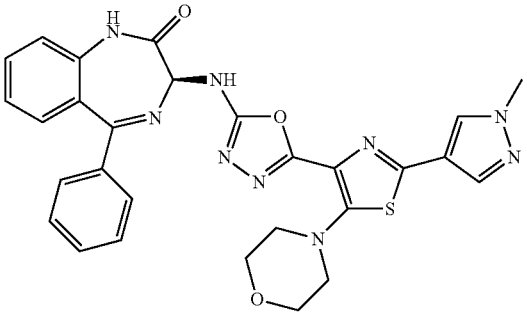 [SMILES: Cn1cc(-c2nc(-c3nnc(N[C@H]4N=C(c5ccccc5)c5ccccc5NC4=O)o3)c(N3CCOCC3)s2)cn1] |
| 401 | 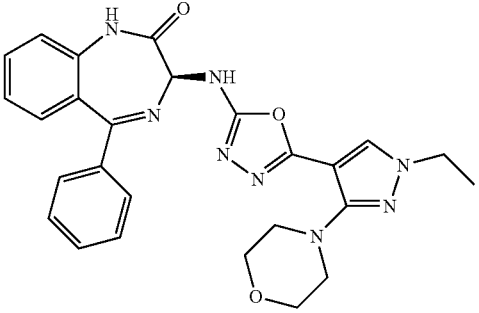 [SMILES: CCn1cc(-c2nnc(N[C@H]3N=C(c4ccccc4)c4ccccc4NC3=O)o2)c(N2CCOCC2)n1] |
| 402 | 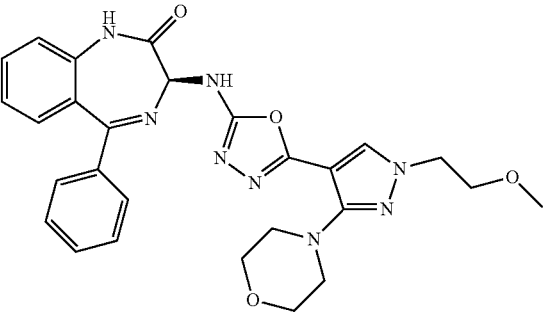 [SMILES: COCCn1cc(-c2nnc(N[C@H]3N=C(c4ccccc4)c4ccccc4NC3=O)o2)c(N2CCOCC2)n1] |
| 403 | 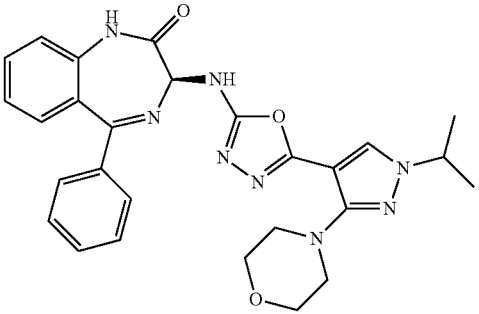 [SMILES: CC(C)n1cc(-c2nnc(N[C@H]3N=C(c4ccccc4)c4ccccc4NC3=O)o2)c(N2CCOCC2)n1] |
| 404 | 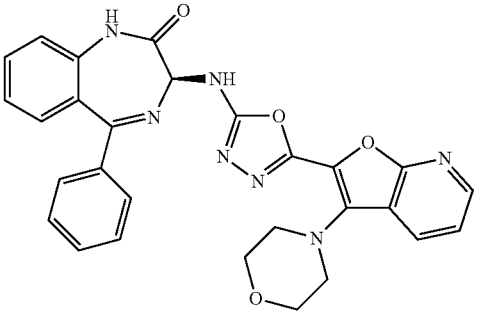 [SMILES: O=C1Nc2ccccc2C(c2ccccc2)=N[C@@H]1Nc1nnc(-c2oc3ncccc3c2N2CCOCC2)o1] |

| Compound | Structure |
|---|---|
| 405 | 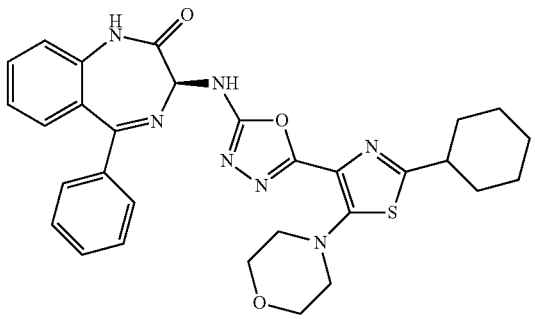 [SMILES: O=C1Nc2ccccc2C(c2ccccc2)=N[C@@H]1Nc1nnc(-c2nc(C3CCCCC3)sc2N2CCOCC2)o1] |
| 406 | 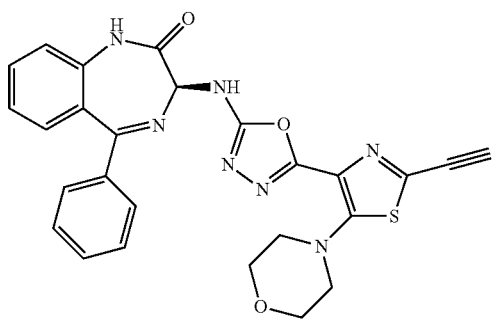 [SMILES: C#Cc1nc(-c2nnc(N[C@H]3N=C(c4ccccc4)c4ccccc4NC3=O)o2)c(N2CCOCC2)s1] |
| 407 | 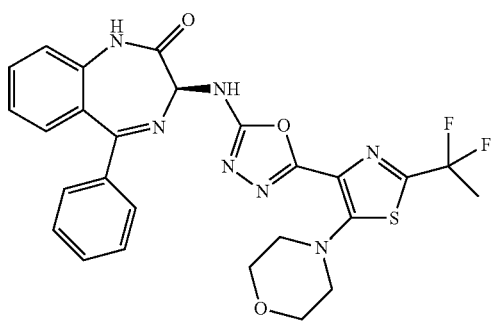 [SMILES: CC(F)(F)c1nc(-c2nnc(N[C@H]3N=C(c4ccccc4)c4ccccc4NC3=O)o2)c(N2CCOCC2)s1] |
| 408 | 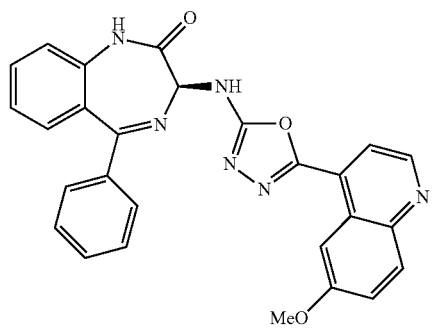 [SMILES: COc1ccc2nccc(-c3nnc(N[C@H]4N=C(c5ccccc5)c5ccccc5NC4=O)o3)c2c1] |

-continued
| Compound | Structure |
|---|---|
| 409 | 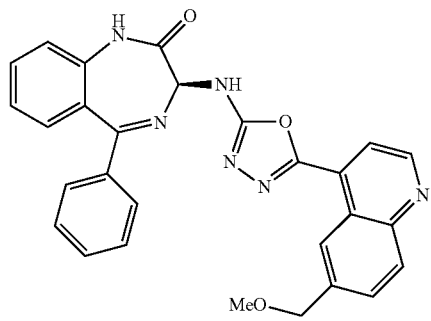 [SMILES: COCc1ccc2nccc(-c3nnc(N[C@H]4N=C(c5ccccc5)c5ccccc5NC4=O)o3)c2c1] |
| 410 | 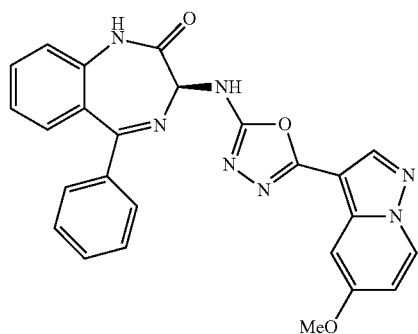 [SMILES: COc1ccn2ncc(-c3nnc(N[C@H]4N=C(c5ccccc5)c5ccccc5NC4=O)o3)c2c1] |
| 411 | 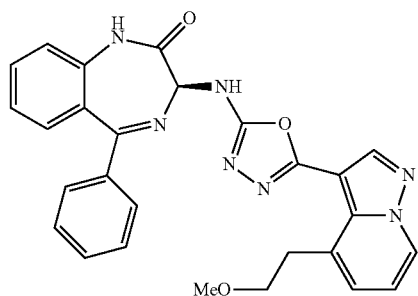 [SMILES: COCCc1cccn2ncc(-c3nnc(N[C@H]4N=C(c5ccccc5)c5ccccc5NC4=O)o3)c12] |
| 412 | 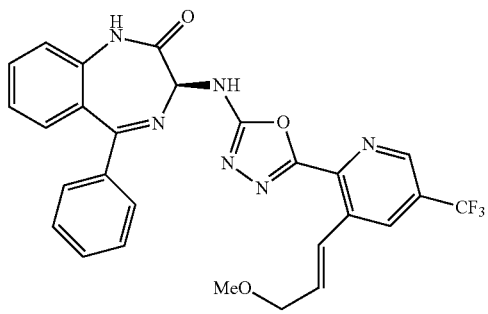 |

-continued
| Compound | Structure |
|---|---|
| 413 | 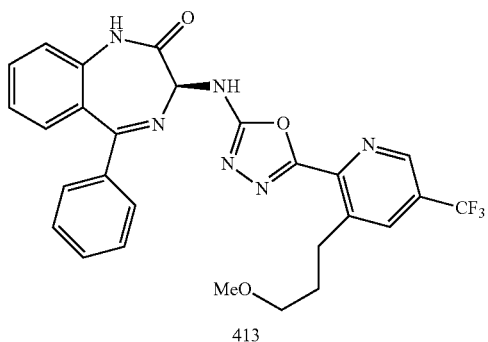 [SMILES: COCCCc1cc(C(F)(F)F)cnc1-c1nnc(N[C@H]2N=C(c3ccccc3)c3ccccc3NC2=O)o1] |
| 414 | 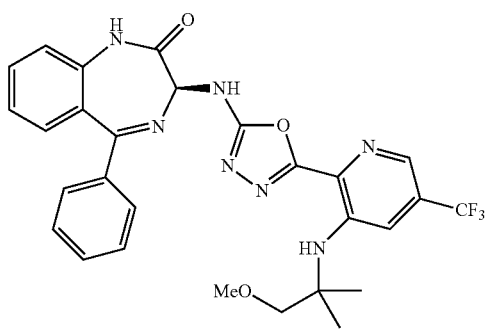 [SMILES: COCC(C)(C)Nc1cc(C(F)(F)F)cnc1-c1nnc(N[C@H]2N=C(c3ccccc3)c3ccccc3NC2=O)o1] |
| 415 | 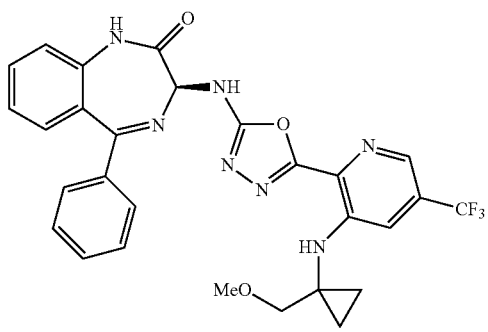 [SMILES: COCC1(Nc2cc(C(F)(F)F)cnc2-c2nnc(N[C@H]3N=C(c4ccccc4)c4ccccc4NC3=O)o2)CC1] |
| 416 | 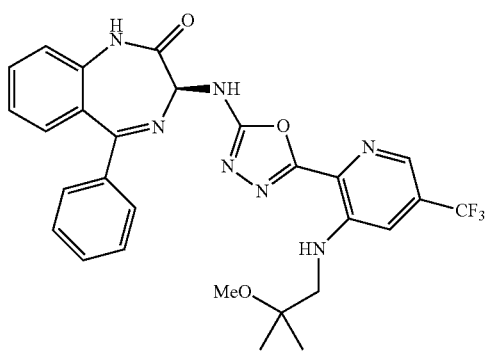 [SMILES: COC(C)(C)CNc1cc(C(F)(F)F)cnc1-c1nnc(N[C@H]2N=C(c3ccccc3)c3ccccc3NC2=O)o1] |

| Compound | Structure |
|---|---|
| 417 | 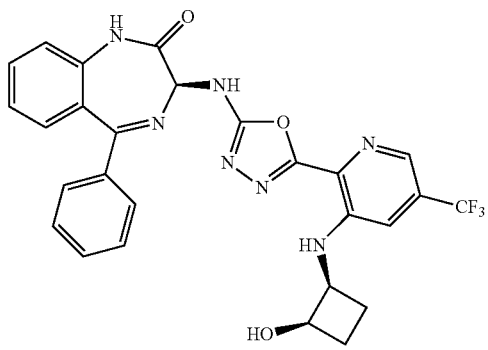 [SMILES: O=C1Nc2ccccc2C(c2ccccc2)=N[C@@H]1Nc1nnc(-c2ncc(C(F)(F)F)cc2N[C@H]2CC[C@H]2O)o1] |
| 418 | 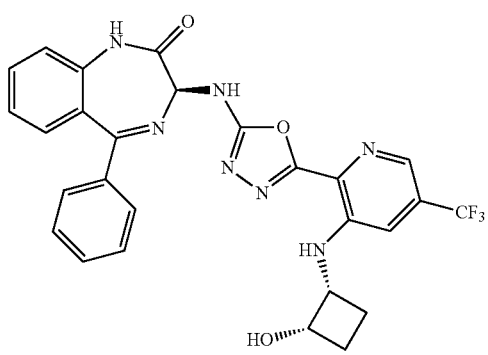 [SMILES: O=C1Nc2ccccc2C(c2ccccc2)=N[C@@H]1Nc1nnc(-c2ncc(C(F)(F)F)cc2N[C@@H]2CC[C@@H]2O)o1] |
| 419 | 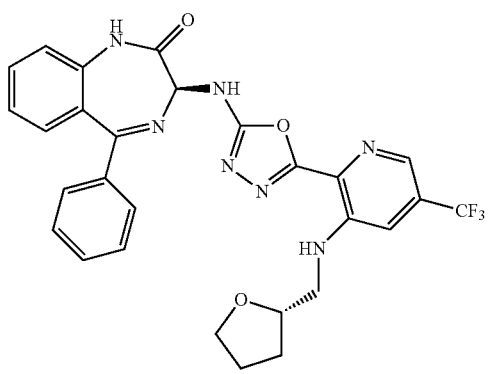 [SMILES: O=C1Nc2ccccc2C(c2ccccc2)=N[C@@H]1Nc1nnc(-c2ncc(C(F)(F)F)cc2NC[C@@H]2CCCO2)o1] |
| 420 | 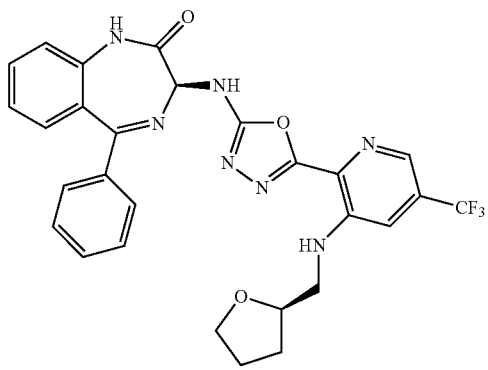 [SMILES: O=C1Nc2ccccc2C(c2ccccc2)=N[C@@H]1Nc1nnc(-c2ncc(C(F)(F)F)cc2NC[C@H]2CCCO2)o1] |

| Compound | Structure |
|---|---|
| 421 | 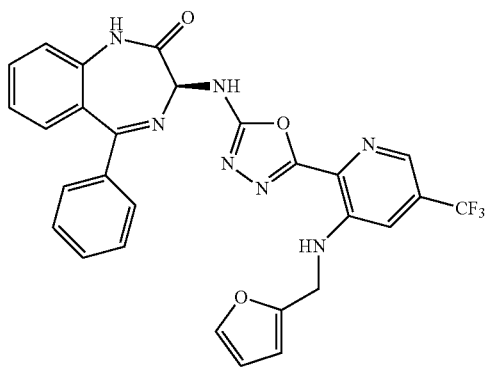 [SMILES: O=C1Nc2ccccc2C(c2ccccc2)=N[C@@H]1Nc1nnc(-c2ncc(C(F)(F)F)cc2NCc2ccco2)o1] |
| 422 | 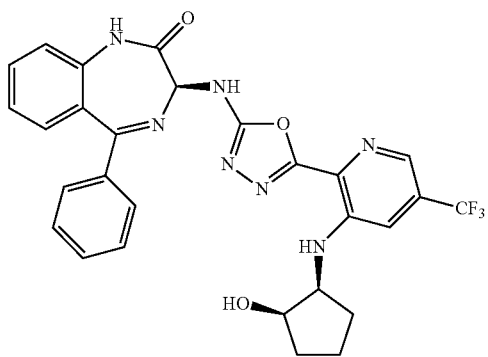 [SMILES: O=C1Nc2ccccc2C(c2ccccc2)=N[C@@H]1Nc1nnc(-c2ncc(C(F)(F)F)cc2N[C@H]2CCC[C@H]2O)o1] |
| 423 | 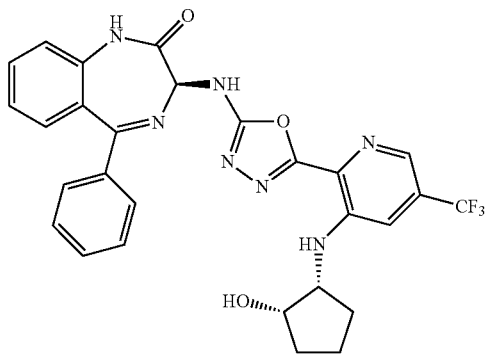 [SMILES: O=C1Nc2ccccc2C(c2ccccc2)=N[C@@H]1Nc1nnc(-c2ncc(C(F)(F)F)cc2N[C@@H]2CCC[C@@H]2O)o1] |
| 424 | 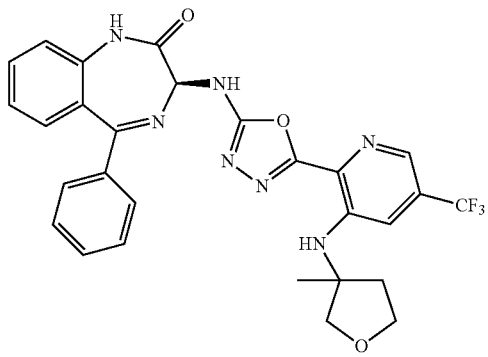 [SMILES: CC1(Nc2cc(C(F)(F)F)cnc2-c2nnc(N[C@H]3N=C(c4ccccc4)c4ccccc4NC3=O)o2)CCOC1] |

| Compound | Structure |
|---|---|
| 425 | 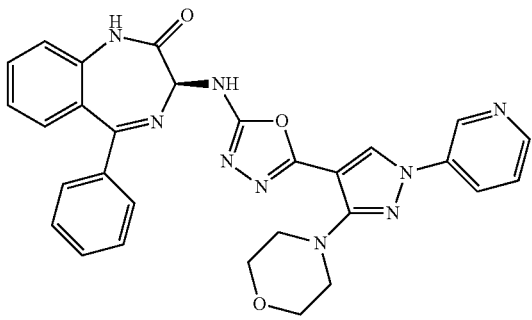 [SMILES: O=C1Nc2ccccc2C(c2ccccc2)=N[C@@H]1Nc1nnc(-c2cn(-c3cccnc3)nc2N2CCOCC2)o1] |
| 426 | 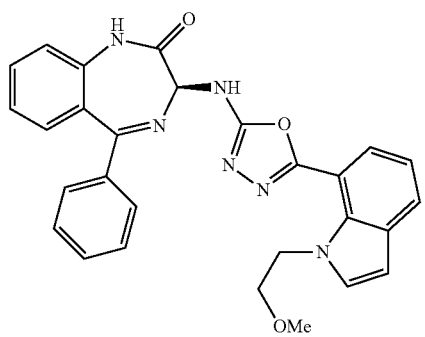 [SMILES: COCCn1ccc2cccc(-c3nnc(N[C@H]4N=C(c5ccccc5)c5ccccc5NC4=O)o3)c21] |
| 427 | 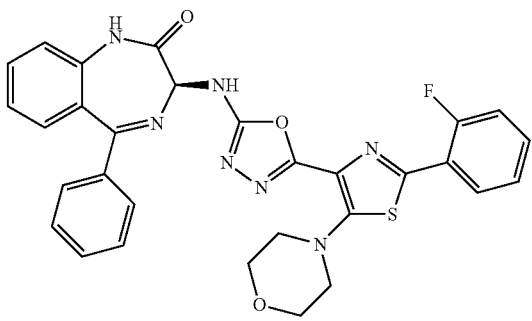 [SMILES: O=C1Nc2ccccc2C(c2ccccc2)=N[C@@H]1Nc1nnc(-c2nc(-c3ccccc3F)sc2N2CCOCC2)o1] |
| 428 | 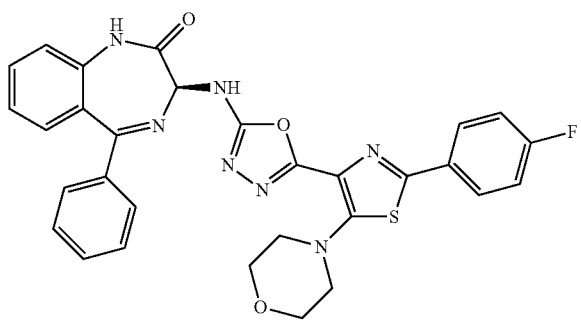 [SMILES: O=C1Nc2ccccc2C(c2ccccc2)=N[C@@H]1Nc1nnc(-c2nc(-c3ccc(F)cc3)sc2N2CCOCC2)o1] |

-continued
| Compound | Structure |
|---|---|
| 429 | 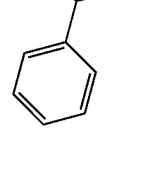 |
| 430 | 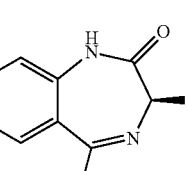 |
| 431 | 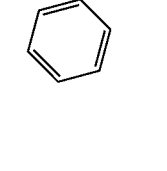 |
| 432 | 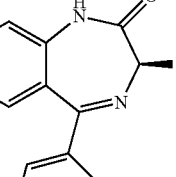 |
| 433 | 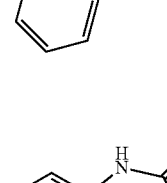 |

-continued

| Compound | Structure |
|---|---|
| 434 | 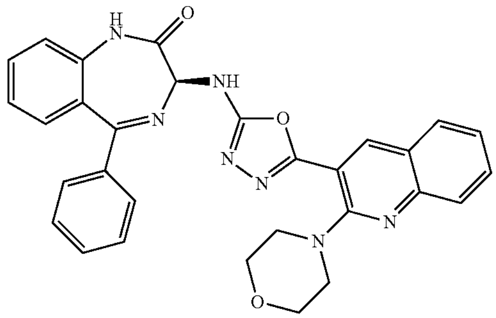 [SMILES: O=C1Nc2ccccc2C(c2ccccc2)=N[C@@H]1Nc1nnc(-c2cc3ccccc3nc2N2CCOCC2)o1] |
| 435 | 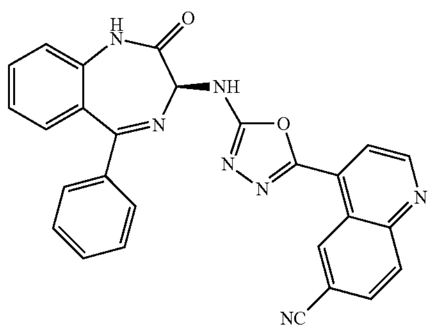 [SMILES: N#Cc1ccc2nccc(-c3nnc(N[C@H]4N=C(c5ccccc5)c5ccccc5NC4=O)o3)c2c1] |
| 436 | 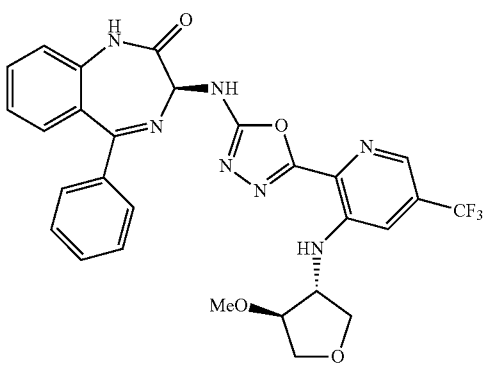 [SMILES: CO[C@@H]1COC[C@H]1Nc1cc(C(F)(F)F)cnc1-c1nnc(N[C@H]2N=C(c3ccccc3)c3ccccc3NC2=O)o1] |
| 437 | 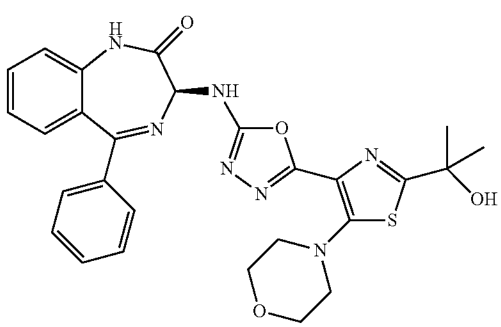 [SMILES: CC(C)(O)c1nc(-c2nnc(N[C@H]3N=C(c4ccccc4)c4ccccc4NC3=O)o2)c(N2CCOCC2)s1] |

-continued
| Compound | Structure |
|---|---|
| 438 | 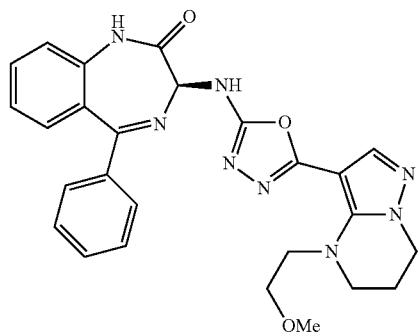 [SMILES: COCCN1CCCn2ncc(-c3nnc(N[C@H]4N=C(c5ccccc5)c5ccccc5NC4=O)o3)c21] |
| 439 | 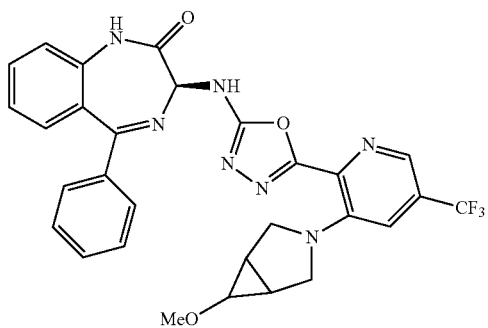 [SMILES: COC1C2CN(c3cc(C(F)(F)F)cnc3-c3nnc(N[C@H]4N=C(c5ccccc5)c5ccccc5NC4=O)o3)CC21] |
| 440 | 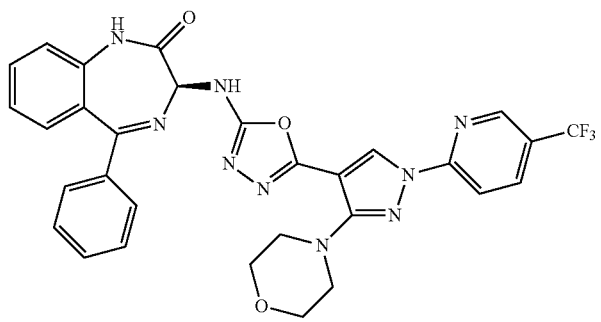 |
| 441 | 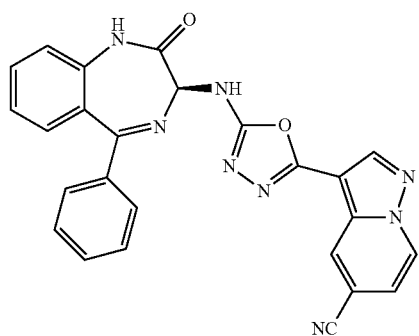 [SMILES: N#Cc1ccn2ncc(-c3nnc(N[C@H]4N=C(c5ccccc5)c5ccccc5NC4=O)o3)c2c1] |

| Compound | Structure |
|---|---|
| 442 | 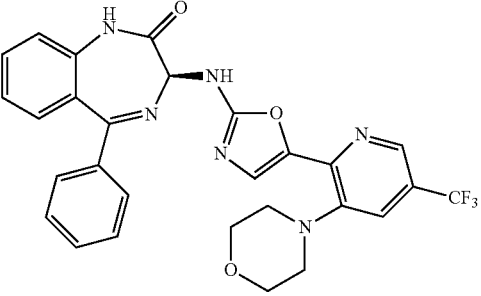 [SMILES: O=C1Nc2ccccc2C(c2ccccc2)=N[C@@H]1Nc1ncc(-c2ncc(C(F)(F)F)cc2N2CCOCC2)o1] |
| 443 | 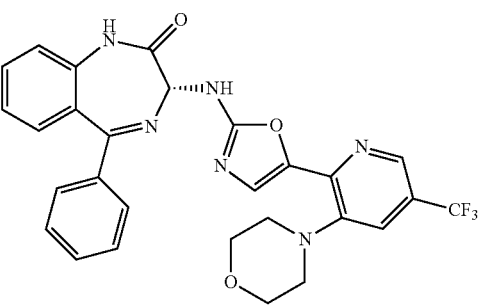 [SMILES: O=C1Nc2ccccc2C(c2ccccc2)=N[C@H]1Nc1ncc(-c2ncc(C(F)(F)F)cc2N2CCOCC2)o1] |
| 444 | 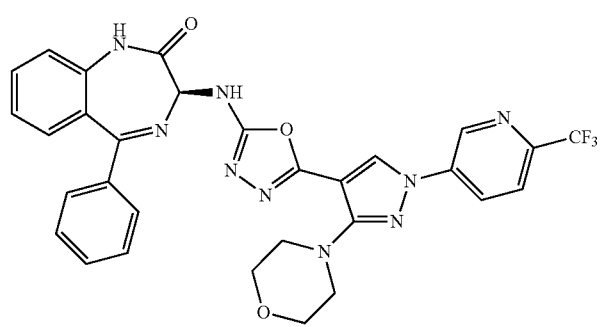 [SMILES: O=C1Nc2ccccc2C(c2ccccc2)=N[C@@H]1Nc1nnc(-c2cn(-c3ccc(C(F)(F)F)nc3)nc2N2CCOCC2)o1] |
| 445 | 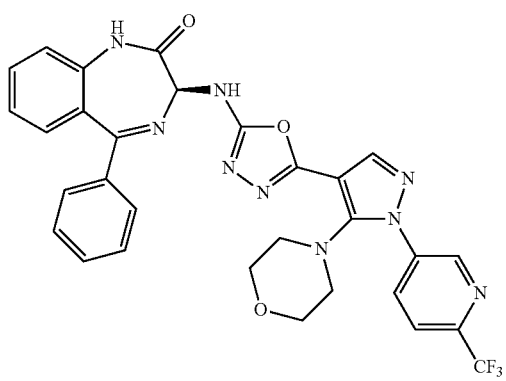 [SMILES: O=C1Nc2ccccc2C(c2ccccc2)=N[C@@H]1Nc1nnc(-c2cnn(-c3ccc(C(F)(F)F)nc3)c2N2CCOCC2)o1] |

US 9,957,281 B2
619
-continued
| Compound | Structure |
|---|---|
| 446 | 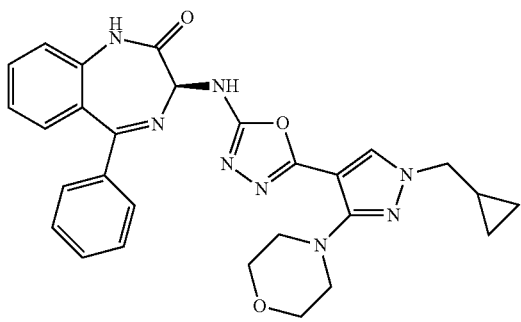 [SMILES: O=C1Nc2ccccc2C(c2ccccc2)=N[C@@H]1Nc1nnc(-c2cn(CC3CC3)nc2N2CCOCC2)o1] |
| 447 | 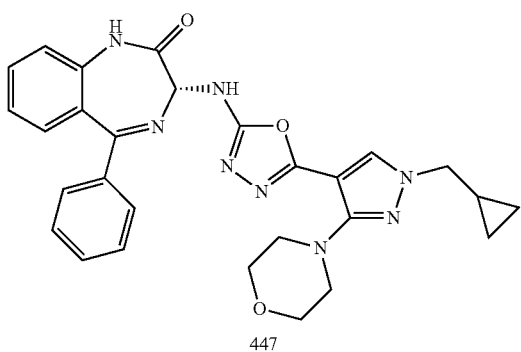 [SMILES: O=C1Nc2ccccc2C(c2ccccc2)=N[C@H]1Nc1nnc(-c2cn(CC3CC3)nc2N2CCOCC2)o1] |
| 448 | 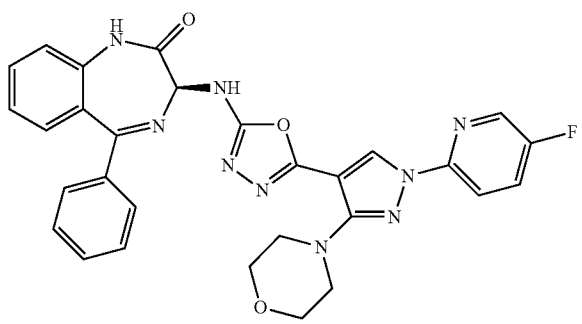 [SMILES: O=C1Nc2ccccc2C(c2ccccc2)=N[C@@H]1Nc1nnc(-c2cn(-c3ccc(F)cn3)nc2N2CCOCC2)o1] |
| 449 | 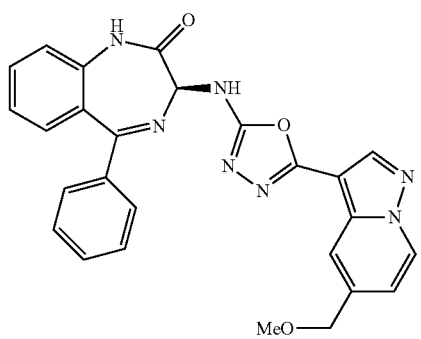 [SMILES: COCc1ccn2ncc(-c3nnc(N[C@H]4N=C(c5ccccc5)c5ccccc5NC4=O)o3)c2c1] |

| Compound | Structure |
|---|---|
| 450 | 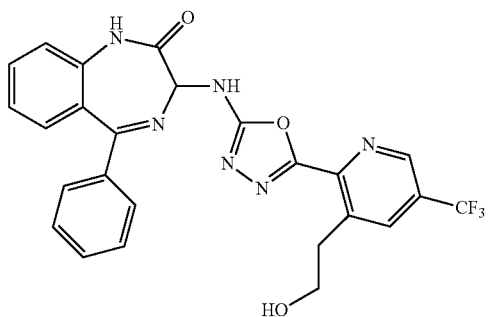 [SMILES: O=C1Nc2ccccc2C(c2ccccc2)=NC1Nc1nnc(-c2ncc(C(F)(F)F)cc2CCO)o1] |
| 451 | 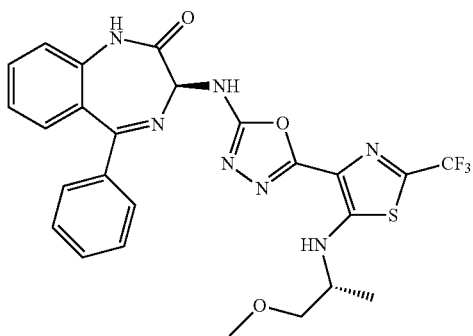 [SMILES: COC[C@@H](C)Nc1sc(C(F)(F)F)nc1-c1nnc(N[C@H]2N=C(c3ccccc3)c3ccccc3NC2=O)o1] |
| 452 | 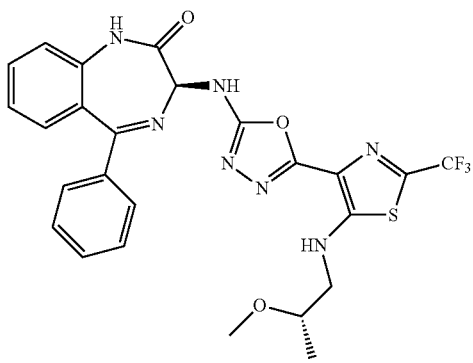 [SMILES: CO[C@@H](C)CNc1sc(C(F)(F)F)nc1-c1nnc(N[C@H]2N=C(c3ccccc3)c3ccccc3NC2=O)o1] |
| 453 | 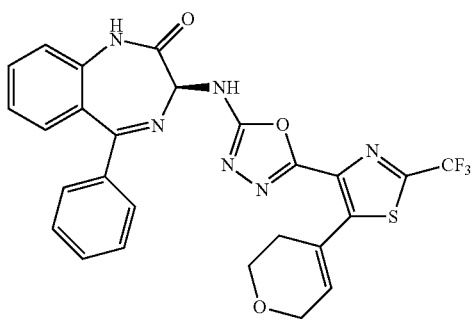 [SMILES: O=C1Nc2ccccc2C(c2ccccc2)=N[C@@H]1Nc1nnc(-c2nc(C(F)(F)F)sc2C2=CCOCC2)o1] |

| Compound | Structure |
|---|---|
| 454 | 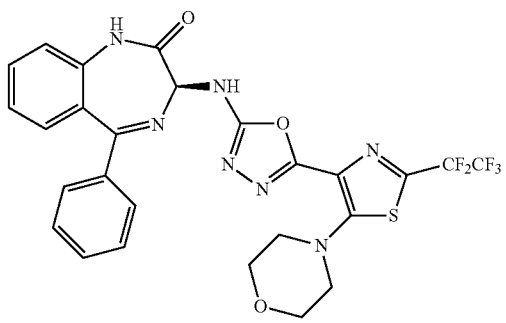 |
| 455 | 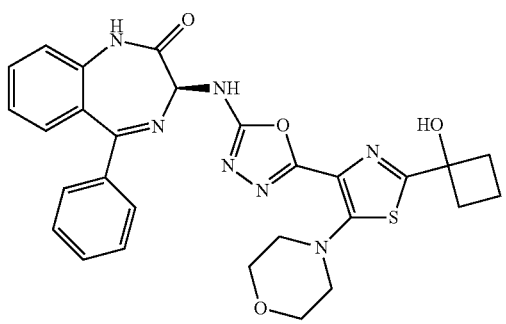 |
| 456 | 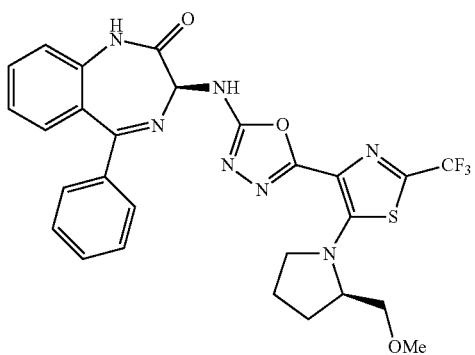 [SMILES: COC[C@H]1CCCN1c1sc(C(F)(F)F)nc1-c1nnc(N[C@H]2N=C(c3ccccc3)c3ccccc3NC2=O)o1] |
| 457 | 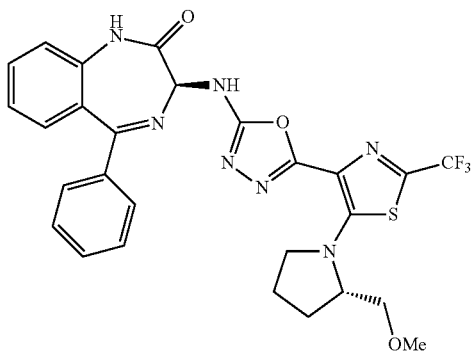 [SMILES: COC[C@@H]1CCCN1c1sc(C(F)(F)F)nc1-c1nnc(N[C@H]2N=C(c3ccccc3)c3ccccc3NC2=O)o1] |

| Compound | Structure |
|---|---|
| 458 | 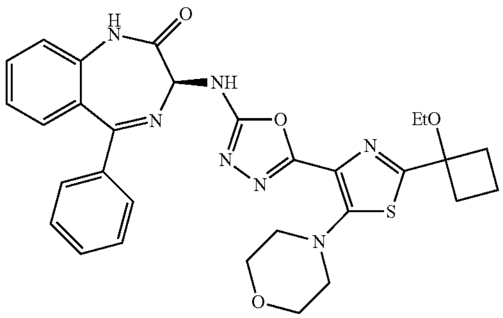 [SMILES: CCOC1(c2nc(-c3nnc(N[C@H]4N=C(c5ccccc5)c5ccccc5NC4=O)o3)c(N3CCOCC3)s2)CCC1] |
| 459 | 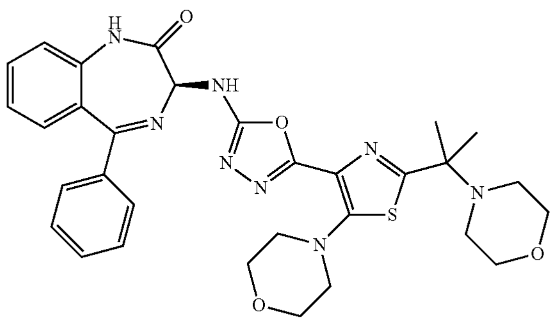 [SMILES: CC(C)(c1nc(-c2nnc(N[C@H]3N=C(c4ccccc4)c4ccccc4NC3=O)o2)c(N2CCOCC2)s1)N1CCOCC1] |
| 460 | 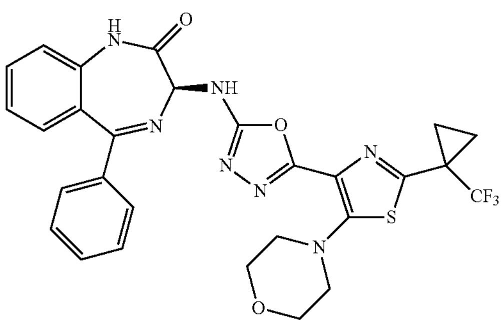 [SMILES: O=C1Nc2ccccc2C(c2ccccc2)=N[C@@H]1Nc1nnc(-c2nc(C3(C(F)(F)F)CC3)sc2N2CCOCC2)o1] |
| 461 | 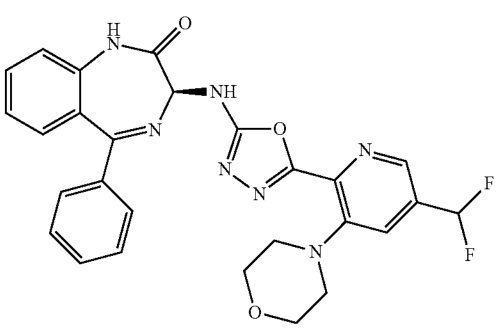 [SMILES: O=C1Nc2ccccc2C(c2ccccc2)=N[C@@H]1Nc1nnc(-c2ncc(C(F)F)cc2N2CCOCC2)o1] |
| 462 | 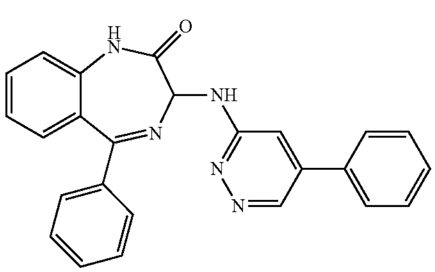 [SMILES: O=C1Nc2ccccc2C(c2ccccc2)=NC1Nc1cc(-c2ccccc2)cnn1] |

-continued
| Compound | Structure |
|---|---|
| 463 | 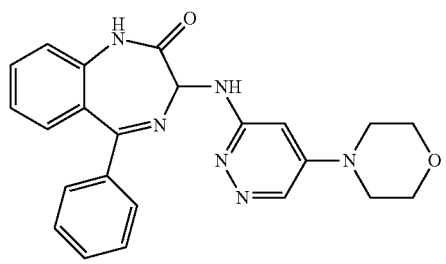 |
| 464 | 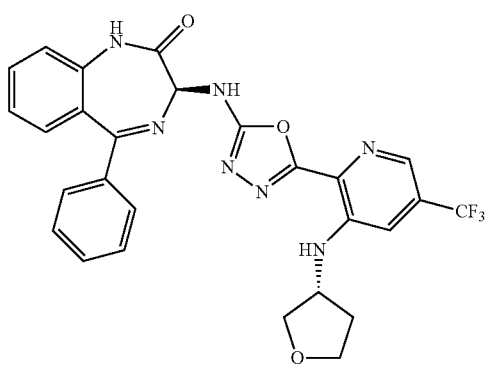 [SMILES: O=C1Nc2ccccc2C(c2ccccc2)=N[C@@H]1Nc1nnc(-c2ncc(C(F)(F)F)cc2N[C@@H]2CCOC2)o1] |
| 465 | 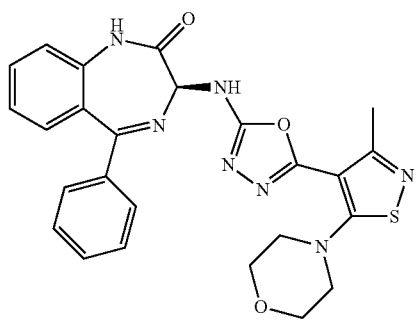 [SMILES: Cc1nsc(N2CCOCC2)c1-c1nnc(N[C@H]2N=C(c3ccccc3)c3ccccc3NC2=O)o1] |
| 466 | 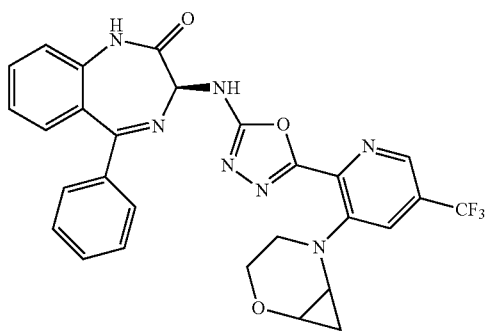 [SMILES: O=C1Nc2ccccc2C(c2ccccc2)=N[C@@H]1Nc1nnc(-c2ncc(C(F)(F)F)cc2N2CCOC3CC32)o1] |

| Compound | Structure |
|---|---|
| 467 | 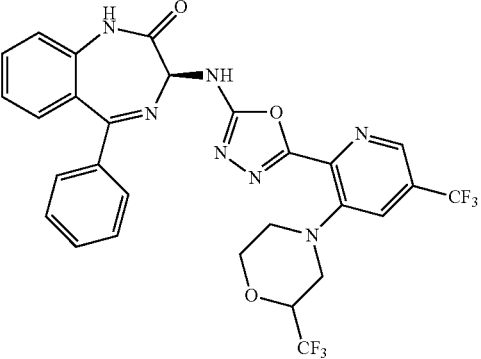 [SMILES: O=C1Nc2ccccc2C(c2ccccc2)=N[C@@H]1Nc1nnc(-c2ncc(C(F)(F)F)cc2N2CCOC(C(F)(F)F)C2)o1] |
| 468 | 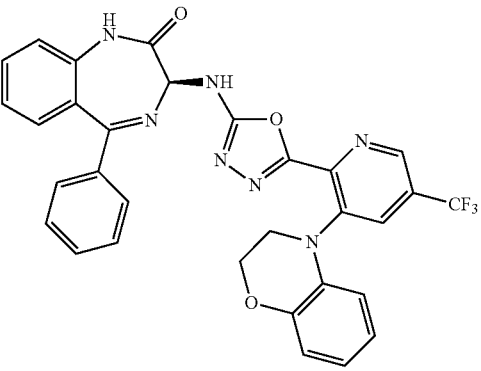 [SMILES: O=C1Nc2ccccc2C(c2ccccc2)=N[C@@H]1Nc1nnc(-c2ncc(C(F)(F)F)cc2N2CCOc3ccccc32)o1] |
| 469 | 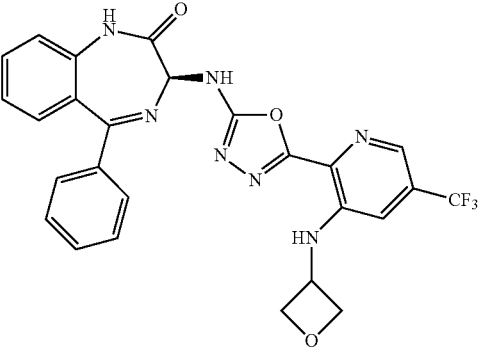 [SMILES: O=C1Nc2ccccc2C(c2ccccc2)=N[C@@H]1Nc1nnc(-c2ncc(C(F)(F)F)cc2NC2COC2)o1] |
| 470 | 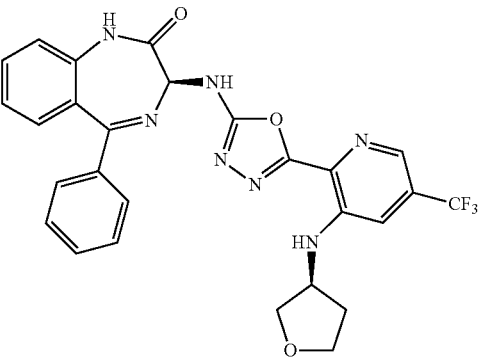 [SMILES: O=C1Nc2ccccc2C(c2ccccc2)=N[C@@H]1Nc1nnc(-c2ncc(C(F)(F)F)cc2N[C@H]2CCOC2)o1] |

| Compound | Structure |
|---|---|
| 471 | 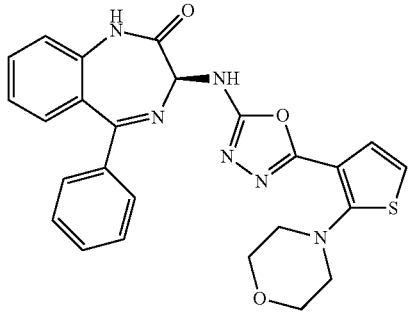 [SMILES: O=C1Nc2ccccc2C(c2ccccc2)=N[C@@H]1Nc1nnc(-c2ccsc2N2CCOCC2)o1] |
| 472 | 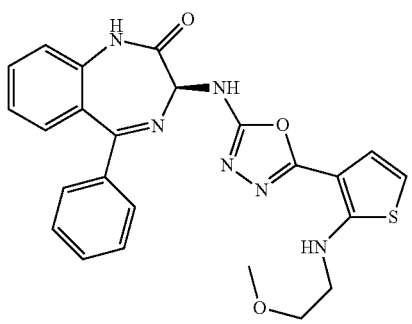 [SMILES: COCCNc1sccc1-c1nnc(N[C@H]2N=C(c3ccccc3)c3ccccc3NC2=O)o1] |
| 473 | 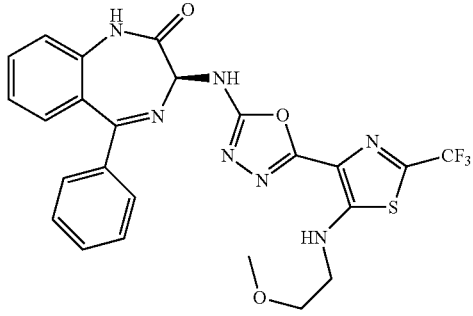 [SMILES: COCCNc1sc(C(F)(F)F)nc1-c1nnc(N[C@H]2N=C(c3ccccc3)c3ccccc3NC2=O)o1] |
| 474 | 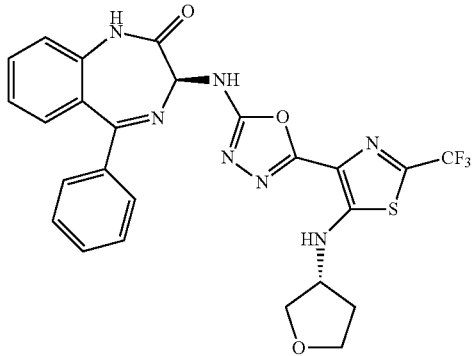 [SMILES: O=C1Nc2ccccc2C(c2ccccc2)=N[C@@H]1Nc1nnc(-c2nc(C(F)(F)F)sc2N[C@@H]2CCOC2)o1] |

| Compound | Structure |
|---|---|
| 475 | 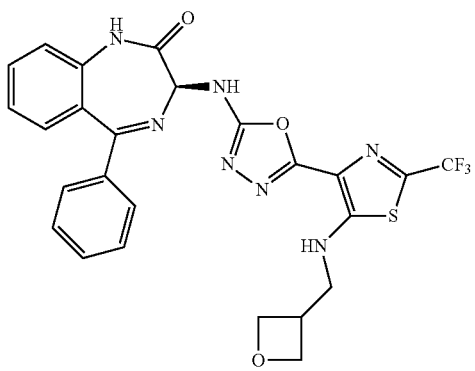 [SMILES: O=C1Nc2ccccc2C(c2ccccc2)=N[C@@H]1Nc1nnc(-c2nc(C(F)(F)F)sc2NCC2COC2)o1] |
| 476 | 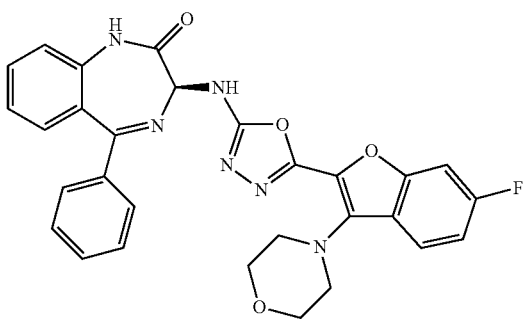 [SMILES: O=C1Nc2ccccc2C(c2ccccc2)=N[C@@H]1Nc1nnc(-c2oc3cc(F)ccc3c2N2CCOCC2)o1] |
| 477 | 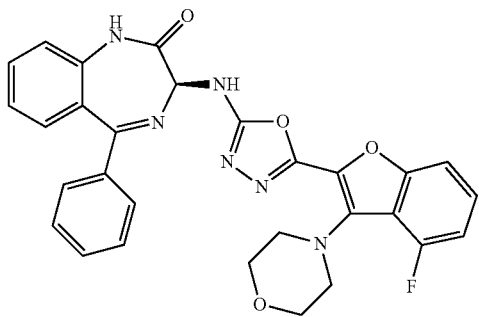 [SMILES: O=C1Nc2ccccc2C(c2ccccc2)=N[C@@H]1Nc1nnc(-c2oc3cccc(F)c3c2N2CCOCC2)o1] |
| 478 | 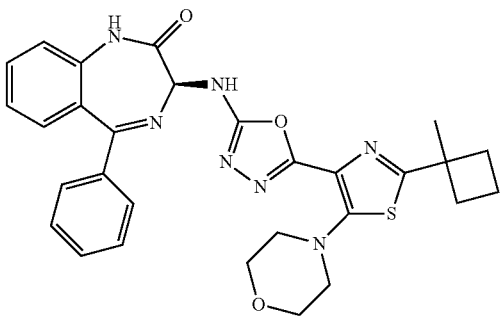 [SMILES: CC1(c2nc(-c3nnc(N[C@H]4N=C(c5ccccc5)c5ccccc5NC4=O)o3)c(N3CCOCC3)s2)CCC1] |

-continued
| Compound | Structure |
|---|---|
| 479 | 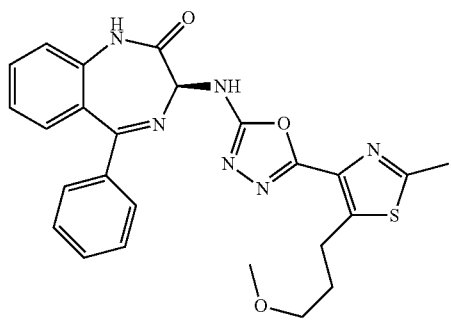 [SMILES: COCCCc1sc(C)nc1-c1nnc(N[C@H]2N=C(c3ccccc3)c3ccccc3NC2=O)o1] |
| 480 | 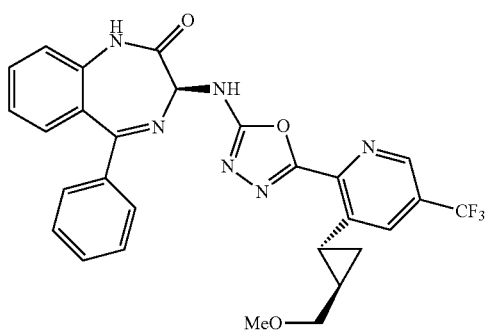 [SMILES: COC[C@@H]1C[C@H]1c1cc(C(F)(F)F)cnc1-c1nnc(N[C@H]2N=C(c3ccccc3)c3ccccc3NC2=O)o1] |
| 481 | 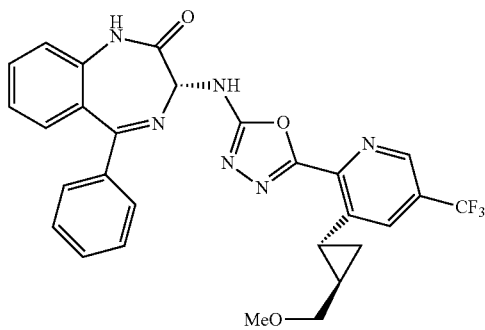 [SMILES: COC[C@@H]1C[C@H]1c1cc(C(F)(F)F)cnc1-c1nnc(N[C@@H]2N=C(c3ccccc3)c3ccccc3NC2=O)o1] |
| 482 | 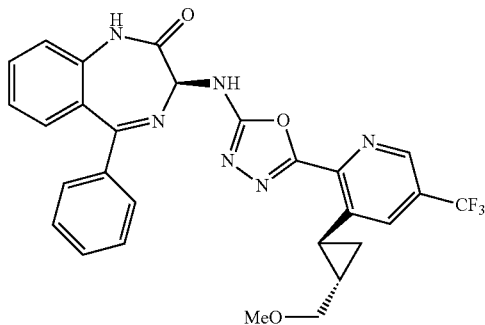 [SMILES: COC[C@H]1C[C@@H]1c1cc(C(F)(F)F)cnc1-c1nnc(N[C@H]2N=C(c3ccccc3)c3ccccc3NC2=O)o1] |

| Compound | Structure |
|---|---|
| 483 | 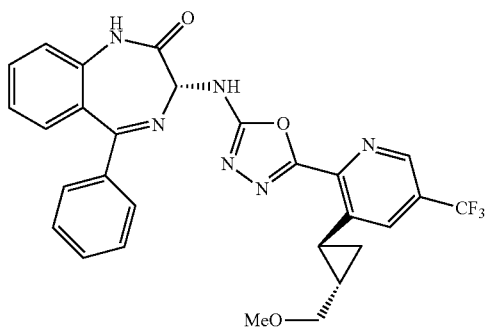 [SMILES: COC[C@H]1C[C@@H]1c1cc(C(F)(F)F)cnc1-c1nnc(N[C@@H]2N=C(c3ccccc3)c3ccccc3NC2=O)o1] |
| 484 | 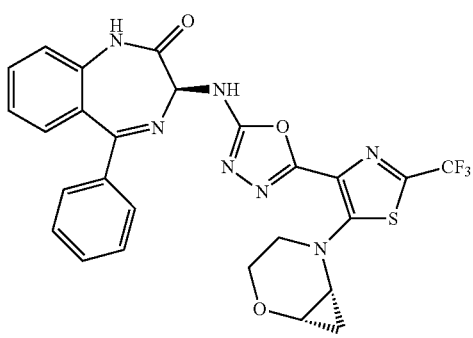 |
| 485 | 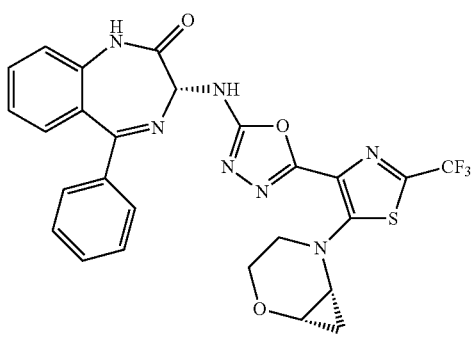 [SMILES: O=C1Nc2ccccc2C(c2ccccc2)=N[C@H]1Nc1nnc(-c2nc(C(F)(F)F)sc2N2CCO[C@H]3C[C@H]32)o1] |
| 486 | 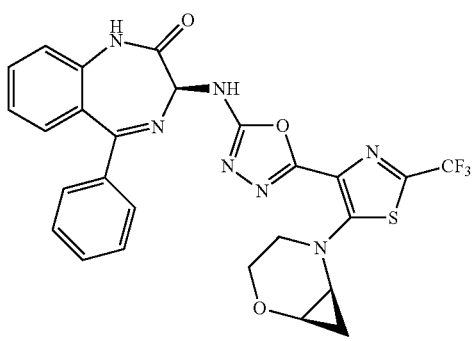 [SMILES: O=C1Nc2ccccc2C(c2ccccc2)=N[C@@H]1Nc1nnc(-c2nc(C(F)(F)F)sc2N2CCO[C@@H]3C[C@@H]32)o1] |

| Compound | Structure |
|---|---|
| 487 | 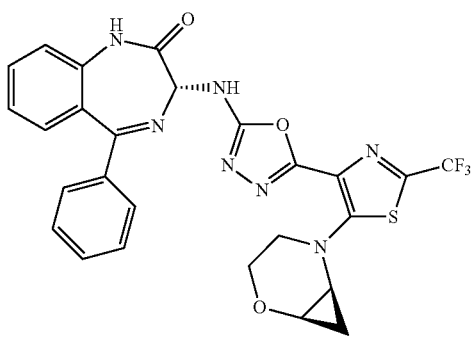 [SMILES: O=C1Nc2ccccc2C(c2ccccc2)=N[C@H]1Nc1nnc(-c2nc(C(F)(F)F)sc2N2CCO[C@@H]3C[C@@H]32)o1] |
| 488 | 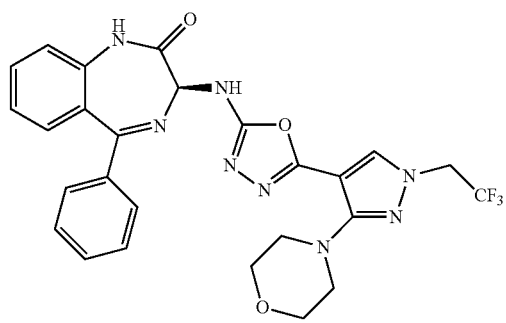 [SMILES: O=C1Nc2ccccc2C(c2ccccc2)=N[C@@H]1Nc1nnc(-c2cn(CC(F)(F)F)nc2N2CCOCC2)o1] |
| 489 | 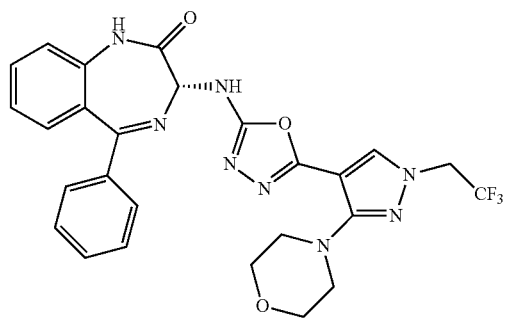 [SMILES: O=C1Nc2ccccc2C(c2ccccc2)=N[C@H]1Nc1nnc(-c2cn(CC(F)(F)F)nc2N2CCOCC2)o1] |
| 490 | 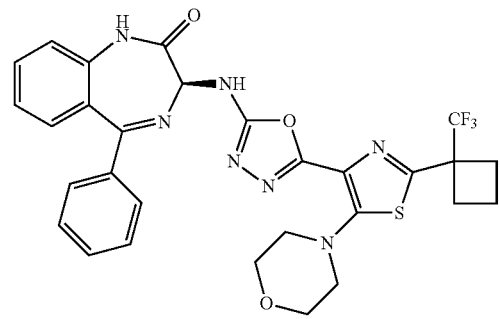 [SMILES: O=C1Nc2ccccc2C(c2ccccc2)=N[C@@H]1Nc1nnc(-c2nc(C3(C(F)(F)F)CCC3)sc2N2CCOCC2)o1] |

| Compound | Structure |
|---|---|
| 491 | 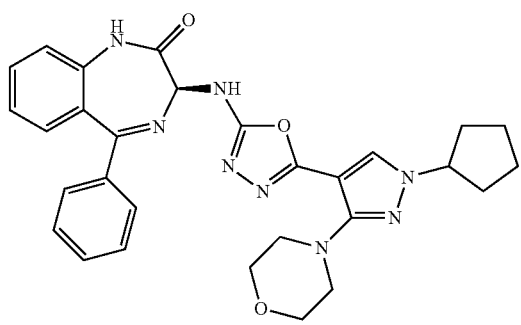 [SMILES: O=C1Nc2ccccc2C(c2ccccc2)=N[C@@H]1Nc1nnc(-c2cn(C3CCCC3)nc2N2CCOCC2)o1] |
| 492 | 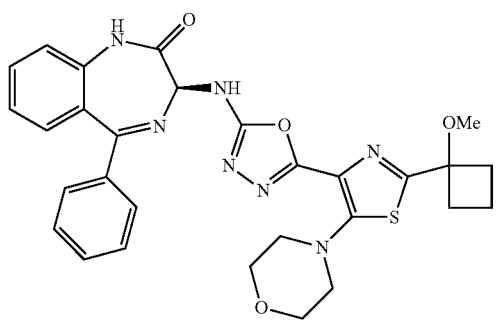 [SMILES: COC1(c2nc(-c3nnc(N[C@H]4N=C(c5ccccc5)c5ccccc5NC4=O)o3)c(N3CCOCC3)s2)CCC1] |
| 493 | 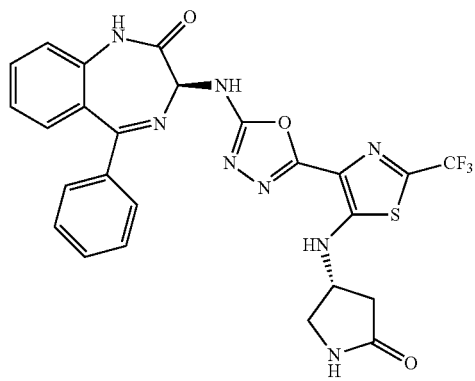 [SMILES: O=C1C[C@@H](Nc2sc(C(F)(F)F)nc2-c2nnc(N[C@H]3N=C(c4ccccc4)c4ccccc4NC3=O)o2)CN1] |
| 494 | 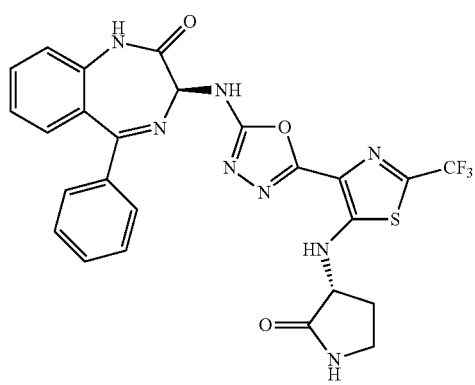 [SMILES: O=C1Nc2ccccc2C(c2ccccc2)=N[C@@H]1Nc1nnc(-c2nc(C(F)(F)F)sc2N[C@@H]2CCNC2=O)o1] |

| Compound | Structure |
|---|---|
| 495 | 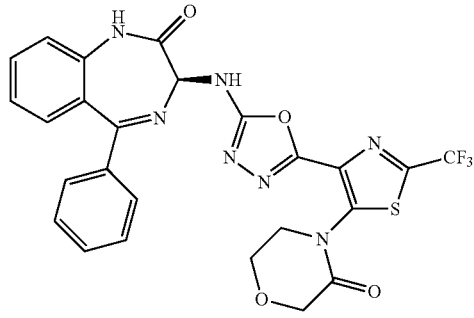 [SMILES: O=C1Nc2ccccc2C(c2ccccc2)=N[C@@H]1Nc1nnc(-c2nc(C(F)(F)F)sc2N2CCOCC2=O)o1] |
| 496 | 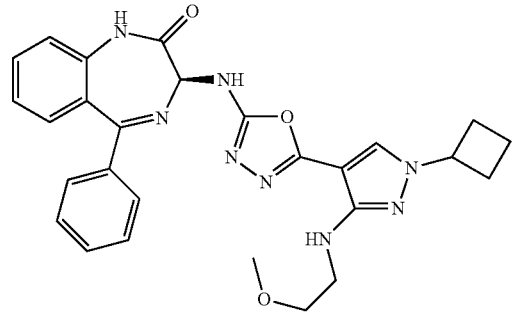 [SMILES: COCCNc1nn(C2CCC2)cc1-c1nnc(N[C@H]2N=C(c3ccccc3)c3ccccc3NC2=O)o1] |
| 497 | 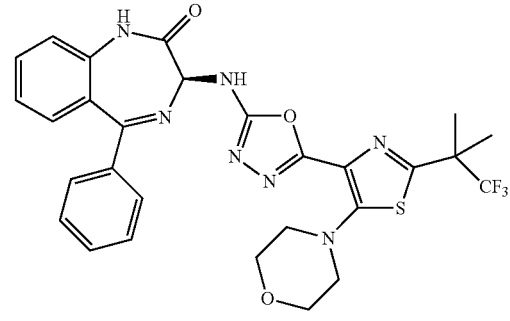 [SMILES: CC(C)(c1nc(-c2nnc(N[C@H]3N=C(c4ccccc4)c4ccccc4NC3=O)o2)c(N2CCOCC2)s1)C(F)(F)F] |
| 498 | 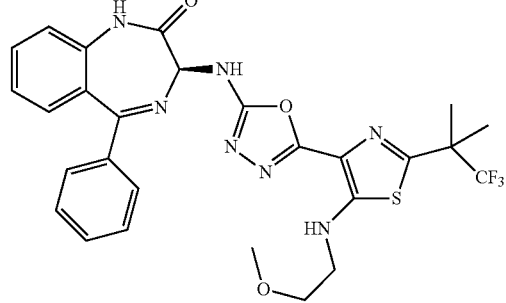 |

| Compound | Structure |
|---|---|
| 499 | 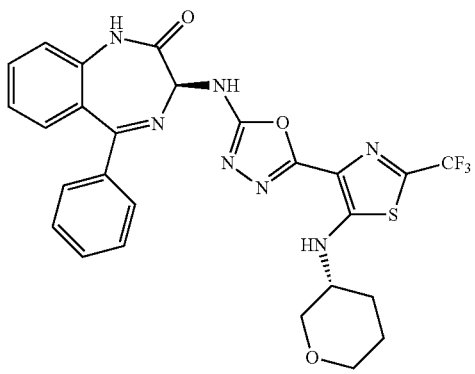 [SMILES: O=C1Nc2ccccc2C(c2ccccc2)=N[C@@H]1Nc1nnc(-c2nc(C(F)(F)F)sc2N[C@@H]2CCCOC2)o1] |
| 500 | 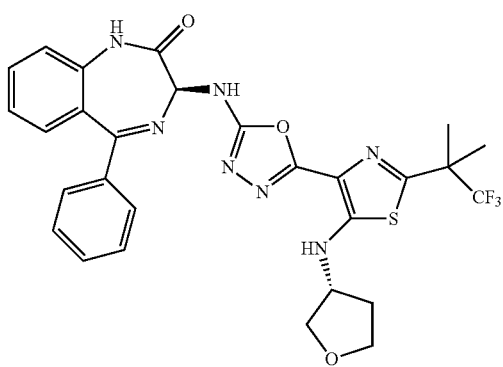 [SMILES: CC(C)(c1nc(-c2nnc(N[C@H]3N=C(c4ccccc4)c4ccccc4NC3=O)o2)c(N[C@@H]2CCOC2)s1)C(F)(F)F] |
| 501 | 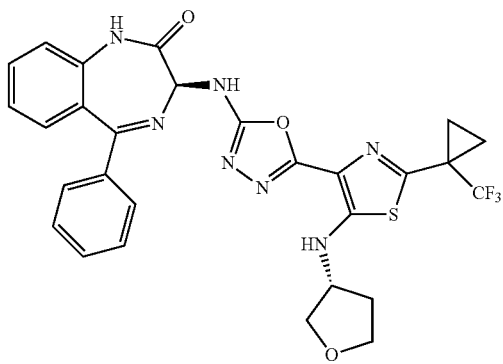 [SMILES: O=C1Nc2ccccc2C(c2ccccc2)=N[C@@H]1Nc1nnc(-c2nc(C3(C(F)(F)F)CC3)sc2N[C@@H]2CCOC2)o1] |
| 502 | 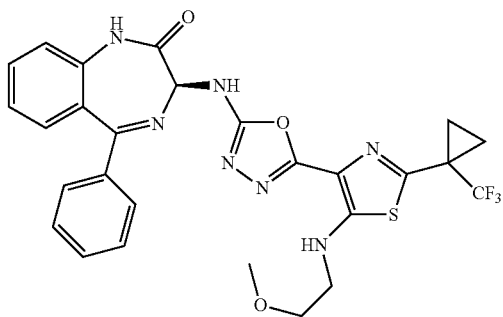 [SMILES: COCCNc1sc(C2(C(F)(F)F)CC2)nc1-c1nnc(N[C@H]2N=C(c3ccccc3)c3ccccc3NC2=O)o1] |

| Compound | Structure |
|---|---|
| 503 | 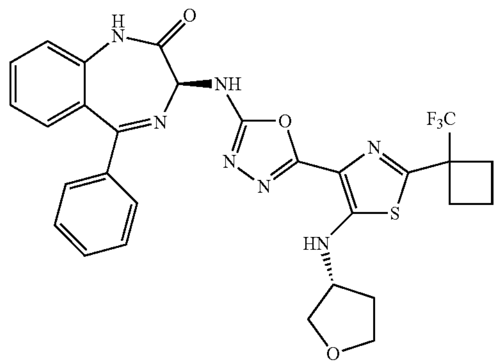 [SMILES: O=C1Nc2ccccc2C(c2ccccc2)=N[C@@H]1Nc1nnc(-c2nc(C3(C(F)(F)F)CCC3)sc2N[C@@H]2CCOC2)o1] |
| 504 | 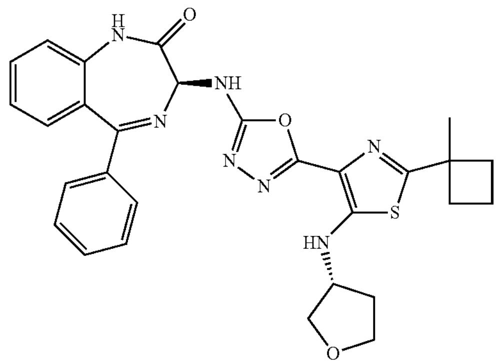 [SMILES: CC1(c2nc(-c3nnc(N[C@H]4N=C(c5ccccc5)c5ccccc5NC4=O)o3)c(N[C@@H]3CCOC3)s2)CCC1] |
| 505 | 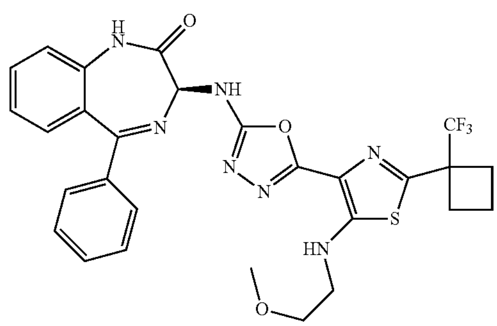 [SMILES: COCCNc1sc(C2(C(F)(F)F)CCC2)nc1-c1nnc(N[C@H]2N=C(c3ccccc3)c3ccccc3NC2=O)o1] |
| 506 | 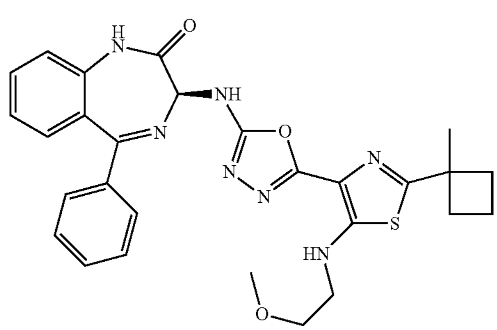 [SMILES: COCCNc1sc(C2(C)CCC2)nc1-c1nnc(N[C@H]2N=C(c3ccccc3)c3ccccc3NC2=O)o1] |

| Compound | Structure |
|---|---|
| 507 | 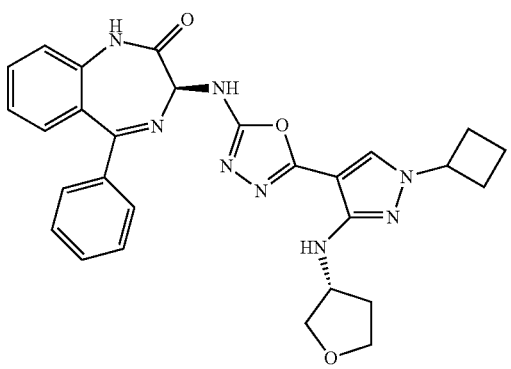 [SMILES: O=C1Nc2ccccc2C(c2ccccc2)=N[C@@H]1Nc1nnc(-c2cn(C3CCC3)nc2N[C@@H]2CCOC2)o1] |
| 508 | 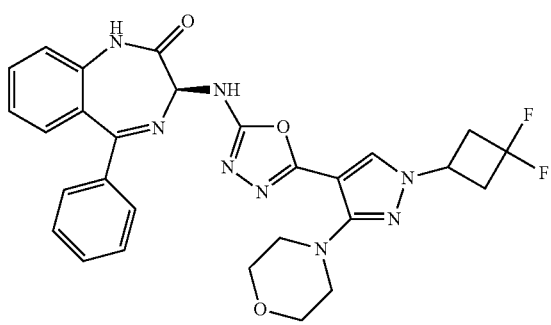 [SMILES: O=C1Nc2ccccc2C(c2ccccc2)=N[C@@H]1Nc1nnc(-c2cn(C3CC(F)(F)C3)nc2N2CCOCC2)o1] |
| 509 | 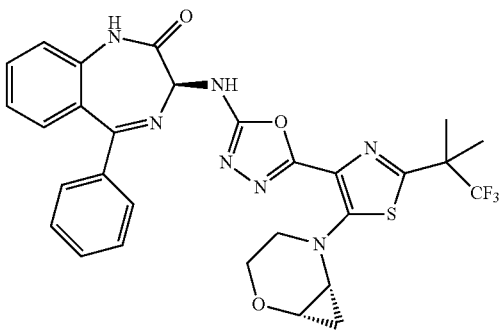 [SMILES: CC(C)(c1nc(-c2nnc(N[C@H]3N=C(c4ccccc4)c4ccccc4NC3=O)o2)c(N2CCO[C@H]3C[C@H]32)s1)C(F)(F)F] |
| 510 | 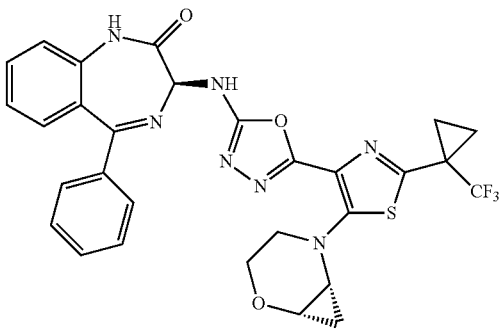 [SMILES: O=C1Nc2ccccc2C(c2ccccc2)=N[C@@H]1Nc1nnc(-c2nc(C3(C(F)(F)F)CC3)sc2N2CCO[C@H]3C[C@H]32)o1] |

-continued
| Compound | Structure |
|---|---|
| 511 | 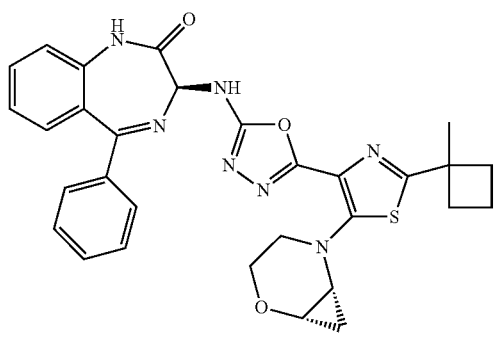 [SMILES: CC1(c2nc(-c3nnc(N[C@H]4N=C(c5ccccc5)c5ccccc5NC4=O)o3)c(N3CCO[C@H]4C[C@H]43)s2)CCC1] |
| 512 | 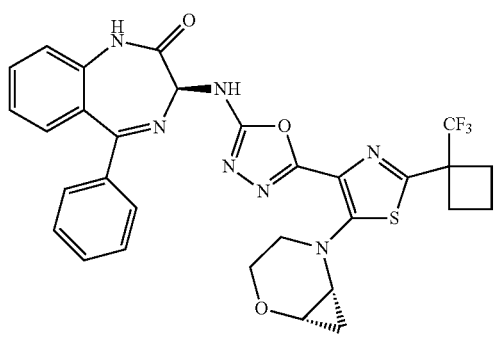 [SMILES: O=C1Nc2ccccc2C(c2ccccc2)=N[C@@H]1Nc1nnc(-c2nc(C3(C(F)(F)F)CCC3)sc2N2CCO[C@H]3C[C@H]32)o1] |
| 513 | 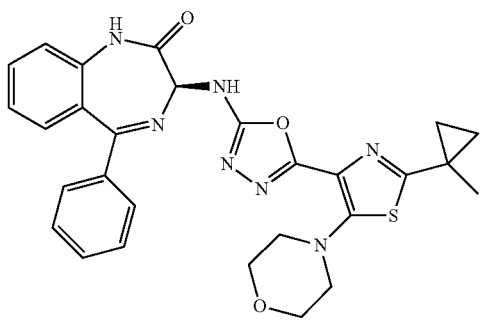 [SMILES: CC1(c2nc(-c3nnc(N[C@H]4N=C(c5ccccc5)c5ccccc5NC4=O)o3)c(N3CCOCC3)s2)CC1] |
| 514 | 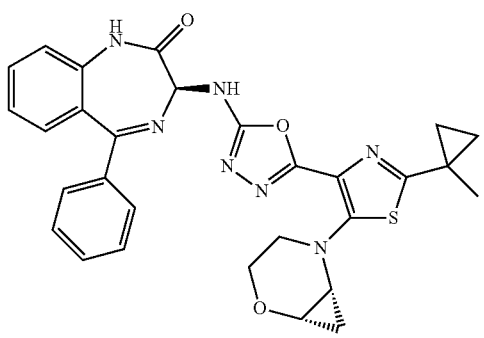 [SMILES: CC1(c2nc(-c3nnc(N[C@H]4N=C(c5ccccc5)c5ccccc5NC4=O)o3)c(N3CCO[C@H]4C[C@H]43)s2)CC1] |

| Compound | Structure |
|---|---|
| 515 | 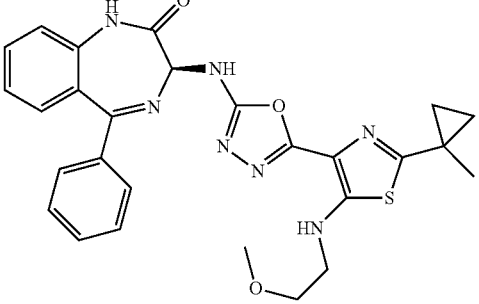 |
| 516 | 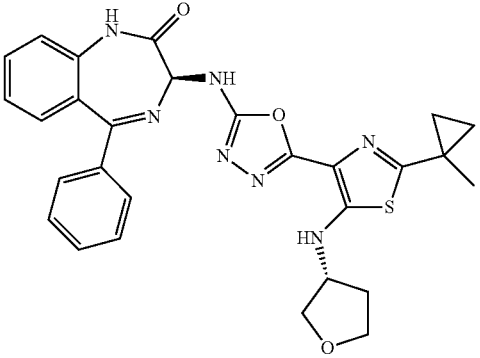 [SMILES: CC1(c2nc(-c3nnc(N[C@H]4N=C(c5ccccc5)c5ccccc5NC4=O)o3)c(N[C@@H]3CCOC3)s2)CC1] |
| 517 | 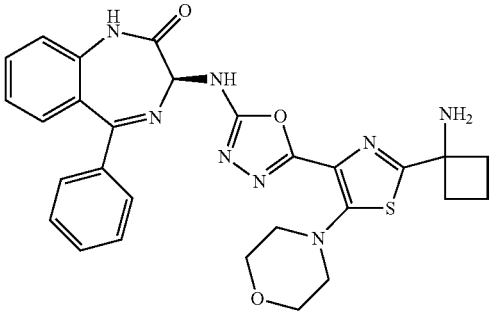 |
| 518 | 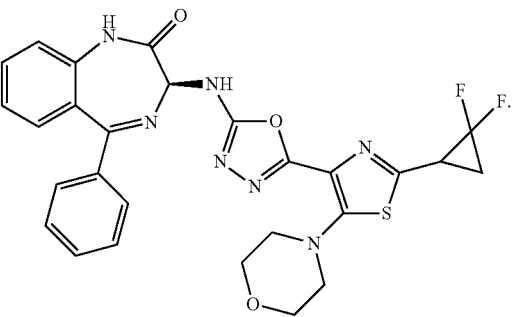 [SMILES: O=C1Nc2ccccc2C(c2ccccc2)=N[C@@H]1Nc1nnc(-c2nc(C3CC3(F)F)sc2N2CCOCC2)o1] |

11. A pharmaceutical composition, comprising a compound according to claim 1, or a pharmaceutically acceptable salt thereof, and a pharmaceutically acceptable carrier, diluent or excipient.

12. A method of treating an RSV infection in a subject in need thereof, comprising administering to the subject a therapeutically effective amount of a compound or a combination of compounds of claim 1.

13. The method of claim 12, further comprising administering to the subject an additional therapeutic agent selected from steroid anti-inflammatory compounds and nonsteroid anti-inflammatory compounds.

14. The method of claim 12, wherein the subject has concomitant RSV and influenza infections, said method further comprising administering to the subject an anti-influenza compound.

15. The method of claim 13, wherein the compound and the additional therapeutic agent are co-formulated.

16. The compound of claim 1, represented by Formula (VIa-1), (VIa-2), (VIa-3), (VIa-4), (VIb-1), (VIb-2), (VIb-3), or (VIb-4,)
(VIa-1)
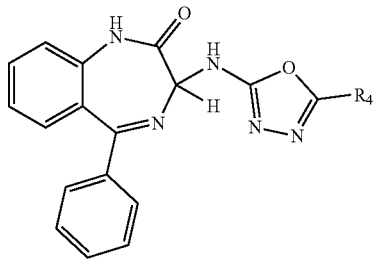
(VIa-2)
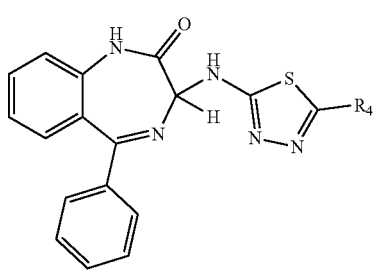
(VIa-3)
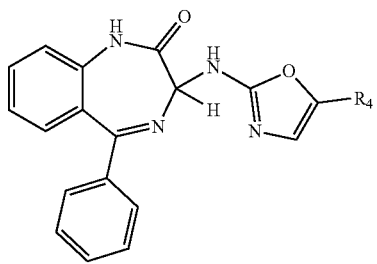
(VIa-4)
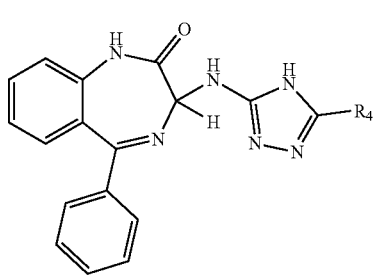
(VIb-1)
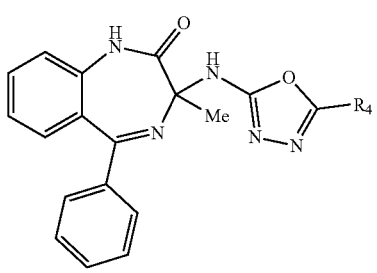
(VIb-2)
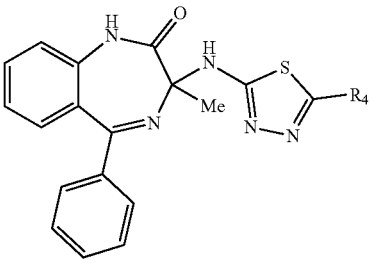
(VIb-3)
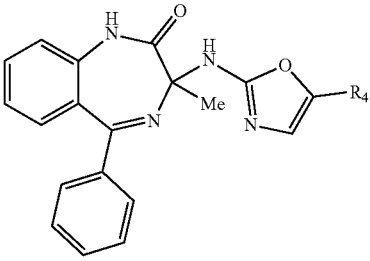
(VIb-4)
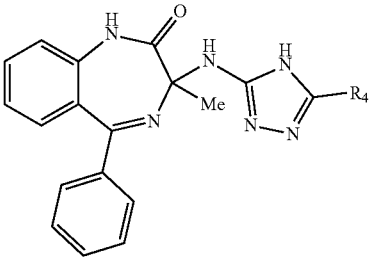
or a pharmaceutically acceptable salt thereof, wherein
$R_4$ is selected from the groups below,
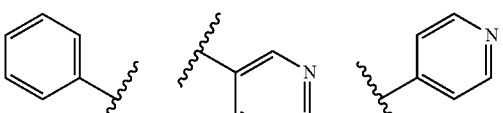
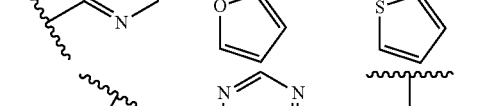
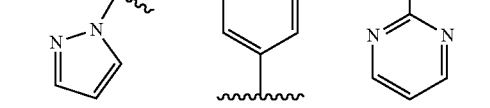
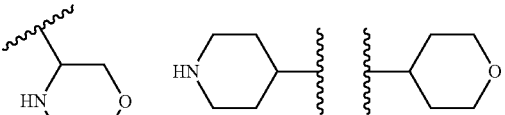
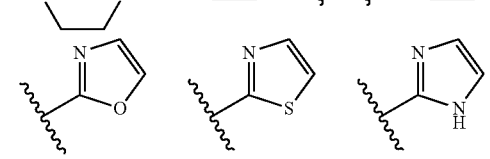

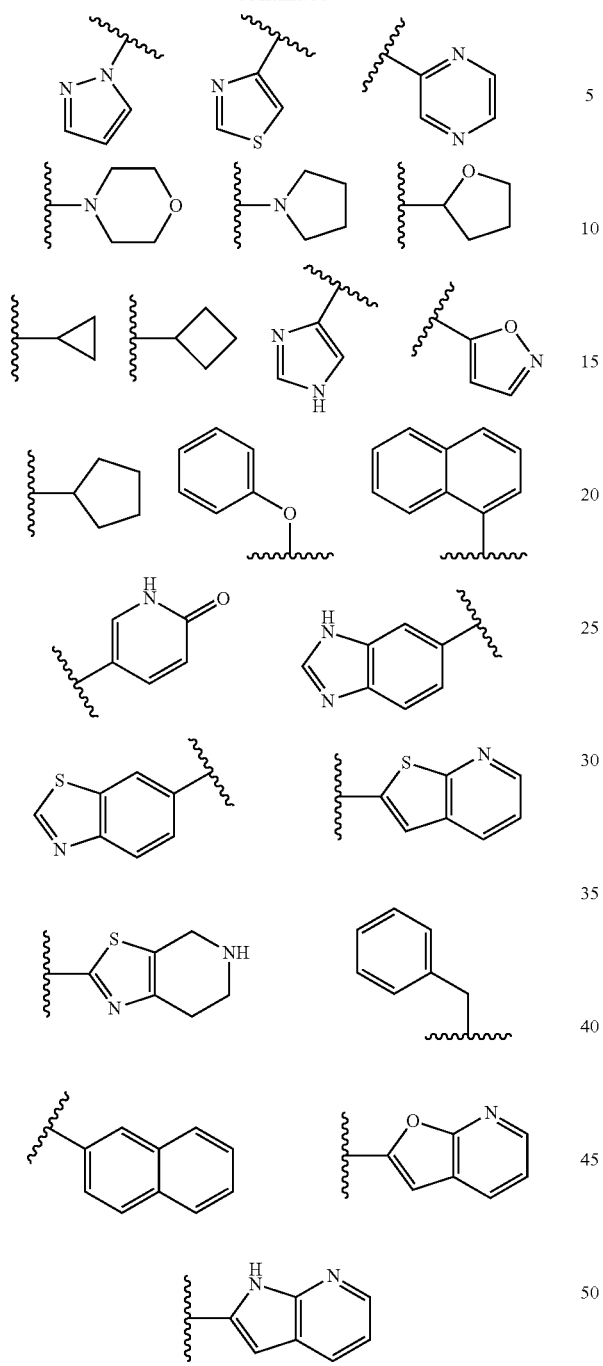

each of which is optionally substituted with one to three substituents independently selected from halo, —CH$_3$, —CF$_3$, —OCF$_3$, —CN, —NH$_2$, —OH, —CH$_2$N(CH$_3$)$_2$, —C(O)CH$_3$, —NH—(C$_1$-C$_6$)alkyl, —NH—(C$_1$-C$_6$)alkyl-(C$_1$-C$_6$)alkoxy, —SO$_2$—(C$_1$-C$_6$)alkyl, —SO$_2$—NH—(C$_1$-C$_6$)alkyl, —NH—SO$_2$—(C$_1$-C$_6$)alkyl, 3- to 12-membered heterocyclic, aryl, heteroaryl, —C$_1$-C$_8$-alkyl, —C$_1$-C$_8$-alkenyl, —C$_3$-C$_8$-cycloalkyl, —C$_3$-C$_8$-cycloalkenyl, and —C$_1$-C$_8$-alkoxy.

17. The compound of claim 1, represented by Formula (VIa-1), (VIa-2), (VIa-3), (VIa-4), (VIb-1), (VIb-2), (VIb-3), or (VIb-4,)

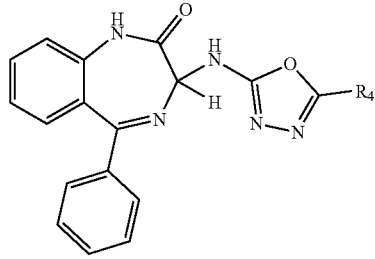
(VIa-1)

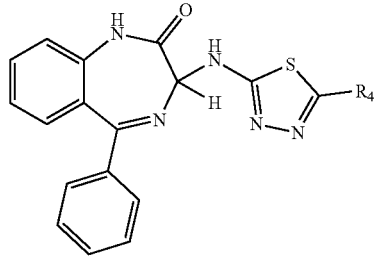
(VIa-2)

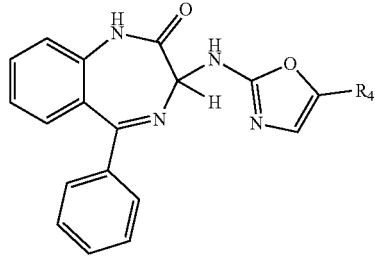
(VIa-3)

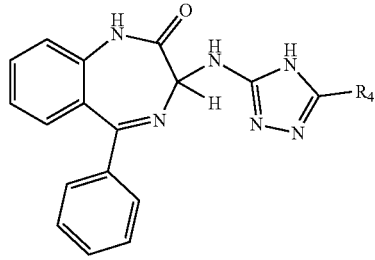
(VIa-4)

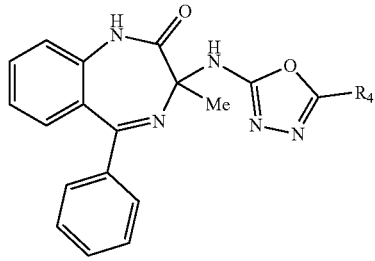
(VIb-1)

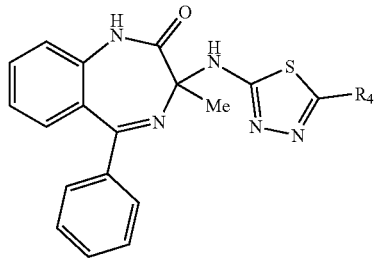
(VIb-2)

(VIb-3)
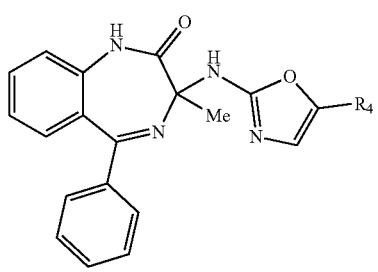
(VIb-4)
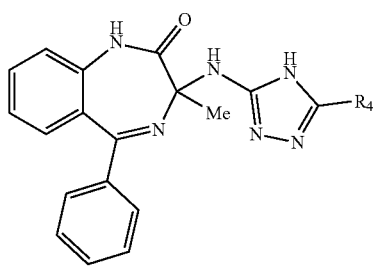
or a pharmaceutically acceptable salt thereof,
wherein
$R_4$ is selected from the groups below,
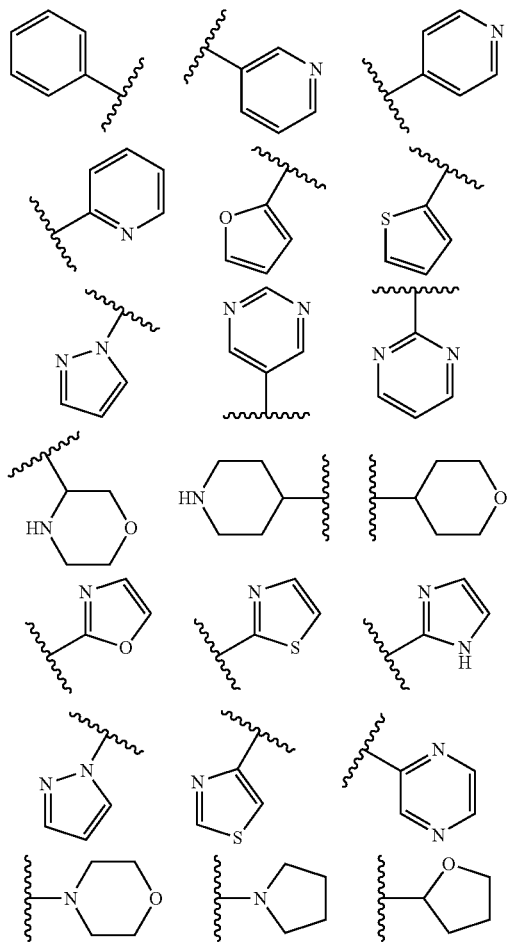
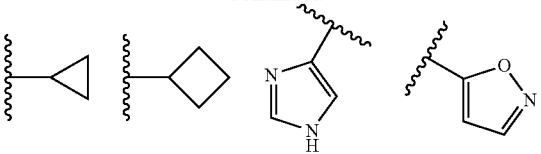
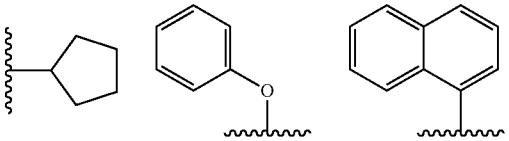
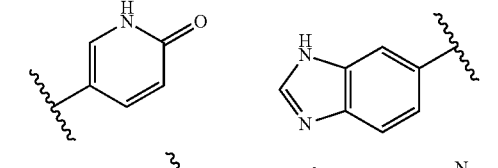
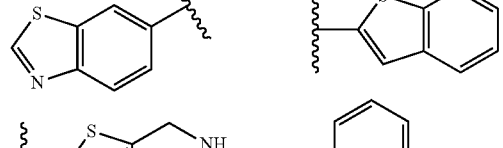
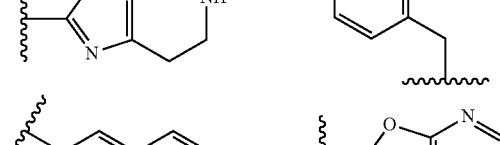
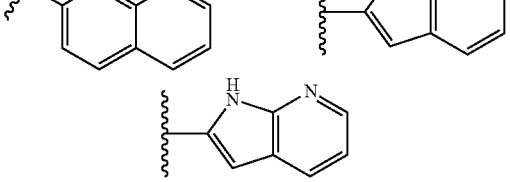
each of which is optionally substituted with one to three substituents independently selected from $CH_3$, CN, fluoro, chloro, $CH_3O$—, $CH_3C(O)$—, $CH_3OCH_2$—, $CH_3OCH_2CH_2O$—, —$CF_3$, $CF_3O$—,
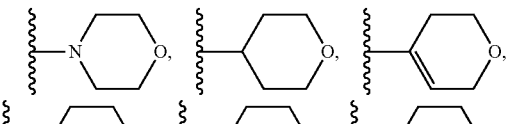
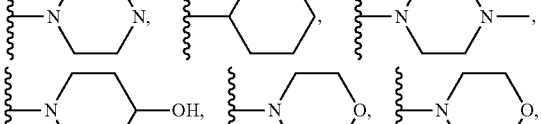
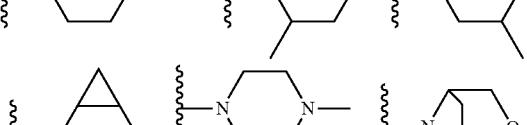
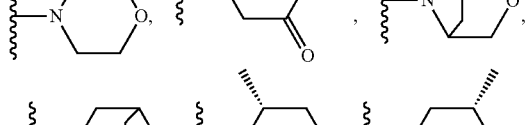
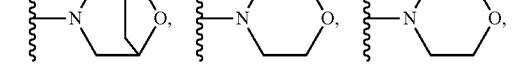

-continued
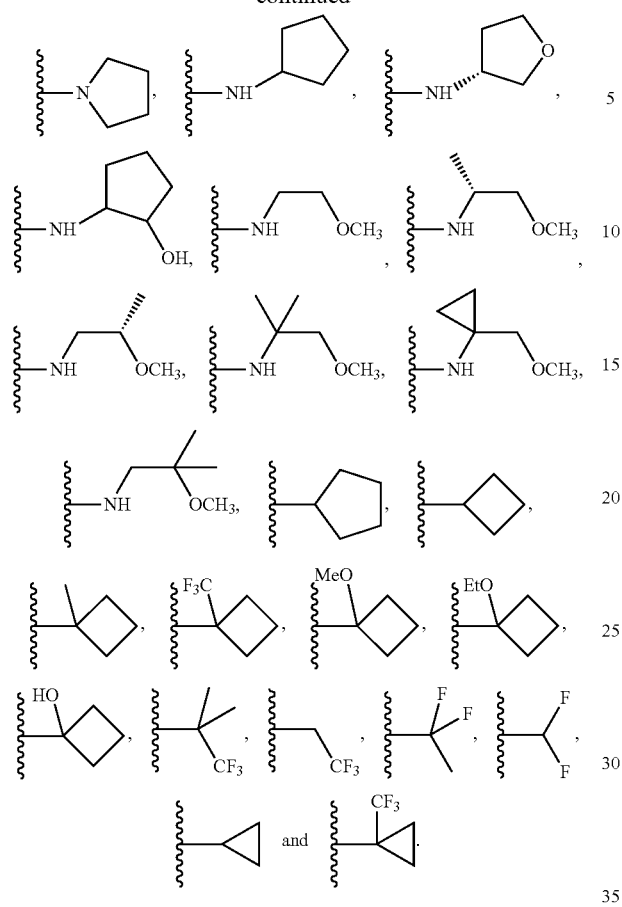
18. A compound represented by Formula (VIa-1), (VIa-2), (VIa-3), (VIa-4), (VIb-1), (VIb-2), (VIb-3), or (VIb-4,)
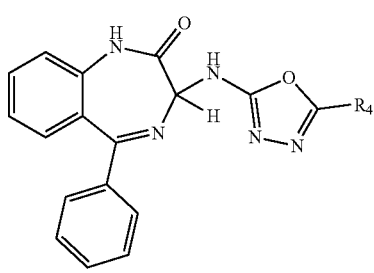
(VIa-1)
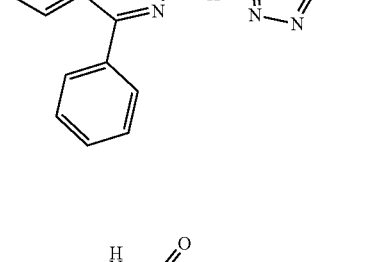
(VIa-2)
-continued
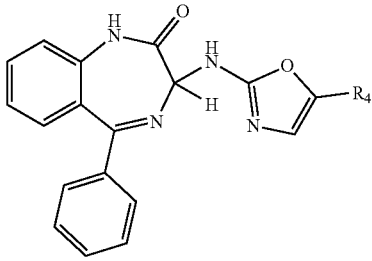
(VIa-3)
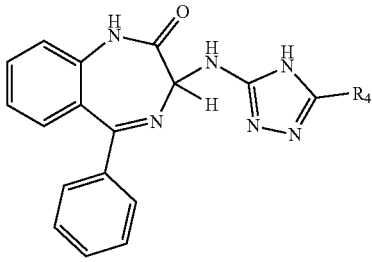
(VIa-4)
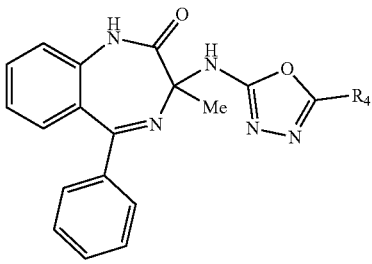
(VIb-1)
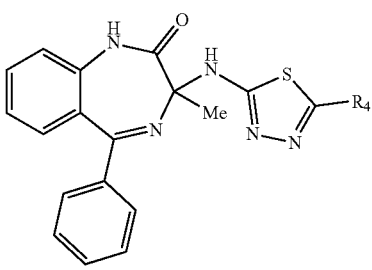
(VIb-2)
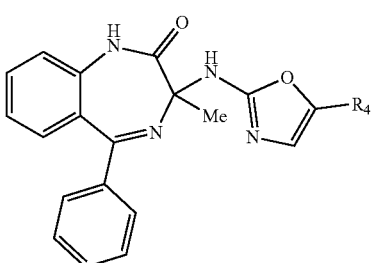
(VIb-3)
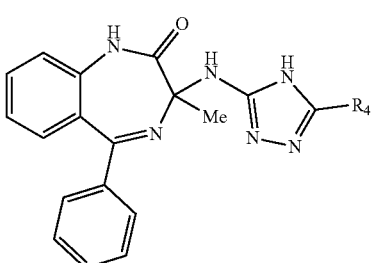
(VIb-4)
or a pharmaceutically acceptable salt thereof, wherein
R₄ is selected from the groups in the table below,
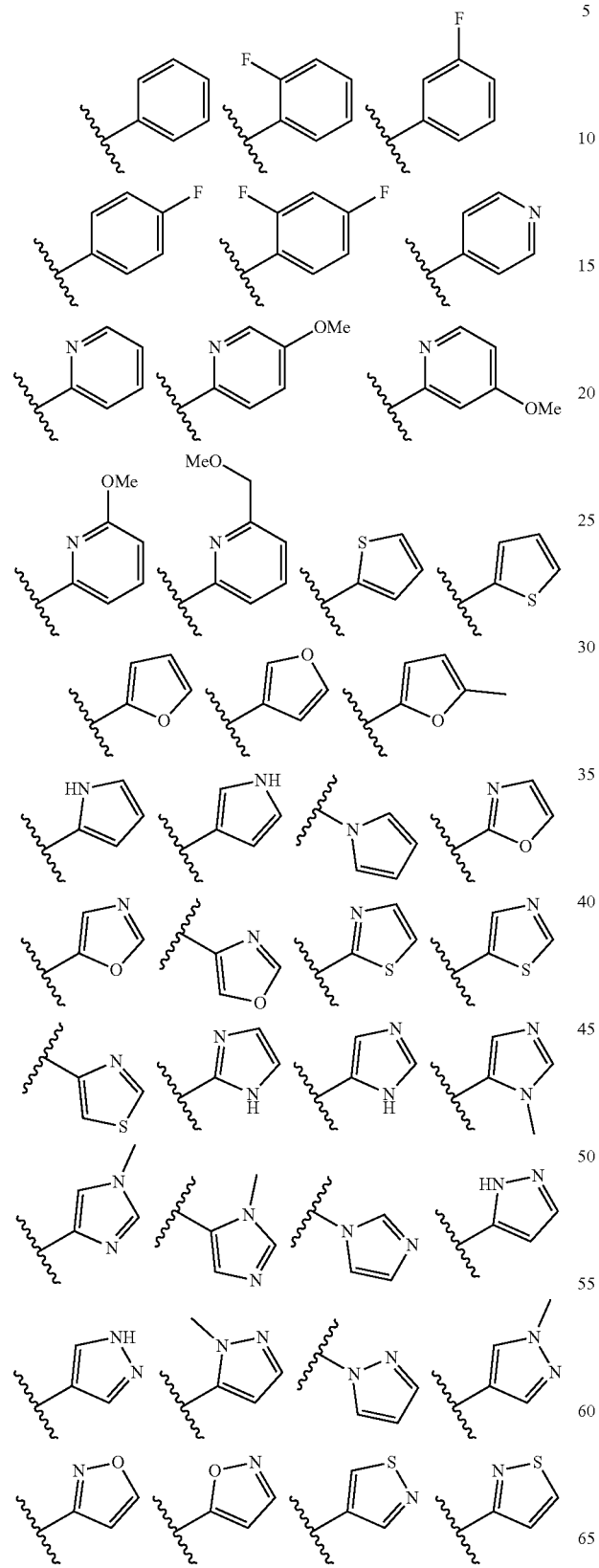
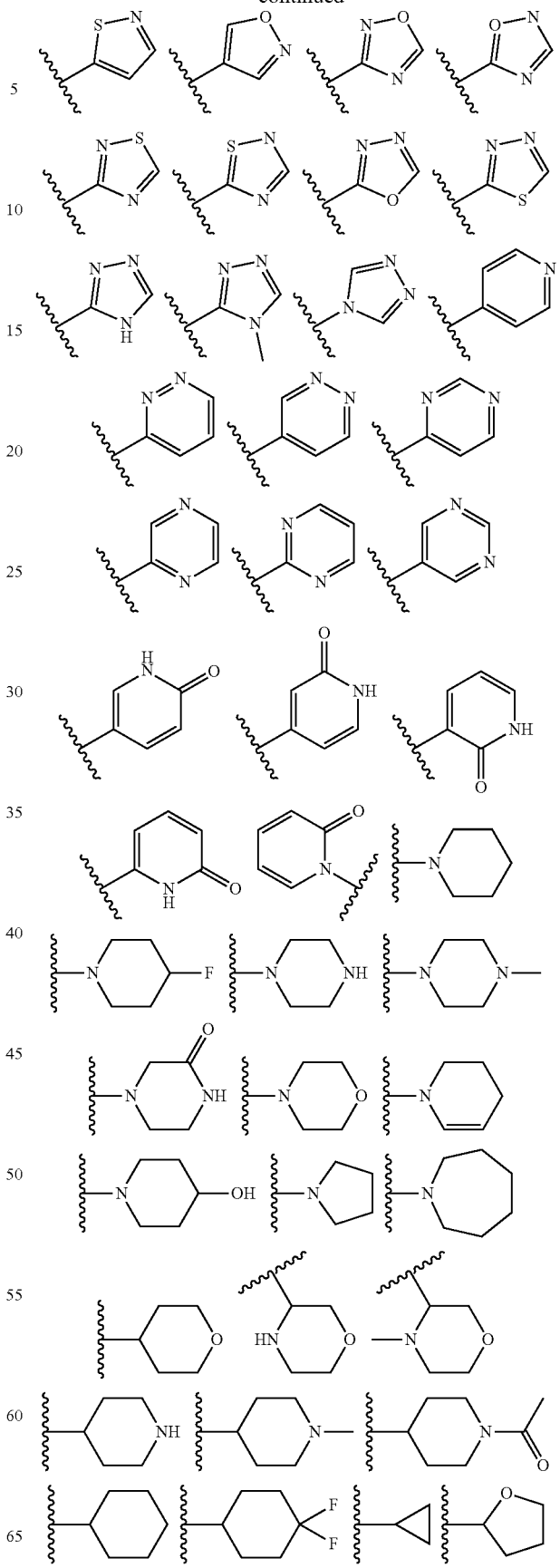

665
-continued
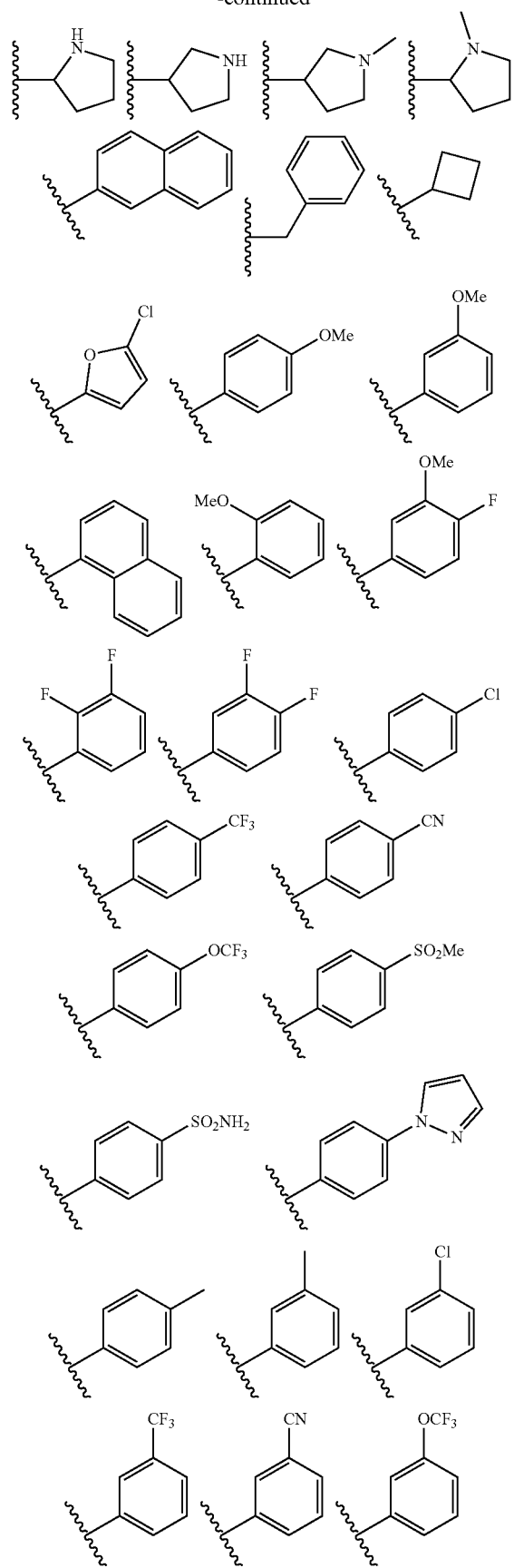
666
-continued
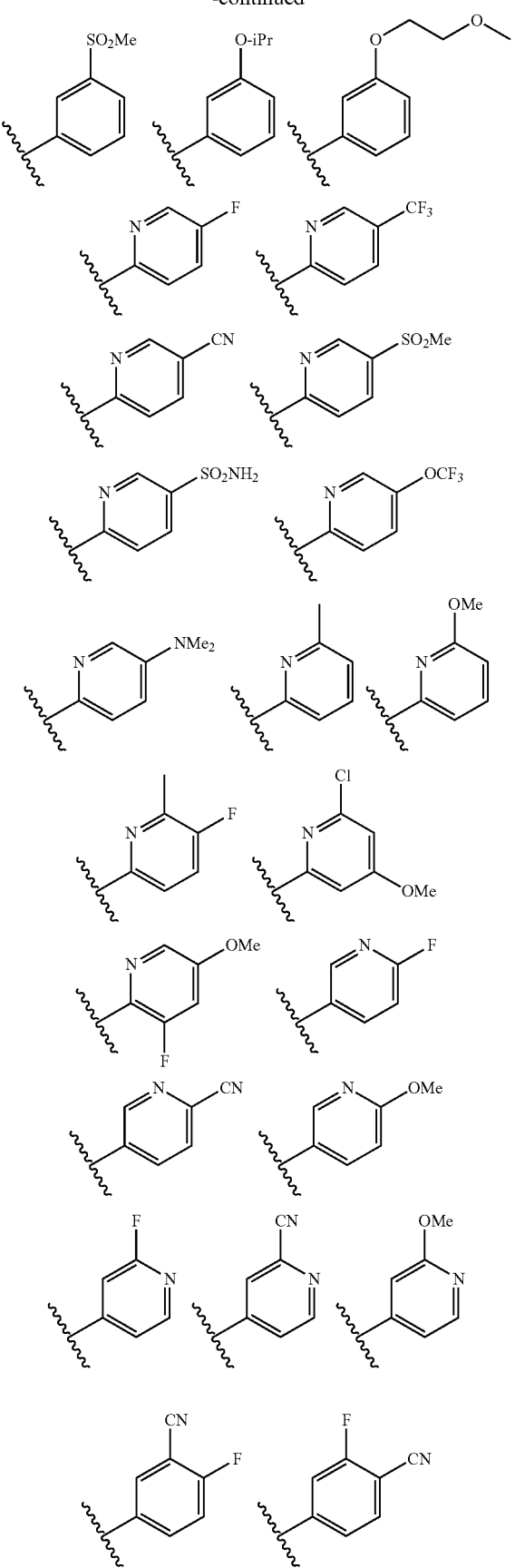

667
-continued
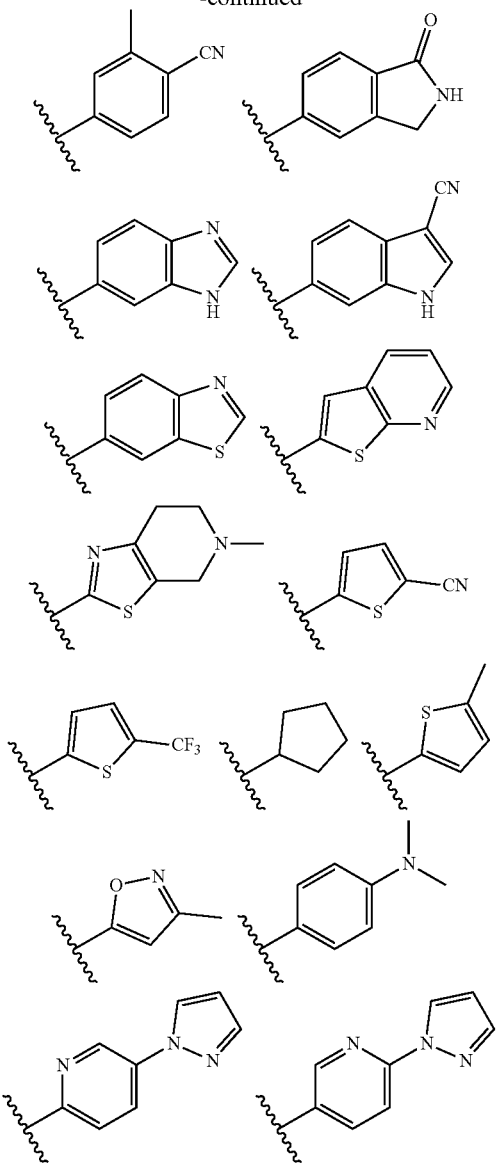
668
-continued
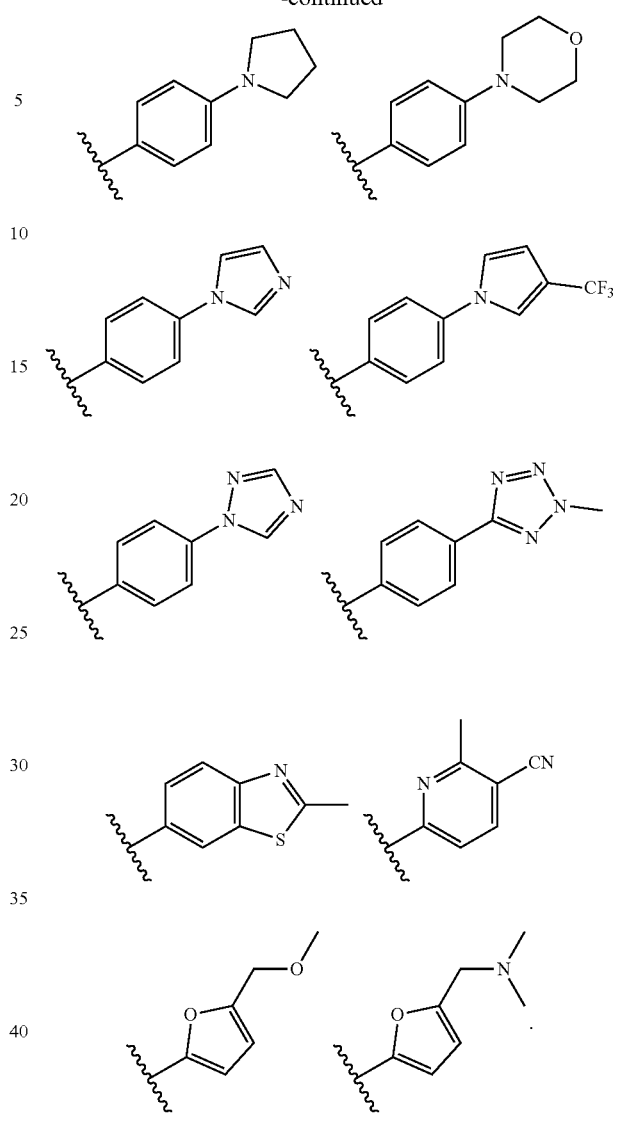
* * * * *

UNITED STATES PATENT AND TRADEMARK OFFICE
CERTIFICATE OF CORRECTION

PATENT NO. : 9,957,281 B2
APPLICATION NO. : 15/216119
DATED : May 1, 2018
INVENTOR(S) : Brian C. Shook et al.

It is certified that error appears in the above-identified patent and that said Letters Patent is hereby corrected as shown below:

In the Claims

At Column 581

In Claim 10, at structure 364, delete " 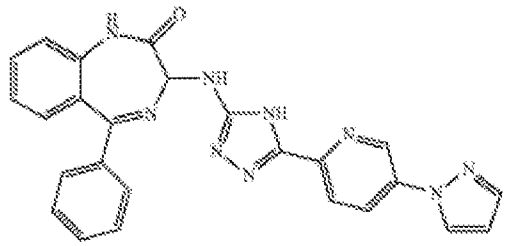 " and insert -- 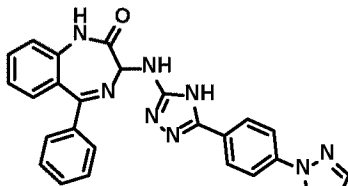 --; and At Column 583

In Claim 10, at structure 372, delete " 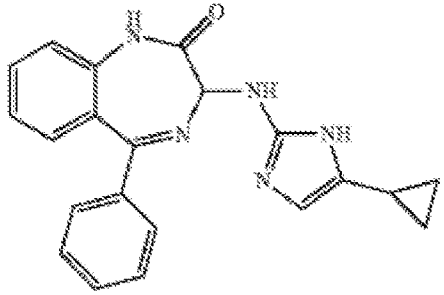 " and insert

Signed and Sealed this
Fourth Day of December, 2018

Andrei Iancu
*Director of the United States Patent and Trademark Office*

CERTIFICATE OF CORRECTION (continued)
U.S. Pat. No. 9,957,281 B2

-- 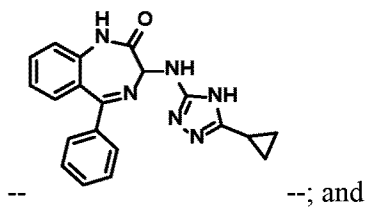 --; and

At Column 668

In Claim 18, at Line 15, delete second structure " 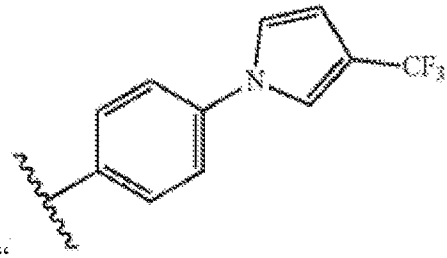 " and insert

-- 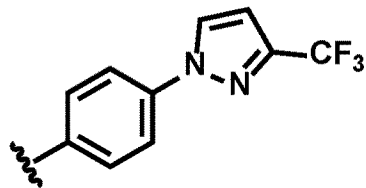 --.